United States Patent
Sheppard et al.

(10) Patent No.: US 11,643,388 B2
(45) Date of Patent: May 9, 2023

(54) INHIBITORS OF ALPHA 2 BETA 1 INTEGRIN AND METHODS OF USE THEREOF

(71) Applicants: The Regents of the University of California, Oakland, CA (US); ShangPharma Innovation Inc., South San Francisco, CA (US)

(72) Inventors: Dean Sheppard, Oakland, CA (US); William F. DeGrado, San Francisco, CA (US); Aparna Sundaram, San Francisco, CA (US); Hyunil Jo, Lafayette, CA (US); Richard Beresis, San Francisco, CA (US); Marc Adler, Orinda, CA (US)

(73) Assignees: The Regents of the University of California, Oakland, CA (US); ShangPharma Innovation Inc., South San Francisco, CA (US)

( * ) Notice: Subject to any disclaimer, the term of this patent is extended or adjusted under 35 U.S.C. 154(b) by 0 days.

(21) Appl. No.: 17/246,014

(22) Filed: Apr. 30, 2021

(65) Prior Publication Data
US 2022/0411366 A1 Dec. 29, 2022

Related U.S. Application Data

(60) Provisional application No. 63/019,023, filed on May 1, 2020.

(51) Int. Cl.
| | |
|---|---|
| *C07C 275/26* | (2006.01) |
| *C07C 275/24* | (2006.01) |
| *A61P 11/06* | (2006.01) |
| *C07D 205/04* | (2006.01) |
| *C07D 213/73* | (2006.01) |
| *C07D 217/02* | (2006.01) |
| *C07D 217/06* | (2006.01) |
| *C07D 239/84* | (2006.01) |

(52) U.S. Cl.
CPC ............ *C07C 275/26* (2013.01); *A61P 11/06* (2018.01); *C07C 275/24* (2013.01); *C07D 205/04* (2013.01); *C07D 213/73* (2013.01); *C07D 217/02* (2013.01); *C07D 217/06* (2013.01); *C07D 239/84* (2013.01)

(58) Field of Classification Search
CPC ...... C07C 275/26; C07C 275/24; A61P 11/06; C07D 205/04; C07D 213/73; C07D 217/02; C07D 217/06; C07D 239/84
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,946,778 A | 8/1990 | Ladner et al. | |
| 5,034,506 A | 7/1991 | Summerton et al. | |
| 5,235,033 A | 8/1993 | Summerton et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 8,258,159 B2 | 9/2012 | DeGrado et al. | |
| 8,946,159 B2 | 2/2015 | Feng | |
| 2009/0197861 A1 | 8/2009 | DeGrado et al. | |
| 2010/0179119 A1 | 7/2010 | DeGrado et al. | |
| 2016/0376266 A1 | 12/2016 | DeGrado et al. | |
| 2021/0387986 A1 | 12/2021 | Sheppard et al. | |

FOREIGN PATENT DOCUMENTS

| | | |
|---|---|---|
| EP | 0 308 936 A2 | 3/1989 |
| EP | 0 308 936 A3 | 3/1989 |
| EP | 0 308 936 B1 | 3/1989 |
| JP | 2003-277340 | 10/2003 |
| WO | WO-91/00360 A1 | 1/1991 |
| WO | WO-92/20373 A1 | 11/1992 |
| WO | WO-93/08829 A1 | 5/1993 |
| WO | WO-2006/133338 A1 | 12/2006 |
| WO | WO-2017/173302 A2 | 10/2017 |
| WO | WO-2017/173302 A3 | 10/2017 |
| WO | WO-2019/178248 A1 | 9/2019 |
| WO | WO-2021/222789 A1 | 11/2021 |

OTHER PUBLICATIONS

RN1057712-00-1, registry database compound, 2008.*
Benayoun, L. et al. (May 15, 2003, e-published Jan. 16, 2003). "Airway structural alterations selectively associated with severe asthma," *Am J Respir Crit Care Med* 167(10):1360-1368.
Berger, P. et al. (Nov. 2003). "Tryptase-stimulated human airway smooth muscle cells induce cytokine synthesis and mast cell Chemotaxis," *FASEB J* 17(14):2139-2141.
Borza, C.M. et al. (Jun. 2012, e-published Mar. 22, 2012). "Inhibition of integrin α2β1 ameliorates glomerular injury," *J Am Soc Nephrol* 23(6):1027-1038.
Brightling, C.E. et al. (May 2012, e-published Dec. 22, 2011). "Lung damage and airway remodelling in severe asthma," *Clin Exp Allergy* 42(5):638-649.
Chiba, Y. et al. (Feb. 2009, e-published Aug. 7, 2008). "Interleukin-13 augments bronchial smooth muscle contractility with an upregulation of RhoA protein," *Am J Respir Cell Mol Biol* 40(2):159-167.
Choi, S. et al. (Nov. 1, 2007, e-published Oct. 4, 2007). "Small molecule inhibitors of integrin $\alpha_2\beta_1$," *J Med Chem* 50(22):5457-5462.

(Continued)

*Primary Examiner* — Sun Jae Yoo
(74) *Attorney, Agent, or Firm* — Mintz, Levin, Cohn, Ferris, Glovsky and Popeo, P.C.

(57) ABSTRACT

Disclosed herein, inter alia, are inhibitors of alpha 2 beta 1 integrin and methods of using the same.

20 Claims, No Drawings
Specification includes a Sequence Listing.

(56) References Cited

OTHER PUBLICATIONS

Cole, S.P.C. et al. (1985). "The EBV-Hybridoma Technique and Its Application to Human Lung Cancer," *Monoclonal Antibodies and Cancer Therapy* pp. 77-96.
Halland, N. et al. (Jan. 10, 2014, e-published Feb. 13, 2014). "Small Macrocycles as Highly Active Integrin α2β1 Antagonists," *ACS Medicinal Chemistry Letters* 5(2):193-198.
Holgate, S.T. (Sep. 2011). "Pathophysiology of asthma: what has our current understanding taught us about new therapeutic approaches?" *J Allergy Clin Immunol* 128(3):495-505.
International Search Report dated Jul. 5, 2019, for PCT Application No. PCT/US2019/022078, filed Mar. 13, 2019, 4 pages.
International Search Report dated Oct. 12, 2021 for PCT Application No. PCT/US2021/030233, filed Apr. 30, 2021, 5 pages.
Jones. P.T. et al. (May 29-Jun. 4, 1986). "Replacing the complementarity-determining regions in a human antibody with those from a mouse," *Nature* 321(6069):522-525.
Kudo, M. et al. (Mar. 4, 2012). "IL-17A produced by αβ T cells drives airway hyper-responsiveness in mice and enhances mouse and human airway smooth muscle contraction," *Nat Med* 18(4)547-554.
Liu, S. et al. (Jun. 15, 2021). "Integrin α2β1 regulates collagen I tethering to modulate hyperresponsiveness in reactive airway disease models," *J Clin Invest* 131(12):e138140.
Marcus-Sakura, C.J. (Aug. 1, 1988). "Techniques for using antisense oligodeoxyribonucleotides to study gene expression," *Anal. Biochem.* 172(2):289-295.
McCafferty, J. et al. (Dec. 6, 1990). "Phage antibodies: filamentous phage displaying antibody variable domains," *Nature* 348(6301):552-554.
Mehta, D. et al. (Sep. 15, 1999). "Actin polymerization stimulated by contractile activation regulates force development in canine tracheal smooth muscle," *J Physiol* 519(Pt 3):829-840.
Miller, M.W. et al. (Jan. 20, 2009, e-published Jan. 13, 2009). "Small-molecule inhibitors of integrin alpha2beta1 that prevent pathological thrombus formation via an allosteric mechanism," *Proc Natl Acad Sci USA* 106(3):719-724.
Presta, L. (1992). "Antibody engineering," *Curr Opin Struc Biol* 2(4):593-596.
Sundaram, A. et al. (Jan. 3, 2017, e-published Dec. 5, 2016). "Targeting integrin α5β1 ameliorates severe airway hyperresponsiveness in experimental asthma," *J Clin Invest* 127(1):365-374.
Suresh. M.R. et al. (1986). "Bispecific monoclonal antibodies from hybrid hybridomas," *Methods Enzymol* 121:210-228.
Tang,D. et al. "Mechanosensitive tyrosine phosphorylation of paxillin and focal adhesion kinase in tracheal smooth muscle," *Am J Physiol* 276(1):C250-C258.
Traunecker, A. et al. (Dec. 1991). "Bispecific single chain molecules (Janusins) target cytotoxic lymphocytes on HIV infected cells," *EMBO J* 10(12):3655-3659.
Verhoeyen, M. et al. (Mar. 25, 1988). "Reshaping human antibodies: grafting an antilysozyme activity," *Science* 239(4847):1534-1536.
Wenzel, S.E. (Aug. 26, 2006). "Asthma: defining of the persistent adult phenotypes," *Lancet* 368(9537):804-813.
World Health Organization. Global surveillance, prevention and control of chronic respiratory diseases: a comprehensive approach. 2007, 155 pages.
Written Opinion dated Jul. 5, 2019, for PCT Application No. PCT/US2019/022078, filed Mar. 13, 2019, 6 pages.
Written Opinion dated Oct. 12, 2021 for PCT Application No. PCT/US2021/030233, filed Apr. 30, 2021, 6 pages.

\* cited by examiner

INHIBITORS OF ALPHA 2 BETA 1 INTEGRIN AND METHODS OF USE THEREOF

CROSS-REFERENCES TO RELATED APPLICATIONS

This application claims the benefit of U.S. Provisional Application No. 63/019,023, filed May 1, 2020, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant no. U54 HL 119893 awarded by The National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-683001US_Sequence_Listing_ST25.txt, created Apr. 23, 2021, 17,613 bytes, machine format IBM-PC, MS Windows operating system, is hereby incorporated by reference.

BACKGROUND

Severe asthma accounts for approximately 10% of the 300 million people worldwide that carry a diagnosis of asthma. These patients have persistent symptoms of exaggerated airway narrowing despite maximal medical therapy including anti-inflammatories (inhaled and oral corticosteroids, leukotriene inhibitors, and antibodies to IgE), and muscle-targeted therapies (beta-adrenergic agonists). Despite the initial promise of biologic therapies that target specific cytokine mediators of both T2 high and T2 low asthma, early clinical trials have shown inconsistent benefit only in a small subset of severe asthmatics. Meanwhile, there have been no significant advances in therapies that directly target airway smooth muscle in over half a century. It is clear that novel approaches that specifically target smooth muscle are required. Currently available muscle-targeted therapies have focused on the classical actin-myosin machinery contributing to force generation. We recently identified a parallel pathway involved in tension transmission from the cell to the extracellular matrix, and found that disruption of specific integrin interactions with matrix proteins can effectively impair tension transmission in airway smooth muscle, a critical step for airway narrowing in asthma. Disclosed herein, inter alia, are solutions to these and other problems in the art.

BRIEF SUMMARY

In an aspect is provided a compound, or a pharmaceutically acceptable salt thereof or a prodrug thereof, having the formula:

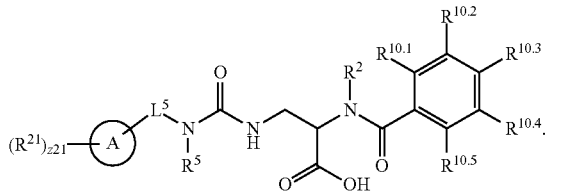

(I)

Ring A is cycloalkyl, heterocycloalkyl, aryl, or heteroaryl.
$R^2$ is hydrogen or substituted or unsubstituted alkyl.
$R^5$ is hydrogen or unsubstituted $C_1$-$C_3$ alkyl.
$L^5$ is a bond or unsubstituted $C_1$-$C_3$ alkylene.
$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $-C(O)R^{10.2C}$, $-C(O)OR^{10.2C}$, $-C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, $-L^{10.2}-R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$, $-L^{10.3}-R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$, $-L^{10.4}-R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.1A}C(O)R^{10.5C}$, $-NR^{10.5A}C(O)OR^{10.5C}$, $-NR^{10.1A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{21}$ is independently oxo, halogen, $-CX^{21}{}_3$, $-CHX^{21}{}_2$, $-CH_2X^{21}$, $-OCX^{21}{}_3$, $-OCH_2X^{21}$, $-OCHX^{21}{}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl substituted or unsubstituted cycloalkyl, substituted or unsubstituted heterocycloalkyl, substituted or unsubstituted aryl, or substituted or unsubstituted heteroaryl.

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, $-C(S)-$, substituted or unsubstituted alkylene, or substituted or unsubstituted heteroalkylene.

$R^{22}$, $R^{23}$, and $R^{24}$ are independently substituted or unsubstituted cycloalkyl, substituted or unsubstituted heterocycloalkyl, substituted or unsubstituted aryl, or substituted or unsubstituted heteroaryl.

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.4A}$, $R^{10.4B}$, $R^{10.4C}$, $R^{10.4D}$, $R^{10.5A}$, $R^{10.5B}$, $R^{10.5C}$, $R^{10.5D}$, $R^{21A}$, $R^{21B}$, $R^{21C}$, and $R^{21D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$, substituents bonded to the same nitrogen atom may be joined to form a substituted or unsubstituted heterocycloalkyl or substituted or unsubstituted heteroaryl.

The variables n10.1, n10.2, n10.3, n10.4, n10.5, and n21 are independently an integer from 0 to 4.

The variables m10.1, m10.2, m10.3, m10.4, m10.5, m21, v10.1, v10.2, v10.3, v10.4, v10.5, and v21 are independently 1 or 2.

$X^{10.1}$, $X^{10.2}$, $X^{10.3}$, $X^{10.4}$, $X^{10.5}$, and $X^{21}$ are independently $-F$, $-Cl$, $-Br$, or $-I$.

The variable z21 is an integer from 0 to 11.

At least one of $R^{10.1}$ or $R^{10.5}$ is not hydrogen.

At least one of $R^{10.2}$, $R^{10.3}$, or $R^{10.4}$ is $-L^{10.2}-R^{22}$, $-L^{10.3}-R^{23}$, or $-L^{10.4}-R^{24}$, respectively.

In an aspect is provided a compound, or a pharmaceutically acceptable salt thereof or a prodrug thereof, having the formula:

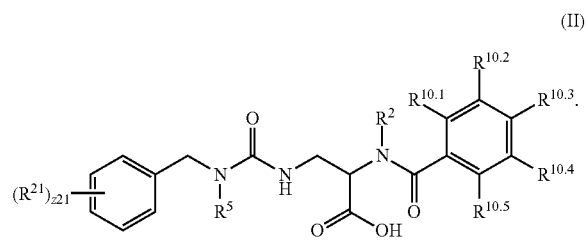

(II)

$R^2$, $R^5$, $R^{10.1}$, $R^{10.2}$, $R^{10.3}$, $R^{10}$, $R^{10.5}$, and $R^{21}$ are as described herein, including in embodiments. The variable z21 is an integer from 0 to 5. At least one of $R^{10.1}$ or $R^{10.5}$ is not hydrogen.

In an aspect is provided a compound, or a pharmaceutically acceptable salt thereof or a prodrug thereof, having the formula:

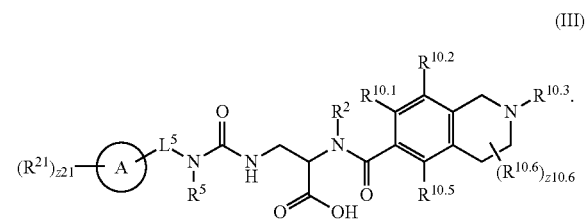

(III)

Ring A, $R^2$, $R^5$, $L^5$, $R^{10.1}$, $R^{10.2}$, $R^{10.3}$, $R^{10.5}$, $R^{21}$, and z21 are as described herein, including in embodiments. At least one of $R^{10.1}$ or $R^{10.5}$ is not hydrogen.

$R^{10.6}$ is independently oxo, halogen, $-CX^{10.6}{}_3$, $-CHX^{10.6}{}_2$, $-CH_2X^{10.6}$, $-OCX^{10.6}{}_3$, $-OCH_2X^{10.6}$, $-OCHX^{10.6}{}_2$, $-CN$, $-SO_{n10.6}R^{10.6D}$, $-SO_{v10.6}NR^{10.6A}R^{10.6B}$, $-NHC(O)NR^{10.6A}R^{10.6B}$, $-N(O)_{m10.6}$, $-NR^{10.6A}R^{10.6B}$, $-C(O)R^{10.6C}$, $-C(O)OR^{10.6C}$, $-C(O)NR^{10.6A}R^{10.6B}$, $-OR^{10.6D}$, $-SR^{10.6D}$, $-NR^{10.6A}SO_2R^{10.6D}$, $-NR^{10.6A}C(O)R^{10.6C}$, $-NR^{10.6A}C(O)OR^{10.6C}$, $-NR^{10.6A}OR^{10.6C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10.6A}$, $R^{10.6B}$, $R^{10.6C}$, and $R^{10.6D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.6A}$ and $R^{10.6B}$ substituents bonded to the same nitrogen atom may be joined to form a substituted or unsubstituted heterocycloalkyl or substituted or unsubstituted heteroaryl.

The variable n10.6 is an integer from 0 to 4.

The variables m10.6 and v10.6 are independently 1 or 2. $X^{10.6}$ is —F, —Cl, —Br, or —I.

The variable z10.6 is an integer from 0 to 6.

In an aspect is provided a compound, or a pharmaceutically acceptable salt thereof or a prodrug thereof, having the formula:

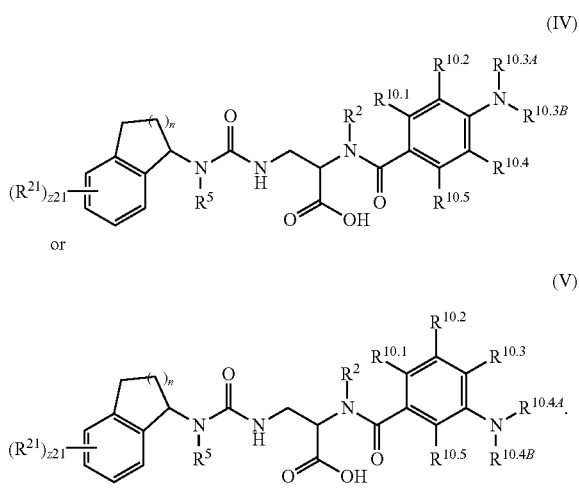

$R^2$, $R^5$, $R^{10.1}$, $R^{10.3A}$, $R^{10.3B}$, $R^{10.4A}$, $R^{10.4B}$, $R^{10.5}$, and $R^{21}$ are as described herein, including in embodiments. $R^{10.2}$, $R^{10.3}$, and $R^{10.4}$ are independently hydrogen, halogen, or —CF$_3$. The variable z21 is an integer from 0 to 9. The variable n is an integer from 0 to 3. At least one of $R^{10.1}$ or $R^{10.5}$ is not hydrogen.

In an aspect is provided a pharmaceutical composition including a compound described herein, or pharmaceutically acceptable salt thereof or a prodrug thereof, and a pharmaceutically acceptable excipient.

In an aspect is provided a method of treating asthma, the method including administering to a subject in need thereof an effective amount of a compound described herein, or a pharmaceutically acceptable salt thereof or a prodrug thereof.

In an aspect is provided a method of treating an inflammatory disease, the method including administering to a subject in need thereof an effective amount of a compound described herein, or a pharmaceutically acceptable salt thereof or a prodrug thereof.

In an aspect is provided a method of treating an autoimmune disease, the method including administering to a subject in need thereof an effective amount of a compound described herein, or a pharmaceutically acceptable salt thereof or a prodrug thereof.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. In embodiments, the alkyl is fully saturated. In embodiments, the alkyl is monounsaturated. In embodiments, the alkyl is polyunsaturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. In embodiments, an alkenylene includes one or more double bonds. In embodiments, an alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. In embodiments, a heteroalkenylene includes one or more double bonds. In embodiments, a heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N, and S. The 5 membered ring can contain zero or one double bond and one, two or three heteroatoms selected from the group consisting of O, N, and S. The 6 or 7 membered ring contains zero, one or two double bonds and one, two or three heteroatoms selected from the group consisting of O, N, and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5.6-fused ring heteroarylene refers to two rings fused together, wherein one ring has 5 members and the other ring has 6 members, and wherein at least one ring is a heteroaryl ring. Likewise, a 6.6-fused ring heteroarylene refers to two rings fused together, wherein one ring has 6 members and the other ring has 6 members, and wherein at least one ring is a heteroaryl ring. And a 6.5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzooxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

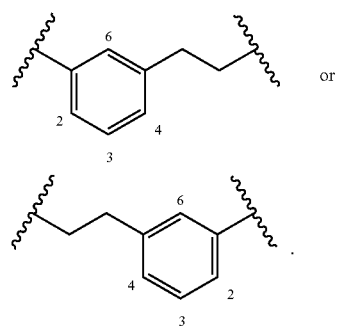

An alkylarylene moiety may be substituted (e.g., with a substituent group) on the alkylene moiety or the arylene linker (e.g., at carbons 2, 3, 4, or 6) with halogen, oxo, $-N_3$, $-CF_3$, $-CCl_3$, $-CBr_3$, $-Cl_3$, $-CN$, $-CHO$, $-OH$, $-NH_2$, $-COOH$, $-CONH_2$, $-NO_2$, $-SH$, $-SO_2CH_3$, $-SO_3H$, $-OSO_3H$, $-SO_2NH_2$, $-NHNH_2$, $-ONH_2$, $-NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

The term "alkylsulfonyl," as used herein, means a moiety having the formula $-S(O_2)-R'$, where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'C(O)NR"R''', —NR"C(O)$_2$R', —NRC(NR'R"R''')=NR'''', —NRC(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)OR", —NR'OR", —N$_3$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'C(O)NR"R''', —NR"C(O)$_2$R', —NRC(NR'R"R''')=NR'''', —NRC(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the application (e.g., Examples section, claims, embodiments, FIGURES, or tables below).

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$ respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$ $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g., $R^{1.3}$, $R^{2.3}$, $R^{3.3}$, $R^{4.3}$, $R^{5.3}$ ... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

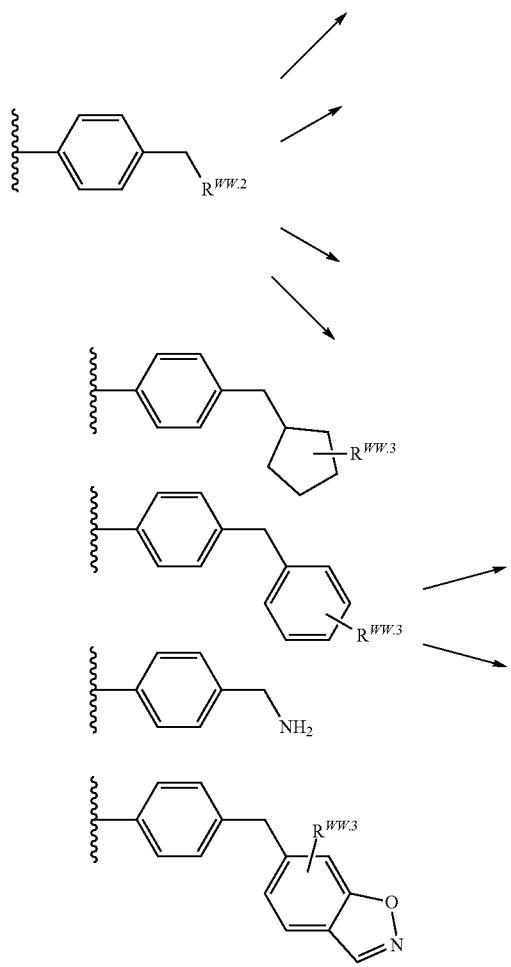

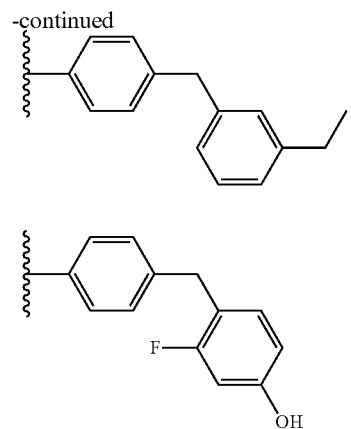

$R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW}$ is independently $-F$, $-Cl$, $-Br$, or $-I$.

$R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{LWW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}_3$, —$CHX^{LWW.2}_{22}$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, —$OCHX^{LWW.3}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, —$SO_2$—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example: (a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; and (o) biotin conjugate can react with avidin or streptavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an", as used in herein means one or more. In addition, the phrase "substituted with a[n]", as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl", the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Pb, $^{212}$Bi, $^{213}$Bi, $^{223}$Ra, and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb, and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, or L$^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

An "α2β1-inhibitor" or "α2β1 inhibitor" or "alpha 2 beta 1 inhibitor" as used herein refers to a substance, agent, or composition (e.g., a compound, nucleic acid, polynucleotide, peptide, or protein) capable of reducing the activity of α2β1 integrin when compared to a control compound (e.g., known to have no reduction in α2β1 integrin activity) or the absence of the α2β1-inhibitor compound. An "α2β1-inhibitor compound" or "α2β1 inhibitor compound" or "alpha 2 beta 1 inhibitor compound" refers to a compound (e.g., compound described herein) that reduce the activity of α2β1 integrin when compared to a control, such as absence of the compound or a compound with known inactivity.

"Specific," "specifically", "specificity", or the like of a composition (e.g., a compound, nucleic acid, polynucleotide, peptide, or protein) refers to the composition's ability to discriminate between particular molecular targets to a significantly greater extent than other proteins in the cell (e.g., a compound having specificity towards α2β1 integrin binds to α2β1 integrin whereas the same compound displays little-to-no binding to other integrins such as αvβ1, α8β1, α5β1, αvβ3, αvβ5, or αvβ6). An "α2β1-specific compound" or "α2β1 specific compound" or "alpha 2 beta 1 specific compound" refers to a compound (e.g., compound described herein) having specificity towards α2β1 integrin.

The term "selective" or "selectivity" or the like of a compound refers to the composition's (e.g., a compound, nucleic acid, polynucleotide, peptide, or protein) ability to cause a particular action in a particular molecular target (e.g., a compound having selectivity toward α2β1 integrin would inhibit only α2β1). An "α2β1-selective compound" or "α2β1 selective compound" or "alpha 2 beta 1 selective compound" refers to a compound (e.g., compounds described herein) having selectivity towards α2β1 integrin.

The terms "polypeptide", "peptide", and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist", "activator", "upregulator", etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor", "repressor", "antagonist", or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease means that the disease is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components. For example, binding of a thioredoxin protein with a compound as described herein may reduce the interactions between the thioredoxin protein and downstream effectors or signaling pathway components, resulting in changes in cell growth, proliferation, or survival.

In this disclosure, "comprises", "comprising", "containing", and "having" and the like can have the meaning ascribed to them in U.S. Patent law and can mean "includes", "including", and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with a compound, pharmaceutical composition, or method provided herein. In some embodiments, the disease is asthma. The disease may be airway hyperresponsiveness. The disease may be airway hyperresponsiveness in asthma. The disease may be angiogenesis. The disease may be an autoimmune disease (e.g., scleroderma, lupus, diabetes, or rheumatoid arthritis). The disease may be an inflammatory disease (e.g., autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis).

As used herein, the term "inflammatory disease" refers to a disease or condition characterized by aberrant inflammation (e.g., an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, and atopic dermatitis.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, treating refers to treating a subject having a disease.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of a disease or disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "bind" and "bound" as used herein is used in accordance with its plain and ordinary meaning and refers to the association between atoms or molecules. The association can be covalent (e.g., by a covalent bond or linker) or non-covalent (e.g., electrostatic interactions (e.g., ionic bond, hydrogen bond, or halogen bond), van der Waals interactions (e.g., dipole-dipole, dipole-induced dipole, or London dispersion), ring stacking (pi effects), hydrophobic interactions, and the like).

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der Waals bond(s)/interactions, hydrogen bond(s), polar bond(s), or combinations or mixtures thereof).

As used herein, the term "asthma" refers to any disease or condition characterized by inflammation within the circulatory system, often accompanied with wheezing, airway restriction, shortness of breath, chest tightness, and coughing. In embodiments, asthma is characterized by airway hyperresponsiveness. In embodiments, asthma is airway hyperresponsiveness. Asthma may refer inflammation in the bronchi and bronchioles. Asthma may refer to atopic asthma. Asthma may refer to non-atopic asthma.

The compounds described herein may be prodrugs. The term "prodrug" when referring to a prodrug described herein (e.g., $\alpha 2\beta 1$-inhibitor compound moiety bonded to a prodrug moiety) refers to the compound including the $\alpha 2\beta 1$-inhibitor compound moiety and the prodrug moiety. A "prodrug moiety" is the portion of a prodrug that may be cleaved from the prodrug resulting in an increased activity of the non-prodrug moiety portion of the prodrug, for example an $\alpha 2\beta 1$-inhibitor compound having increased $\alpha 2\beta 1$-inhibitor activity relative to the prodrug of the α2β1-inhibitor compound. In embodiments, the compounds described herein are prodrugs, wherein the prodrug moiety is the component of the compound that is not an α2β1-inhibitor compound moiety and is released from the α2β1-inhibitor compound moiety upon degradation of the prodrug.

In embodiments, the prodrug of a compound described herein may be a prodrug having a prodrug moiety attached to the —C(O)OH group. The prodrug moiety is typically selected to be labile in vivo, thereby revealing the —C(O)OH group. In embodiments, an α2β1-inhibitor compound is a compound described herein and a prodrug of the α2β1-inhibitor compound is the identical compound except the hydrogen in the —C(O)OH group is not a hydrogen. A person having ordinary skill in the art would understand that the α2β1 inhibitor compound moiety includes only those compounds compatible with the chemistry provided herein for connecting the α2β1-inhibitor compound moiety to the prodrug moiety and for release of the α2β1-inhibitor compound from the compound (prodrug) (e.g., in vivo). In embodiments, degradation of the prodrug releases an active agent (e.g., α2β1-inhibitor compound). In such compounds, the resulting active agent includes a higher level of activity compared to the level of activity of the intact prodrug.

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of α subunits (from about 120 to about 170 kDa in size) and β subunits (from about 90 to about 100 kDa in size).

The terms "α2β1", "alpha 2 beta 1", "α2β1 integrin", and "alpha 2 beta 1 integrin" refer to an integrin comprised of α2 subunit and a β1 subunit and is used according to its common, ordinary meaning. "α2β1" refers to proteins of the same or similar names, homologs, isoforms, and functional fragments thereof, so long as such fragments retain α2β1 integrin activity. The term includes any recombinant or naturally-occurring form of α2β1, or an α2β1 preprotein, or variants thereof that maintain α2β1 activity (e.g., within at least 30%, 40%, 50%, 60%, 70%, 80%, 90%, 95%, or 100% activity compared to wildtype α2β1). In embodiments, α2 has the protein sequence corresponding to RefSeq NP_002194.2. In embodiments, α2 has the protein sequence corresponding to the proteolytically processed mature version of RefSeq NP_002194.2. In embodiments, α2 has the amino acid sequence corresponding to nucleic acid sequence of the reference number NM_002203.3. In embodiments, α2 has the following amino acid sequence:

```
                                              (SEQ ID NO:1)
MGPERTGAAPLPLLLVLALSQGILNCCLAYNVGLPEAKIFSGPSSEQFG

YAVQQFINPKGNWLLVGSPWSGFPENRMGDVYKCPVDLSTATCEKLNLQ

TSTSIPNVTEMKTNMSLGLILTRNMGTGGFLTCGPLWAQQCGNQYYTTG

VCSDISPDFQLSASFSPATQPCPSLIDVVVVCDESNSIYPWDAVKNFLE

KFVQGLDIGPTKTQVGLIQYANNPRVVFNLNTYKTKEEMIVATSQTSQY

GGDLINTFGAIQYARKYAYSAASGGRRSATKVMVVVTDGESHDGSMLKA

VIDQCNHDNILRFGIAVLGYLNRNALDTKNLIKEIKAIASIPTERYFFN

VSDEAALLEKAGTLGEQIFSIEGTVQGGDNFQMEMSQVGFSADYSSQND

ILMLGAVGAFGWSGTIVQKTSHGHLIFPKQAFDQILQDRNHSSYLGYSV

AAISTGESTHFVAGAPRANYTGQIVLYSVNENGNITVIQAHRGDQIGSY

FGSVLCSVDVDKDTITDVLLVGAPMYMSDLKKEEGRVYLFTIKKGILGQ

HQFLEGPEGIENTRFGSAIAALSDINMDGFNDVIVGSPLENQNSGAVYI

YNGHQGTIRTKYSQKILGSDGAFRSHLQYFGRSLDGYGDLNGDSITDVS

IGAFGQVVQLWSQSIADVAIEASFTPEKITLVNKNAQIILKLCFSAKFR

PTKQNNQVAIVYNITLDADGFSSRVTSRGLFKENNERCLQKNMVVNQAQ

SCPEHIIYIQEPSDVVNSLDLRVDISLENPGTSPALEAYSETAKVFSIP

FHKDCGEDGLCISDLVLDVRQIPAAQEQPFIVSNQNKRLTFSVTLKNKR

ESAYNTGIVVDFSENLFFASFSLPVDGTEVTCQVAASQKSVACDVGYPA

LKREQQVTFTINFDFNLQNLQNQASLSFQALSESQEENKADNLVNLKIP

LLYDAEIHLTRSTNINFYEISSDGNVPSIVHSFEDVGPKFIFSLKVTTG

SVPVSMATVIIHIPQYTKEKNPLMYLTGVQTDKAGDISCNADINPLKIG

QTSSSVSFKSENFRHTKELNCRTASCSNVTCWLKDVHMKGEYFVNVTTR

IWNGTFASSTFQTVQLTAAAEINTYNPEIYVIEDNTVTIPLMIMKPDEK

AEVPTGVIIGSIIAGILLLLALVAILWKLGFFKRKYEKMTKNPDEIDET

TELSS.
```

In embodiments, β1 has the protein sequence corresponding to RefSeq NP_002202.2 In embodiments, β1 has the amino acid sequence corresponding to the reference number GI: 19743813. In embodiments, β1 has the following amino acid sequence:

```
                                              (SEQ ID NO:2)
MNLQPIFWIGLISSVCCVFAQTDENRCLKANAKSCGECIQAGPNCGWCT

NSTFLQEGMPTSARCDDLEALKKKGCPPDDIENPRGSKDIKKNKNVTNR

SKGTAEKLKPEDITQIQPQQLVLRLRSGEPQTFTLKFKRAEDYPIDLYY

LMDLSYSMKDDLENVKSLGTDLMNEMRRITSDFRIGFGSFVEKTVMPYI

STTPAKLRNPCTSEQNCTSPFSYKNVLSLTNKGEVFNELVGKQRISGNL

DSPEGGFDAIMQVAVCGSLIGWRNVTRLLVFSTDAGFHFAGDGKLGGIV

LPNDGQCHLENNMYTMSHYYDYPSIAHLVQKLSENNIQTIFAVTEEFQP

VYKELKNLIPKSAVGTLSANSSNVIQLIIDAYNSLSSEVILENGKLSEG

VTISYKSYCKNGVNGTGENGRKCSNISIGDEVQFEISITSNKCPKKDSD

SFKIRPLGFTEEVEVILQYICECECQSEGIPESPKCHEGNGTFECGACR

CNEGRVGRHCECSTDEVNSEDMDAYCRKENSSEICSNNGECVCGQCVCR

KRDNTNEIYSGKFCECDNFNCDRSNGLICGGNGVCKCRVCECNPNYTGS

ACDCSLDTSTCEASNGQICNGRGICECGVCKCTDPKFQGQTCEMCQTCL

GVCAEHKECVQCRAFNKGEKKDTCTQECSYFNITKVESRDKLPQPVQPD

PVSHCKEKDVDDCWFYFTYSVNGNNEVMVHVVENPECPTGPDIIPIVAG

VVAGIVLIGLALLLIWKLLMIIHDRREFAKFEKEKMNAKWDTGENPIYK

SAVTTVVNPKYEGK.
```

II. Compounds

In an aspect is provided a compound, or a pharmaceutically acceptable salt thereof or a prodrug thereof, having the formula:

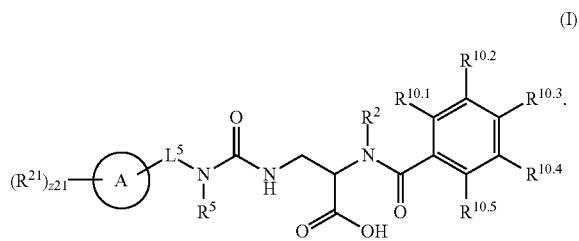

(I)

Ring A is cycloalkyl, heterocycloalkyl, aryl, or heteroaryl.

$R^2$ is hydrogen or substituted or unsubstituted alkyl (e.g., $C_1$-$C_8$, $C_1$-$C_6$, $C_1$-$C_4$, or $C_1$-$C_2$).

$R^5$ is hydrogen or unsubstituted $C_1$-$C_3$ alkyl.

$L^5$ is a bond or unsubstituted $C_1$-$C_3$ alkylene.

$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $N(O)_{m10.2}$, $-NR^{10.2A}R^{10.2B}$, $-C(O)R^{10.2C}$, $-C(O)OR^{10.2C}$, $-C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$,-$L^{10.2}$-$R^{22}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$,-$L^{10.3}$-$R^{23}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$,-$L^{10.4}$-$R^{24}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.1A}C(O)R^{10.5C}$, $-NR^{10.5A}C(O)OR^{10.5C}$, $-NR^{10.5A}OR^{10.5C}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, $-C(S)-$, substituted or unsubstituted alkylene (e.g., $C_1$-$C_8$, $C_1$-$C_6$, $C_1$-$C_4$, or $C_1$-$C_2$), or substituted or unsubstituted heteroalkylene (e.g., 2 to 8 membered, 2 to 6 membered, 4 to 6 membered, or 2 to 3 membered).

$R^{22}$, $R^{23}$, and $R^{24}$ are independently substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.4A}$, $R^{10.4B}$, $R^{10.4C}$, $R^{10.4D}$, $R^{10.5A}$, $R^{10.5B}$, $R^{10.5C}$, $R^{10.5D}$, $R^{21A}$, $R^{21B}$, $R^{21C}$, and $R^{21D}$ are independently hydrogen, halogen, —CCl₃, —CBr₃, —CF₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); $R^{10.1A}$ and $R^{10.1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{10.2A}$ and $R^{10.2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{10.3A}$ and $R^{10.3B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{10.4A}$ and $R^{10.4B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{10.5A}$ and $R^{10.5B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered); $R^{21A}$ and $R^{21B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

The variables n10.1, n10.2, n10.3, n10.4, n10.5, and n21 are independently an integer from 0 to 4.

The variables m10.1, m10.2, m10.3, m10.4, m10.5, m21, v10.1, v10.2, v10.3, v10.4, v10.5, and v21 are independently 1 or 2.

$X^{10.1}$, $X^{10.2}$, $X^{10.3}$, $X^{10.4}$, $X^{10.5}$, and $X^{21}$ are independently —F, —Cl, —Br, or —I.

The variable z21 is an integer from 0 to 11.

At least one of $R^{10.1}$ or $R^{10.5}$ is not hydrogen.

At least one of $R^{10.2}$, $R^{10.3}$, or $R^{10.4}$ is -$L^{10.2}$-$R^{22}$, -$L^{10.3}$-$R^{23}$, or -$L^{10.4}$-$R^{24}$, respectively.

In embodiments, the prodrug thereof may be a prodrug having a prodrug moiety attached to the —C(O)OH group. The prodrug moiety is typically selected to be labile in vivo, thereby revealing the —C(O)OH group.

In an aspect is provided a compound, or a pharmaceutically acceptable salt thereof or a prodrug thereof, having the formula:

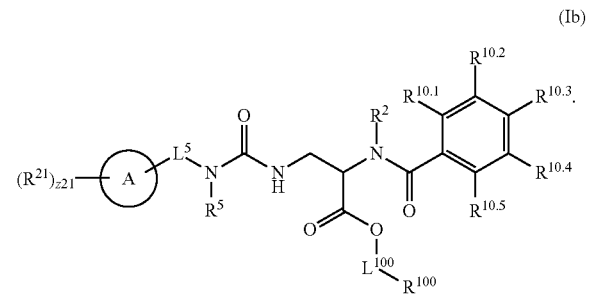

(Ib)

Ring A, $R^2$, $R^5$, $R^{10.1}$, $R^{10.2}$, $R^{10.3}$, $R^{10.4}$, $R^{10.5}$, $R^{21}$, $L^5$, and z21 are as described herein, including in embodiments. At least one of $R^{10.1}$ or $R^{10.5}$ is not hydrogen. At least one of $R^{10.2}$, $R^{10.3}$, or $R^{10.4}$ is -$L^{10.2}$-$R^{22}$, -$L^{10.3}$-$R^{23}$, or -$L^{10.4}$-$R^{24}$, respectively, wherein $L^{10.2}$, $R^{22}$, $L^{10.3}$, $R^{23}$, $L^{10.4}$, and $R^{24}$ are as described herein, including in embodiments.

$L^{100}$ is a bond, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, or 2 to 3 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^{100}$ is hydrogen, halogen, —CX$^{100}_3$, —CHX$^{100}_2$, —CH₂X$^{100}$, —OCX$^{100}_3$, —OCH₂X$^{100}$, —OCHX$^{100}_2$, —CN, —SO$_{n100}$R$^{100D}$, —SO$_{v100}$NR$^{100A}$R$^{100B}$, —NHC(O)NR$^{100A}$R$^{100B}$, —N(O)$_{m100}$, —NR$^{100A}$R$^{100B}$, —C(O)R$^{100C}$, —C(O)OR$^{100C}$, —C(O)NR$^{100A}$R$^{100B}$, —OR$^{100D}$, —SR$^{100D}$, —NR$^{100A}$SO₂R$^{100D}$, —NR$^{100A}$C(O)R$^{100C}$, —NR$^{100A}$C(O)OR$^{100C}$, —NR$^{100A}$OR$^{100C}$, —N₃, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{100A}$, $R^{100B}$, $R^{100C}$, and $R^{100D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —C OOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —O CHI$_2$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, or 2 to 3 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered); $R^{100A}$ and $R^{100B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

The variable n100 is an integer from 0 to 4.

The variables m100 and v100 are independently 1 or 2.

$X^{100}$ is independently —F, —Cl, —Br, or —I.

In embodiments, a substituted $L^{100}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{100}$ is substituted with a plurality of groups selected from substituent groups, size-limited substituent groups, and lower substituent groups; each substituent group, size-limited substituent group, and/or lower substituent group may optionally be different. In embodiments, when $L^{100}$ is substituted, it is substituted with at least one substituent group. In embodiments, when $L^{100}$ is substituted, it is substituted with at least one size-limited substituent group. In embodiments, when $L^{100}$ is substituted, it is substituted with at least one lower substituent group.

In embodiments, a substituted $R^{100}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100}$ is substituted with a plurality of groups selected from substituent groups, size-limited substituent groups, and lower substituent groups; each substituent group, size-limited substituent group, and/or lower substituent group may optionally be different. In embodiments, when $R^{100}$ is substituted, it is substituted with at least one substituent group. In embodiments, when $R^{100}$ is substituted, it is substituted with at least one size-limited substituent group. In embodiments, when $R^{100}$ is substituted, it is substituted with at least one lower substituent group.

In embodiments, a substituted $R^{100A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100A}$ is substituted with a plurality of groups selected from substituent groups, size-limited substituent groups, and lower substituent groups; each substituent group, size-limited substituent group, and/or lower substituent group may optionally be different. In embodiments, when $R^{100A}$ is substituted, it is substituted with at least one substituent group. In embodiments, when $R^{100A}$ is substituted, it is substituted with at least one size-limited substituent group. In embodiments, when $R^{100A}$ is substituted, it is substituted with at least one lower substituent group.

In embodiments, a substituted $R^{100B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100B}$ is substituted with a plurality of groups selected from substituent groups, size-limited substituent groups, and lower substituent groups; each substituent group, size-limited substituent group, and/or lower substituent group may optionally be different. In embodiments, when $R^{100B}$ is substituted, it is substituted with at least one substituent group. In embodiments, when $R^{100B}$ is substituted, it is substituted with at least one size-limited substituent group. In embodiments, when R"" is substituted, it is substituted with at least one lower substituent group.

In embodiments, a substituted ring formed when $R^{100A}$ and $R^{100B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{100A}$ and $R^{100B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{100A}$ and $R^{100B}$ substituents bonded to the same nitrogen atom are joined is substituted, it is substituted with at least one substituent group. In embodiments, when the substituted ring formed when $R^{100A}$ and $R^{100B}$ substituents bonded to the same nitrogen atom are joined is substituted, it is substituted with at least one size-limited substituent group. In embodiments, when the substituted ring formed when $R^{100A}$ and $R^{100B}$ substituents bonded to the same nitrogen atom are joined is substituted, it is substituted with at least one lower substituent group.

In embodiments, a substituted $R^{100C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{100C}$ is substituted with a plurality of groups selected from substituent groups, size-limited substituent groups, and lower substituent groups; each substituent group, size-limited substituent group, and/or lower substituent group may optionally be different. In embodiments, when $R^{100C}$ is substituted, it is substituted with at least one substituent group. In embodiments, when $R^{100C}$ is substituted, it is substituted with at least one size-limited substituent group. In embodiments, when $R^{100C}$ is substituted, it is substituted with at least one lower substituent group.

In embodiments, a substituted $R^{100D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group;

wherein if the substituted $R^{100D}$ is substituted with a plurality of groups selected from substituent groups, size-limited substituent groups, and lower substituent groups; each substituent group, size-limited substituent group, and/or lower substituent group may optionally be different. In embodiments, when $R^{100D}$ is substituted, it is substituted with at least one substituent group. In embodiments, when $R^{100D}$ is substituted, it is substituted with at least one size-limited substituent group. In embodiments, when $R^{100D}$ is substituted, it is substituted with at least one lower substituent group.

In embodiments, $L^{100}$ is a bond or unsubstituted $C_1$-$C_4$ alkylene. In embodiments, $L^{100}$ is a bond. In embodiments, $L^{100}$ is an unsubstituted $C_1$-$C_4$ alkylene. In embodiments, $L^{100}$ is unsubstituted methylene. In embodiment $L^{100}$ is unsubstituted ethylene. In embodiments, $L^{100}$ is unsubstituted propylene. In embodiments, $L^{100}$ is unsubstituted butylene.

In embodiments, $R^{100}$ is hydrogen, substituted or unsubstituted $C_1$-$C_4$ alkyl, substituted or unsubstituted 2 to 10 membered heteroalkyl, substituted or unsubstituted 3 to 8 membered heterocycloalkyl, or substituted or unsubstituted 5 to 6 membered heteroaryl. In embodiments, $R^{100}$ is hydrogen. In embodiments, $R^{100}$ is unsubstituted methyl. In embodiments, $R^{100}$ is unsubstituted ethyl. In embodiments, $R^{100}$ is unsubstituted propyl. In embodiments, $R^{100}$ is unsubstituted n-propyl. In embodiments, $R^{100}$ is unsubstituted isopropyl. In embodiments, $R^{100}$ is unsubstituted butyl. In embodiments, $R^{100}$ is unsubstituted n-butyl. In embodiments, $R^{100}$ is unsubstituted tert-butyl. In embodiments, $R^{100}$ is substituted or unsubstituted 2 to 10 membered heteroalkyl. In embodiments, $R^{100}$ is oxo-substituted 2 to 10 membered heteroalkyl. In embodiments, $R^{100}$ is

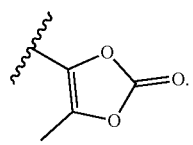

In embodiments, $R^{100}$ is substituted or unsubstituted 3 to 8 membered heterocycloalkyl. In embodiments, $R^{100}$ is substituted or unsubstituted 5 to 6 membered heteroaryl. In embodiments, $R^{100}$ is

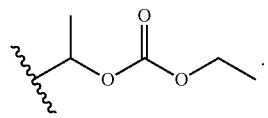 [SMILES: *C(C)OC(=O)OCC]

In embodiments, Ring A is cycloalkyl. In embodiments, Ring A is heterocycloalkyl. In embodiments, Ring A is aryl. In embodiments, Ring A is heteroaryl. In embodiments, Ring A is a fused bicyclic cycloalkyl or phenyl. In embodiments, Ring A is a fused bicyclic cycloalkyl. In embodiments, Ring A is a phenyl.

In embodiments,

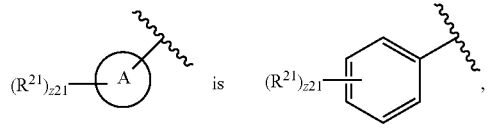

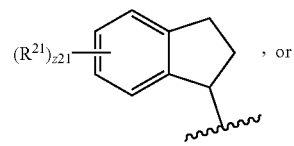

$R^{21}$ and z21 are as described herein, including in embodiments. In embodiments,

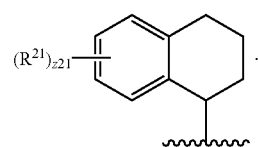

$R^{21}$ and z21 are as described herein, including in embodiments. In embodiments,

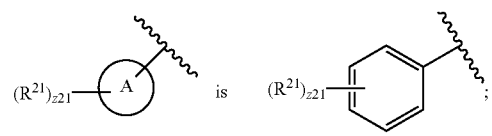

$R^{21}$ and z21 are as described herein, including in embodiments,

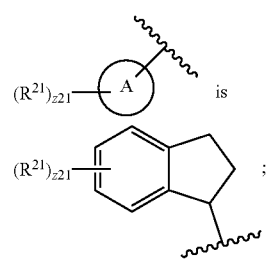

$R^{21}$ and z21 are as described herein, including in embodiments.

In embodiments,
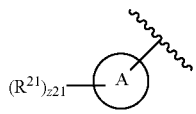
is
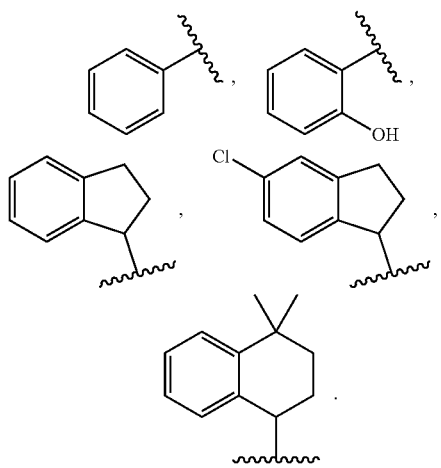
In embodiments,
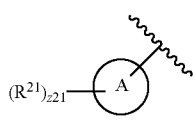
is
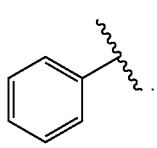.
In embodiments,
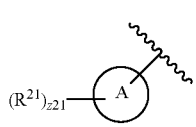
is
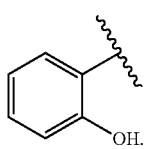.
In embodiments,
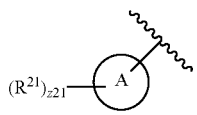
is
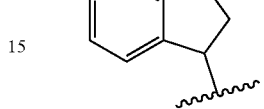
In embodiments,
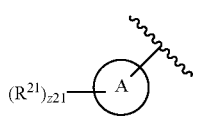
is
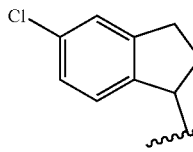.
In embodiments,
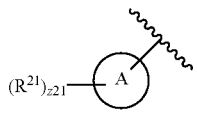
is
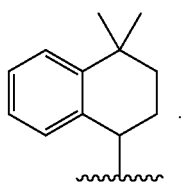 [SMILES: *C1CCC(C)(C)c2ccccc21].
In embodiments,
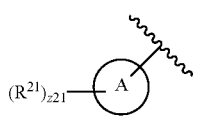

is

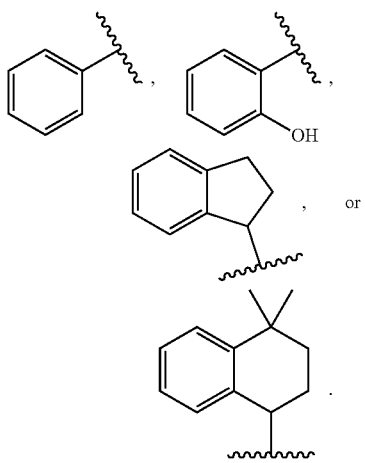

In embodiments,

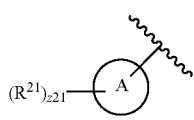

is

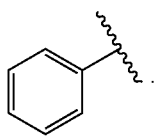 [SMILES: *c1ccccc1]

In embodiments,

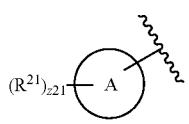

is

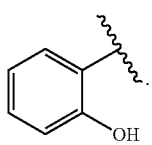

In embodiments,

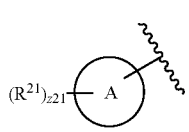

is

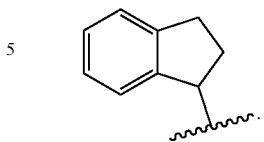

In embodiments,

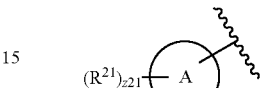

is

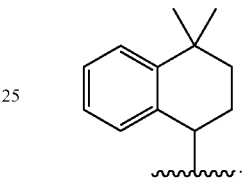

In embodiments, a substituted $R^{21}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21}$ is substituted with a plurality of groups selected from substituent groups, size-limited substituent groups, and lower substituent groups; each substituent group, size-limited substituent group, and/or lower substituent group may optionally be different. In embodiments, when $R^{21}$ is substituted, it is substituted with at least one substituent group. In embodiments, when $R^{21}$ is substituted, it is substituted with at least one size-limited substituent group. In embodiments, when $R^{21}$ is substituted, it is substituted with at least one lower substituent group.

In embodiments, a substituted $R^{21A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21A}$ is substituted with a plurality of groups selected from substituent groups, size-limited substituent groups, and lower substituent groups; each substituent group, size-limited substituent group, and/or lower substituent group may optionally be different. In embodiments, when $R^{21A}$ is substituted, it is substituted with at least one substituent group. In embodiments, when $R^{21A}$ is substituted, it is substituted with at least one size-limited substituent group. In embodiments, when $R^{21A}$ is substituted, it is substituted with at least one lower substituent group.

In embodiments, a substituted $R^{21B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21B}$ is substituted with a plurality of groups selected from substituent groups, size-limited substituent groups; each substituent group, size-limited substituent group, and/or lower substituent group may optionally be different. In embodiments, when $R^{21B}$ is substituted, it is substituted with at least one substituent group. In embodiments, when $R^{21B}$ is substituted, it is substituted with at least one size-limited substituent group. In embodiments, when $R^{21B}$ is substituted, it is substituted with at least one lower substituent group.

In embodiments, a substituted ring formed when $R^{21A}$ and $R^{21B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{21A}$ and $R^{21B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{21A}$ and $R^{21B}$ substituents bonded to the same nitrogen atom are joined is substituted, it is substituted with at least one substituent group. In embodiments, when the substituted ring formed when $R^{21A}$ and $R^{21B}$, substituents bonded to the same nitrogen atom are joined is substituted, it is substituted with at least one size-limited substituent group. In embodiments, when the substituted ring formed when $R^{21A}$ and $R^{21B}$ substituents bonded to the same nitrogen atom are joined is substituted, it is substituted with at least one lower substituent group.

In embodiments, a substituted $R^{21C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21C}$ is substituted with a plurality of groups selected from substituent groups, size-limited substituent groups, and lower substituent groups; each substituent group, size-limited substituent group, and/or lower substituent group may optionally be different. In embodiments, when $R^{21C}$ is substituted, it is substituted with at least one substituent group. In embodiments, when $R^{21C}$ is substituted, it is substituted with at least one size-limited substituent group. In embodiments, when $R^{21C}$ is substituted, it is substituted with at least one lower substituent group.

In embodiments, a substituted $R^{21D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21D}$ is substituted with a plurality of groups selected from substituent groups, size-limited substituent groups, and lower substituent groups; each substituent group, size-limited substituent group, and/or lower substituent group may optionally be different. In embodiments, when $R^{21D}$ is substituted, it is substituted with at least one substituent group. In embodiments, when $R^{21D}$ is substituted, it is substituted with at least one size-limited substituent group. In embodiments, when $R^{21D}$ is substituted, it is substituted with at least one lower substituent group.

In embodiments, $R^{21}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, or 2 to 3 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{21}$ is independently halogen, —OH, or substituted or unsubstituted C$_1$-C$_4$ alkyl. In embodiments, $R^{21}$ is independently —OH or unsubstituted methyl. In embodiments, $R^{21}$ is independently halogen. In embodiments, $R^{21}$ is independently —F. In embodiments, $R^{21}$ is independently —Cl. In embodiments, $R^{21}$ is independently —Br. In embodiments, $R^{21}$ is independently —I. In embodiments, $R^{21}$ is independently —OH. In embodiments, $R^{21}$ is independently substituted or unsubstituted alkyl. In embodiments, $R^{21}$ is independently substituted or unsubstituted C$_1$-C$_4$ alkyl. In embodiments, $R^{21}$ is independently unsubstituted methyl. In embodiments, $R^{21}$ is independently unsubstituted ethyl. In embodiments, $R^{21}$ is independently unsubstituted propyl. In embodiments, $R^{21}$ is independently unsubstituted n-propyl. In embodiments, $R^{21}$ is independently unsubstituted isopropyl. In embodiments, $R^{21}$ is independently unsubstituted butyl. In embodiments, $R^{21}$ is independently unsubstituted n-butyl. In embodiments, $R^{21}$ is independently unsubstituted tert-butyl. In embodiments, $R^{21}$ is independently substituted or unsubstituted heteroalkyl. In embodiments, $R^{21}$ is independently substituted or unsubstituted 2 to 5 membered heteroalkyl. In embodiments, $R^{21}$ is independently unsubstituted methoxy. In embodiments, $R^{21}$ is independently unsubstituted ethoxy. In embodiments, $R^{21}$ is independently unsubstituted propoxy. In embodiments, $R^{21}$ is independently unsubstituted n-propoxy. In embodiments, $R^{21}$ is independently unsubstituted isopropoxy. In embodiments, $R^{21}$ is independently unsubstituted butoxy. In embodiments, $R^{21}$ is independently unsubstituted n-butoxy. In embodiments, $R^{21}$ is independently unsubstituted tert-butoxy.

In embodiments, z21 is 0. In embodiments, z21 is 1. In embodiments, z21 is 2. In embodiments, z21 is 3. In embodiments, z21 is 4. In embodiments, z21 is 5. In embodiments, z21 is 6. In embodiments, z21 is 7. In embodiments, z21 is 8. In embodiments, z21 is 9. In embodiments, z21 is 10. In embodiments, z21 is 11. In embodiments, z21 is an integer from 0 to 3.

In embodiments, a substituted $R^2$ (e.g., substituted alkyl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^2$ is hydrogen or unsubstituted C$_1$-C$_3$ alkyl. In embodiments, $R^2$ is hydrogen. In embodiments, $R^2$ is unsubstituted methyl. In embodiments, $R^2$ is unsubstituted ethyl. In embodiments, $R^2$ is unsubstituted propyl. In embodiments, $R^2$ is unsubstituted n-propyl. In embodiments, $R^2$ is unsubstituted isopropyl.

In embodiments, $R^5$ is hydrogen. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted n-propyl. In embodiments, $R^5$ is unsubstituted isopropyl.

In embodiments, $L^5$ is a bond. In embodiments, $L^5$ is unsubstituted methylene. In embodiments, $L^5$ is unsubstituted ethylene. In embodiments, $L^5$ is unsubstituted propylene. In embodiments, $L^5$ is unsubstituted n-propylene. In embodiments, $L^5$ is unsubstituted isopropylene.

In embodiments, a substituted $R^{10.1}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.1}$ is substituted with a plurality of groups selected from substituent groups, size-limited substituent groups, and lower substituent groups; each substituent group, size-limited substituent group, and/or lower substituent group may optionally be different. In embodiments, when $R^{10.1}$ is substituted, it is substituted with at least one substituent group. In embodiments, when $R^{10.1}$ is substituted, it is substituted with at least one size-limited substituent group. In embodiments, when $R^{10.1}$ is substituted, it is substituted with at least one lower substituent group.

In embodiments, a substituted $R^{10.1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.1A}$ is substituted with a plurality of groups selected from substituent groups, size-limited substituent groups, and lower substituent groups; each substituent group, size-limited substituent group, and/or lower substituent group may optionally be different. In embodiments, when $R^{10.1A}$ is substituted, it is substituted with at least one substituent group. In embodiments, when $R^{10.1A}$ is substituted, it is substituted with at least one size-limited substituent group. In embodiments, when $R^{10.1A}$ is substituted, it is substituted with at least one lower substituent group.

In embodiments, a substituted $R^{10.1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.1B}$ is substituted with a plurality of groups selected from substituent groups, size-limited substituent groups, and lower substituent groups; each substituent group, size-limited substituent group, and/or lower substituent group may optionally be different. In embodiments, when $R^{10.1B}$ is substituted, it is substituted with at least one substituent group. In embodiments, when $R^{10.1B}$ is substituted, it is substituted with at least one size-limited substituent group. In embodiments, when $R^{10.1B}$ is substituted, it is substituted with at least one lower substituent group.

In embodiments, a substituted ring formed when $R^{10.1A}$ and $R^{10.1B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.1A}$ and $R^{10.1B}$, substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.1A}$ and $R^{10.1B}$ substituents bonded to the same nitrogen atom are joined is substituted, it is substituted with at least one substituent group. In embodiments, when the substituted ring formed when $R^{10.1A}$ and $R^{10.1B}$ substituents bonded to the same nitrogen atom are joined is substituted, it is substituted with at least one size-limited substituent group. In embodiments, when the substituted ring formed when $R^{10.1A}$ and $R^{10.1B}$ substituents bonded to the same nitrogen atom are joined is substituted, it is substituted with at least one lower substituent group.

In embodiments, a substituted $R^{10.1C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.1C}$ is substituted with a plurality of groups selected from substituent groups, size-limited substituent groups, and lower substituent groups; each substituent group, size-limited substituent group, and/or lower substituent group may optionally be different. In embodiments, when $R^{10.1C}$ is substituted, it is substituted with at least one substituent group. In embodiments, when $R^{10.1C}$ is substituted, it is substituted with at least one size-limited substituent group. In embodiments, when $R^{10.1C}$ is substituted, it is substituted with at least one lower substituent group.

In embodiments, a substituted $R^{10.1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.1D}$ is substituted with a plurality of groups selected from substituent groups, size-limited substituent groups, and lower substituent groups; each substituent group, size-limited substituent group, and/or lower substituent group may optionally be different. In embodiments, when $R^{10.1D}$ is substituted, it is substituted with at least one substituent group. In embodiments, when $R^{10.1D}$ is substituted, it is substituted with at least one size-limited substituent group. In embodiments, when $R^{10.1D}$ is substituted, it is substituted with at least one lower substituent group.

In embodiments, $R^{10.1}$ is hydrogen, halogen, —CCl₃, —CBr₃, —CF₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{10.1}$ is halogen, substituted or unsubstituted $C_1$-$C_5$ alkyl, or substituted or unsubstituted 2 to 5 membered heteroalkyl. In embodiments, $R^{10.1}$ is halogen or unsubstituted methyl. In embodiments, $R^{10.1}$ is halogen. In embodiments, $R^{10.1}$ is —F. In embodiments, $R^{10.1}$ is —Cl. In embodiments, $R^{10.1}$ is —Br. In embodiments, $R^{10.1}$ is —I. In embodiments, $R^{10.1}$ is substituted or unsubstituted $C_1$-$C_5$ alkyl. In embodiments, $R^{10.1}$ is unsubstituted methyl. In embodiments, $R^{10.1}$ is unsubstituted ethyl. In embodiments, $R^{10.1}$ is unsubstituted propyl. In embodiments, $R^{10.1}$ is unsubstituted n-propyl. In embodiments, $R^{10.1}$ is unsubstituted isopropyl. In embodiments, $R^{10.1}$ is unsubstituted butyl. In embodiments, $R^{10.1}$ is unsubstituted n-butyl. In embodiments, $R^{10.1}$ is unsubstituted tert-butyl. In embodiments, $R^{10.1}$ is substituted or unsubstituted 2 to 5 membered heteroalkyl. In embodiments, $R^{10.1}$ is unsubstituted methoxy. In embodiments, $R^{10.1}$ is unsubstituted ethoxy. In embodiments, $R^{10.1}$ is unsubstituted propoxy. In embodiments, $R^{10.1}$ is unsubstituted n-propoxy. In embodiments, $R^{10.1}$ is unsubstituted isopropoxy. In embodiments, $R^{10.1}$ is unsubstituted butoxy. In embodiments, $R^{10.1}$ is unsubstituted n-butoxy. In embodiments, $R^{10.1}$ is unsubstituted tert-butoxy. In embodiments, $R^{10.1}$ is hydrogen.

In embodiments, a substituted $R^{10.2}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.2}$ is substituted with a plurality of groups selected from substituent groups, size-limited substituent groups, and lower substituent groups; each substituent group, size-limited substituent group, and/or lower substituent group may optionally be different. In embodiments, when $R^{10.2}$ is substituted, it is substituted with at least one substituent group. In embodiments, when $R^{10.2}$ is substituted, it is substituted with at least one size-limited substituent group. In embodiments, when $R^{10.2}$ is substituted, it is substituted with at least one lower substituent group.

In embodiments, a substituted $R^{10.2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.2A}$ is substituted with a plurality of groups selected from substituent groups, size-limited substituent groups, and lower substituent groups; each substituent group, size-limited substituent group, and/or lower substituent group may optionally be different. In embodiments, when $R^{10.2A}$ is substituted, it is substituted with at least one substituent group. In embodiments, when $R^{10.2A}$ is substituted, it is substituted with at least one size-limited substituent group. In embodiments, when $R^{10.2A}$ is substituted, it is substituted with at least one lower substituent group.

In embodiments, a substituted $R^{10.2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.2B}$ is substituted with a plurality of groups selected from substituent groups, size-limited substituent groups, and lower substituent groups; each substituent group, size-limited substituent group, and/or lower substituent group may optionally be different. In embodiments, when $R^{10.2B}$ is substituted, it is substituted with at least one substituent group. In embodiments, when $R^{10.2B}$ is substituted, it is substituted with at least one size-limited substituent group. In embodiments, when $R^{10.2B}$ is substituted, it is substituted with at least one lower substituent group.

In embodiments, a substituted ring formed when $R^{10.2A}$ and $R^{10.2B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.2A}$ and $R^{10.2B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.2A}$ and $R^{10.2B}$ substituents bonded to the same nitrogen atom are joined is substituted, it is substituted with at least one substituent group. In embodiments, when the substituted ring formed when $R^{10.2A}$ and $R^{10.2B}$ substituents bonded to the same nitrogen atom are joined is substituted, it is substituted with at least one size-limited substituent group. In embodiments, when the substituted ring formed when $R^{10.2A}$ and $R^{10.2B}$ substituents bonded to the same nitrogen atom are joined is substituted, it is substituted with at least one lower substituent group.

In embodiments, a substituted $R^{10.2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.2C}$ is substituted with a plurality of groups selected from substituent groups, size-limited substituent groups, and lower substituent groups; each substituent group, size-limited substituent group, and/or lower substituent group may optionally be different. In embodiments, when $R^{10.2C}$ is substituted, it is substituted with at least one substituent group. In embodiments, when $R^{10.2C}$ is substituted, it is substituted with at least one size-limited substituent group. In embodiments, when $R^{10.2C}$ is substituted, it is substituted with at least one lower substituent group.

In embodiments, a substituted $R^{10.2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.2D}$ is substituted with a plurality of groups selected from substituent groups, size-limited substituent groups, and lower substituent groups; each substituent group, size-limited substituent group, and/or lower substituent group may optionally be different. In embodiments, when $R^{10.2D}$ is substituted, it is substituted with at least one substituent group. In embodiments, when $R^{10.2D}$ is substituted, it is substituted with at least one size-limited substituent group. In embodiments, when $R^{10.2D}$ is substituted, it is substituted with at least one lower substituent group.

In embodiments, $R^{10.2}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCBr_3$, —OCF$_3$, —OCl$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, or 2 to 3 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^{10.2}$ is hydrogen or -L$^{10.2}$-R$^{22}$; L$^{10.2}$ and R$^{22}$ are as described herein, including in embodiments. In embodiments, R$^{10.2}$ is hydrogen. In embodiments, R$^{10.2}$ is -L$^{10.2}$-R$^{22}$; L$^{10.2}$ and R$^{22}$ are as described herein, including in embodiments.

In embodiments, a substituted L$^{10.2}$ (e.g., substituted alkylene and/or substituted heteroalkylene) is substituted with at least one substituent group, size-limited substituent group, or lower substituent group; wherein if the substituted L$^{10.2}$ is substituted with a plurality of groups selected from substituent groups, size-limited substituent groups, and lower substituent groups; each substituent group, size-limited substituent group, and/or lower substituent group may optionally be different. In embodiments, when L$^{10.2}$ is substituted, it is substituted with at least one substituent group. In embodiments, when L$^{10.2}$ is substituted, it is substituted with at least one size-limited substituent group. In embodiments, when L$^{10.2}$ is substituted, it is substituted with at least one lower substituent group.

In embodiments, L$^{10.2}$ is a bond, —NH—, —O—, —C(O)—, —NHC(O)O—, —NHS(O)$_2$—, or substituted or unsubstituted 2 to 5 membered heteroalkylene. In embodiments, L$^{10.2}$ is substituted or unsubstituted 2 to 5 membered heteroalkylene.

In embodiments, L$^{10.2}$ is a bond, —NH—, —O—, —C(O)—, —NHC(O)O—, —NHS(O)$_2$—, In embodiments, L$^{10.2}$ is a bond. In embodiments, L$^{10.2}$ is —NH—. In embodiments, L$^{10.2}$ is —O—. In embodiments, L$^{10.2}$ is —C(O)—. In embodiments, L$^{10.2}$ is —NHC(O)O—. In embodiments, L$^{10.2}$ is —NHS(O)$_2$—. In embodiments, L$^{10.2}$ is

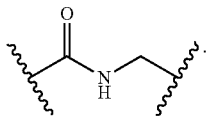

In embodiments, L$^{10.2}$ is

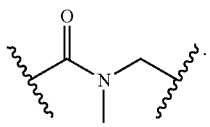

In embodiments, L is

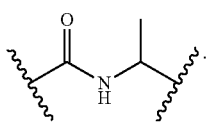 [SMILES: *C(=O)NC(*)C]

In embodiments, L$^{10.2}$ is

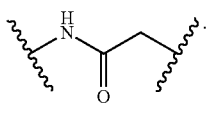

In embodiments, L$^{10.2}$ is

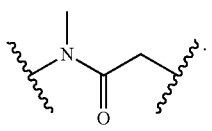

In embodiments, L$^{10.2}$ is

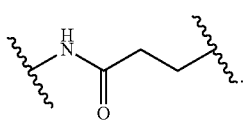 [SMILES: *CCC(=O)N*]

In embodiments, L$^{10.2}$ is

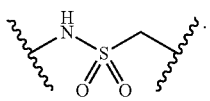

In embodiments, $L^{10.2}$ is

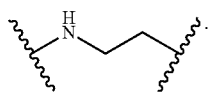

In embodiments, $L^{10.2}$ is

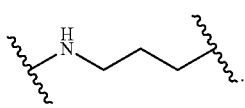 [SMILES: *CCCN*]

In embodiments, $L^{10.2}$ is

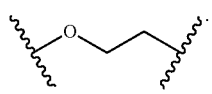 [SMILES: *CCO*]

In embodiments, $L^{10.2}$ is

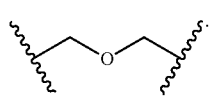

In embodiments, a substituted $R^{22}$ (e.g., substituted cycloalkyl, substituted heterocycloalkyl, substituted aryl, and/or substituted heteroaryl) is substituted with at least one substituent group, size-limited substituent group, or lower substituent group; wherein if the substituted $R^{22}$ is substituted with a plurality of groups selected from substituent groups, size-limited substituent groups, and lower substituent groups; each substituent group, size-limited substituent group, and/or lower substituent group may optionally be different. In embodiments, when $R^{22}$ is substituted, it is substituted with at least one substituent group. In embodiments, when $R^{22}$ is substituted, it is substituted with at least one size-limited substituent group. In embodiments, when $R^{22}$ is substituted, it is substituted with at least one lower substituent group.

In embodiments, $R^{22}$ is $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{22}$ is

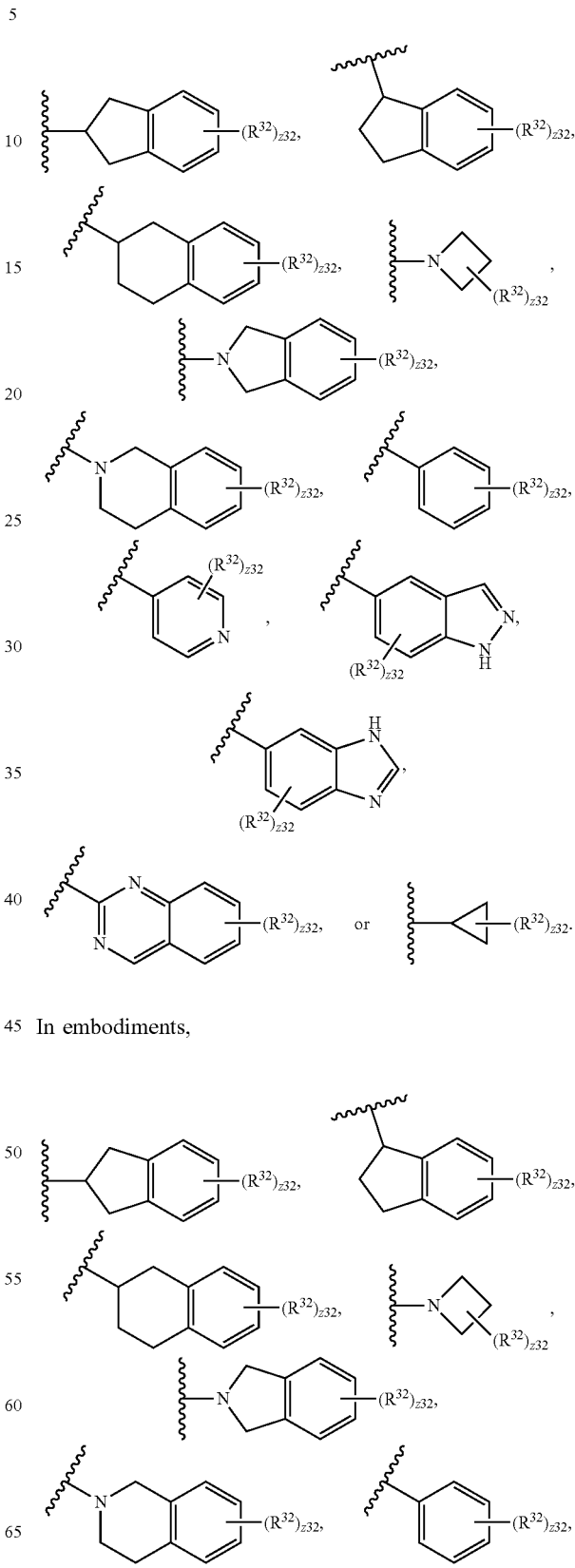

In embodiments,

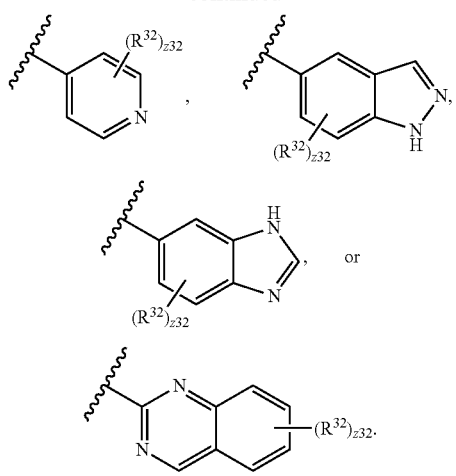

$R^{32}$ is as described herein, including in embodiments. The variable z32 is an integer from 0 to 10. In embodiments, $R^{22}$ is

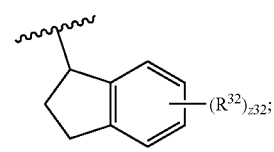

$R^{32}$ and z32 are as described herein, including in embodiments. In embodiments, $R^{22}$ is

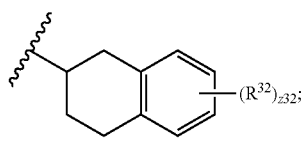

$R^{32}$ and z32 are as described herein, including in embodiments. In embodiments, $R^{22}$ is

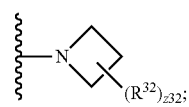

$R^{32}$ and z32 are as described herein, including in embodiments. In embodiments, $R^{22}$ is

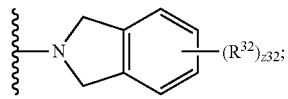

$R^{32}$ and z32 are as described herein, including in embodiments. In embodiments, $R^{22}$ is

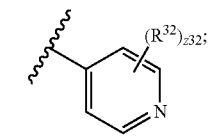

$R^{32}$ and z32 are as described herein, including in embodiments. In embodiments, $R^{22}$ is

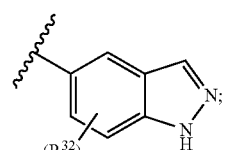

$R^{32}$ and z32 are as described herein, including in embodiments. In embodiments, $R^{22}$ is

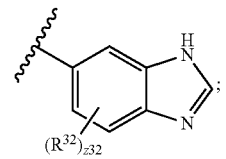

$R^{32}$ and z32 are as described herein, including in embodiments. In embodiments, $R^{22}$ is $R^{32}$ and z32 are as described herein, including in embodiments. In embodiments, $R^{22}$ is

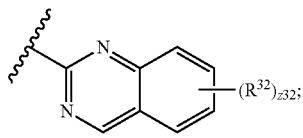

$R^{32}$ and z32 are as described herein, including in embodiments. In embodiments, $R^{22}$ is

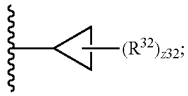

$R^{32}$ and z32 are as described herein, including in embodiments.

In embodiments, a substituted $R^{32}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{32}$ is substituted with a plurality of groups selected from substituent groups, size-limited substituent groups, and lower substituent groups; each substituent group, size-limited substituent group, and/or lower substituent group may optionally be different. In embodiments, when $R^{32}$ is substituted, it is substituted with at least one substituent group. In embodiments, when $R^{32}$ is substituted, it is substituted with at least one size-limited substituent group. In embodiments, when $R^{32}$ is substituted, it is substituted with at least one lower substituent group.

In embodiments, $R^{32}$ is independently halogen, $-CF_3$, $-OH$, $-NH_2$, substituted or unsubstituted $C_1$-$C_4$ alkyl, substituted or unsubstituted 2 to 5 membered heteroalkyl, or substituted or unsubstituted phenyl. In embodiments, $R^{32}$ is independently halogen. In embodiments, $R^{32}$ is independently —F. In embodiments, $R^{32}$ is independently —Cl. In embodiments, $R^{32}$ is independently —Br. In embodiments, $R^{32}$ is independently —I. In embodiments, $R^{32}$ is independently —$CF_3$. In embodiments, $R^{32}$ is independently —$CHF_2$. In embodiments, $R^{32}$ is independently —$CH_2F$. In embodiments, $R^{32}$ is independently —OH. In embodiments, $R^{32}$ is independently —$NH_2$. In embodiments, $R^{32}$ is independently —CN. In embodiments, $R^{32}$ is independently substituted or unsubstituted $C_1$-$C_4$ alkyl. In embodiments, $R^{32}$ is independently unsubstituted methyl. In embodiments, $R^{32}$ is independently unsubstituted ethyl. In embodiments, $R^{32}$ is independently unsubstituted propyl. In embodiments, $R^{32}$ is independently unsubstituted n-propyl. In embodiments, $R^{32}$ is independently unsubstituted isopropyl. In embodiments, $R^{32}$ is independently unsubstituted butyl. In embodiments, $R^{32}$ is independently unsubstituted n-butyl. In embodiments, $R^{32}$ is independently unsubstituted tert-butyl. In embodiments, $R^{32}$ is independently substituted or unsubstituted 2 to 5 membered heteroalkyl. In embodiments, $R^{32}$ is independently unsubstituted methoxy. In embodiments, $R^{32}$ is independently unsubstituted ethoxy. In embodiments, $R^{32}$ is independently unsubstituted propoxy. In embodiments, $R^{32}$ is independently unsubstituted n-propoxy. In embodiments, $R^{32}$ is independently unsubstituted isopropoxy. In embodiments, $R^{32}$ is independently unsubstituted butoxy. In embodiments, $R^{32}$ is independently unsubstituted n-butoxy. In embodiments, $R^{32}$ is independently unsubstituted tert-butoxy. In embodiments, $R^{32}$ is independently substituted or unsubstituted phenyl.

In embodiments, z32 is 0. In embodiments, z32 is 1. In embodiments, z32 is 2. In embodiments, z32 is 3. In embodiments, z32 is 4. In embodiments, z32 is 5. In embodiments, z32 is 6. In embodiments, z32 is 7. In embodiments, z32 is 8. In embodiments, z32 is 9. In embodiments, z32 is 10.

In embodiments, $R^{22}$ is

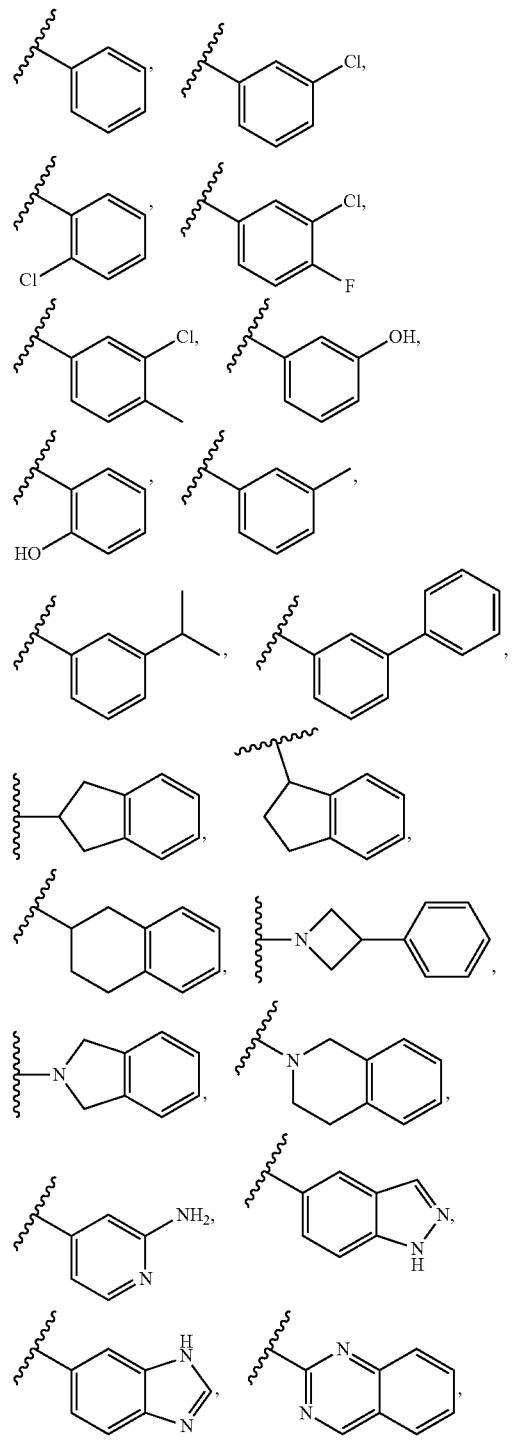

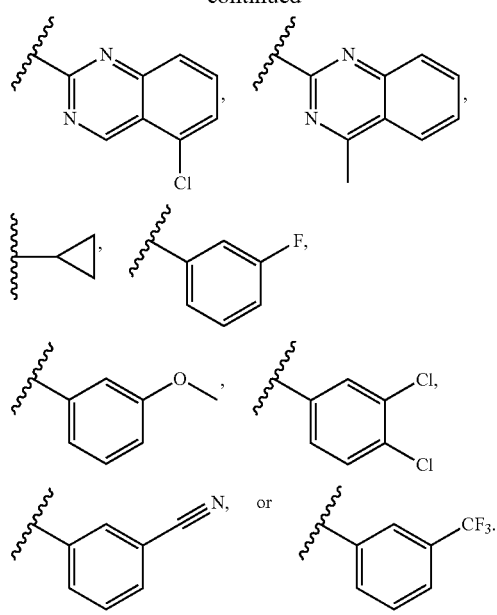
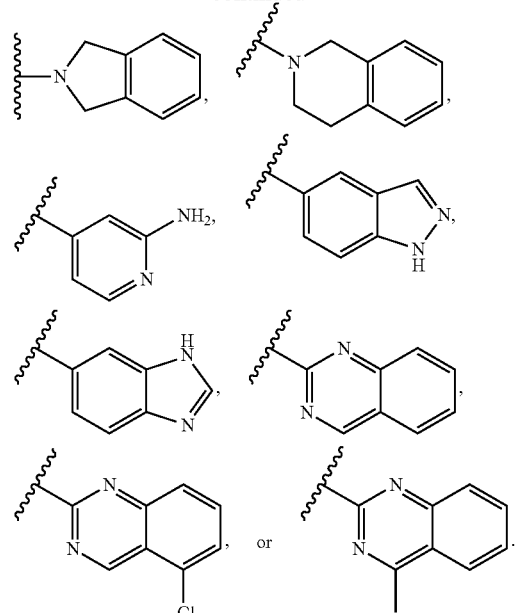
In embodiments, R²² is
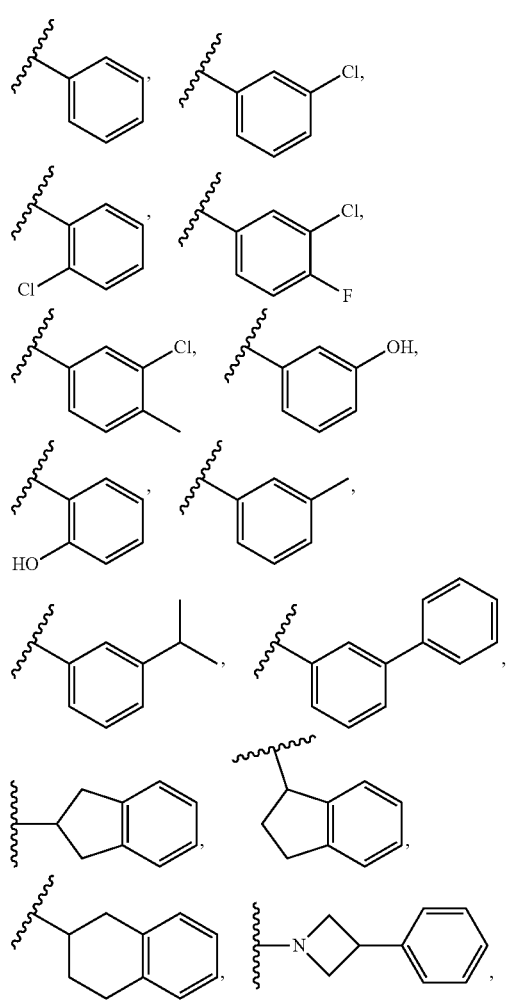
In embodiments, R²² is
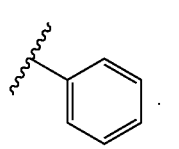
In embodiments, R²² is
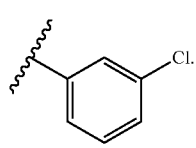 [SMILES: *c1cccc(Cl)c1]
In embodiments, R²² is
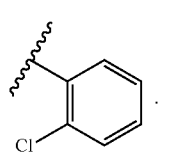
In embodiments, R²² is
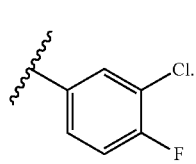 [SMILES: *c1ccc(F)c(Cl)c1]

In embodiments, $R^{22}$ is
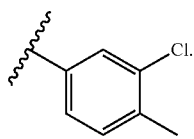 [SMILES: *c1ccc(C)c(Cl)c1]
In embodiments, $R^{22}$ is
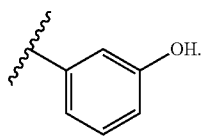 [SMILES: *c1cccc(O)c1]
In embodiments, $R^{22}$ is
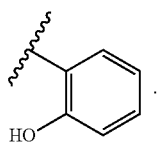
In embodiments, $R^{22}$ is
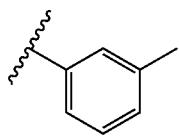
In embodiments, $R^{22}$ is
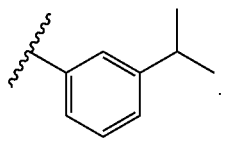 [SMILES: *c1cccc(C(C)C)c1]
In embodiments, $R^{22}$ is
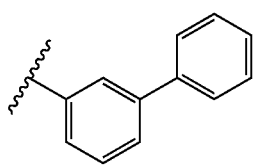
In embodiments, $R^{22}$ is
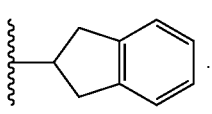 [SMILES: *C1Cc2ccccc2C1]
In embodiments, $R^{22}$ is
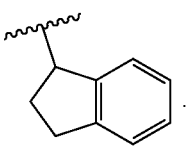 [SMILES: *C1CCc2ccccc21]
In embodiments, $R^{22}$ is
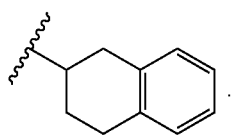 [SMILES: *C1CCc2ccccc2C1]
In embodiments, $R^{22}$ is
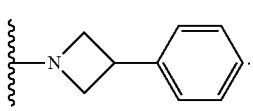 [SMILES: *N1CC(c2ccccc2)C1]
In embodiments, $R^{22}$ is
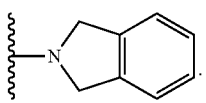 [SMILES: *N1Cc2ccccc2C1]
In embodiments, $R^{22}$ is
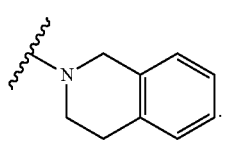 [SMILES: *N1CCc2ccccc2C1]
In embodiments, $R^{22}$ is
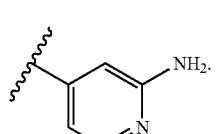
In embodiments, $R^{22}$ is
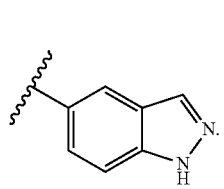

In embodiments, R²² is

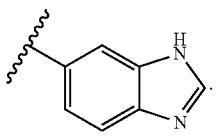 [SMILES: *c1ccc2nc[nH]c2c1]

In embodiments, R²² is

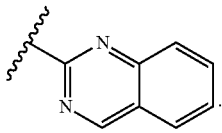 [SMILES: *c1ncc2ccccc2n1]

In embodiments, R²² is

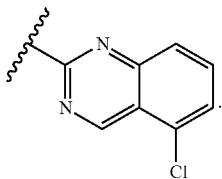 [SMILES: *c1ncc2c(Cl)cccc2n1]

In embodiments, R²² is

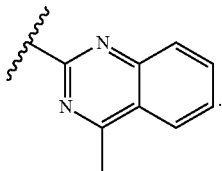 [SMILES: *c1nc(C)c2ccccc2n1]

In embodiments, R²² is

In embodiments, R²² is

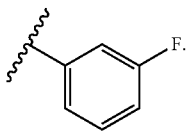 [SMILES: *c1cccc(F)c1]

In embodiments, R²² is

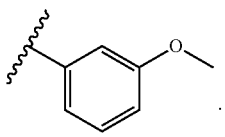 [SMILES: *c1cccc(OC)c1]

In embodiments, R²² is

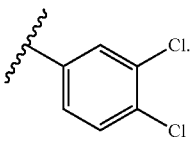 [SMILES: *c1ccc(Cl)c(Cl)c1]

In embodiments, R²² is

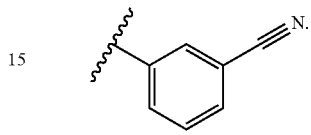

In embodiments, R²² is

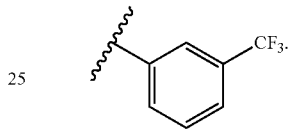

In embodiments, a substituted $R^{10.3}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.3}$ is substituted with a plurality of groups selected from substituent groups, size-limited substituent groups, and lower substituent groups; each substituent group, size-limited substituent group, and/or lower substituent group may optionally be different. In embodiments, when $R^{10.3}$ is substituted, it is substituted with at least one substituent group. In embodiments, when $R^{10.3}$ is substituted, it is substituted with at least one size-limited substituent group. In embodiments, when $R^{10.3}$ is substituted, it is substituted with at least one lower substituent group.

In embodiments, a substituted $R^{10.3A}$, (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.3A}$ is substituted with a plurality of groups selected from substituent groups, size-limited substituent groups, and lower substituent groups; each substituent group, size-limited substituent group, and/or lower substituent group may optionally be different. In embodiments, when $R^{10.3A}$ is substituted, it is substituted with at least one substituent group. In embodiments, when $R^{10.3A}$, is substituted, it is substituted with at least one size-limited substituent group. In embodiments, when $R^{10.3A}$, is substituted, it is substituted with at least one lower substituent group.

In embodiments, a substituted $R^{10.3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.3B}$ is substituted with a plurality of groups selected from substituent groups, size-limited substituent groups, and lower substituent groups;

each substituent group, size-limited substituent group, and/or lower substituent group may optionally be different. In embodiments, when $R^{10.3B}$ is substituted, it is substituted with at least one substituent group. In embodiments, when $R^{10.3B}$ is substituted, it is substituted with at least one size-limited substituent group. In embodiments, when $R^{10.3B}$ is substituted, it is substituted with at least one lower substituent group.

In embodiments, a substituted ring formed when $R^{10.3A}$, and $R^{10.3B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.3A}$, and $R^{10.3B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.3A}$, and $R^{10.3B}$ substituents bonded to the same nitrogen atom are joined is substituted, it is substituted with at least one substituent group. In embodiments, when the substituted ring formed when $R^{10.3A}$, and $R^{10.3B}$ substituents bonded to the same nitrogen atom are joined is substituted, it is substituted with at least one size-limited substituent group. In embodiments, when the substituted ring formed when $R^{10.3A}$, and $R^{10.3B}$ substituents bonded to the same nitrogen atom are joined is substituted, it is substituted with at least one lower substituent group.

In embodiments, a substituted $R^{10.3C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.3C}$ is substituted with a plurality of groups selected from substituent groups, size-limited substituent groups, and lower substituent groups; each substituent group, size-limited substituent group, and/or lower substituent group may optionally be different. In embodiments, when $R^{10.3C}$ is substituted, it is substituted with at least one substituent group. In embodiments, when $R^{10.3C}$ is substituted, it is substituted with at least one size-limited substituent group. In embodiments, when $R^{10.3C}$ is substituted, it is substituted with at least one lower substituent group.

In embodiments, a substituted $R^{10.3D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.3D}$ is substituted with a plurality of groups selected from substituent groups, size-limited substituent groups, and lower substituent groups; each substituent group, size-limited substituent group, and/or lower substituent group may optionally be different. In embodiments, when $R^{10.3D}$ is substituted, it is substituted with at least one substituent group. In embodiments, when $R^{10.3D}$ is substituted, it is substituted with at least one size-limited substituent group. In embodiments, when $R^{10.3D}$ is substituted, it is substituted with at least one lower substituent group.

In embodiments, $R^{10.3}$ is hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{10.3}$ is hydrogen or -$L^{10.3}$-$R^{23}$; $L^{10.3}$ and $R^{23}$ are as described herein, including in embodiments. In embodiments, $R^{10.3}$ is hydrogen. In embodiments, $R^{10.3}$ is -$L^{10.3}$-$R^{23}$; $L^{10.3}$ and $R^{23}$ are as described herein, including in embodiments.

In embodiments, a substituted $L^{10.3}$ (e.g., substituted alkylene and/or substituted heteroalkylene) is substituted with at least one substituent group, size-limited substituent group, or lower substituent group; wherein if the substituted $L^{10.3}$ is substituted with a plurality of groups selected from substituent groups, size-limited substituent groups, and lower substituent groups; each substituent group, size-limited substituent group, and/or lower substituent group may optionally be different. In embodiments, when $L^{10.3}$ is substituted, it is substituted with at least one substituent group. In embodiments, when $L^{10.3}$ is substituted, it is substituted with at least one size-limited substituent group. In embodiments, when $L^{10.3}$ is substituted, it is substituted with at least one lower substituent group.

In embodiments, $L^{10.3}$ is a bond, —NH—, —O—, —C(O)—, —NHC(O)O—, —NHS(O)$_2$—, or substituted or unsubstituted 2 to 5 membered heteroalkylene. In embodiments, $L^{10.3}$ is substituted or unsubstituted 2 to 5 membered heteroalkylene.

In embodiments, $L^{10.3}$ is a bond, —NH—, —O—, —C(O)—, —NHC(O)O—, —NHS(O)$_2$—,

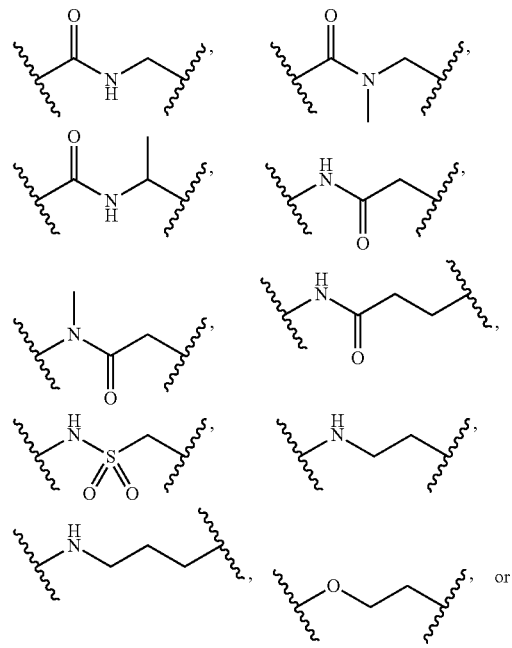

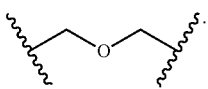

In embodiments, $L^{10.3}$ is a bond. In embodiments, $L^{10.3}$ is —NH—. In embodiments, $L^{10.3}$ is —O—. In embodiments, $L^{10.3}$ is —C(O)—. In embodiments, $L^{10.3}$ is —NHC(O)O—. In embodiments, $L^{10.3}$ is —NHS(O)$_2$—. In embodiments, $L^{10.3}$ is

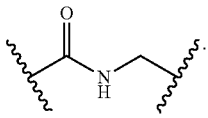 [SMILES: *CNC(*)=O]

In embodiments, $L^{13}$ is

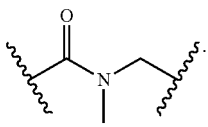 [SMILES: *CN(C)C(*)=O]

In embodiments, $L^{10.3}$ is

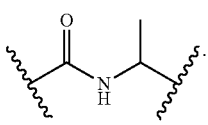 [SMILES: *C(=O)NC(*)C]

In embodiments, $L^{10.3}$ is

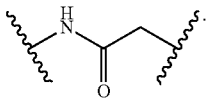

In embodiments, $L^{10.3}$ is

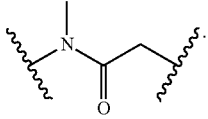 [SMILES: *CC(=O)N(*)C]

In embodiments, $L^{10.3}$ is

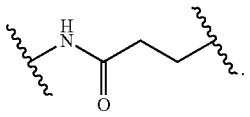 [SMILES: *CCC(=O)N*]

In embodiments, $L^{10.3}$ is

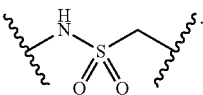 [SMILES: *CS(=O)(=O)N*]

In embodiments, $L^{10.3}$ is

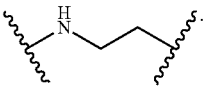 [SMILES: *CCN*]

In embodiments, $L^{10.3}$ is

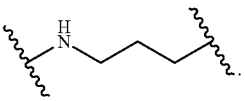

In embodiments, $L^{10.3}$ is

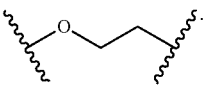 [SMILES: *CCO*]

In embodiments, $L^{10.3}$ is

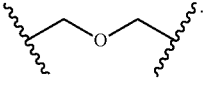 [SMILES: *COC*]

In embodiments, a substituted $R^{23}$ (e.g., substituted cycloalkyl, substituted heterocycloalkyl, substituted aryl, and/or substituted heteroaryl) is substituted with at least one substituent group, size-limited substituent group, or lower substituent group; wherein if the substituted $R^{23}$ is substituted with a plurality of groups selected from substituent groups, size-limited substituent groups, and lower substituent groups; each substituent group, size-limited substituent group, and/or lower substituent group may optionally be different. In embodiments, when $R^{23}$ is substituted, it is substituted with at least one substituent group. In embodiments, when $R^{23}$ is substituted, it is substituted with at least one size-limited substituent group. In embodiments, when $R^{23}$ is substituted, it is substituted with at least one lower substituent group.

In embodiments, $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCH$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., C$_1$-C$_8$, C$_1$-C$_6$, C$_1$-C$_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{23}$ is

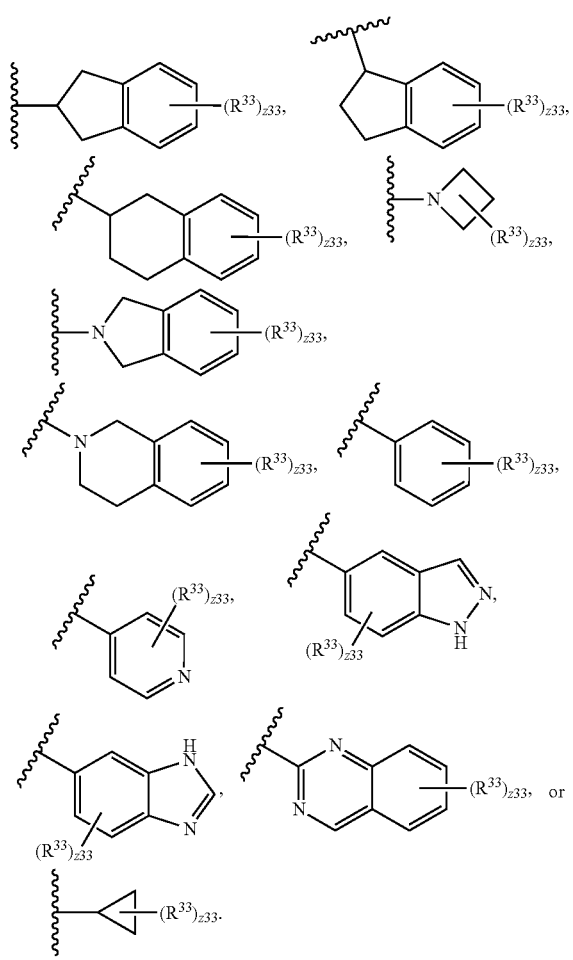

In embodiments, $R^{23}$ is

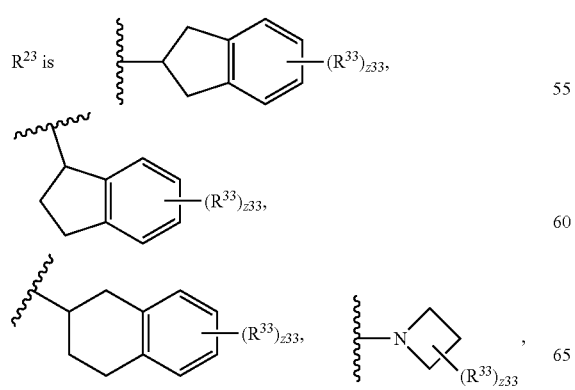

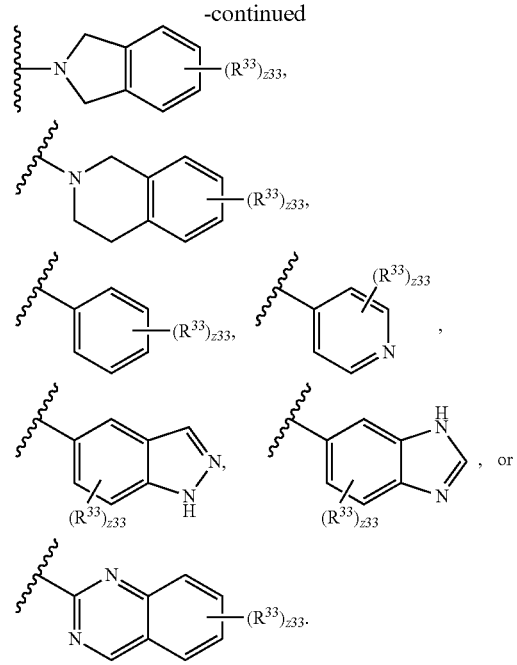

$R^{33}$ is as described herein, including in embodiments. The variable z33 is an integer from 0 to 10. In embodiments, $R^{23}$ is

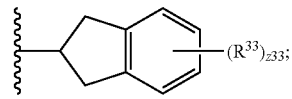

$R^{33}$ and z33 are as described herein, including in embodiments. In embodiments, $R^{23}$ is

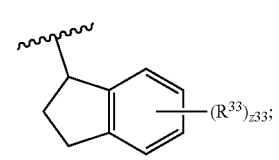

$R^{33}$ and z33 are as described herein, including in embodiments. In embodiments, $R^{23}$ is

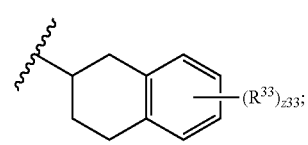

$R^{33}$ and z33 are as described herein, including in embodiments. In embodiments, $R^{23}$ is

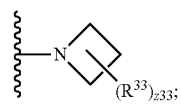

$R^{33}$ and z33 are as described herein, including in embodiments. In embodiments, $R^{23}$ is

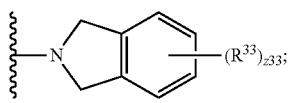

$R^{33}$ and z33 are as described herein, including in embodiments. In embodiments, $R^{23}$ is

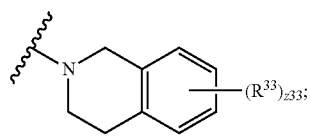

$R^{33}$ and z33 are as described herein, including in embodiments. In embodiments, $R^{23}$ is

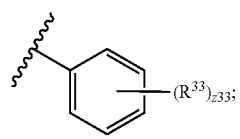

$R^{33}$ and z33 are as described herein, including in embodiments. In embodiments, $R^{23}$ is

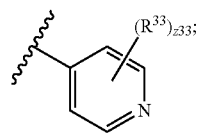

$R^{33}$ and z33 are as described herein, including in embodiments. In embodiments, $R^{23}$ is

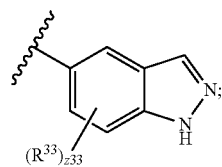

$R^{33}$ and z33 are as described herein, including in embodiments. In embodiments, $R^{23}$ is

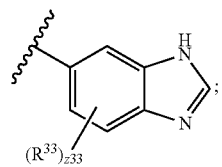

$R^{33}$ and z33 are as described herein, including in embodiments. In embodiments, $R^{23}$ is

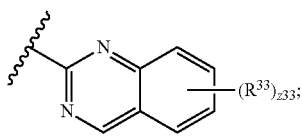

$R^{33}$ and z33 are as described herein, including in embodiments. In embodiments, $R^{23}$ is

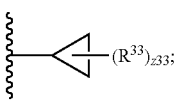

$R^{33}$ and z33 are as described herein, including in embodiments.

In embodiments, a substituted $R^{33}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{33}$ is substituted with a plurality of groups selected from substituent groups, size-limited substituent groups, and lower substituent groups; each substituent group, size-limited substituent group, and/or lower substituent group may optionally be different. In embodiments, when $R^{33}$ is substituted, it is substituted with at least one substituent group. In embodiments, when $R^{33}$ is substituted, it is substituted with at least one size-limited substituent group. In embodiments, when $R^{33}$ is substituted, it is substituted with at least one lower substituent group.

In embodiments, $R^{33}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl. In embodiments, $R^{33}$ is independently halogen. In embodiments, $R^{33}$ is independently —F. In embodiments, $R^{33}$ is independently —Cl. In embodiments, $R^{33}$ is independently —Br. In embodiments, $R^{33}$ is independently —I. In embodiments, $R^{33}$ is independently —$CF_3$. In embodiments, $R^{33}$ is independently —$CHF_2$. In embodiments, $R^{33}$ is independently —$CH_2F$. In embodiments, $R^{33}$ is independently —OH. In embodiments, $R^{33}$ is independently —$NH_2$. In embodiments, $R^{33}$ is independently —CN. In embodiments, $R^{33}$ is independently substituted or unsubstituted $C_1$-$C_4$ alkyl. In embodiments, $R^{33}$ is independently unsubstituted methyl. In embodiments, $R^{33}$ is independently unsubstituted ethyl. In embodiments, $R^{33}$ is independently unsubstituted propyl. In embodiments, $R^{33}$ is independently unsubstituted n-propyl. In embodiments, $R^{33}$ is independently unsubstituted isopropyl. In embodiments, $R^{33}$ is independently unsubstituted butyl. In embodiments, $R^{33}$ is independently unsubstituted n-butyl. In embodiments, $R^{33}$ is independently unsubstituted tert-butyl. In embodiments, $R^{33}$ is independently substituted or unsubstituted 2 to 5 membered heteroalkyl. In embodiments, $R^{33}$ is independently unsubstituted methoxy. In embodiments, $R^{33}$ is independently unsubstituted ethoxy. In embodiments, $R^{33}$ is independently unsubstituted propoxy. In embodiments, $R^{33}$ is independently unsubstituted n-propoxy. In embodiments, $R^{33}$ is independently unsubstituted isopropoxy. In embodiments, $R^{33}$ is independently unsubstituted butoxy. In embodiments, $R^{33}$ is independently unsubstituted n-butoxy. In embodiments, $R^{33}$ is independently unsubstituted tert-butoxy. In embodiments, $R^{33}$ is independently substituted or unsubstituted phenyl.

In embodiments, z33 is 0. In embodiments, z33 is 1. In embodiments, z33 is 2. In embodiments, z33 is 3. In embodiments, z33 is 4. In embodiments, z33 is 5. In embodiments, z33 is 6. In embodiments, z33 is 7. In embodiments, z33 is 8. In embodiments, z33 is 9. In embodiments, z33 is 10.

In embodiments, $R^{23}$ is

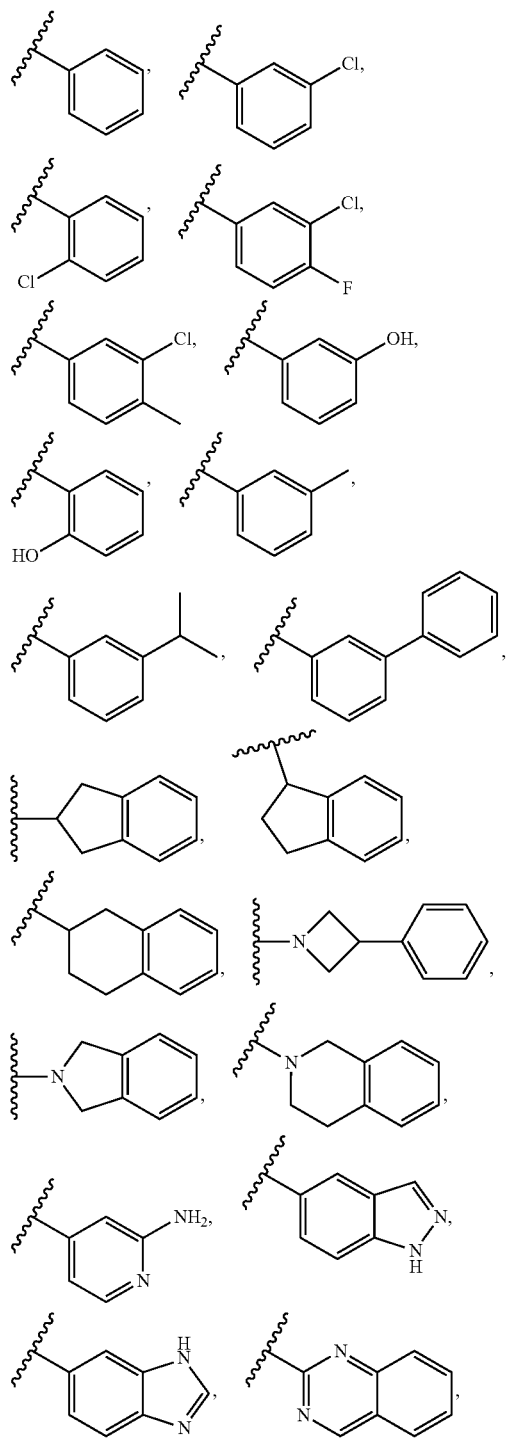

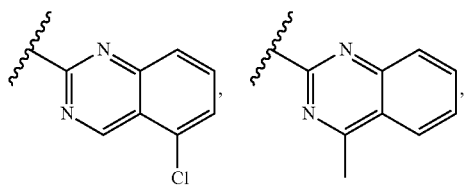

-continued

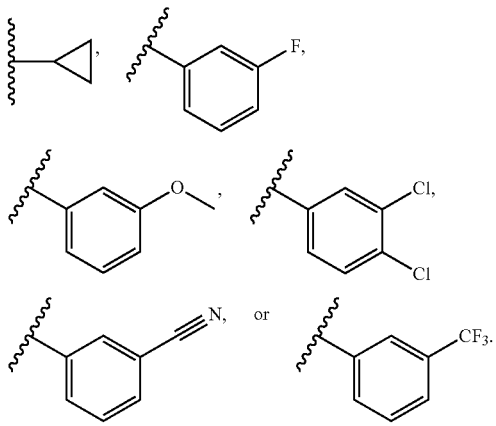

In embodiments, $R^{23}$ is

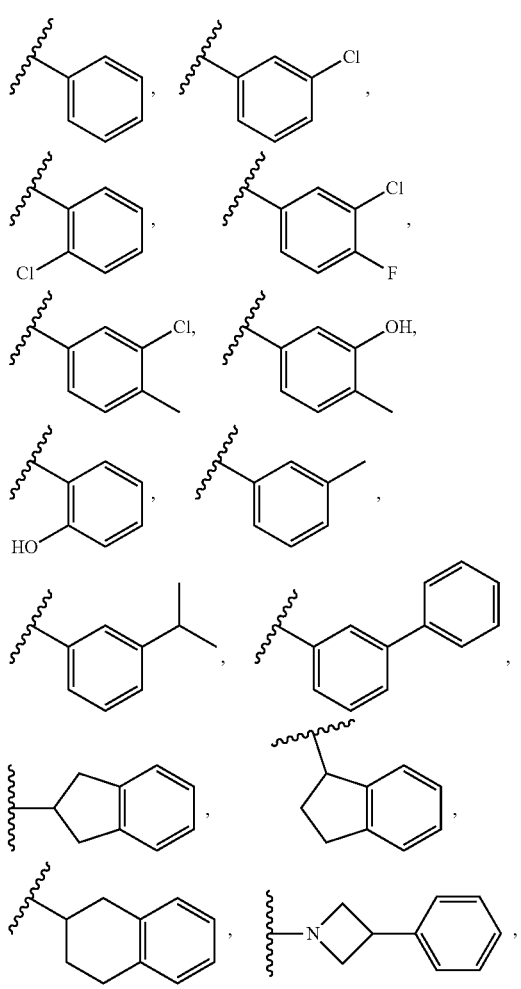

-continued
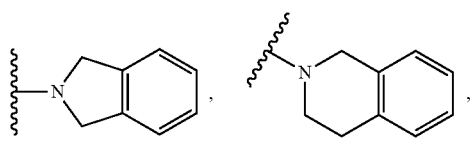
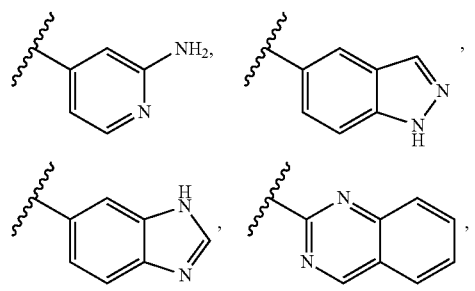
, or
In embodiments, $R^{23}$ is
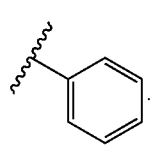
In embodiments, $R^{23}$ is
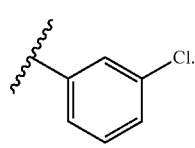 [SMILES: *c1cccc(Cl)c1]
In embodiments, $R^{23}$ is
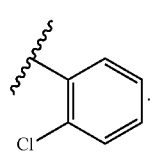
In embodiments, $R^{23}$ is
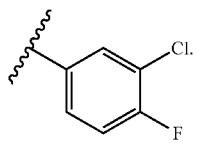
In embodiments, $R^{23}$ is
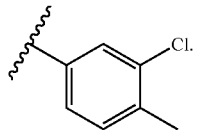 [SMILES: *c1ccc(C)c(Cl)c1]
In embodiments, $R^{23}$ is
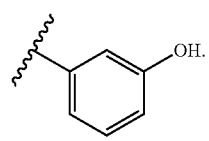
In embodiments, $R^{23}$ is
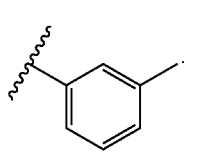 [SMILES: *c1cccc(C)c1]
In embodiments, $R^{23}$ is
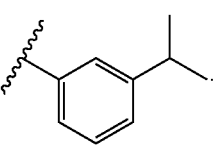 [SMILES: *c1cccc(C(C)C)c1]
In embodiments, $R^{23}$ is
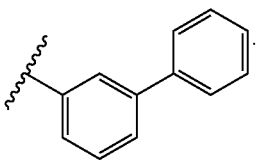 [SMILES: *c1cccc(-c2ccccc2)c1]

In embodiments, $R^{23}$ is
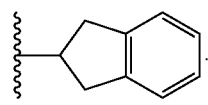
In embodiments, $R^{23}$ is
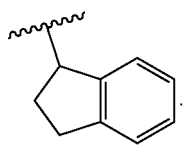
In embodiments, $R^{23}$ is
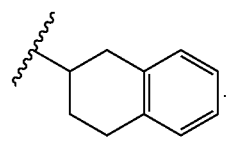 [SMILES: *C1CCc2ccccc2C1]
In embodiments, $R^{23}$ is
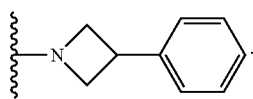 [SMILES: *N1CC(c2ccccc2)C1]
In embodiments, $R^{23}$ is
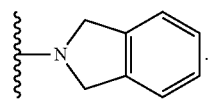
In embodiments, $R^{23}$ is
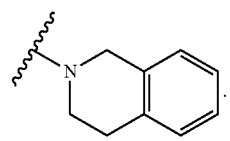 [SMILES: *N1CCc2ccccc2C1]
In embodiments, $R^{23}$ is
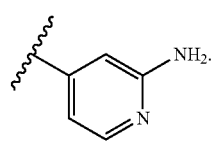 [SMILES: *c1ccnc(N)c1]
In embodiments, $R^{23}$ is
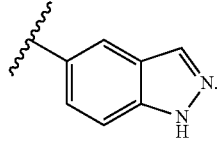 [SMILES: *c1ccc2[nH]ncc2c1]
In embodiments, $R^{23}$ is
In embodiments, $R^{23}$ is
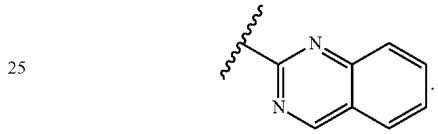
In embodiments, $R^{23}$ is
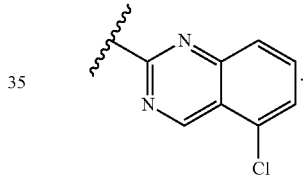
In embodiments, $R^{23}$ is
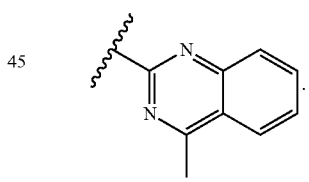
In embodiments, $R^{23}$ is
In embodiments, $R^{23}$ is
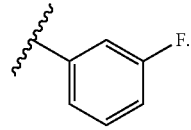 [SMILES: *c1cccc(F)c1]

In embodiments, $R^{23}$ is

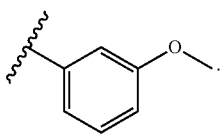 [SMILES: *c1cccc(OC)c1]

In embodiments, $R^{23}$ is

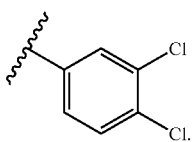 [SMILES: *c1ccc(Cl)c(Cl)c1]

In embodiments, $R^{23}$ is

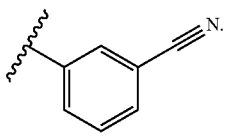 [SMILES: *c1cccc(C#N)c1]

In embodiments, $R^{23}$ is

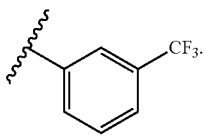 [SMILES: *c1cccc(C(F)(F)F)c1]

In embodiments, a substituted $R^{10.4}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.4}$ is substituted with a plurality of groups selected from substituent groups, size-limited substituent groups, and lower substituent groups; each substituent group, size-limited substituent group, and/or lower substituent group may optionally be different. In embodiments, when $R^{10.4}$ is substituted, it is substituted with at least one substituent group. In embodiments, when $R^{10.4}$ is substituted, it is substituted with at least one size-limited substituent group. In embodiments, when $R^{10.4}$ is substituted, it is substituted with at least one lower substituent group.

In embodiments, a substituted $R^{10.4A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.4A}$ is substituted with a plurality of groups selected from substituent groups, size-limited substituent groups, and lower substituent groups; each substituent group, size-limited substituent group, and/or lower substituent group may optionally be different. In embodiments, when $R^{10.4A}$ is substituted, it is substituted with at least one substituent group. In embodiments, when $R^{10.4A}$ is substituted, it is substituted with at least one size-limited substituent group. In embodiments, when $R^{10.4A}$ is substituted, it is substituted with at least one lower substituent group.

In embodiments, a substituted $R^{10.4B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.4B}$ is substituted with a plurality of groups selected from substituent groups, size-limited substituent groups, and lower substituent groups; each substituent group, size-limited substituent group, and/or lower substituent group may optionally be different. In embodiments, when $R^{10.4B}$ is substituted, it is substituted with at least one substituent group. In embodiments, when $R^{10.4B}$ is substituted, it is substituted with at least one size-limited substituent group. In embodiments, when $R^{10.4B}$ is substituted, it is substituted with at least one lower substituent group.

In embodiments, a substituted ring formed when $R^{10.4A}$ and $R^{10.4B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.4A}$ and $R^{10.4B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.4A}$ and $R^{10.4B}$ substituents bonded to the same nitrogen atom are joined is substituted, it is substituted with at least one substituent group. In embodiments, when the substituted ring formed when $R^{10.4A}$ and $R^{10.4B}$ substituents bonded to the same nitrogen atom are joined is substituted, it is substituted with at least one size-limited substituent group. In embodiments, when the substituted ring formed when $R^{10.4A}$ and $R^{10.4B}$ substituents bonded to the same nitrogen atom are joined is substituted, it is substituted with at least one lower substituent group.

In embodiments, a substituted $R^{10.4C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.4C}$ is substituted with a plurality of groups selected from substituent groups, size-limited substituent groups, and lower substituent groups; each substituent group, size-limited substituent group, and/or lower substituent group may optionally be different. In embodiments, when $R^{10.4C}$ is substituted, it is substituted with at least one substituent group. In embodiments, when $R^{10.4C}$ is substituted, it is substituted with at least one size-limited substituent group. In embodiments, when $R^{10.4C}$ is substituted, it is substituted with at least one lower substituent group.

In embodiments, a substituted $R^{10.4D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.4D}$ is substituted with a plurality of groups selected from substituent groups, size-limited substituent groups, and lower substituent groups; each substituent group, size-limited substituent group, and/or lower substituent group may optionally be different. In embodiments, when $R^{10.4D}$ is substituted, it is substituted with at least one substituent group. In embodiments, when $R^{10.4D}$ is substituted, it is substituted with at least one size-limited substituent group. In embodiments, when $R^{10.4D}$ is substituted, it is substituted with at least one lower substituent group.

In embodiments, $R^{10.4}$ is hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{10.4}$ is hydrogen or -$L^{10.4}$-$R^{24}$; $L^{10.4}$ and $R^{24}$ are as described herein, including in embodiments. In embodiments, $R^{10.4}$ is hydrogen. In embodiments, $R^{10.4}$ is -$L^{10.4}$-$R^{24}$; $L^{10.4}$ and $R^{24}$ are as described herein, including in embodiments.

In embodiments, a substituted $L^{10.4}$ (e.g., substituted alkylene and/or substituted heteroalkylene) is substituted with at least one substituent group, size-limited substituent group, or lower substituent group; wherein if the substituted $L^{10.4}$ is substituted with a plurality of groups selected from substituent groups, size-limited substituent groups, and lower substituent groups; each substituent group, size-limited substituent group, and/or lower substituent group may optionally be different. In embodiments, when $L^{10.4}$ is substituted, it is substituted with at least one substituent group. In embodiments, when $L^{10.4}$ is substituted, it is substituted with at least one size-limited substituent group. In embodiments, when $L^{10.4}$ is substituted, it is substituted with at least one lower substituent group.

In embodiments, $L^{10.4}$ is a bond, $-NH-$, $-O-$, $-C(O)-$, $-NHC(O)O-$, $-NHS(O)_2-$, or substituted or unsubstituted 2 to 5 membered heteroalkylene. In embodiments, $L^{10.4}$ is substituted or unsubstituted 2 to 5 membered heteroalkylene.

In embodiments, $L^{10.4}$ is a bond, $-NH-$, $-O-$, $-C(O)-$, $-NHC(O)O-$, $-NHS(O)_2-$,

, 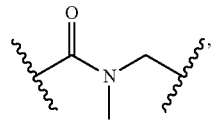,

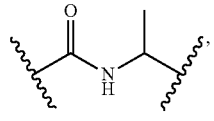, 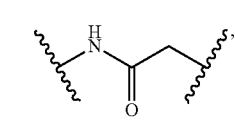,

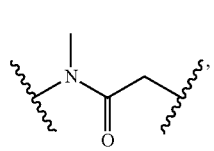, 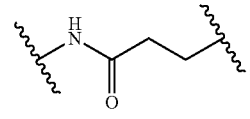,

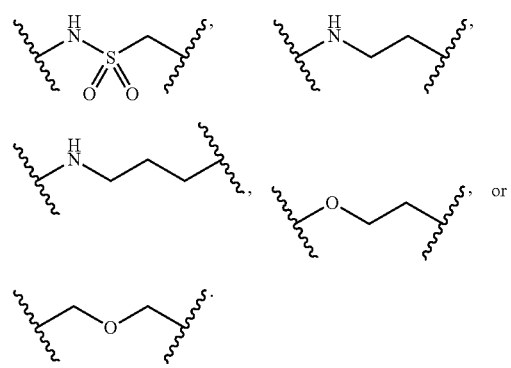

In embodiments, $L^{10.4}$ is a bond. In embodiments, $L^{10.4}$ is $-NH-$. In embodiments, $L^{10.4}$ is $-O-$. In embodiments, $L^{10.4}$ is $-C(O)-$. In embodiments, $L^{10.4}$ is $-NHC(O)O-$. In embodiments, $L^{10.4}$ is $-NHS(O)_2-$. In embodiments, $L^{10.4}$ is

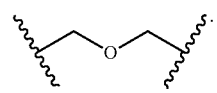

In embodiments, $L^{10.4}$ is

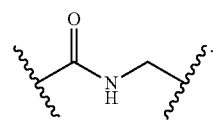 [SMILES: *CNC(*)=O]

In embodiments, $L^{10.4}$ is

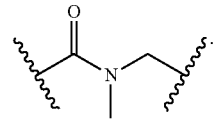 [SMILES: *CN(C)C(*)=O]

In embodiments, $L^{10.4}$ is

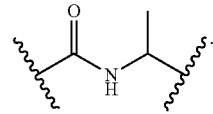

In embodiments, $L^{10.4}$ is

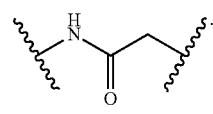

In embodiments, $L^{10.4}$ is

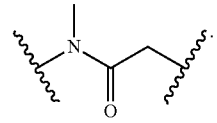 [SMILES: *CC(=O)N(*)C]

In embodiments, $L^{10.4}$ is

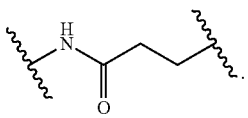 [SMILES: *CCC(=O)N*]

In embodiments, $L^{10.4}$ is

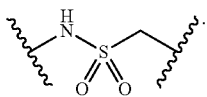

In embodiments, $L^{10.4}$ is

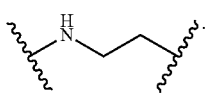 [SMILES: *CCN*]

In embodiments, $L^{10.4}$ is

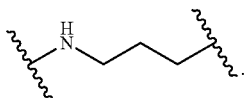 [SMILES: *CCCN*]

In embodiments, $L^{10.4}$ is

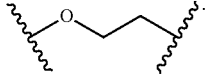

In embodiments, $L^{10.4}$ is

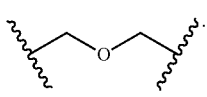

In embodiments, a substituted $R^{24}$ (e.g., substituted cycloalkyl, substituted heterocycloalkyl, substituted aryl, and/or substituted heteroaryl) is substituted with at least one substituent group, size-limited substituent group, or lower substituent group; wherein if the substituted $R^{24}$ is substituted with a plurality of groups selected from substituent groups, size-limited substituent groups, and lower substituent groups; each substituent group, size-limited substituent group, and/or lower substituent group may optionally be different. In embodiments, when $R^{24}$ is substituted, it is substituted with at least one substituent group. In embodiments, when $R^{24}$ is substituted, it is substituted with at least one size-limited substituent group. In embodiments, when $R^{24}$ is substituted, it is substituted with at least one lower substituent group.

In embodiments, $R^{24}$ is $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{24}$ is

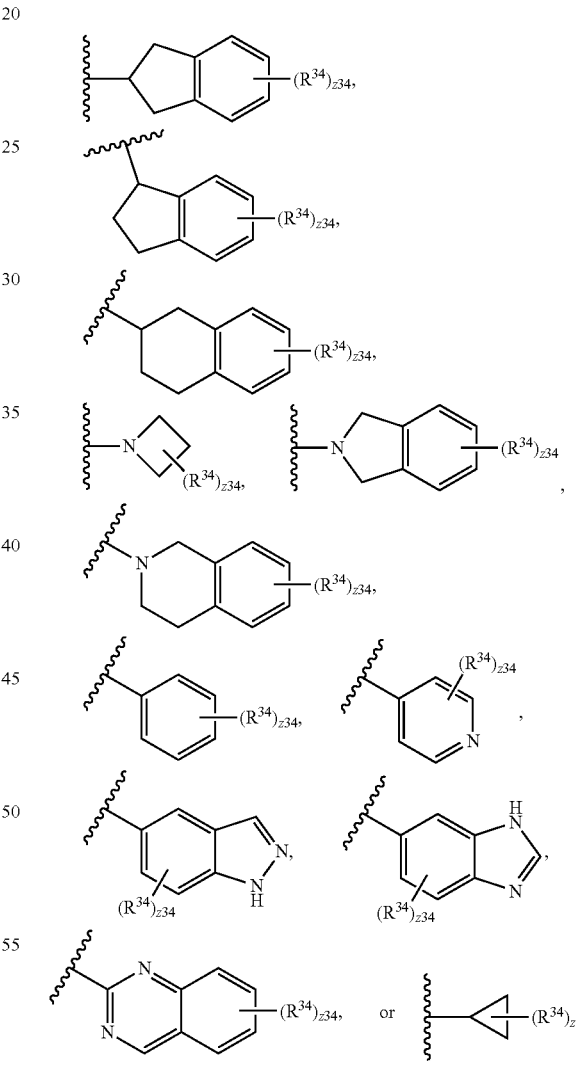

In embodiments,

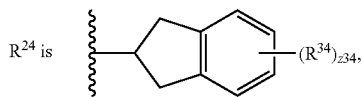

$R^{24}$ is

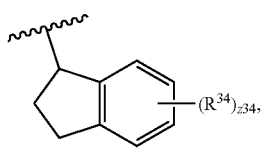

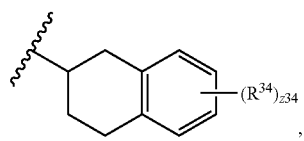 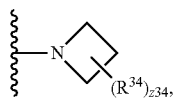

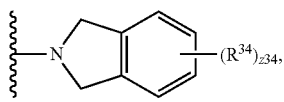

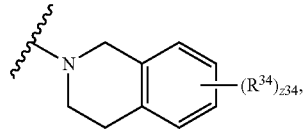

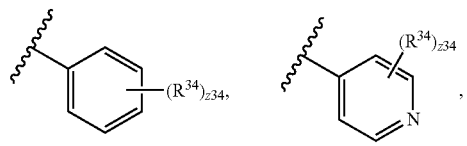

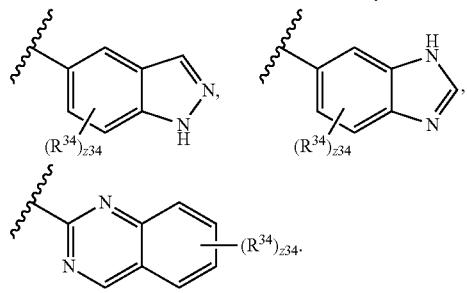

or $R^{34}$ is as described herein, including in embodiments. The variable z34 is an integer from 0 to 10. In embodiments, $R^{24}$ is

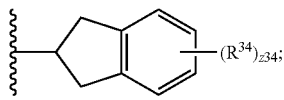

$R^{34}$ and z34 are as described herein, including in embodiments. In embodiments, $R^{24}$ is

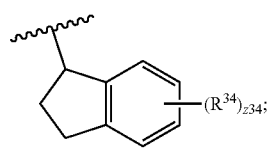

$R^{34}$ and z34 are as described herein, including in embodiments. In embodiments, $R^{24}$ is

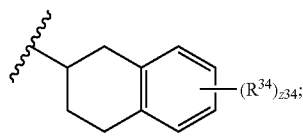

$R^{34}$ and z34 are as described herein, including in embodiments. In embodiments, $R^{24}$ is

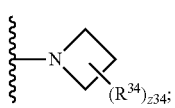

$R^{34}$ and z34 are as described herein, including in embodiments. In embodiments, $R^{24}$ is

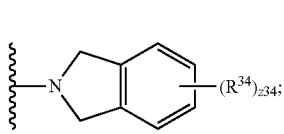

$R^{34}$ and z34 are as described herein, including in embodiments. In embodiments, $R^{24}$ is

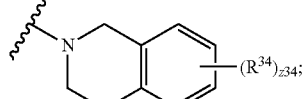

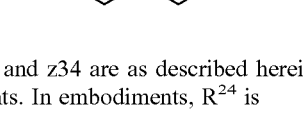

$R^{34}$ and z34 are as described herein, including in embodiments. In embodiments, $R^{24}$ is

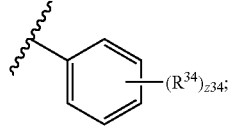

$R^{34}$ and z34 are as described herein, including in embodiments. In embodiments, $R^{24}$ is

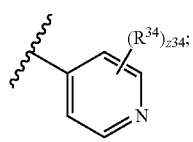

$R^{34}$ and z34 are as described herein, including in embodiments. In embodiments, $R^{24}$ is

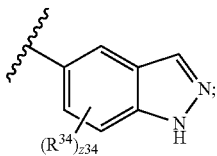

$R^{34}$ and z34 are as described herein, including in embodiments. In embodiments, $R^{24}$ is

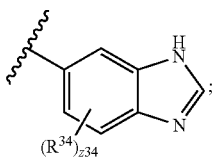

$R^{34}$ and z34 are as described herein, including in embodiments. In embodiments, $R^{24}$ is

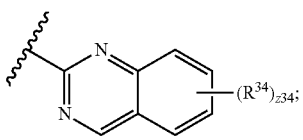

$R^{34}$ and z34 are as described herein, including in embodiments. In embodiments, $R^{24}$ is

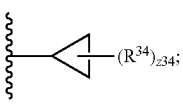

$R^{34}$ and z34 are as described herein, including in embodiments.

In embodiments, a substituted $R^{34}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{34}$ is substituted with a plurality of groups selected from substituent groups, size-limited substituent groups, and lower substituent groups; each substituent group, size-limited substituent group, and/or lower substituent group may optionally be different. In embodiments, when $R^{34}$ is substituted, it is substituted with at least one substituent group. In embodiments, when $R^{34}$ is substituted, it is substituted with at least one size-limited substituent group. In embodiments, when $R^{34}$ is substituted, it is substituted with at least one lower substituent group.

In embodiments, $R^{34}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl. In embodiments, $R^{34}$ is independently halogen. In embodiments, $R^{34}$ is independently —F. In embodiments, $R^{34}$ is independently —Cl. In embodiments, $R^{34}$ is independently —Br. In embodiments, $R^{34}$ is independently —I. In embodiments, $R^{34}$ is independently —$CF_3$. In embodiments, $R^{34}$ is independently —$CHF_2$. In embodiments, $R^{34}$ is independently —$CH_2F$. In embodiments, $R^{34}$ is independently —OH. In embodiments, $R^{34}$ is independently —$NH_2$. In embodiments, $R^{34}$ is independently —CN. In embodiments, $R^{34}$ is independently substituted or unsubstituted $C_1$-$C_4$ alkyl. In embodiments, $R^{34}$ is independently unsubstituted methyl. In embodiments, $R^{34}$ is independently unsubstituted ethyl. In embodiments, $R^{34}$ is independently unsubstituted propyl. In embodiments, $R^{34}$ is independently unsubstituted n-propyl. In embodiments, $R^{34}$ is independently unsubstituted isopropyl. In embodiments, $R^{34}$ is independently unsubstituted butyl. In embodiments, $R^{34}$ is independently unsubstituted n-butyl. In embodiments, $R^{34}$ is independently unsubstituted tert-butyl. In embodiments, $R^{34}$ is independently substituted or unsubstituted 2 to 5 membered heteroalkyl. In embodiments, $R^{34}$ is independently unsubstituted methoxy. In embodiments, $R^{34}$ is independently unsubstituted ethoxy. In embodiments, $R^{34}$ is independently unsubstituted propoxy. In embodiments, $R^{34}$ is independently unsubstituted n-propoxy. In embodiments, $R^{34}$ is independently unsubstituted isopropoxy. In embodiments, $R^{34}$ is independently unsubstituted butoxy. In embodiments, $R^{34}$ is independently unsubstituted n-butoxy. In embodiments, $R^{34}$ is independently unsubstituted tert-butoxy. In embodiments, $R^{34}$ is independently substituted or unsubstituted phenyl.

In embodiments, z34 is 0. In embodiments, z34 is 1. In embodiments, z34 is 2. In embodiments, z34 is 3. In embodiments, z34 is 4. In embodiments, z34 is 5. In embodiments, z34 is 6. In embodiments, z34 is 7. In embodiments, z34 is 8. In embodiments, z34 is 9. In embodiments, z34 is 10.

In embodiments, $R^{24}$ is

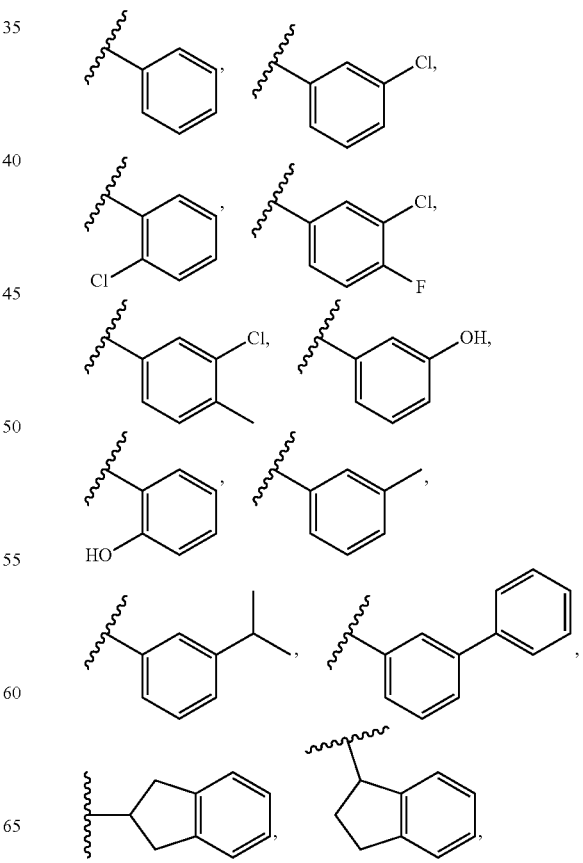

97
-continued
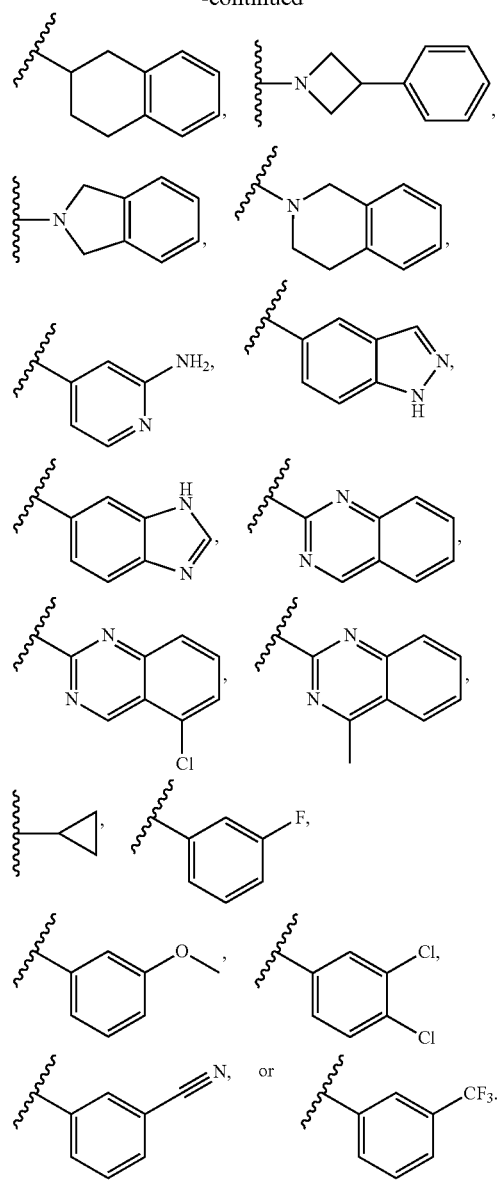
In embodiments, $R^{24}$ is
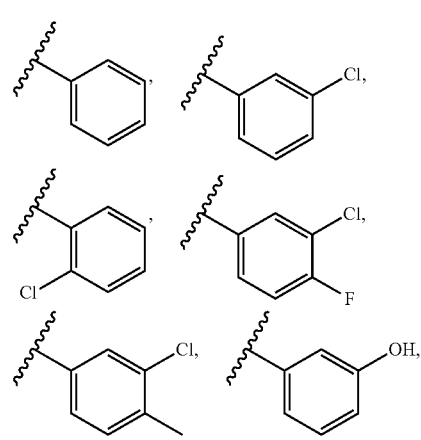
98
-continued
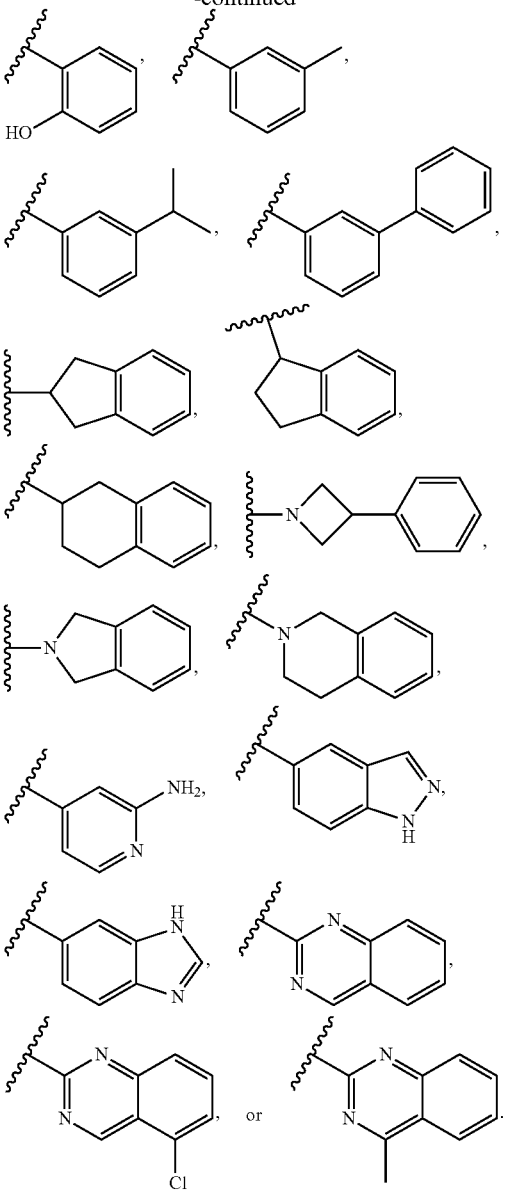
In embodiments, $R^{24}$ is
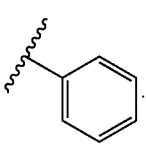 [SMILES: *c1ccccc1]
In embodiments, $R^{24}$ is
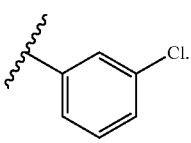 [SMILES: *c1cccc(Cl)c1]

In embodiments, $R^{24}$ is
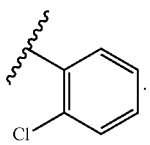 [SMILES: *c1ccccc1Cl]
In embodiments, $R^{24}$ is
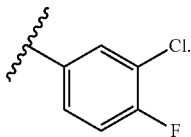 [SMILES: *c1ccc(F)c(Cl)c1]
In embodiments, $R^{24}$ is
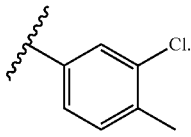 [SMILES: *c1ccc(C)c(Cl)c1]
In embodiments, $R^{24}$ is
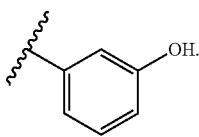 [SMILES: *c1cccc(O)c1]
In embodiments, $R^{24}$ is
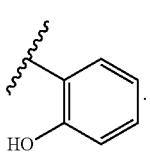
In embodiments, $R^{24}$ is
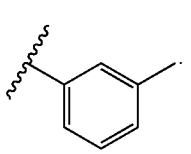 [SMILES: *c1cccc(C)c1]
In embodiments, $R^{24}$ is
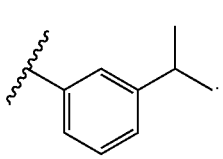 [SMILES: *c1cccc(C(C)C)c1]
In embodiments, $R^{24}$ is
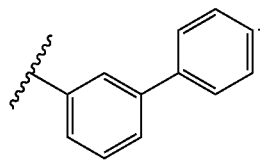 [SMILES: *c1cccc(-c2ccccc2)c1]
In embodiments, $R^{24}$ is
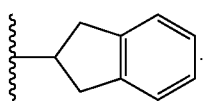
In embodiments, $R^{24}$ is
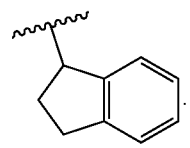
In embodiments, $R^{24}$ is
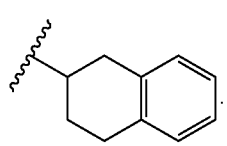 [SMILES: *C1CCc2ccccc2C1]
In embodiments, $R^{24}$ is
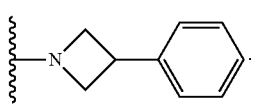 [SMILES: *N1CC(c2ccccc2)C1]
In embodiments, $R^{24}$ is
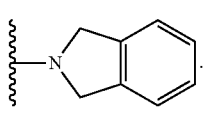 [SMILES: *N1Cc2ccccc2C1]
In embodiments, $R^{24}$ is
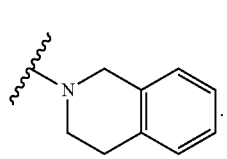 [SMILES: *N1CCc2ccccc2C1]

In embodiments, R$^{24}$ is

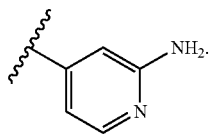 [SMILES: *c1ccnc(N)c1]

In embodiments, R$^{24}$ is

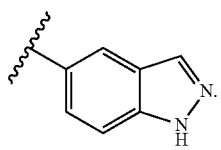 [SMILES: *c1ccc2[nH]ncc2c1]

In embodiments, R$^{24}$ is

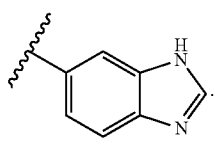 [SMILES: *c1ccc2nc[nH]c2c1]

In embodiments, R$^{24}$ is

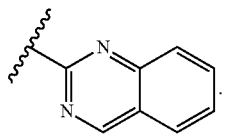 [SMILES: *c1ncc2ccccc2n1]

In embodiments, R$^{24}$ is

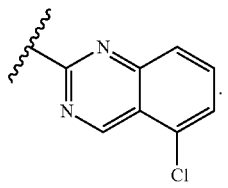 [SMILES: *c1ncc2c(Cl)cccc2n1]

In embodiments, R$^{24}$ is

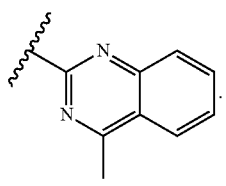 [SMILES: *c1nc(C)c2ccccc2n1]

In embodiments, R$^{24}$ is

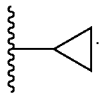

In embodiments, R$^{24}$ is

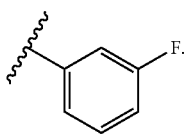 [SMILES: *c1cccc(F)c1]

In embodiments, R$^{24}$ is

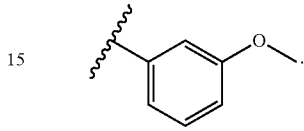

In embodiments, R$^{24}$ is

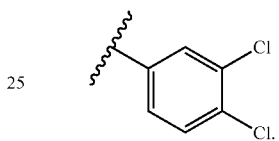

In embodiments, R$^{24}$ is

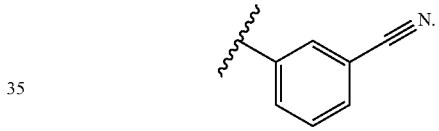

In embodiments, R$^{24}$ is

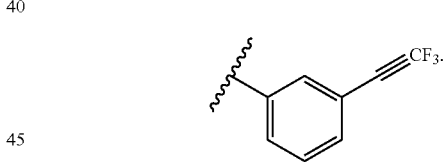

In embodiments, a substituted R$^{10.5}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{10.5}$ is substituted with a plurality of groups selected from substituent groups, size-limited substituent groups, and lower substituent groups; each substituent group, size-limited substituent group, and/or lower substituent group may optionally be different. In embodiments, when R$^{10.5}$ is substituted, it is substituted with at least one substituent group. In embodiments, when R$^{10.5}$ is substituted, it is substituted with at least one size-limited substituent group. In embodiments, when R$^{10.5}$ is substituted, it is substituted with at least one lower substituent group.

In embodiments, a substituted R$^{10.5A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.5A}$ is substituted with a plurality of groups selected from substituent groups, size-limited substituent groups, and lower substituent groups; each substituent group, size-limited substituent group, and/or lower substituent group may optionally be different. In embodiments, when $R^{10.5A}$ is substituted, it is substituted with at least one substituent group. In embodiments, when $R^{10.5A}$ is substituted, it is substituted with at least one size-limited substituent group. In embodiments, when $R^{10.5A}$ is substituted, it is substituted with at least one lower substituent group.

In embodiments, a substituted $R^{10.5B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.5B}$ is substituted with a plurality of groups selected from substituent groups, size-limited substituent groups, and lower substituent groups; each substituent group, size-limited substituent group, and/or lower substituent group may optionally be different. In embodiments, when $R^{10.5B}$ is substituted, it is substituted with at least one substituent group. In embodiments, when $R^{10.5B}$ is substituted, it is substituted with at least one size-limited substituent group. In embodiments, when $R^{10.5B}$ is substituted, it is substituted with at least one lower substituent group.

In embodiments, a substituted ring formed when $R^{10.5A}$ and $R^{10.5B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.5A}$ and $R^{10.5B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.5A}$ and $R^{10.5B}$ substituents bonded to the same nitrogen atom are joined is substituted, it is substituted with at least one substituent group. In embodiments, when the substituted ring formed when $R^{10.5A}$ and $R^{10.5B}$ substituents bonded to the same nitrogen atom are joined is substituted, it is substituted with at least one size-limited substituent group. In embodiments, when the substituted ring formed when $R^{10.5A}$ and $R^{10.5B}$ substituents bonded to the same nitrogen atom are joined is substituted, it is substituted with at least one lower substituent group.

In embodiments, a substituted $R^{10.5C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.5C}$ is substituted with a plurality of groups selected from substituent groups, size-limited substituent groups, and lower substituent groups; each substituent group, size-limited substituent group, and/or lower substituent group may optionally be different. In embodiments, when $R^{10.5C}$ is substituted, it is substituted with at least one substituent group. In embodiments, when $R^{10.5C}$ is substituted, it is substituted with at least one size-limited substituent group. In embodiments, when $R^{10.5C}$ is substituted, it is substituted with at least one lower substituent group.

In embodiments, a substituted $R^{10.5D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.5D}$ is substituted with a plurality of groups selected from substituent groups, size-limited substituent groups, and lower substituent groups; each substituent group, size-limited substituent group, and/or lower substituent group may optionally be different. In embodiments, when $R^{10.5D}$ is substituted, it is substituted with at least one substituent group. In embodiments, when $R^{10.5D}$ is substituted, it is substituted with at least one size-limited substituent group. In embodiments, when $R^{10.5D}$ is substituted, it is substituted with at least one lower substituent group.

In embodiments, $R^{10.5}$ is hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^{10.5}$ is hydrogen, halogen, substituted or unsubstituted $C_1$-$C_5$ alkyl, or substituted or unsubstituted 2 to 5 membered heteroalkyl. In embodiments, $R^{10.5}$ is halogen, substituted or unsubstituted $C_1$-$C_5$ alkyl, or substituted or unsubstituted 2 to 5 membered heteroalkyl. In embodiments, $R^{10.5}$ is halogen or unsubstituted methyl. In embodiments, $R^{10.5}$ is halogen. In embodiments, $R^{10.5}$ is —F. In embodiments, $R^{10.5}$ is —Cl. In embodiments, $R^{10.5}$ is —Br. In embodiments, $R^{10.5}$ is —I. In embodiments, $R^{10.5}$ is substituted or unsubstituted $C_1$-$C_5$ alkyl. In embodiments, $R^{10.5}$ is unsubstituted methyl. In embodiments, $R^{10.5}$ is unsubstituted ethyl. In embodiments, $R^{10.5}$ is unsubstituted propyl. In embodiments, $R^{10.5}$ is unsubstituted n-propyl. In embodiments, $R^{10.5}$ is unsubstituted isopropyl. In embodiments, $R^{10.5}$ is unsubstituted butyl. In embodiments, $R^{10.5}$ is unsubstituted n-butyl. In embodiments, $R^{10.5}$ is unsubstituted tert-butyl. In embodiments, $R^{10.5}$ is substituted or unsubstituted 2 to 5 membered heteroalkyl. In embodiments, $R^{10.5}$ is unsubstituted methoxy. In embodiments, $R^{10.5}$ is unsubstituted ethoxy. In embodiments, $R^{10.5}$ is unsubstituted propoxy. In embodiments, $R^{10.5}$ is unsubstituted n-propoxy. In embodiments, $R^{10.5}$ is unsubstituted isopropoxy. In embodiments, $R^{10.5}$ is unsubstituted butoxy. In embodiments, $R^{10.5}$ is unsubstituted n-butoxy. In embodiments, $R^{10.5}$ is unsubstituted tert-butoxy.

In embodiments, the compound has the formula
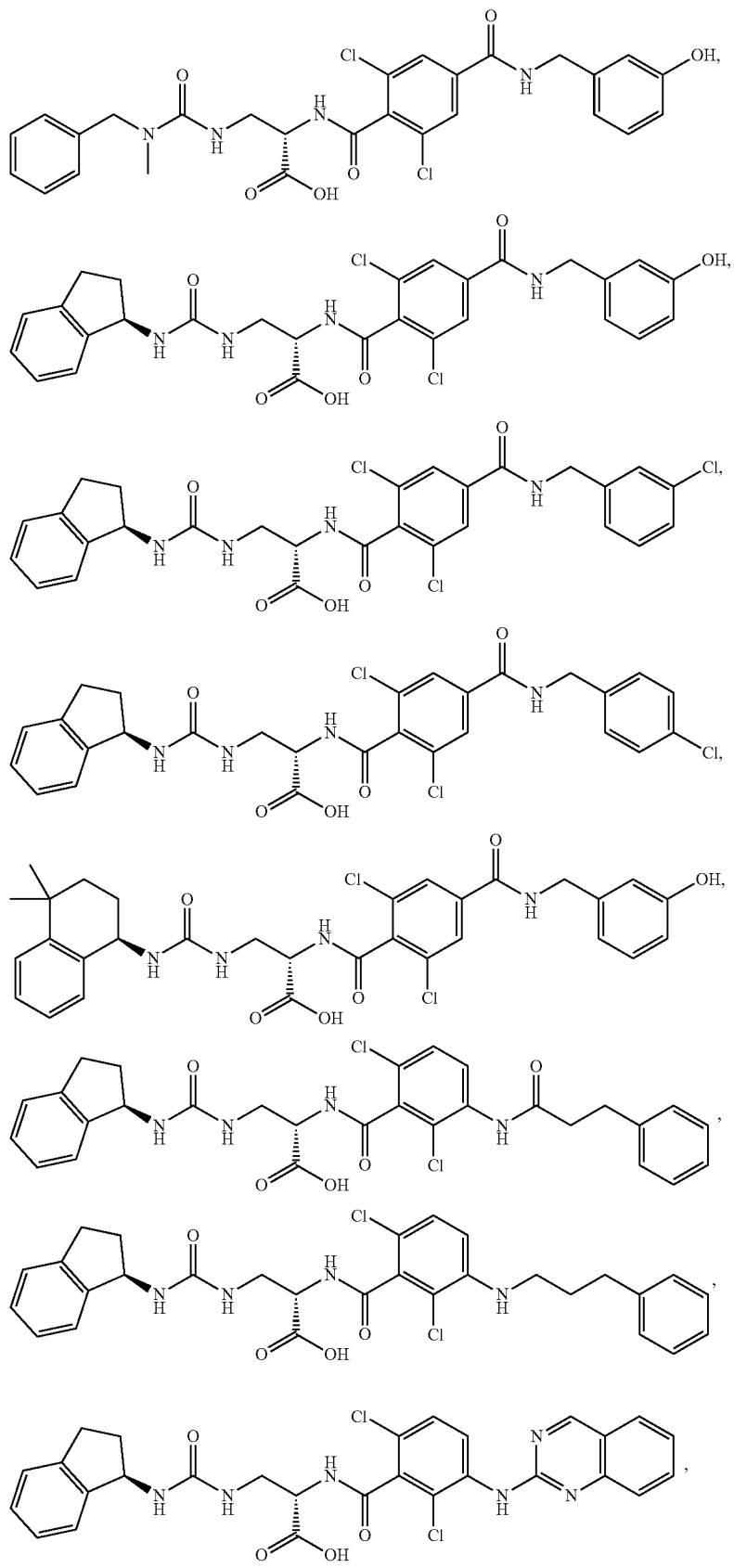

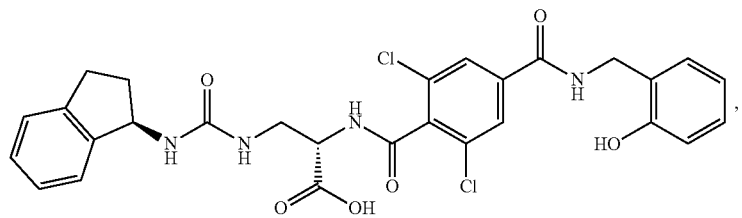
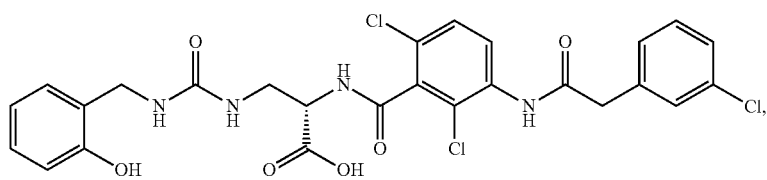
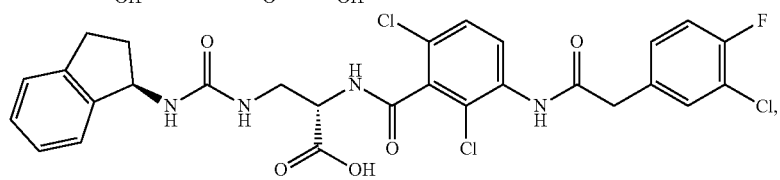
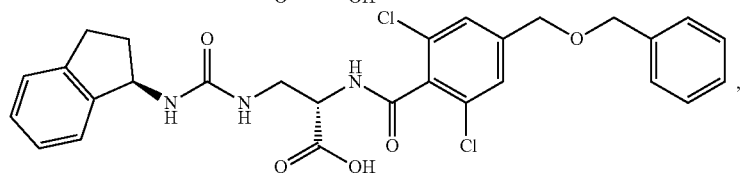
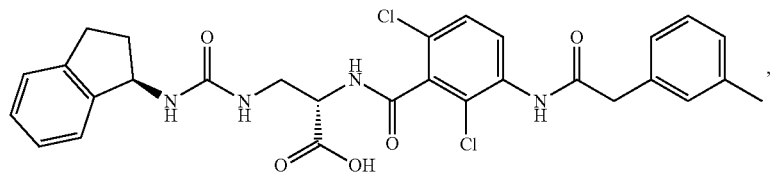
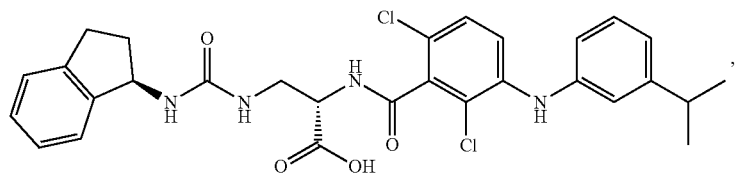
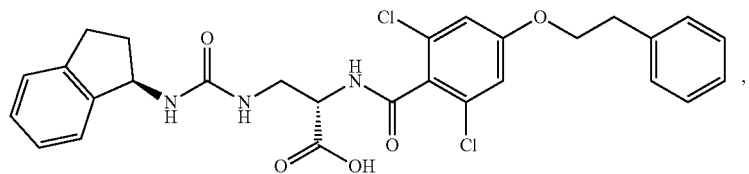
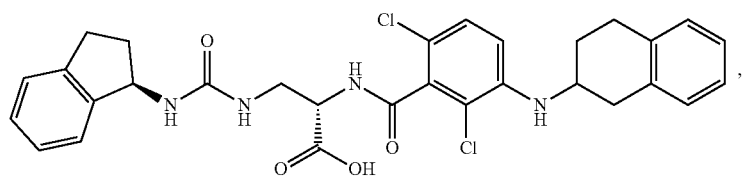
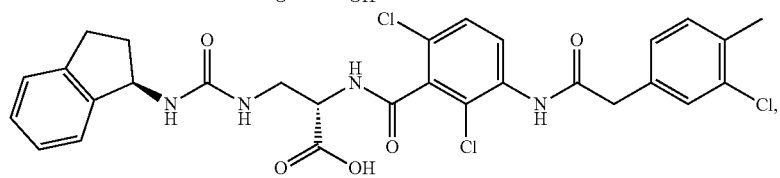

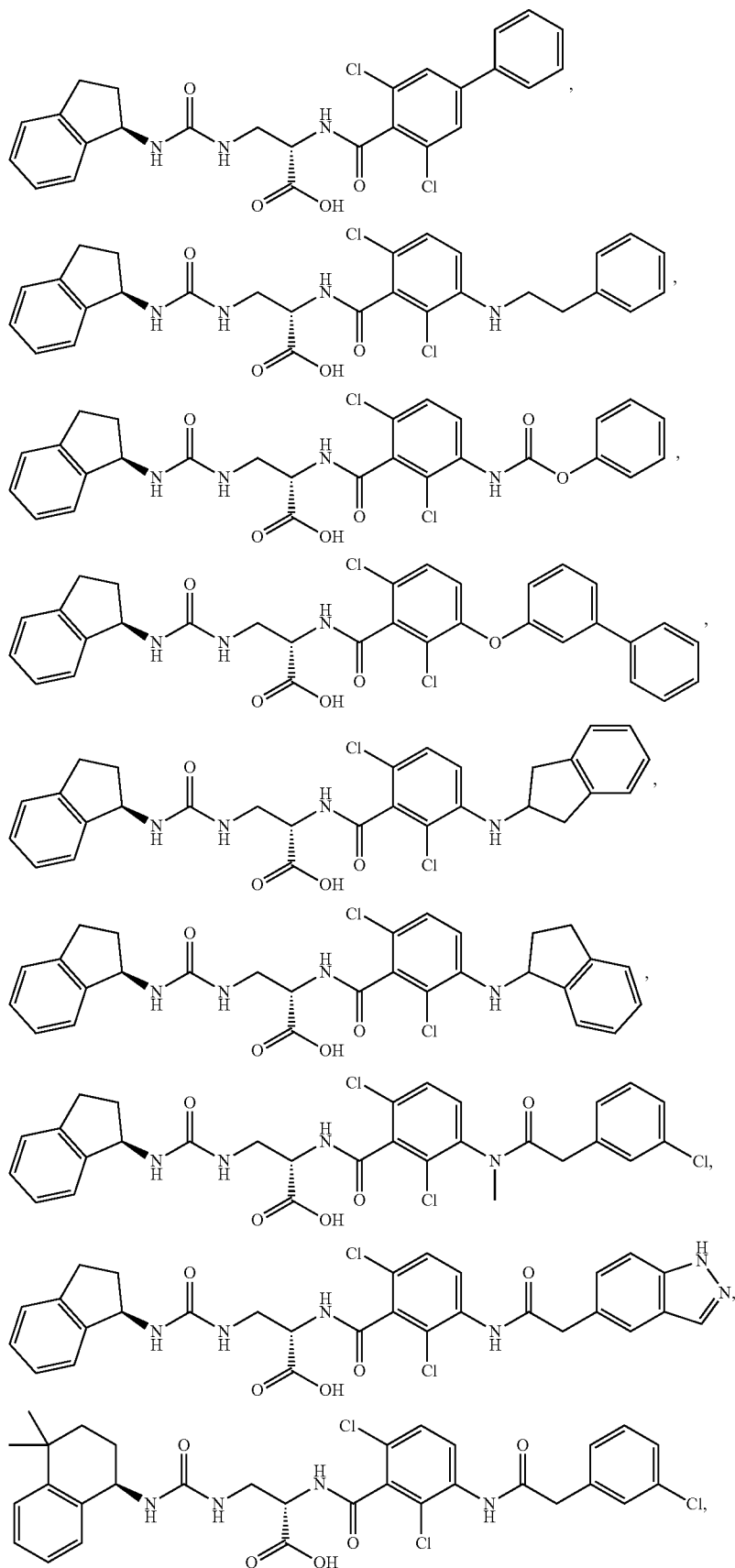

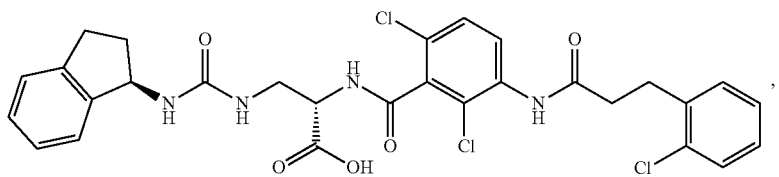
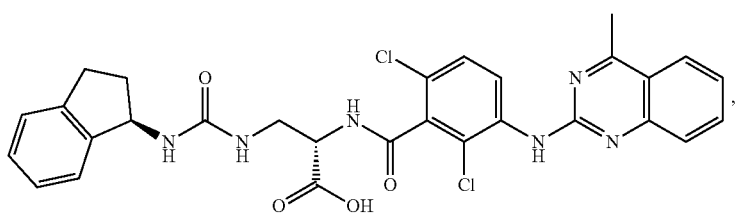
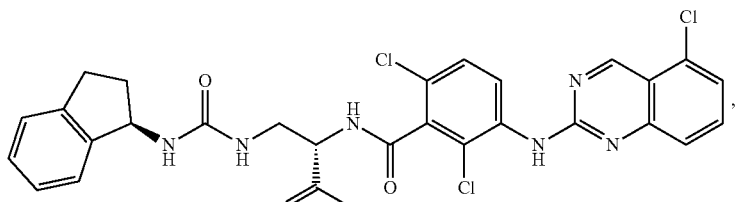
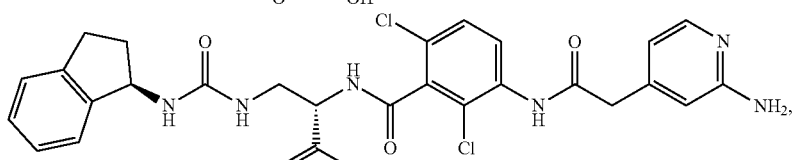
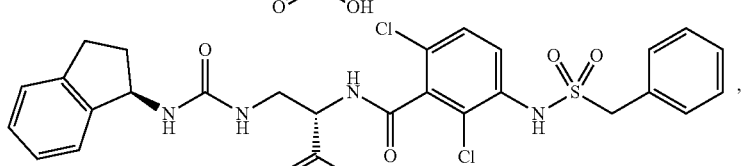
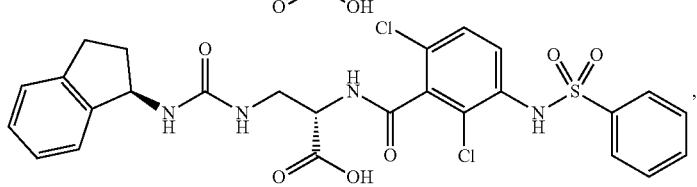
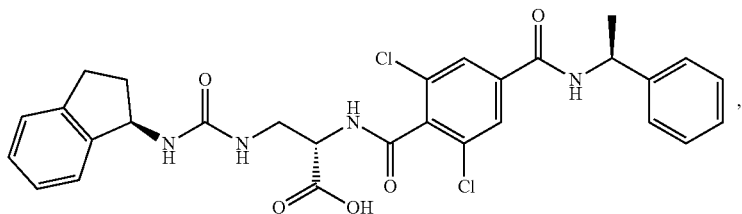
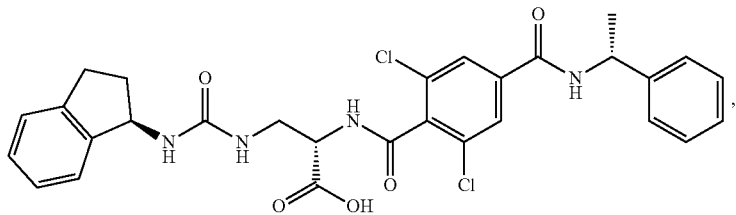

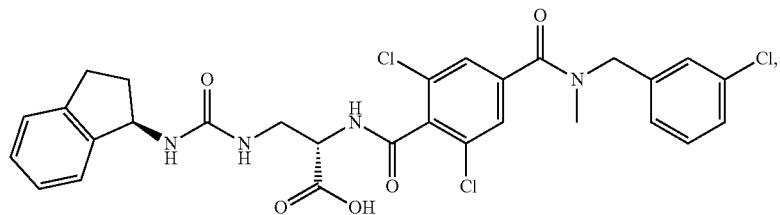
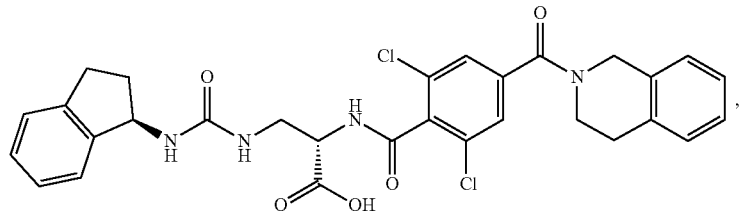
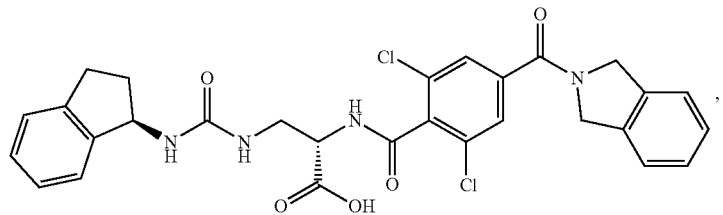
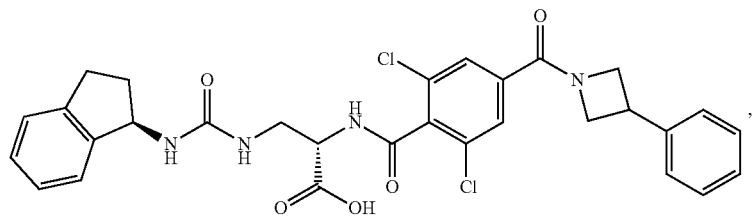
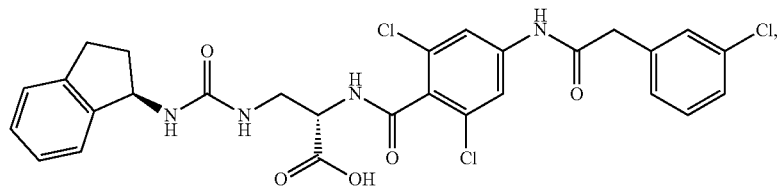
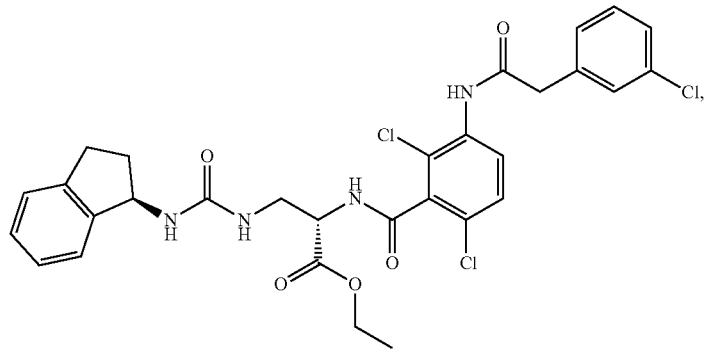
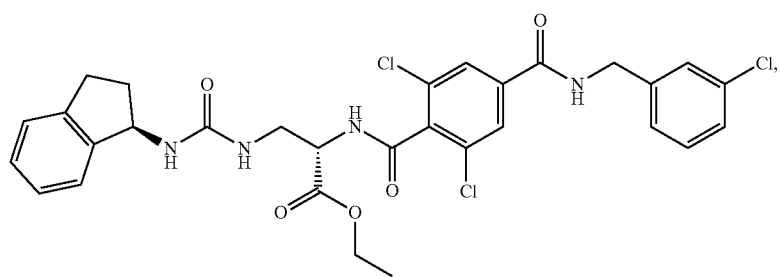

-continued
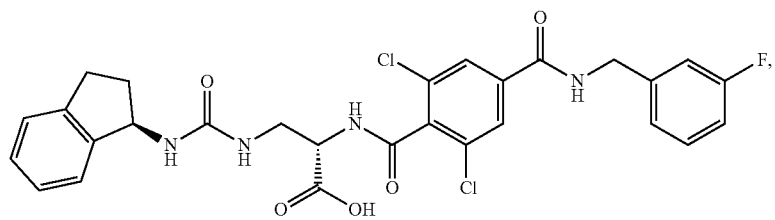
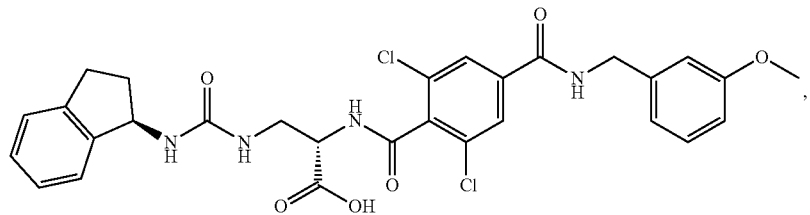
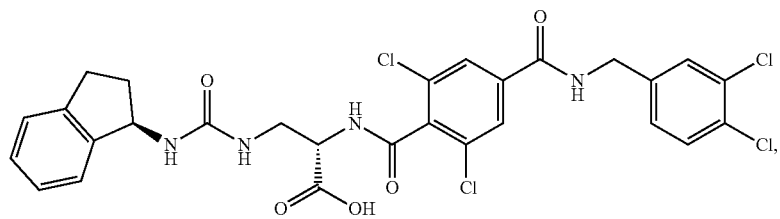
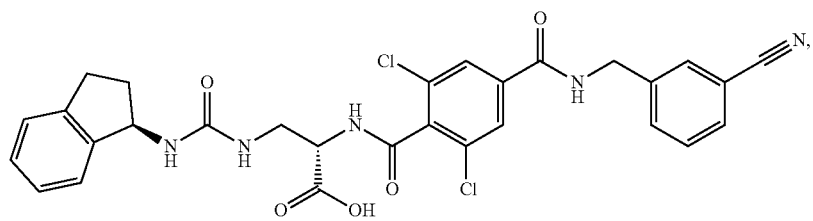
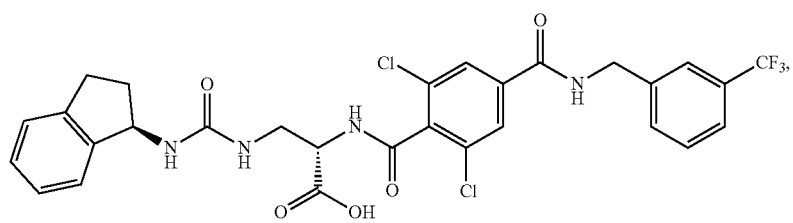
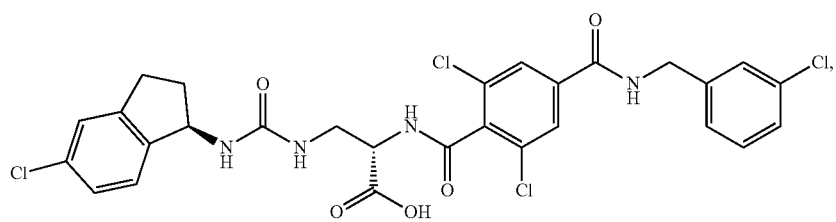
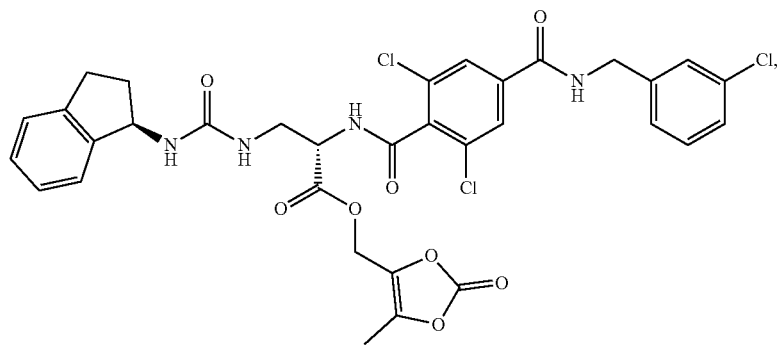
or

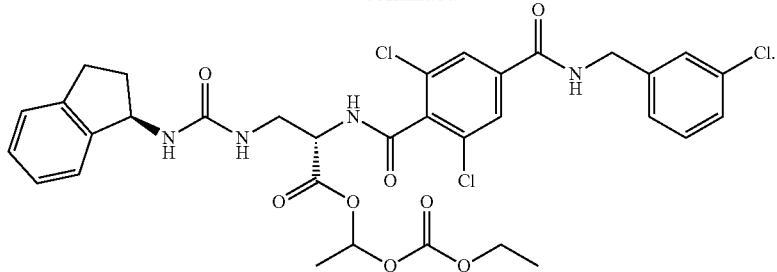
In embodiments, the compound has the formula
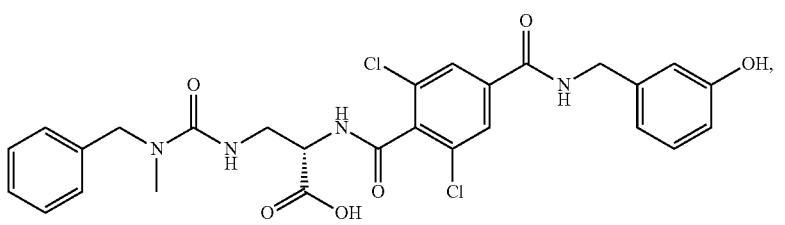
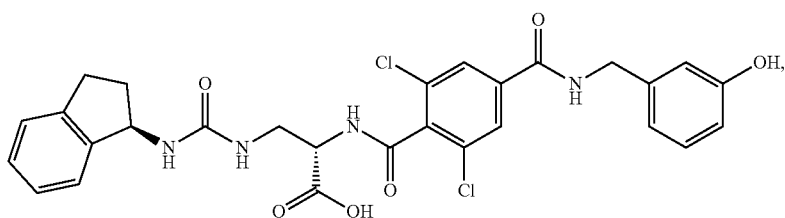
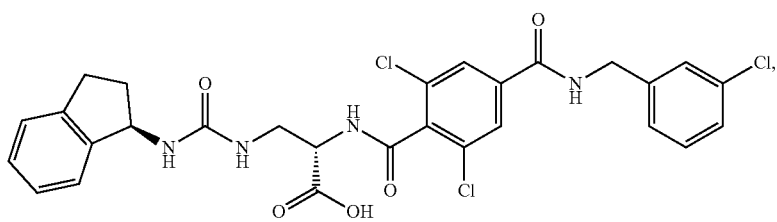
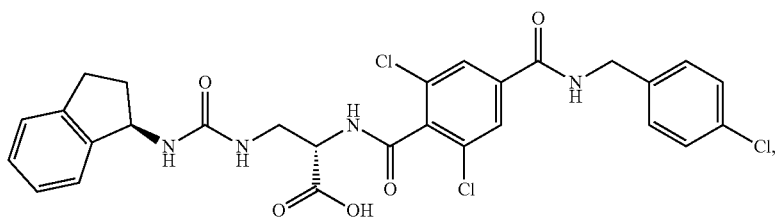
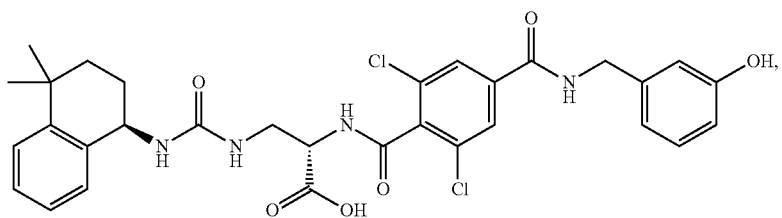
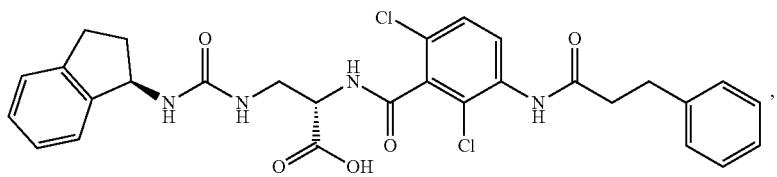

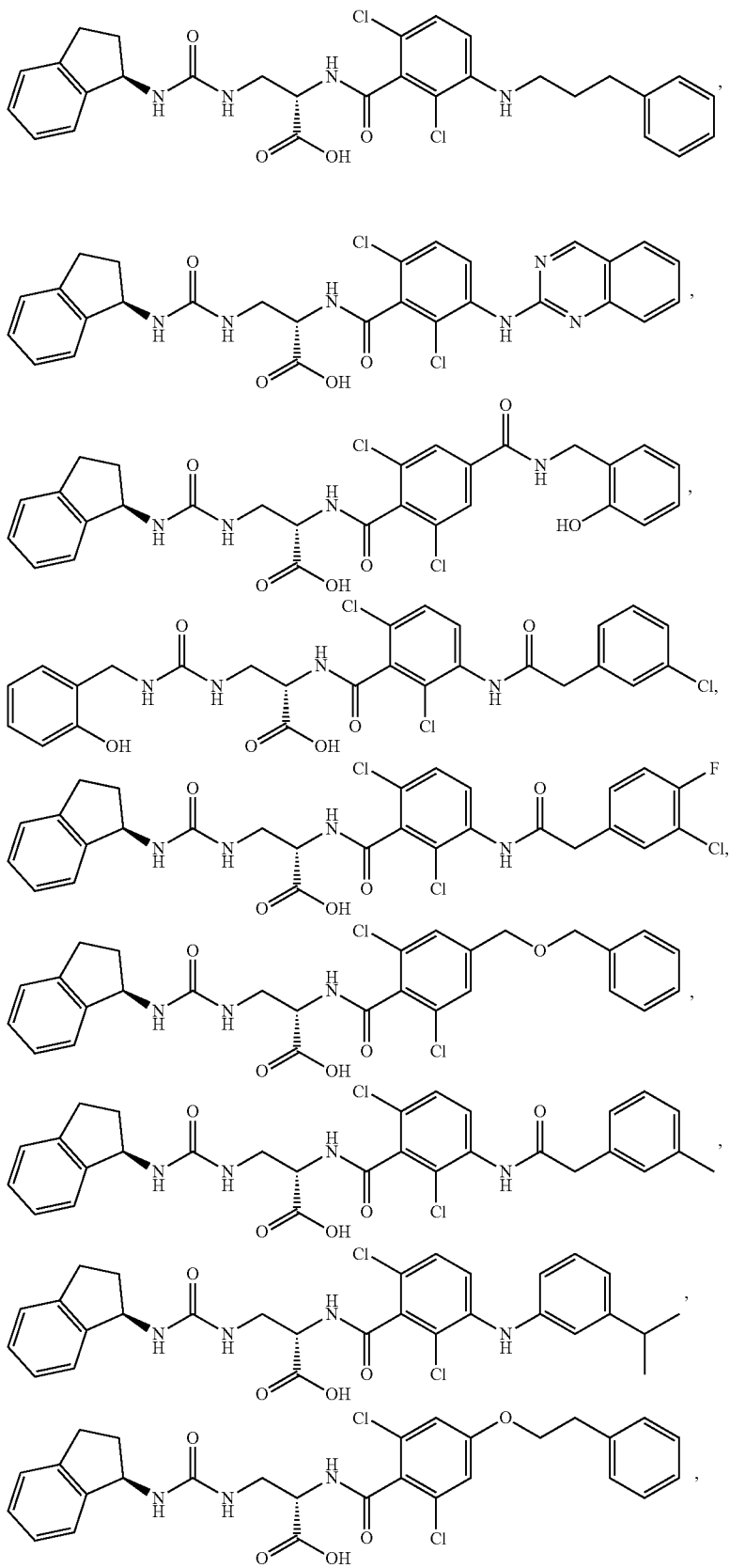

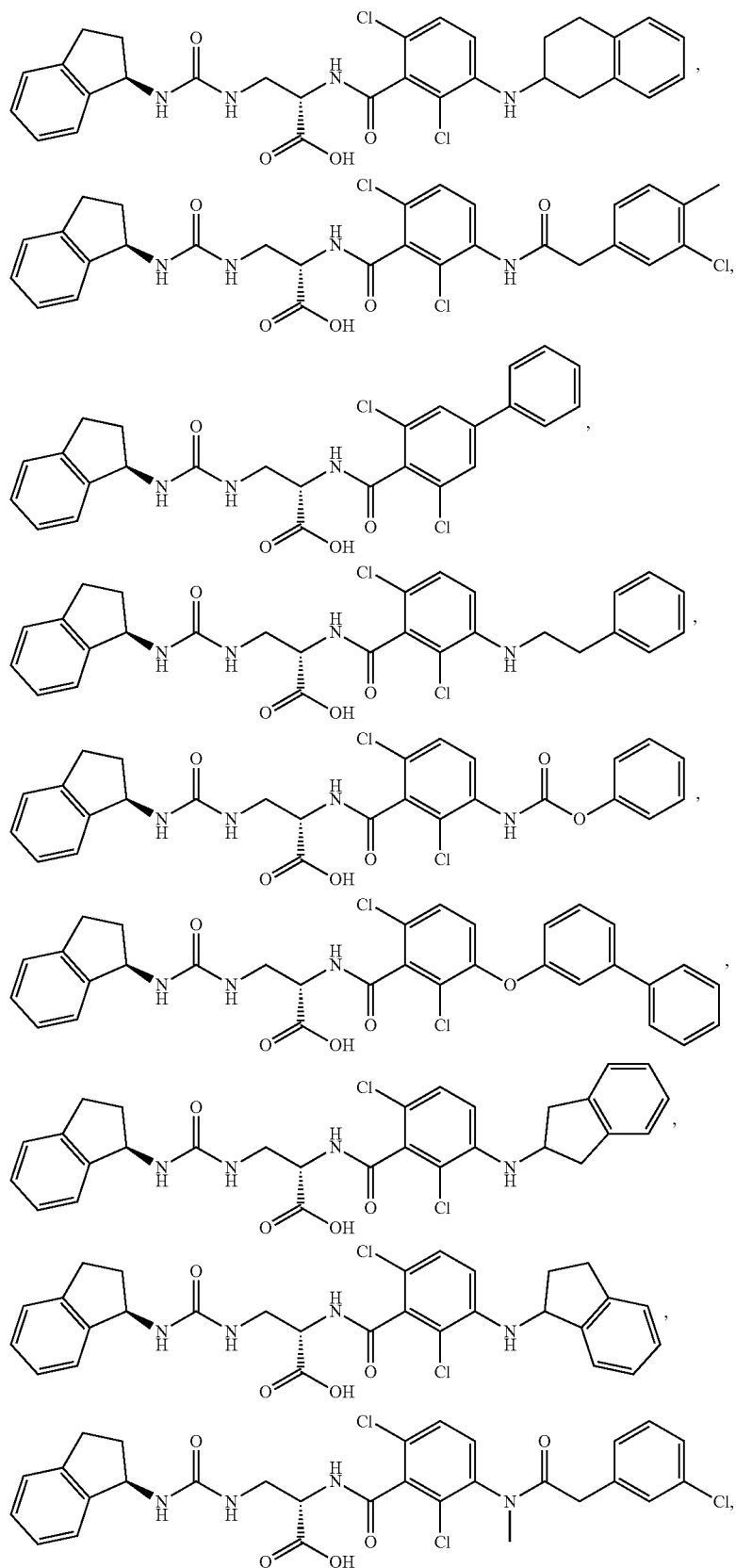

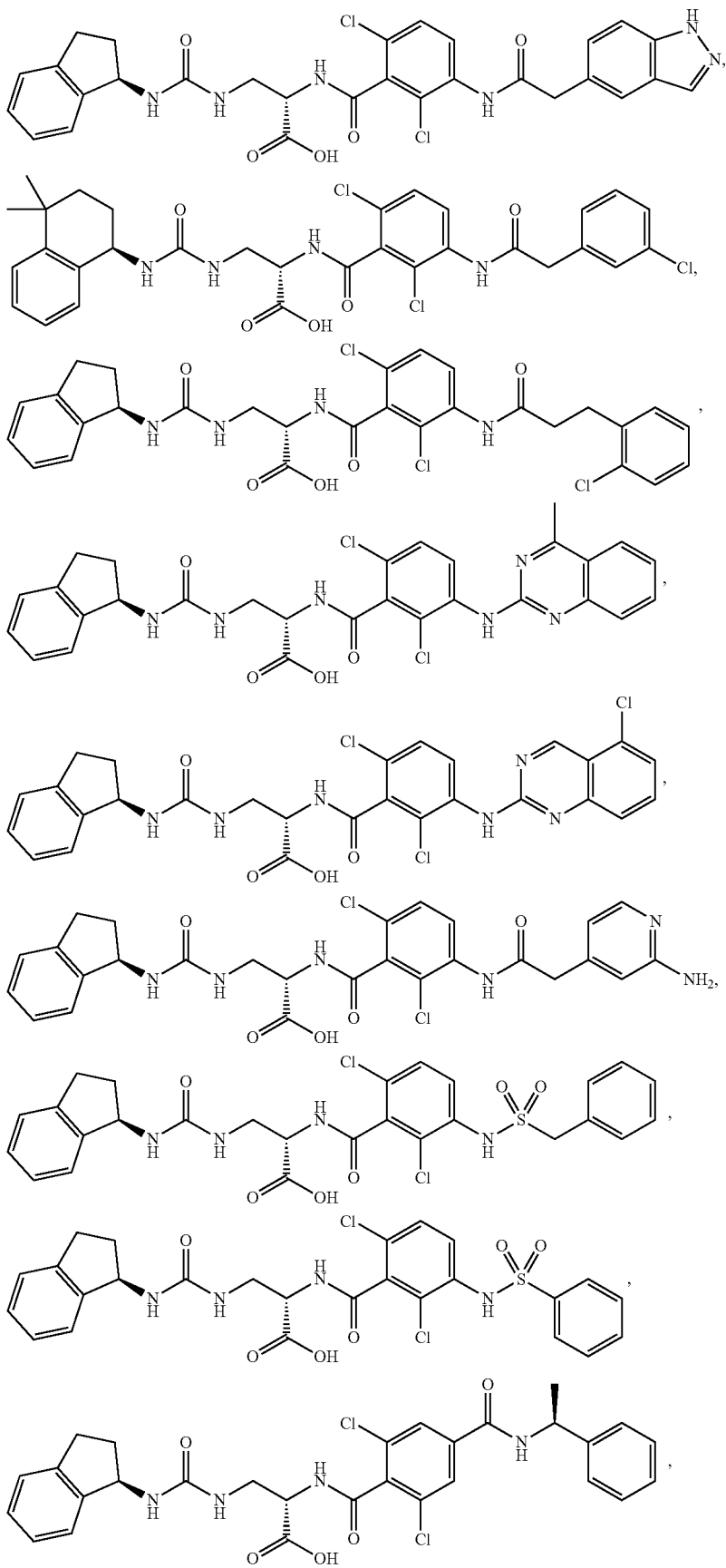

-continued

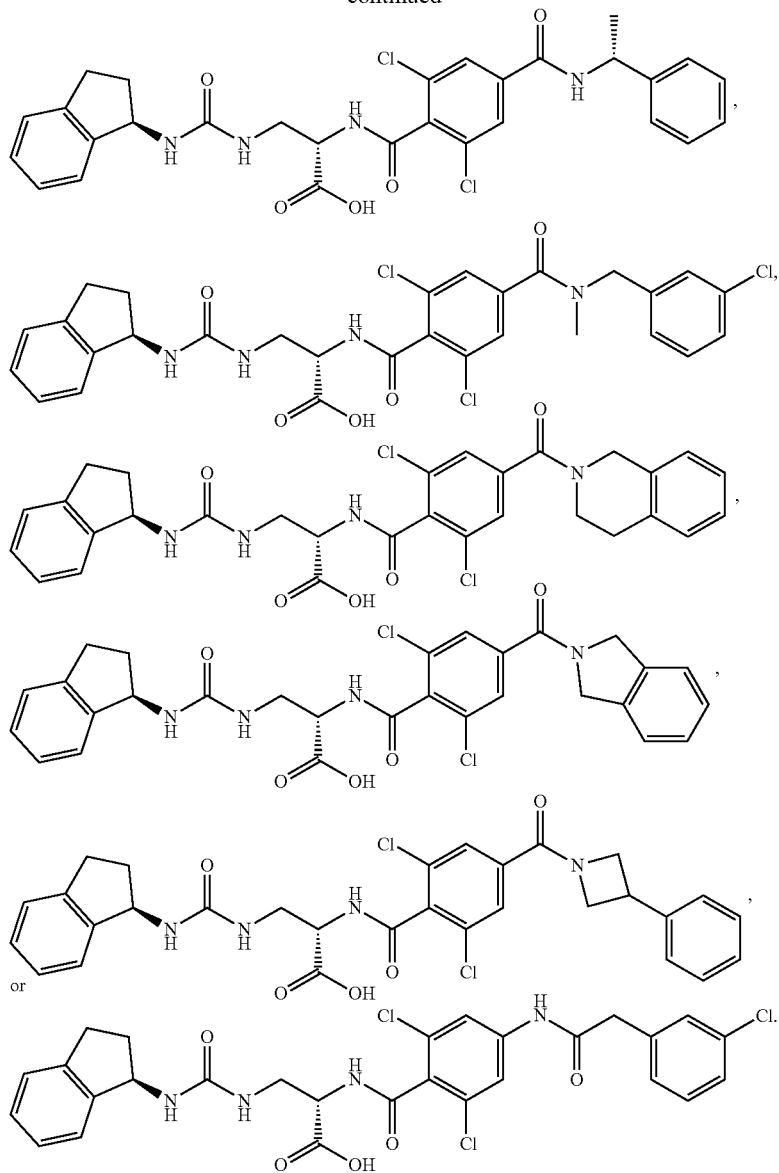

In an aspect is provided a compound, or a pharmaceutically acceptable salt thereof or a prodrug thereof, having the formula:

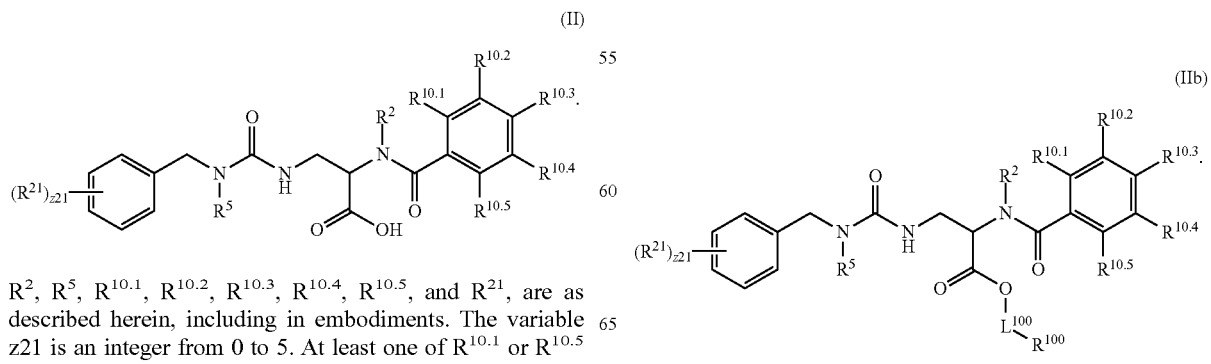

$R^2$, $R^5$, $R^{10.1}$, $R^{10.2}$, $R^{10.3}$, $R^{10.4}$, $R^{10.5}$, and $R^{21}$, are as described herein, including in embodiments. The variable z21 is an integer from 0 to 5. At least one of $R^{10.1}$ or $R^{10.5}$ is not hydrogen.

In an aspect is provided a compound, or a pharmaceutically acceptable salt thereof or a prodrug thereof, having the formula:

$R^2$, $R^5$, $R^{10.1}$, $R^{10.2}$, $R^{10.3}$, $R^{10.4}$, $R^{10.5}$, $R^{21}$, $R^{100}$, and $L^{100}$ are as described herein, including in embodiments. The variable z21 is an integer from 0 to 5. At least one of $R^{10.1}$ or $R^{10.5}$ is not hydrogen.

In embodiments, the compound has the formula

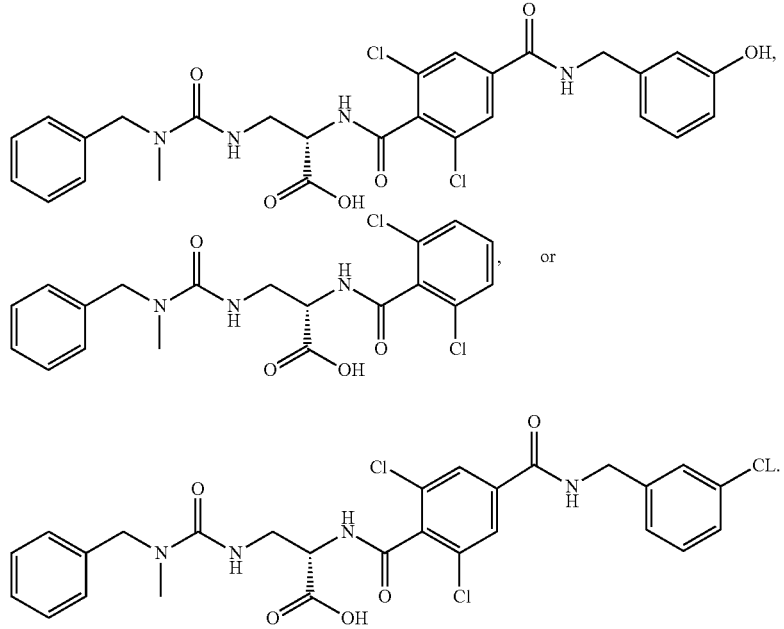

In an aspect is provided a compound, or a pharmaceutically acceptable salt thereof or a prodrug thereof, having the formula:

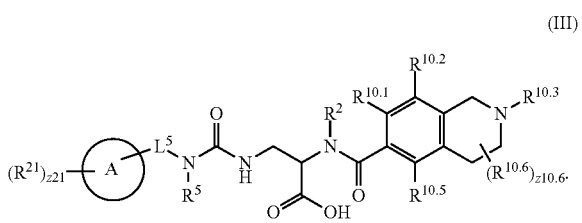

(III)

Ring A, $R^2$, $R^5$, $L^5$, $R^{10.1}$, $R^{10.2}$, $R^{10.3}$, $R^{10.5}$, $R^{21}$, and z21 are as described herein, including in embodiments. At least one of $R^{10.1}$ or $R^{10.5}$ is not hydrogen.

$R^{10.6}$ is independently oxo, halogen, $-CX^{10.6}_3$, $-CHX^{10.6}_2$, $-CH_2X^{10.6}$, $-OCX^{10.6}_3$, $-OCH_2X^{10.6}$, $-OCHX^{10.6}_2$, $-CN$, $-SO_{v10.6}R^{10.6D}$, $SO_{v10.6}NR^{10.6A}R^{10.6B}$, $-NHC(O)NR^{10.6A}R^{10.6B}$, $-N(O)_{m10.6}$, $-NR^{10.6A}R^{10.6B}$, $-C(O)R^{10.6C}$, $-C(O)OR^{10.6C}$, $-C(O)NR^{10.6A}R^{10.6B}$, $-OR^{10.6D}$, $-SR^{10.6D}$, $-NR^{10.6A}SO_2R^{10.6D}$, $-NR^{10.6A}C(O)R^{10.6C}$, $NR^{10.6A}C(O)OR^{10.6C}$, $-NR^{10.6A}OR^{10.6C}$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$R^{10.6A}$, $R^{10.6B}$, $R^{10.6C}$, and $R^{10.6D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, or 2 to 3 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); $R^{10.6A}$ and $R^{10.6B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

The variable n10.6 is an integer from 0 to 4.

The variables m10.6 and v10.6 are independently 1 or 2.

$X^{10.6}$ is independently $-F$, $-Cl$, $-Br$, or $-I$.

The variable z10.6 is an integer from 0 to 6.

In embodiments, the compound has the formula:

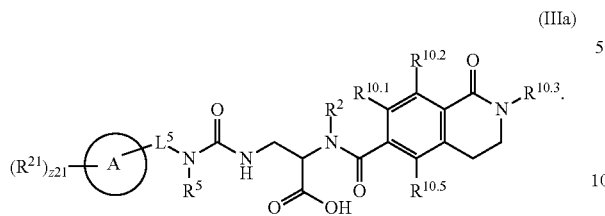
(IIIa)

Ring A, $R^2$, $R^5$, $L^5$, $R^{10.1}$, $R^{10.2}$, $R^{10.3}$, $R^{10.5}$, $R^{21}$, and z21 are as described herein, including in embodiments.

In an aspect is provided a compound, or a pharmaceutically acceptable salt thereof or a prodrug thereof, having the formula:

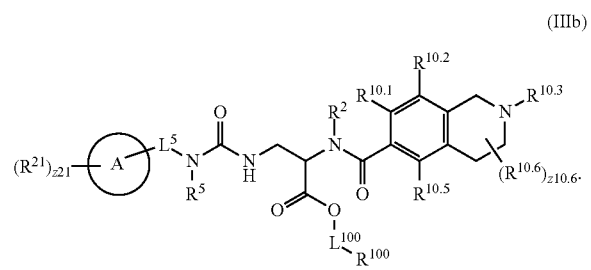
(IIIb)

Ring A, $R^2$, $R^5$, $L^5$, $R^{10.1}$, $R^{10.2}$, $R^{10.3}$, $R^{10.5}$, $R^{10.6}$, $R^{21}$, $R^{100}$, $L^{100}$, z10.6, and z21 are as described herein, including in embodiments.

In embodiments, $R^{10.3}$ is hydrogen, —C(O)$R^{10.3C}$, —SO$_{n10.3}$$R^{10.3D}$, or -$L^{10.3}$-$R^{23}$; $R^{10.3C}$, $R^{10.3D}$, n10.3, $L^{10.3}$, and $R^{23}$ are as described herein, including in embodiments. In embodiments, $R^{10.3}$ is hydrogen, —C(O)$R^{10.3C}$, or -$L^{10.3}$-$R^{23}$; $R^{10.3C}$, $L^{10.3}$, and $R^{23}$ are as described herein, including in embodiments. In embodiments, $R^{10.3}$ is hydrogen. In embodiments, $R^{10.3}$ is —C(O)$R^{10.3C}$; $R^{10.3C}$ is as described herein, including in embodiments. In embodiments, $R^{10.3}$ is —SO$_{n10.3}$$R^{10.3D}$; $R^{10.3D}$ and n10.3 are as described herein, including in embodiments. In embodiments, $R^{10.3}$ is —SO$_2$$R^{10.3D}$; $R^{10.3D}$ is as described herein, including in embodiments. In embodiments, $R^{10.3}$ is -$L^{10.3}$-$R^{23}$; $L^{10.3}$ and $R^{23}$ are as described herein, including in embodiments.

In embodiments, $R^{10.3C}$ is substituted or unsubstituted $C_1$-$C_4$ alkyl or substituted or unsubstituted phenyl. In embodiments, $R^{10.3C}$ is substituted or unsubstituted $C_1$-$C_4$ alkyl. In embodiments, $R^{10.3C}$ is unsubstituted methyl. In embodiments, $R^{10.3C}$ is unsubstituted ethyl. In embodiments, $R^{10.3C}$ is unsubstituted propyl. In embodiments, $R^{10.3C}$ is unsubstituted n-propyl. In embodiments, $R^{10.3C}$ is unsubstituted isopropyl. In embodiments, $R^{10.3C}$ is unsubstituted butyl. In embodiments, $R^{10.3C}$ is unsubstituted n-butyl. In embodiments, $R^{10.3C}$ is unsubstituted tert-butyl. In embodiments, $R^{10.3C}$ is substituted or unsubstituted phenyl. In embodiments, $R^{10.3C}$ is halogen-substituted phenyl. In embodiments, $R^{10.3C}$ is chloro-substituted phenyl. In embodiments, $R^{10.3C}$ is

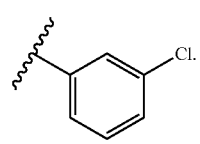 [SMILES: *c1cccc(Cl)c1]

In embodiments, $R^{10.3C}$ is

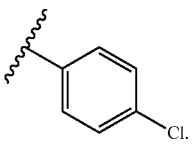 [SMILES: *c1ccc(Cl)cc1]

In embodiments, $R^{10.3C}$ is unsubstituted phenyl.

In embodiments, $R^{10.3D}$ is substituted or unsubstituted $C_1$-$C_4$ alkyl or substituted or unsubstituted phenyl. In embodiments, $R^{10.3D}$ is substituted or unsubstituted $C_1$-$C_4$ alkyl. In embodiments, $R^{10.3D}$ is unsubstituted methyl. In embodiments, $R^{10.3D}$ is unsubstituted ethyl. In embodiments, $R^{10.3D}$ is unsubstituted propyl. In embodiments, $R^{10.3D}$ is unsubstituted n-propyl. In embodiments, $R^{10.3D}$ is unsubstituted isopropyl. In embodiments, $R^{10.3D}$ is unsubstituted butyl. In embodiments, $R^{10.3D}$ is unsubstituted n-butyl. In embodiments, $R^{10.3D}$ is unsubstituted tert-butyl. In embodiments, $R^{10.3D}$ is substituted or unsubstituted phenyl. In embodiments, $R^{10.3D}$ is unsubstituted phenyl.

In embodiments, $L^{10.3}$ is —C(O)—, —S(O)$_2$—, or unsubstituted $C_1$-$C_4$ alkylene. In embodiments, $L^{10.3}$ is —C(O)—. In embodiments, $L^{10.3}$ is —S(O)$_2$—. In embodiments, $L^{10.3}$ is unsubstituted methylene. In embodiments, $L^{10.3}$ is unsubstituted alkynylene. In embodiments, $L^{10.3}$ is

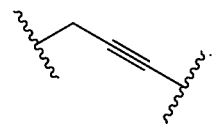 [SMILES: *C#CC*]

In embodiments, $L^{10.3}$ is —C(O)—, —S(O)$_2$—, or unsubstituted methylene. In embodiments, $L^{10.3}$ is —C(O)—. In embodiments, $L^{10.3}$ is —S(O)$_2$—. In embodiments, $L^{10.3}$ is unsubstituted methylene.

In embodiments, $R^{23}$ is

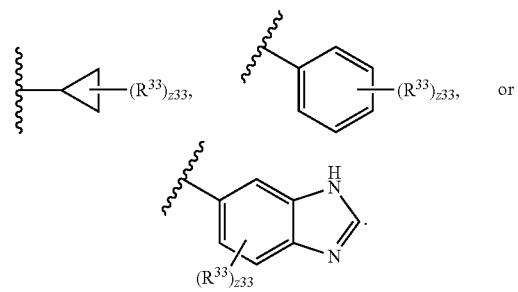

The symbol z33 is an integer from 0 to 5.

In embodiments, $R^{23}$ is

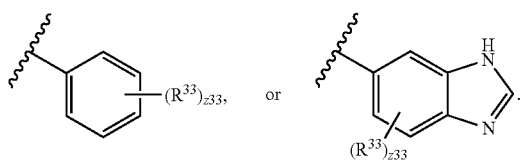

The symbol z33 is an integer from 0 to 5.

In embodiments, $R^{23}$ is

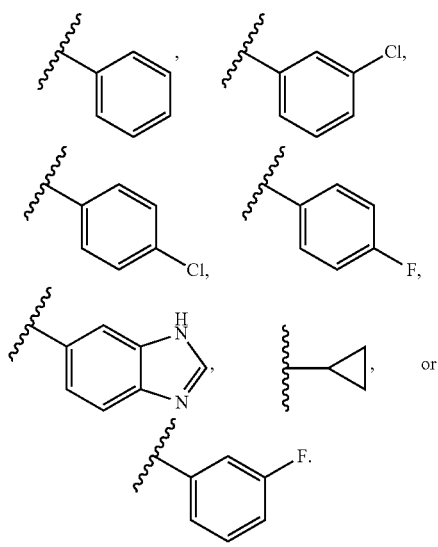

In embodiments, $R^{23}$ is

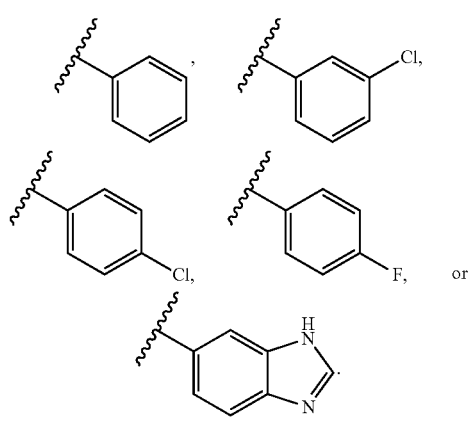

In embodiments, a substituted $R^{10.6}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.6}$ is substituted with a plurality of groups selected from substituent groups, size-limited substituent groups, and lower substituent groups; each substituent group, size-limited substituent group, and/or lower substituent group may optionally be different. In embodiments, when $R^{10.6}$ is substituted, it is substituted with at least one substituent group. In embodiments, when $R^{10.6}$ is substituted, it is substituted with at least one size-limited substituent group. In embodiments, when $R^{10.6}$ is substituted, it is substituted with at least one lower substituent group.

In embodiments, a substituted $R^{10.6A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.6A}$ is substituted with a plurality of groups selected from substituent groups, size-limited substituent groups, and lower substituent groups; each substituent group, size-limited substituent group, and/or lower substituent group may optionally be different. In embodiments, when $R^{10.6A}$ is substituted, it is substituted with at least one substituent group. In embodiments, when $R^{10.6A}$ is substituted, it is substituted with at least one size-limited substituent group. In embodiments, when $R^{10.6A}$ is substituted, it is substituted with at least one lower substituent group.

In embodiments, a substituted $R^{10.6B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.6B}$ is substituted with a plurality of groups selected from substituent groups, size-limited substituent groups, and lower substituent groups; each substituent group, size-limited substituent group, and/or lower substituent group may optionally be different. In embodiments, when $R^{10.6B}$ is substituted, it is substituted with at least one substituent group. In embodiments, when $R^{10.6B}$ is substituted, it is substituted with at least one size-limited substituent group. In embodiments, when $R^{10.6B}$ is substituted, it is substituted with at least one lower substituent group.

In embodiments, a substituted ring formed when $R^{10.6A}$ and $R^{10.6B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{10.6A}$ and $R^{10.6B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{10.6A}$ and $R^{10.6B}$ substituents bonded to the same nitrogen atom are joined is substituted, it is substituted with at least one substituent group. In embodiments, when the substituted ring formed when $R^{10.6A}$ and $R^{10.6B}$ substituents bonded to the same nitrogen atom are joined is substituted, it is substituted with at least one size-limited substituent group. In embodiments, when the substituted ring formed when $R^{10.6A}$ and $R^{10.6B}$ substituents bonded to the same nitrogen atom are joined is substituted, it is substituted with at least one lower substituent group.

In embodiments, a substituted $R^{10.6C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.6C}$ is substituted with a plurality of groups selected from substituent groups, size-limited substituent groups, and lower substituent groups; each substituent group, size-limited substituent group, and/or lower substituent group may optionally be different. In embodiments, when $R^{10.6C}$ is substituted, it is substituted with at least one substituent group. In embodiments, when $R^{10.6C}$ is substituted, it is substituted with at least one size-limited substituent group. In embodiments, when $R^{10.6C}$ is substituted, it is substituted with at least one lower substituent group.

In embodiments, a substituted $R^{10.6D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10.6D}$ is substituted with a plurality of groups selected from substituent groups, size-limited substituent groups, and lower substituent groups; each substituent group, size-limited substituent group, and/or lower substituent group may optionally be different. In embodiments, when $R^{10.6D}$ is substituted, it is substituted with at least one substituent group. In embodiments, when $R^{10.6D}$ is substituted, it is substituted with at least one size-limited substituent group. In embodiments, when $R^{10.6D}$ is substituted, it is substituted with at least one lower substituent group.

In embodiments, $R^{10.6}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, or 2 to 3 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, $R^{10.6}$ is independently oxo.

In embodiments, z10.6 is 0. In embodiments, z10.6 is 1. In embodiments, z10.6 is 2. In embodiments, z10.6 is 3. In embodiments, z10.6 is 4. In embodiments, z10.6 is 5. In embodiments, z10.6 is 6.

In embodiments, the compound has the formula

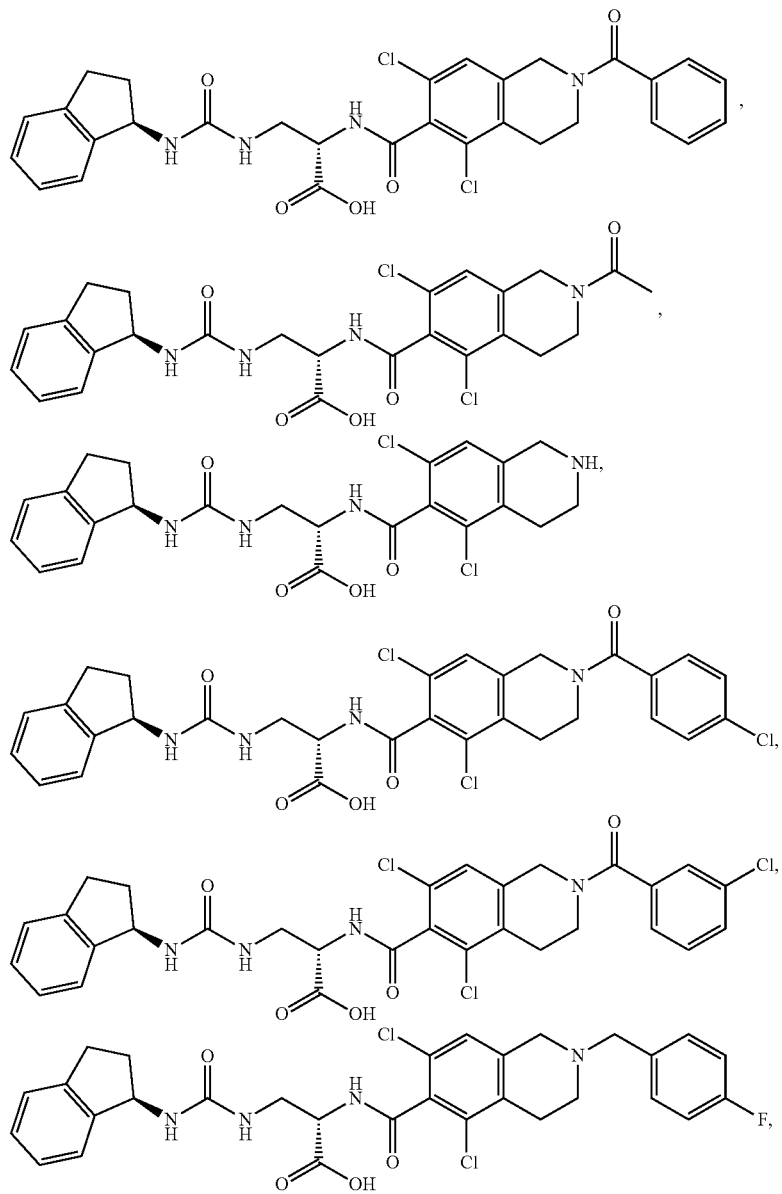

-continued
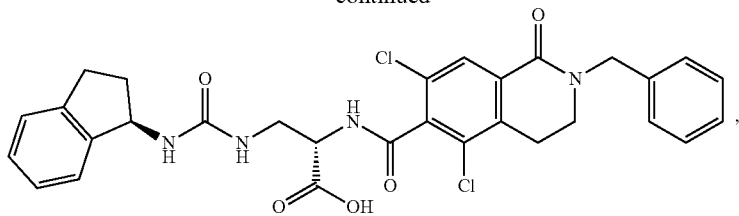,
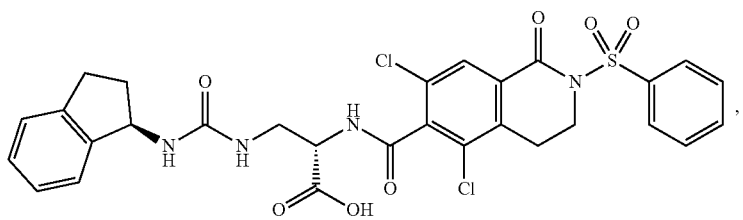,
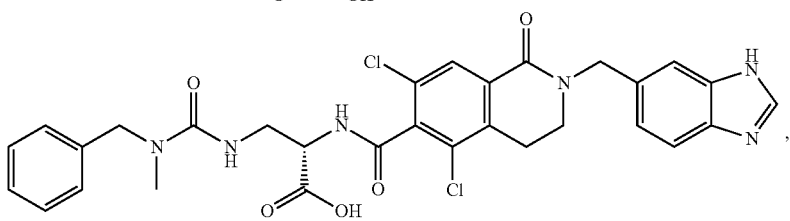,
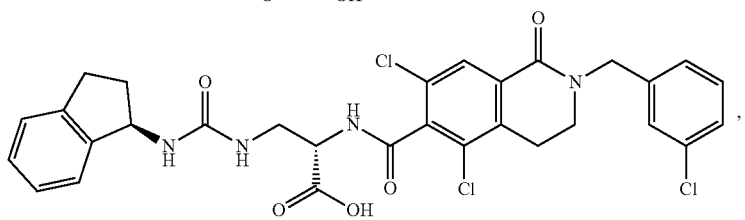,
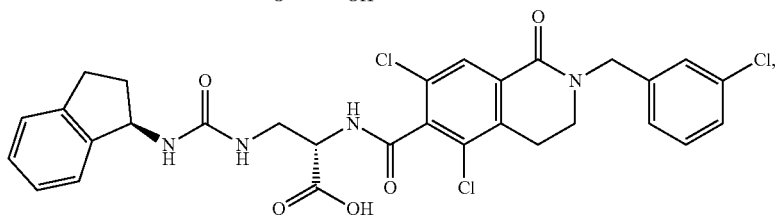,
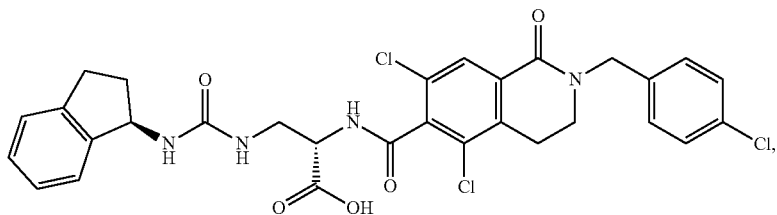,
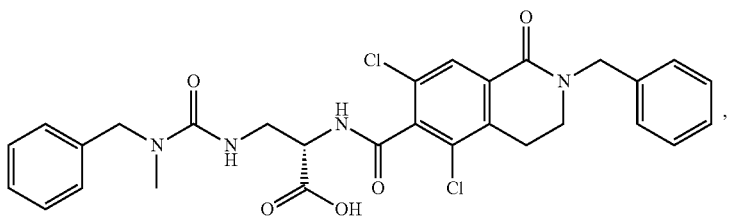,
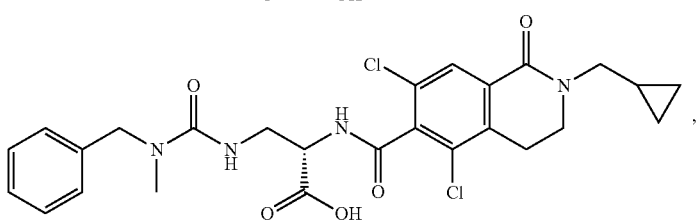,

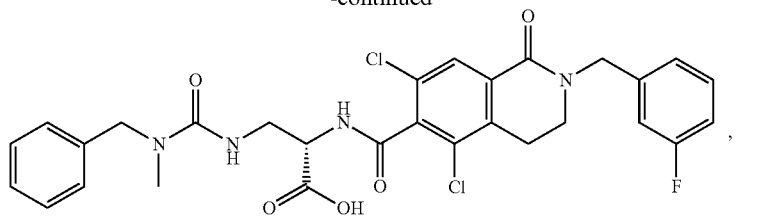
,
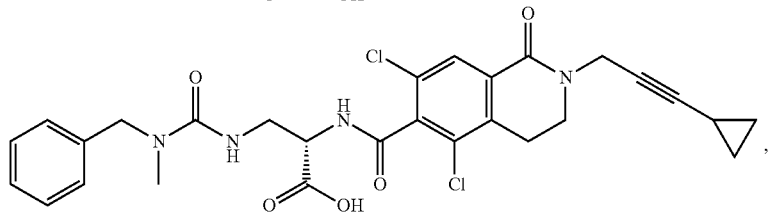
or
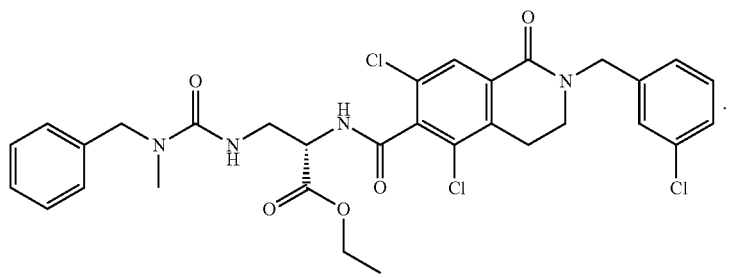
.
In embodiments, the compound has the formula
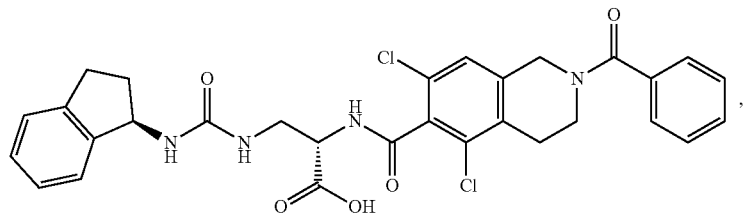
,
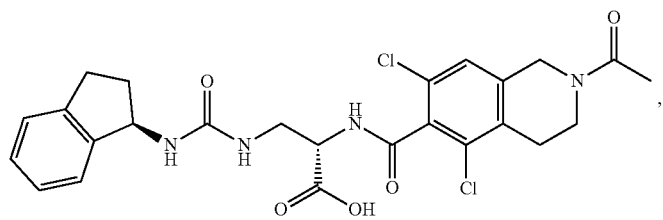
,
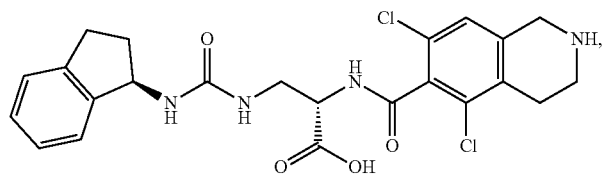
,
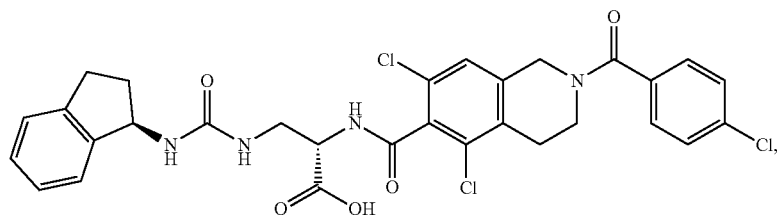
, -continued
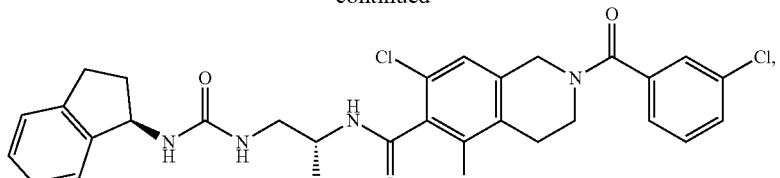
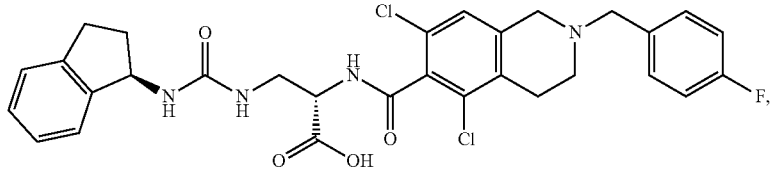
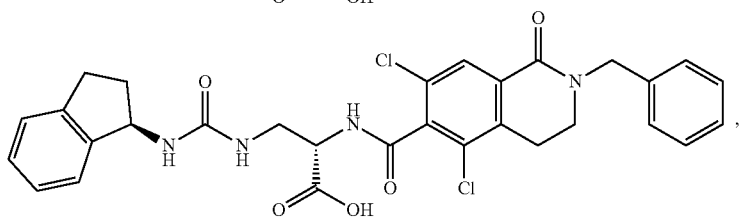
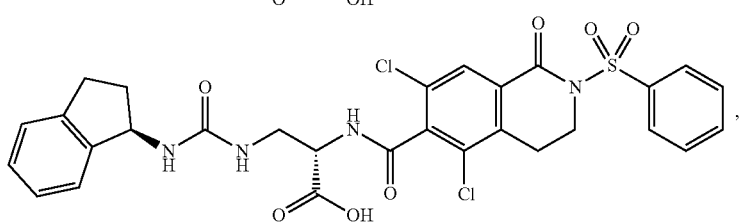
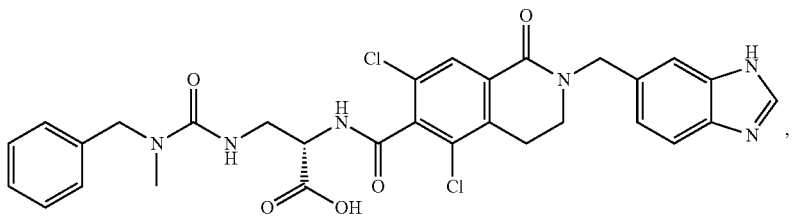
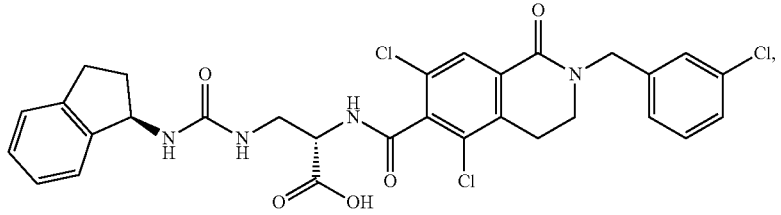
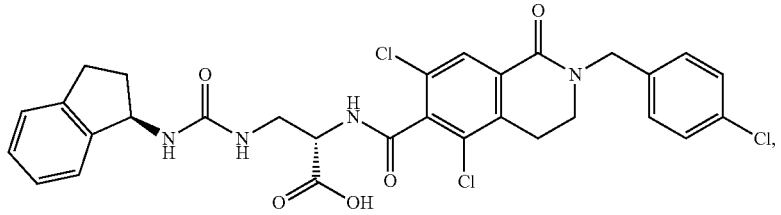
or
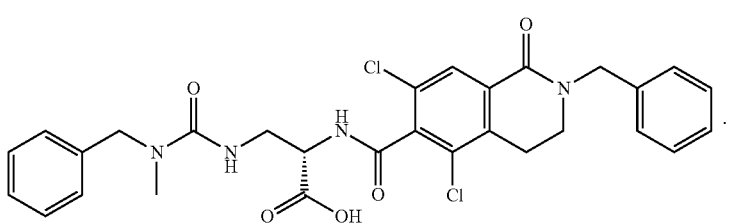

In an aspect is provided a compound, or a pharmaceutically acceptable salt thereof or a prodrug thereof, having the formula:

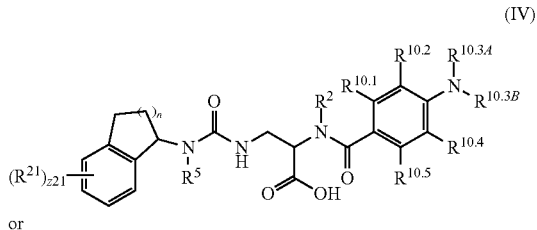

(IV)

or

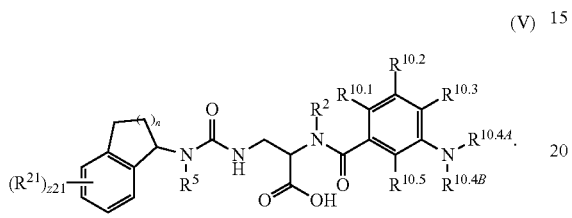

(V)

$R^2$, $R^5$, $R^{10.1}$, $R^{10.3A}$, $R^{10.3B}$, $R^{10.4A}$, $R^{10.4B}$, $R^{10.5}$ and $R^{21}$ are as described herein, including in embodiments. $R^{10.2}$, $R^{10.3}$ and $R^{10.4}$ are independently hydrogen, halogen, or —$CF_3$. The variable z21 is an integer from 0 to 9. The variable n is an integer from 0 to 3. At least one of $R^{10.1}$ or $R^{10.5}$ is not hydrogen.

In embodiments, the compound has the formula:

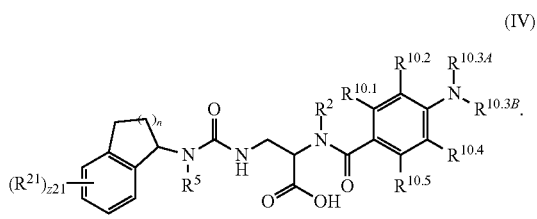

(IV)

$R^2$, $R^5$, $R^{10.1}$, $R^{10.2}$, $R^{10.3A}$, $R^{10.3B}$, $R^{10.4}$, $R^{10.5}$, $R^{21}$, z21, and n are as described herein, including in embodiments.

In embodiments, the compound has the formula:

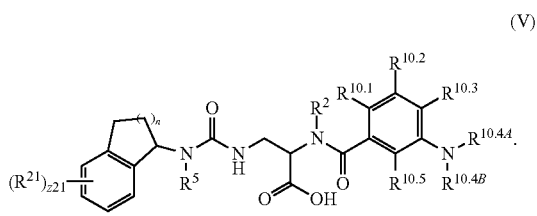

(V)

$R^2$, $R^5$, $R^{10.1}$, $R^{10.2}$, $R^{10.3}$, $R^{10.4A}$, $R^{10.4B}$, $R^{10.5}$, $R^{21}$, z21, and n are as described herein, including in embodiments.

In embodiments, $R^{10.2}$, $R^{10.3}$, and $R^{10.4}$ are independently deuterium, halogen, or —$CF_3$.

In embodiments, $R^{10.2}$ is deuterium, halogen, or —$CF_3$. In embodiments, $R^{10.2}$ is deuterium. In embodiments, $R^{10.2}$ is halogen. In embodiments, $R^{10.2}$ is —F. In embodiments, $R^{10.2}$ is —Cl. In embodiments, $R^{10.2}$ is —Br. In embodiments, $R^{10.2}$ is —I. In embodiments, $R^{10.2}$ is —$CF_3$.

In embodiments, $R^{10.3}$ is deuterium, halogen, or —$CF_3$. In embodiments, $R^{10}3$ is deuterium. In embodiments, $R^{10.3}$ is halogen. In embodiments, $R^{10.3}$ is —F. In embodiments, $R^{10.3}$ is —Cl. In embodiments, $R^{10.3}$ is —Br. In embodiments, $R^{10.3}$ is —I. In embodiments, $R^{10.3}$ is —$CF_3$.

In embodiments, $R^{10.4}$ is deuterium, halogen, or —$CF_3$. In embodiments, $R^{10.4}$ is deuterium. In embodiments, $R^{10.4}$ is halogen. In embodiments, $R^{10.4}$ is —F. In embodiments, $R^{10.4}$ is —Cl. In embodiments, $R^{10.4}$ is —Br. In embodiments, $R^{10.4}$ is —I. In embodiments, $R^{10.4}$ is —$CF_3$.

In embodiments, n is 0. In embodiments, n is 1. In embodiments, n is 2. In embodiments, n is 3.

In embodiments, the compound has the formula:

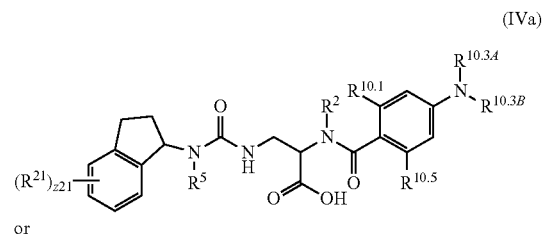

(IVa)

or

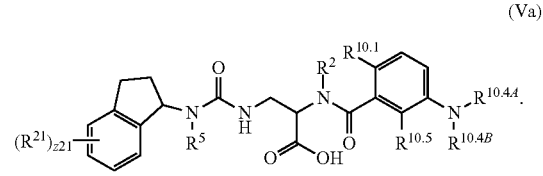

(Va)

$R^2$, $R^5$, $R^{10.1}$, $R^{10.3B}$, $R^{10.3B}$, $R^{10.4A}$, $R^{10.4B}$, $R^{10.5}$, $R^{21}$, and z21 are as described herein, including in embodiments.

In an aspect is provided a compound, or a pharmaceutically acceptable salt thereof or a prodrug thereof, having the formula:

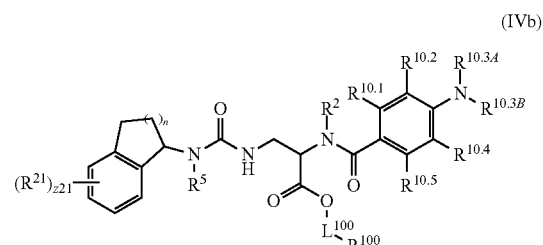

(IVb)

or

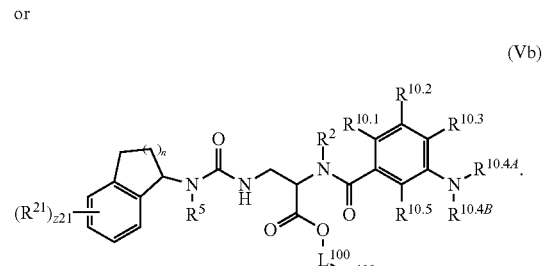

(Vb)

$R^2$, $R^5$, $R^{10.1}$, $R^{10.3A}$, $R^{10.3B}$, $R^{10.4A}$, $R^{10.4B}$, $R^{10.5}$, $R^{21}$, $R^{100}$, and $L^{100}$ are as described herein, including in embodiments. $R^{10.2}$, $R^{10.3}$, and $R^{10.4}$ are independently hydrogen, halogen, or —$CF_3$. The variable z21 is an integer from 0 to 9. The variable n is an integer from 0 to 3. At least one of $R^{10.1}$ or $R^{10.5}$ is not hydrogen.

In embodiments, $R^{10.3A}$, and $R^{10.3B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

In embodiments, $R^{10.3A}$ is hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl. In embodiments, $R^{10.3A}$, is hydrogen, $R^{33}$-substituted or unsubstituted $C_1$-$C_5$ alkyl, $R^{33}$-substituted or unsubstituted 2 to 5 membered heteroalkyl, $R^{33}$-substituted or unsubstituted $C_6$-$C_{10}$ aryl, or $R^{33}$-substituted or unsubstituted 5 to 10 membered heteroaryl; $R^{33}$ is as described herein, including in embodiments. In embodiments, $R^{10.3A}$, is hydrogen. In embodiments, $R^{10.3A}$, is $R^{33}$-substituted or unsubstituted $C_1$-$C_5$ alkyl. In embodiments, $R^{10.3A}$, is $R^{33}$-substituted methyl. In embodiments, $R^{10.3A}$, is an unsubstituted methyl. In embodiments, $R^{10.3A}$ is $R^{33}$-substituted ethyl. In embodiments, $R^{10.3A}$ is an unsubstituted ethyl. In embodiments, $R^{10.3A}$ is $R^{33}$-substituted propyl. In embodiments, $R^{10.3A}$ is an unsubstituted propyl. In embodiments, $R^{10.3A}$ is $R^{33}$-substituted n-propyl. In embodiments, $R^{10.3A}$, is an unsubstituted n-propyl. In embodiments, $R^{10.3A}$ is $R^{33}$-substituted isopropyl. In embodiments, $R^{10.3A}$, is an unsubstituted isopropyl. In embodiments, $R^{10.3A}$, is $R^{33}$-substituted n-butyl. In embodiments, $R^{10.3A}$ is an unsubstituted n-butyl. In embodiments, $R^{10.3A}$ is $R^{33}$-substituted tert-butyl. In embodiments, $R^{10.3A}$ is an unsubstituted tert-butyl. In embodiments, $R^{10.3A}$, is $R^{33}$-substituted or unsubstituted 2 to 5 membered heteroalkyl. In embodiments, $R^{10.3A}$ is $R^{33}$-substituted or unsubstituted $C_6$-$C_{10}$ aryl. In embodiments, $R^{10.3A}$ is $R^{33}$-substituted or unsubstituted phenyl. In embodiments, $R^{10.3A}$, is $R^{33}$-substituted or unsubstituted 5 to 10 membered heteroaryl. In embodiments, $R^{10.3A}$, is unsubstituted 5 to 10 membered heteroaryl. In embodiments, $R^{10.3A}$ is unsubstituted quinazolinyl.

In embodiments, $R^{10.3B}$ is hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl. In embodiments, $R^{10.3B}$ is hydrogen, $R^{33}$-substituted or unsubstituted $C_1$-$C_5$ alkyl, $R^{33}$-substituted or unsubstituted 2 to 5 membered heteroalkyl, $R^{33}$-substituted or unsubstituted $C_6$-$C_{10}$ aryl, or $R^{33}$-substituted or unsubstituted 5 to 10 membered heteroaryl; $R^{33}$ is as described herein, including in embodiments. In embodiments, $R^{10.3B}$ is hydrogen. In embodiments, $R^{10.3B}$ is $R^{33}$-substituted or unsubstituted $C_1$-$C_5$ alkyl. In embodiments, $R^{10.3B}$ is $R^{33}$-substituted methyl. In embodiments, $R^{10.3B}$ is an unsubstituted methyl. In embodiments, $R^{10.3B}$ is $R^{33}$-substituted ethyl. In embodiments, $R^{10.3B}$ is an unsubstituted ethyl. In embodiments, $R^{10.3B}$ is $R^{33}$-substituted propyl. In embodiments, $R^{10.3B}$ is an unsubstituted propyl. In embodiments, $R^{10.3B}$ is $R^{33}$-substituted n-propyl. In embodiments, $R^{10.3B}$ is an unsubstituted n-propyl. In embodiments, $R^{10.3B}$ is R"-substituted isopropyl. In embodiments, $R^{10.3B}$ is an unsubstituted isopropyl. In embodiments, $R^{10.3B}$ is $R^{33}$-substituted n-butyl. In embodiments, $R^{10.3B}$ is an unsubstituted n-butyl. In embodiments, $R^{10.3B}$ is $R^{33}$-substituted tert-butyl. In embodiments, $R^{10.3B}$ is an unsubstituted tert-butyl. In embodiments, $R^{10.3B}$ is $R^{33}$-substituted or unsubstituted 2 to 5 membered heteroalkyl. In embodiments, $R^{10.3B}$ is $R^{33}$-substituted or unsubstituted $C_6$-$C_{10}$ aryl. In embodiments, $R^{10.3B}$ is $R^{33}$-substituted or unsubstituted phenyl. In embodiments, $R^{10.3B}$ is $R^{33}$-substituted or unsubstituted 5 to 10 membered heteroaryl. In embodiments, $R^{10.3B}$ is unsubstituted 5 to 10 membered heteroaryl. In embodiments, $R^{10.3B}$ is unsubstituted quinazolinyl.

In embodiments, $R^{33}$ is independently a substituted or unsubstituted $C_6$-$C_{10}$ aryl, or substituted or unsubstituted 5 to 10 membered heteroaryl. In embodiments, $R^{33}$ is independently a substituted or unsubstituted phenyl. In embodiments, $R^{33}$ is independently a substituted or unsubstituted naphthyl. In embodiments, $R^{33}$ is independently a substituted or unsubstituted 5 to 10 membered heteroaryl. In embodiments, $R^{33}$ is independently an unsubstituted 5 to 10 membered heteroaryl. In embodiments, $R^{33}$ is independently an unsubstituted quinazolinyl.

In embodiments,

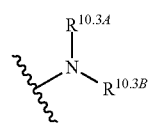

is —$NH_2$,

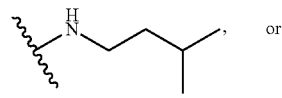

or

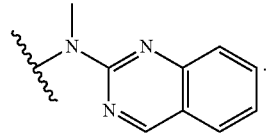

In embodiments,

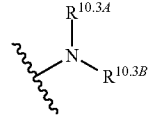

is —$NH_2$. In embodiments,

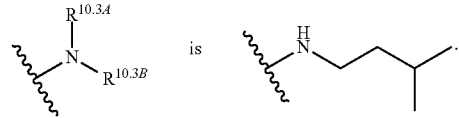

In embodiments,

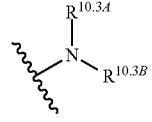

is

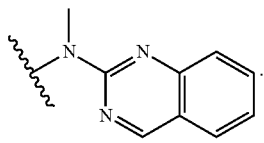 [SMILES: *N(C)c1ncc2ccccc2n1]

In embodiments, $R^{10.3A}$, and $R^{10.3B}$ substituents bonded to the same nitrogen atom are joined to form a substituted or unsubstituted heterocycloalkyl or substituted or unsubstituted heteroaryl. In embodiments, $R^{10.3A}$, and $R^{10.3B}$ substituents bonded to the same nitrogen atom are joined to form an $R^{33}$-substituted or unsubstituted heterocycloalkyl or $R^{33}$-substituted or unsubstituted heteroaryl; $R^{33}$ is as described herein, including in embodiments.

In embodiments,

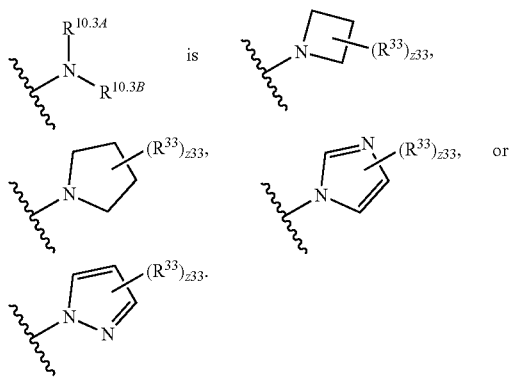

$R^{33}$ is as described herein, including in embodiments. The variable z33 is an integer from 0 to 8. In embodiments,

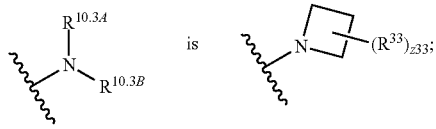

$R^{33}$ and z33 are as described herein, including in embodiments. In embodiments,

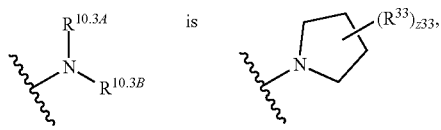

$R^{33}$ and z33 are as described herein, including in embodiments. In embodiments,

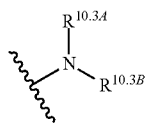

is

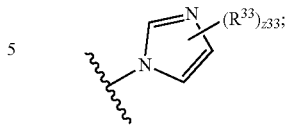

$R^{33}$ and z33 are as described herein, including in embodiments. In embodiments,

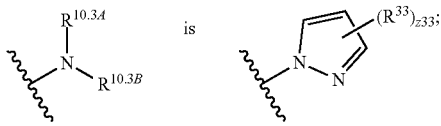

$R^{33}$ and z33 are as described herein, including in embodiments.

In embodiments, $R^{33}$ is independently a substituted or unsubstituted $C_6$-$C_{10}$ aryl. In embodiments, $R^{33}$ is independently a substituted or unsubstituted phenyl. In embodiments, $R^{33}$ is independently a substituted phenyl. In embodiments, $R^{33}$ is independently an unsubstituted phenyl.

In embodiments,

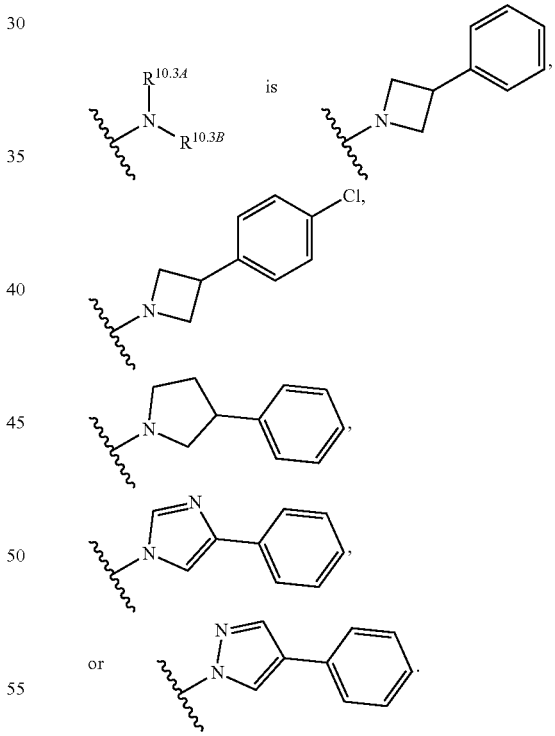

In embodiments,

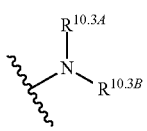

is

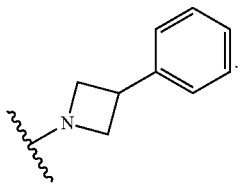 [SMILES: *N1CC(c2ccccc2)C1]

In embodiments,

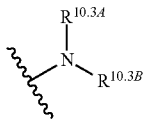

is

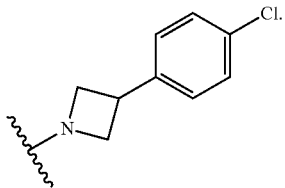 [SMILES: *N1CC(c2ccc(Cl)cc2)C1]

In embodiments,

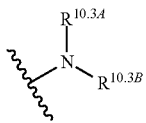

is

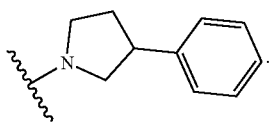

In embodiments,

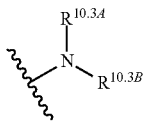

is

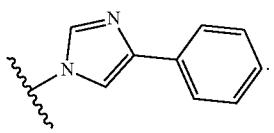 [SMILES: *n1cnc(-c2ccccc2)c1]

In embodiments,

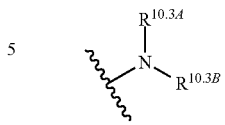

is

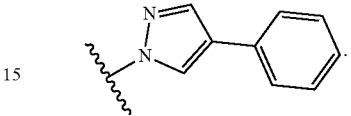

In embodiments, $R^{10.4A}$ and $R^{10.4B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

In embodiments, $R^{10.4A}$ is hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl. In embodiments, $R^{10.4A}$ is hydrogen, $R^{34}$-substituted or unsubstituted $C_1$-$C_5$ alkyl, $R^{34}$-substituted or unsubstituted 2 to 5 membered heteroalkyl, $R^{34}$-substituted or unsubstituted $C_6$-$C_{10}$ aryl, or $R^{34}$-substituted or unsubstituted 5 to 10 membered heteroaryl; $R^{34}$ is as described herein, including in embodiments. In embodiments, $R^{10.4A}$ is hydrogen. In embodiments, $R^{10.4A}$ is $R^{34}$-substituted or unsubstituted $C_1$-$C_5$ alkyl. In embodiments, $R^{10.4A}$ is $R^{34}$-substituted methyl. In embodiments, $R^{10.4A}$ is an unsubstituted methyl. In embodiments, $R^{10.4A}$ is $R^{34}$-substituted ethyl. In embodiments, $R^{10.4A}$ is an unsubstituted ethyl. In embodiments, $R^{10.4A}$ is $R^{34}$-substituted propyl. In embodiments, $R^{10.4A}$ is an unsubstituted propyl. In embodiments, $R^{10.4A}$ is $R^{34}$-substituted n-propyl. In embodiments, $R^{10.4A}$ is an unsubstituted n-propyl. In embodiments, $R^{10.4A}$ is $R^{34}$-substituted isopropyl. In embodiments, $R^{10.4A}$ is an unsubstituted isopropyl. In embodiments, $R^{10.4A}$ is $R^{34}$-substituted n-butyl. In embodiments, $R^{10.4A}$ is an unsubstituted n-butyl. In embodiments, $R^{10.4A}$ is $R^{34}$-substituted tert-butyl. In embodiments, $R^{10.4A}$ is an unsubstituted tert-butyl. In embodiments, $R^{10.4A}$ is $R^{34}$-substituted or unsubstituted 2 to 5 membered heteroalkyl. In embodiments, $R^{10.4A}$ is $R^{34}$-substituted or unsubstituted $C_6$-$C_{10}$ aryl. In embodiments, $R^{10.4A}$ is $R^{34}$-substituted or unsubstituted phenyl. In embodiments, $R^{10.4A}$ is $R^{34}$-substituted or unsubstituted 5 to 10 membered heteroaryl. In embodiments, $R^{10.4A}$ is unsubstituted 5 to 10 membered heteroaryl. In embodiments, $R^{10.4A}$ is unsubstituted quinazolinyl.

In embodiments, $R^{10.4B}$ is hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl. In embodiments, $R^{10.4B}$ is hydrogen, $R^{34}$-substituted or unsubstituted $C_1$-$C_5$ alkyl, $R^{34}$-substituted or unsubstituted 2 to 5 membered heteroalkyl, $R^{34}$-substituted or unsubstituted $C_6$-$C_{10}$ aryl, or $R^{34}$-substituted or unsubstituted 5 to 10 membered heteroaryl; $R^{34}$ is as described herein, including in embodiments. In embodiments, $R^{10.4B}$ is hydrogen. In embodiments, $R^{10.4B}$ is $R^{34}$-substituted or unsubstituted $C_1$-$C_5$ alkyl. In embodiments, $R^{10.4B}$ is $R^{34}$-substituted methyl. In embodiments, $R^{10.4B}$ is an unsubstituted methyl. In embodiments, $R^{10.4B}$ is $R^{34}$-substituted ethyl. In embodiments, $R^{10.4B}$ is an unsubstituted ethyl. In embodiments, $R^{10.4B}$ is $R^{34}$-substituted propyl. In embodiments, $R^{10.4B}$ is an unsubstituted propyl. In embodiments, $R^{10.4B}$ is $R^{34}$-substituted n-propyl. In embodiments, $R^{10.4B}$ is an unsubstituted n-propyl. In embodiments, $R^{10.4B}$ is $R^{34}$-substituted isopropyl. In embodiments, $R^{10.4B}$ is an unsubstituted isopropyl. In embodiments, $R^{10.4B}$ is $R^{34}$-substituted n-butyl. In embodiments, $R^{10.4B}$ is an unsubstituted n-butyl. In embodiments, $R^{10.4B}$ is $R^{34}$-substituted tert-butyl. In embodiments, $R^{10.4B}$ is an unsubstituted tert-butyl. In embodiments, $R^{10.4B}$ is $R^{34}$-substituted or unsubstituted 2 to 5 membered heteroalkyl. In embodiments, $R^{10.4B}$ is $R^{34}$-substituted or unsubstituted $C_6$-$C_{10}$ aryl. In embodiments, $R^{10.4B}$ is $R^{34}$-substituted or unsubstituted phenyl. In embodiments, $R^{10.4B}$ is $R^{34}$-substituted or unsubstituted 5 to 10 membered heteroaryl. In embodiments, $R^{10.4B}$ is unsubstituted 5 to 10 membered heteroaryl. In embodiments, $R^{10.4B}$ is unsubstituted quinazolinyl.

In embodiments, $R^{34}$ is independently a substituted or unsubstituted $C_6$-$C_{10}$ aryl, or substituted or unsubstituted 5 to 10 membered heteroaryl. In embodiments, $R^{34}$ is independently a substituted or unsubstituted phenyl. In embodiments, $R^{34}$ is independently a substituted or unsubstituted naphthyl. In embodiments, $R^{34}$ is independently a substituted or unsubstituted 5 to membered heteroaryl. In embodiments, $R^{34}$ is independently an unsubstituted 5 to 10 membered heteroaryl. In embodiments, $R^{34}$ is independently an unsubstituted quinazolinyl.

In embodiments,

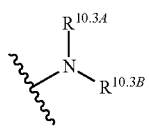

is —NH$_2$,

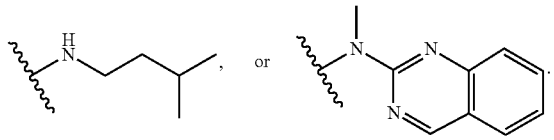

In embodiments,

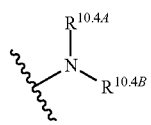

is —NH$_2$. In embodiments,

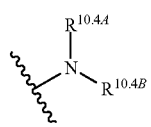

is

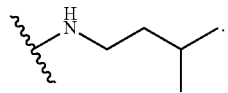 [SMILES: *NCCC(C)C]

In embodiments,

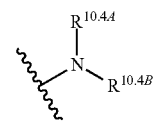

is

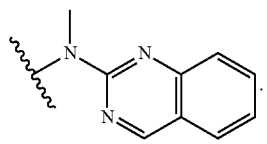 [SMILES: *N(C)c1ncc2ccccc2n1]

In embodiments, $R^{10.4A}$ and $R^{10.4B}$ substituents bonded to the same nitrogen atom are joined to form a substituted or unsubstituted heterocycloalkyl or substituted or unsubstituted heteroaryl. In embodiments, $R^{10.4A}$ and $R^{10.4B}$ substituents bonded to the same nitrogen atom are joined to form an $R^{34}$-substituted or unsubstituted heterocycloalkyl or $R^{34}$-substituted or unsubstituted heteroaryl; $R^{34}$ is as described herein, including in embodiments.

In embodiments,

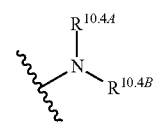

is

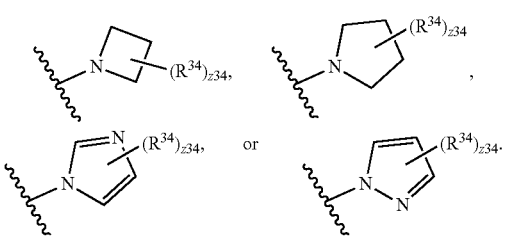

$R^{34}$ is as described herein, including in embodiments. The variable z34 is an integer from 0 to 8. In embodiments,

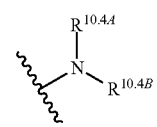

is

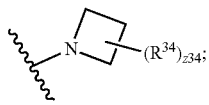

R³⁴ and z34 are as described herein, including in embodiments. In embodiments,

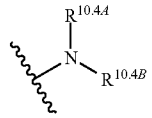

is

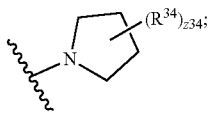

R³⁴ and z34 are as described herein, including in embodiments. In embodiments,

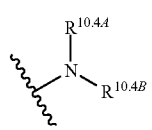

is

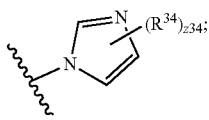

R³⁴ and z34 are as described herein, including in embodiments. In embodiments,

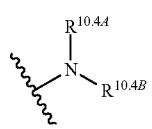

is

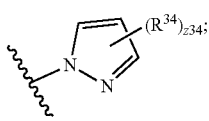

R³⁴ and z34 are as described herein, including in embodiments.

In embodiments, R³⁴ is independently a substituted or unsubstituted $C_6$-$C_{10}$ aryl. In embodiments, R³⁴ is independently a substituted or unsubstituted phenyl. In embodiments, R³⁴ is independently a substituted phenyl. In embodiments, R³⁴ is independently an unsubstituted phenyl.

In embodiments,

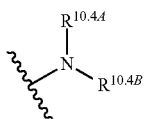

is

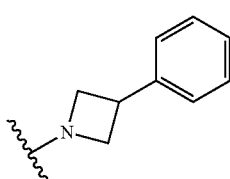

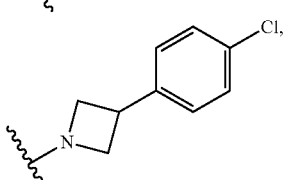

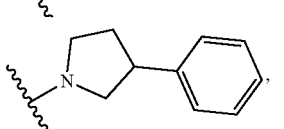

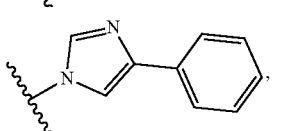

or

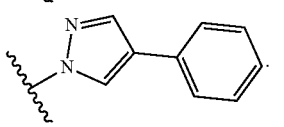

In embodiments,

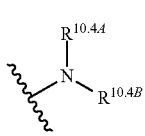

is

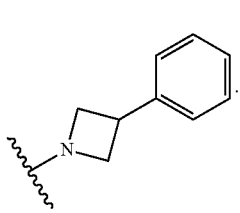 [SMILES: *N1CC(c2ccccc2)C1]

In embodiments,
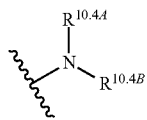
is
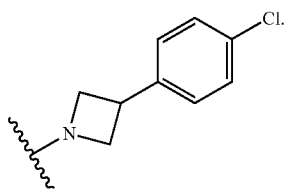
In embodiments,
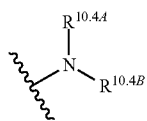
is
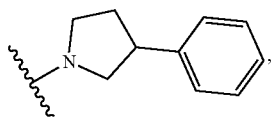 [SMILES: *N1CCC(c2ccccc2)C1]
In embodiments,
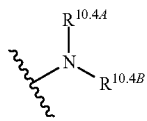
is
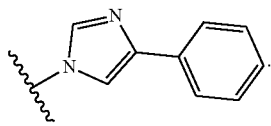 [SMILES: *n1cnc(-c2ccccc2)c1]
In embodiments,
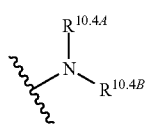
is
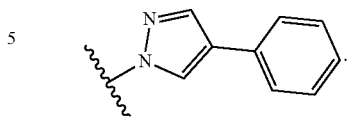
In embodiments, the compound has the formula
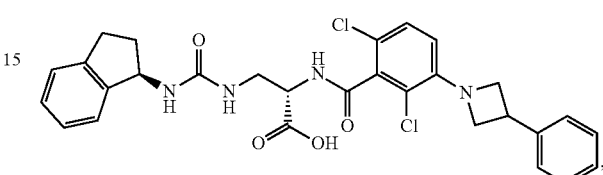
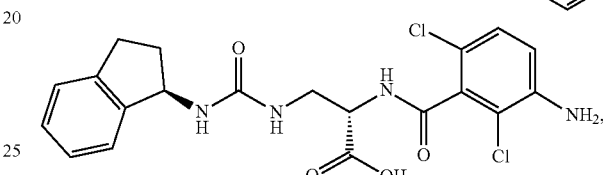
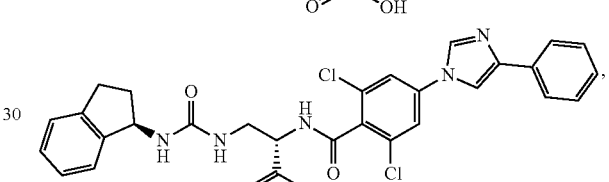
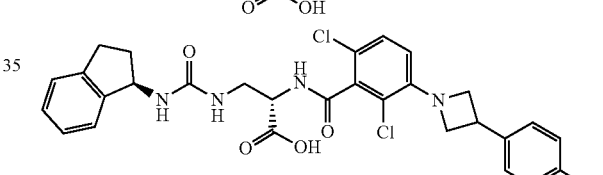
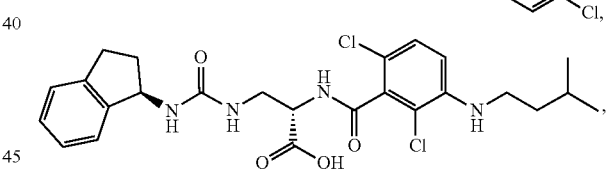
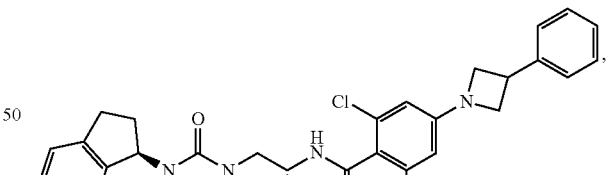
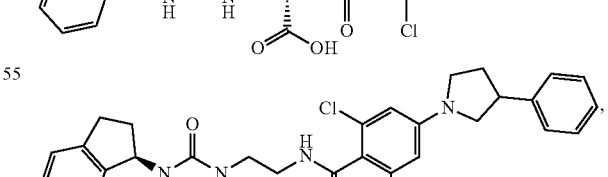
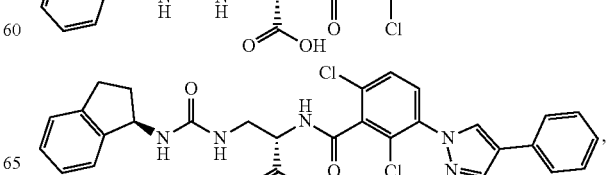

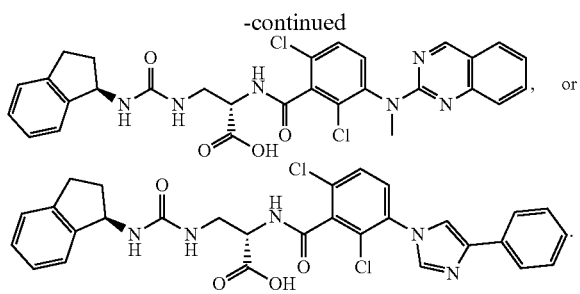
, or

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{10.1}$ is substituted, $R^{10.1}$ is substituted with one or more first substituent groups denoted by $R^{10.1.1}$ as explained in the definitions section above in the description of "first substituent group(s)". In embodiments, when an $R^{10.1.1}$ substituent group is substituted, the $R^{10.1.1}$ substituent group is substituted with one or more second substituent groups denoted by $R^{10.1.2}$ as explained in the definitions section above in the description of "first substituent group(s)". In embodiments, when an $R^{10.1.2}$ substituent group is substituted, the $R^{10.1.2}$ substituent group is substituted with one or more third substituent groups denoted by $R^{10.1.3}$ as explained in the definitions section above in the description of "first substituent group(s)". In the above embodiments, $R^{10.1}$, $R^{10.1}$, $R^{10.1.2}$, and $R^{10.1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.1}$, $R^{10.1}$, $R^{10.1.2}$, and $R^{10.1.3}$, respectively.

In embodiments, when $R^{10.1A}$ is substituted, $R^{10.1A}$ is substituted with one or more first substituent groups denoted by $R^{10.1A.1}$ as explained in the definitions section above in the description of "first substituent group(s)". In embodiments, when an $R^{10.1A.1}$ substituent group is substituted, the $R^{10.1A.1}$ substituent group is substituted with one or more second substituent groups denoted by $R^{10.1A.2}$ as explained in the definitions section above in the description of "first substituent group(s)". In embodiments, when an $R^{10.1A.2}$ substituent group is substituted, the $R^{10.1A.2}$ substituent group is substituted with one or more third substituent groups denoted by $R^{10.1A.3}$ as explained in the definitions section above in the description of "first substituent group(s)". In the above embodiments, $R^{10.1A}$, $R^{10.1A.1}$, $R^{10.1A.2}$, and $R^{10.1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.1A}$, $R^{10.1A.1}$, $R^{10.1A.2}$, and $R^{10.1A.3}$, respectively.

In embodiments, when $R^{10.1B}$ is substituted, $R^{10.1B}$ is substituted with one or more first substituent groups denoted by $R^{10.1B.1}$ as explained in the definitions section above in the description of "first substituent group(s)". In embodiments, when an $R^{10.1B.1}$ substituent group is substituted, the $R^{10.1B.1}$ substituent group is substituted with one or more second substituent groups denoted by $R^{10.1B.2}$ as explained in the definitions section above in the description of "first substituent group(s)". In embodiments, when an $R^{10.1B.2}$ substituent group is substituted, the $R^{10.1B.2}$ substituent group is substituted with one or more third substituent groups denoted by $R^{10.1B}0.3$ as explained in the definitions section above in the description of "first substituent group(s)". In the above embodiments, $R^{10.1B}$, $R^{10.1B.1}$, $R^{10.1B.2}$, and $R^{10.1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.1B}$, $R^{10.1B.1}$, $R^{10.1B.2}$, and $R^{10.1B.3}$, respectively.

In embodiments, when $R^{10.1A}$ and $R^{10.1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.1A.1}$ as explained in the definitions section above in the description of "first substituent group(s)". In embodiments, when an $R^{10.1A.1}$ substituent group is substituted, the $R^{10.1A.1}$ substituent group is substituted with one or more second substituent groups denoted by $R^{10.1A.2}$ as explained in the definitions section above in the description of "first substituent group(s)". In embodiments, when an $R^{10.1A.2}$ substituent group is substituted, the $R^{10.1A.2}$ substituent group is substituted with one or more third substituent groups denoted by $R^{10.1A.3}$ as explained in the definitions section above in the description of "first substituent group(s)". In the above embodiments, $R^{10.1A.1}$, $R^{10.1A.2}$, and $R^{10.1A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.1A.1}$, $R^{10.1A.2}$, and $R^{10.1A.3}$, respectively.

In embodiments, when $R^{10.1A}$ and $R^{10.1B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.1B.1}$ as explained in the definitions section above in the description of "first substituent group(s)". In embodiments, when an $R^{10.1B.1}$ substituent group is substituted, the $R^{10.1B.1}$ substituent group is substituted with one or more second substituent groups denoted by $R^{10.1B.2}$ as explained in the definitions section above in the description of "first substituent group(s)". In embodiments, when an $R^{10.1B.2}$ substituent group is substituted, the $R^{10.1B.2}$ substituent group is substituted with one or more third substituent groups denoted by $R^{10.1B.3}$ as explained in the definitions section above in the description of "first substituent group(s)". In the above embodiments, $R^{10.1B.1}$, $R^{10.1B.2}$, and $R^{10.1B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.1B.1}$, $R^{10.1B.2}$, and $R^{10.1B.3}$, respectively.

In embodiments, when $R^{10.1C}$ is substituted, $R^{10.1C}$ is substituted with one or more first substituent groups denoted by $R^{10.1C.1}$ as explained in the definitions section above in the description of "first substituent group(s)". In embodiments, when an $R^{10.1C.1}$ substituent group is substituted, the $R^{10.1C.1}$ substituent group is substituted with one or more second substituent groups denoted by $R^{10.1C.2}$ as explained in the definitions section above in the description of "first substituent group(s)". In embodiments, when an $R^{10.1C.2}$ substituent group is substituted, the $R^{10.1C.2}$ substituent group is substituted with one or more third substituent groups denoted by $R^{10.1C.3}$ as explained in the definitions section above in the description of "first substituent group(s)". In the above embodiments, $R^{10.1C}$, $R^{10.1C.1}$, $R^{10.1C.2}$, and $R^{10.1C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.1C}$, $R^{10.1C.1}$, $R^{10.1C.2}$, and $R^{10.1C.3}$, respectively.

In embodiments, when $R^{10.1D}$ is substituted, $R^{10.1D}$ is substituted with one or more first substituent groups denoted by $R^{10.1D.1}$ as explained in the definitions section above in the description of "first substituent group(s)". In embodiments, when an $R^{10.1D.1}$ substituent group is substituted, the $R^{10.1D.1}$ substituent group is substituted with one or more second substituent groups denoted by $R^{10.1D.2}$ as explained in the definitions section above in the description of "first substituent group(s)". In embodiments, when an $R^{10.1D.2}$ substituent group is substituted, the $R^{10.1D.2}$ substituent group is substituted with one or more third substituent groups denoted by $R^{10.1D.3}$ as explained in the definitions section above in the description of "first substituent group(s)". In the above embodiments, $R^{10.1D}$, $R^{10.1D.1}$, $R^{10.1D.2}$, and $R^{10.1D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.1D}$, $R^{10.1D.1}$, $R^{10.1D.2}$, and $R^{10.1D.3}$, respectively.

In embodiments, when $R^{10.2}$ is substituted, $R^{10.2}$ is substituted with one or more first substituent groups denoted by $R^{10.2.1}$ as explained in the definitions section above in the description of "first substituent group(s)". In embodiments, when an $R^{10.2.1}$ substituent group is substituted, the $R^{10.2.1}$ substituent group is substituted with one or more second substituent groups denoted by $R^{10.2.2}$ as explained in the definitions section above in the description of "first substituent group(s)". In embodiments, when an $R^{10.2.2}$ substituent group is substituted, the $R^{10.2.2}$ substituent group is substituted with one or more third substituent groups denoted by $R^{10.2.3}$ as explained in the definitions section above in the description of "first substituent group(s)". In the above embodiments, $R^{10.2}$, $R^{10.2.1}$, $R^{10.2.2}$, and $R^{10.2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.2}$, $R^{10.2.1}$, $R^{10.2.2}$, and $R^{10.2.3}$, respectively.

In embodiments, when $R^{10.2A}$ is substituted, $R^{10.2A}$ is substituted with one or more first substituent groups denoted by $R^{10.2A.1}$ as explained in the definitions section above in the description of "first substituent group(s)". In embodiments, when an $R^{10.2A.1}$ substituent group is substituted, the $R^{10.2A.1}$ substituent group is substituted with one or more second substituent groups denoted by $R^{10.2A.2}$ as explained in the definitions section above in the description of "first substituent group(s)". In embodiments, when an $R^{10.2A.2}$ substituent group is substituted, the $R^{10.2A.2}$ substituent group is substituted with one or more third substituent groups denoted by $R^{10.2A.3}$ as explained in the definitions section above in the description of "first substituent group(s)". In the above embodiments, $R^{10.2A}$, $R^{10.2A.1}$, $R^{10.2A.2}$, and $R^{10.2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.2A}$, $R^{10.2A.1}$, $R^{10.2A.2}$, and $R^{10.2A.3}$, respectively.

In embodiments, when $R^{10.2B}$ is substituted, $R^{10.2B}$ is substituted with one or more first substituent groups denoted by $R^{10.2B.1}$ as explained in the definitions section above in the description of "first substituent group(s)". In embodiments, when an $R^{10.2B.1}$ substituent group is substituted, the $R^{10.2B.1}$ substituent group is substituted with one or more second substituent groups denoted by $R^{10.2B.2}$ as explained in the definitions section above in the description of "first substituent group(s)". In embodiments, when an $R^{10.2B.2}$ substituent group is substituted, the $R^{10.2B.2}$ substituent group is substituted with one or more third substituent groups denoted by $R^{10.2B.3}$ as explained in the definitions section above in the description of "first substituent group(s)". In the above embodiments, $R^{10.2B}$, $R^{10.2B.1}$, $R^{10.2B.2}$, and $R^{10.2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.2B}$, $R^{10.2B.1}$, $R^{10.2B.2}$, and $R^{10.2B.3}$, respectively.

In embodiments, when $R^{10.2A}$ and $R^{10.2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.2A.1}$ as explained in the definitions section above in the description of "first substituent group(s)". In embodiments, when an $R^{10.2A.1}$ substituent group is substituted, the $R^{10.2A.1}$ substituent group is substituted with one or more second substituent groups denoted by $R^{10.2A.2}$ as explained in the definitions section above in the description of "first substituent group(s)". In embodiments, when an $R^{10.2A.2}$ substituent group is substituted, the $R^{10.2A.2}$ substituent group is substituted with one or more third substituent groups denoted by $R^{10.2A.3}$ as explained in the definitions section above in the description of "first substituent group(s)". In the above embodiments, $R^{10.2A.1}$, $R^{10.2A.2}$, and $R^{10.2A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.2A.1}$, $R^{10.2A.2}$, and $R^{10.2A.3}$, respectively.

In embodiments, when $R^{10.2A}$ and $R^{10.2B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.2B.1}$ as explained in the definitions section above in the description of "first substituent group(s)". In embodiments, when an $R^{10.2B.1}$ substituent group is substituted, the $R^{10.2B.1}$ substituent group is substituted with one or more second substituent groups denoted by $R^{10.2B.2}$ as explained in the definitions section above in the description of "first substituent group(s)". In embodiments, when an $R^{10.2B.2}$ substituent group is substituted, the $R^{10.2B.2}$ substituent group is substituted with one or more third substituent groups denoted by $R^{10.2B.3}$ as explained in the definitions section above in the description of "first substituent group(s)". In the above embodiments, $R^{10.2B.1}$, $R^{10.2B.2}$, and $R^{10.2B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.2B.1}$, $R^{10.2B.2}$, and $R^{10.2B.3}$, respectively.

In embodiments, when $R^{10.2C}$ is substituted, $R^{10.2C}$ is substituted with one or more first substituent groups denoted by $R^{10.2C.1}$ as explained in the definitions section above in the description of "first substituent group(s)". In embodiments, when an $R^{10.2C.1}$ substituent group is substituted, the $R^{10.2C.1}$ substituent group is substituted with one or more second substituent groups denoted by $R^{10.2C.2}$ as explained in the definitions section above in the description of "first substituent group(s)". In embodiments, when an $R^{10.2C.2}$ substituent group is substituted, the $R^{10.2C.2}$ substituent group is substituted with one or more third substituent groups denoted by $R^{10.2C.3}$ as explained in the definitions section above in the description of "first substituent group(s)". In the above embodiments, $R^{10.2C}$, $R^{10.2C.1}$, $R^{10.2C.2}$, and $R^{10.2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.2C}$, $R^{10.2C.1}$, $R^{10.2C.2}$, and $R^{10.2C.3}$, respectively.

In embodiments, when $R^{10.2D}$, is substituted, $R^{10.2D}$, is substituted with one or more first substituent groups denoted by $R^{10.2D.1}$ as explained in the definitions section above in the description of "first substituent group(s)". In embodiments, when an $R^{10.2D.1}$ substituent group is substituted, the $R^{10.2D.1}$ substituent group is substituted with one or more second substituent groups denoted by $R^{10.2D.2}$ as explained in the definitions section above in the description of "first substituent group(s)". In embodiments, when an $R^{10.2D.2}$ substituent group is substituted, the $R^{10.2D.2}$ substituent group is substituted with one or more third substituent groups denoted by $R^{10.2D.3}$ as explained in the definitions section above in the description of "first substituent group(s)". In the above embodiments, $R^{10.2D}$, $R^{10.2D.1}$, $R^{10.2D.2}$, and $R^{10.2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.2D}$, $R^{10.2D.1}$, $R^{10.2D.2}$, and $R^{10.2D.3}$, respectively.

In embodiments, when $R^{10.3}$ is substituted, $R^{10.3}$ is substituted with one or more first substituent groups denoted by $R^{10.3.1}$ as explained in the definitions section above in the description of "first substituent group(s)". In embodiments, when an $R^{10.3.1}$ substituent group is substituted, the $R^{10.3.1}$ substituent group is substituted with one or more second substituent groups denoted by $R^{10.3.2}$ as explained in the definitions section above in the description of "first substituent group(s)". In embodiments, when an $R^{10.3.2}$ substituent group is substituted, the $R^{10.3.2}$ substituent group is substituted with one or more third substituent groups denoted by $R^{10.3.3}$ as explained in the definitions section above in the description of "first substituent group(s)". In the above embodiments, $R^{10.3}$, $R^{10.3.1}$, $R^{10.3.2}$, and $R^{10.3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.3}$, $R^{10.3.1}$, $R^{10.3.2}$, and $R^{10.3.3}$, respectively.

In embodiments, when $R^{10.3A}$, is substituted, $R^{10.3A}$, is substituted with one or more first substituent groups denoted by $R^{10.3A.1}$ as explained in the definitions section above in the description of "first substituent group(s)". In embodiments, when an $R^{10.3A.1}$ substituent group is substituted, the $R^{10.3A.1}$ substituent group is substituted with one or more second substituent groups denoted by $R^{10.3A.2}$ as explained in the definitions section above in the description of "first substituent group(s)". In embodiments, when an $R^{10.3A.2}$ substituent group is substituted, the $R^{10.3A.2}$ substituent group is substituted with one or more third substituent groups denoted by $R^{10.3A.3}$ as explained in the definitions section above in the description of "first substituent group(s)". In the above embodiments, $R^{10.3A}$, $R^{10.3A.1}$, $R^{10.3A.2}$, and $R^{10.3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.3A}$, $R^{10.3A.1}$, $R^{10.3A.2}$, and $R^{10.3A.3}$, respectively.

In embodiments, when $R^{10.3B}$ is substituted, $R^{10.3B}$ is substituted with one or more first substituent groups denoted by $R^{10.3B.1}$ as explained in the definitions section above in the description of "first substituent group(s)". In embodiments, when an $R^{10.3B.1}$ substituent group is substituted, the $R^{10.3B.1}$ substituent group is substituted with one or more second substituent groups denoted by $R^{10.3B.2}$ as explained in the definitions section above in the description of "first substituent group(s)". In embodiments, when an $R^{10.3B.2}$ substituent group is substituted, the $R^{10.3B.2}$ substituent group is substituted with one or more third substituent groups denoted by $R^{10.3B.3}$ as explained in the definitions section above in the description of "first substituent group(s)". In the above embodiments, $R^{10.3B}$, $R^{10.3B.1}$, $R^{10.3B.2}$, and $R^{10.3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.3B}$, $R^{10.3B.1}$, $R^{10.3B.2}$, and $R^{10.3B.3}$, respectively.

In embodiments, when $R^{10.3A}$, and $R^{10.3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.3A.1}$ as explained in the definitions section above in the description of "first substituent group(s)". In embodiments, when an $R^{10.3A.1}$ substituent group is substituted, the $R^{10.3A.1}$ substituent group is substituted with one or more second substituent groups denoted by $R^{10.3A.2}$ as explained in the definitions section above in the description of "first substituent group(s)". In embodiments, when an $R^{10.3A.2}$ substituent group is substituted, the $R^{10.3A.2}$ substituent group is substituted with one or more third substituent groups denoted by $R^{10.3A3}$ as explained in the definitions section above in the description of "first substituent group(s)". In the above embodiments, $R^{10.3A.1}$, $R^{10.3A.2}$, and $R^{10.3A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.3A.1}$, $R^{10.3A.2}$, and $R^{10.3A.3}$, respectively.

In embodiments, when $R^{10.3A}$, and $R^{10.3B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.3B.1}$ as explained in the definitions section above in the description of "first substituent group(s)". In embodiments, when an $R^{10.3B.1}$ substituent group is substituted, the $R^{10.3B.1}$ substituent group is substituted with one or more second substituent groups denoted by $R^{10.3B.2}$ as explained in the definitions section above in the description of "first substituent group(s)". In embodiments, when an $R^{10.3B.2}$ substituent group is substituted, the $R^{10.3B.2}$ substituent group is substituted with one or more third substituent groups denoted by $R^{10.3B.3}$ as explained in the definitions section above in the description of "first substituent group(s)". In the above embodiments, $R^{10.3B.1}$, $R^{10.3B.2}$, and $R^{10.3B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.3B.1}$, $R^{10.3B.2}$, and $R^{10.3B.3}$, respectively.

In embodiments, when $R^{10.3C}$ is substituted, $R^{10.3C}$ is substituted with one or more first substituent groups denoted by $R^{10.3C.1}$ as explained in the definitions section above in the description of "first substituent group(s)". In embodiments, when an $R^{10.3C.1}$ substituent group is substituted, the $R^{10.3C.1}$ substituent group is substituted with one or more second substituent groups denoted by $R^{10.3C.2}$ as explained in the definitions section above in the description of "first substituent group(s)". In embodiments, when an $R^{10.3C.2}$ substituent group is substituted, the $R^{10.3C.2}$ substituent group is substituted with one or more third substituent groups denoted by $R^{10.3C.3}$ as explained in the definitions section above in the description of "first substituent group(s)". In the above embodiments, $R^{10.3C}$, $R^{10.3C.1}$, $R^{10.3C.2}$, and $R^{10.3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.3C}$, $R^{10.3C.1}$, $R^{10.3C.2}$, and $R^{10.3C.3}$, respectively.

In embodiments, when $R^{10.3D}$ is substituted, $R^{10.3D}$ is substituted with one or more first substituent groups denoted by $R^{10.3D.1}$ as explained in the definitions section above in the description of "first substituent group(s)". In embodiments, when an $R^{10.3D.1}$ substituent group is substituted, the $R^{10.3D.1}$ substituent group is substituted with one or more second substituent groups denoted by $R^{10.3D.2}$ as explained in the definitions section above in the description of "first substituent group(s)". In embodiments, when an $R^{10.3D.2}$ substituent group is substituted, the $R^{10.3D.2}$ substituent group is substituted with one or more third substituent groups denoted by $R^{10.3D.3}$ as explained in the definitions section above in the description of "first substituent group(s)". In the above embodiments, $R^{10.3D}$, $R^{10.3D.1}$, $R^{10.3D.2}$, and $R^{10.3D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.3D}$, $R^{10.3D.1}$, $R^{10.3D.2}$, and $R^{10.3D.3}$, respectively.

In embodiments, when $R^{10.4}$ is substituted, $R^{10.4}$ is substituted with one or more first substituent groups denoted by $R^{10.4.1}$ as explained in the definitions section above in the description of "first substituent group(s)". In embodiments, when an $R^{10.4.1}$ substituent group is substituted, the $R^{10.4.1}$ substituent group is substituted with one or more second substituent groups denoted by $R^{10.4.2}$ as explained in the definitions section above in the description of "first substituent group(s)". In embodiments, when an $R^{10.4.2}$ substituent group is substituted, the $R^{10.4.2}$ substituent group is substituted with one or more third substituent groups denoted by $R^{10.4.3}$ as explained in the definitions section above in the description of "first substituent group(s)". In the above embodiments, $R^{10.4}$, $R^{10.4.1}$, $R^{10.4.2}$, and $R^{10.4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.4}$, $R^{10.4.1}$, $R^{10.4.2}$, and $R^{10.4.3}$, respectively.

In embodiments, when $R^{10.4A}$ is substituted, $R^{10.4A}$ is substituted with one or more first substituent groups denoted by $R^{10.4A.1}$ as explained in the definitions section above in the description of "first substituent group(s)". In embodiments, when an $R^{10.4A.1}$ substituent group is substituted, the $R^{10.4A.1}$ substituent group is substituted with one or more second substituent groups denoted by $R^{10.4A.2}$ as explained in the definitions section above in the description of "first substituent group(s)". In embodiments, when an $R^{10.4A.2}$ substituent group is substituted, the $R^{10.4A.2}$ substituent group is substituted with one or more third substituent groups denoted by $R^{10.4A.3}$ as explained in the definitions section above in the description of "first substituent group(s)". In the above embodiments, $R^{10.4A}$, $R^{10.4A.1}$, $R^{10.4A.2}$, and $R^{10.4A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.4A}$, $R^{10.4A.1}$, $R^{10.4A.2}$, and $R^{10.4A.3}$, respectively.

In embodiments, when $R^{10.4B}$ is substituted, $R^{10.4B}$ is substituted with one or more first substituent groups denoted by $R^{10.4B.1}$ as explained in the definitions section above in the description of "first substituent group(s)". In embodiments, when an $R^{10.4B.1}$ substituent group is substituted, the $R^{10.4B.1}$ substituent group is substituted with one or more second substituent groups denoted by $R^{10.4B.2}$ as explained in the definitions section above in the description of "first substituent group(s)". In embodiments, when an $R^{10.4B.2}$ substituent group is substituted, the $R^{10.4B.2}$ substituent group is substituted with one or more third substituent groups denoted by $R^{10.4B.3}$ as explained in the definitions section above in the description of "first substituent group(s)". In the above embodiments, $R^{10.4B}$, $R^{10.4B.1}$, $R^{10.4B.2}$, and $R^{10.4B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.4B}$, $R^{10.4B.1}$, $R^{10.4B.2}$, and $R^{10.4B.3}$, respectively.

In embodiments, when $R^{10.4A}$ and $R^{10.4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.4A.1}$ as explained in the definitions section above in the description of "first substituent group(s)". In embodiments, when an $R^{10.4A.1}$ substituent group is substituted, the $R^{10.4A.1}$ substituent group is substituted with one or more second substituent groups denoted by $R^{10.4A.2}$ as explained in the definitions section above in the description of "first substituent group(s)". In embodiments, when an $R^{10.4A.2}$ substituent group is substituted, the $R^{10.4A.2}$ substituent group is substituted with one or more third substituent groups denoted by $R^{10.4A.3}$ as explained in the definitions section above in the description of "first substituent group(s)". In the above embodiments, $R^{10.4A.1}$, $R^{10.4A.2}$, and $R^{10.4A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.4A.1}$, $R^{10.4A.2}$, and $R^{10.4A.3}$, respectively.

In embodiments, when $R^{10.4A}$ and $R^{10.4B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.4B.1}$ as explained in the definitions section above in the description of "first substituent group(s)". In embodiments, when an $R^{10.4B.1}$ substituent group is substituted, the $R^{10.4B.1}$ substituent group is substituted with one or more second substituent groups denoted by $R^{10.4B.2}$ as explained in the definitions section above in the description of "first substituent group(s)". In embodiments, when an $R^{10.4B.2}$ substituent group is substituted, the $R^{10.4B.2}$ substituent group is substituted with one or more third substituent groups denoted by $R^{10.4B.3}$ as explained in the definitions section above in the description of "first substituent group(s)". In the above embodiments, $R^{10.4B.1}$, $R^{10.4B.2}$, and $R^{10.4B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.4B.1}$, $R^{10.4B.2}$, and $R^{10.4B.3}$, respectively.

In embodiments, when $R^{10.4C}$ is substituted, $R^{10.4C}$ is substituted with one or more first substituent groups denoted by $R^{10.4C.1}$ as explained in the definitions section above in the description of "first substituent group(s)". In embodiments, when an $R^{10.4C.1}$ substituent group is substituted, the $R^{10.4C.1}$ substituent group is substituted with one or more second substituent groups denoted by $R^{10.4C.2}$ as explained in the definitions section above in the description of "first substituent group(s)". In embodiments, when an $R^{10.4C.2}$ substituent group is substituted, the $R^{10.4C.2}$ substituent group is substituted with one or more third substituent groups denoted by $R^{10.4C.3}$ as explained in the definitions section above in the description of "first substituent group(s)". In the above embodiments, $R^{10.4C}$, $R^{10.4C.1}$, $R^{10.4C.2}$, and $R^{10.4C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.4C}$, $R^{10.4C.1}$, $R^{10.4C.2}$, and $R^{10.4C.3}$, respectively.

In embodiments, when $R^{10.4D}$ is substituted, $R^{10.4D}$ is substituted with one or more first substituent groups denoted by $R^{10.4D.1}$ as explained in the definitions section above in the description of "first substituent group(s)". In embodiments, when an $R^{10.4D.1}$ substituent group is substituted, the $R^{10.4D.1}$ substituent group is substituted with one or more second substituent groups denoted by $R^{10.4D.2}$ as explained in the definitions section above in the description of "first substituent group(s)". In embodiments, when an $R^{10.4D.2}$ substituent group is substituted, the $R^{10.4D.2}$ substituent group is substituted with one or more third substituent groups denoted by $R^{10.4D.3}$ as explained in the definitions section above in the description of "first substituent group(s)". In the above embodiments, $R^{10.4D}$, $R^{10.4D.1}$, $R^{10.4D.2}$, and $R^{10.4D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.4D}$, $R^{10.4D.1}$, $R^{10.4D.2}$, and $R^{10.4D.3}$, respectively.

In embodiments, when $R^{10.5}$ is substituted, $R^{10.5}$ is substituted with one or more first substituent groups denoted by $R^{10.5.1}$ as explained in the definitions section above in the description of "first substituent group(s)". In embodiments, when an $R^{10.5.1}$ substituent group is substituted, the $R^{10.5.1}$ substituent group is substituted with one or more second substituent groups denoted by $R^{10.5.2}$ as explained in the definitions section above in the description of "first substituent group(s)". In embodiments, when an $R^{10.5.2}$ substituent group is substituted, the $R^{10.5.2}$ substituent group is substituted with one or more third substituent groups denoted by $R^{10.5.3}$ as explained in the definitions section above in the description of "first substituent group(s)". In the above embodiments, $R^{10.5}$, $R^{10.5.1}$, $R^{10.5.2}$, and $R^{10.5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.5}$, $R^{10.5.1}$, $R^{10.5.2}$, and $R^{10.5.3}$, respectively.

In embodiments, when $R^{10.5A}$ is substituted, $R^{10.5A}$ is substituted with one or more first substituent groups denoted by $R^{10.5A.1}$ as explained in the definitions section above in the description of "first substituent group(s)". In embodiments, when an $R^{10.5A.1}$ substituent group is substituted, the $R^{10.5A.1}$ substituent group is substituted with one or more second substituent groups denoted by $R^{10.5A.2}$ as explained in the definitions section above in the description of "first substituent group(s)". In embodiments, when an $R^{10.5A.2}$ substituent group is substituted, the $R^{10.5A.2}$ substituent group is substituted with one or more third substituent groups denoted by $R^{10.5A.3}$ as explained in the definitions section above in the description of "first substituent group(s)". In the above embodiments, $R^{10.5A}$, $R^{10.5A.1}$, $R^{10.5A.2}$, and $R^{10.5A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.5A}$, $R^{10.5A.1}$, $R^{10.5A.2}$, and $R^{10.5A.3}$, respectively.

In embodiments, when $R^{10.5B}$ is substituted, $R^{10.5B}$ is substituted with one or more first substituent groups denoted by $R^{10.5B.1}$ as explained in the definitions section above in the description of "first substituent group(s)". In embodiments, when an $R^{10.5B.1}$ substituent group is substituted, the $R^{10.5B.1}$ substituent group is substituted with one or more second substituent groups denoted by $R^{10.5B.2}$ as explained in the definitions section above in the description of "first substituent group(s)". In embodiments, when an $R^{10.5B.2}$ substituent group is substituted, the $R^{10.5B.2}$ substituent group is substituted with one or more third substituent groups denoted by $R^{10.5B.3}$ as explained in the definitions section above in the description of "first substituent group(s)". In the above embodiments, $R^{10.5B}$, $R^{10.5B.1}$, $R^{10.5B.2}$, and $R^{10.5B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.5B}$, $R^{10.5B.1}$, $R^{10.5B.2}$, and $R^{10.5B.3}$, respectively.

In embodiments, when $R^{10.5A}$ and $R^{10.5B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.5A.1}$ as explained in the definitions section above in the description of "first substituent group(s)". In embodiments, when an $R^{10.5A.1}$ substituent group is substituted, the $R^{10.5A.1}$ substituent group is substituted with one or more second substituent groups denoted by $R^{10.5A.2}$ as explained in the definitions section above in the description of "first substituent group(s)". In embodiments, when an $R^{10.5A.2}$ substituent group is substituted, the $R^{10.5A.2}$ substituent group is substituted with one or more third substituent groups denoted by $R^{10.5A.3}$ as explained in the definitions section above in the description of "first substituent group(s)". In the above embodiments, $R^{10.5A.1}$, $R^{10.5A.2}$, and $R^{10.5A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.5A.1}$, $R^{10.5A.2}$, and $R^{10.5A.3}$, respectively.

In embodiments, when $R^{10.5A}$ and $R^{10.5B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.5B.1}$ as explained in the definitions section above in the description of "first substituent group(s)". In embodiments, when an $R^{10.5B.1}$ substituent group is substituted, the $R^{10.5B.1}$ substituent group is substituted with one or more second substituent groups denoted by $R^{10.5B.2}$ as explained in the definitions section above in the description of "first substituent group(s)". In embodiments, when an $R^{10.5B.2}$ substituent group is substituted, the $R^{10.5B.2}$ substituent group is substituted with one or more third substituent groups denoted by $R^{10.5B.3}$ as explained in the definitions section above in the description of "first substituent group(s)". In the above embodiments, $R^{10.5B.1}$, $R^{10.5B.2}$, and $R^{10.5B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.5B.1}$, $R^{10.5B.2}$, and $R^{10.5B.3}$, respectively.

In embodiments, when $R^{10.5C}$ is substituted, $R^{10.5C}$ is substituted with one or more first substituent groups denoted by $R^{10.5C.1}$ as explained in the definitions section above in the description of "first substituent group(s)". In embodiments, when an $R^{10.5C.1}$ substituent group is substituted, the $R^{10.5C.1}$ substituent group is substituted with one or more second substituent groups denoted by $R^{10.5C.2}$ as explained in the definitions section above in the description of "first substituent group(s)". In embodiments, when an $R^{10.5C.2}$ substituent group is substituted, the $R^{10.5C.2}$ substituent group is substituted with one or more third substituent groups denoted by $R^{10.1C.3}$ as explained in the definitions section above in the description of "first substituent group(s)". In the above embodiments, $R^{10.5C}$, $R^{10.5C.1}$, $R^{10.5C.2}$, and $R^{10.5C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.5C}$, $R^{10.5C.1}$, $R^{10.5C.2}$, and $R^{10.5C.3}$, respectively.

In embodiments, when $R^{10.5D}$ is substituted, $R^{10.5D}$ is substituted with one or more first substituent groups denoted by $R^{10.5D.1}$ as explained in the definitions section above in the description of "first substituent group(s)". In embodiments, when an $R^{10.5D.1}$ substituent group is substituted, the $R^{10.5D.1}$ substituent group is substituted with one or more second substituent groups denoted by $R^{10.5D.2}$ as explained in the definitions section above in the description of "first substituent group(s)". In embodiments, when an $R^{10.5D.2}$ substituent group is substituted, the $R^{10.5D.2}$ substituent group is substituted with one or more third substituent groups denoted by $R^{10.5D.3}$ as explained in the definitions section above in the description of "first substituent group(s)". In the above embodiments, $R^{10.5D}$, $R^{10.5D.1}$, $R^{10.5D.2}$, and $R^{10.5D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.5D}$, $R^{10.5D.1}$, $R^{10.5D.2}$, and $R^{10.5D.3}$, respectively.

In embodiments, when $R^{10.6}$ is substituted, $R^{10.6}$ is substituted with one or more first substituent groups denoted by $R^{10.6.1}$ as explained in the definitions section above in the description of "first substituent group(s)". In embodiments, when an $R^{10.6.1}$ substituent group is substituted, the $R^{10.6.1}$ substituent group is substituted with one or more second substituent groups denoted by $R^{10.6.2}$ as explained in the definitions section above in the description of "first substituent group(s)". In embodiments, when an $R^{10.6.2}$ substituent group is substituted, the $R^{10.6.2}$ substituent group is substituted with one or more third substituent groups denoted by $R^{10.6.3}$ as explained in the definitions section above in the description of "first substituent group(s)". In the above embodiments, $R^{10.6}$, $R^{10.6.1}$, $R^{10.6.2}$, and $R^{10.6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.6}$, $R^{10.6.1}$, $R^{10.6.2}$, and $R^{10.6.3}$, respectively.

In embodiments, when $R^{10.6A}$ is substituted, $R^{10.6A}$ is substituted with one or more first substituent groups denoted by $R^{10.6A.1}$ as explained in the definitions section above in the description of "first substituent group(s)". In embodiments, when an $R^{10.6A.1}$ substituent group is substituted, the $R^{10.6A.1}$ substituent group is substituted with one or more second substituent groups denoted by $R^{10.6A.2}$ as explained in the definitions section above in the description of "first substituent group(s)". In embodiments, when an $R^{10.6A.2}$ substituent group is substituted, the $R^{10.6A.2}$ substituent group is substituted with one or more third substituent groups denoted by $R^{10.6A.3}$ as explained in the definitions section above in the description of "first substituent group(s)". In the above embodiments, $R^{10.6A}$, $R^{10.6A.1}$, $R^{10.6A.2}$, and $R^{10.6A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.6A}$, $R^{10.6A.1}$, $R^{10.6A.2}$, and $R^{10.6A.3}$, respectively.

In embodiments, when $R^{10.6B}$ is substituted, $R^{10.6B}$ is substituted with one or more first substituent groups denoted by $R^{10.6B.1}$ as explained in the definitions section above in the description of "first substituent group(s)". In embodiments, when an $R^{10.6B.1}$ substituent group is substituted, the $R^{10.6B.1}$ substituent group is substituted with one or more second substituent groups denoted by $R^{10.6B.2}$ as explained in the definitions section above in the description of "first substituent group(s)". In embodiments, when an $R^{10.6B.2}$ substituent group is substituted, the $R^{10.6B.2}$ substituent group is substituted with one or more third substituent groups denoted by $R^{10.6B.3}$ as explained in the definitions section above in the description of "first substituent group(s)". In the above embodiments, $R^{10.6B}$, $R^{10.6B.1}$, $R^{10.6B.2}$, and $R^{10.6B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.6B}$, $R^{10.6B.1}$, $R^{10.6B.2}$, and $R^{10.6B.3}$, respectively.

In embodiments, when $R^{10.6A}$ and $R^{10.6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.6A.1}$ as explained in the definitions section above in the description of "first substituent group(s)". In embodiments, when an $R^{10.6A.1}$ substituent group is substituted, the $R^{10.6A.1}$ substituent group is substituted with one or more second substituent groups denoted by $R^{10.6A.2}$ as explained in the definitions section above in the description of "first substituent group(s)". In embodiments, when an $R^{10.6A.2}$ substituent group is substituted, the $R^{10.6A.2}$ substituent group is substituted with one or more third substituent groups denoted by $R^{10.6A.3}$ as explained in the definitions section above in the description of "first substituent group(s)". In the above embodiments, $R^{10.6A.1}$, $R^{10.6A.2}$, and $R^{10.6A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.6A.1}$, $R^{10.6A.2}$, and $R^{10.6A.3}$, respectively.

In embodiments, when $R^{10.6A}$ and $R^{10.6B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{10.6B.1}$ as explained in the definitions section above in the description of "first substituent group(s)". In embodiments, when an $R^{10.6B.1}$ substituent group is substituted, the $R^{10.6B.1}$ substituent group is substituted with one or more second substituent groups denoted by $R^{10.6B.2}$ as explained in the definitions section above in the description of "first substituent group(s)". In embodiments, when an $R^{10.6B.2}$ substituent group is substituted, the $R^{10.6B.2}$ substituent group is substituted with one or more third substituent groups denoted by $R^{10.6B.3}$ as explained in the definitions section above in the description of "first substituent group(s)". In the above embodiments, $R^{10.6B.1}$, $R^{10.6B.2}$, and $R^{10.6B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{10.6B.1}$, $R^{10.6B.2}$, and $R^{10.6B.3}$, respectively.

In embodiments, when $R^{10.6C}$ is substituted, $R^{10.6C}$ is substituted with one or more first substituent groups denoted by $R^{10.6C.1}$ as explained in the definitions section above in the description of "first substituent group(s)". In embodiments, when an $R^{10.6C.1}$ substituent group is substituted, the $R^{10.6C.1}$ substituent group is substituted with one or more second substituent groups denoted by $R^{10.6C.2}$ as explained in the definitions section above in the description of "first substituent group(s)". In embodiments, when an $R^{10.6C.2}$ substituent group is substituted, the $R^{10.6C.2}$ substituent group is substituted with one or more third substituent groups denoted by $R^{10.6C.3}$ as explained in the definitions section above in the description of "first substituent group(s)". In the above embodiments, $R^{10.6C}$, $R^{10.6C.1}$, $R^{10.6C.2}$, and $R^{10.6C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.6C}$, $R^{10.6C.1}$, $R^{10.6C.2}$, and $R^{10.6C.3}$, respectively.

In embodiments, when $R^{10.6D}$ is substituted, $R^{10.6D}$ is substituted with one or more first substituent groups denoted by $R^{10.6D.1}$ as explained in the definitions section above in the description of "first substituent group(s)". In embodiments, when an $R^{10.6D.1}$ substituent group is substituted, the $R^{10.6D.1}$ substituent group is substituted with one or more second substituent groups denoted by $R^{10.6D.2}$ as explained in the definitions section above in the description of "first substituent group(s)". In embodiments, when an $R^{10.6D.2}$ substituent group is substituted, the $R^{10.6D.2}$ substituent group is substituted with one or more third substituent groups denoted by $R^{10.6D.3}$ as explained in the definitions section above in the description of "first substituent group(s)". In the above embodiments, $R^{10.6D}$, $R^{10.6D.1}$, $R^{10.6D.2}$, and $R^{10.6D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10.6D}$, $R^{10.6D.1}$, $R^{10.6D.2}$, and $R^{10.6D.3}$, respectively.

In embodiments, when $R^{21}$ is substituted, $R^{21}$ is substituted with one or more first substituent groups denoted by $R^{21.1}$ as explained in the definitions section above in the description of "first substituent group(s)". In embodiments, when an $R^{21.1}$ substituent group is substituted, the $R^{21.1}$ substituent group is substituted with one or more second substituent groups denoted by $R^{21.2}$ as explained in the definitions section above in the description of "first substituent group(s)". In embodiments, when an $R^{21.2}$ substituent group is substituted, the $R^{21.2}$ substituent group is substituted with one or more third substituent groups denoted by $R^{21.3}$ as explained in the definitions section above in the description of "first substituent group(s)". In the above embodiments, $R^{21}$, $R^{21.1}$, $R^{21.2}$, and $R^{21.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21}$, $R^{21.1}$, $R^{21.2}$, and $R^{21.3}$, respectively.

In embodiments, when $R^{21A}$ is substituted, $R^{21A}$ is substituted with one or more first substituent groups denoted by $R^{21A.1}$ as explained in the definitions section above in the description of "first substituent group(s)". In embodiments, when an $R^{21A.1}$ substituent group is substituted, the $R^{21A.1}$ substituent group is substituted with one or more second substituent groups denoted by $R^{21A.2}$ as explained in the definitions section above in the description of "first substituent group(s)". In embodiments, when an $R^{21A.2}$ substituent group is substituted, the $R^{21A.2}$ substituent group is substituted with one or more third substituent groups denoted by $R^{21A.3}$ as explained in the definitions section above in the description of "first substituent group(s)". In the above embodiments, $R^{21A}$, $R^{21A.1}$, $R^{21A.2}$, and $R^{21A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21A}$, $R^{21A.1}$, $R^{21A.2}$, and $R^{21A.3}$, respectively.

In embodiments, when $R^{21B}$ is substituted, $R^{21B}$ is substituted with one or more first substituent groups denoted by $R^{21B.1}$ as explained in the definitions section above in the description of "first substituent group(s)". In embodiments, when an $R^{21B.1}$ substituent group is substituted, the $R^{21B.1}$ substituent group is substituted with one or more second substituent groups denoted by $R^{21B.2}$ as explained in the definitions section above in the description of "first substituent group(s)". In embodiments, when an $R^{21B.2}$ substituent group is substituted, the $R^{21B.2}$ substituent group is substituted with one or more third substituent groups denoted by $R^{21B.3}$ as explained in the definitions section above in the description of "first substituent group(s)". In the above embodiments, $R^{21B}$, $R^{21B.1}$, $R^{21B.2}$, and $R^{21B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21B}$, $R^{21B.1}$, $R^{21B.2}$, and $R^{21B.3}$, respectively.

In embodiments, when $R^{21A}$ and $R^{21B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{21A.1}$ as explained in the definitions section above in the description of "first substituent group(s)". In embodiments, when an $R^{21A.1}$ substituent group is substituted, the $R^{21A.1}$ substituent group is substituted with one or more second substituent groups denoted by $R^{21A.2}$ as explained in the definitions section above in the description of "first substituent group(s)". In embodiments, when an $R^{21A.2}$ substituent group is substituted, the $R^{21A.2}$ substituent group is substituted with one or more third substituent groups denoted by $R^{21A.3}$ as explained in the definitions section above in the description of "first substituent group(s)". In the above embodiments, $R^{21A.1}$, $R^{21A.2}$, and $R^{21A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{21A.1}$, $R^{21A.2}$, and $R^{21A.3}$, respectively.

In embodiments, when $R^{21A}$ and $R^{21B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{21B.1}$ as explained in the definitions section above in the description of "first substituent group(s)". In embodiments, when an $R^{21B.1}$ substituent group is substituted, the $R^{21B.1}$ substituent group is substituted with one or more second substituent groups denoted by $R^{21B.2}$ as explained in the definitions section above in the description of "first substituent group(s)". In embodiments, when an $R^{21B.2}$ substituent group is substituted, the $R^{21B.2}$ substituent group is substituted with one or more third substituent groups denoted by $R^{21B.3}$ as explained in the definitions section above in the description of "first substituent group(s)". In the above embodiments, $R^{21B.1}$, $R^{21B.2}$, and $R^{21B.3}$ have values corresponding to the values of $R^{WW.1}$, $R^{WW.2}$ and $R^{WW.3}$, respectively, as explained in the definitions section above in the description of "first substituent group(s)", wherein $R^{WW.1}$, $R^{WW.2}$, and $R^{WW.3}$ correspond to $R^{21B.1}$, $R^{21B.2}$, and $R^{21B.3}$ respectively.

In embodiments, when $R^{21C}$ is substituted, $R^{21C}$ is substituted with one or more first substituent groups denoted by $R^{21C.1}$ as explained in the definitions section above in the description of "first substituent group(s)". In embodiments, when an $R^{21C.1}$ substituent group is substituted, the $R^{21C.1}$ substituent group is substituted with one or more second substituent groups denoted by $R^{21C.2}$ as explained in the definitions section above in the description of "first substituent group(s)". In embodiments, when an $R^{21C.2}$ substituent group is substituted, the $R^{21C.2}$ substituent group is substituted with one or more third substituent groups denoted by $R^{21C}$ as explained in the definitions section above in the description of "first substituent group(s)". In the above embodiments, $R^{21C}$, $R^{21C.1}$, $R^{21C.2}$, and $R^{21C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21C}$, $R^{21C.1}$, $R^{21C.2}$, and $R^{21C.3}$, respectively.

In embodiments, when $R^{21D}$ is substituted, $R^{21D}$ is substituted with one or more first substituent groups denoted by $R^{21D.1}$ as explained in the definitions section above in the description of "first substituent group(s)". In embodiments, when an $R^{21D.1}$ substituent group is substituted, the $R^{21D.1}$ substituent group is substituted with one or more second substituent groups denoted by $R^{21D.2}$ as explained in the definitions section above in the description of "first substituent group(s)". In embodiments, when an $R^{21D.2}$ substituent group is substituted, the $R^{21D.2}$ substituent group is substituted with one or more third substituent groups denoted by $R^{21D.3}$ as explained in the definitions section above in the description of "first substituent group(s)". In the above embodiments, $R^{21D}$, $R^{21D.1}$, $R^{21D.2}$, and $R^{21D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21D}$, $R^{21D.1}$, $R^{21D.2}$, and $R^{21D.3}$, respectively.

In embodiments, when $R^{22}$ is substituted, $R^{22}$ is substituted with one or more first substituent groups denoted by $R^{22.1}$ as explained in the definitions section above in the description of "first substituent group(s)". In embodiments, when an $R^{22.1}$ substituent group is substituted, the $R^{22.1}$ substituent group is substituted with one or more second substituent groups denoted by $R^{22.2}$ as explained in the definitions section above in the description of "first substituent group(s)". In embodiments, when an $R^{22.2}$ substituent group is substituted, the $R^{22.2}$ substituent group is substituted with one or more third substituent groups denoted by $R^{22.3}$ as explained in the definitions section above in the description of "first substituent group(s)". In the above embodiments, $R^{22}$, $R^{22.1}$, $R^{22.2}$, and $R^{22.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22}$, $R^{22.1}$, $R^{22.2}$, and $R^{22.3}$, respectively.

In embodiments, when $R^{23}$ is substituted, $R^{23}$ is substituted with one or more first substituent groups denoted by $R^{23.1}$ as explained in the definitions section above in the description of "first substituent group(s)". In embodiments, when an $R^{23.1}$ substituent group is substituted, the $R^{23.1}$ substituent group is substituted with one or more second substituent groups denoted by $R^{23.2}$ as explained in the definitions section above in the description of "first substituent group(s)". In embodiments, when an $R^{23.2}$ substituent group is substituted, the $R^{23.2}$ substituent group is substituted with one or more third substituent groups denoted by $R^{23.3}$ as explained in the definitions section above in the description of "first substituent group(s)". In the above embodiments, $R^{23}$, $R^{23.1}$, $R^{23.2}$, and $R^{23.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23}$, $R^{23.1}$, $R^{23.2}$, and $R^{23.3}$, respectively.

In embodiments, when $R^{24}$ is substituted, $R^{24}$ is substituted with one or more first substituent groups denoted by $R^{24.1}$ as explained in the definitions section above in the description of "first substituent group(s)". In embodiments, when an $R^{24.1}$ substituent group is substituted, the $R^{24.1}$ substituent group is substituted with one or more second substituent groups denoted by $R^{24.2}$ as explained in the definitions section above in the description of "first substituent group(s)". In embodiments, when an $R^{24.2}$ substituent group is substituted, the $R^{24.2}$ substituent group is substituted with one or more third substituent groups denoted by $R^{24.3}$ as explained in the definitions section above in the description of "first substituent group(s)". In the above embodiments, $R^{24}$, $R^{24.1}$, $R^{24.2}$, and $R^{24.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{24}$, $R^{24.1}$, $R^{24.2}$, and $R^{24.3}$, respectively.

In embodiments, when $R^{32}$ is substituted, $R^{32}$ is substituted with one or more first substituent groups denoted by $R^{32.1}$ as explained in the definitions section above in the description of "first substituent group(s)". In embodiments, when an $R^{32.1}$ substituent group is substituted, the $R^{32.1}$ substituent group is substituted with one or more second substituent groups denoted by $R^{32.2}$ as explained in the definitions section above in the description of "first substituent group(s)". In embodiments, when an $R^{32.2}$ substituent group is substituted, the $R^{32.2}$ substituent group is substituted with one or more third substituent groups denoted by $R^{32.3}$ as explained in the definitions section above in the description of "first substituent group(s)". In the above embodiments, $R^{32}$, $R^{32.1}$, $R^{32.2}$, and $R^{32.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{32}$, $R^{32.1}$, $R^{32.2}$, and $R^{32.3}$, respectively.

In embodiments, when $R^{33}$ is substituted, $R^{33}$ is substituted with one or more first substituent groups denoted by $R^{33.1}$ as explained in the definitions section above in the description of "first substituent group(s)". In embodiments, when an $R^{33.1}$ substituent group is substituted, the $R^{33.1}$ substituent group is substituted with one or more second substituent groups denoted by $R^{33.2}$ as explained in the definitions section above in the description of "first substituent group(s)". In embodiments, when an $R^{33.2}$ substituent group is substituted, the $R^{33.2}$ substituent group is substituted with one or more third substituent groups denoted by $R^{33.3}$ as explained in the definitions section above in the description of "first substituent group(s)". In the above embodiments, $R^{33}$, $R^{33.1}$, $R^{33.2}$, and $R^{33.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{33}$, $R^{33.1}$, $R^{33.2}$, and $R^{33.3}$, respectively.

In embodiments, when $R^{34}$ is substituted, $R^{34}$ is substituted with one or more first substituent groups denoted by $R^{34.1}$ as explained in the definitions section above in the description of "first substituent group(s)". In embodiments, when an $R^{34.1}$ substituent group is substituted, the $R^{34.1}$ substituent group is substituted with one or more second substituent groups denoted by $R^{34.2}$ as explained in the definitions section above in the description of "first substituent group(s)". In embodiments, when an $R^{34.2}$ substituent group is substituted, the $R^{34.2}$ substituent group is substituted with one or more third substituent groups denoted by $R^{34.3}$ as explained in the definitions section above in the description of "first substituent group(s)". In the above embodiments, $R^{34}$, $R^{34.1}$, $R^{34.2}$, and $R^{34.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{34}$, $R^{34.1}$, $R^{34.2}$, and $R^{34.3}$, respectively.

In embodiments, when $R^{100}$ is substituted, $R^{100}$ is substituted with one or more first substituent groups denoted by $R^{100.1}$ as explained in the definitions section above in the description of "first substituent group(s)". In embodiments, when an $R^{100.1}$ substituent group is substituted, the $R^{100.1}$ substituent group is substituted with one or more second substituent groups denoted by $R^{100.2}$ as explained in the definitions section above in the description of "first substituent group(s)". In embodiments, when an $R^{100.2}$ substituent group is substituted, the $R^{100.2}$ substituent group is substituted with one or more third substituent groups denoted by $R^{100.3}$ as explained in the definitions section above in the description of "first substituent group(s)". In the above embodiments, $R^{100}$, $R^{100.1}$, $R^{100.2}$, and $R^{100.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{100}$, $R^{100.1}$, $R^{100.2}$, and $R^{100.3}$, respectively.

In embodiments, when $R^{100A}$ is substituted, $R^{100A}$ is substituted with one or more first substituent groups denoted by $R^{100A.1}$ as explained in the definitions section above in the description of "first substituent group(s)". In embodiments, when an $R^{100A.1}$ substituent group is substituted, the $R^{100A.1}$ substituent group is substituted with one or more second substituent groups denoted by $R^{100A.2}$ as explained in the definitions section above in the description of "first substituent group(s)". In embodiments, when an $R^{100A.2}$ substituent group is substituted, the $R^{100A.2}$ substituent group is substituted with one or more third substituent groups denoted by $R^{100A.3}$ as explained in the definitions section above in the description of "first substituent group(s)". In the above embodiments, $R^{100A}$, $R^{100A.1}$, $R^{100A.2}$, and $R^{100A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{100A}$, $R^{100A.1}$, $R^{100A.2}$, and $R^{100A.3}$, respectively.

In embodiments, when $R^{100B}$ is substituted, $R^{100B}$ is substituted with one or more first substituent groups denoted by $R^{100B.1}$ as explained in the definitions section above in the description of "first substituent group(s)". In embodiments, when an $R^{100B.1}$ substituent group is substituted, the $R^{100B.1}$ substituent group is substituted with one or more second substituent groups denoted by $R^{100B.2}$ as explained in the definitions section above in the description of "first substituent group(s)". In embodiments, when an $R^{100B.2}$ substituent group is substituted, the $R^{100B.2}$ substituent group is substituted with one or more third substituent groups denoted by $R^{100B.3}$ as explained in the definitions section above in the description of "first substituent group(s)". In the above embodiments, $R^{100B}$, $R^{100B.1}$, $R^{100B.2}$, and $R^{100B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{100B}$, $R^{100B.1}$, $R^{100B.2}$, and $R^{100B.3}$, respectively.

In embodiments, when $R^{100A}$ and $R^{100B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{100A.1}$ as explained in the definitions section above in the description of "first substituent group(s)". In embodiments, when an $R^{100A.1}$ substituent group is substituted, the $R^{100A.1}$ substituent group is substituted with one or more second substituent groups denoted by $R^{100A.2}$ as explained in the definitions section above in the description of "first substituent group(s)". In embodiments, when an $R^{100A.2}$ substituent group is substituted, the $R^{100A.2}$ substituent group is substituted with one or more third substituent groups denoted by $R^{100A.3}$ as explained in the definitions section above in the description of "first substituent group(s)". In the above embodiments, $R^{100A.1}$, $R^{100A.2}$, and $R^{100A.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{100A.1}$, $R^{100A.2}$, and $R^{100A.3}$, respectively.

In embodiments, when $R^{100A}$ and $R^{100B}$ substituents bonded to the same nitrogen atom are optionally joined to form a moiety that is substituted (e.g., a substituted heterocycloalkyl or substituted heteroaryl), the moiety is substituted with one or more first substituent groups denoted by $R^{100B.1}$ as explained in the definitions section above in the description of "first substituent group(s)". In embodiments, when an $R^{100B.1}$ substituent group is substituted, the $R^{100B.1}$ substituent group is substituted with one or more second substituent groups denoted by $R^{100B.2}$ as explained in the definitions section above in the description of "first substituent group(s)". In embodiments, when an $R^{100B.2}$ substituent group is substituted, the $R^{100B.2}$ substituent group is substituted with one or more third substituent groups denoted by $R^{100B.3}$ as explained in the definitions section above in the description of "first substituent group(s)". In the above embodiments, $R^{100B.1}$, $R^{100B.2}$, and $R^{100B.3}$ have values corresponding to the values of $R^{WW.1}$, $R^{WW.2}$, and $R^{WW.3}$, respectively, as explained in the definitions section above in the description of "first substituent group(s)", wherein $R^{WW.1}$, $R^{WW.2}$, and $R^{WW.3}$ correspond to $R^{100B.1}$, $R^{100B.2}$, and $R^{100B.3}$, respectively.

In embodiments, when $R^{100C}$ is substituted, $R^{100C}$ is substituted with one or more first substituent groups denoted by $R^{100C.1}$ as explained in the definitions section above in the description of "first substituent group(s)". In embodiments, when an $R^{100C.1}$ substituent group is substituted, the $R^{100C.1}$ substituent group is substituted with one or more second substituent groups denoted by $R^{100C.2}$ as explained in the definitions section above in the description of "first substituent group(s)". In embodiments, when an $R^{100C.2}$ substituent group is substituted, the $R^{100C.2}$ substituent group is substituted with one or more third substituent groups denoted by $R^{100C.3}$ as explained in the definitions section above in the description of "first substituent group(s)". In the above embodiments, $R^{100C}$, $R^{100C.1}$, $R^{100C.2}$, and $R^{100C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{100C}$, $R^{100C.1}$, $R^{100C.2}$, and $R^{100C.3}$, respectively.

In embodiments, when $R^{100D}$ is substituted, $R^{100D}$ is substituted with one or more first substituent groups denoted by $R^{100D}$ as explained in the definitions section above in the description of "first substituent group(s)". In embodiments, when an $R^{100D.1}$ substituent group is substituted, the $R^{100D.1}$ substituent group is substituted with one or more second substituent groups denoted by $R^{100D.2}$ as explained in the definitions section above in the description of "first substituent group(s)". In embodiments, when an $R^{100D.2}$ substituent group is substituted, the $R^{100D.2}$ substituent group is substituted with one or more third substituent groups denoted by $R^{100D.3}$ as explained in the definitions section above in the description of "first substituent group(s)". In the above embodiments, $R^{100D}$, $R^{100D.1}$, $R^{100D.2}$, and $R^{100D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{100D}$, $R^{100D.1}$, $R^{100D.2}$, and $R^{100D.3}$, respectively.

In embodiments, when $L^{10.2}$ is substituted, $L^{10.2}$ is substituted with one or more first substituent groups denoted by $R^{L10.2.1}$ as explained in the definitions section above in the description of "first substituent group(s)". In embodiments, when an $R^{L10.2.1}$ substituent group is substituted, the $R^{L10.2.1}$ substituent group is substituted with one or more second substituent groups denoted by $R^{L10.2.2}$ as explained in the definitions section above in the description of "first substituent group(s)". In embodiments, when an $R^{L10.2.2}$ substituent group is substituted, the $R^{L10.2.2}$ substituent group is substituted with one or more third substituent groups denoted by $R^{L10.2.3}$ as explained in the definitions section above in the description of "first substituent group(s)". In the above embodiments, $L^{10.2}$, $R^{L10.2.1}$, $R^{L10.2.2}$, and $R^{L10.2.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{10.2}$, $R^{L10.2.1}$, $R^{L10.2.2}$, and $R^{L10.2.3}$, respectively.

In embodiments, when $L^{10.3}$ is substituted, $L^{10.3}$ is substituted with one or more first substituent groups denoted by $R^{L10.3.1}$ as explained in the definitions section above in the description of "first substituent group(s)". In embodiments, when an $R^{L10.3.1}$ substituent group is substituted, the $R^{L10.3.1}$ substituent group is substituted with one or more second substituent groups denoted by $R^{L10.3.2}$ as explained in the definitions section above in the description of "first substituent group(s)". In embodiments, when an $R^{L10.3.2}$ substituent group is substituted, the $R^{L10.3.2}$ substituent group is substituted with one or more third substituent groups denoted by $R^{L10.3.3}$ as explained in the definitions section above in the description of "first substituent group(s)". In the above embodiments, $L^{10.3}$, $R^{L10.3.1}$, $R^{L10.3.2}$, and $R^{L10.3.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{10.3}$, $R^{L10.3.1}$, $R^{L10.3.2}$, and $R^{L10.3.3}$, respectively.

In embodiments, when $L^{10.4}$ is substituted, $L^{10.4}$ is substituted with one or more first substituent groups denoted by $R^{L10.4.1}$ as explained in the definitions section above in the description of "first substituent group(s)". In embodiments, when an $R^{L10.4.1}$ substituent group is substituted, the $R^{L10.4.1}$ substituent group is substituted with one or more second substituent groups denoted by $R^{L10.4.2}$ as explained in the definitions section above in the description of "first substituent group(s)". In embodiments, when an $R^{L10.4.2}$ substituent group is substituted, the $R^{L10.4.2}$ substituent group is substituted with one or more third substituent groups denoted by $R^{L10.4.3}$ as explained in the definitions section above in the description of "first substituent group(s)". In the above embodiments, $L^{10.4}$, $R^{L10.4.1}$, $R^{L10.4.2}$, and $R^{L10.4.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{10.4}$, $R^{L10.4.1}$, $R^{L10.4.2}$, and $R^{L10.4.3}$, respectively.

In embodiments, when $L^{100}$ is substituted, $L^{100}$ is substituted with one or more first substituent groups denoted by $R^{L100.1}$ as explained in the definitions section above in the description of "first substituent group(s)". In embodiments, when an $R^{L100.1}$ substituent group is substituted, the $R^{L100.1}$ substituent group is substituted with one or more second substituent groups denoted by $R^{L100.2}$ as explained in the definitions section above in the description of "first substituent group(s)". In embodiments, when an $R^{L100.2}$ substituent group is substituted, the $R^{L100.2}$ substituent group is substituted with one or more third substituent groups denoted by $R^{L100.3}$ as explained in the definitions section above in the description of "first substituent group(s)". In the above embodiments, $L^{100}$, $R^{L100.1}$, $R^{L100.2}$, and $R^{L100.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{100}$, $R^{L100.1}$, $R^{L100.2}$, and $R^{L100.3}$, respectively.

In embodiments, the compound is

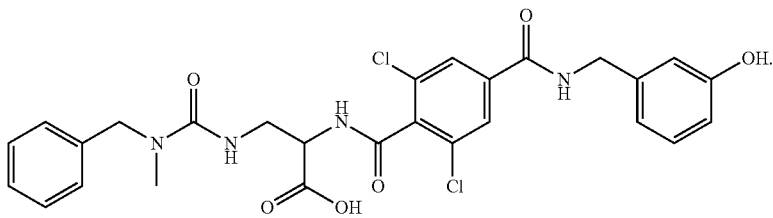 [SMILES: CN(Cc1ccccc1)C(=O)NCC(NC(=O)c1c(Cl)cc(C(=O)NCc2cccc(O)c2)cc1Cl)C(=O)O]

In embodiments, the compound is

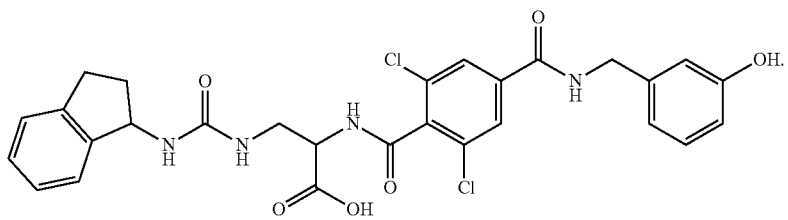 [SMILES: O=C(NCC(NC(=O)c1c(Cl)cc(C(=O)NCc2cccc(O)c2)cc1Cl)C(=O)O)NC1CCc2ccccc21]

In embodiments, the compound is

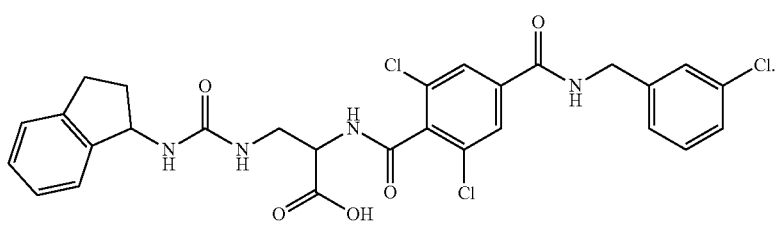 [SMILES: O=C(NCC(NC(=O)c1c(Cl)cc(C(=O)NCc2cccc(Cl)c2)cc1Cl)C(=O)O)NC1CCc2ccccc21]

In embodiments, the compound is

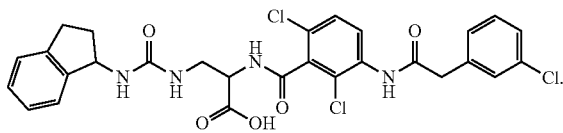

In embodiments, the compound is

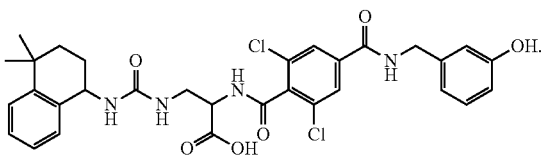 [SMILES: CC1(C)CCC(NC(=O)NCC(NC(=O)c2c(Cl)cc(C(=O)NCc3cccc(O)c3)cc2Cl)C(=O)O)c2ccccc21]

In embodiments, the compound is

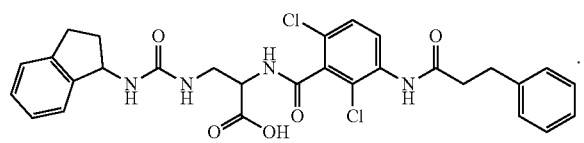 [SMILES: O=C(CCc1ccccc1)Nc1ccc(Cl)c(C(=O)NC(CNC(=O)NC2CCc3ccccc32)C(=O)O)c1Cl]

In embodiments, the compound is

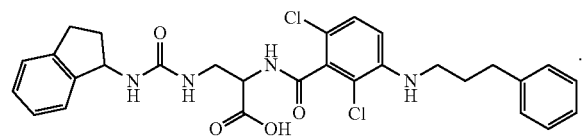 [SMILES: O=C(NCC(NC(=O)c1c(Cl)ccc(NCCCc2ccccc2)c1Cl)C(=O)O)NC1CCc2ccccc21]

In embodiments, the compound is

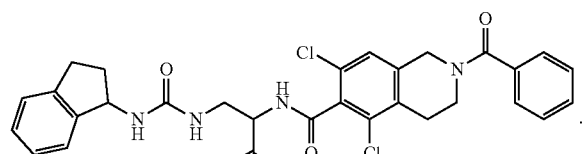

In embodiments, the compound is


In embodiments, the compound is

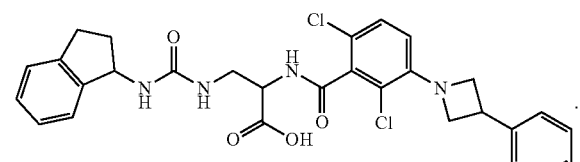

In embodiments, the compound is

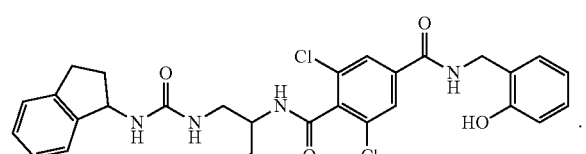

In embodiments, the compound is


In embodiments, the compound is

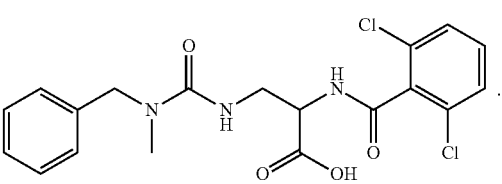 [SMILES: CN(Cc1ccccc1)C(=O)NCC(NC(=O)c1c(Cl)cccc1Cl)C(=O)O]

In embodiments, the compound is

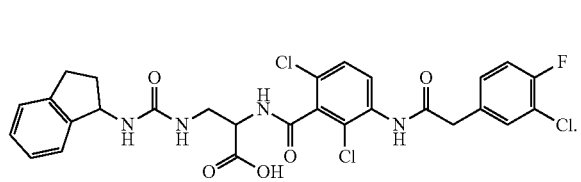 [SMILES: O=C(Cc1ccc(F)c(Cl)c1)Nc1ccc(Cl)c(C(=O)NC(CNC(=O)NC2CCc3ccccc32)C(=O)O)c1Cl]

In embodiments, the compound is

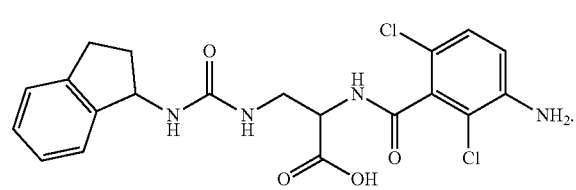 [SMILES: Nc1ccc(Cl)c(C(=O)NC(CNC(=O)NC2CCc3ccccc32)C(=O)O)c1Cl]

In embodiments, the compound is

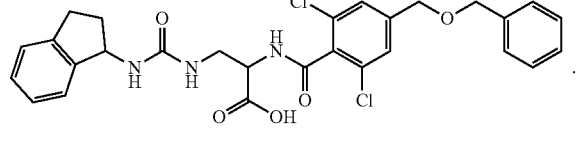

In embodiments, the compound is

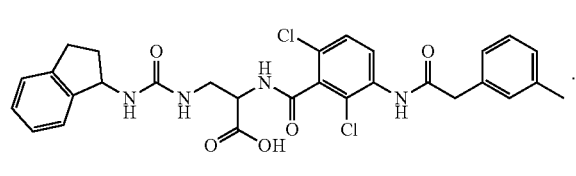 [SMILES: Cc1cccc(CC(=O)Nc2ccc(Cl)c(C(=O)NC(CNC(=O)NC3CCc4ccccc43)C(=O)O)c2Cl)c1]

In embodiments, the compound is

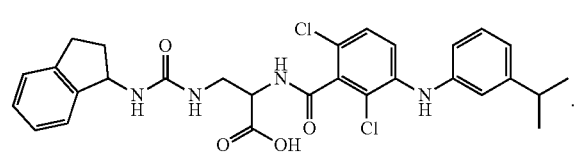 [SMILES: CC(C)c1cccc(Nc2ccc(Cl)c(C(=O)NC(CNC(=O)NC3CCc4ccccc43)C(=O)O)c2Cl)c1]

In embodiments, the compound is

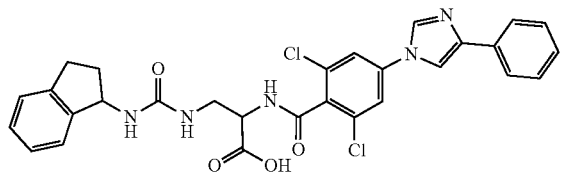

In embodiments, the compound is

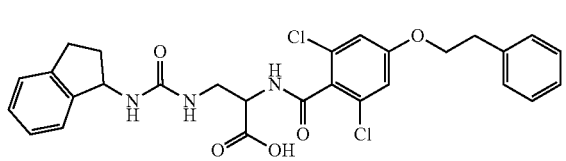

In embodiments, the compound is

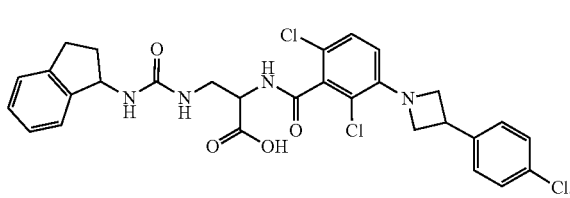 [SMILES: O=C(NCC(NC(=O)c1c(Cl)ccc(N2CC(c3ccc(Cl)cc3)C2)c1Cl)C(=O)O)NC1CCc2ccccc21]

In embodiments, the compound is

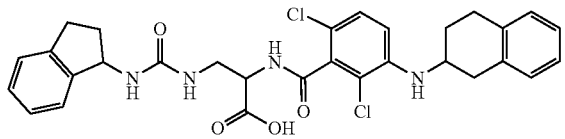

In embodiments, the compound is

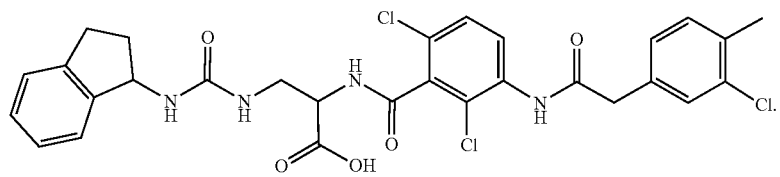 [SMILES: Cc1ccc(CC(=O)Nc2ccc(Cl)c(C(=O)NC(CNC(=O)NC3CCc4ccccc43)C(=O)O)c2Cl)cc1Cl]

In embodiments, the compound is

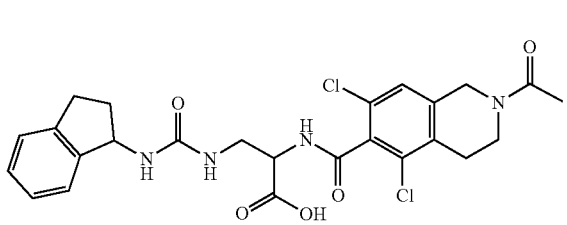

In embodiments, the compound is

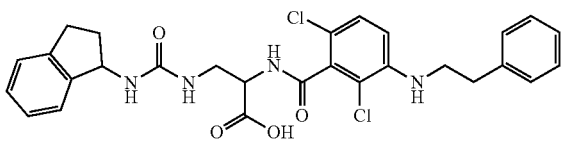

In embodiments, the compound is

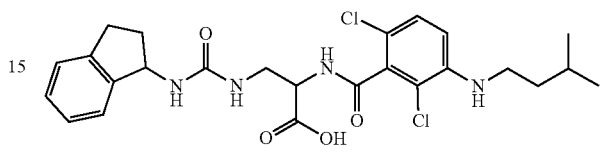

In embodiments, the compound is

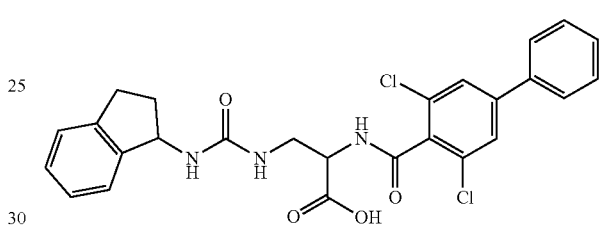

In embodiments, the compound is

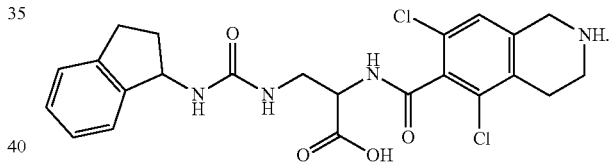

In embodiments, the compound is

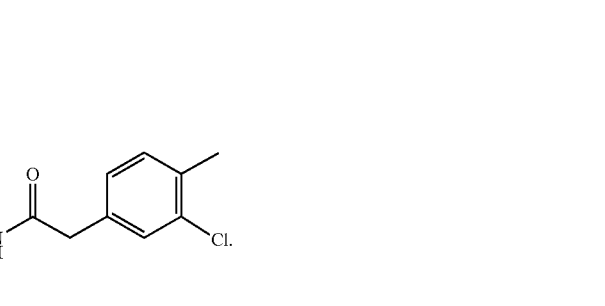

In embodiments, the compound is

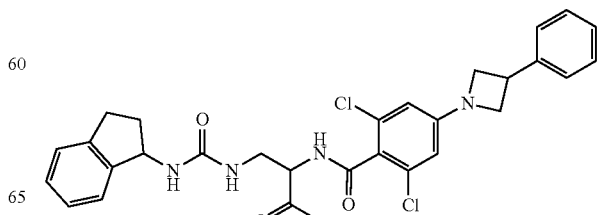

181
In embodiments, the compound is
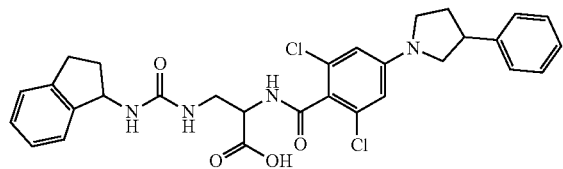
In embodiments, the compound is
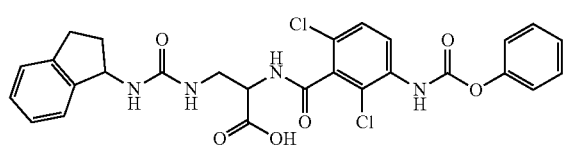
In embodiments, the compound is
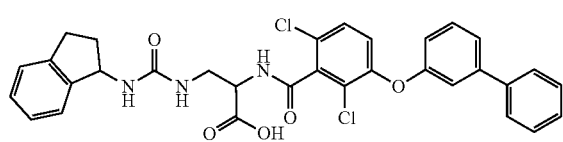
In embodiments, the compound is
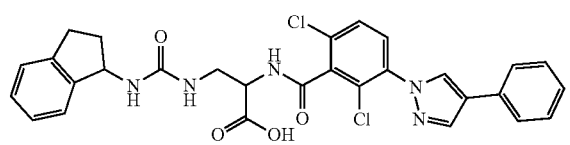
182
In embodiments, the compound is
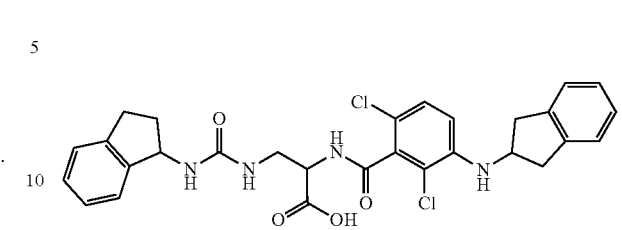
In embodiments, the compound is

In embodiments, the compound is
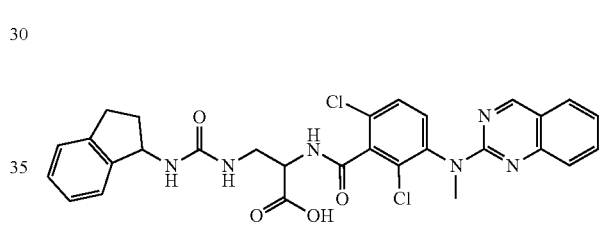
In embodiments, the compound is
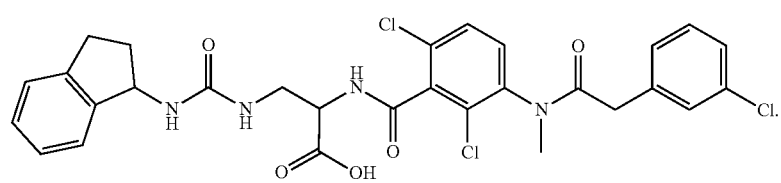 [SMILES: CN(C(=O)Cc1cccc(Cl)c1)c1ccc(Cl)c(C(=O)NC(CNC(=O)NC2CCc3ccccc32)C(=O)O)c1Cl]
In embodiments, the compound is
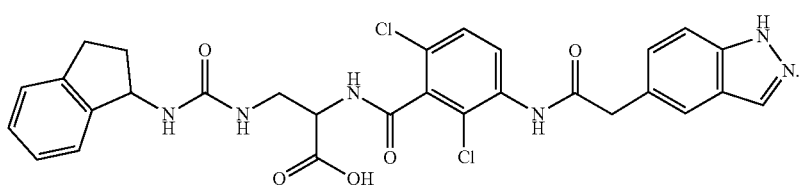 [SMILES: O=C(Cc1ccc2[nH]ncc2c1)Nc1ccc(Cl)c(C(=O)NC(CNC(=O)NC2CCc3ccccc32)C(=O)O)c1Cl]

In embodiments, the compound is
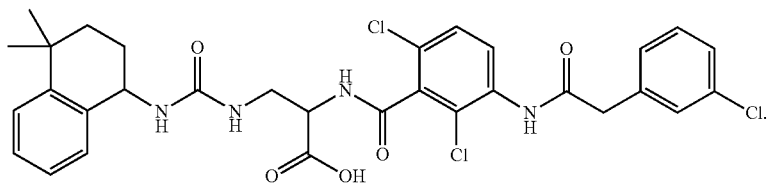 [SMILES: CC1(C)CCC(NC(=O)NCC(NC(=O)c2c(Cl)ccc(NC(=O)Cc3cccc(Cl)c3)c2Cl)C(=O)O)c2ccccc21]
In embodiments, the compound is
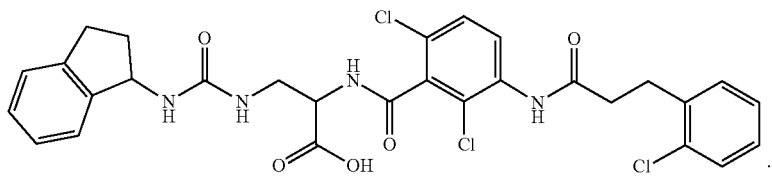 [SMILES: O=C(CCc1ccccc1Cl)Nc1ccc(Cl)c(C(=O)NC(CNC(=O)NC2CCc3ccccc32)C(=O)O)c1Cl]
In embodiments, the compound is
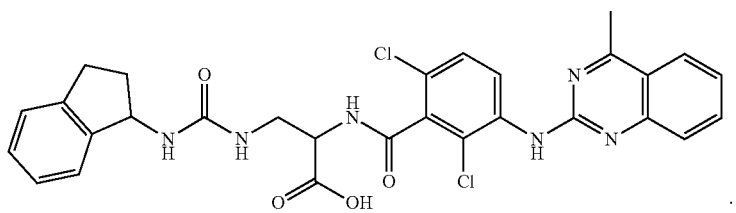 [SMILES: Cc1nc(Nc2ccc(Cl)c(C(=O)NC(CNC(=O)NC3CCc4ccccc43)C(=O)O)c2Cl)nc2ccccc12]
In embodiments, the compound is
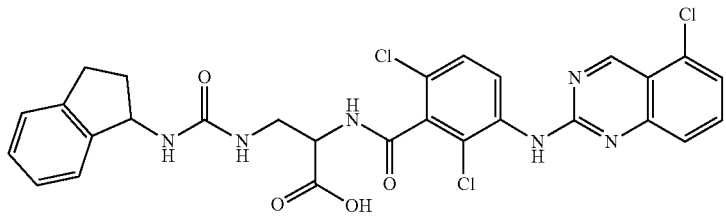
In embodiments, the compound is
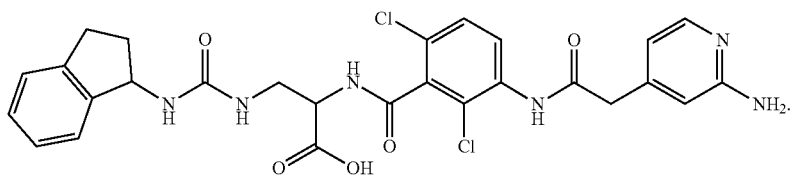 [SMILES: Nc1cc(CC(=O)Nc2ccc(Cl)c(C(=O)NC(CNC(=O)NC3CCc4ccccc43)C(=O)O)c2Cl)ccn1]

In embodiments, the compound is
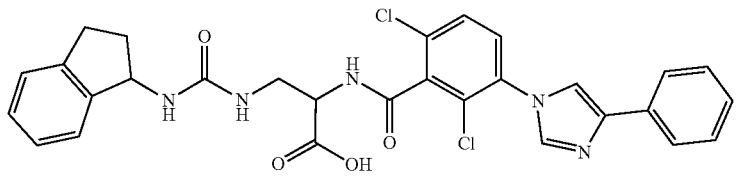
In embodiments, the compound is
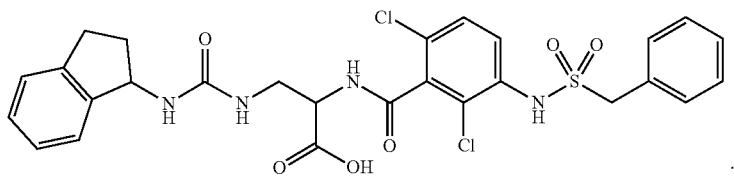 [SMILES: O=C(NCC(NC(=O)c1c(Cl)ccc(NS(=O)(=O)Cc2ccccc2)c1Cl)C(=O)O)NC1CCc2ccccc21]
In embodiments, the compound is
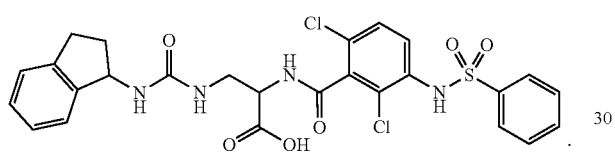
In embodiments, the compound is
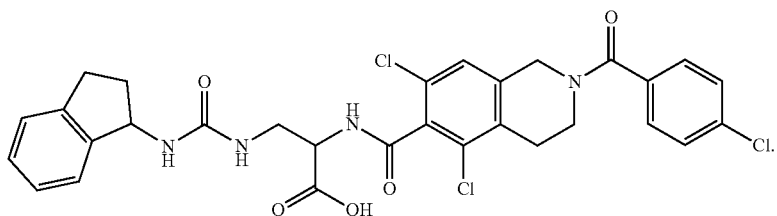 [SMILES: O=C(NCC(NC(=O)c1c(Cl)cc2c(c1Cl)CCN(C(=O)c1ccc(Cl)cc1)C2)C(=O)O)NC1CCc2ccccc21]
In embodiments, the compound is
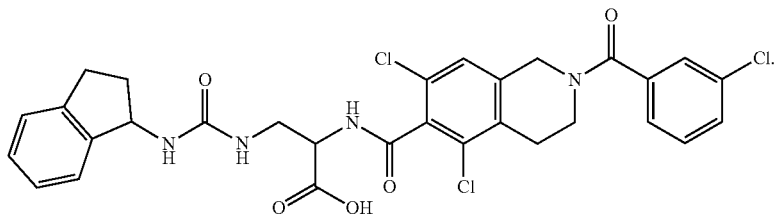 [SMILES: O=C(NCC(NC(=O)c1c(Cl)cc2c(c1Cl)CCN(C(=O)c1cccc(Cl)c1)C2)C(=O)O)NC1CCc2ccccc21]
In embodiments, the compound is
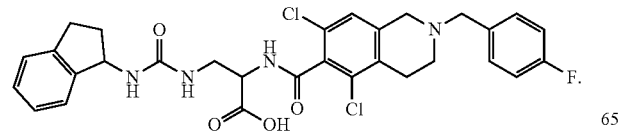

In embodiments, the compound is
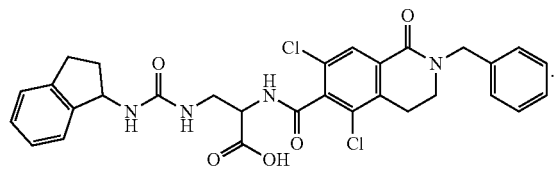 [SMILES: O=C(NCC(NC(=O)c1c(Cl)cc2c(c1Cl)CCN(Cc1ccccc1)C2=O)C(=O)O)NC1CCc2ccccc21]
In embodiments, the compound is
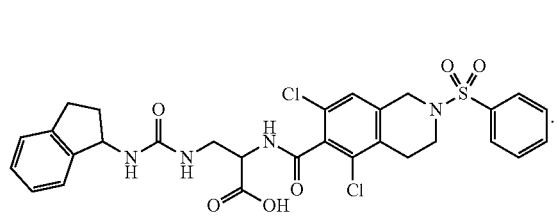 [SMILES: O=C(NCC(NC(=O)c1c(Cl)cc2c(c1Cl)CCN(S(=O)(=O)c1ccccc1)C2)C(=O)O)NC1CCc2ccccc21]
In embodiments, the compound is
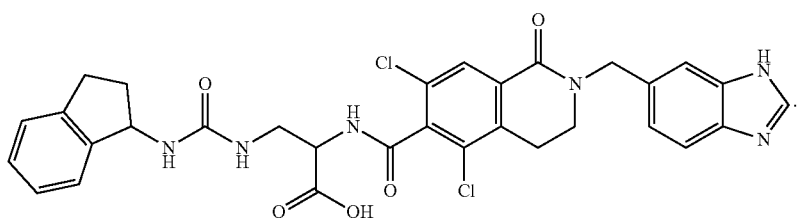 [SMILES: O=C(NCC(NC(=O)c1c(Cl)cc2c(c1Cl)CCN(Cc1ccc3nc[nH]c3c1)C2=O)C(=O)O)NC1CCc2ccccc21]
In embodiments, the compound is
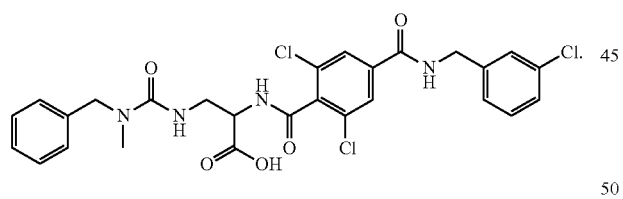
In embodiments, the compound is
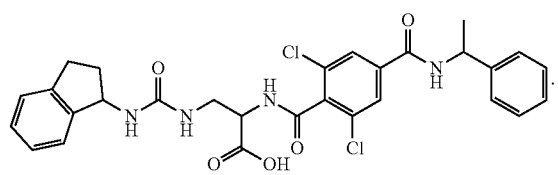 [SMILES: CC(NC(=O)c1cc(Cl)c(C(=O)NC(CNC(=O)NC2CCc3ccccc32)C(=O)O)c(Cl)c1)c1ccccc1]
In embodiments, the compound is
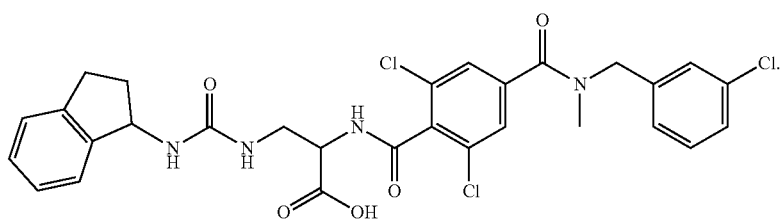 [SMILES: CN(Cc1cccc(Cl)c1)C(=O)c1cc(Cl)c(C(=O)NC(CNC(=O)NC2CCc3ccccc32)C(=O)O)c(Cl)c1]

In embodiments, the compound is
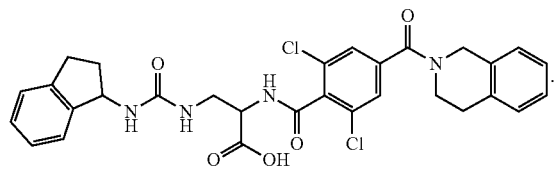 [SMILES: O=C(NCC(NC(=O)c1c(Cl)cc(C(=O)N2CCc3ccccc3C2)cc1Cl)C(=O)O)NC1CCc2ccccc21]
In embodiments, the compound is
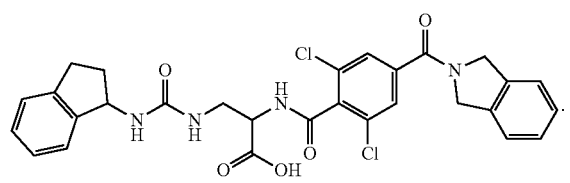 [SMILES: O=C(NCC(NC(=O)c1c(Cl)cc(C(=O)N2Cc3ccccc3C2)cc1Cl)C(=O)O)NC1CCc2ccccc21]
In embodiments, the compound is

In embodiments, the compound is
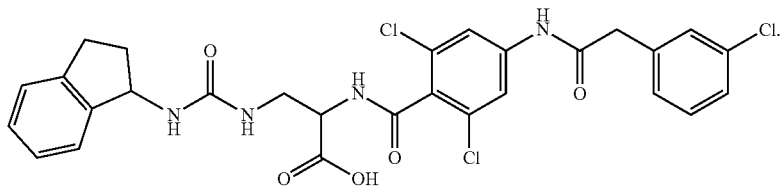 [SMILES: O=C(Cc1cccc(Cl)c1)Nc1cc(Cl)c(C(=O)NC(CNC(=O)NC2CCc3ccccc32)C(=O)O)c(Cl)c1]
In embodiments, the compound is
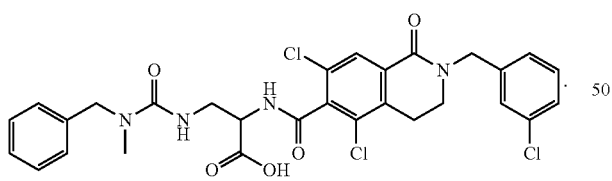
In embodiments, the compound is
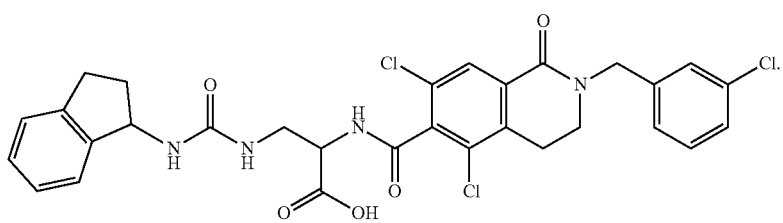 [SMILES: O=C(NCC(NC(=O)c1c(Cl)cc2c(c1Cl)CCN(Cc1cccc(Cl)c1)C2=O)C(=O)O)NC1CCc2ccccc21]

In embodiments, the compound is
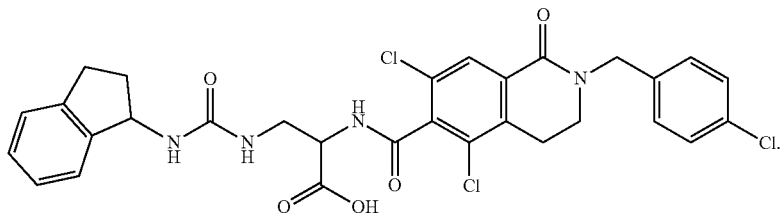 [SMILES: O=C(NCC(NC(=O)c1c(Cl)cc2c(c1Cl)CCN(Cc1ccc(Cl)cc1)C2=O)C(=O)O)NC1CCc2ccccc21]
In embodiments, the compound is
In embodiments, the compound is
In embodiments, the compound is
In embodiments, the compound is
In embodiments, the compound is
In embodiments, the compound is
In embodiments, the compound is
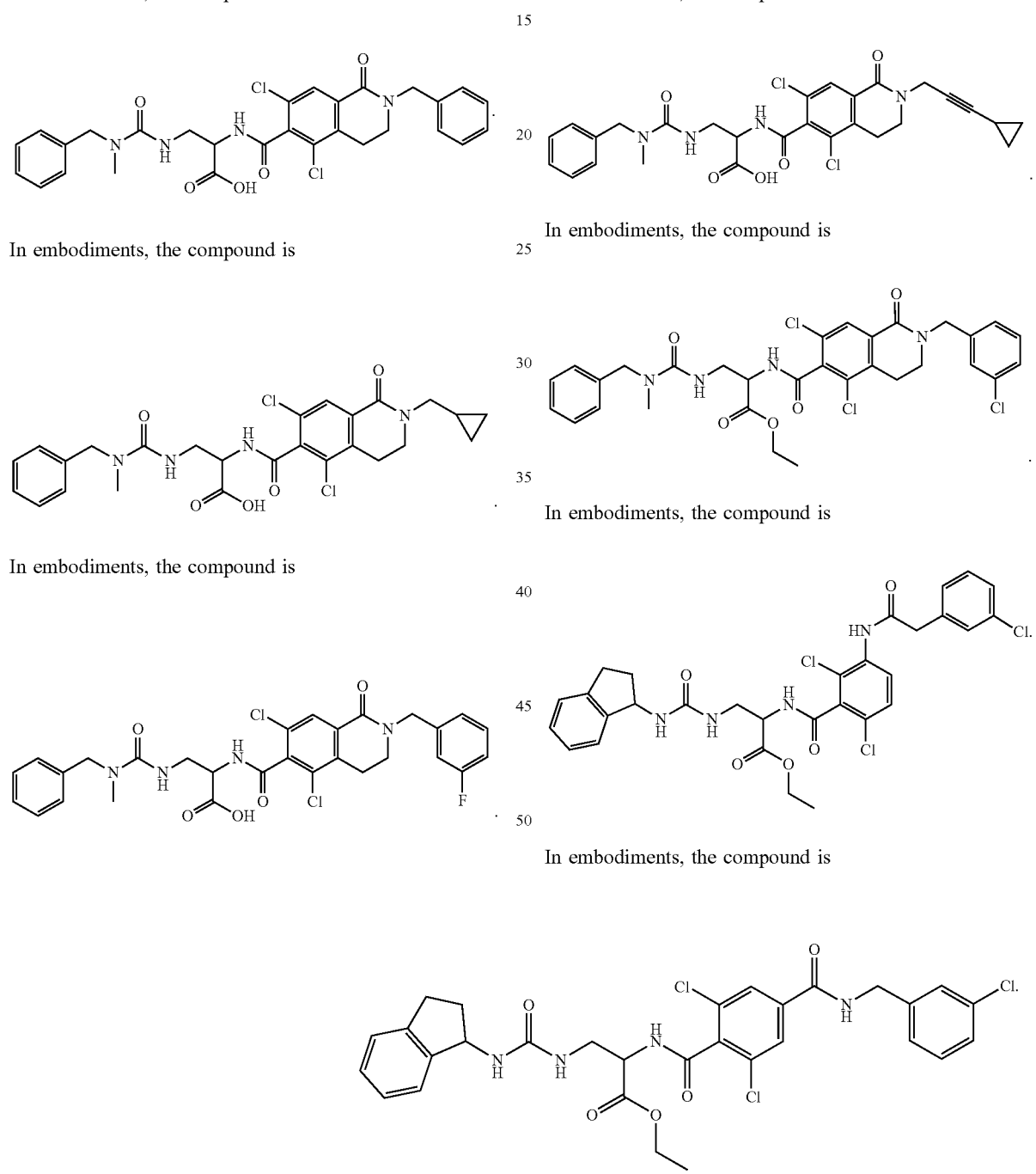

In embodiments, the compound is
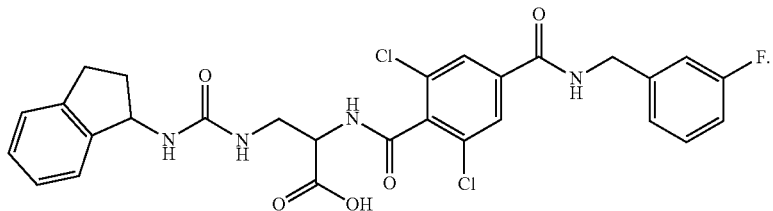 [SMILES: O=C(NCC(NC(=O)c1c(Cl)cc(C(=O)NCc2cccc(F)c2)cc1Cl)C(=O)O)NC1CCc2ccccc21]
In embodiments, the compound is
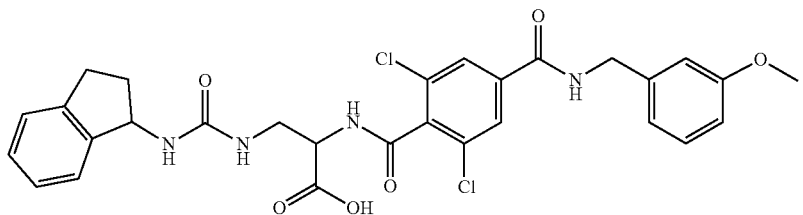
In embodiments, the compound is
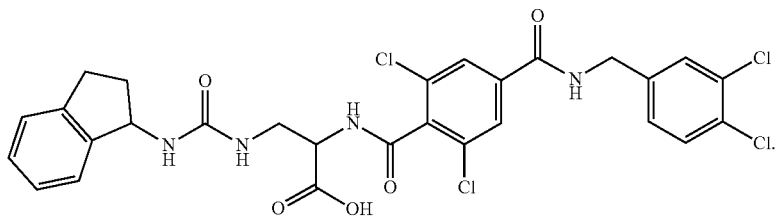 [SMILES: O=C(NCC(NC(=O)c1c(Cl)cc(C(=O)NCc2ccc(Cl)c(Cl)c2)cc1Cl)C(=O)O)NC1CCc2ccccc21]
In embodiments, the compound is
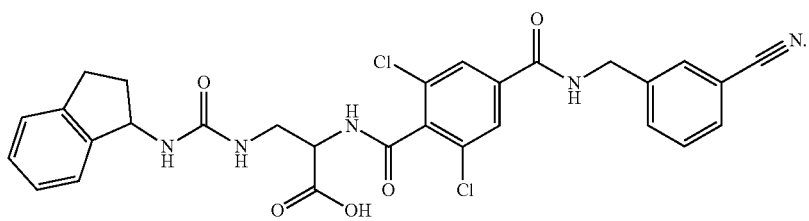 [SMILES: N#Cc1cccc(CNC(=O)c2cc(Cl)c(C(=O)NC(CNC(=O)NC3CCc4ccccc43)C(=O)O)c(Cl)c2)c1]
In embodiments, the compound is
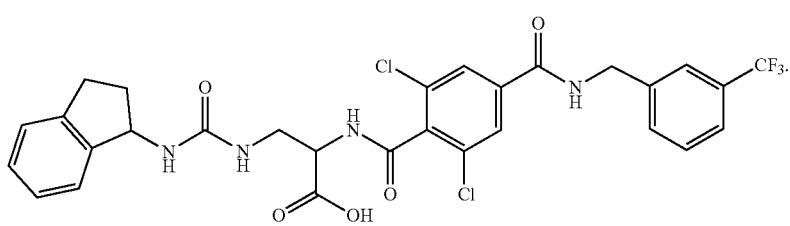 [SMILES: O=C(NCC(NC(=O)c1c(Cl)cc(C(=O)NCc2cccc(C(F)(F)F)c2)cc1Cl)C(=O)O)NC1CCc2ccccc21]

In embodiments, the compound is
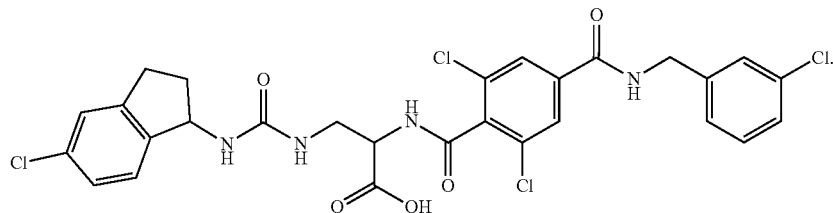 [SMILES: O=C(NCC(NC(=O)c1c(Cl)cc(C(=O)NCc2cccc(Cl)c2)cc1Cl)C(=O)O)NC1CCc2cc(Cl)ccc21]
In embodiments, the compound is
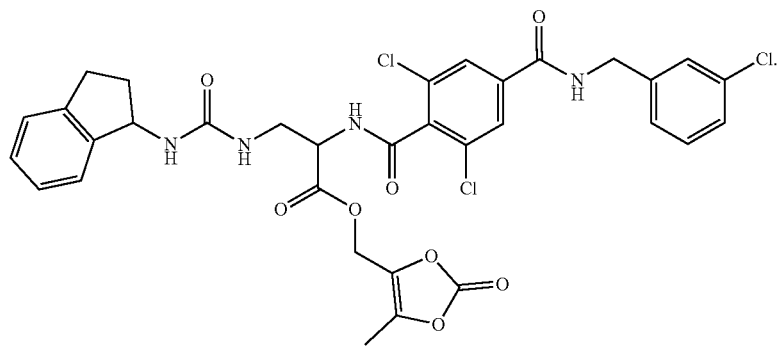 [SMILES: Cc1oc(=O)oc1COC(=O)C(CNC(=O)NC1CCc2ccccc21)NC(=O)c1c(Cl)cc(C(=O)NCc2cccc(Cl)c2)cc1Cl]
In embodiments, the compound is
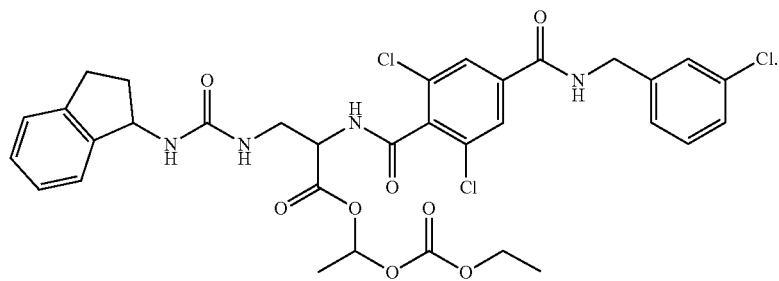 [SMILES: CCOC(=O)OC(C)OC(=O)C(CNC(=O)NC1CCc2ccccc21)NC(=O)c1c(Cl)cc(C(=O)NCc2cccc(Cl)c2)cc1Cl]
In embodiments, the compound is
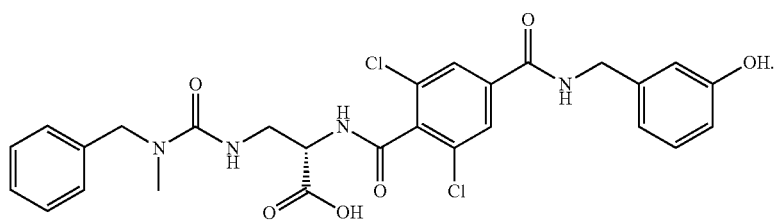 [SMILES: CN(Cc1ccccc1)C(=O)NC[C@H](NC(=O)c1c(Cl)cc(C(=O)NCc2cccc(O)c2)cc1Cl)C(=O)O]

(SU15210-0186-01). In embodiments, the compound is
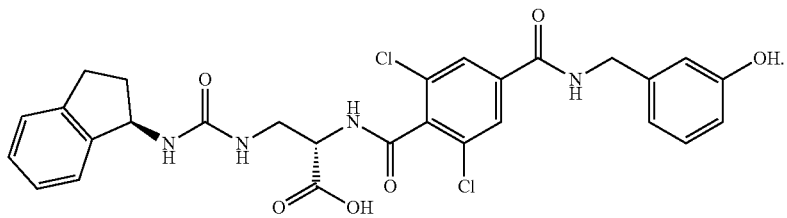
(SU15210-0095-01)
In embodiments, the compound is
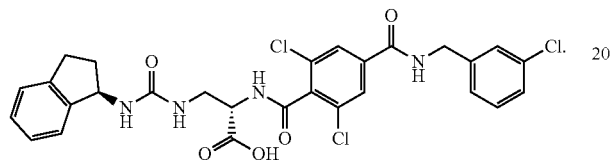
(SU15210-0185-01)
In embodiments, the compound is
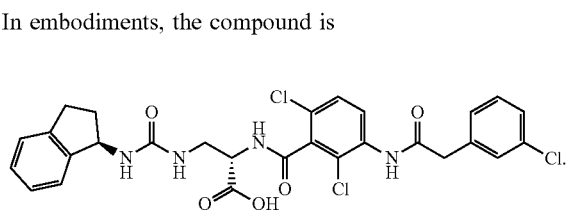
(SU15210-0099-01)
In embodiments, the compound is
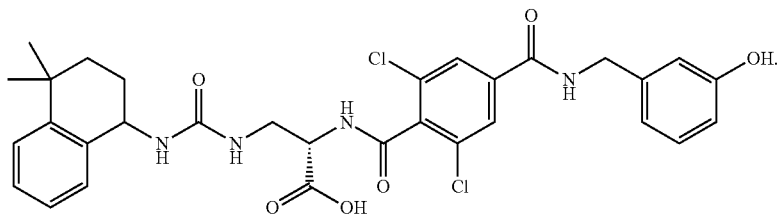
(SU15210-0187-01)
In embodiments, the compound is
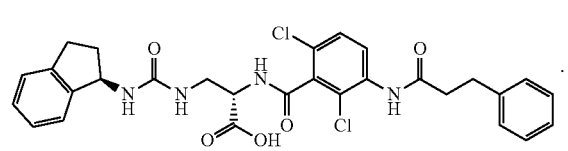
(SU15210-0124-01)
In embodiments, the compound is
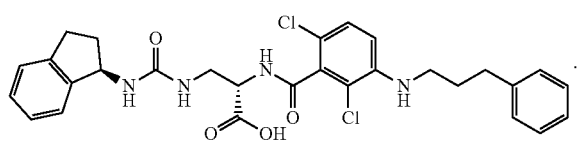
(SU15210-0098-01)

In embodiments, the compound is
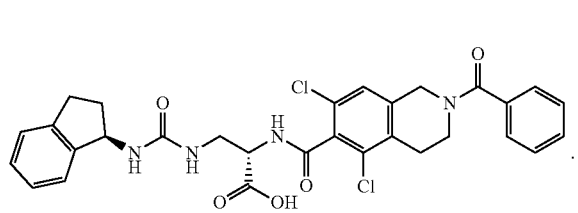
(SU15210-0173-01)
In embodiments, the compound is
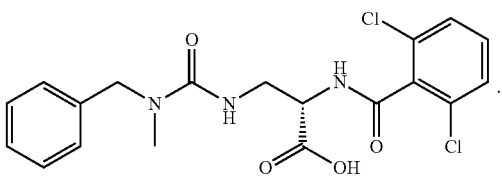
(SU15210-0167-01)
In embodiments, the compound is
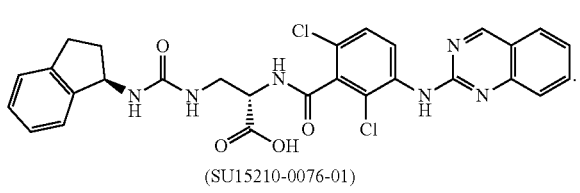 [SMILES: O=C(NC[C@H](NC(=O)c1c(Cl)ccc(Nc2ncc3ccccc3n2)c1Cl)C(=O)O)N[C@@H]1CCc2ccccc21]
(SU15210-0076-01)
In embodiments, the compound is
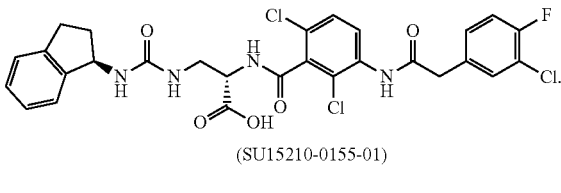 [SMILES: O=C(Cc1ccc(F)c(Cl)c1)Nc1ccc(Cl)c(C(=O)N[C@@H](CNC(=O)N[C@@H]2CCc3ccccc32)C(=O)O)c1Cl]
(SU15210-0155-01)
In embodiments, the compound is
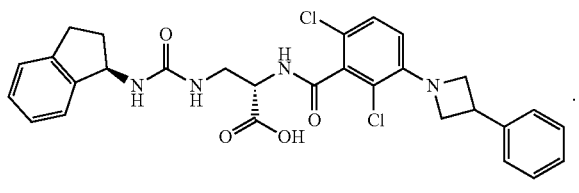
(SU15210-0080-01)
In embodiments, the compound is
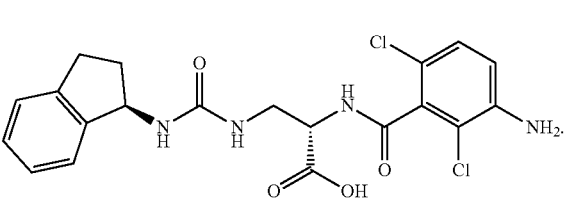
(SU15210-0084-01)
In embodiments, the compound is
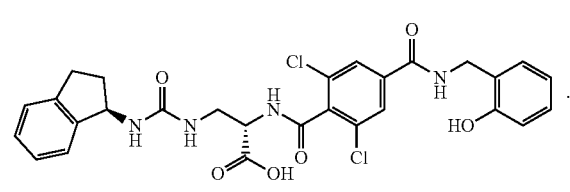
(SU15210-0172-01)
In embodiments, the compound is
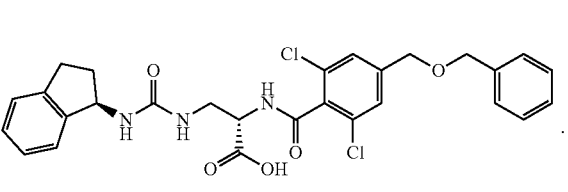
(SU15210-0189-01)
In embodiments, the compound is
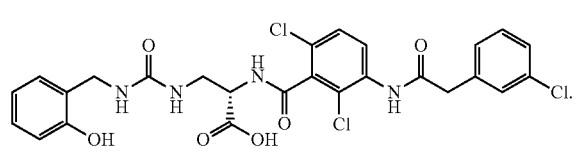
(SU15210-0159-01)
In embodiments, the compound is
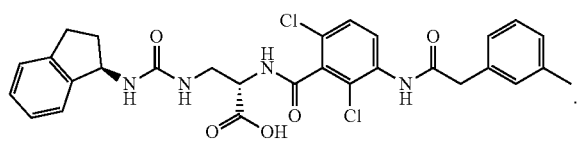
(SU15210-0156-01)

201
In embodiments, the compound is
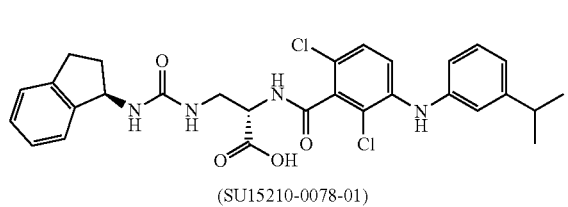
(SU15210-0078-01)
In embodiments, the compound is
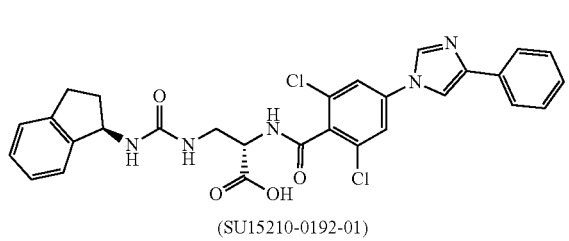
(SU15210-0192-01)
In embodiments, the compound is
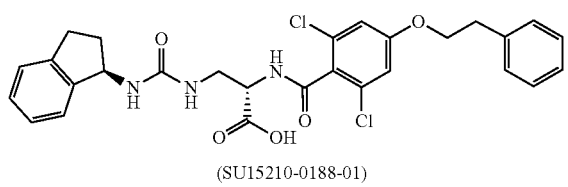
(SU15210-0188-01)
In embodiments, the compound is
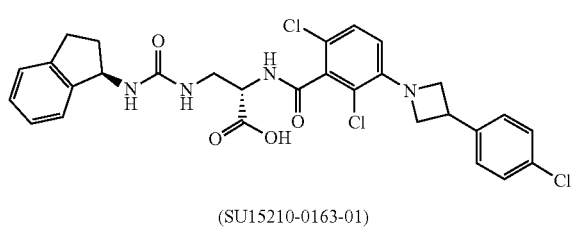 [SMILES: O=C(NC[C@H](NC(=O)c1c(Cl)ccc(N2CC(c3ccc(Cl)cc3)C2)c1Cl)C(=O)O)N[C@@H]1CCc2ccccc21]
(SU15210-0163-01)
202
In embodiments, the compound is
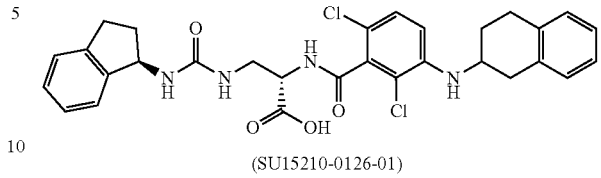
(SU15210-0126-01)
In embodiments, the compound is
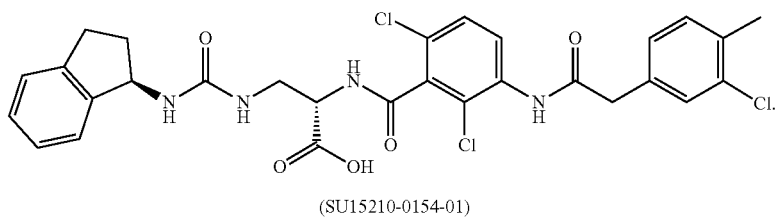 [SMILES: Cc1ccc(CC(=O)Nc2ccc(Cl)c(C(=O)N[C@@H](CNC(=O)N[C@@H]3CCc4ccccc43)C(=O)O)c2Cl)cc1Cl]
(SU15210-0154-01)
In embodiments, the compound is
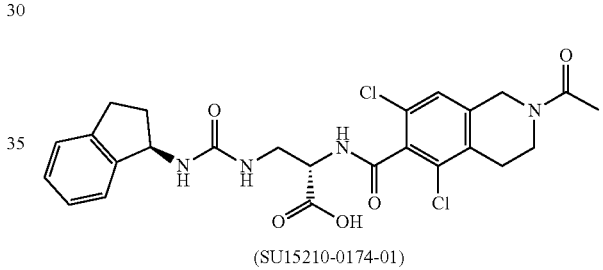
(SU15210-0174-01)
In embodiments, the compound is
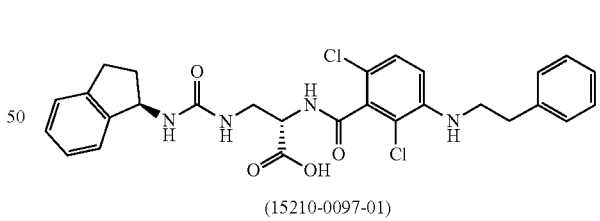
(15210-0097-01)
In embodiments, the compound is
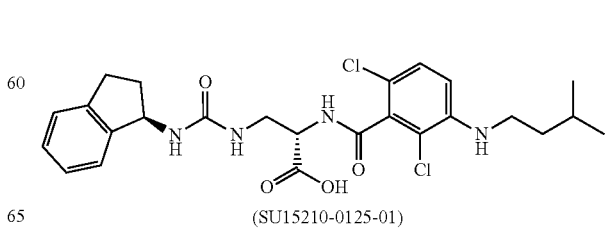
(SU15210-0125-01)

In embodiments, the compound is
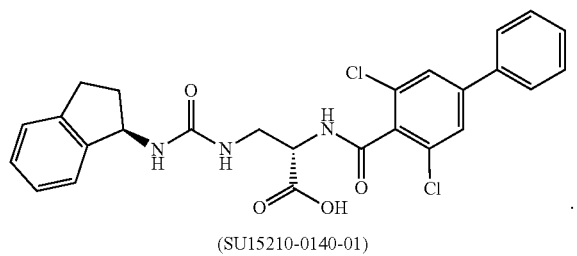 [SMILES: O=C(NC[C@H](NC(=O)c1c(Cl)cc(-c2ccccc2)cc1Cl)C(=O)O)N[C@@H]1CCc2ccccc21]
(SU15210-0140-01)
In embodiments, the compound is
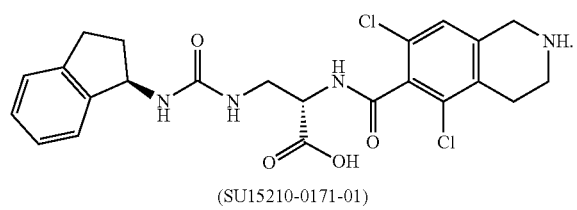 [SMILES: O=C(NC[C@H](NC(=O)c1c(Cl)cc2c(c1Cl)CCNC2)C(=O)O)N[C@@H]1CCc2ccccc21]
(SU15210-0171-01)
In embodiments, the compound is
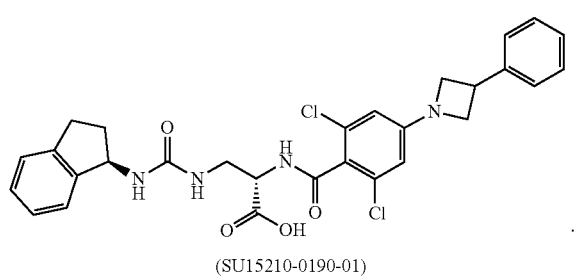 [SMILES: O=C(NC[C@H](NC(=O)c1c(Cl)cc(N2CC(c3ccccc3)C2)cc1Cl)C(=O)O)N[C@@H]1CCc2ccccc21]
(SU15210-0190-01)
In embodiments, the compound is
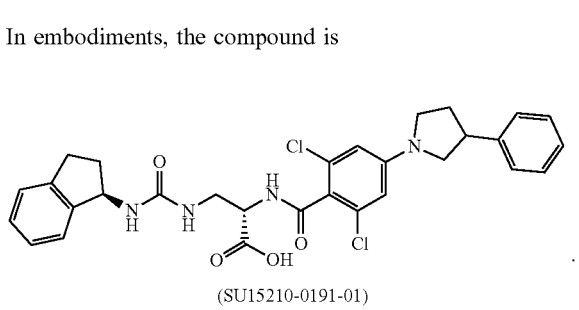
(SU15210-0191-01)
In embodiments, the compound is
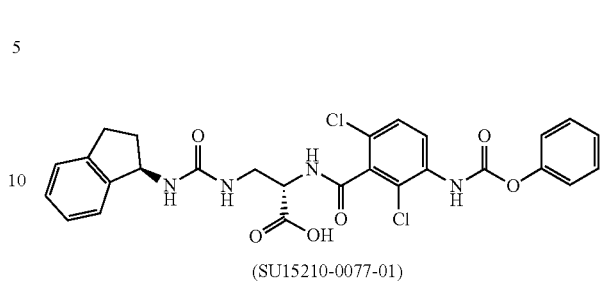
(SU15210-0077-01)
In embodiments, the compound is
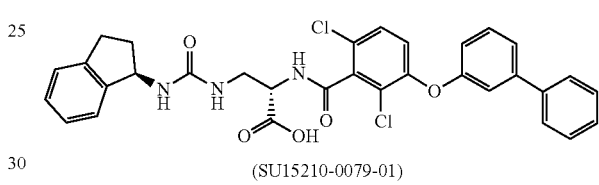
(SU15210-0079-01)
In embodiments, the compound is
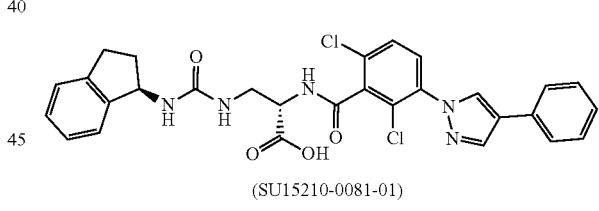
(SU15210-0081-01)
In embodiments, the compound is
(SU15210-0127-01)
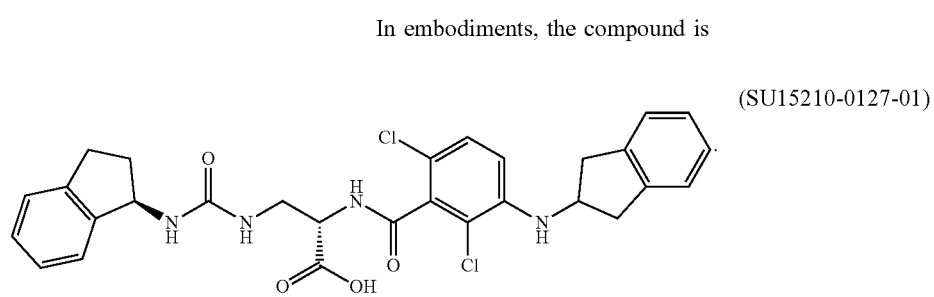

In embodiments, the compound is
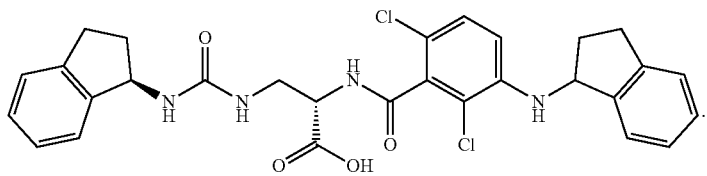
(SU15210-0128-01)
In embodiments, the compound is
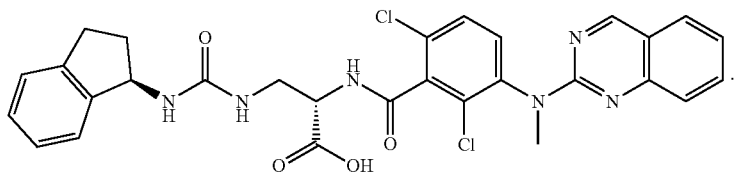
(SU15210-0145-01)
In embodiments, the compound is
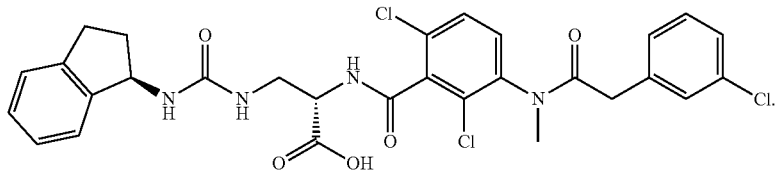
(SU15210-0146-01)
In embodiments, the compound is
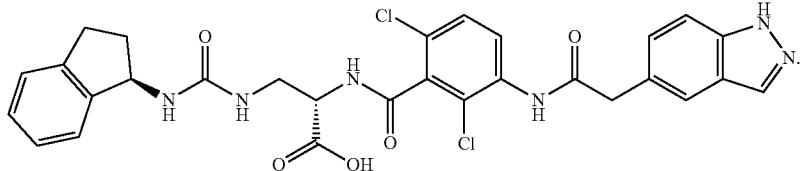
(SU15210-0157-01)
In embodiments, the compound is
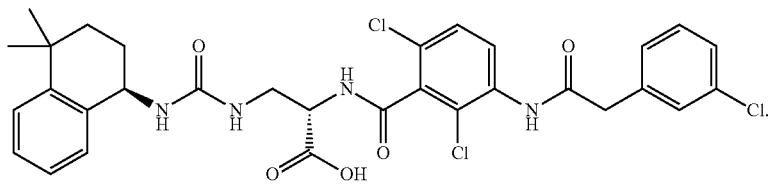
(SU15210-0158-01)

In embodiments, the compound is
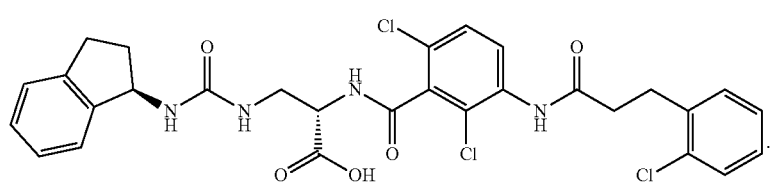
(SU15210-0160-01)
In embodiments, the compound is
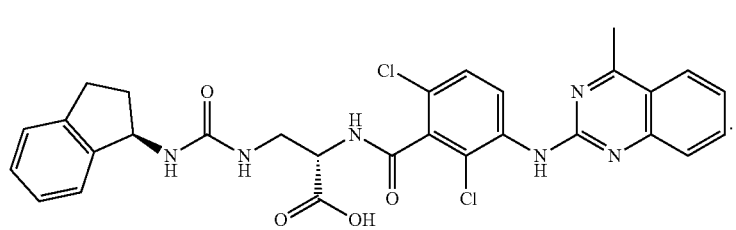
(SU15210-0161-01)
In embodiments, the compound is
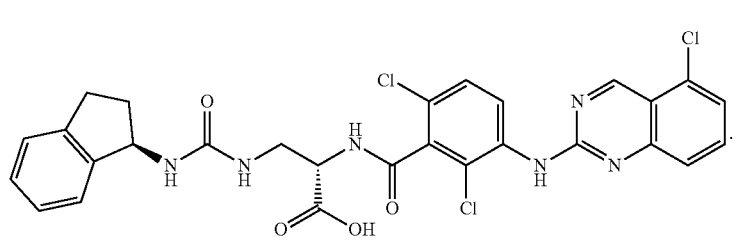
(SU15210-0162-01)
In embodiments, the compound is
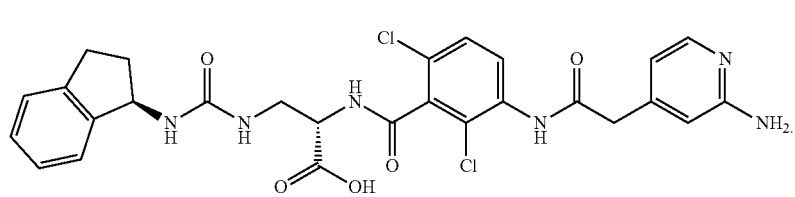
(SU15210-0165-01)
In embodiments, the compound is
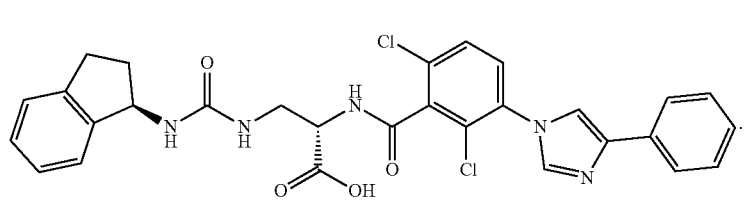
(SU15210-0175-01)

In embodiments, the compound is
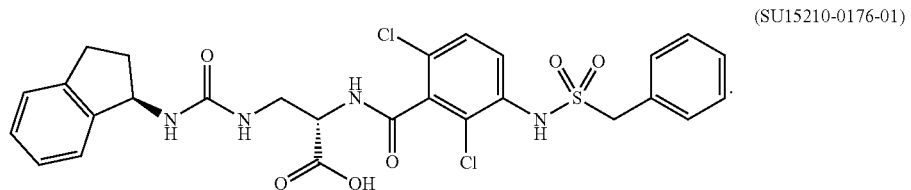 [SMILES: O=C(NC[C@H](NC(=O)c1c(Cl)ccc(NS(=O)(=O)Cc2ccccc2)c1Cl)C(=O)O)N[C@@H]1CCc2ccccc21]
(SU15210-0176-01)
In embodiments, the compound is
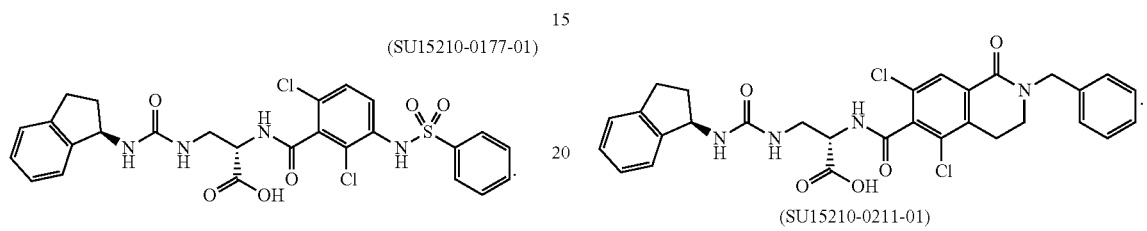
(SU15210-0177-01)
In embodiments, the compound is
(SU15210-0211-01)
In embodiments, the compound is
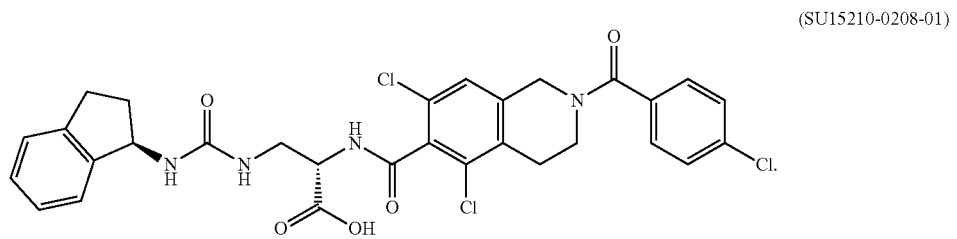 [SMILES: O=C(NC[C@H](NC(=O)c1c(Cl)cc2c(c1Cl)CCN(C(=O)c1ccc(Cl)cc1)C2)C(=O)O)N[C@@H]1CCc2ccccc21]
(SU15210-0208-01)
In embodiments, the compound is
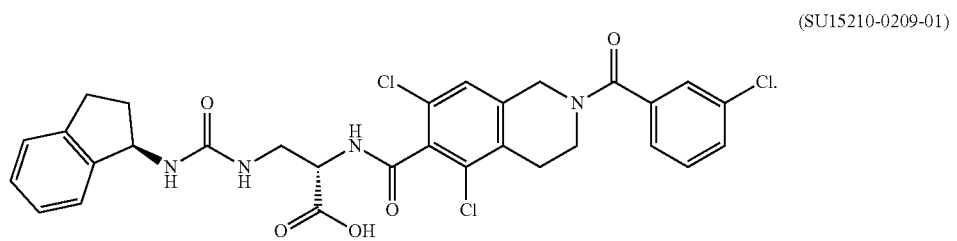 [SMILES: O=C(NC[C@H](NC(=O)c1c(Cl)cc2c(c1Cl)CCN(C(=O)c1cccc(Cl)c1)C2)C(=O)O)N[C@@H]1CCc2ccccc21]
(SU15210-0209-01)
In embodiments, the compound is
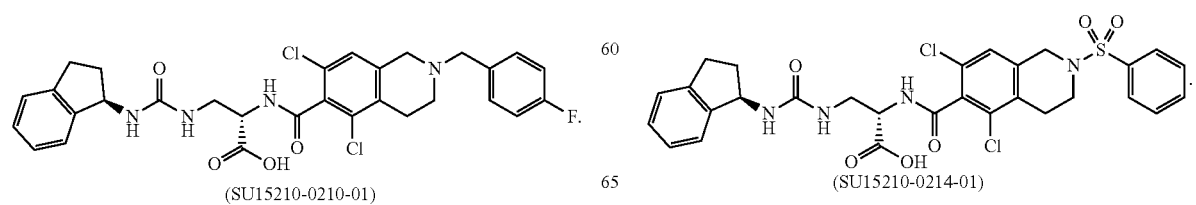
(SU15210-0210-01)
In embodiments, the compound is
(SU15210-0214-01)

In embodiments, the compound is
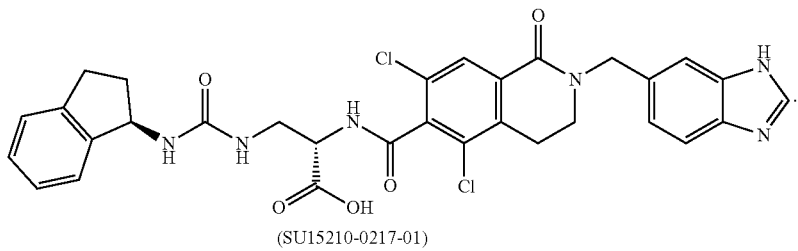 [SMILES: O=C(NC[C@H](NC(=O)c1c(Cl)cc2c(c1Cl)CCN(Cc1ccc3nc[nH]c3c1)C2=O)C(=O)O)N[C@@H]1CCc2ccccc21]
(SU15210-0217-01)
In embodiments, the compound is

(SU15210-0223-01) (SU15210-0227-01)
In embodiments, the compound is
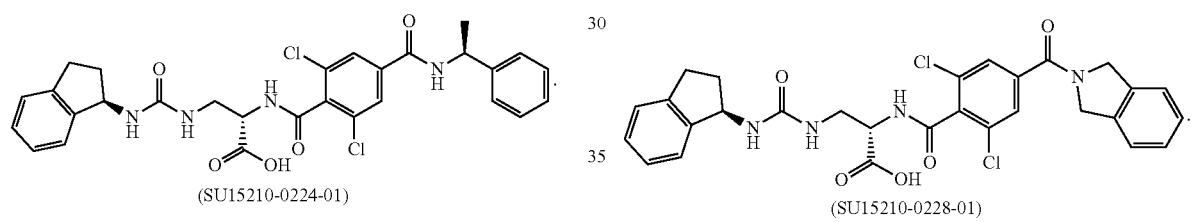
(SU15210-0224-01) (SU15210-0228-01)
In embodiments, the compound is
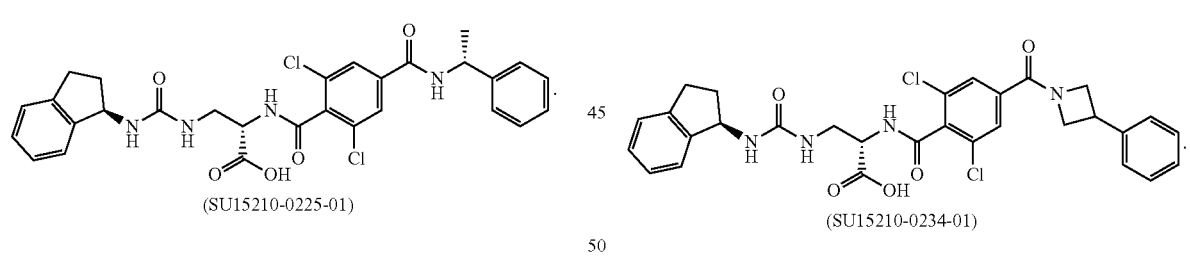
(SU15210-0225-01) (SU15210-0234-01)
In embodiments, the compound is
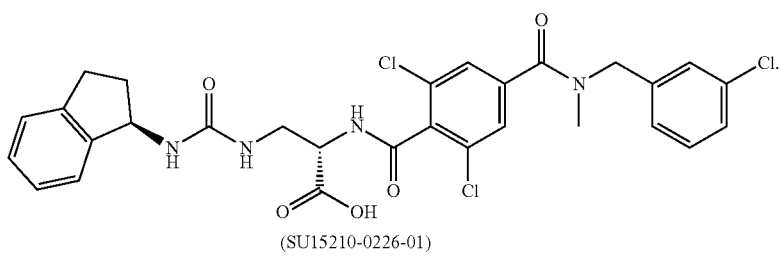 [SMILES: CN(Cc1cccc(Cl)c1)C(=O)c1cc(Cl)c(C(=O)N[C@@H](CNC(=O)N[C@@H]2CCc3ccccc32)C(=O)O)c(Cl)c1]
(SU15210-0226-01)

In embodiments, the compound is
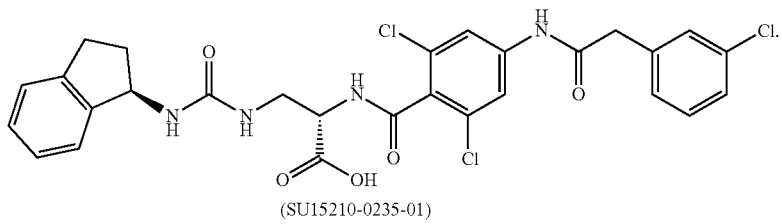 [SMILES: O=C(Cc1cccc(Cl)c1)Nc1cc(Cl)c(C(=O)N[C@@H](CNC(=O)N[C@@H]2CCc3ccccc32)C(=O)O)c(Cl)c1]
(SU15210-0235-01)
In embodiments, the compound is
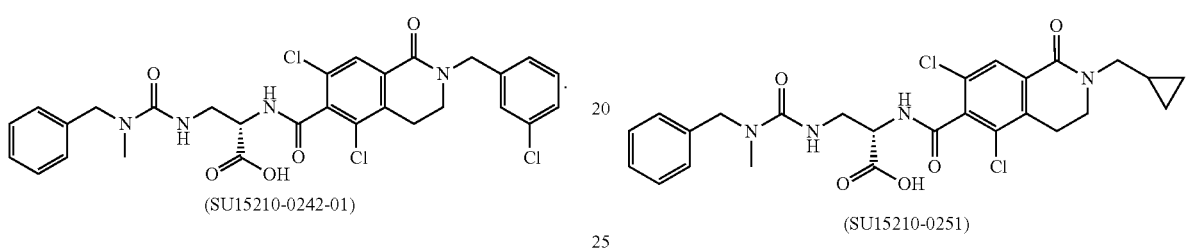
(SU15210-0242-01)      (SU15210-0251)
In embodiments, the compound is
In embodiments, the compound is
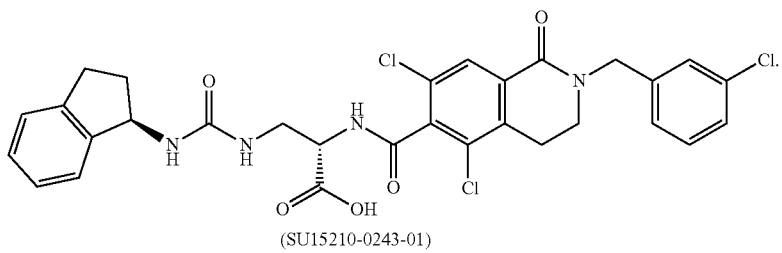 [SMILES: O=C(NC[C@H](NC(=O)c1c(Cl)cc2c(c1Cl)CCN(Cc1cccc(Cl)c1)C2=O)C(=O)O)N[C@@H]1CCc2ccccc21]
(SU15210-0243-01)
In embodiments, the compound is
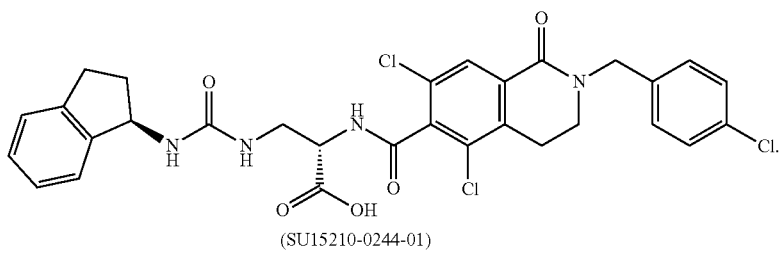 [SMILES: O=C(NC[C@H](NC(=O)c1c(Cl)cc2c(c1Cl)CCN(Cc1ccc(Cl)cc1)C2=O)C(=O)O)N[C@@H]1CCc2ccccc21]
(SU15210-0244-01)
In embodiments, the compound is
In embodiments, the compound is
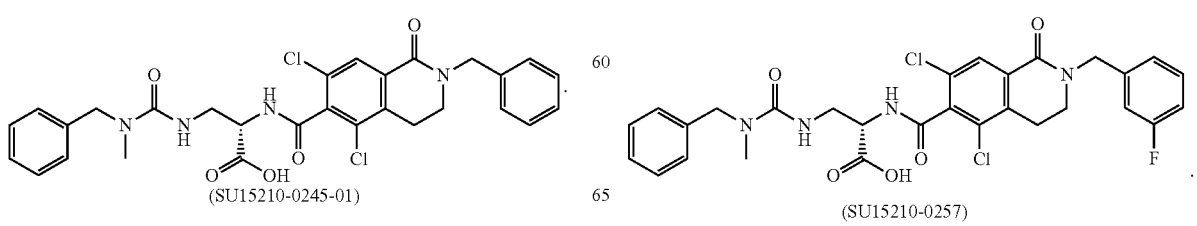
(SU15210-0245-01)      (SU15210-0257)

In embodiments, the compound is
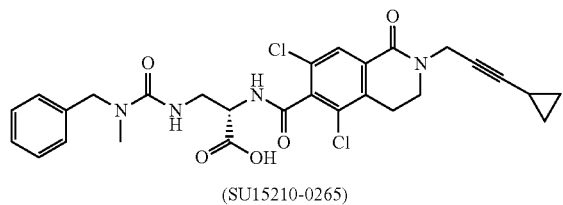
(SU15210-0265)
In embodiments, the compound is
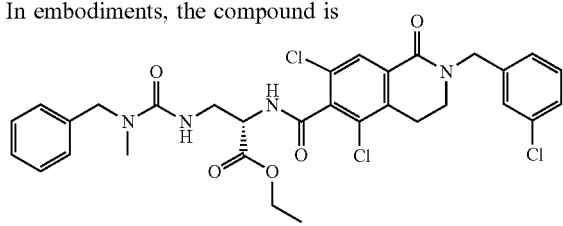
(SU15210-0270-01)
In embodiments, the compound is
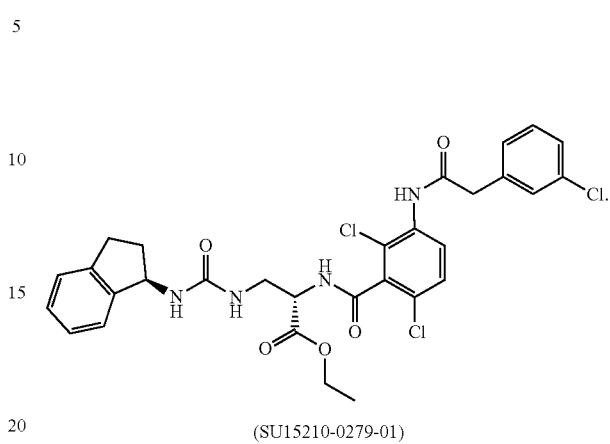
(SU15210-0279-01)
In embodiments, the compound is
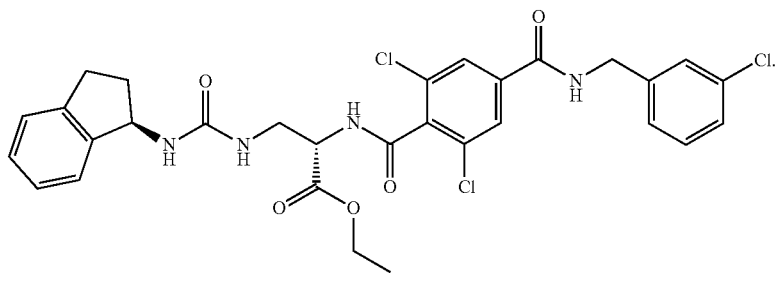
(SU15210-0289)
In embodiments, the compound is
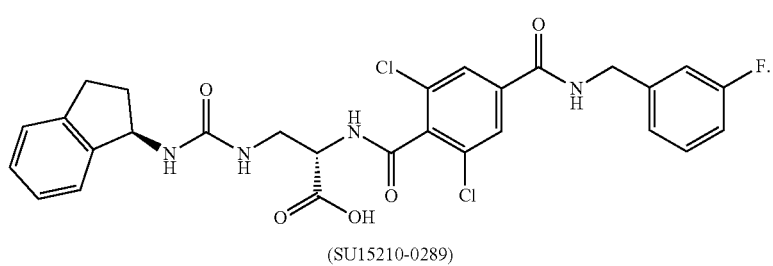 [SMILES: O=C(NC[C@H](NC(=O)c1c(Cl)cc(C(=O)NCc2cccc(F)c2)cc1Cl)C(=O)O)N[C@@H]1CCc2ccccc21]
(SU15210-0289)
In embodiments, the compound is
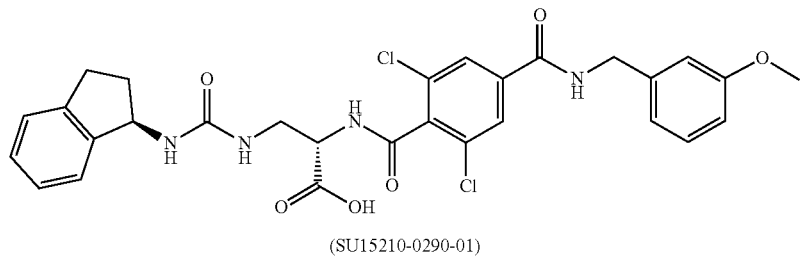
(SU15210-0290-01)

In embodiments, the compound is
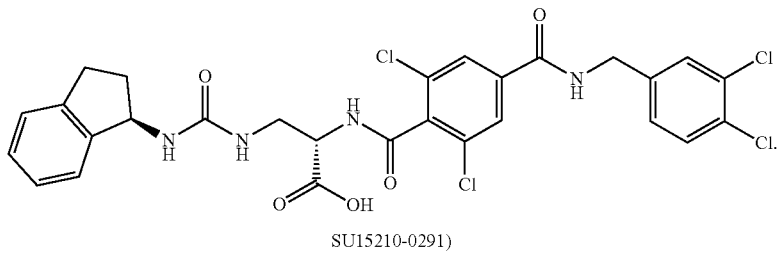 [SMILES: O=C(NC[C@H](NC(=O)c1c(Cl)cc(C(=O)NCc2ccc(Cl)c(Cl)c2)cc1Cl)C(=O)O)N[C@@H]1CCc2ccccc21]
SU15210-0291)
In embodiments, the compound is
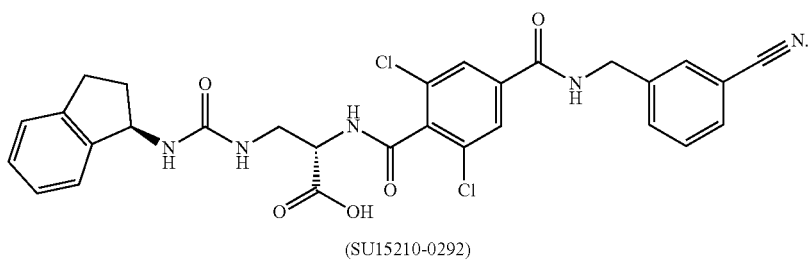 [SMILES: N#Cc1cccc(CNC(=O)c2cc(Cl)c(C(=O)N[C@@H](CNC(=O)N[C@@H]3CCc4ccccc43)C(=O)O)c(Cl)c2)c1]
(SU15210-0292)
In embodiments, the compound is
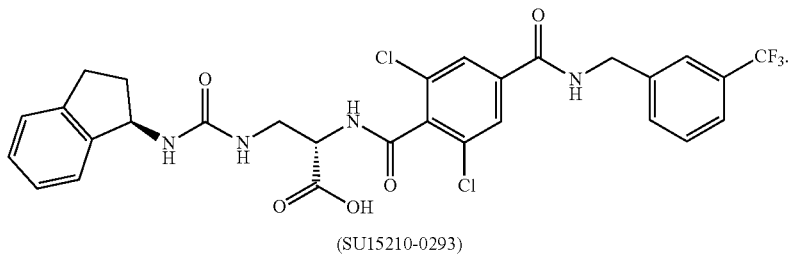 [SMILES: O=C(NC[C@H](NC(=O)c1c(Cl)cc(C(=O)NCc2cccc(C(F)(F)F)c2)cc1Cl)C(=O)O)N[C@@H]1CCc2ccccc21]
(SU15210-0293)
In embodiments, the compound is
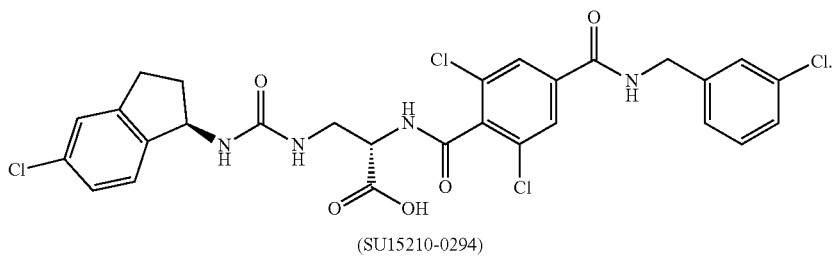 [SMILES: O=C(NC[C@H](NC(=O)c1c(Cl)cc(C(=O)NCc2cccc(Cl)c2)cc1Cl)C(=O)O)N[C@@H]1CCc2cc(Cl)ccc21]
(SU15210-0294)

In embodiments, the compound is

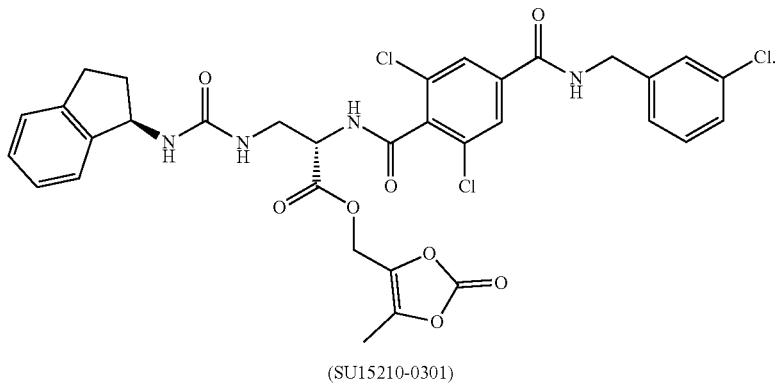 [SMILES: Cc1oc(=O)oc1COC(=O)[C@H](CNC(=O)N[C@@H]1CCc2ccccc21)NC(=O)c1c(Cl)cc(C(=O)NCc2cccc(Cl)c2)cc1Cl]

(SU15210-0301)

In embodiments, the compound is

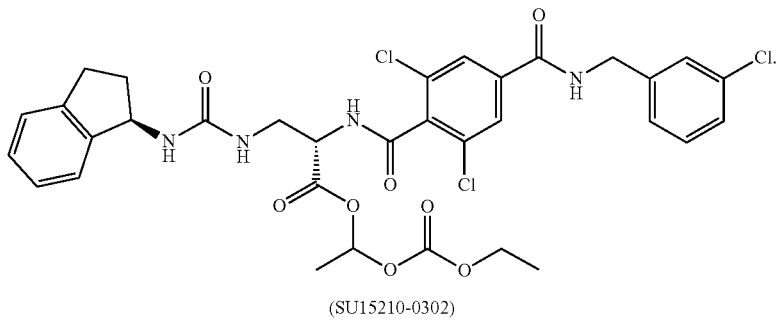 [SMILES: CCOC(=O)OC(C)OC(=O)[C@H](CNC(=O)N[C@@H]1CCc2ccccc21)NC(=O)c1c(Cl)cc(C(=O)NCc2cccc(Cl)c2)cc1Cl]

(SU15210-0302)

In embodiments, the compound is useful as a comparator compound. In embodiments, the comparator compound can be used to assess the activity of a test compound as set forth in an assay described herein (e.g., in the examples section, FIGURES, or tables).

In embodiments, the compound is a compound described herein (e.g., in an aspect, embodiment, example, table, FIGURE, or claim).

III. Pharmaceutical Compositions

In an aspect is provided a pharmaceutical composition including a compound described herein, or pharmaceutically acceptable salt thereof or a prodrug thereof, and a pharmaceutically acceptable excipient.

In embodiments of the pharmaceutical compositions, the compound, or pharmaceutically acceptable salt thereof or a prodrug thereof, is included in a therapeutically effective amount.

In embodiments, the pharmaceutical composition includes a second agent (e.g., therapeutic agent). In embodiments, the pharmaceutical composition includes a second agent (e.g., therapeutic agent) in a therapeutically effective amount. In embodiments, the second agent is an agent for treating asthma. In embodiments, the second agent is an anti-inflammatory agent. In embodiments, the second agent is an anti-autoimmune disease agent.

IV. Methods of Use

In an aspect is provided a method of treating asthma, the method including administering to a subject in need thereof an effective amount of a compound described herein, or a pharmaceutically acceptable salt thereof or a prodrug thereof. In embodiments, the method includes administering to a subject in need thereof a therapeutically effective amount of a compound described herein, or a pharmaceutically acceptable salt thereof or a prodrug thereof.

In embodiments, the asthma is severe asthma. In embodiments, the asthma is acute severe asthma. In embodiments, the asthma is moderate asthma.

In embodiments, the administering is by inhalation.

In an aspect is provided a method of treating an inflammatory disease, the method including administering to a subject in need thereof an effective amount of a compound described herein, or a pharmaceutically acceptable salt thereof or a prodrug thereof. In embodiments, the method includes administering to a subject in need thereof a therapeutically effective amount of a compound described herein, or a pharmaceutically acceptable salt thereof or a prodrug thereof.

In embodiments, the inflammatory disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis.

In an aspect is provided a method of treating an autoimmune disease, the method including administering to a subject in need thereof an effective amount of a compound described herein, or a pharmaceutically acceptable salt thereof or a prodrug thereof. In embodiments, the method includes administering to a subject in need thereof a therapeutically effective amount of a compound described herein, or a pharmaceutically acceptable salt thereof or a prodrug thereof.

In embodiments, the autoimmune disease is arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis.

In embodiments, the method includes administering a second agent (e.g., therapeutic agent). In embodiments, the method includes administering a second agent (e.g., therapeutic agent) in a therapeutically effective amount. In embodiments, the second agent is an anti-inflammatory agent.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A compound, or a pharmaceutically acceptable salt thereof or a prodrug thereof, having the formula:

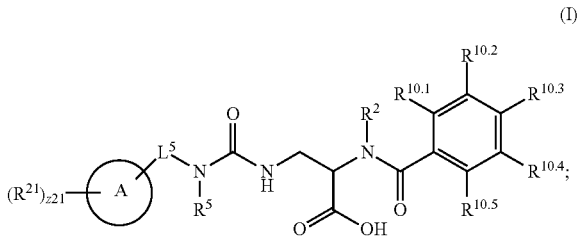

(I)

wherein
Ring A is cycloalkyl, heterocycloalkyl, aryl, or heteroaryl;
$R^2$ is hydrogen or substituted or unsubstituted alkyl;
$R^5$ is hydrogen or unsubstituted $C_1$-$C_3$ alkyl;
$L^5$ is a bond or unsubstituted $C_1$-$C_3$ alkylene;
$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $-C(O)R^{10.2C}$, $-C(O)OR^{10.2C}$, $-C(O)NR^{10.2A}R^{10.2B}$, $-OR^{10.2D}$, $-SR^{10.2D}$, $TNR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, $-L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$, $-L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$, $-L^{10.4}$-$R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $-NR^{10.5A}C(O)OR^{10.5C}$, $-NR^{10.5A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $-SR^{21D}$ $NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, —NHS(O)$_2$—, —S(O)$_2$NH—, —C(S)—, substituted or unsubstituted alkylene, or substituted or unsubstituted heteroalkylene;

R$^{22}$, R$^{23}$, and R$^{24}$ are independently substituted or unsubstituted cycloalkyl, substituted or unsubstituted heterocycloalkyl, substituted or unsubstituted aryl, or substituted or unsubstituted heteroaryl;

R$^{10.1A}$, R$^{10.1B}$, R$^{10.1C}$, R$^{10.1D}$, R$^{10.2A}$, R$^{10.2B}$, R$^{10.2C}$, R$^{10.2D}$, R$^{10.3A}$, R$^{10.3B}$, R$^{10.3C}$, R$^{10.3D}$, R$^{10.4A}$, R$^{10.4B}$, R$^{10.4C}$, R$^{10.4D}$, R$^{10.5A}$, R$^{10.5B}$, R$^{10.5C}$, R$^{10.5D}$, R$^{21A}$, R$^{21B}$, R$^{21C}$, and R$^{21D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10.1A}$ and R$^{10.1B}$ substituents bonded to the same nitrogen atom may be joined to form a substituted or unsubstituted heterocycloalkyl or substituted or unsubstituted heteroaryl; R$^{10.2A}$ and R$^{10.2B}$ substituents bonded to the same nitrogen atom may be joined to form a substituted or unsubstituted heterocycloalkyl or substituted or unsubstituted heteroaryl; R$^{10.3A}$, and R$^{10.3B}$ substituents bonded to the same nitrogen atom may be joined to form a substituted or unsubstituted heterocycloalkyl or substituted or unsubstituted heteroaryl; R$^{10.4A}$ and R$^{10.4B}$ substituents bonded to the same nitrogen atom may be joined to form a substituted or unsubstituted heterocycloalkyl or substituted or unsubstituted heteroaryl; R$^{10.5A}$ and R$^{10.5B}$ substituents bonded to the same nitrogen atom may be joined to form a substituted or unsubstituted heterocycloalkyl or substituted or unsubstituted heteroaryl; R$^{21A}$ and R$^{21B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, and n21 are independently an integer from 0 to 4;

m10.1, m10.2, m10.3, m10.4, m10.5, m21, v10.1, v10.2, v10.3, v10.4, v10.5, and v21 are independently 1 or 2;

X$^{10.1}$, X$^{10.2}$, X$^{10.3}$, X$^{10.4}$, X$^{10.5}$, and X$^{21}$ are independently —F, —Cl, —Br, or —I;

z21 is an integer from 0 to 11;

wherein at least one of R$^{10.1}$ or R$^{10.5}$ is not hydrogen; and wherein at least one of R$^{10.2}$, R$^{10.3}$, or R$^{10.4}$ is -L$^{10.2}$-R$^{22}$, -L$^{10.3}$-R$^{23}$, or -L$^{10.4}$-R$^{24}$, respectively.

Embodiment P2. The compound of embodiment P1, wherein Ring A is a fused bicyclic cycloalkyl or phenyl.

Embodiment P3. The compound of embodiment P1, wherein

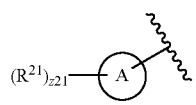

is

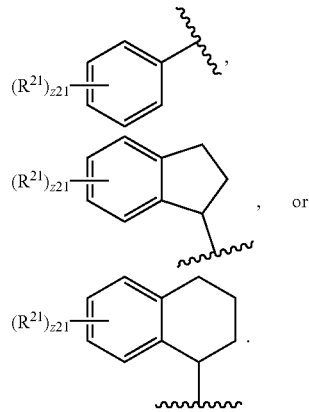

Embodiment P4. The compound of one of embodiments P1 to P3, wherein R$^{21}$ is independently halogen, —OH, or substituted or unsubstituted C$_1$-C$_4$ alkyl.

Embodiment P5. The compound of one of embodiments P1 to P3, wherein R$^{21}$ is independently —OH or unsubstituted methyl.

Embodiment P6. The compound of one of embodiments P1 to P5, wherein z21 is an integer from 0 to 3.

Embodiment P7. The compound of embodiment P1, wherein

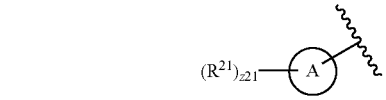

is

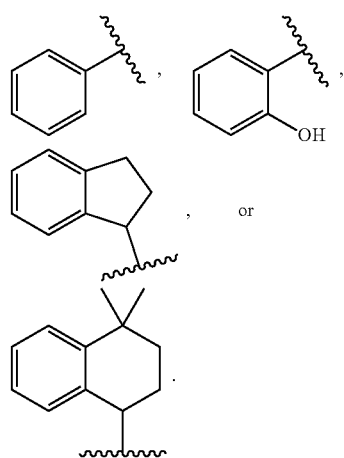

Embodiment P8. The compound of one of embodiments P1 to P7, wherein R$^2$ is hydrogen or unsubstituted C$_1$-C$_3$ alkyl.

Embodiment P9. The compound of one of embodiments P1 to P7, wherein R$^2$ is hydrogen.

Embodiment P10. The compound of one of embodiments P1 to P7, wherein R$^2$ is unsubstituted methyl.

Embodiment P11. The compound of one of embodiments P1 to P10, wherein R$^5$ is hydrogen.

Embodiment P12. The compound of one of embodiments P1 to P10, wherein $R^5$ is unsubstituted methyl.

Embodiment P13. The compound of one of embodiments P1 to P12, wherein $L^5$ is a bond.

Embodiment P14. The compound of one of embodiments P1 to P12, wherein $L^5$ is unsubstituted methylene.

Embodiment P15. The compound of one of embodiments P1 to P14, wherein $R^{10.1}$ is halogen, substituted or unsubstituted $C_1$-$C_5$ alkyl, or substituted or unsubstituted 2 to 5 membered heteroalkyl.

Embodiment P16. The compound of one of embodiments P1 to P14, wherein $R^{10.1}$ is halogen or unsubstituted methyl.

Embodiment P17. The compound of one of embodiments P1 to P14, wherein $R^{10.1}$ is —Cl.

Embodiment P18. The compound of one of embodiments P1 to P17, wherein $R^{10.2}$ is hydrogen or -$L^{10.2}$-$R^{22}$.

Embodiment P19. The compound of embodiment P18, wherein $L^{10.2}$ is a bond, —NH—, —O—, —C(O)—, —NHC(O)O—, —NHS(O)$_2$—, or substituted or unsubstituted 2 to 5 membered heteroalkylene.

Embodiment P20. The compound of embodiment P18, wherein $L^{10.2}$ is a bond, —NH—, —O—, —C(O)—, —NC(O)O—, —NHS(O)$_2$—,

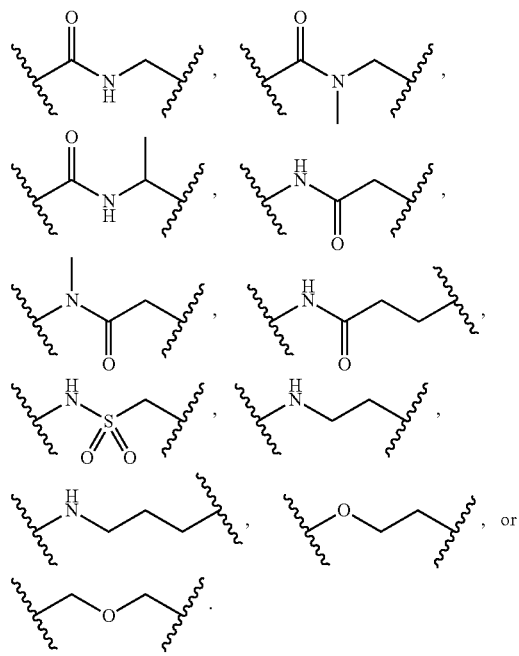

.

Embodiment P21. The compound of one of embodiments P1 to P20, wherein $R^{22}$ is $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl; and $R^{32}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P22. The compound of embodiment P21, wherein $R^{22}$ is

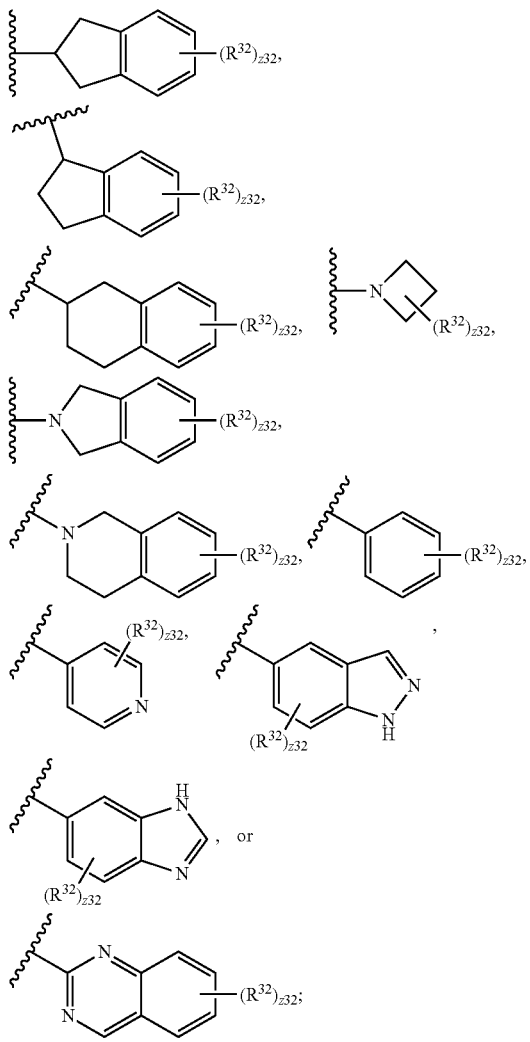

and z32 is an integer from 0 to 10.

Embodiment P23. The compound of one of embodiments P21 to P22, wherein $R^{32}$ is independently halogen, —CF$_3$, —OH, —NH$_2$, substituted or unsubstituted $C_1$-$C_4$ alkyl, substituted or unsubstituted 2 to 5 membered heteroalkyl, or substituted or unsubstituted phenyl.

Embodiment P24. The compound of one of embodiments P1 to P21, wherein $R^{22}$ is

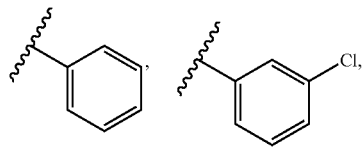

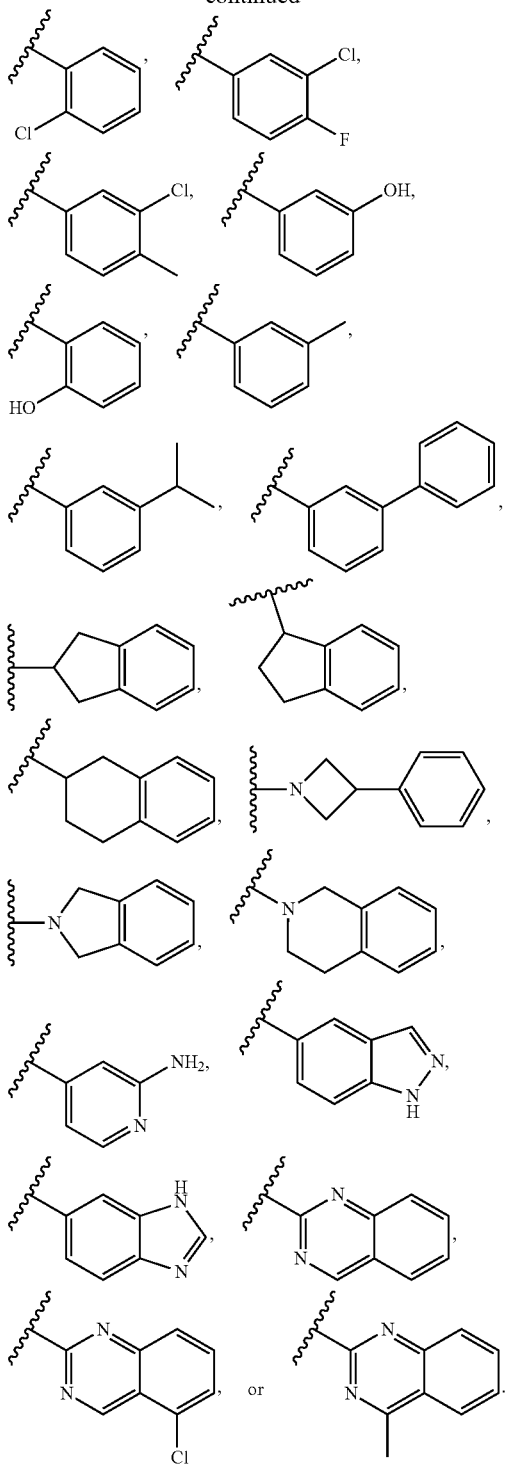

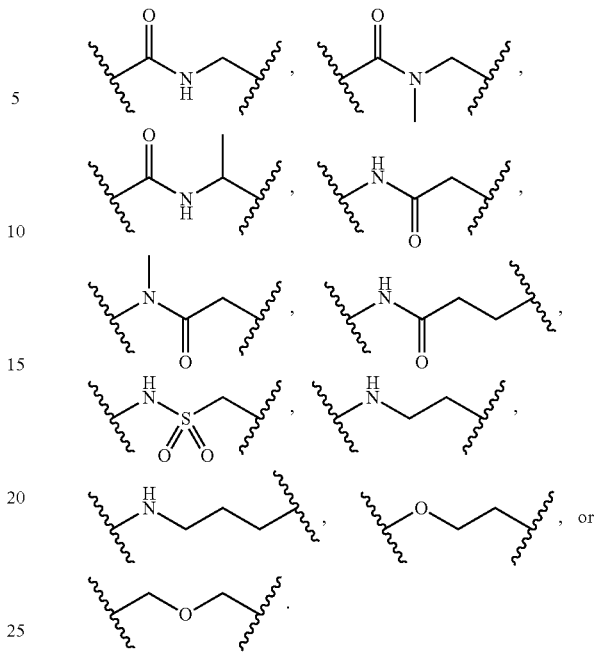

Embodiment P25. The compound of one of embodiments P1 to P24, wherein $R^{10.3}$ is hydrogen or -$L^{10.3}$-$R^{23}$.

Embodiment P26. The compound of one of embodiments P1 to P25, wherein $L^{10.3}$ is a bond, —NH—, —O—, —C(O)—, —NHC(O)O—, —NHS(O)$_2$—, or substituted or unsubstituted 2 to 5 membered heteroalkylene.

Embodiment P27. The compound of one of embodiments P1 to P25, wherein $L^{10.3}$ is a bond, —NH—, —O—, —C(O)—, —NHC(O)O—, —NHS(O)$_2$—, Embodiment P28. The compound of one of embodiments P1 to P27, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P29. The compound of embodiment P28, wherein $R^{23}$ is

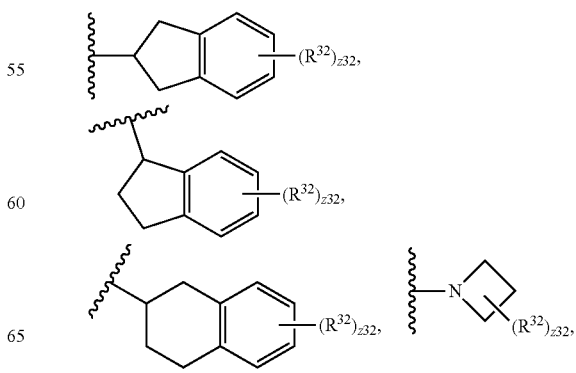

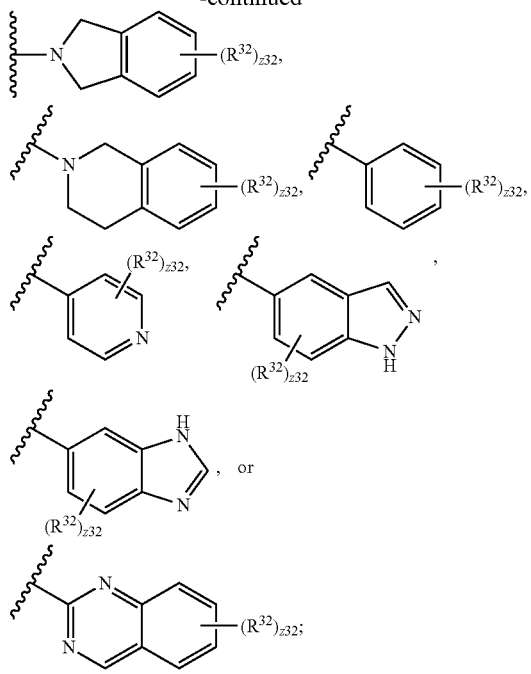

and
z33 is an integer from 0 to 10.

Embodiment P30. The compound of one of embodiments P28 to P29, wherein $R^{33}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl.

Embodiment P31. The compound of one of embodiments P1 to P28, wherein $R^{23}$ is

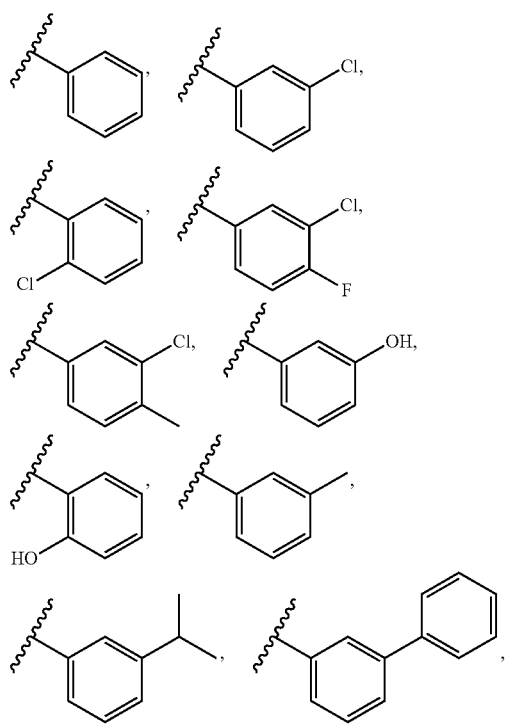

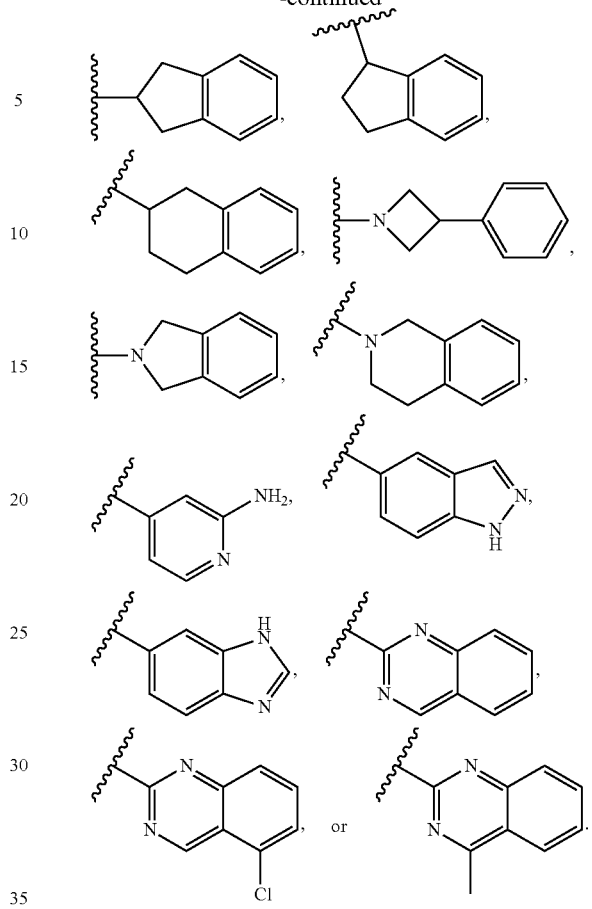

Embodiment P32. The compound of one of embodiments P1 to P31, wherein $R^{10.4}$ is hydrogen or -$L^{10.4}$-$R^{24}$.

Embodiment P33. The compound of one of embodiments P1 to P32, wherein $L^{10.4}$ is a bond, —NH—, —O—, —C(O)—, —NHC(O)O—, —NHS(O)$_2$—, or substituted or unsubstituted 2 to 5 membered heteroalkylene.

Embodiment P34. The compound of one of embodiments P1 to P32, wherein $L^{10.4}$ is a bond, —NH—, —O—, —C(O)—, —NHC(O)O—, —NHS(O)$_2$—,

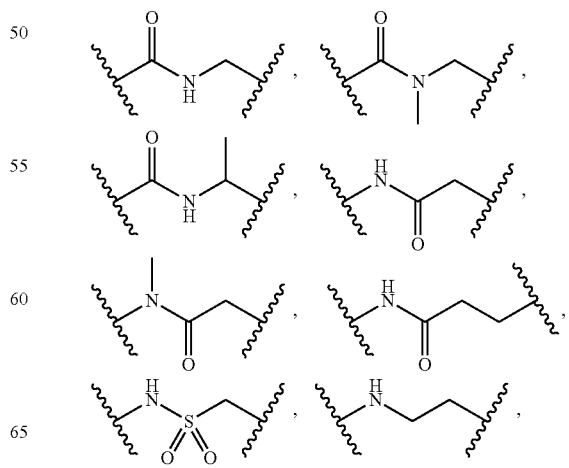

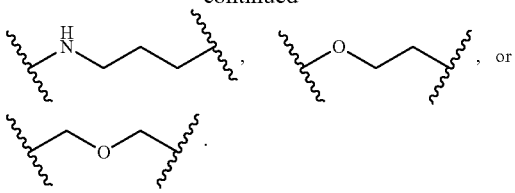, 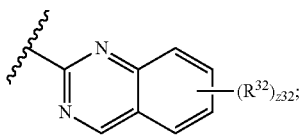

Embodiment P35. The compound of one of embodiments P1 to P34, wherein $R^{24}$ is $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl; and $R^{34}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P36. The compound of embodiment P35, wherein $R^{24}$ is

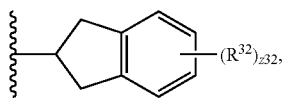

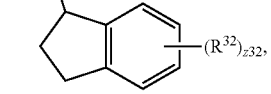

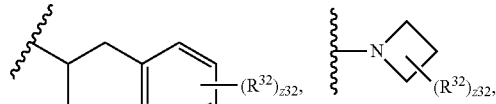

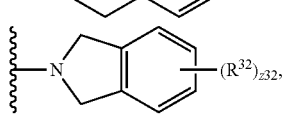

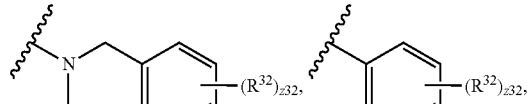

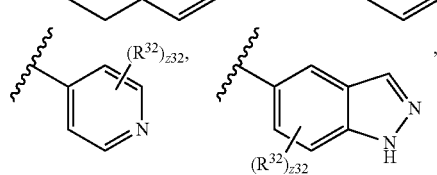

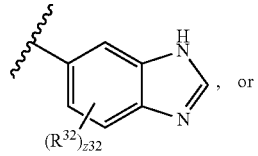, or and z34 is an integer from 0 to 10.

Embodiment P37. The compound of one of embodiments P35 to P36, wherein $R^{34}$ is independently halogen, —CF$_3$, —OH, —NH$_2$, substituted or unsubstituted C$_1$-C$_4$ alkyl, substituted or unsubstituted 2 to 5 membered heteroalkyl, or substituted or unsubstituted phenyl.

Embodiment P38. The compound of one of embodiments P1 to P35, wherein $R^{24}$ is

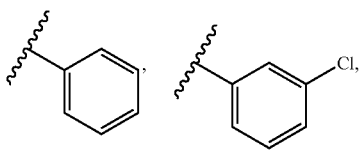

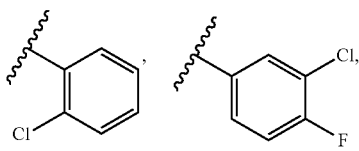

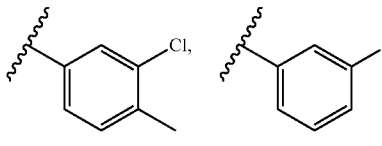

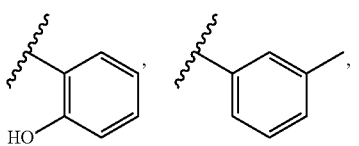

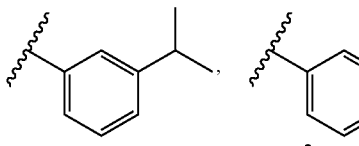

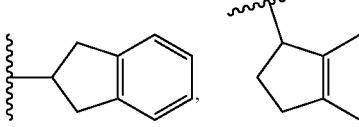

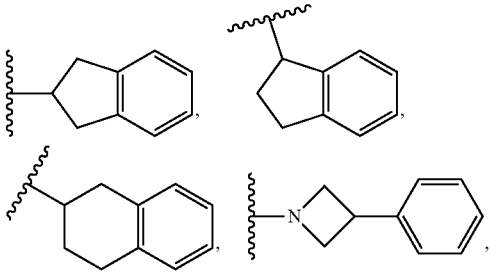

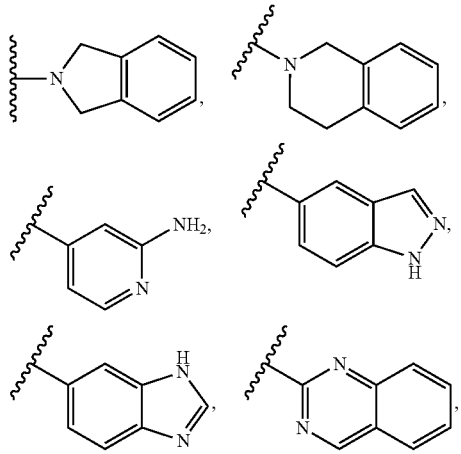
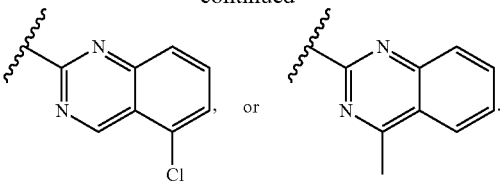

Embodiment P39. The compound of one of embodiments P1 to P38, wherein $R^{10.5}$ is hydrogen, halogen, substituted or unsubstituted $C_1$-$C_5$ alkyl, or substituted or unsubstituted 2 to 5 membered heteroalkyl.

Embodiment P40. The compound of one of embodiments P1 to P38, wherein $R^{10.5}$ is halogen or unsubstituted methyl.

Embodiment P41. The compound of one of embodiments P1 to P38, wherein $R^{10.5}$ is —Cl.

Embodiment P42. The compound of embodiment P1, having the formula

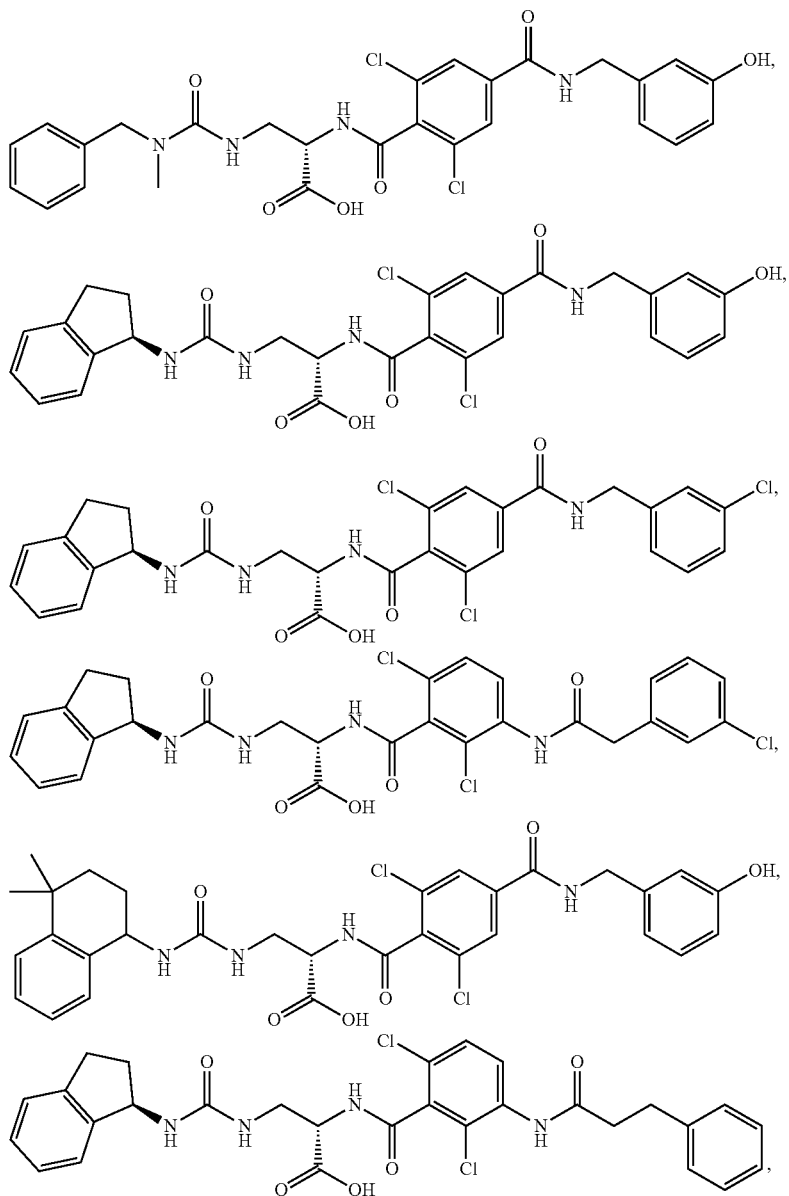

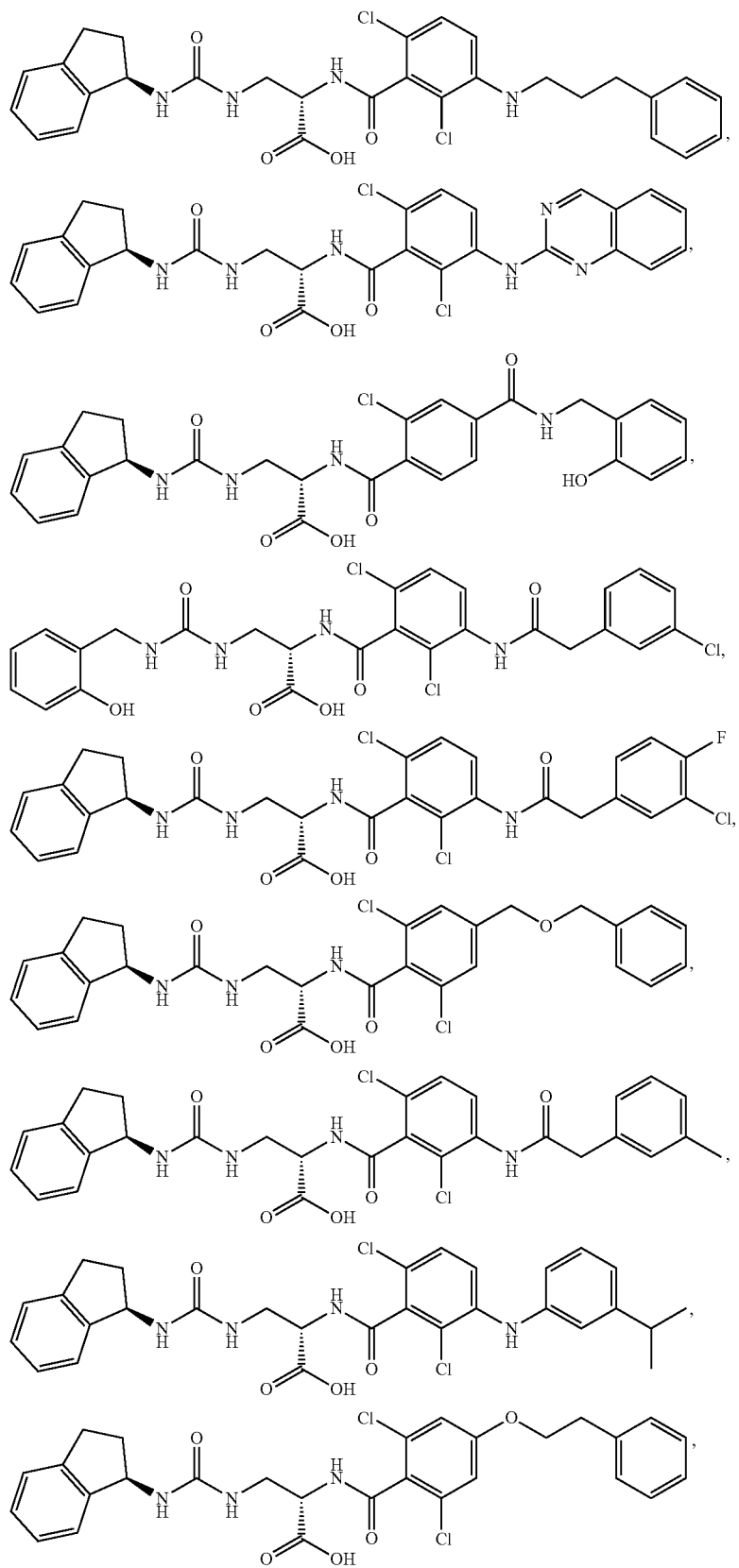

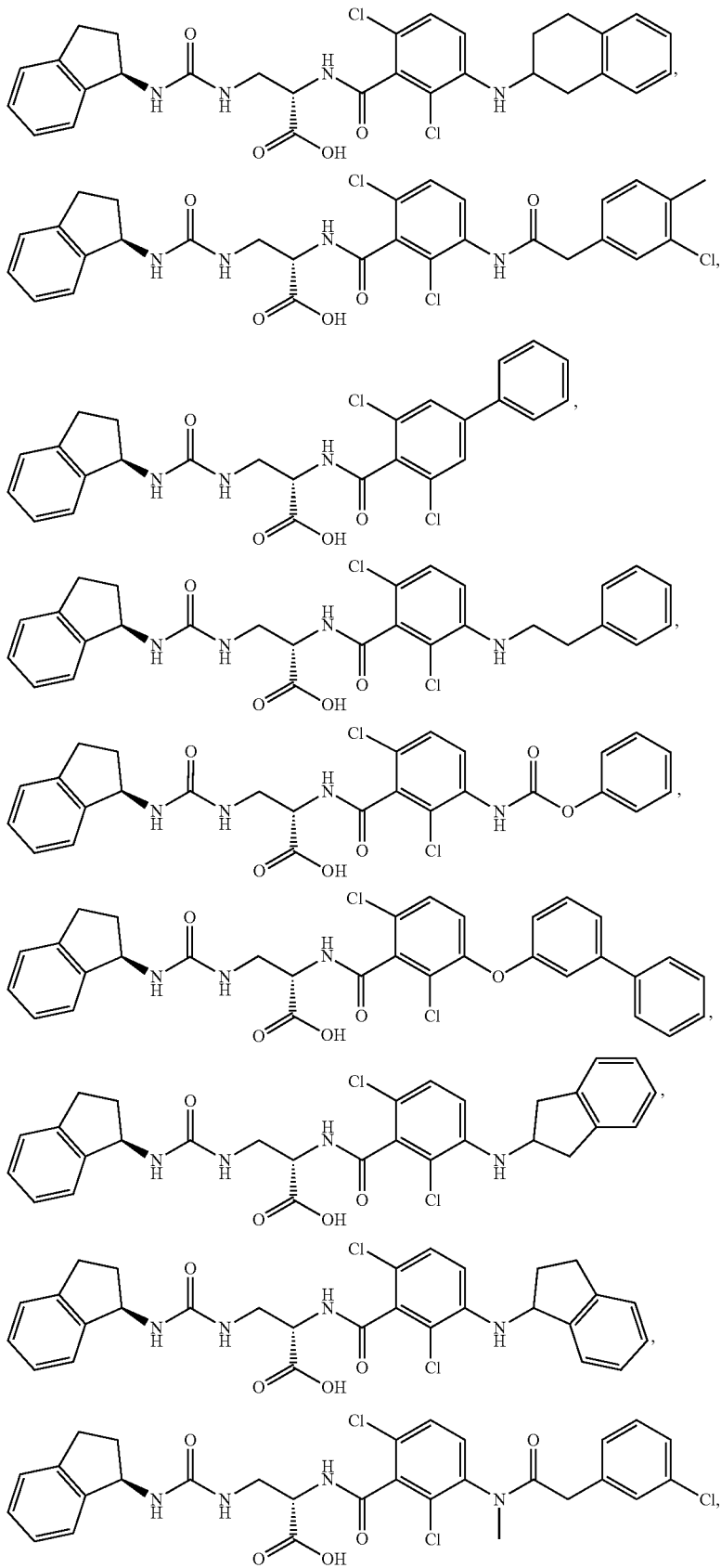

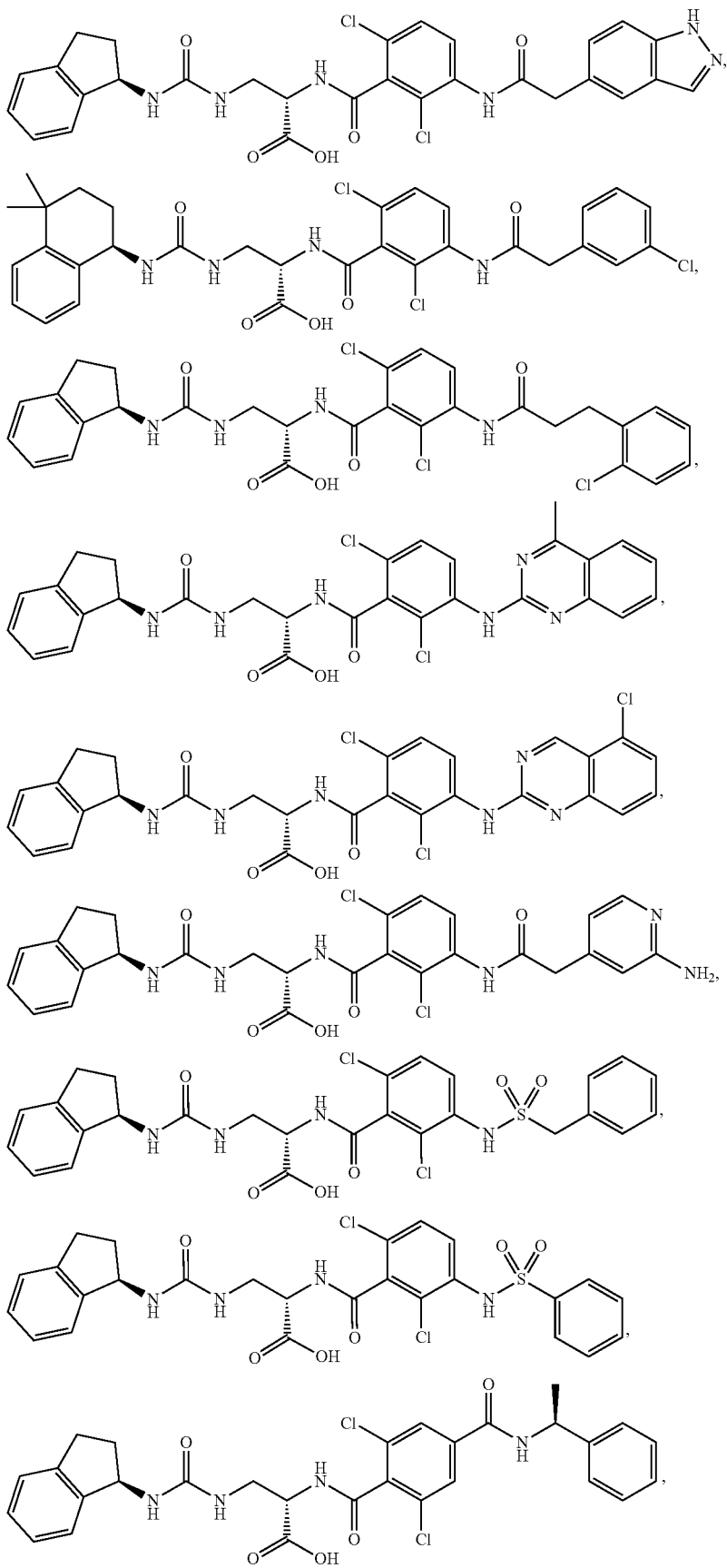

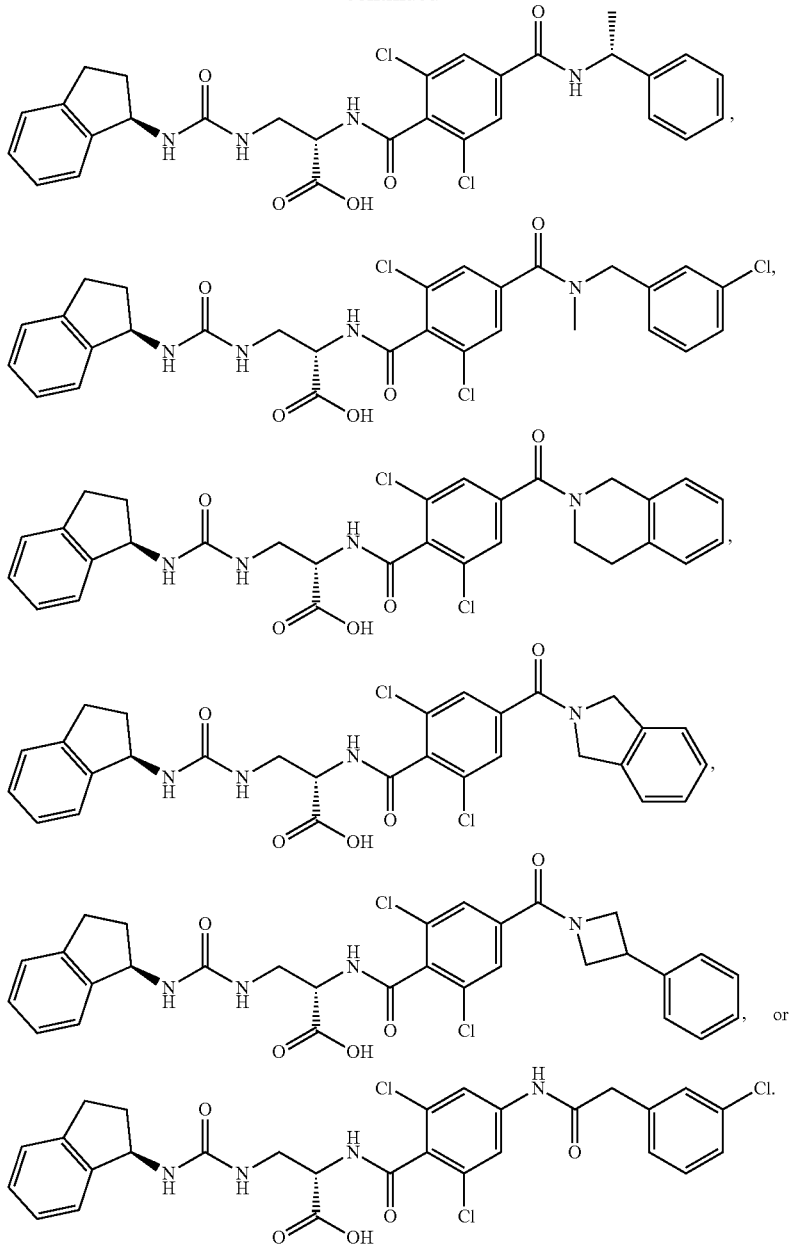

Embodiment P43. A compound, or a pharmaceutically acceptable salt thereof or a prodrug thereof, having the formula:

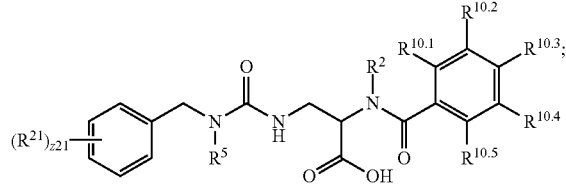

(II)

wherein
R$^2$ is hydrogen or substituted or unsubstituted alkyl;
R$^5$ is unsubstituted C$_1$-C$_3$ alkyl;
R$^{10.1}$ is hydrogen, halogen, —CX$^{10.1}{}_3$, —CHX$^{10.1}{}_2$, —CH$_2$X$^{10.1}$, —OCX$^{10.1}{}_3$, —OCH$_2$X$^{10.1}$, —OCHX$^{10.1}{}_2$, —CN, —SO$_{m10.1}$R$^{10.1D}$, —SO$_{v10.1}$NR$^{10.1A}$R$^{10.1B}$, —NHC(O)NR$^{10.1A}$R$^{10.1B}$, —N(O)$_{m10.1}$, —NR$^{10.1A}$R$^{10.1B}$, —C(O)R$^{10.1C}$, —C(O)OR$^{10.1C}$, —C(O)NR$^{10.1A}$R$^{10.1B}$, —OR$^{10.1D}$, —SR$^{10.1D}$, —NR$^{10.1A}$SO$_2$R$^{10.1D}$, —NR$^{10.1A}$C(O)R$^{10.1C}$, —NR$^{10.1A}$C(O)OR$^{10.1C}$, —NR$^{10.1A}$OR$^{10.1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{10.2}$ is hydrogen, halogen, —CX$^{10.2}{}_3$, —CHX$^{10.2}{}_2$, —CH$_2$X$^{10.2}$, —OCX$^{10.2}{}_3$, —OCH$_2$X$^{10.2}$, —OCHX$^{10.2}{}_2$, —CN, —SO$_{m10.2}$R$^{10.2D}$, —SO$_{v10.2}$NR$^{10.2A}$R$^{10.2B}$, —NHC (O)NR$^{10.2A}$R$^{10.2B}$, N(O)$_{m10.2}$, —NR$^{10.2A}$R$^{10.2B}$, —C(O)R$^{10.2C}$, —C(O)OR$^{10.2C}$, C(O)NR$^{10.2A}$R$^{10.2B}$, —OR$^{10.2D}$, —SR$^{10.2D}$, —NR$^{10.2A}$SO$_2$R$^{10.2D}$, —NR$^{10.2A}$C(O)R$^{10.2C}$, —NR$^{10.2A}$C(O)OR$^{10.2C}$, —NR$^{10.2A}$OR$^{10.2C}$, —N$_3$, -L$^{10.2}$-R$^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10.3}$ is hydrogen, halogen, —CX$^{10.3}_3$, —CHX$^{10.3}_2$, —CH$_2$X$^{10.3}$, —OCX$^{10.3}_3$, —OCH$_2$X$^{10.3}$, —OCHX$^{10.3}_2$, —CN, —SO$_{n10.3}$R$^{10.3D}$, —SO$_{v10.3}$NR$^{10.3A}$R$^{10.3B}$, —NHC(O)NR$^{10.3A}$R$^{10.3B}$, —N(O)$_{m10.3}$, —NR$^{10.3A}$R$^{10.3B}$, —C(O)R$^{10.3C}$, —C(O)OR$^{10.3C}$, —C(O)NR$^{10.3A}$R$^{10.3B}$, —OR$^{10.3D}$, —SR$^{10.3D}$, —NR$^{10.3A}$SO$_2$R$^{10.3D}$, —NR$^{10.3A}$C(O)R$^{10.3C}$, —NR$^{10.3A}$C(O)OR$^{10.3C}$, —NR$^{10.3A}$OR$^{10.3C}$, —N$_3$, -L$^{10.3}$-R$^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10.4}$ is hydrogen, halogen, —CX$^{10.4}_3$, —CHX$^{10.4}_2$, —CH$_2$X$^{10.4}$, —OCX$^{10.4}_3$, —OCH$_2$X$^{10.4}$, —OCHX$^{10.4}_2$, —CN, —SO$_{n10.4}$R$^{10.4D}$, —SO$_{v10.4}$NR$^{10.4A}$R$^{10.4B}$, —NHC(O)NR$^{10.4A}$R$^{10.4B}$, —N(O)$_{m10.4}$, —NR$^{10.4A}$R$^{10.4B}$, —C(O)R$^{10.4C}$, —C(O)OR$^{10.4C}$, —C(O)NR$^{10.4A}$R$^{10.4B}$, —OR$^{10.4D}$, —SR$^{10.4D}$, —NR$^{10.4A}$SO$_2$R$^{10.4D}$, —NR$^{10.4A}$C(O)R$^{10.4C}$, —NR$^{10.4A}$C(O)OR$^{10.4C}$, —NR$^{10.4A}$OR$^{10.4C}$, —N$_3$, -L$^{10.4}$-R$^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10.5}$ is hydrogen, halogen, —CX$^{10.5}_3$, —CHX$^{10.5}_2$, —CH$_2$X$^{10.5}$, —OCX$^{10.5}_3$, —OCH$_2$X$^{10.5}$, —OCHX$^{10.5}_2$, —CN, —SO$_{n10.5}$R$^{10.5D}$, —SO$_{v10.5}$NR$^{10.5A}$R$^{10.5B}$, —NHC(O)NR$^{10.5A}$R$^{10.5B}$, N(O)$_{m10.5}$, —NR$^{10.5A}$R$^{10.5B}$, —C(O)R$^{10.5C}$, —C(O)OR$^{10.5C}$, —C(O)NR$^{10.5A}$R$^{10.5B}$, —OR$^{10.5D}$, —SR$^{10.5D}$, —NR$^{10.5A}$SO$_2$R$^{10.5D}$, —NR$^{10.5A}$C(O)R$^{10.5C}$, —NR$^{10.5A}$C(O)OR$^{10.5C}$, —NR$^{10.1A}$OR$^{10.5C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21}$ is independently oxo, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O)R$^{21C}$, —C(O)OR$^{21C}$, —C(O)NR$^{21A}$R$^{21B}$, —OR$^{21D}$, —SR$^{21D}$, —NR$^{21A}$SO$_2$R$^{21D}$, —NR$^{21A}$C(O)R$^{21C}$, —NR$^{21A}$C(O)OR$^{21C}$, —NR$^{21A}$OR$^{21C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L$^{10.2}$, L$^{10.3}$, and L$^{10.4}$ are independently a bond, —NH—, —S—, —O—, —C(O)—, —C(O)O—, —OC(O)—, —NHC(O)—, —C(O)NH—, —NHC(O)O—, —OC(O)NH—, —NHC(O)NH—, —NHC(NH)NH—, —S(O)$_2$—, —NHS(O)$_2$—, —S(O)$_2$NH—, substituted or unsubstituted alkylene, or substituted or unsubstituted heteroalkylene;

R$^{22}$, R$^{23}$ and R$^{24}$ are independently substituted or unsubstituted cycloalkyl, substituted or unsubstituted heterocycloalkyl, substituted or unsubstituted aryl, or substituted or unsubstituted heteroaryl;

R$^{10.1A}$, R$^{10.1B}$, R$^{10.1C}$, R$^{10.1D}$, R$^{10.2A}$, R$^{10.2B}$, R$^{10.2C}$, R$^{10.2D}$, R$^{10.3A}$, R$^{10.3B}$, R$^{10.3C}$, R$^{10.3D}$, R$^{10.4A}$, R$^{10.4B}$, R$^{10.4C}$, R$^{10.4D}$, R$^{10.5A}$, R$^{10.5B}$, R$^{10.5C}$, R$^{10.5D}$, R$^{21A}$, R$^{21B}$, R$^{21C}$, and R$^{21D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10.1A}$ and R$^{10.1B}$ substituents bonded to the same nitrogen atom may be joined to form a substituted or unsubstituted heterocycloalkyl or substituted or unsubstituted heteroaryl; R$^{10.2A}$ and R$^{10.2B}$ substituents bonded to the same nitrogen atom may be joined to form a substituted or unsubstituted heterocycloalkyl or substituted or unsubstituted heteroaryl; R$^{10.3A}$, and R$^{10.3B}$ substituents bonded to the same nitrogen atom may be joined to form a substituted or unsubstituted heterocycloalkyl or substituted or unsubstituted heteroaryl; R$^{10.4A}$ and R$^{10.4B}$ substituents bonded to the same nitrogen atom may be joined to form a substituted or unsubstituted heterocycloalkyl or substituted or unsubstituted heteroaryl; R$^{10.5A}$ and R$^{10.5B}$ substituents bonded to the same nitrogen atom may be joined to form a substituted or unsubstituted heterocycloalkyl or substituted or unsubstituted heteroaryl; R$^{21A}$ and R$^{21B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, and n21 are independently an integer from 0 to 4; m10.1, m10.2, m10.3, m10.4, m10.5, m21, v10.1, v10.2, v10.3, v10.4, v10.5, and v21 are independently 1 or 2;

X$^{10.1}$, X$^{10.2}$, X$^{10.3}$, X$^{10.4}$, X$^{10.5}$, and X$^{21}$ are independently —F, —Cl, —Br, or —I;

z21 is an integer from 0 to 5; and wherein at least one of R$^{10.1}$ or R$^{10.5}$ is not hydrogen.

Embodiment P44. The compound of embodiment P43, wherein R$^5$ is unsubstituted methyl.

Embodiment P45. The compound of one of embodiments P43 to P44, wherein R$^2$ is hydrogen or unsubstituted C$_1$-C$_3$ alkyl.

Embodiment P46. The compound of one of embodiments P43 to P44, wherein R$^2$ is hydrogen.

Embodiment P47. The compound of one of embodiments P43 to P44, wherein R$^2$ is unsubstituted methyl.

Embodiment P48. The compound of one of embodiments P43 to P47, wherein R$^{21}$ is independently halogen, —OH, or substituted or unsubstituted C$_1$-C$_4$ alkyl.

Embodiment P49. The compound of one of embodiments P43 to P47, wherein R$^{21}$ is independently —OH or unsubstituted methyl.

Embodiment P50. The compound of one of embodiments P43 to P47, wherein z21 is 0.

Embodiment P51. The compound of one of embodiments P43 to P50, wherein R$^{10.1}$ is halogen, substituted or unsubstituted C$_1$-C$_5$ alkyl, or substituted or unsubstituted 2 to 5 membered heteroalkyl.

Embodiment P52. The compound of one of embodiments P43 to P50, wherein R$^{10.1}$ is halogen or unsubstituted methyl.

Embodiment P53. The compound of one of embodiments P43 to P50, wherein R$^{10.1}$ is —Cl.

Embodiment P54. The compound of one of embodiments P43 to P53, wherein R$^{10.2}$ is hydrogen or -L$^{10.2}$-R$^{22}$.

Embodiment P55. The compound of one of embodiments P43 to P54, wherein $L^{10.2}$ is a bond, —NH—, —O—, —C(O)—, —NHC(O)O—, —NHS(O)$_2$—, or substituted or unsubstituted 2 to 5 membered heteroalkylene.

Embodiment P56. The compound of one of embodiments P43 to P54, wherein $L^{10.2}$ is a bond, —NH—, —O—, —C(O)—, —NHC(O)O—, —NHS(O)$_2$—,

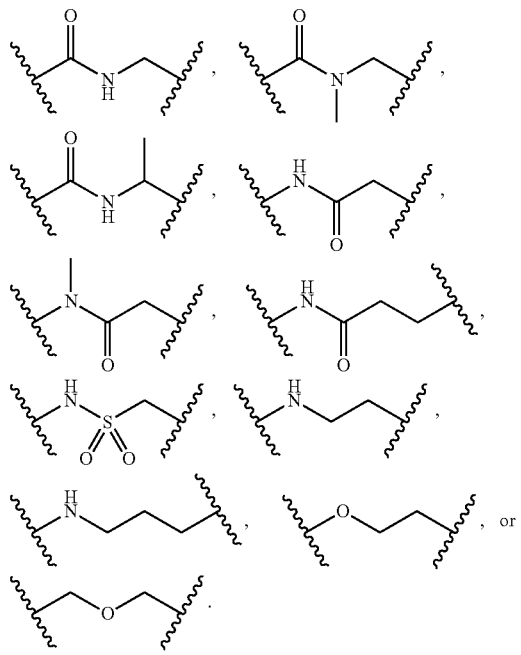

Embodiment P57. The compound of one of embodiments P43 to P56, wherein $R^{22}$ is $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl; and $R^{32}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P58. The compound of embodiment P57, wherein $R^{22}$ is

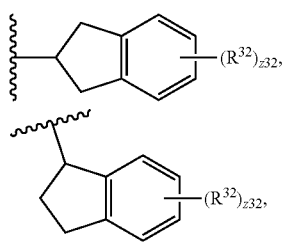

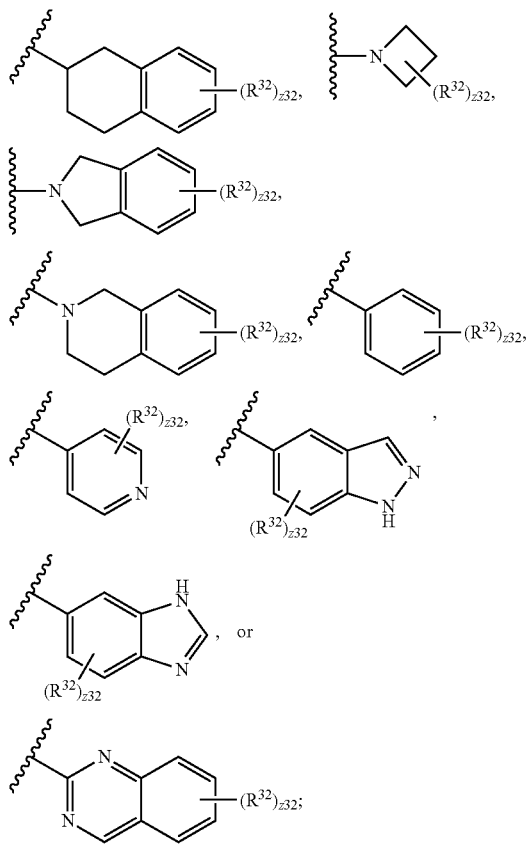

and z32 is an integer from 0 to 10.

Embodiment P59. The compound of one of embodiments P57 to P58, wherein $R^{32}$ is independently halogen, —CF$_3$, —OH, —NH$_2$, substituted or unsubstituted C$_1$-C$_4$ alkyl, substituted or unsubstituted 2 to 5 membered heteroalkyl, or substituted or unsubstituted phenyl.

Embodiment P60. The compound of one of embodiments P43 to P57, wherein $R^{22}$ is

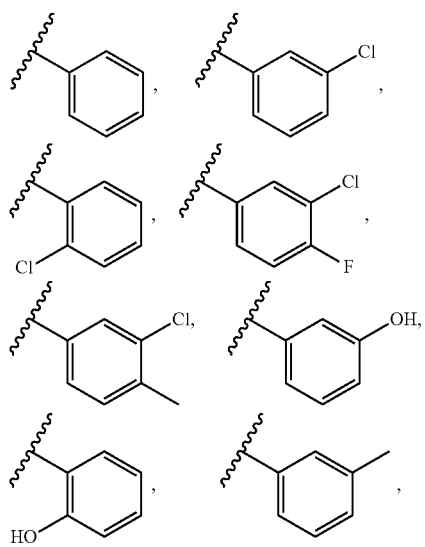

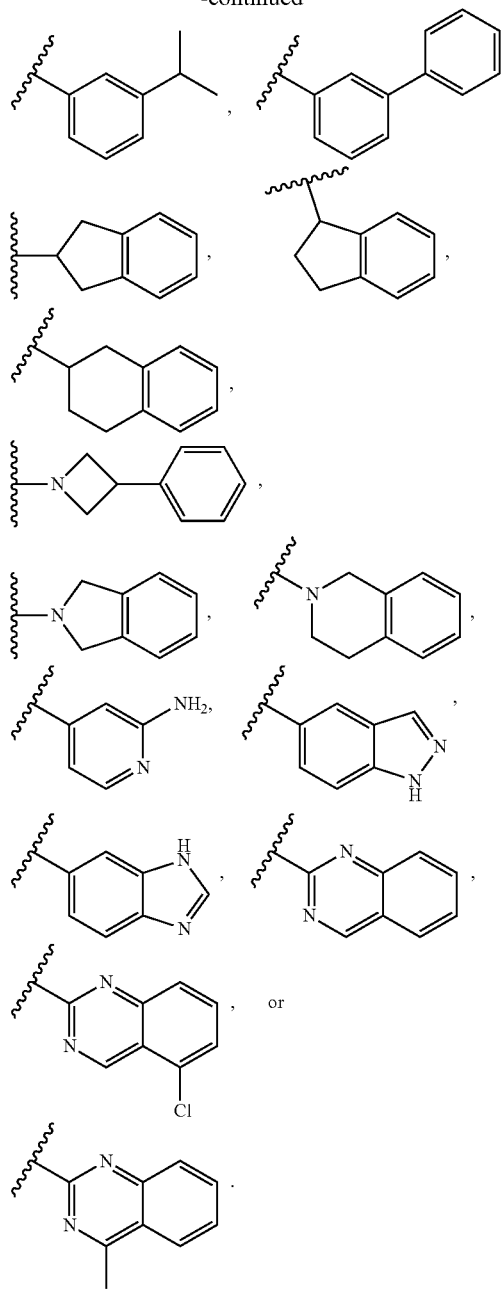

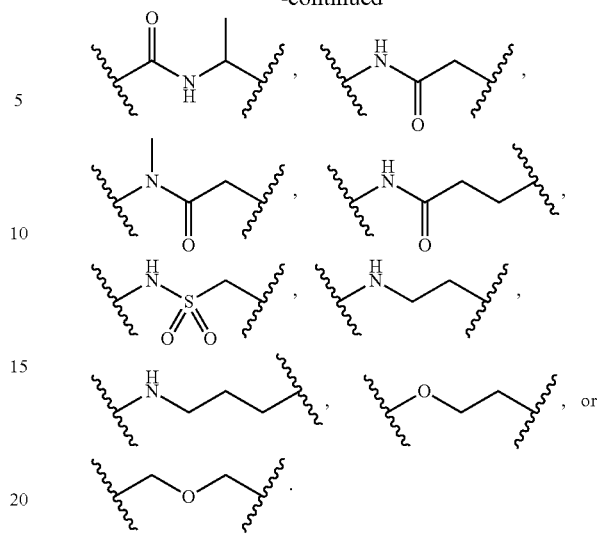

Embodiment P61. The compound of one of embodiments P43 to P60, wherein $R^{10.3}$ is hydrogen or -$L^{10.3}$-$R^{23}$.

Embodiment P62. The compound of one of embodiments P43 to P61, wherein $L^{10.3}$ is a bond, —NH—, —O—, —C(O)—, —NHC(O)O—, —NHS(O)$_2$—, or substituted or unsubstituted 2 to 5 membered heteroalkylene.

Embodiment P63. The compound of one of embodiments P43 to P61, wherein $L^{10.3}$ is a bond, NH—, —O—, —C(O)—, —NHC(O)O—, —NHS(O)$_2$—, Embodiment P64. The compound of one of embodiments P43 to P63, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P65. The compound of embodiment P64, wherein $R^{23}$ is

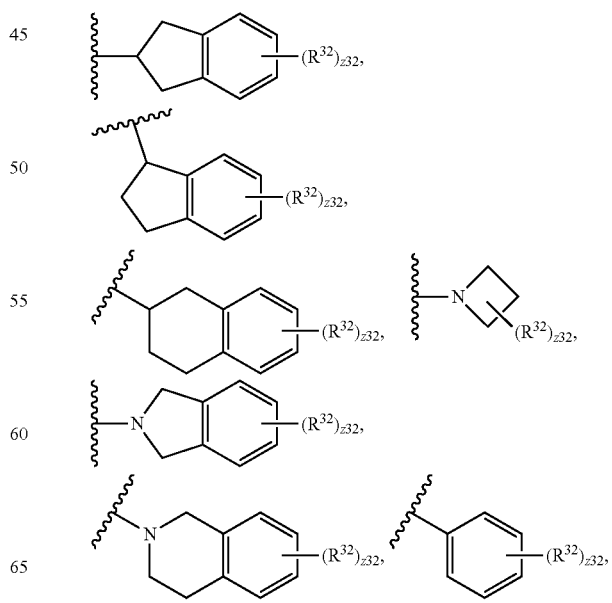

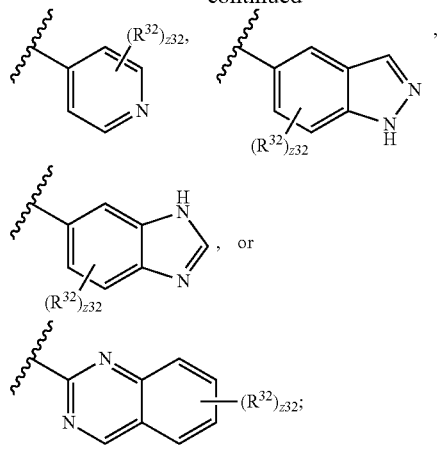

and z33 is an integer from 0 to 10.

Embodiment P66. The compound of one of embodiments P64 to P65, wherein $R^{33}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl.

Embodiment P67. The compound of one of embodiments P43 to P64, wherein $R^{23}$ is

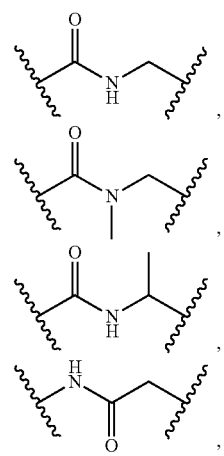

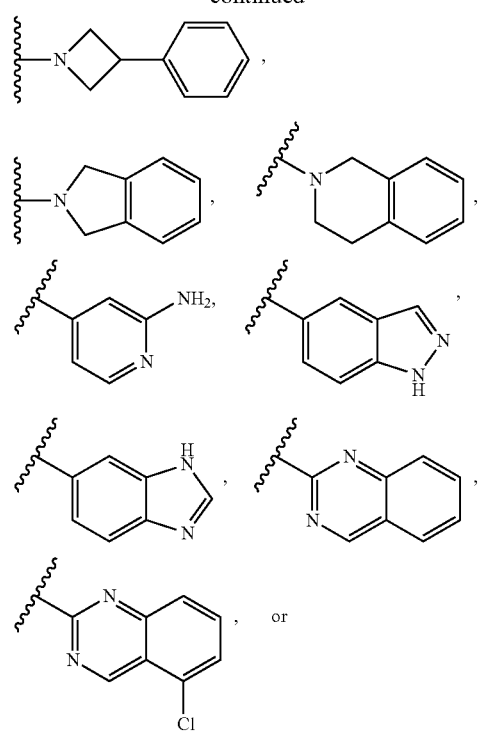

Embodiment P68. The compound of one of embodiments P43 to P67, wherein $R^{10.4}$ is hydrogen or -$L^{10.4}$-$R^{24}$.

Embodiment P69. The compound of one of embodiments P43 to P68, wherein $L^{10.4}$ is a bond, —NH—, —O—, —C(O)—, —NHC(O)O—, —NHS(O)$_2$—, or substituted or unsubstituted 2 to 5 membered heteroalkylene.

Embodiment P70. The compound of one of embodiments P43 to P68, wherein $L^{10.4}$ is a bond, NH—, —O—, —C(O)—, —NHC(O)O—, —NHS(O)$_2$—,

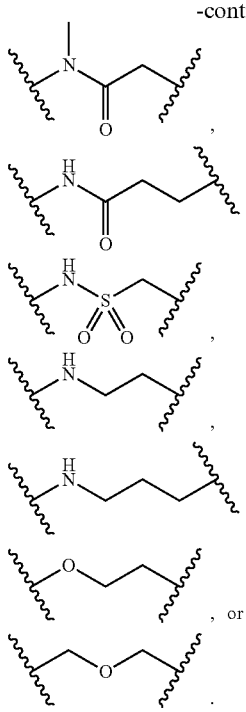

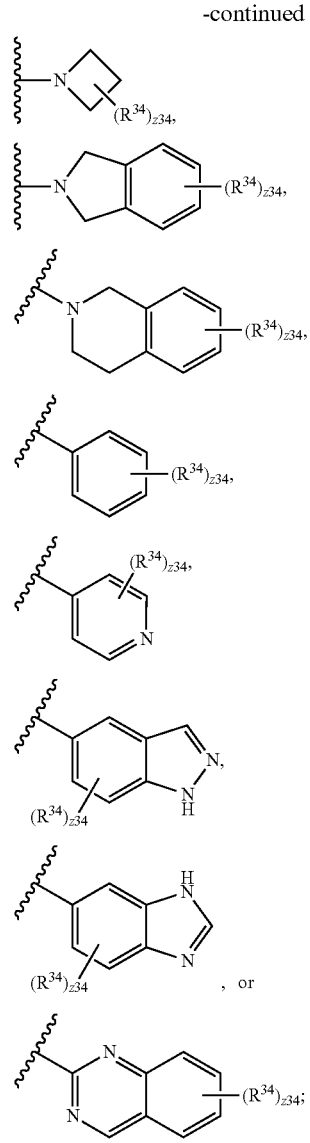

Embodiment P71. The compound of one of embodiments P43 to P70, wherein $R^{24}$ is $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl; and $R^{34}$ is independently oxo, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P72. The compound of embodiment P71, wherein $R^{24}$ is

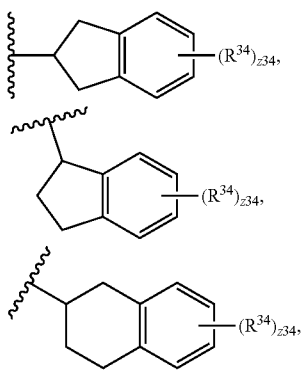

and z34 is an integer from 0 to 10.

Embodiment P73. The compound of one of embodiments P71 to P72, wherein $R^{34}$ is independently halogen, $-CF_3$, $-OH$, $-NH_2$, substituted or unsubstituted $C_1$-$C_4$ alkyl, substituted or unsubstituted 2 to 5 membered heteroalkyl, or substituted or unsubstituted phenyl.

Embodiment P74. The compound of one of embodiments P43 to P71, wherein $R^{24}$ is

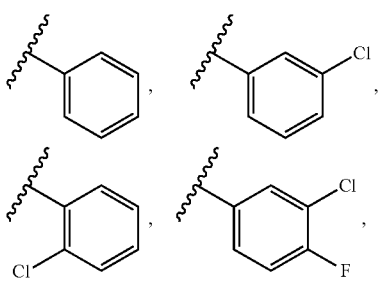

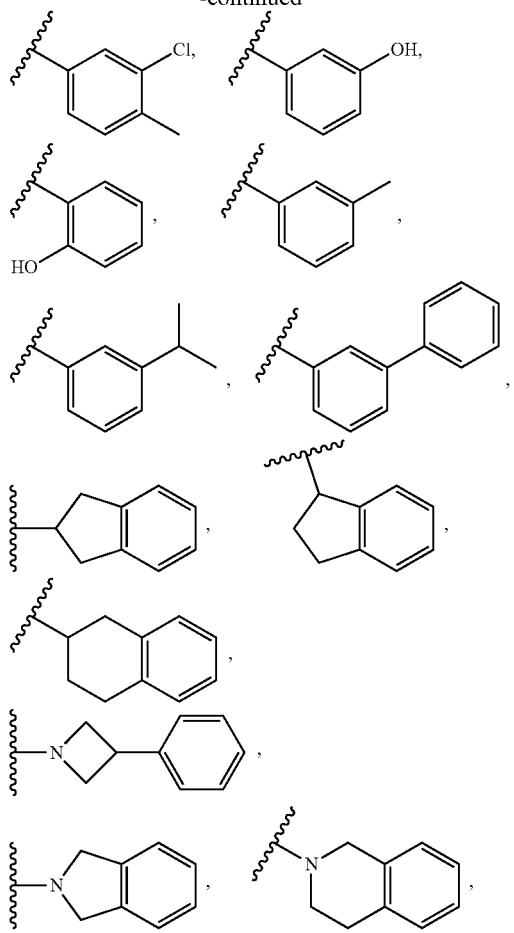

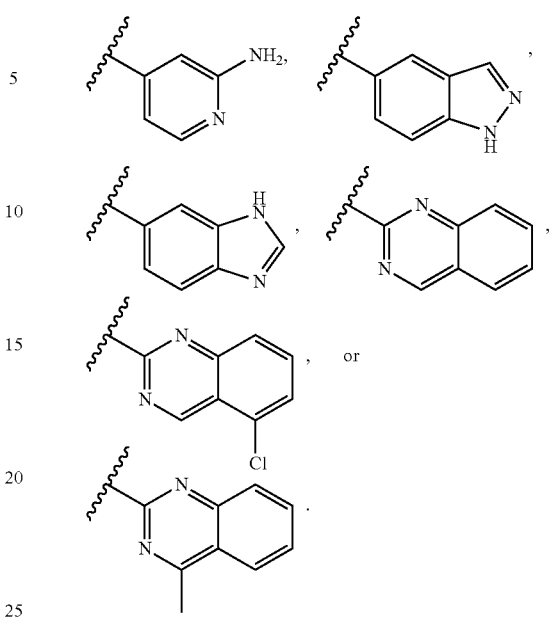

Embodiment P75. The compound of one of embodiments P43 to P74, wherein $R^{10.5}$ is halogen, substituted or unsubstituted $C_1$-$C_5$ alkyl, or substituted or unsubstituted 2 to 5 membered heteroalkyl.

Embodiment P76. The compound of one of embodiments P43 to P74, wherein $R^{10.5}$ is halogen or unsubstituted methyl.

Embodiment P77. The compound of one of embodiments P43 to P74, wherein $R^{10.5}$ is —Cl.

Embodiment P78. The compound of embodiment P43, having the formula

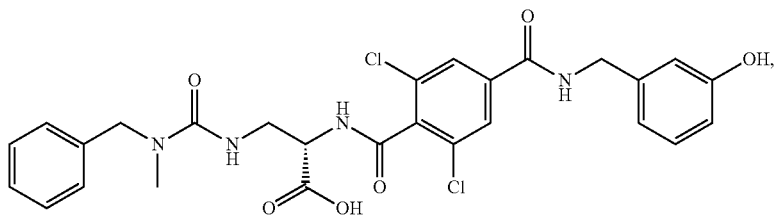

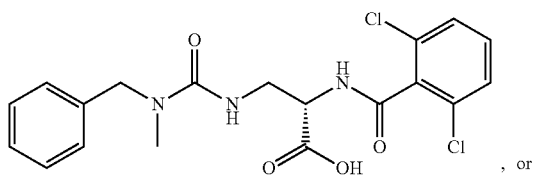

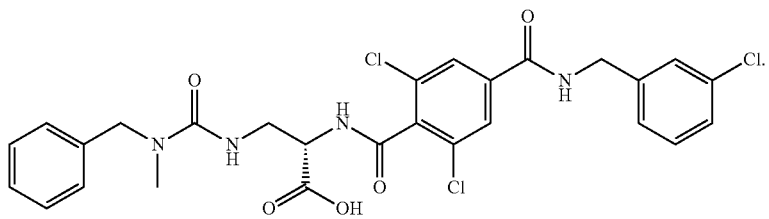

Embodiment P79. A compound, or a pharmaceutically acceptable salt thereof or a prodrug thereof, having the formula:

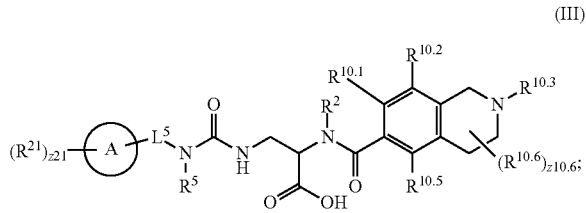

(III)

wherein

Ring A is cycloalkyl, heterocycloalkyl, aryl, or heteroaryl;
$R^2$ is hydrogen or substituted or unsubstituted alkyl;
$R^5$ is hydrogen or unsubstituted $C_1$-$C_3$ alkyl;
$L^5$ is a bond or unsubstituted $C_1$-$C_3$ alkylene;
$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $-C(O)R^{10.2C}$, $-C(O)OR^{10.2C}$, $-C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, $-L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$, $-L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.5}$ is hydrogen, halogen, $-CX^{10.5}_3$, $-CHX^{10.5}$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.1A}C(O)R^{10.5C}$, $-NR^{10.5A}C(O)OR^{10.5C}$, $-NR^{10A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.6}$ is independently oxo, halogen, $-CX^{10.6}_3$, $-CHX^{10.6}_2$, $-CH_2X^{10.6}$, $-OCX^{10.6}_3$, $-OCH_2X^{10.6}$, $-OCHX^{10.6}_2$, $-CN$, $-SO_{n10.6}R^{10.6D}$, $-SO_{v10.6}NR^{10.6A}R^{10.6B}$, $-NHC(O)NR^{10.6A}R^{10.6B}$, $-N(O)_{m10.6}$, $-NR^{10.6A}R^{10.6B}$, $-C(O)R^{10.6C}$, $-C(O)OR^{10.6C}$, $-C(O)NR^{10.6A}R^{10.6B}$, $-OR^{10.6D}$, $-SR^{10.6D}$, $-NR^{10.6A}SO_2R^{10.6D}$, $-NR^{10.6A}C(O)R^{10.6C}$, $NR^{10.6A}C(O)OR^{10.6C}$, $-NR^{10.6A}OR^{10.6C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^{10.2}$ and $L^{10.3}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, substituted or unsubstituted alkylene, or substituted or unsubstituted heteroalkylene;
$R^{22}$ and $R^{23}$ are independently substituted or unsubstituted cycloalkyl, substituted or unsubstituted heterocycloalkyl, substituted or unsubstituted aryl, or substituted or unsubstituted heteroaryl;
$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.5A}$, $R^{10.5B}$, $R^{10.5C}$, $R^{10.5D}$, $R^{10.6A}$, $R^{10.6B}$, $R^{10.6C}$, $R^{10.6D}$, $R^{21A}$, $R^{21B}$, $R^{21C}$, and $R^{21D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$, and $R^{10.3B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{10.6A}$ and $R^{10.6B}$ substituents bonded to the same nitrogen atom may be joined to form a substituted or unsubstituted heterocycloalkyl or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl;

n10.1, n10.2, n10.3, n10.5, n10.6, and n21 are independently an integer from 0 to 4; m10.1, m10.2, m10.3, m10.5, m10.6, m21, v10.1, v10.2, v10.3, v10.5, v10.6, and v21 are independently 1 or 2;

$X^{10.1}$, $X^{10.2}$, $X^{10.3}$, $X^{10.5}$, $X^{10.6}$, and $X^{21}$ are independently —F, —Cl, —Br, or —I;

z10.6 is an integer from 0 to 6;

z21 is an integer from 0 to 11; and wherein at least one of $R^{10.1}$ or $R^{10.5}$ is not hydrogen.

Embodiment P80. The compound of embodiment P79, wherein Ring A is a fused bicyclic cycloalkyl or phenyl.

Embodiment P81. The compound of embodiment P79, wherein

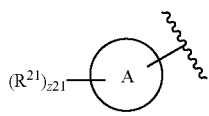

is

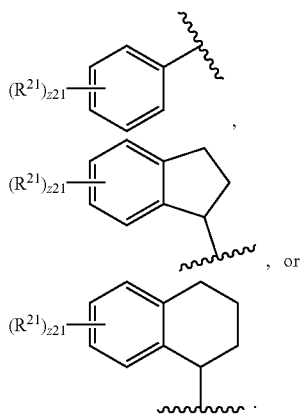

, or

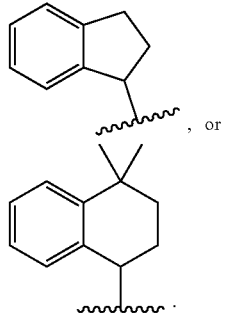

Embodiment P82. The compound of one of embodiments P79 to P81, wherein $R^{21}$ is independently halogen, —OH, or substituted or unsubstituted $C_1$-$C_4$ alkyl.

Embodiment P83. The compound of one of embodiments P79 to P81, wherein $R^{21}$ is independently —OH or unsubstituted methyl.

Embodiment P84. The compound of one of embodiments P79 to P83, wherein z21 is an integer from 0 to 3.

Embodiment P85. The compound of embodiment P79, wherein

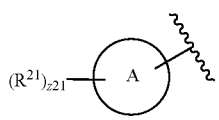

is

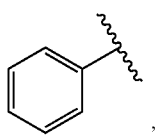

,

Embodiment P86. The compound of one of embodiments P79 to P85, wherein $R^2$ is hydrogen or unsubstituted $C_1$-$C_3$ alkyl.

Embodiment P87. The compound of one of embodiments P79 to P85, wherein $R^2$ is hydrogen.

Embodiment P88. The compound of one of embodiments P79 to P85, wherein $R^2$ is unsubstituted methyl.

Embodiment P89. The compound of one of embodiments P79 to P88, wherein $R^5$ is hydrogen.

Embodiment P90. The compound of one of embodiments P79 to P88, wherein $R^5$ is unsubstituted methyl.

Embodiment P91. The compound of one of embodiments P79 to P90, wherein $L^5$ is a bond.

Embodiment P92. The compound of one of embodiments P79 to P90, wherein $L^5$ is unsubstituted methylene.

Embodiment P93. The compound of one of embodiments P79 to P90, wherein $R^{10.1}$ is halogen, substituted or unsubstituted $C_1$-$C_5$ alkyl, or substituted or unsubstituted 2 to 5 membered heteroalkyl.

Embodiment P94. The compound of one of embodiments P79 to P90, wherein $R^{10.1}$ is halogen or unsubstituted methyl.

Embodiment P95. The compound of one of embodiments P79 to P90, wherein $R^{10.1}$ is —Cl.

Embodiment P96. The compound of one of embodiments P79 to P94, wherein $R^{12}$ is hydrogen.

Embodiment P97. The compound of one of embodiments P79 to P96, wherein $R^{10.3}$ is hydrogen, —C(O)$R^{10.3C}$, or -$L^{10.3}R^{23}$.

Embodiment P98. The compound of embodiment P97, wherein $R^{10.3C}$ is substituted or unsubstituted $C_1$-$C_4$ alkyl or substituted or unsubstituted phenyl.

Embodiment P99. The compound of embodiment P97, wherein $R^{10.3C}$ is unsubstituted methyl.

Embodiment P100. The compound of embodiment P97, wherein $L^{10.3}$ is —C(O)—, —S(O)$_2$—, or unsubstituted methylene.

Embodiment P101. The compound of embodiment P97 or embodiment P100, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P102. The compound of embodiment P101, wherein $R^{23}$ is

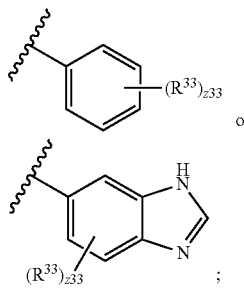

and z33 is an integer from 0 to 5.

Embodiment P103. The compound of one of embodiments P101 to P102, wherein $R^{33}$ is independently halogen.

Embodiment P104. The compound of embodiment P101, wherein $R^{23}$ is

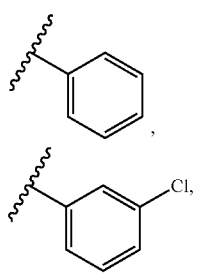

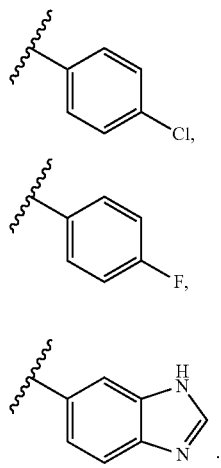

Embodiment P105. The compound of one of embodiments P79 to P104, wherein $R^{10.5}$ is halogen, substituted or unsubstituted $C_1$-$C_5$ alkyl, or substituted or unsubstituted 2 to 5 membered heteroalkyl.

Embodiment P106. The compound of one of embodiments P79 to P104, wherein $R^{10.5}$ is halogen or unsubstituted methyl.

Embodiment P107. The compound of one of embodiments P79 to P104, wherein $R^{10.5}$ is —Cl.

Embodiment P108. The compound of one of embodiments P79 to P107, wherein $R^{10.6}$ is independently oxo.

Embodiment P109. The compound of embodiment P79, having the formula

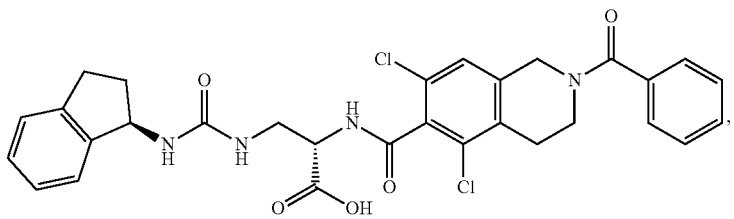

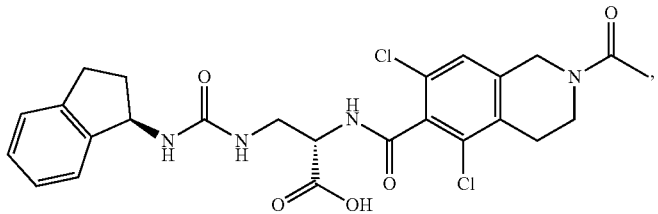

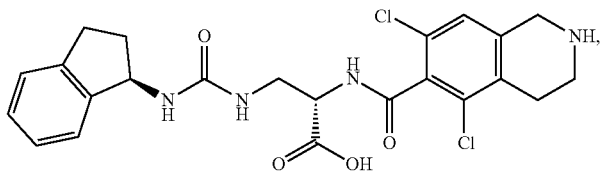

-continued
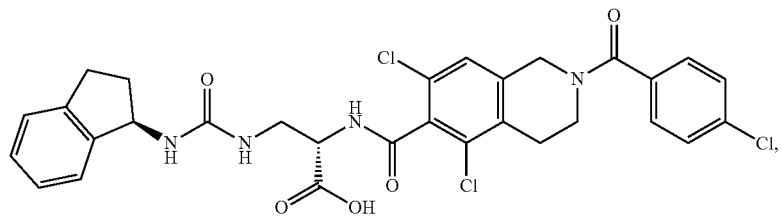
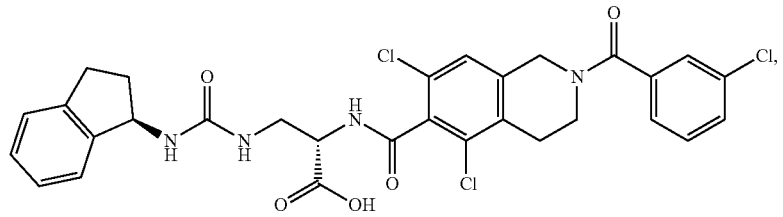
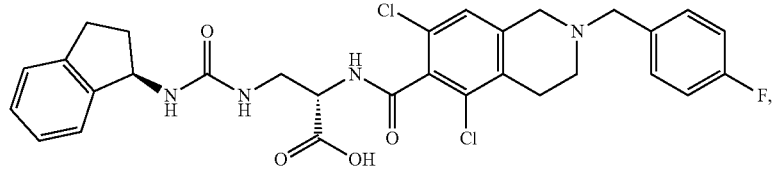
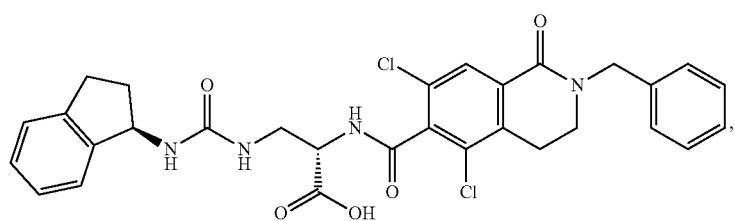
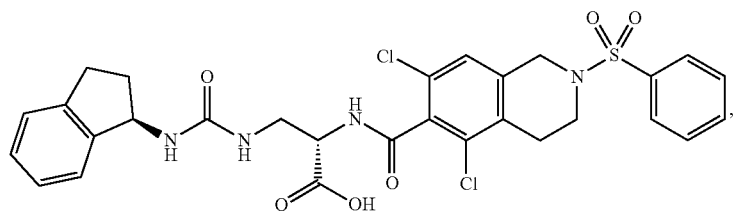
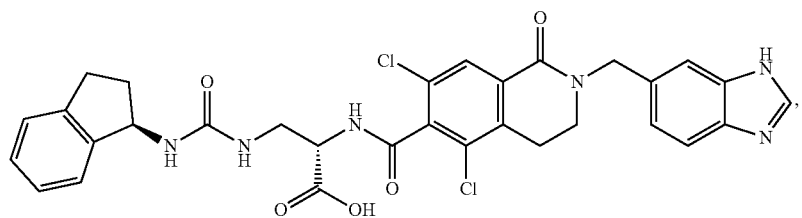
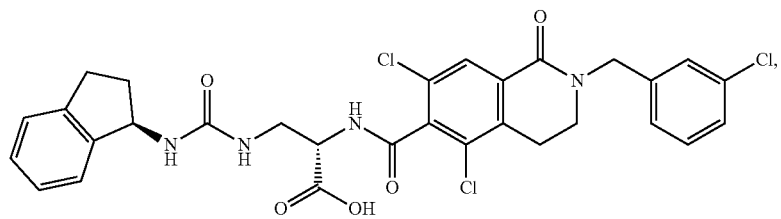
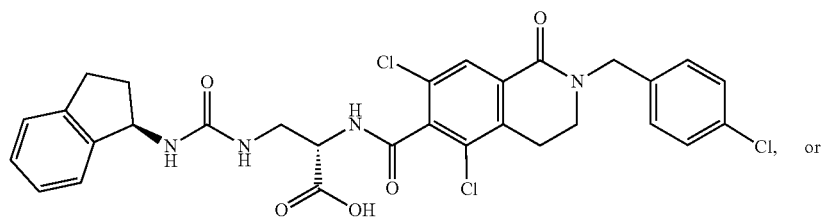, or -continued

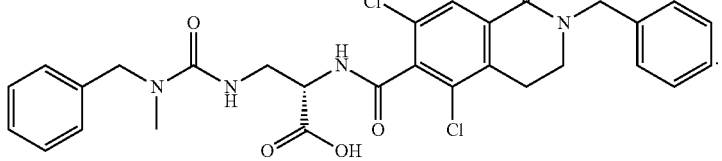

Embodiment P110. A compound, or a pharmaceutically acceptable salt thereof or a prodrug thereof, having the formula:

(IV)

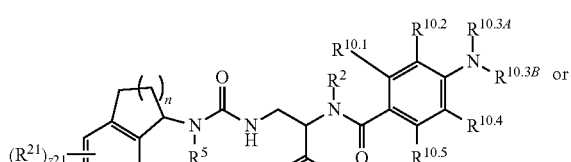

or (V)

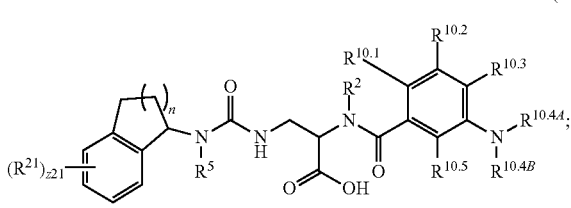

wherein $R^2$ is hydrogen or substituted or unsubstituted alkyl;

$R^5$ is hydrogen or unsubstituted $C_1$-$C_3$ alkyl;

$R^{10.1}$ is hydrogen, halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10.1}R^{10.1D}$, —$SO_{v10.1}NR^{10.1A}R^{10.1B}$, —NHC(O)$NR^{10.1A}R^{10.1B}$, —N(O)$_{m10.1}$, —$NR^{10.1A}R^{10.1B}$, —C(O)$R^{10.1C}$, —C(O)$OR^{10.1C}$, —C(O)$NR^{10.1A}R^{10.1B}$, —$OR^{10.1D}$, —$SR^{10.1D}$, —$NR^{10.1A}SO_2R^{10.1D}$, —$NR^{10.1A}C(O)R^{10.1C}$, —$NR^{10.1A}C(O)OR^{10.1C}$, —$NR^{10.1A}OR^{10.1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$, $R^{10.3}$, and $R^{10.4}$ are independently hydrogen, halogen, or —$CF_3$;

$R^{10.5}$ is hydrogen, halogen, —$CX^{10.5}_3$, —$CHX^{10.5}_2$, —$CH_2X^{10.5}$, —$OCX^{10.5}_3$, —$OCH_2X^{10.5}$, —$OCHX^{10.5}_2$, —CN, —$SO_{n10.5}R^{10.5D}$, —$SO_{v10.5}NR^{10.5A}R^{10.5B}$, —NHC(O)$NR^{10.5A}R^{10.5B}$, —N(O)$_{m10.5}$, —$NR^{10.5A}R^{10.5B}$, —C(O)$R^{10.5C}$, —C(O)$OR^{10.5C}$, C(O)$NR^{10.5A}R^{10.5B}$, —$OR^{10.5D}$, —$SR^{10.5D}$, —$NR^{10.5A}SO_2R^{10.5D}$, —$NR^{10.1A}C(O)R^{10.5C}$, $NR^{10.5A}C(O)OR^{10.5C}$, —$NR^{10.5A}OR^{10.5C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21D}$, —$SO_{v21}NR^{21A}R^{21B}$, —NHC(O)$NR^{21A}R^{21B}$, —N(O)$_{m21}$, —$NR^{21A}R^{21B}$, C(O)$R^{21C}$, —C(O)$OR^{21C}$, —C(O)$NR^{21A}R^{21B}$, —$OR^{21D}$, —$SR^{21D}$ $NR^{21A}SO_2R^{21D}$, —$NR^{21A}C(O)R^{21C}$, —$NR^{21A}C(O)OR^{21C}$, —$NR^{21A}OR^{21C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.3A}$, $R^{10.3B}$, $R^{10.4A}$, $R^{10.4B}$, $R^{10.5A}$, $R^{10.5B}$, $R^{10.5C}$, $R^{10.5D}$, $R^{21A}$, $R^{21B}$, $R^{21C}$, and $R^{21D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.3A}$, and $R^{10.3B}$ substituents bonded to the same nitrogen atom may be joined to form a substituted or unsubstituted heterocycloalkyl or substituted or unsubstituted heteroaryl; $R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$, substituents bonded to the same nitrogen atom may be joined to form a substituted or unsubstituted heterocycloalkyl or substituted or unsubstituted heteroaryl;

n10.1, n10.5, and n21 are independently an integer from 0 to 4;

m10.1, m10.5, m21, v10.1, v10.5, and v21 are independently 1 or 2;

$X^{10.1}$, $X^{10.5}$, and $X^{21}$ are independently —F, —Cl, —Br, or —I;

z21 is an integer from 0 to 9;

n is an integer from 0 to 3; and wherein at least one of $R^{10.1}$ or $R^{10.5}$ is not hydrogen.

Embodiment P111. The compound of embodiment P110, wherein $R^{10.2}$, $R^{10.3}$, and $R^{10.4}$ are independently deuterium, halogen, or —$CF_3$.

Embodiment P112. The compound of embodiment P110, having the formula:

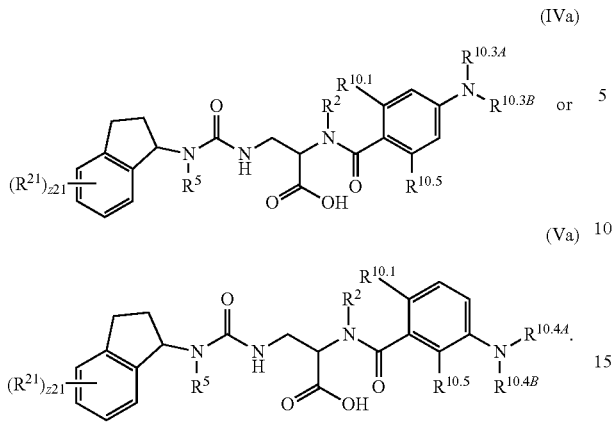

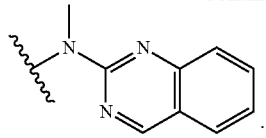

Embodiment P113. The compound of one of embodiments P110 to P112, wherein $R^5$ is hydrogen.

Embodiment P114. The compound of one of embodiments P110 to P113, wherein $R^2$ is hydrogen or unsubstituted $C_1$-$C_3$ alkyl.

Embodiment P115. The compound of one of embodiments P110 to P113, wherein $R^2$ is hydrogen.

Embodiment P116. The compound of one of embodiments P110 to P113, wherein $R^2$ is unsubstituted methyl.

Embodiment P117. The compound of one of embodiments P110 to P116, wherein $R^{21}$ is independently halogen, —OH, or substituted or unsubstituted $C_1$-$C_4$ alkyl.

Embodiment P118. The compound of one of embodiments P110 to P116, wherein $R^{21}$ is independently —OH or unsubstituted methyl.

Embodiment P119. The compound of one of embodiments P110 to P117, wherein z21 is 0 to 3.

Embodiment P120. The compound of one of embodiments P110 to P119, wherein $R^{10.1}$ is halogen, substituted or unsubstituted $C_1$-$C_5$ alkyl, or substituted or unsubstituted 2 to 5 membered heteroalkyl.

Embodiment P121. The compound of one of embodiments P110 to P119, wherein $R^{10.1}$ is halogen or unsubstituted methyl.

Embodiment P122. The compound of one of embodiments P110 to P119, wherein $R^{10.1}$ is —Cl.

Embodiment P123. The compound of one of embodiments P110 to P122, wherein $R^{10.3A}$, and $R^{10.3B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

Embodiment P124. The compound of embodiment P123, wherein

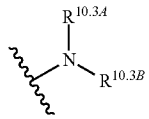

is

—NH$_2$,

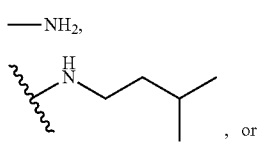, or

Embodiment P125. The compound of one of embodiments P110 to P122, wherein $R^{10.3A}$, and $R^{10.3B}$ substituents bonded to the same nitrogen atom are joined to form a substituted or unsubstituted heterocycloalkyl or substituted or unsubstituted heteroaryl.

Embodiment P126. The compound of one of embodiments P110 to P122, wherein $R^{10.3A}$, and $R^{10.3B}$ substituents bonded to the same nitrogen atom are joined to form an $R^{33}$-substituted or unsubstituted heterocycloalkyl or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P127. The compound of embodiment P126, wherein

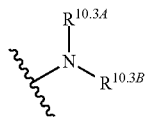

is

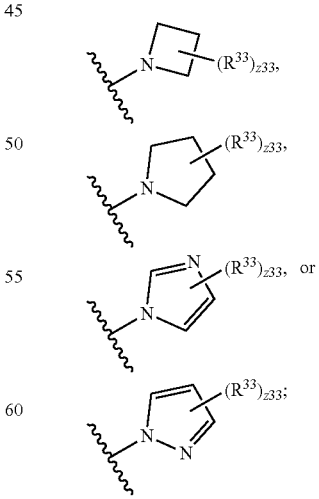

and z33 is an integer from 0 to 8.

Embodiment P128. The compound of one of embodiments P126 to P127, wherein $R^{33}$ is independently a substituted or unsubstituted phenyl.

Embodiment P129. The compound of embodiment P126, wherein

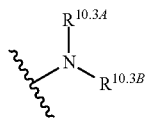

is

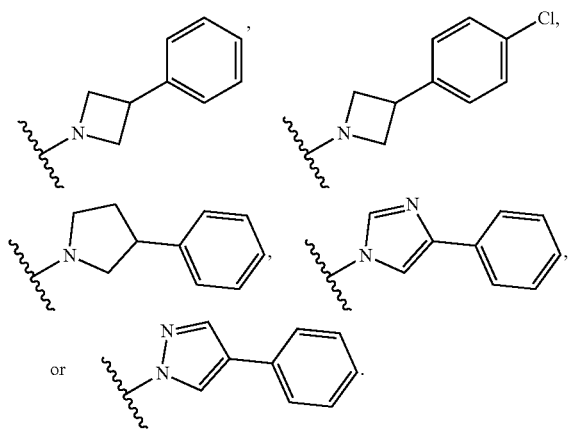

Embodiment P130. The compound of one of embodiments P110 to P122, wherein $R^{10.4A}$ and $R^{10.4B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

Embodiment P131. The compound of embodiment P130, wherein

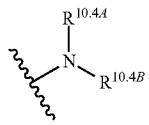

is

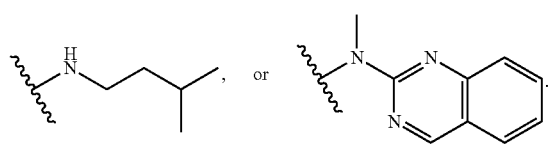

Embodiment P132. The compound of one of embodiments P110 to P122, wherein $R^{10.4A}$ and $R^{10.4B}$ substituents bonded to the same nitrogen atom are joined to form a substituted or unsubstituted heterocycloalkyl or substituted or unsubstituted heteroaryl.

Embodiment P133. The compound of one of embodiments P110 to P122, wherein $R^{10.4A}$ and $R^{10.4B}$ substituents bonded to the same nitrogen atom are joined to form an $R^{34}$-substituted or unsubstituted heterocycloalkyl or $R^{34}$-substituted or unsubstituted heteroaryl; and $R^{34}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P134. The compound of embodiment P133, wherein

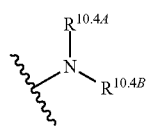

is

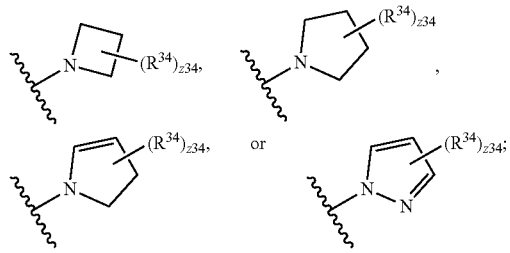

and z34 is an integer from 0 to 8.

Embodiment P135. The compound of one of embodiments P133 to P134, wherein $R^{34}$ is independently a substituted or unsubstituted phenyl.

Embodiment P136. The compound of embodiment P133, wherein

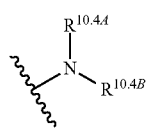

is

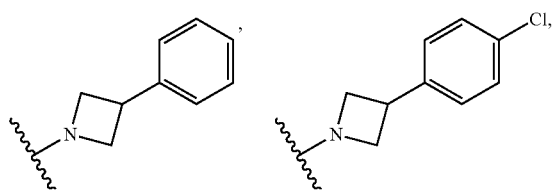

-continued

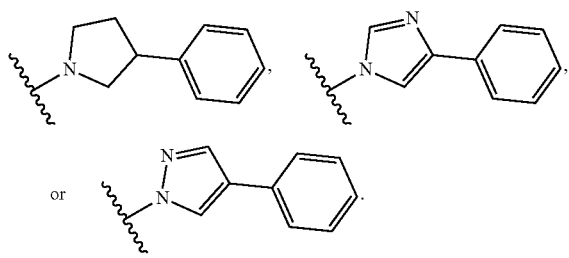

or

Embodiment P137. The compound of one of embodiments P110 to P136, wherein $R^{10.5}$ is halogen, substituted or unsubstituted $C_1$-$C_5$ alkyl, or substituted or unsubstituted 2 to 5 membered heteroalkyl.

Embodiment P138. The compound of one of embodiments P110 to P136, wherein $R^{10.5}$ is halogen or unsubstituted methyl.

Embodiment P139. The compound of one of embodiments P110 to P136, wherein $R^{10.5}$ is —Cl.

Embodiment P140. The compound of embodiment P110, having the formula

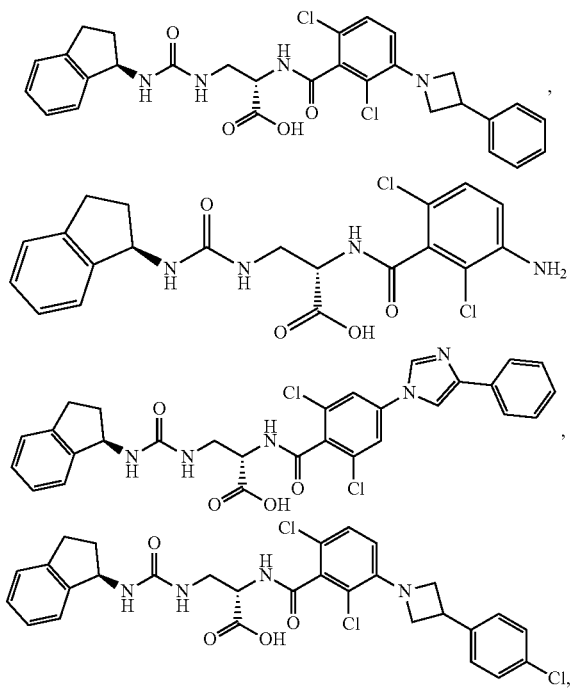

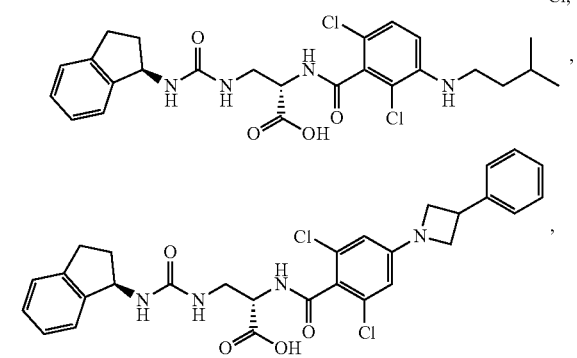

-continued

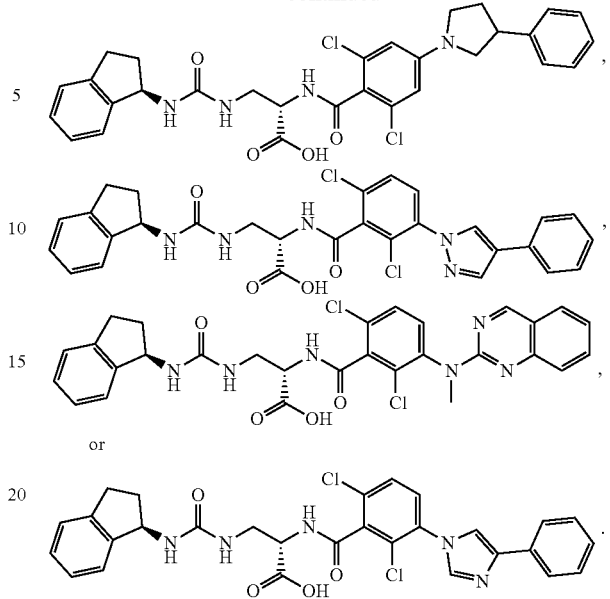

or

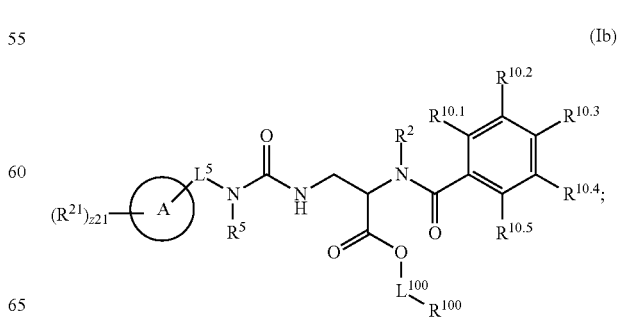

Embodiment P141. A pharmaceutical composition comprising a compound of one of embodiments P1 to P140, or a pharmaceutically acceptable salt thereof or a prodrug thereof, and a pharmaceutically acceptable excipient.

Embodiment P142. A method of treating asthma, the method comprising administering to a subject in need thereof an effective amount of a compound of one of embodiments P1 to P140, or a pharmaceutically acceptable salt thereof or a prodrug thereof.

Embodiment P143. A method of treating an inflammatory disease, the method comprising administering to a subject in need thereof an effective amount of a compound of one of embodiments P1 to P140, or a pharmaceutically acceptable salt thereof or a prodrug thereof.

Embodiment P144. A method of treating an autoimmune disease, the method comprising administering to a subject in need thereof an effective amount of a compound of one of embodiments P1 to P140, or a pharmaceutically acceptable salt thereof or a prodrug thereof.

VI. Additional Embodiments

Embodiment 1. A compound, or a pharmaceutically acceptable salt thereof or a prodrug thereof, having the formula:

(Ib)

wherein

Ring A is cycloalkyl, heterocycloalkyl, aryl, or heteroaryl;

$R^2$ is hydrogen or substituted or unsubstituted alkyl;

$R^5$ is hydrogen or unsubstituted $C_1$-$C_3$ alkyl;

$L^5$ is a bond or unsubstituted $C_1$-$C_3$ alkylene;

$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $-C(O)R^{10.2C}$, $-C(O)OR^{10.2C}$, $-C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, $-L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$,-$L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$,-$L^{10.4}$-$R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $-NR^{10.5A}C(O)OR^{10.5C}$, $-NR^{10.1A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, $-C(S)-$, substituted or unsubstituted alkylene, or substituted or unsubstituted heteroalkylene;

$R^{22}$, $R^{23}$, and $R^{24}$ are independently substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, $-CX^{100}_3$, $-CHX^{100}_2$, $-CH_2X^{100}$, $-OCX^{100}_3$, $-OCH_2X^{100}$, $-OCHX^{100}_2$, $-CN$, $-SO_{n100}R^{100D}$, $-SO_{v100}NR^{100A}R^{100B}$, $-NHC(O)NR^{100A}R^{100B}$, $-N(O)_{m100}$, $-NR^{100A}R^{100B}$, $-C(O)R^{100C}$, $-C(O)OR^{100C}$, $-C(O)NR^{100A}R^{100B}$, $-OR^{100D}$, $-SR^{100D}$, $-NR^{100A}SO_2R^{100D}$, $-NR^{100A}C(O)R^{100C}$, $-NR^{100A}C(O)OR^{100C}$, $-NR^{100A}OR^{100C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.4A}$, $R^{10.4B}$, $R^{10.4C}$, $R^{10.4D}$, $R^{10.5A}$, $R^{10.5B}$, $R^{10.5C}$, $R^{10.5D}$, $R^{21A}$, $R^{21B}$, $R^{21C}$, $R^{21D}$, $R^{100A}$, $R^{100B}$, $R^{100C}$, and $R^{100D}$, are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, n21, and n100 are independently an integer from 0 to 4;

m10.1, m10.2, m10.3, m10.4, m10.5, m21, m100, v10.1, v10.2, v10.3, v10.4, v10.5, v21, and v100 are independently 1 or 2;

$X^{10.1}$, $X^{10.2}$, $X^{10.3}$, $X^{10.4}$, $X^{10.5}$, $X^{21}$, and $X^{100}$ are independently —F, —Cl, —Br, or —I;

z21 is an integer from 0 to 11;

wherein at least one of $R^{10.1}$ or $R^{10.5}$ is not hydrogen; and wherein at least one of $R^{10.2}$, $R^{10.3}$, or $R^{10.4}$ is -$L^{10.2}$-$R^{22}$, -$L^{10.3}$-$R^{23}$, or -$L^{10.4}$-$R^{24}$, respectively.

Embodiment 2. The compound of embodiment 1, having the formula:

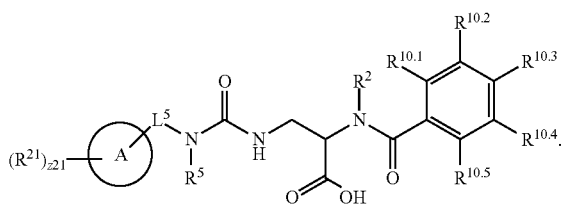

I

Embodiment 3. The compound of one of embodiments 1 to 2, wherein Ring A is a fused bicyclic cycloalkyl or phenyl.

Embodiment 4. The compound of one of embodiments 1 to 2, wherein

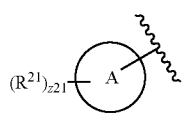

is

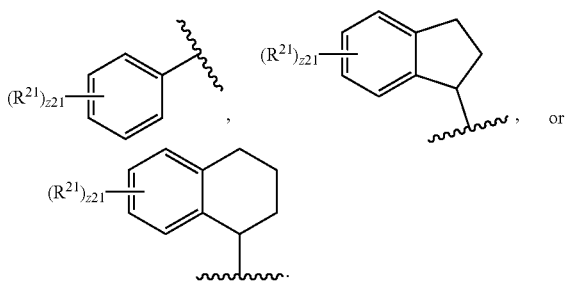

Embodiment 5. The compound of one of embodiments 1 to 4, wherein $R^{21}$ is independently halogen, —OH, or substituted or unsubstituted $C_1$-$C_4$ alkyl.

Embodiment 6. The compound of one of embodiments 1 to 4, wherein $R^{21}$ is independently —OH or unsubstituted methyl.

Embodiment 7. The compound of one of embodiments 1 to 6, wherein z21 is an integer from 0 to 3.

Embodiment 8. The compound of one of embodiments 1 to 2, wherein

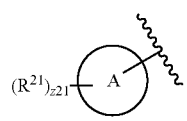

is

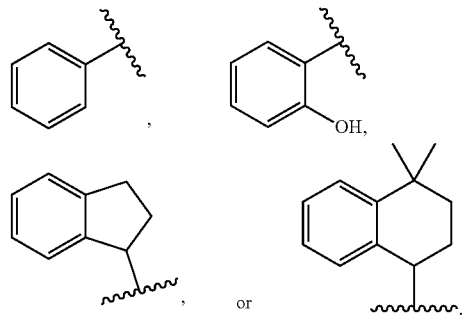

Embodiment 9. The compound of one of embodiments 1 to 8, wherein $R^2$ is hydrogen or unsubstituted $C_1$-$C_3$ alkyl.

Embodiment 10. The compound of one of embodiments 1 to 8, wherein $R^2$ is hydrogen.

Embodiment 11. The compound of one of embodiments 1 to 8, wherein $R^2$ is unsubstituted methyl.

Embodiment 12. The compound of one of embodiments 1 to 11, wherein $R^5$ is hydrogen.

Embodiment 13. The compound of one of embodiments 1 to 11, wherein $R^5$ is unsubstituted methyl.

Embodiment 14. The compound of one of embodiments 1 to 13, wherein $L^5$ is a bond.

Embodiment 15. The compound of one of embodiments 1 to 13, wherein $L^5$ is unsubstituted methylene.

Embodiment 16. The compound of one of embodiments 1 to 15, wherein $R^{10.1}$ is halogen, substituted or unsubstituted $C_1$-$C_5$ alkyl, or substituted or unsubstituted 2 to 5 membered heteroalkyl.

Embodiment 17. The compound of one of embodiments 1 to 15, wherein $R^{10.1}$ is halogen or unsubstituted methyl.

Embodiment 18. The compound of one of embodiments 1 to 15, wherein $R^{10.1}$ is —Cl.

Embodiment 19. The compound of one of embodiments 1 to 18, wherein $R^{10.2}$ is hydrogen or -$L^{10.2}$-$R^{22}$.

Embodiment 20. The compound of embodiment 19, wherein $L^{10.2}$ is a bond, —NH—, —O—, —C(O)—, —NHC(O)O—, —NHS(O)$_2$—, or substituted or unsubstituted 2 to 5 membered heteroalkylene.

Embodiment 21. The compound of embodiment 19, wherein $L^{10.2}$ is a bond,

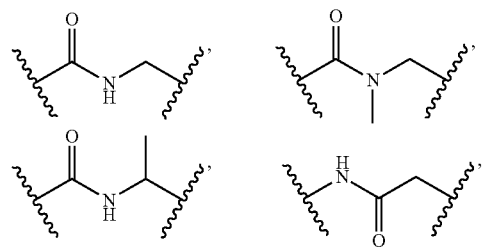

275

-continued

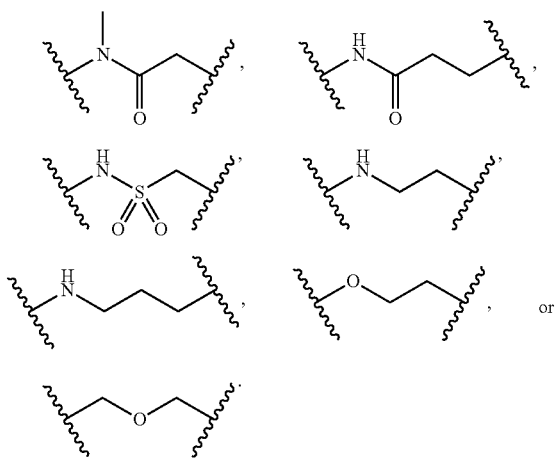

Embodiment 22. The compound of one of embodiments 1 to 21, wherein $R^{22}$ is $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl; and $R^{32}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 23. The compound of embodiment 22, wherein $R^{22}$ is

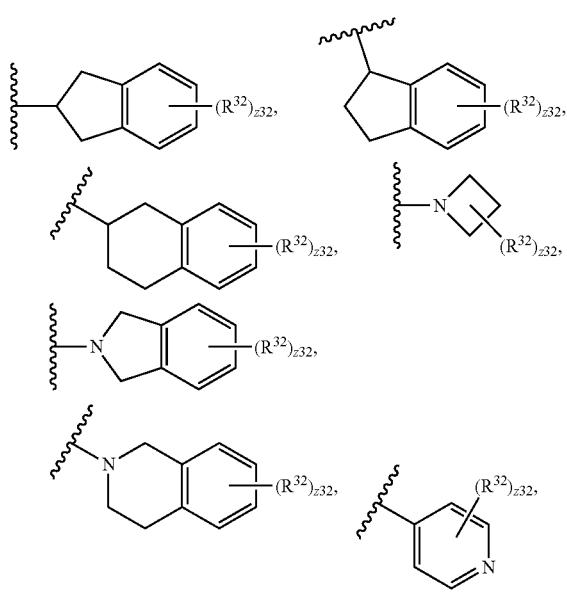

276

-continued

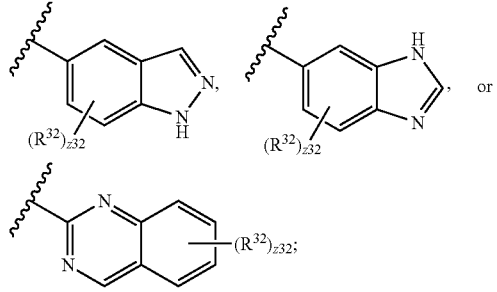

and z32 is an integer from 0 to 10.

Embodiment 24. The compound of one of embodiments 22 to 23, wherein $R^{32}$ is independently halogen, —CF$_3$, —OH, —NH$_2$, substituted or unsubstituted C$_1$-C$_4$ alkyl, substituted or unsubstituted 2 to 5 membered heteroalkyl, or substituted or unsubstituted phenyl.

Embodiment 25. The compound of one of embodiments 1 to 22, wherein $R^{22}$ is

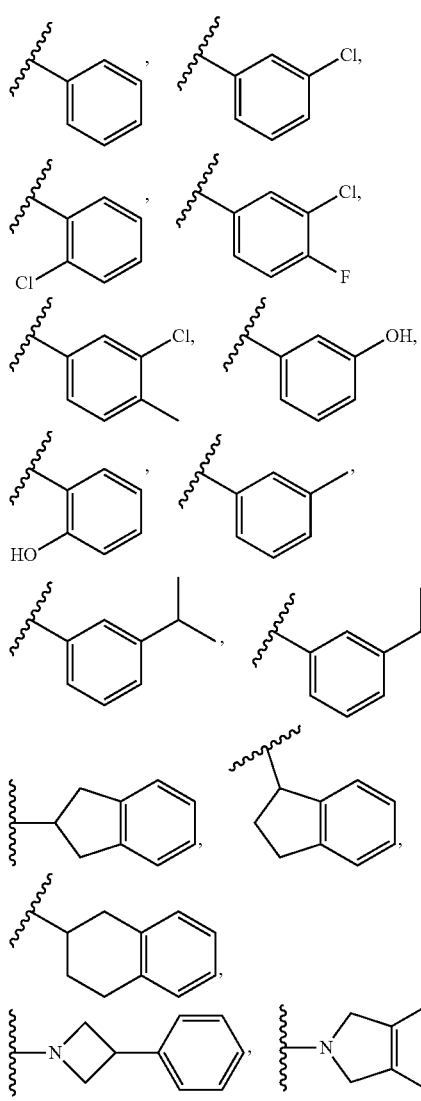

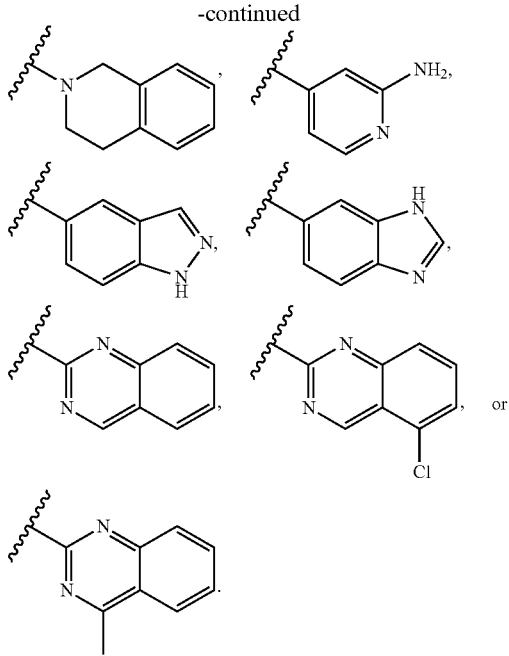

Embodiment 26. The compound of one of embodiments 1 to 25, wherein $R^{10.3}$ is hydrogen or $-L^{10.3}-R^{23}$.

Embodiment 27. The compound of one of embodiments 1 to 26, wherein $L^{10.3}$ is a bond, —NH—, —O—, —C(O)—, —NHC(O)O—, —NHS(O)$_2$—, or substituted or unsubstituted 2 to 5 membered heteroalkylene.

Embodiment 28. The compound of one of embodiments 1 to 26, wherein $L^{10.3}$ is a bond, —NH—, —O—, —C(O)—, —NHC(O)O—, —NHS(O)$_2$—,

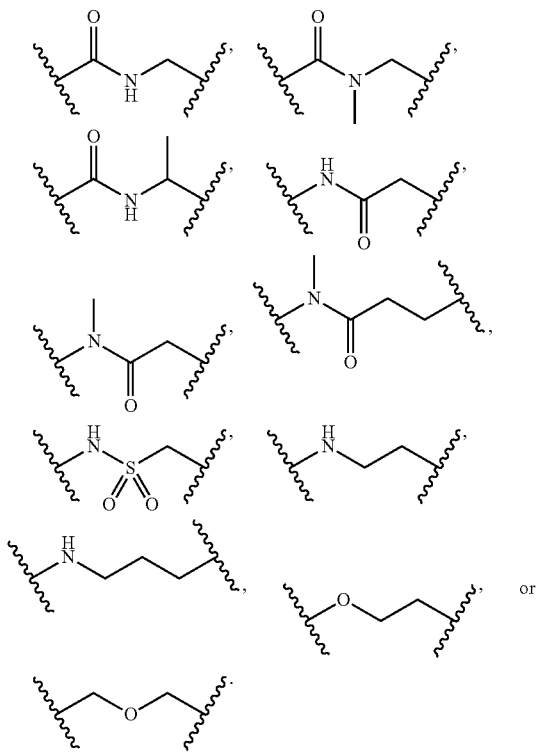

Embodiment 29. The compound of one of embodiments 1 to 28, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 30. The compound of embodiment 29, wherein $R^{23}$ is

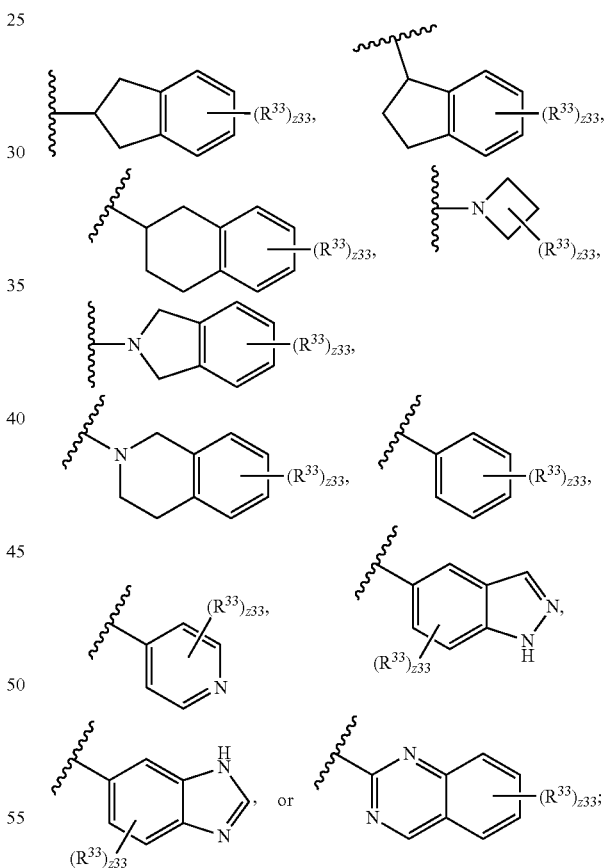

and z33 is an integer from 0 to 10.

Embodiment 31. The compound of one of embodiments 29 to 30, wherein $R^{33}$ is independently halogen, —CF$_3$, —OH, —NH$_2$, substituted or unsubstituted $C_1$-$C_4$ alkyl, substituted or unsubstituted 2 to 5 membered heteroalkyl, or substituted or unsubstituted phenyl.

Embodiment 32. The compound of one of embodiments 1 to 29, wherein $R^{23}$ is

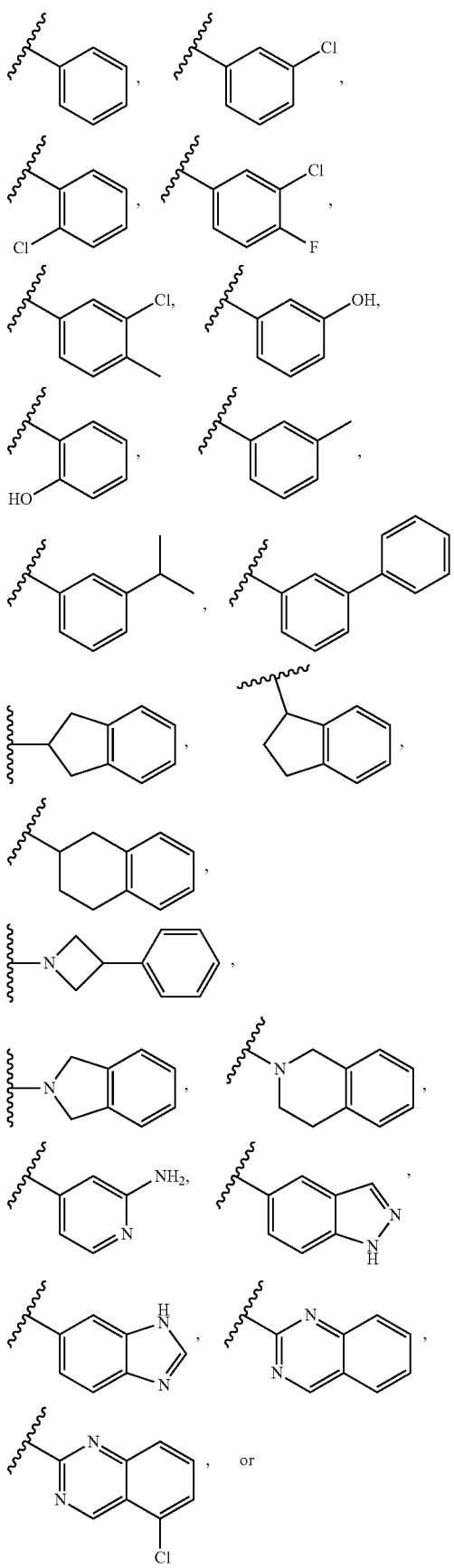
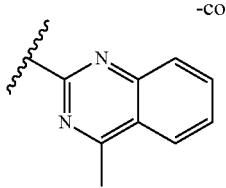

Embodiment 33. The compound of one of embodiments 1 to 32, wherein $R^{10.4}$ is hydrogen or $-L^{10.4}-R^{24}$.

Embodiment 34. The compound of one of embodiments 1 to 33, wherein $L^{10.4}$ is a bond, —NH—, —O—, —C(O)—, —NHC(O)O—, —NHS(O)$_2$—, or substituted or unsubstituted 2 to 5 membered heteroalkylene.

Embodiment 35. The compound of one of embodiments 1 to 33, wherein $L^{10.4}$ is a bond, —NH—, —O—, —C(O)—, —NHC(O)O—, —NHS(O)$_2$—, Embodiment 36. The compound of one of embodiments 1 to 35, wherein $R^{24}$ is $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl; and $R^{34}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 37. The compound of embodiment 36, wherein $R^{24}$ is

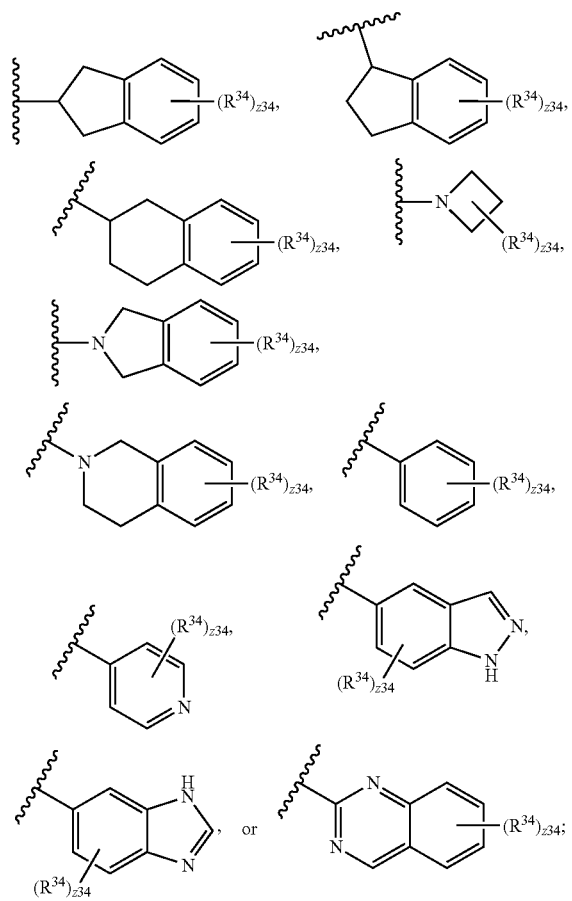

and z34 is an integer from 0 to 10.

Embodiment 38. The compound of one of embodiments 36 to 37, wherein $R^{34}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl.

Embodiment 39. The compound of one of embodiments 1 to 36, wherein $R^{24}$ is

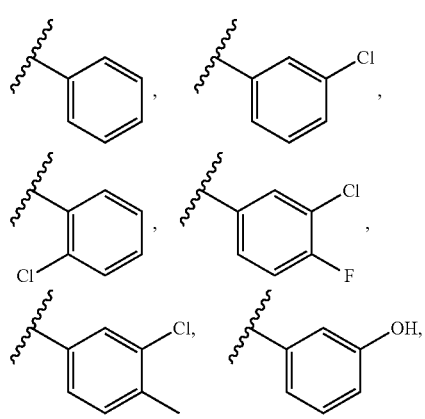

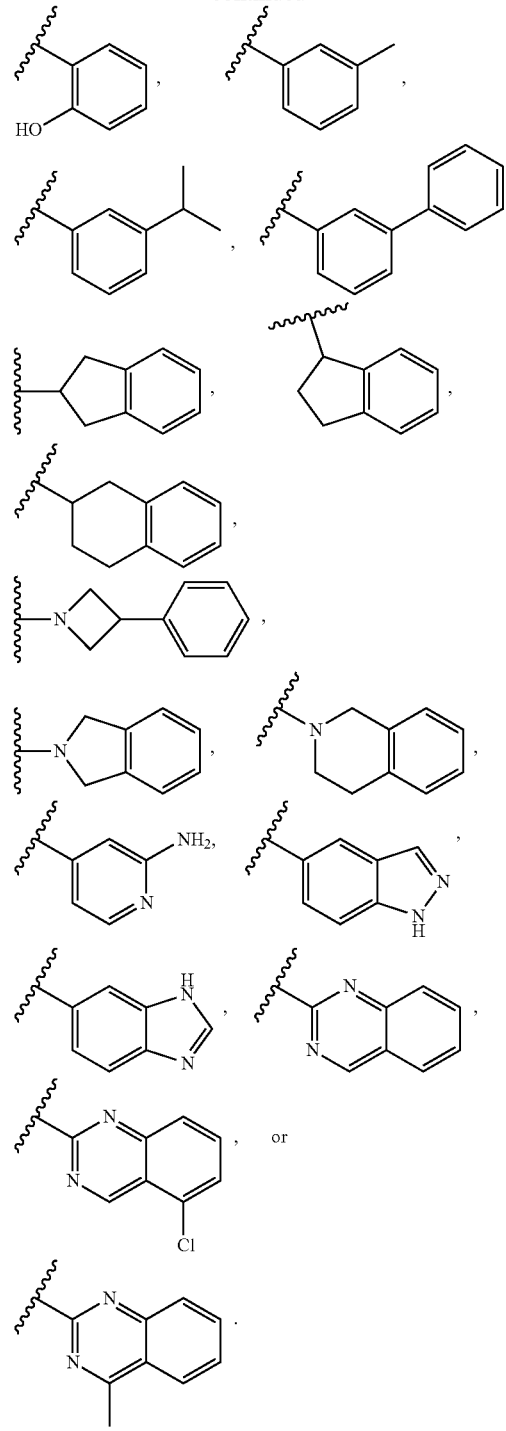

Embodiment 40. The compound of one of embodiments 1 to 39, wherein $R^{10.5}$ is hydrogen, halogen, substituted or unsubstituted $C_1$-$C_5$ alkyl, or substituted or unsubstituted 2 to 5 membered heteroalkyl.

Embodiment 41. The compound of one of embodiments 1 to 39, wherein $R^{10.5}$ is halogen or unsubstituted methyl.

Embodiment 42. The compound of one of embodiments 1 to 39, wherein $R^{10.5}$ is —Cl.

Embodiment 43. The compound of embodiment 1, having the formula

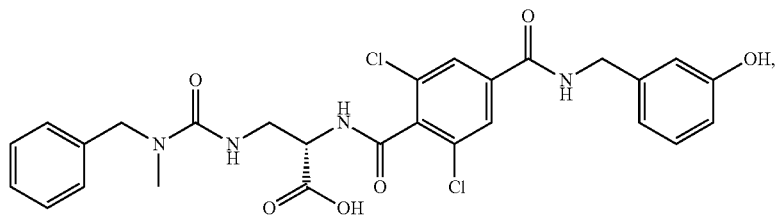
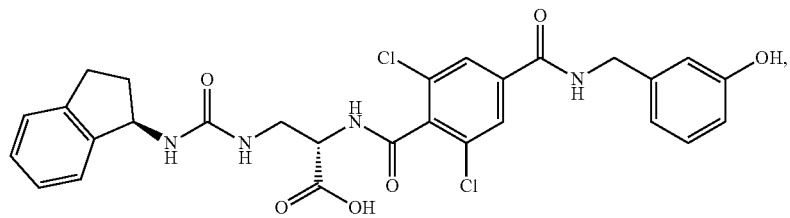
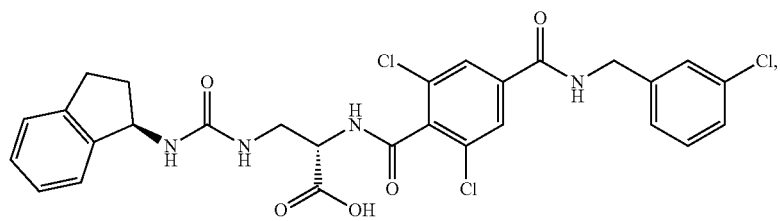
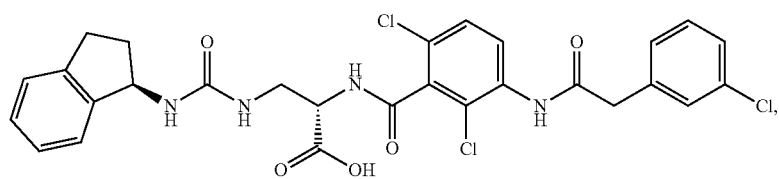
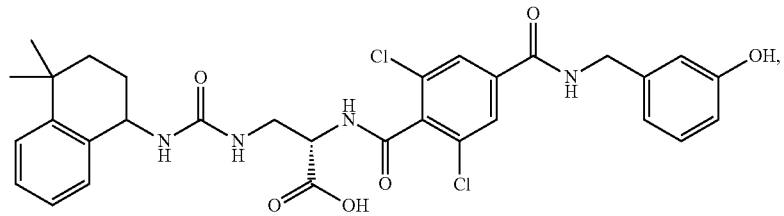
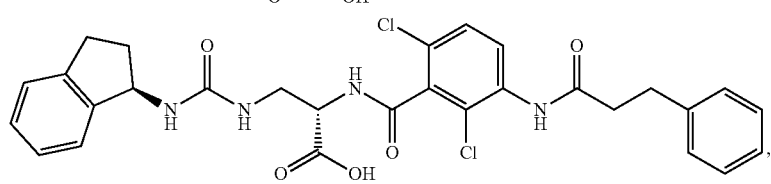
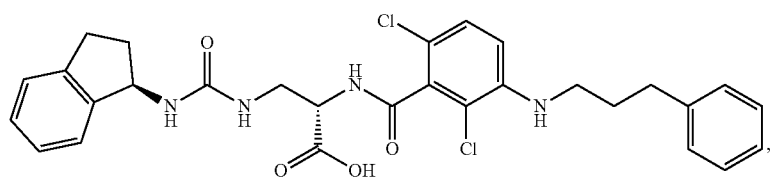
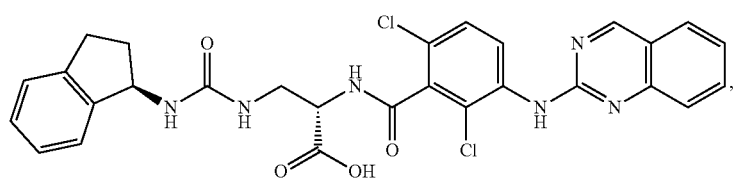

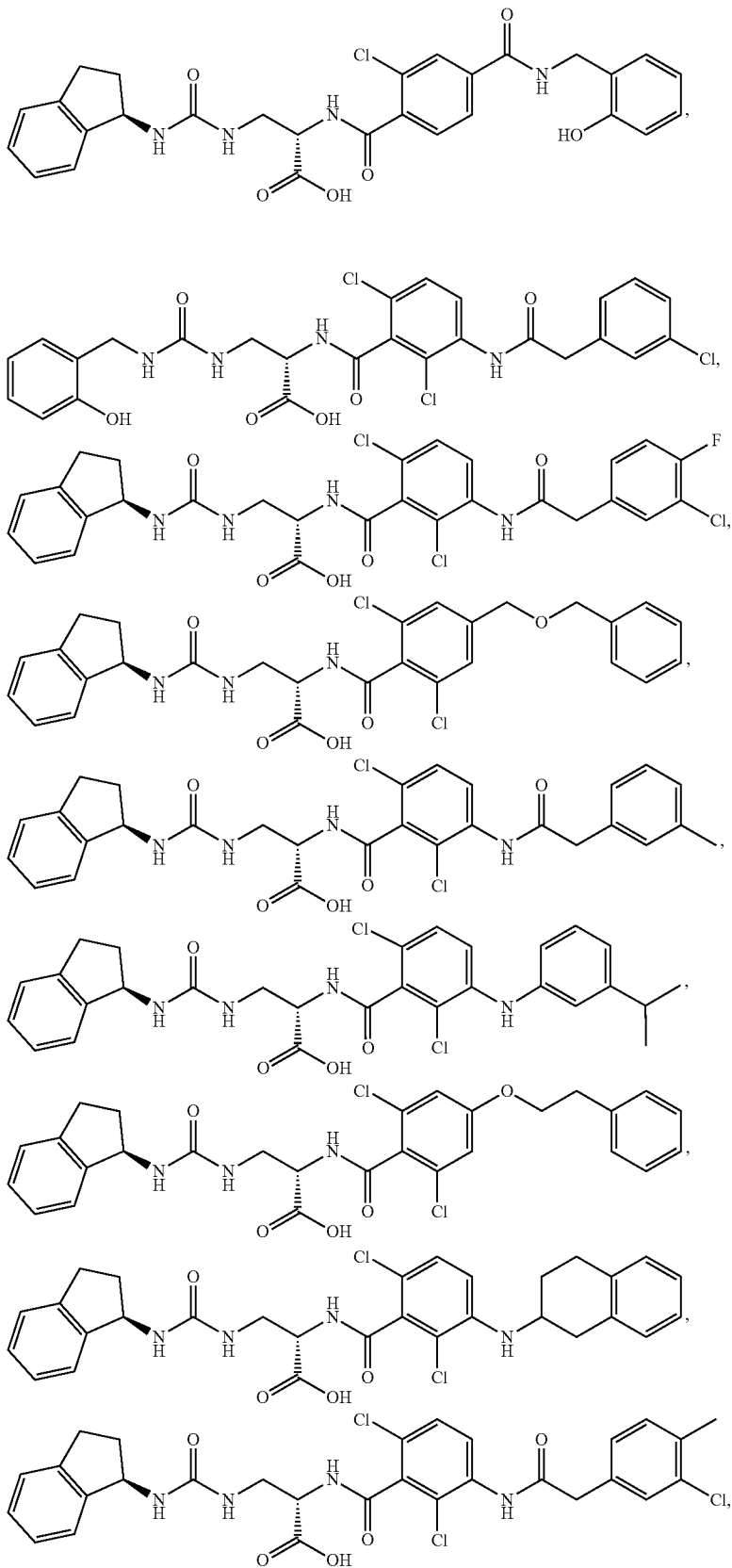

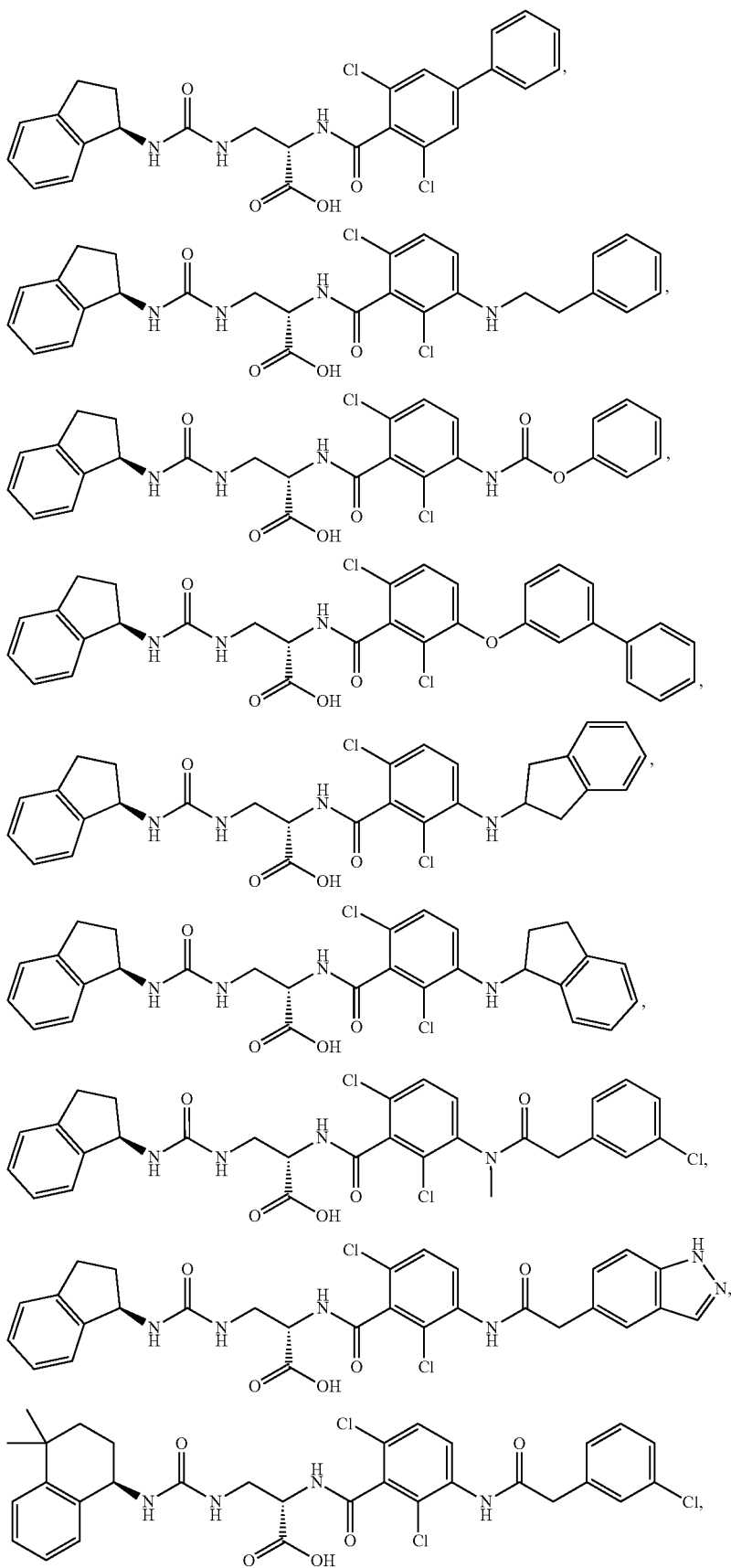

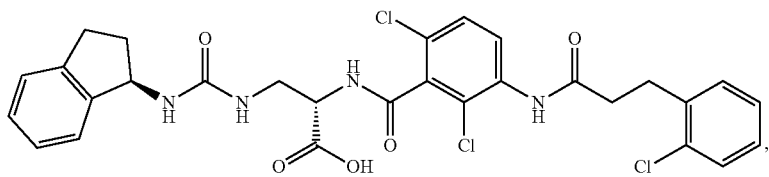
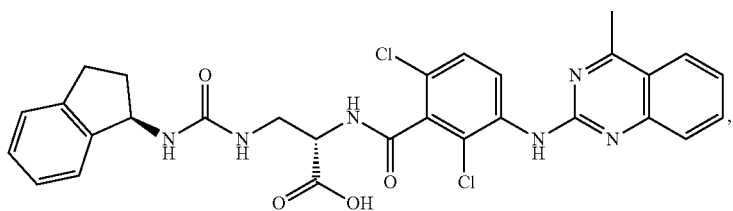
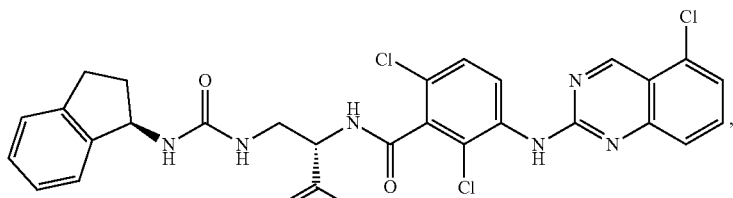
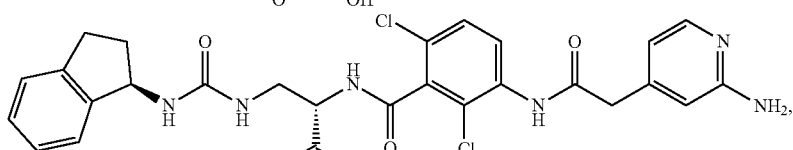
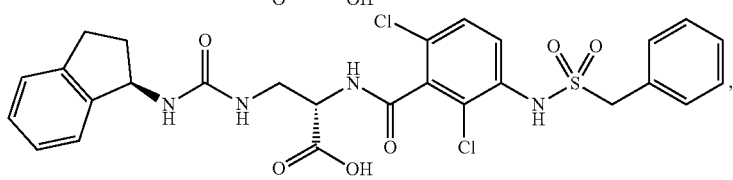
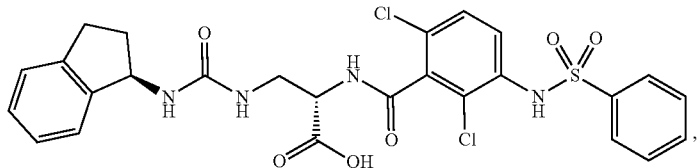
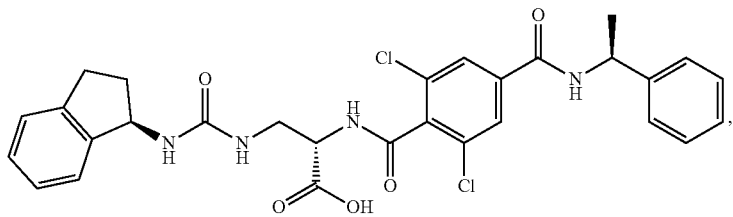
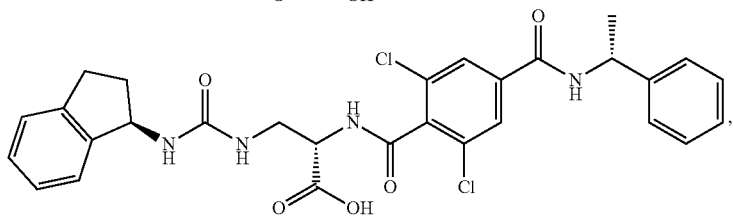

-continued
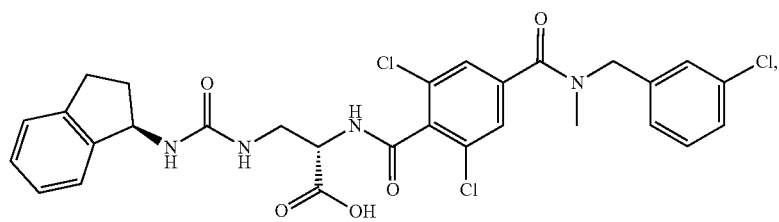
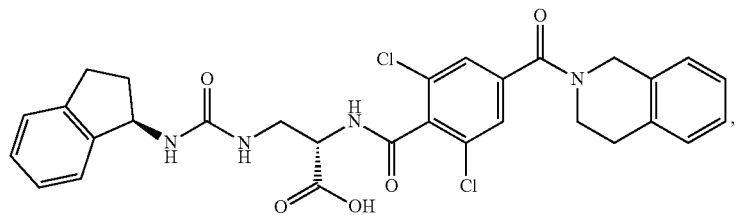
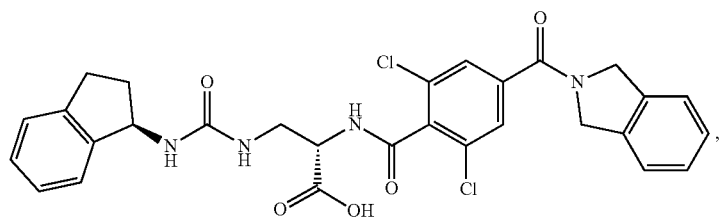
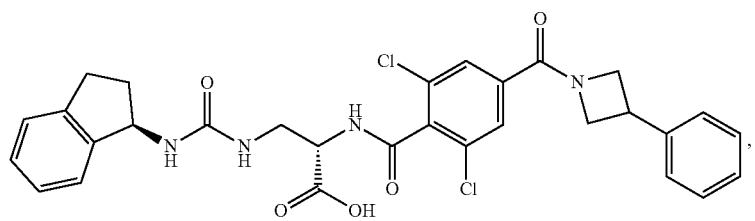
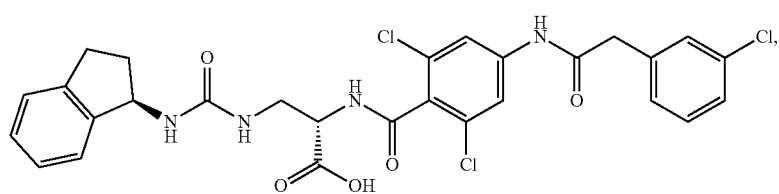 [SMILES: O=C(Cc1cccc(Cl)c1)Nc1cc(Cl)c(C(=O)N[C@@H](CNC(=O)N[C@@H]2CCc3ccccc32)C(=O)O)c(Cl)c1]
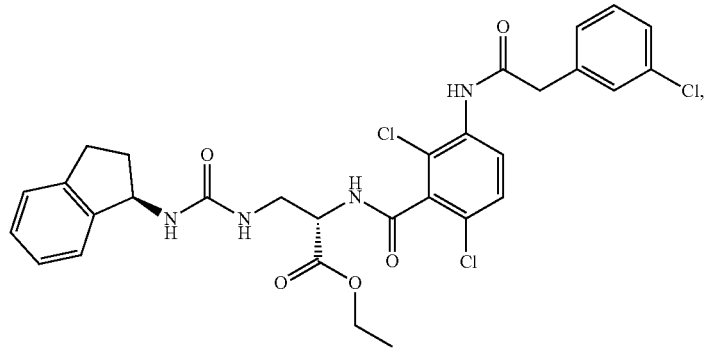
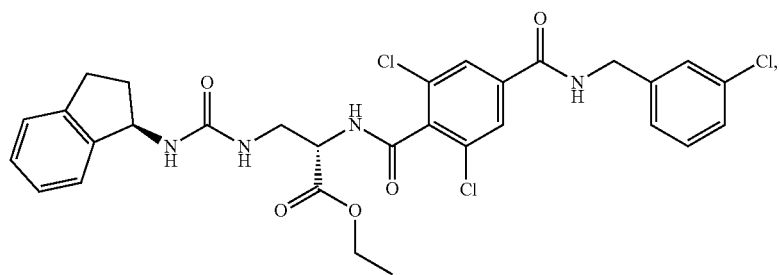

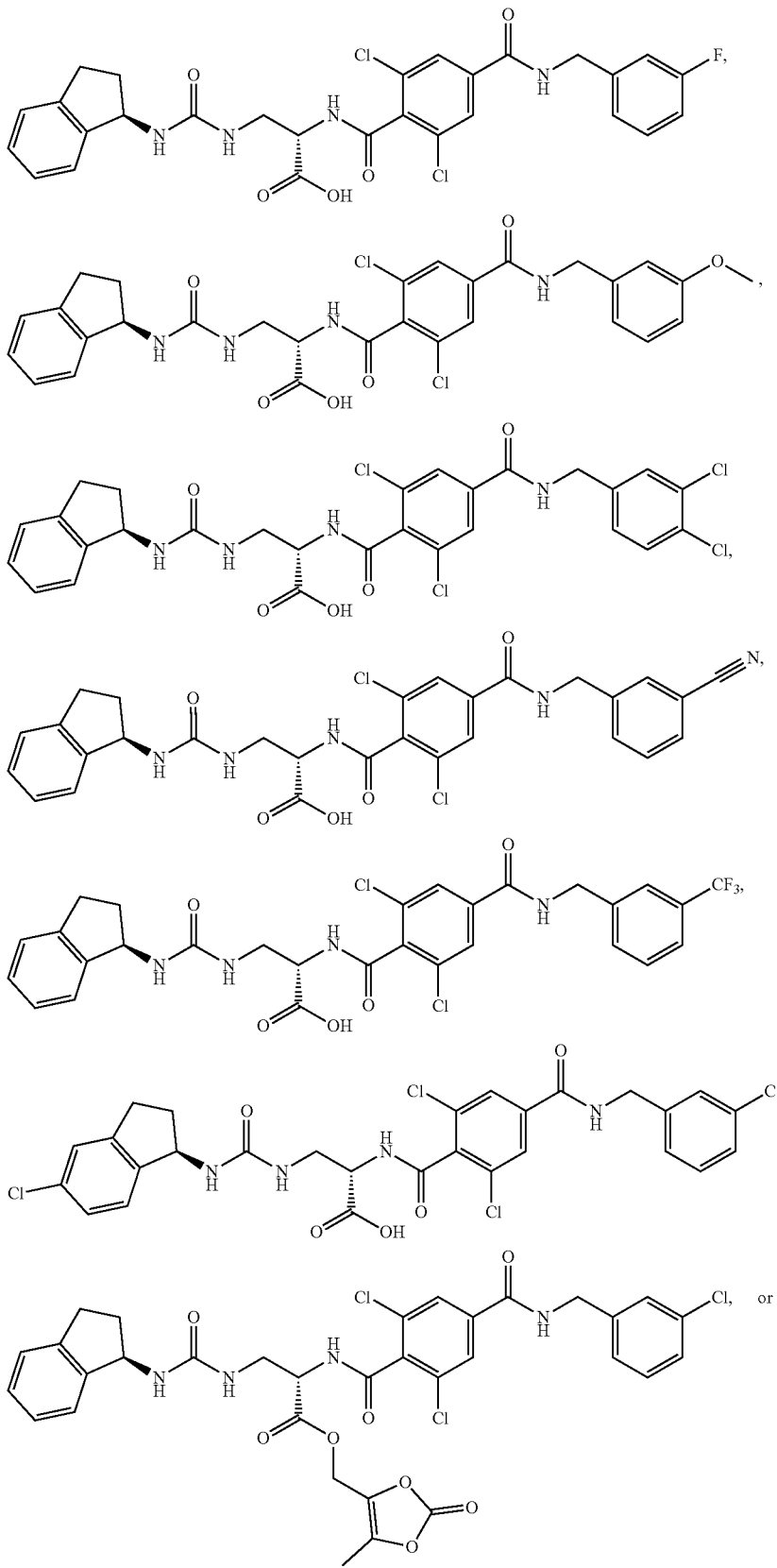

-continued

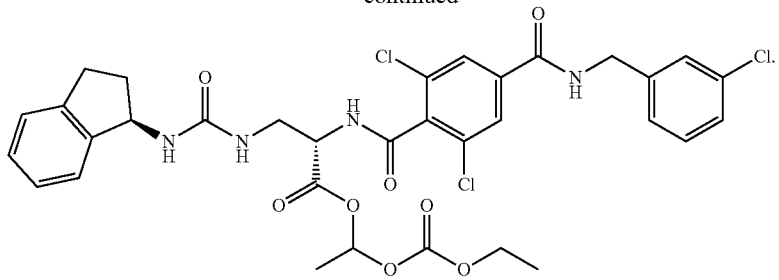

Embodiment 44. A compound, or a pharmaceutically acceptable salt thereof or a prodrug thereof, having the formula:

(IIb)

$$\text{structure with } (R^{21})_{z21}, R^2, R^5, R^{10.1}, R^{10.2}, R^{10.3}, R^{10.4}, R^{10.5}, L^{100}, R^{100}$$

wherein $R^2$ is hydrogen or substituted or unsubstituted alkyl;

$R^5$ is unsubstituted $C_1$-$C_3$ alkyl;

$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $C(O)R^{10.2C}$, $-C(O)OR^{10.2C}$, $-C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$,-$L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$,-$L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$,-$L^{10.4}$-$R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $NR^{10.5A}C(O)OR^{10.5C}$, $-NR^{10.5A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, substituted or unsubstituted alkylene, or substituted or unsubstituted heteroalkylene;

$R^{22}$, $R^{23}$ and $R^{24}$ are independently substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, $-CX^{100}_3$, $-CHX^{100}_2$, $-CH_2X^{100}$, $-OCX^{100}_3$, $-OCH_2X^{100}$, $-OCHX^{100}$, $-CN$, $-SO_{n100}R^{100D}$, $-SO_{v100}NR^{100A}R^{100B}$, $-NHC(O)NR^{100A}R^{100B}$, $-N(O)_{m100}$, $-NR^{100A}R^{100B}$, $-C(O)R^{100C}$, $-C(O)OR^{100C}$, $-C(O)NR^{100A}R^{100B}$, $-OR^{100D}$, —SR$^{100D}$, —NR$^{100A}$SO$_2$R$^{100D}$, —NR$^{100A}$C(O)R$^{100C}$, —NR$^{100A}$C(O)OR$^{100C}$, —NR$^{100A}$OR$^{100C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10.1A}$, R$^{10.1B}$, R$^{10.1C}$, R$^{10.1D}$, R$^{10.2A}$, R$^{10.2B}$, R$^{10.2C}$, R$^{10.2D}$, R$^{10.3A}$, R$^{10.3B}$, R$^{10.3C}$, R$^{10.3D}$, R$^{10.4A}$, R$^{10.4B}$, R$^{10.4C}$, R$^{10.4D}$, R$^{10.5A}$, R$^{10.5B}$, R$^{10.5C}$, R$^{10.5D}$, R$^{21A}$, R$^{21B}$, R$^{21C}$, R$^{21D}$, R$^{100A}$, R$^{100B}$, R$^{100C}$, and R$^{100D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10.1A}$ and R$^{10.1B}$ substituents bonded to the same nitrogen atom may be joined to form a substituted or unsubstituted heterocycloalkyl or substituted or unsubstituted heteroaryl; R$^{10.2A}$ and R$^{10.2B}$ substituents bonded to the same nitrogen atom may be joined to form a substituted or unsubstituted heterocycloalkyl or substituted or unsubstituted heteroaryl; R$^{10.3A}$ and R$^{10.3B}$ substituents bonded to the same nitrogen atom may be joined to form a substituted or unsubstituted heterocycloalkyl or substituted or unsubstituted heteroaryl; R$^{10.4A}$ and R$^{10.4B}$ substituents bonded to the same nitrogen atom may be joined to form a substituted or unsubstituted heterocycloalkyl or substituted or unsubstituted heteroaryl; R$^{10.5A}$ and R$^{10.5B}$ substituents bonded to the same nitrogen atom may be joined to form a substituted or unsubstituted heterocycloalkyl or substituted or unsubstituted heteroaryl; R$^{21A}$ and R$^{21B}$, substituents bonded to the same nitrogen atom may be joined to form a substituted or unsubstituted heterocycloalkyl or substituted or unsubstituted heteroaryl; R$^{100A}$ and R$^{100B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, n21, and n100 are independently an integer from 0 to 4;

m10.1, m10.2, m10.3, m10.4, m10.5, m21, m100, v10.1, v10.2, v10.3, v10.4, v10.5, v21, and v100 are independently 1 or 2;

X$^{10.1}$, X$^{10.2}$, X$^{10.3}$, X$^{10.4}$, X$^{10.5}$, and X$^{21}$ are independently —F, —Cl, —Br, or —I;

z21 is an integer from 0 to 5; and wherein at least one of R$^{10.1}$ or R$^{10.5}$ is not hydrogen.

Embodiment 45. The compound of embodiment 44, having the formula:

(II)

Embodiment 46. The compound of one of embodiments 44 to 45, wherein R$^5$ is unsubstituted methyl.

Embodiment 47. The compound of one of embodiments 44 to 46, wherein R$^2$ is hydrogen or unsubstituted C$_1$-C$_3$ alkyl.

Embodiment 48. The compound of one of embodiments 44 to 46, wherein R$^2$ is hydrogen.

Embodiment 49. The compound of one of embodiments 44 to 46, wherein R$^2$ is unsubstituted methyl.

Embodiment 50. The compound of one of embodiments 44 to 49, wherein R$^{21}$ is independently halogen, —OH, or substituted or unsubstituted C$_1$-C$_4$ alkyl.

Embodiment 51. The compound of one of embodiments 44 to 49, wherein R$^{21}$ is independently —OH or unsubstituted methyl.

Embodiment 52. The compound of one of embodiments 44 to 49, wherein z21 is 0.

Embodiment 53. The compound of one of embodiments 44 to 52, wherein R$^{10.1}$ is halogen, substituted or unsubstituted C$_1$-C$_5$ alkyl, or substituted or unsubstituted 2 to 5 membered heteroalkyl.

Embodiment 54. The compound of one of embodiments 44 to 52, wherein R$^{10.1}$ is halogen or unsubstituted methyl.

Embodiment 55. The compound of one of embodiments 44 to 52, wherein R$^{10.1}$ is —Cl.

Embodiment 56. The compound of one of embodiments 44 to 55, wherein R$^{10.2}$ is hydrogen or -L$^{10.2}$-R$^{22}$.

Embodiment 57. The compound of one of embodiments 44 to 56, wherein L$^{10.2}$ is a bond, —NH—, —O—, —C(O)—, —NHC(O)O—, —NHS(O)$_2$—, or substituted or unsubstituted 2 to 5 membered heteroalkylene.

Embodiment 58. The compound of one of embodiments 44 to 56, wherein L$^{10.2}$ is a bond, —NH—, —O—, —C(O)—, —NHC(O)O—, —NHS(O)$_2$—, Embodiment 59. The compound of one of embodiments 44 to 58, wherein $R^{22}$ is $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl; and $R^{32}$ is independently oxo, halogen, —CCl₃, —CBr₃, —CF₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 60. The compound of embodiment 59, wherein $R^{22}$ is

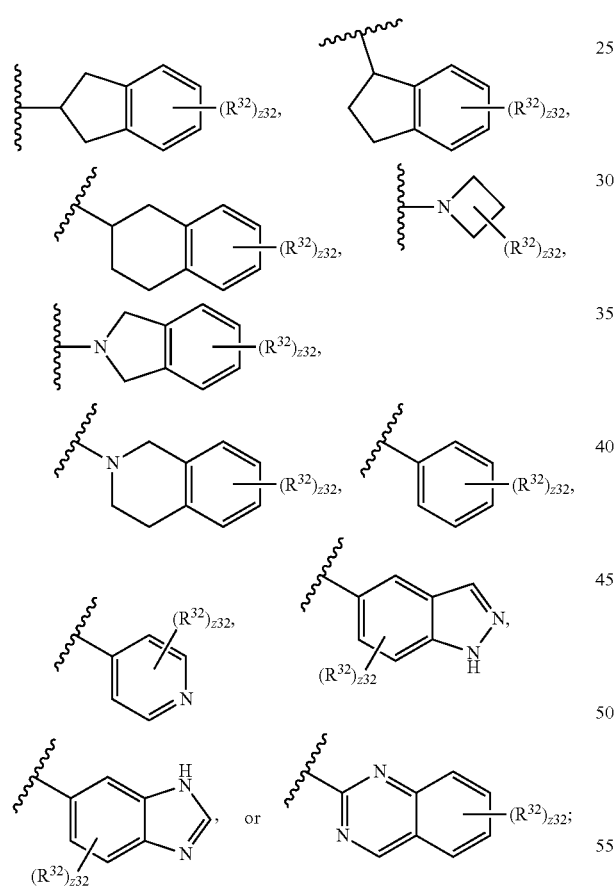

and z32 is an integer from 0 to 10.

Embodiment 61. The compound of one of embodiments 59 to 60, wherein $R^{32}$ is independently halogen, —CF₃, —OH, —NH₂, substituted or unsubstituted C₁-C₄ alkyl, substituted or unsubstituted 2 to 5 membered heteroalkyl, or substituted or unsubstituted phenyl.

Embodiment 62. The compound of one of embodiments 44 to 59, wherein $R^{22}$ is

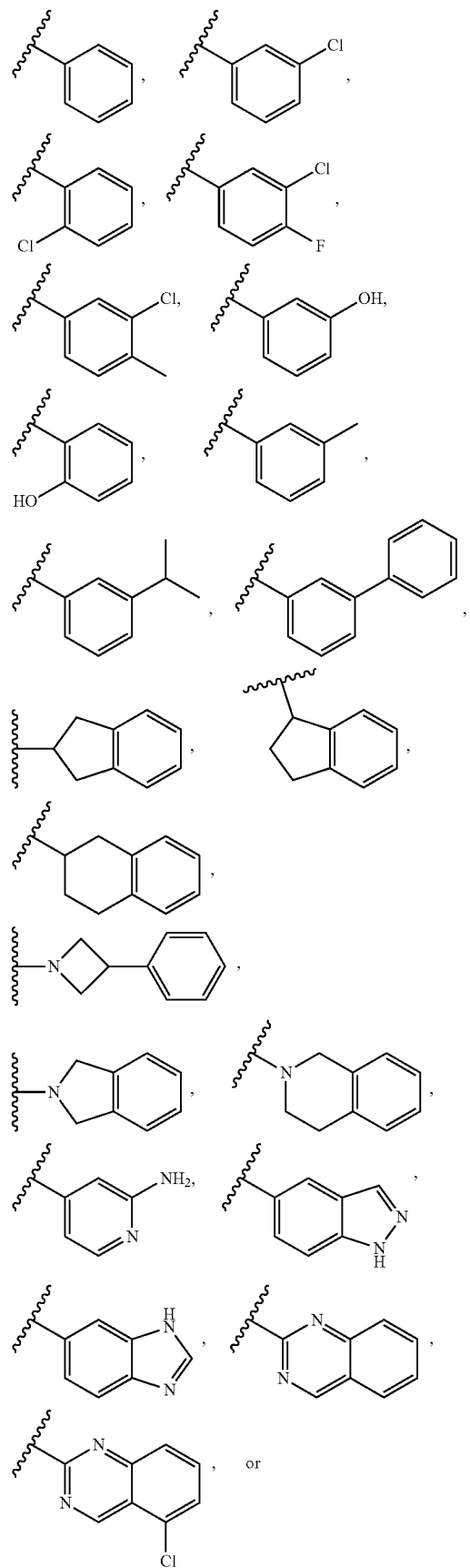

-continued

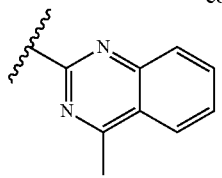

Embodiment 63. The compound of one of embodiments 44 to 62, wherein $R^{10.3}$ is hydrogen or $-L^{10.3}-R^{23}$.

Embodiment 64. The compound of one of embodiments 44 to 63, wherein $L^{10.3}$ is a bond, —NH—, —O—, —C(O)—, —NHC(O)O—, —NHS(O)$_2$—, or substituted or unsubstituted 2 to 5 membered heteroalkylene.

Embodiment 65. The compound of one of embodiments 44 to 63, wherein $L^{10.3}$ is a bond, —NH—, —O—, —C(O)—, —NHC(O)O—, —NHS(O)$_2$—,

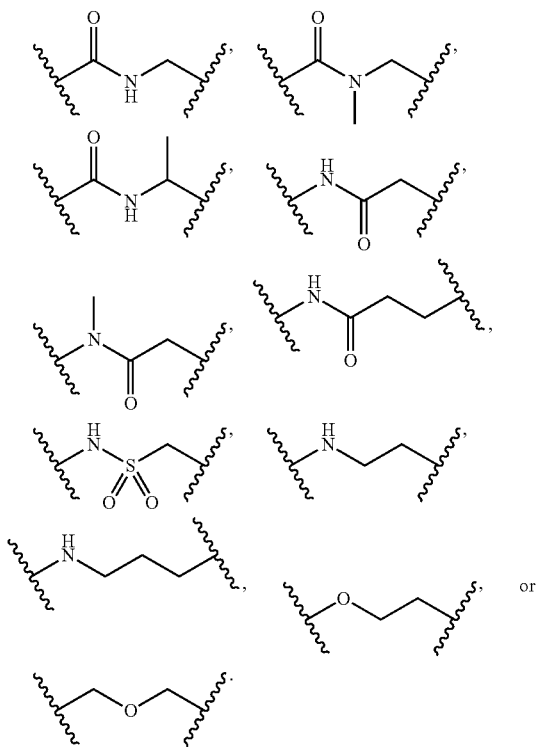

Embodiment 66. The compound of one of embodiments 44 to 65, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 67. The compound of embodiment 66, wherein $R^{23}$ is

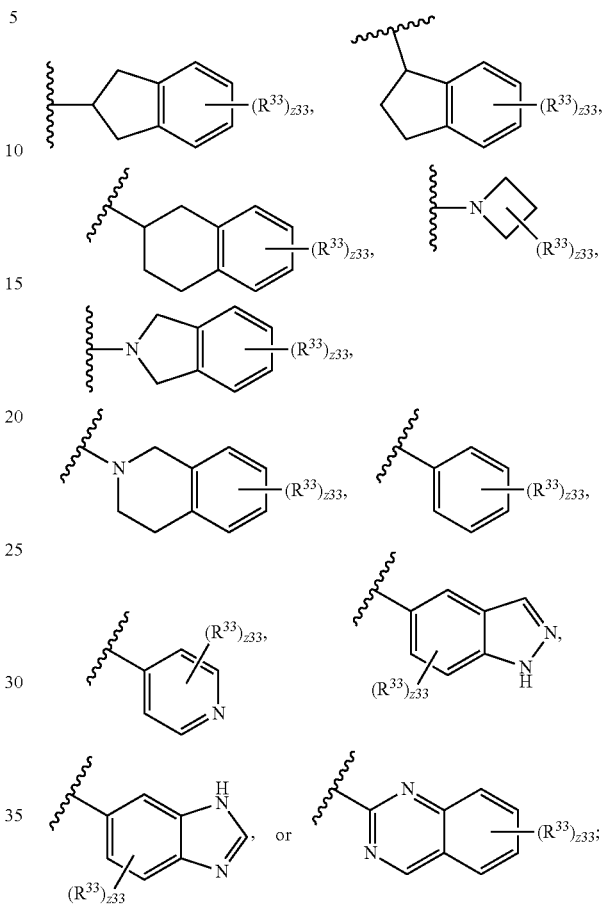

and z33 is an integer from 0 to 10.

Embodiment 68. The compound of one of embodiments 66 to 67, wherein $R^{33}$ is independently halogen, —CF$_3$, —OH, —NH$_2$, substituted or unsubstituted C$_1$-C$_4$ alkyl, substituted or unsubstituted 2 to 5 membered heteroalkyl, or substituted or unsubstituted phenyl.

Embodiment 69. The compound of one of embodiments 44 to 66, wherein $R^{23}$ is

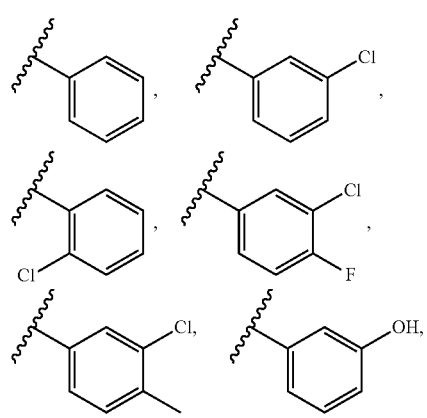

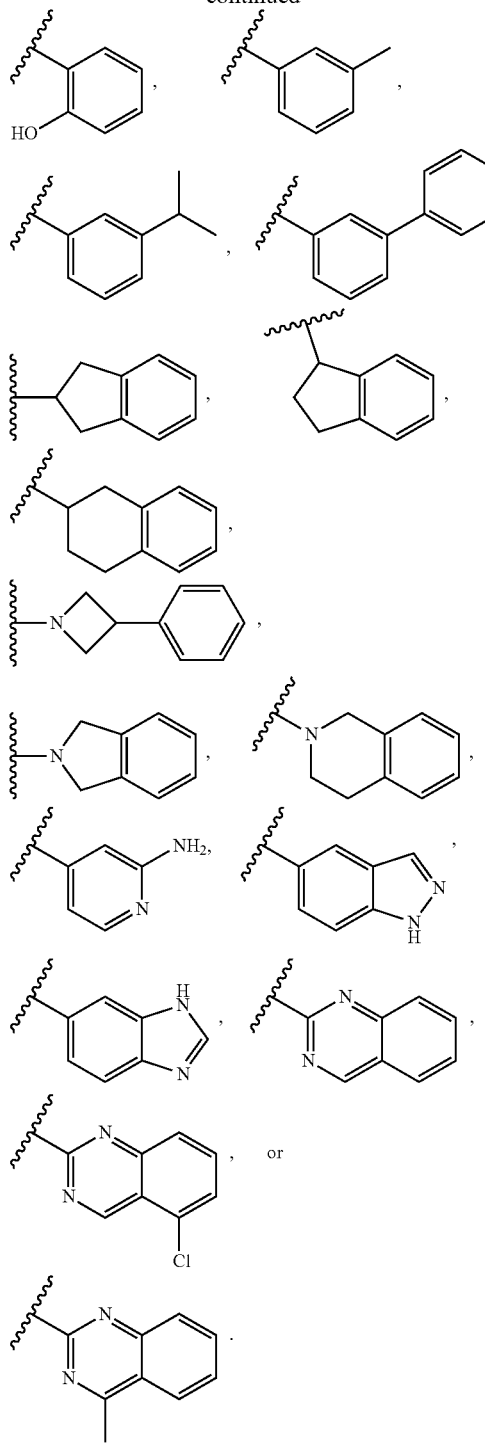

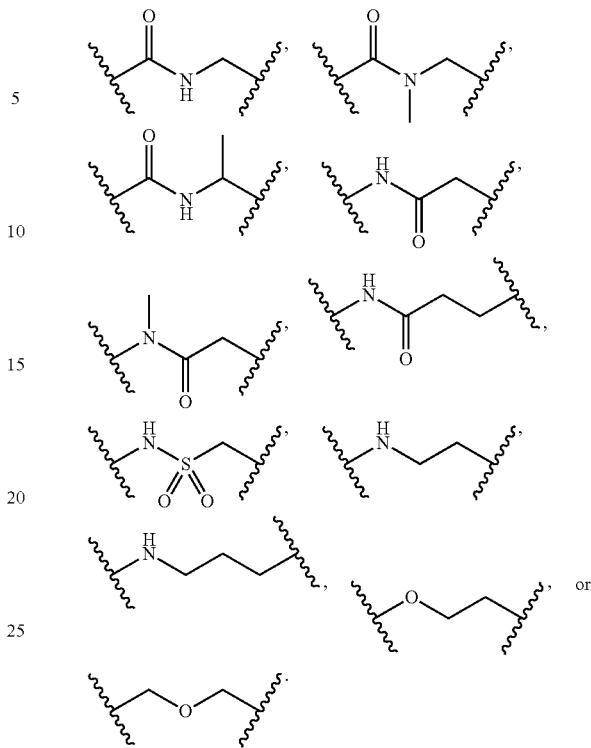

Embodiment 73. The compound of one of embodiments 44 to 72, wherein $R^{24}$ is $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl; and $R^{34}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 74. The compound of embodiment 73, wherein $R^{24}$ is

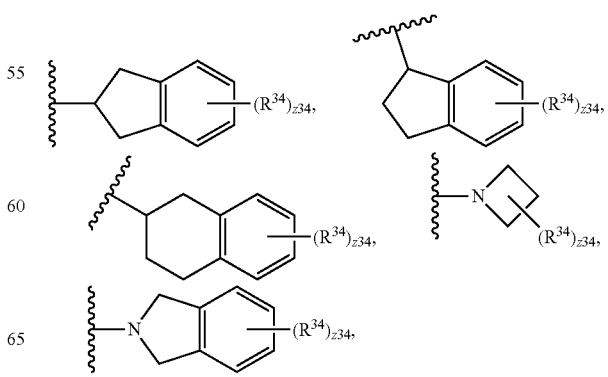

Embodiment 70. The compound of one of embodiments 44 to 69, wherein $R^{10.4}$ is hydrogen or -L$^{10.4}$-R$^{24}$.

Embodiment 71. The compound of one of embodiments 44 to 70, wherein L$^{10.4}$ is a bond, —NH—, —O—, —C(O)—, —NHC(O)O—, —NHS(O)$_2$—, or substituted or unsubstituted 2 to 5 membered heteroalkylene.

Embodiment 72. The compound of one of embodiments 44 to 70, wherein L$^{10.4}$ is a bond, —NH—, —O—, —C(O)—, —NHC(O)O—, —NHS(O)$_2$—,

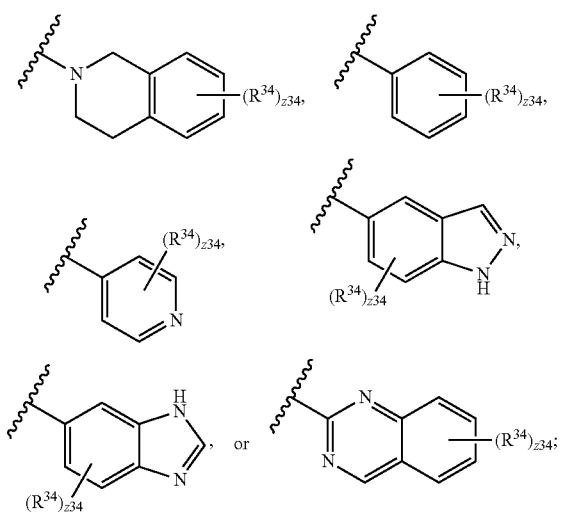

and z34 is an integer from 0 to 10.

Embodiment 75. The compound of one of embodiments 73 to 74, wherein $R^{34}$ is independently halogen, —$CF_3$, —OH, —$NH_2$, substituted or unsubstituted $C_1$-$C_4$ alkyl, substituted or unsubstituted 2 to 5 membered heteroalkyl, or substituted or unsubstituted phenyl.

Embodiment 76. The compound of one of embodiments 44 to 73, wherein $R^{24}$ is

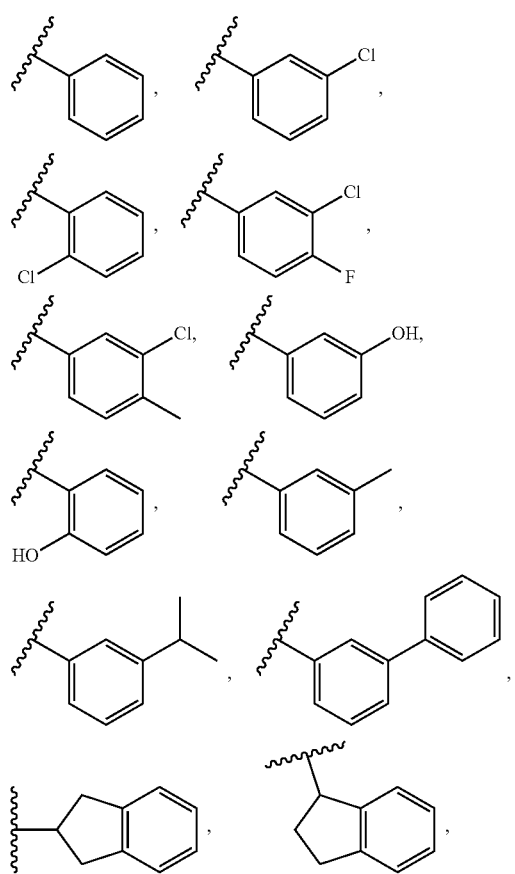

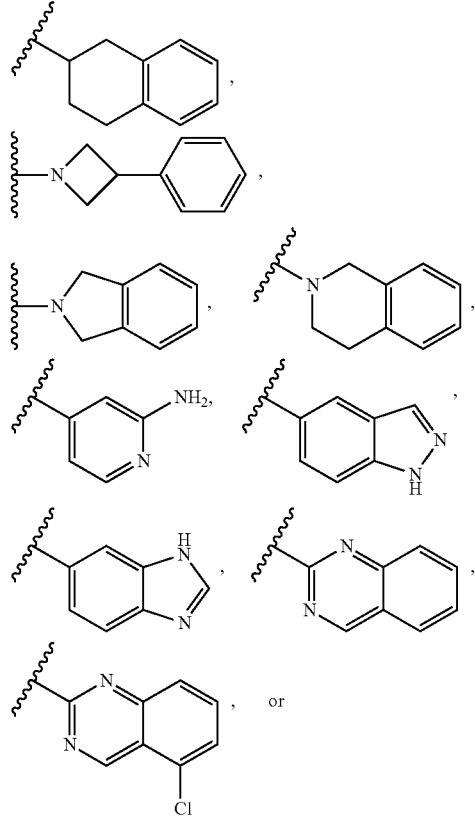

Embodiment 77. The compound of one of embodiments 44 to 76, wherein $R^{10.5}$ is halogen, substituted or unsubstituted $C_1$-$C_5$ alkyl, or substituted or unsubstituted 2 to 5 membered heteroalkyl.

Embodiment 78. The compound of one of embodiments 44 to 76, wherein $R^{10.5}$ is halogen or unsubstituted methyl.

Embodiment 79. The compound of one of embodiments 44 to 76, wherein $R^{10.5}$ is —Cl.

Embodiment 80. The compound of one of embodiments 44 to 45, having the formula

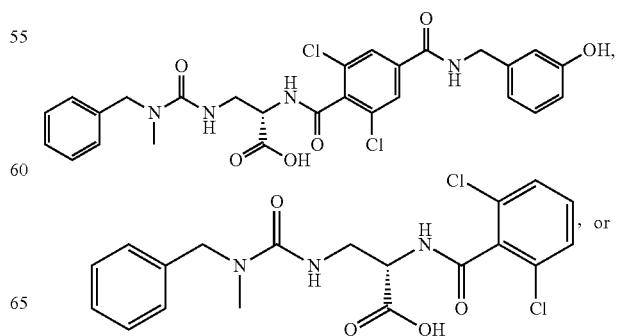

-continued

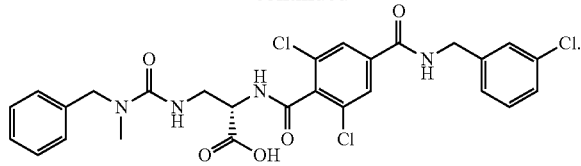

Embodiment 81. A compound, or a pharmaceutically acceptable salt thereof or a prodrug thereof, having the formula:

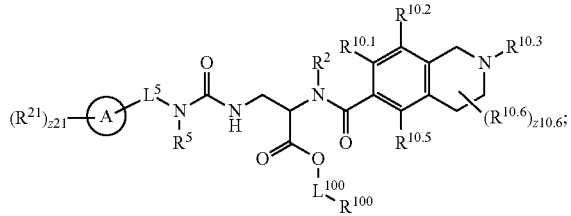

(IIIb)

wherein
Ring A is cycloalkyl, heterocycloalkyl, aryl, or heteroaryl;
$R^2$ is hydrogen or substituted or unsubstituted alkyl;
$R^5$ is hydrogen or unsubstituted $C_1$-$C_3$ alkyl;
$L^5$ is a bond or unsubstituted $C_1$-$C_3$ alkylene;
$R^{10.1}$ is hydrogen, halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10.1}R^{10.1D}$, —$SO_{v10.1}NR^{10.1A}R^{10.1B}$, —NHC(O)NR$^{10.1A}$R$^{10.1B}$, —N(O)$_{m10.1}$, —NR$^{10.1A}$R$^{10.1B}$, —C(O)R$^{10.1C}$, —C(O)OR$^{10.1C}$, —C(O)NR$^{10.1A}$R$^{10.1B}$, —OR$^{10.1D}$, —SR$^{10.1D}$, —NR$^{10.1A}$SO$_2$R$^{10.1D}$, —NR$^{10.1A}$C(O)R$^{10.1C}$, —NR$^{10.1A}$C(O)OR$^{10.1C}$, —NR$^{10.1A}$OR$^{10.1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.2}$ is hydrogen, halogen, —$CX^{10.2}_3$, —$CHX^{10.2}_2$, —$CH_2X^{10.2}$, —$OCX^{10.2}_3$, —$OCH_2X^{10.2}$, —$OCHX^{10.2}_2$, —CN, —$SO_{n10.2}R^{10.2D}$, —$SO_{v10.2}NR^{10.2A}R^{10.2B}$, —NHC(O)NR$^{10.2A}$R$^{10.2B}$, —N(O)$_{m10.2}$, —NR$^{10.2A}$R$^{10.2B}$, —C(O)R$^{10.2C}$, —C(O)OR$^{10.2C}$, —C(O)NR$^{10.2A}$R$^{10.2B}$, —OR$^{10.2D}$, —SR$^{10.2D}$, —NR$^{10.2A}$SO$_2$R$^{10.2D}$, —NR$^{10.2A}$C(O)R$^{10.2C}$, —NR$^{10.2A}$C(O)OR$^{10.2C}$, —NR$^{10.2A}$OR$^{10.2C}$, —N$_3$, -L$^{10.2}$—R$^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.3}$ is hydrogen, halogen, —$CX^{10.3}_3$, —$CHX^{10.3}_2$, —$CH_2X^{10.3}$, —$OCX^{10.3}_3$, —$OCH_2X^{10.3}$, —$OCHX^{10.3}_2$, —CN, —$SO_{n10.3}R^{10.3D}$, —$SO_{v10.3}NR^{10.3A}R^{10.3B}$, —NHC(O)NR$^{10.3A}$R$^{10.3B}$, —N(O)$_{m10.3}$, —NR$^{10.3A}$R$^{10.3B}$, —C(O)R$^{10.3C}$, —C(O)OR$^{10.3C}$, —C(O)NR$^{10.3A}$R$^{10.3B}$, —OR$^{10.3D}$, —SR$^{10.3D}$, —NR$^{10.3A}$SO$_2$R$^{10.3D}$, —NR$^{10.3A}$C(O)R$^{10.3C}$, —NR$^{10.3A}$C(O)OR$^{10.3C}$, —NR$^{10.3A}$OR$^{10.3C}$, —N$_3$, -L$^{10.3}$—R$^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.5}$ is hydrogen, halogen, —$CX^{10.5}_3$, —$CHX^{10.5}_2$, —$CH_2X^{10.5}$, —$OCX^{10.5}_3$, —$OCH_2X^{10.5}$, —$OCHX^{10.5}_2$, —CN, —$SO_{n10.5}R^{10.5D}$, —$SO_{v10.5}NR^{10.5A}R^{10.5B}$, —NHC(O)NR$^{10.5A}$R$^{10.5B}$, —N(O)$_{m10.5}$, —NR$^{10.5A}$R$^{10.5B}$, —C(O)R$^{10.5C}$, —C(O)OR$^{10.5C}$, —C(O)NR$^{10.5A}$R$^{10.5B}$, —OR$^{10.5D}$, —SR$^{10.5D}$, —NR$^{10.5A}$SO$_2$R$^{10.5D}$, —NR$^{10.5A}$C(O)R$^{10.5C}$, —NR$^{10.5A}$C(O)OR$^{10.5C}$, —NR$^{10.5A}$OR$^{10.5C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.6}$ is independently oxo, halogen, —$CX^{10.6}_3$, —$CHX^{10.6}_2$, —$CH_2X^{10.6}$, —$OCX^{10.6}_3$, —$OCH_2X^{10.6}$, —$OCHX^{10.6}_2$, —CN, —$SO_{n10.6}R^{10.6D}$, —$SO_{v10.6}NR^{10.6A}R^{10.6B}$, —NHC(O)NR$^{10.6A}$R$^{10.6B}$, —N(O)$_{m10.6}$, —NR$^{10.6A}$R$^{10.6B}$, —C(O)R$^{10.6C}$, —C(O)OR$^{10.6C}$, —C(O)NR$^{10.6A}$R$^{10.6B}$, —OR$^{10.6D}$, —SR$^{10.6D}$, —NR$^{10.6A}$SO$_2$R$^{10.6D}$, —NR$^{10.6A}$C(O)R$^{10.6C}$, NR$^{10.6A}$C(O)OR$^{10.6C}$, —NR$^{10.6A}$OR$^{10.6C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21D}$, —$SO_{v21}NR^{21A}R^{21B}$, —NHC(O)NR$^{21A}$R$^{21B}$, —N(O)$_{m21}$, —NR$^{21A}$R$^{21B}$, C(O)R$^{21C}$, —C(O)OR$^{21C}$, —C(O)NR$^{21A}$R$^{21B}$, —OR$^{21D}$, —SR$^{21D}$, —NR$^{21A}$SO$_2$R$^{21D}$, —NR$^{21A}$C(O)R$^{21C}$, —NR$^{21A}$C(O)OR$^{21C}$, —NR$^{21A}$OR$^{21C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^{10.2}$ and $L^{10.3}$ are independently a bond, —NH—, —S—, —O—, —C(O)—, —C(O)O—, —OC(O)—, —NHC(O)—, —C(O)NH—, —NHC(O)O—, —OC(O)NH—, —NHC(O)NH—, —NHC(NH)NH—, —S(O)$_2$—, —NHS(O)$_2$—, —S(O)$_2$NH—, substituted or unsubstituted alkylene, or substituted or unsubstituted heteroalkylene;
$R^{22}$ and $R^{23}$ are independently substituted or unsubstituted cycloalkyl, substituted or unsubstituted heterocycloalkyl, substituted or unsubstituted aryl, or substituted or unsubstituted heteroaryl;
$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{100}$ is hydrogen, halogen, —$CX^{100}_3$, —$CHX^{100}_2$, —$CH_2X^{100}$, —$OCX^{100}_3$, —$OCH_2X^{100}$, —$OCHX^{100}_2$, —CN, —$SO_{n100}R^{100D}$, —$SO_{v100}NR^{100A}R^{100B}$, —NHC(O)NR$^{100A}$R$^{100B}$, —N(O)$_{m100}$, —NR$^{100A}$R$^{100B}$, —C(O)R$^{100C}$, —C(O)OR$^{100C}$, —C(O)NR$^{100A}$R$^{100B}$, —OR$^{100D}$, —SR$^{100D}$, —NR$^{100A}$SO$_2$R$^{100D}$, —NR$^{100A}$C(O)R$^{100C}$, —NR$^{100A}$C(O)OR$^{100C}$, —NR$^{100A}$OR$^{100C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.5A}$, $R^{10.5B}$, $R^{10.5C}$, $R^{10.5D}$, $R^{10.6A}$, $R^{10.6B}$, $R^{10.6C}$, $R^{10.6D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{10.6A}$ and $R^{10.6B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.2, n10.3, n10.5, n10.6, n21, and n100 are independently an integer from 0 to 4;

m10.1, m10.2, m10.3, m10.5, m10.6, m21, m100, v10.1, v10.2, v10.3, v10.5, v10.6, v21, and v100 are independently 1 or 2;

$X^{10.1}$, $X^{10.2}$, $X^{10.3}$, $X^{10.5}$, $X^{10.6}$, $X^{21}$, and $X^{100}$ are independently —F, —Cl, —Br, or —I;

z10.6 is an integer from 0 to 6;

z21 is an integer from 0 to 11; and wherein at least one of $R^{10.1}$ or $R^{10.5}$ is not hydrogen.

Embodiment 82. The compound of embodiment 81, having the formula:

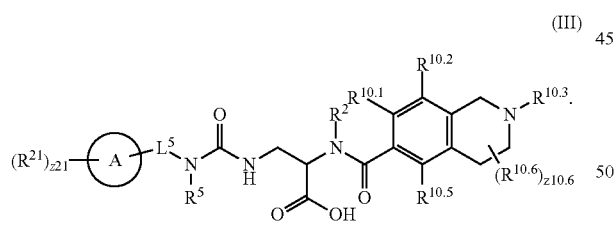

(III)

Embodiment 83. The compound of one of embodiments 81 to 82, wherein Ring A is a fused bicyclic cycloalkyl or phenyl.

Embodiment 84. The compound of one of embodiments 81 to 82, wherein

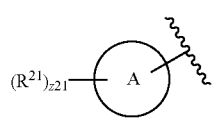

is

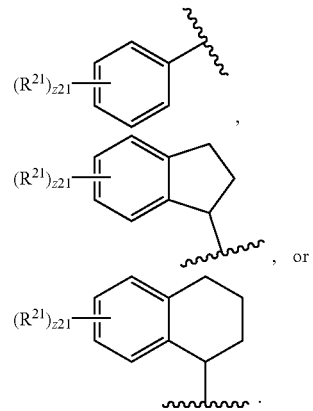

Embodiment 85. The compound of one of embodiments 81 to 84, wherein $R^{21}$ is independently halogen, —OH, or substituted or unsubstituted C$_1$-C$_4$ alkyl.

Embodiment 86. The compound of one of embodiments 81 to 84, wherein $R^{21}$ is independently —OH or unsubstituted methyl.

Embodiment 87. The compound of one of embodiments 81 to 86, wherein z21 is an integer from 0 to 3.

Embodiment 88. The compound of one of embodiments 81 to 82, wherein

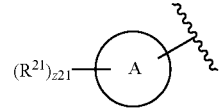

is

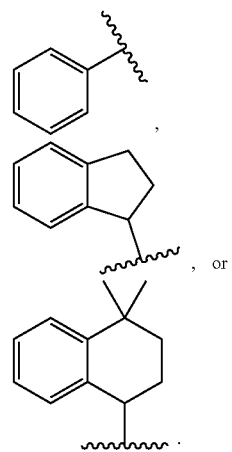

Embodiment 89. The compound of one of embodiments 81 to 88, wherein $R^2$ is hydrogen or unsubstituted C$_1$-C$_3$ alkyl.

Embodiment 90. The compound of one of embodiments 81 to 88, wherein $R^2$ is hydrogen.

Embodiment 91. The compound of one of embodiments 81 to 88, wherein $R^2$ is unsubstituted methyl.

Embodiment 92. The compound of one of embodiments 81 to 91, wherein $R^5$ is hydrogen.

Embodiment 93. The compound of one of embodiments 81 to 91, wherein $R^5$ is unsubstituted methyl.

Embodiment 94. The compound of one of embodiments 81 to 93, wherein $L^5$ is a bond.

Embodiment 95. The compound of one of embodiments 81 to 93, wherein $L^5$ is unsubstituted methylene.

Embodiment 96. The compound of one of embodiments 81 to 93, wherein $R^{10.1}$ is halogen, substituted or unsubstituted $C_1$-$C_5$ alkyl, or substituted or unsubstituted 2 to 5 membered heteroalkyl.

Embodiment 97. The compound of one of embodiments 81 to 93, wherein $R^{10.1}$ is halogen or unsubstituted methyl.

Embodiment 98. The compound of one of embodiments 81 to 93, wherein $R^{10.1}$ is —Cl.

Embodiment 99. The compound of one of embodiments 81 to 98, wherein $R^{102}$ is hydrogen.

Embodiment 100. The compound of one of embodiments 81 to 99, wherein $R^{10.3}$ is hydrogen, —C(O)$R^{10.3C}$, or -$L^{10.3}R^{23}$.

Embodiment 101. The compound of embodiment 100, wherein $R^{10.3C}$ is substituted or unsubstituted $C_1$-$C_4$ alkyl or substituted or unsubstituted phenyl.

Embodiment 102. The compound of embodiment 100, wherein $R^{10.3C}$ is unsubstituted methyl.

Embodiment 103. The compound of embodiment 100, wherein $L^{10.3}$ is —C(O)—, —S(O)$_2$—, or unsubstituted methylene.

Embodiment 104. The compound of embodiment 100 or embodiment 103, wherein $R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 105. The compound of embodiment 104, wherein $R^{23}$ is

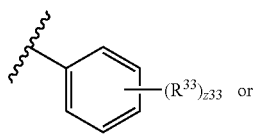 or

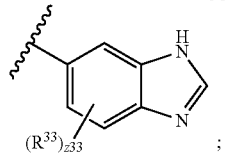

and z33 is an integer from 0 to 5.

Embodiment 106. The compound of one of embodiments 104 to 105, wherein $R^{33}$ is independently halogen.

Embodiment 107. The compound of embodiment 104, wherein $R^{23}$ is

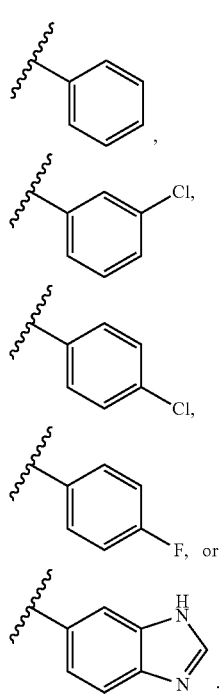

Embodiment 108. The compound of one of embodiments 81 to 107, wherein $R^{10.5}$ is halogen, substituted or unsubstituted $C_1$-$C_5$ alkyl, or substituted or unsubstituted 2 to 5 membered heteroalkyl.

Embodiment 109. The compound of one of embodiments 81 to 107, wherein $R^{10.5}$ is halogen or unsubstituted methyl.

Embodiment 110. The compound of one of embodiments 81 to 107, wherein $R^{10.5}$ is —Cl.

Embodiment 111. The compound of one of embodiments 81 to 110, wherein $R^{10.6}$ is independently oxo.

Embodiment 112. The compound of embodiment 81, having the formula

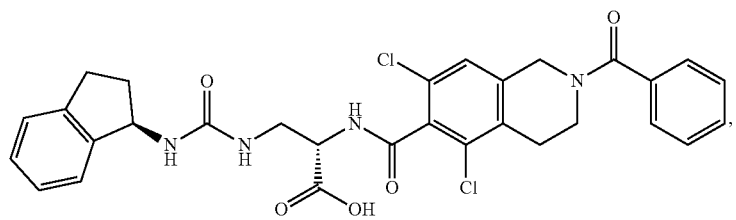

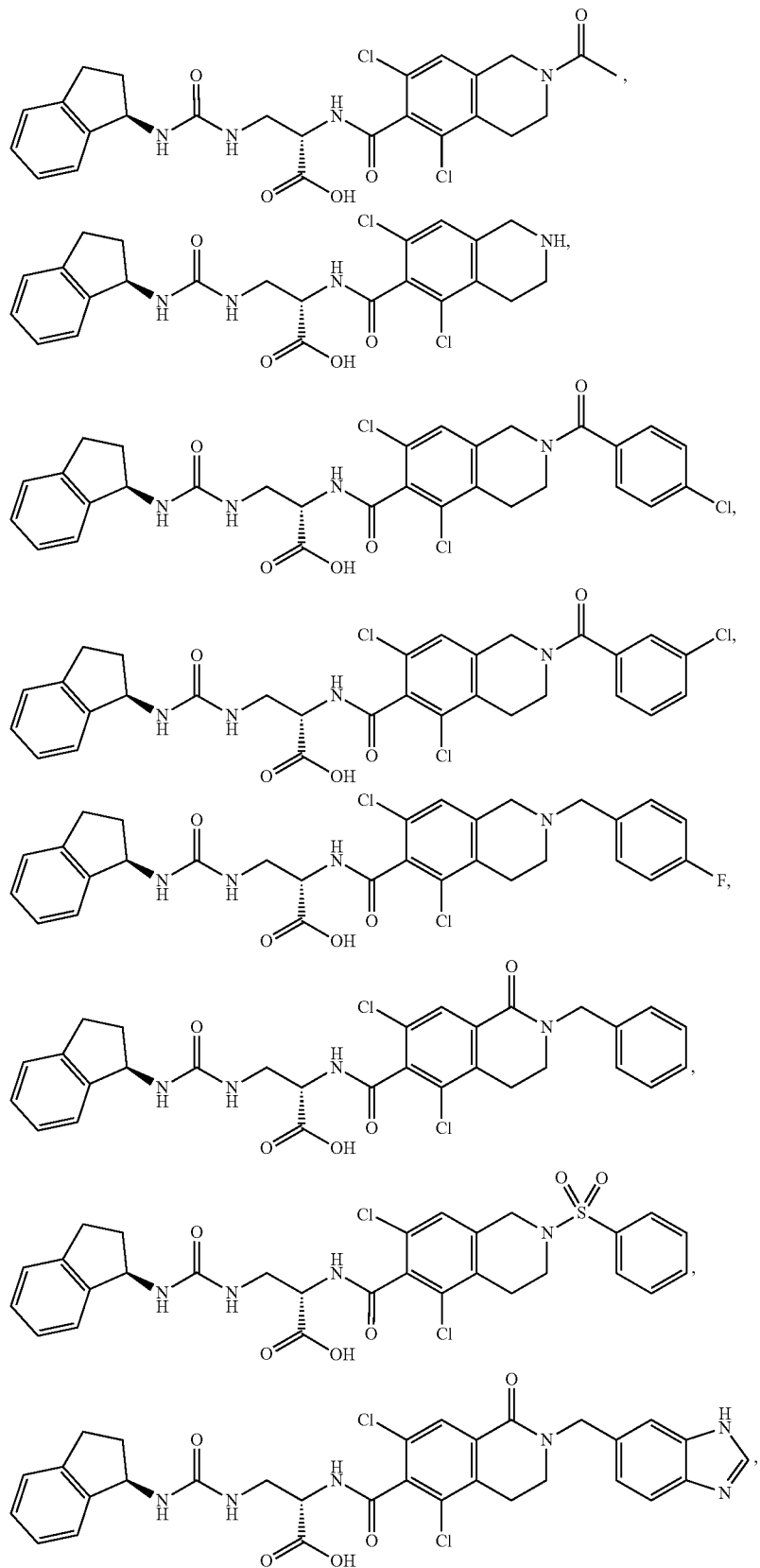

-continued
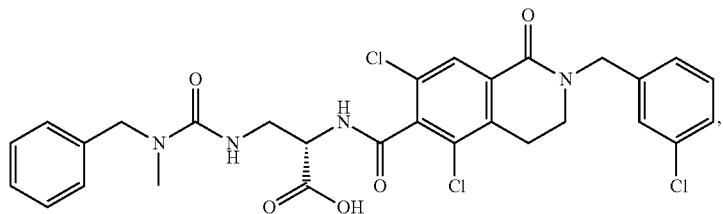,
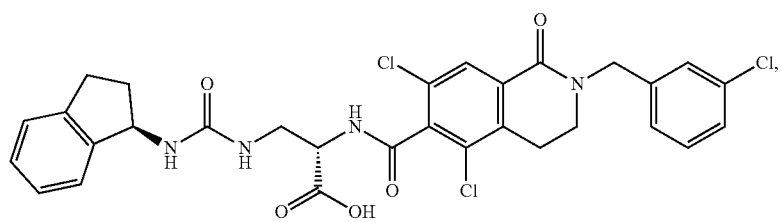,
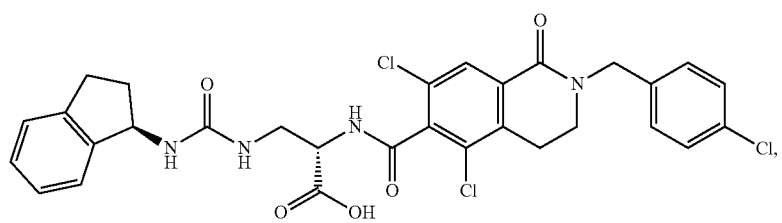,
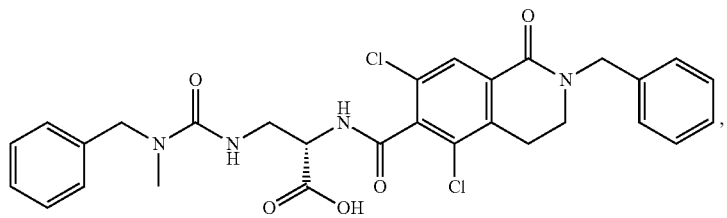,
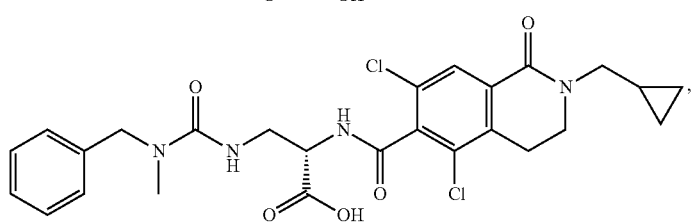,
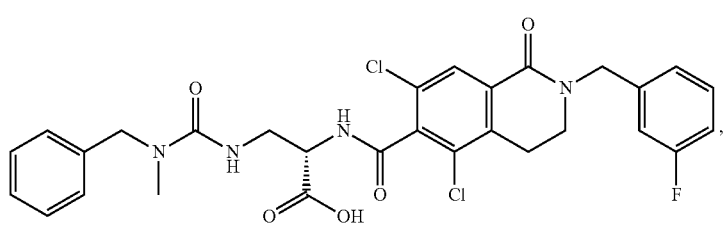,
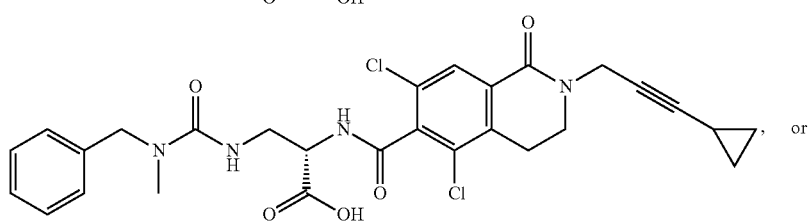, or -continued

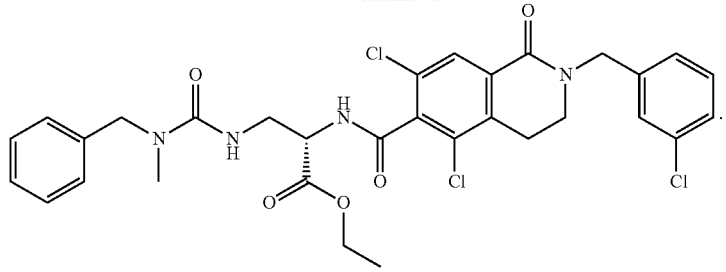

Embodiment 113. A compound, or a pharmaceutically acceptable salt thereof or a prodrug thereof, having the formula:

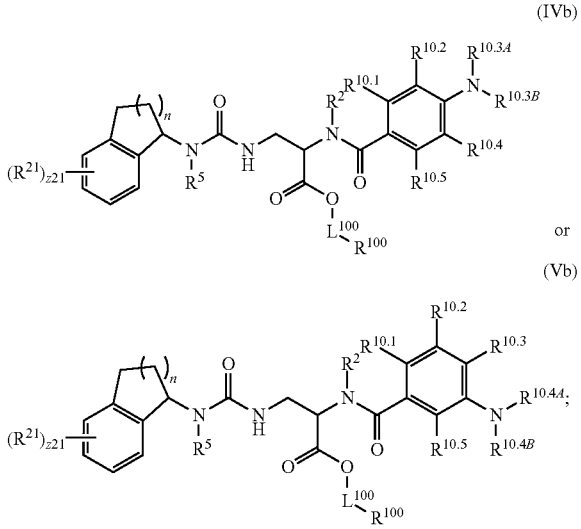

wherein
R² is hydrogen or substituted or unsubstituted alkyl;
R⁵ is hydrogen or unsubstituted $C_1$-$C_3$ alkyl;
$R^{10.1}$ is hydrogen, halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10.1}R^{10.1D}$, —$SO_{v10.1}NR^{10.1A}R^{10.1B}$, —NHC(O)$NR^{10.1A}R^{10.1B}$, —N(O)$_{m10.1}$, —$NR^{10.1A}R^{10.1B}$, —C(O)$R^{10.1C}$, —C(O)O$R^{10.1C}$, —C(O)$NR^{10.1A}R^{10.1B}$, —O$R^{10.1D}$, —S$R^{10.1D}$, —$NR^{10.1A}SO_2R^{10.1D}$, —$NR^{10.1A}C(O)R^{10.1C}$, —$NR^{10.1A}C(O)OR^{10.1C}$, —$NR^{10.1A}OR^{10.1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$, $R^{10.3}$, and $R^{10.4}$ are independently hydrogen, halogen, or —$CF_3$;

$R^{10.5}$ is hydrogen, halogen, —$CX^{10.5}_3$, —$CHX^{10.5}_2$, —$CH_2X^{10.5}$, —$OCX^{10.5}_3$, —$OCH_2X^{10.5}$, —$OCHX^{10.5}_2$, —CN, —$SO_{n10.5}R^{10.5D}$, —$SO_{v10.5}NR^{10.5A}R^{10.5B}$, —NHC(O)$NR^{10.5A}R^{10.5B}$, —N(O)$_{m10.5}$, —$NR^{10.5A}R^{10.5B}$, —C(O)$R^{10.5C}$, C(O)O$R^{10.5C}$, —C(O)$NR^{10.1A}R^{10.1B}$, —O$R^{10.5D}$, —S$R^{10.5D}$, —$NR^{10.5A}SO_2R^{10.5D}$, —$NR^{10.5A}C(O)R^{10.5C}$, —$NR^{10.5A}C(O)OR^{10.5C}$, —$NR^{10.5A}OR^{10.5C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21D}$, —$SO_{v21}NR^{21A}R^{21B}$, —NHC(O)$NR^{21A}R^{21B}$, —N(O)$_{m21}$, —$NR^{21A}R^{21B}$, C(O)$R^{21C}$, —C(O)O$R^{21C}$, —C(O)$NR^{21A}R^{21B}$, —O$R^{21D}$, —S$R^{21D}$, —$NR^{21A}SO_2R^{21D}$, —$NR^{21A}C(O)R^{21C}$, —$NR^{21A}C(O)OR^{21C}$, —$NR^{21A}OR^{21C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, —$CX^{100}_3$, —$CHX^{100}_2$, —$CH_2X^{100}$, —$OCX^{100}_3$, —$OCH_2X^{100}$, —$OCHX^{102}_2$, —CN, —$SO_{n100}R^{100D}$, —$SO_{v100}NR^{100A}R^{100B}$, —NHC(O)$NR^{100A}R^{100B}$, —N(O)$_{m100}$, —$NR^{100A}R^{100B}$, —C(O)$R^{100C}$, —C(O)O$R^{100C}$, —C(O)$NR^{100A}R^{100B}$, —O$R^{100D}$, —S$R^{100D}$, —$NR^{100A}SO_2R^{100D}$, —$NR^{100A}C(O)R^{100C}$, —$NR^{100A}C(O)OR^{100C}$, —$NR^{100A}OR^{100C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.3A}$, $R^{10.3B}$, $R^{10.4A}$, $R^{10.4B}$, $R^{10.5A}$, $R^{10.5B}$, $R^{10.5C}$, $R^{10.5D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.5, n21, and n100 are independently an integer from 0 to 4;

m10.1, m10.5, m21, m100, v10.1, v10.5, v21, and v100 are independently 1 or 2;

$X^{10.1}$, $X^{10.5}$, $X^{21}$, and $X^{100}$ are independently —F, —Cl, —Br, or —I;

z21 is an integer from 0 to 9;

n is an integer from 0 to 3; and wherein at least one of $R^{10}$ or $R^{10.5}$ is not hydrogen.

Embodiment 114. The compound of embodiment 113, having the formula:

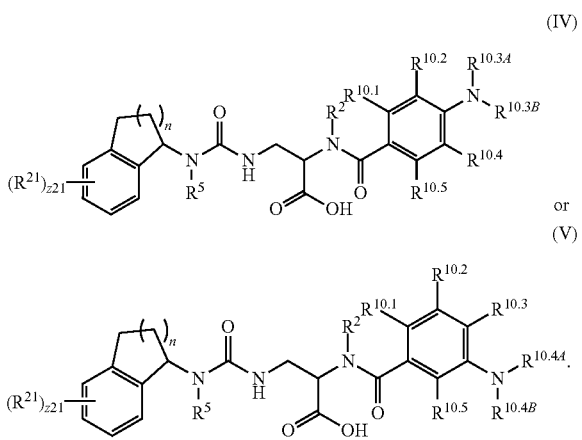

(IV)

or (V)

Embodiment 115. The compound of one of embodiments 113 to 114, wherein $R^{10.2}$, $R^{10.3}$, and $R^{10.4}$ are independently deuterium, halogen, or —CF$_3$.

Embodiment 116. The compound of one of embodiments 113 to 114, having the formula:

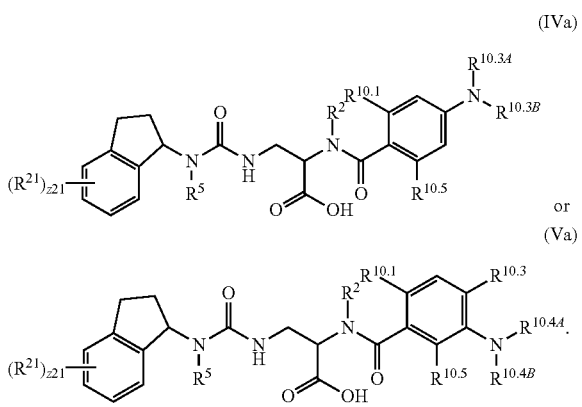

(IVa)

or (Va)

Embodiment 117. The compound of one of embodiments 113 to 116, wherein $R^5$ is hydrogen.

Embodiment 118. The compound of one of embodiments 113 to 117, wherein $R^2$ is hydrogen or unsubstituted $C_1$-$C_3$ alkyl.

Embodiment 119. The compound of one of embodiments 113 to 117, wherein $R^2$ is hydrogen.

Embodiment 120. The compound of one of embodiments 113 to 117, wherein $R^2$ is unsubstituted methyl.

Embodiment 121. The compound of one of embodiments 113 to 120, wherein $R^{21}$ is independently halogen, —OH, or substituted or unsubstituted $C_1$-$C_4$ alkyl.

Embodiment 122. The compound of one of embodiments 113 to 120, wherein $R^{21}$ is independently —OH or unsubstituted methyl.

Embodiment 123. The compound of one of embodiments 113 to 122, wherein z21 is 0 to 3.

Embodiment 124. The compound of one of embodiments 113 to 123, wherein $R^{10.1}$ is halogen, substituted or unsubstituted $C_1$-$C_5$ alkyl, or substituted or unsubstituted 2 to 5 membered heteroalkyl.

Embodiment 125. The compound of one of embodiments 113 to 123, wherein $R^{10.1}$ is halogen or unsubstituted methyl.

Embodiment 126. The compound of one of embodiments 113 to 123, wherein $R^{10.1}$ is —Cl.

Embodiment 127. The compound of one of embodiments 113 to 126, wherein $R^{10.3A}$ and $R^{10.3B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

Embodiment 128. The compound of embodiment 127, wherein

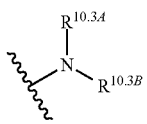

is —NH$_2$,

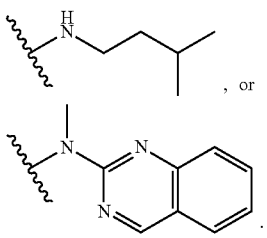

, or

Embodiment 129. The compound of one of embodiments 113 to 126, wherein $R^{10.3A}$ and $R^{10.3B}$ substituents bonded to the same nitrogen atom are joined to form a substituted or unsubstituted heterocycloalkyl or substituted or unsubstituted heteroaryl.

Embodiment 130. The compound of one of embodiments 113 to 126, wherein $R^{10.3A}$ and $R^{10.3B}$ substituents bonded to the same nitrogen atom are joined to form an $R^{33}$-substituted or unsubstituted heterocycloalkyl or $R^{33}$-substituted or unsubstituted heteroaryl; and $R^{33}$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCl₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 131. The compound of embodiment 130, wherein

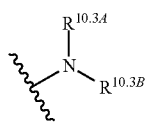

is

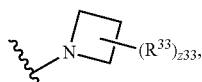

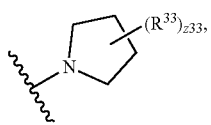

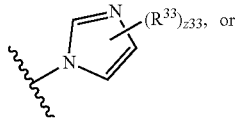

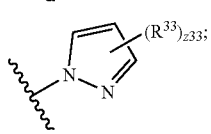

and z33 is an integer from 0 to 8.

Embodiment 132. The compound of one of embodiments 130 to 131, wherein $R^{33}$ is independently a substituted or unsubstituted phenyl.

Embodiment 133. The compound of embodiment 130, wherein

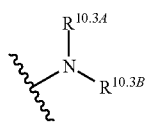

is

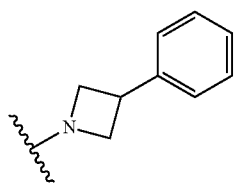

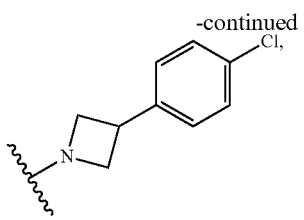

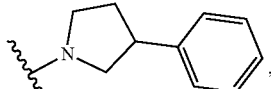

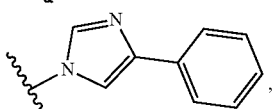

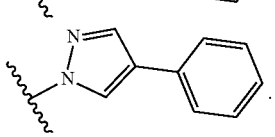

Embodiment 134. The compound of one of embodiments 113 to 126, wherein $R^{10.4A}$ and $R^{10.4B}$ are independently hydrogen, substituted or unsubstituted $C_1$-$C_5$ alkyl, substituted or unsubstituted 2 to 5 membered heteroalkyl, substituted or unsubstituted $C_6$-$C_{10}$ aryl, or substituted or unsubstituted 5 to 10 membered heteroaryl.

Embodiment 135. The compound of embodiment 134, wherein

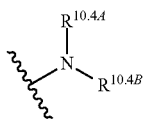

is

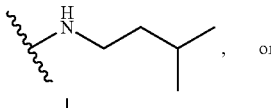

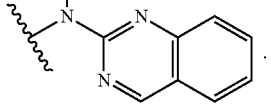

Embodiment 136. The compound of one of embodiments 113 to 126, wherein $R^{10.4A}$ and $R^{10.4B}$ substituents bonded to the same nitrogen atom are joined to form a substituted or unsubstituted heterocycloalkyl or substituted or unsubstituted heteroaryl.

Embodiment 137. The compound of one of embodiments 113 to 126, wherein $R^{10.4A}$ and $R^{10.4B}$ substituents bonded to the same nitrogen atom are joined to form an $R^{34}$-substituted or unsubstituted heterocycloalkyl or $R^{34}$-substituted or unsubstituted heteroaryl; and $R^{34}$ is independently oxo, halogen, —CCl₃, —CBr₃, —CF₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)

NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 138. The compound of embodiment 137, wherein

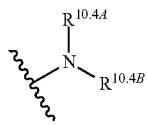

is

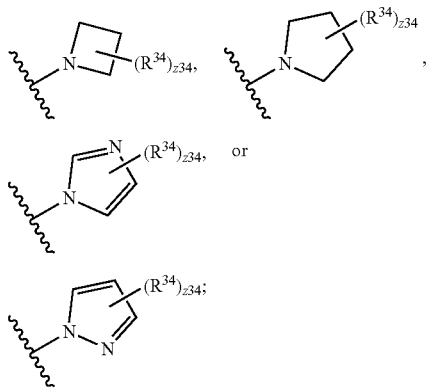

and z34 is an integer from 0 to 8.

Embodiment 139. The compound of one of embodiments 137 to 138, wherein R$^{34}$ is independently a substituted or unsubstituted phenyl.

Embodiment 140. The compound of embodiment 137, wherein

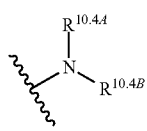

is

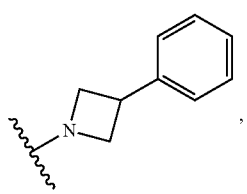

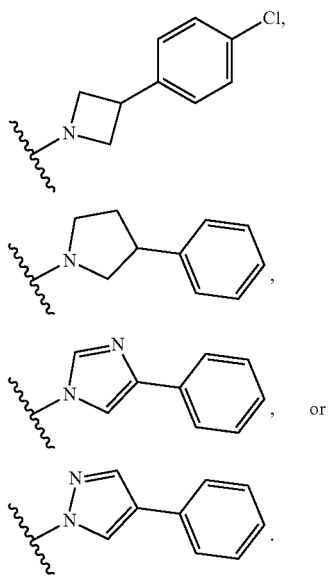

Embodiment 141. The compound of one of embodiments 113 to 140, wherein R$^{10.5}$ is halogen, substituted or unsubstituted C$_1$-C$_5$ alkyl, or substituted or unsubstituted 2 to 5 membered heteroalkyl.

Embodiment 142. The compound of one of embodiments 113 to 140, wherein R$^{10.5}$ is halogen or unsubstituted methyl.

Embodiment 143. The compound of one of embodiments 113 to 140, wherein R$^{10.5}$ is —Cl.

Embodiment 144. The compound of one of embodiments 113 to 114, having the formula

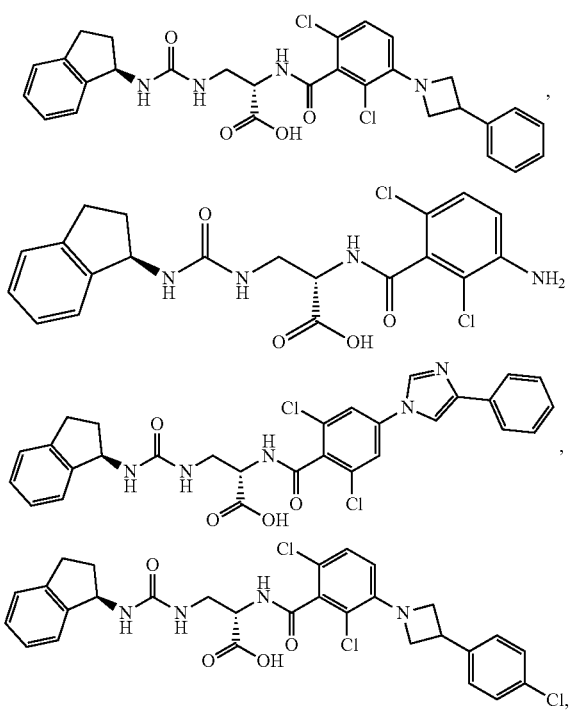

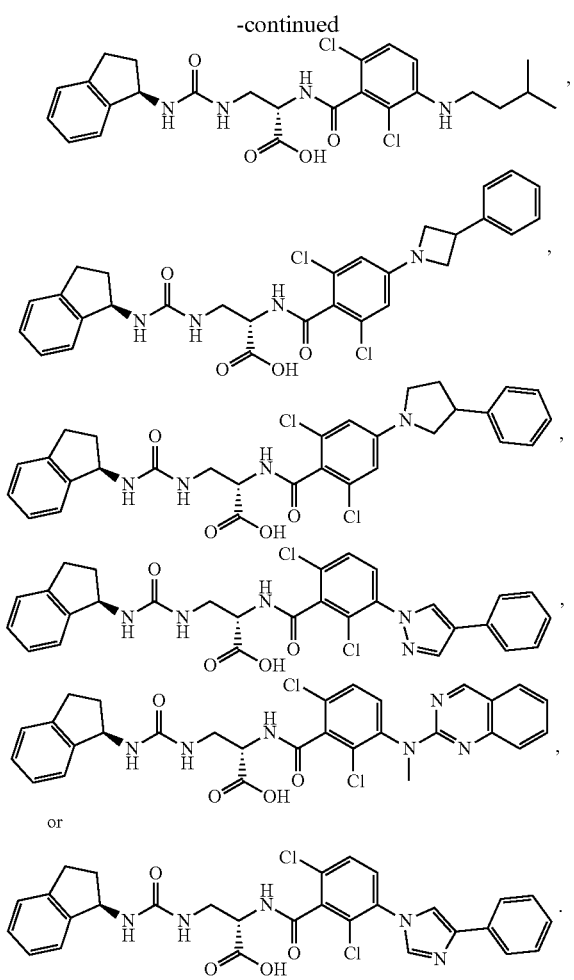

or

Embodiment 145. A pharmaceutical composition comprising a compound of one of embodiments 1 to 144, or a pharmaceutically acceptable salt thereof or a prodrug thereof, and a pharmaceutically acceptable excipient.

Embodiment 146. A method of treating asthma, the method comprising administering to a subject in need thereof an effective amount of a compound of one of embodiments 1 to 144, or a pharmaceutically acceptable salt thereof or a prodrug thereof.

Embodiment 147. A method of treating an inflammatory disease, the method comprising administering to a subject in need thereof an effective amount of a compound of one of embodiments 1 to 144, or a pharmaceutically acceptable salt thereof or a prodrug thereof.

Embodiment 148. A method of treating an autoimmune disease, the method comprising administering to a subject in need thereof an effective amount of a compound of one of embodiments 1 to 144, or a pharmaceutically acceptable salt thereof or a prodrug thereof.

EXAMPLES

Example 1: Small Molecule Inhibitors of Alpha 2 Beta 1 Integrin

Asthma is a life-threatening disease affecting approximately 300 million people worldwide and contributing to 250,000 deaths annually. Although the phenotypes of allergic asthma are heterogeneous, common characteristics include bronchial inflammation, reversible obstruction, and airway hyperreactivity. Current therapies for allergic asthma remain limited (1, 2), despite the increased interest in targeted biologic therapies over the last two decades. Although promising, these biologic therapies have largely been met with limited success in clinical trials. For example, biologics targeting T2 high cytokines such as IL-13 have failed to show statistically significant reductions in asthma exacerbation rates. In T2 low asthma, numerous clinical trials targeting TNF-α, IL-17, GM-CSF, and CXCR2 have failed to show either consistent clinical responses or statistically significant benefits. Due to the fact that biologic therapies offer inhibition of specific cytokine-mediated pathways in asthma, their spectrum of efficacy is much more narrow than standard therapies. In addition, they do not necessarily address all of the clinical objectives of asthma management, necessitating the need for predictive biomarkers for implementation. In this setting, therapeutic advances that directly target the hypercontractile airway smooth muscle that results in bronchoconstriction have been notably lacking. Such muscle-specific therapy would be a particularly attractive therapeutic addition to severe asthmatics with persistent symptoms as well as those with acute exacerbations due to hypercontractile smooth muscle. These target populations number in the millions worldwide, and could be clearly identified by symptoms alone without the need for an accompanying biomarker.

Exaggerated airway narrowing is a central feature of asthma (3), but the mechanisms regulating contraction are incompletely understood. It is known that smooth muscle contraction is driven by calcium-mediated signaling to the actin-myosin contractile apparatus, and that force generation is triggered by stimuli such as methacholine or potassium chloride, enhanced by cytokines such as IL-13 (4) or IL-17A (5, 6), and transmitted via mediators such as myosin light chain kinase and RhoA. Currently available therapies that target smooth muscle contraction work by inhibiting this core pathway, including beta-adrenergic agonists and muscarinic antagonists that inhibit upstream of intracellular calcium release. Other approaches to inhibit this pathway, such as Rho kinase inhibitors, often have unacceptable vascular toxicity.

We disclose herein, inter alia, potent, cell-permeable small molecule alpha 2 beta 1 integrin inhibitors that can reduce cytokine-enhanced contraction in an ex vivo organ bath. Most of the current alpha 2 beta 1 integrin inhibitors suffer from either micromolar potency or poor membrane permeability. Our new compounds have increased potency to a single-digit nanomolar $IC_{50}$ and good permeability, which is highly desirable for orally or inhalation available drug development. Previous alpha 4 beta 1 integrin inhibitors developed for asthma exhibited toxicity. Our compounds have excellent selectivity for alpha 2 beta 1 integrin over alpha 4 beta 1 integrin.

Example 2: Experimental and Characterization Data

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. $^1$H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm×4.6 mm×3.5 um), Flow Rate: 2.0 mL/min, the column temperature: 40° C.

SU15210-0076-01

Route for SU15210-0076-01

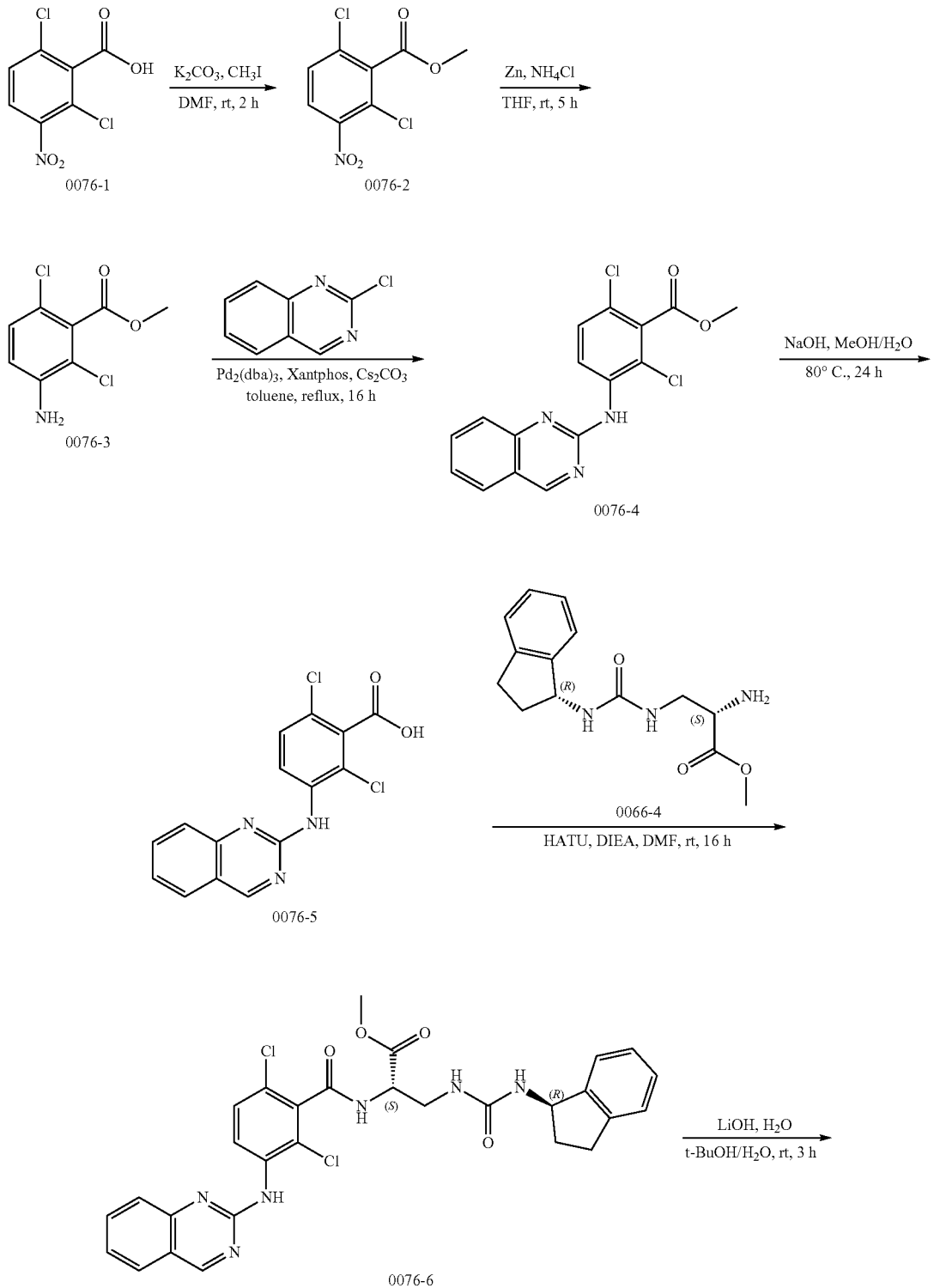

-continued

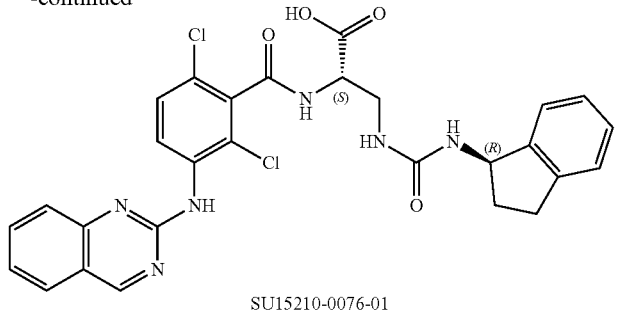

SU15210-0076-01

The Synthesis of Methyl 2,6-dichloro-3-nitrobenzoate (0076-2)

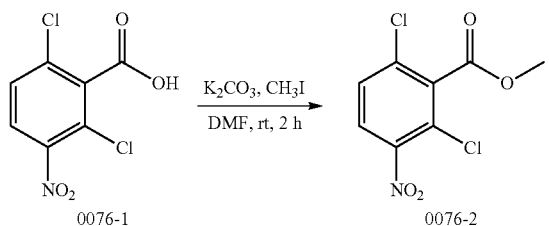

To a stirred solution of compound 0076-1 (5 g, 21.3 mmol) and $K_2CO_3$ (8.8 g, 63.9 mmol) in DMF (50 mL) was added $CH_3I$ (9.1 g, 63.9 mmol). The mixture was stirred at room temperature for 2 h. After the consumption of starting material (by LCMS), the reaction solution was extracted with ethyl acetate, the combined organic phases were dried over anhydrous sodium sulfate, filtered, concentrated in vacuo, purified by column to give the product 0076-2 (5 g, 94% yield) as a yellow solid.

The Synthesis of Methyl 3-amino-2,6-dichlorobenzoate (0076-3)

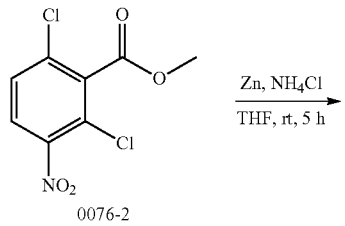

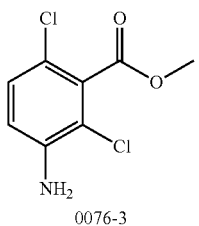

A solution of compound 0076-2 (5 g, 20 mmol), Zn (1.28 g, 200 mmol) and $NH_4Cl$ (3.2 g, 60 mmol) in $THF/H_2O$ (50 mL/10 mL) was stirred at room temperature for 5 h. After the consumption of starting material (by LCMS), the reaction was filtered, the filtrate was added water, extracted with ethyl acetate, the combined organic phases were dried over anhydrous sodium sulfate, filtered, and concentrated in vacuo to give the product 0076-3 (3.9 g, 89% yield) as a yellow solid.

The Synthesis of Methyl 2,6-dichloro-3-(quinazolin-2-ylamino)benzoate (0076-4)

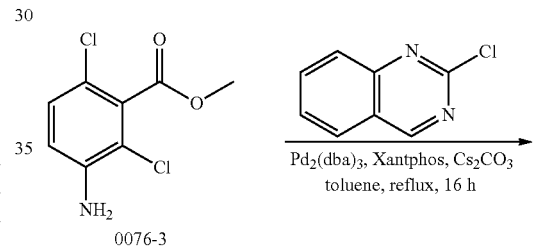

To a stirred solution of $Pd_2(dba)_3$ (236 mg, 0.41 mmol), Xantphos (475 mg, 0.82 mmol) in toluene (20 mL) was added compound 0076-3 (900 mg, 4.1 mmol), 2-chloroquinazoline (806 mg, 4.92 mmol) and $Cs_2CO_3$ (4 g, 12.3 mmol). The mixture was reflux for 16 h. After the consumption of starting material (by LCMS), the reaction solution was added water and extracted with ethyl acetate, the combined organic phases were dried over anhydrous sodium sulfate, filtered, concentrated in vacuo, purified by column to give the product 0076-4 (700 mg, 49% yield) as a yellow solid.

The Synthesis of 2,6-dichloro-3-(quinazolin-2-ylamino)benzoic Acid (0076-5)

The Synthesis of (S)-methyl 2-(2,6-dichloro-3-(quinazolin-2-ylamino)benzamido)-3-(3-((R)-2,3-dihydro-1H-inden-1-yl)ureido)propanoate (0076-6)

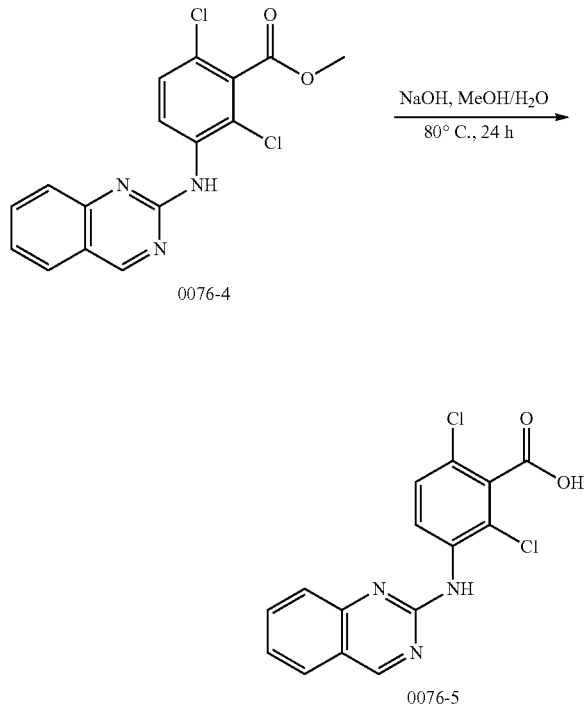

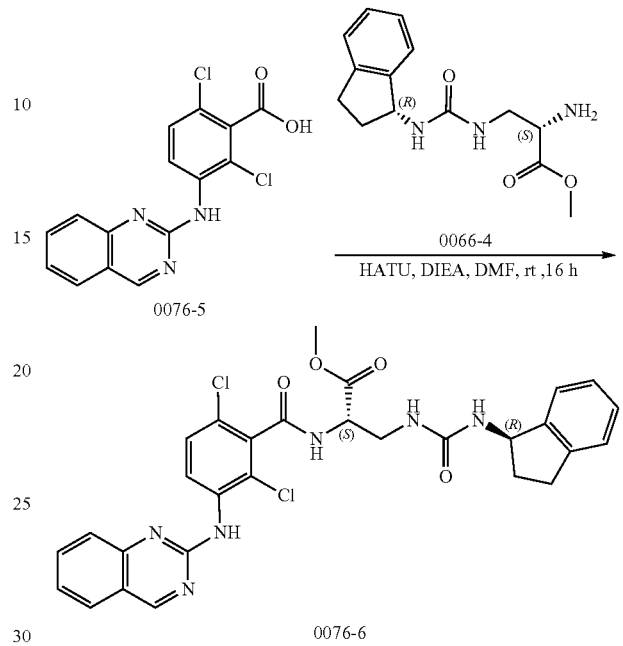

The mixture of 0076-4 (500 mg, 1.44 mmol) and NaOH (576 mg, 14.4 mmol) in MeOH/H₂O (4/1, 15 mL) was stirred at 80° C. for 24 h. Then the reaction mixture was acided with 1 M HCl until pH reached 6.0. The resulting mixture was concentrated in vacuo, purified by prep-HPLC to give the product 0076-5 (340 mg, 70.8% yield) as a yellow solid.

To a stirred solution of compound 0076-5 (340 mg, 1.02 mmol), 0066-4 (283 mg, 1.02 mmol) and HATU (464 mg, 1.22 mmol) in DMF (10 ml) was added DIEA (395 mg, 3.06 mmol). The mixture was stirred at room temperature for 16 h. After the consumption of starting material (by LCMS), the reaction solution was added water and extracted with DCM, the combined organic phases were dried over anhydrous sodium sulfate, filtered, concentrated in vacuo, purified by column (DCM:EA=3:1) to give the desired product 0076-6 (450 mg, 74.5% yield) as a white solid.

The Synthesis of (S)-2-(2,6-dichloro-3-(quinazolin-2-ylamino)benzamido)-3-(3-((R)-2,3-dihydro-1H-inden-1-yl)ureido)propanoic Acid (SU15210-0076-01)

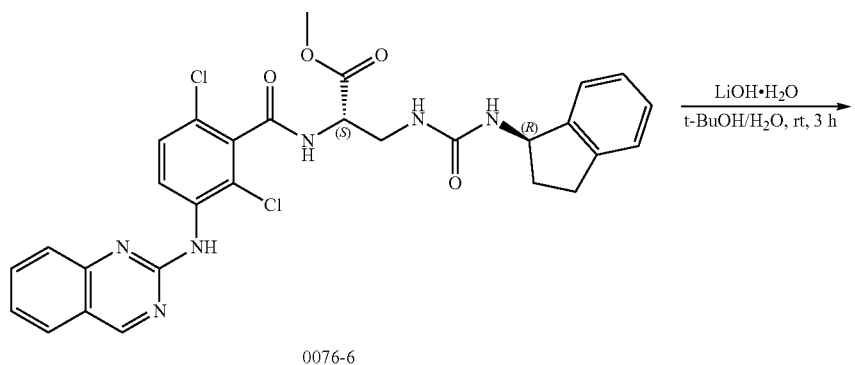

-continued

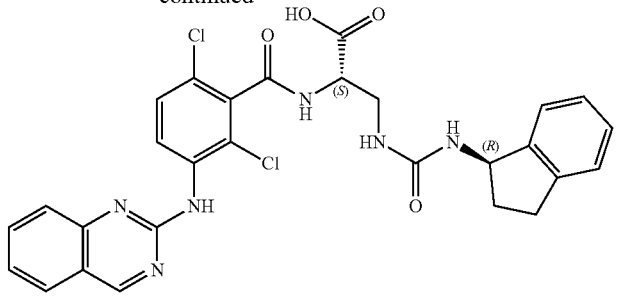

SU15210-0076-01

The mixture of 0076-6 (200 mg, 0.34 mmol) and LiOH.H₂O (143 mg, 3.4 mmol) in t-BuOH/H₂O (2/1, 10 mL) was stirred at room temperature for 3 h. Then the reaction mixture was acided with 1 M HCl until pH reached 6.0. The resulting mixture was concentrated in vacuo, purified by column (DCM:MeOH=15:1) to give the product SU15210-0076-01 (26 mg, 13% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 100%, Rt=1.668 min; MS Calcd.: 579.43; MS Found: 579.1 [M+H]⁺.

¹H NMR (400 MHz, DMSO-d₆) δ 9.32 (s, 1H), 9.01 (s, 1H), 8.15 (d, J=8.8 Hz, 1H), 8.04 (bs, 1H), 7.93 (d, J=8.0 Hz, 1H), 7.77-7.82 (m, 1H), 7.59 (d, J=8.4 Hz, 1H), 7.48 (d, J=8.8 Hz, 1H), 7.40 (t, J=7.2 Hz, 1H), 7.08-7.20 (m, 4H), 6.77 (s, 1H), 5.92 (s, 1H), 5.03-5.10 (m, 1H), 4.15 (s, 1H), 3.51-3.59 (m, 1H), 3.37-3.43 (m, 1H), 2.65-2.85 (m, 2H), 2.29-2.35 (m, 1H), 1.60-1.70 (m, 1H).

SU15210-0078-01

Route for SU15210-0078-01

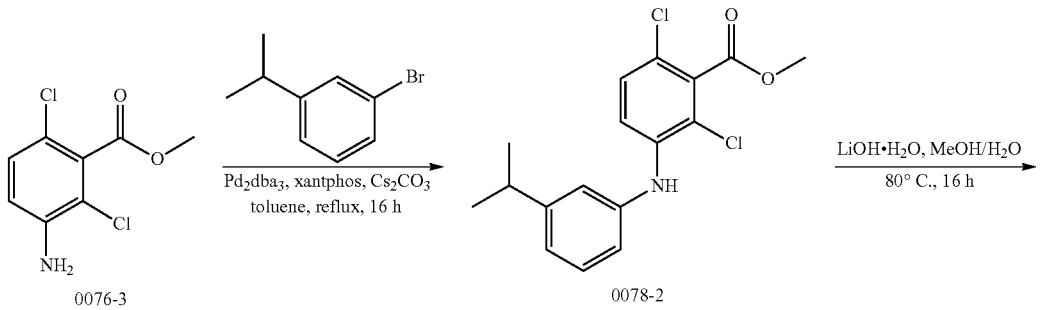

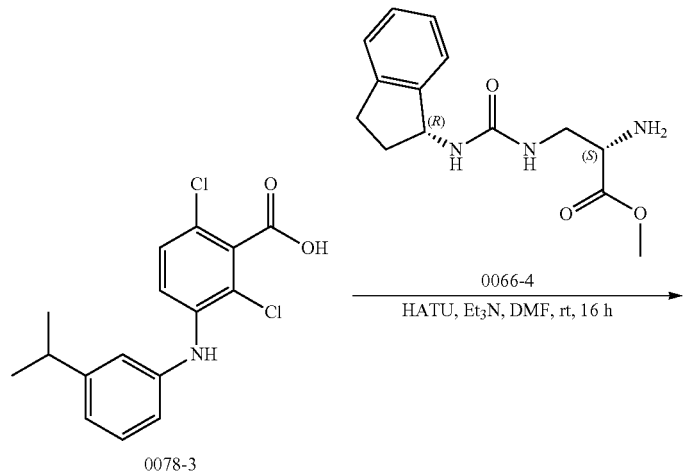

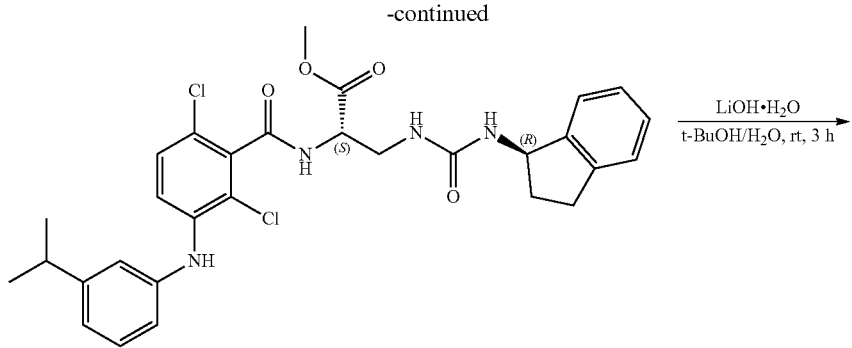

0078-4

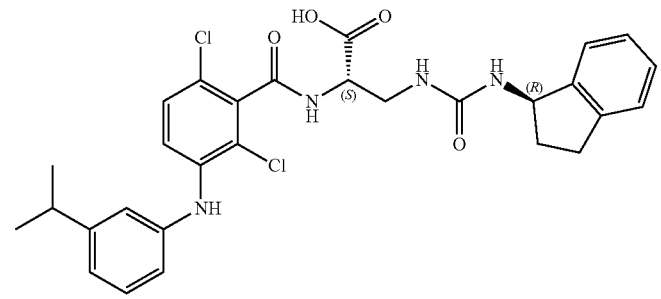

SU15210-0078-01

The Synthesis of Methyl 2,6-dichloro-3-(3-isopropylphenylamino)benzoate (0078-2)

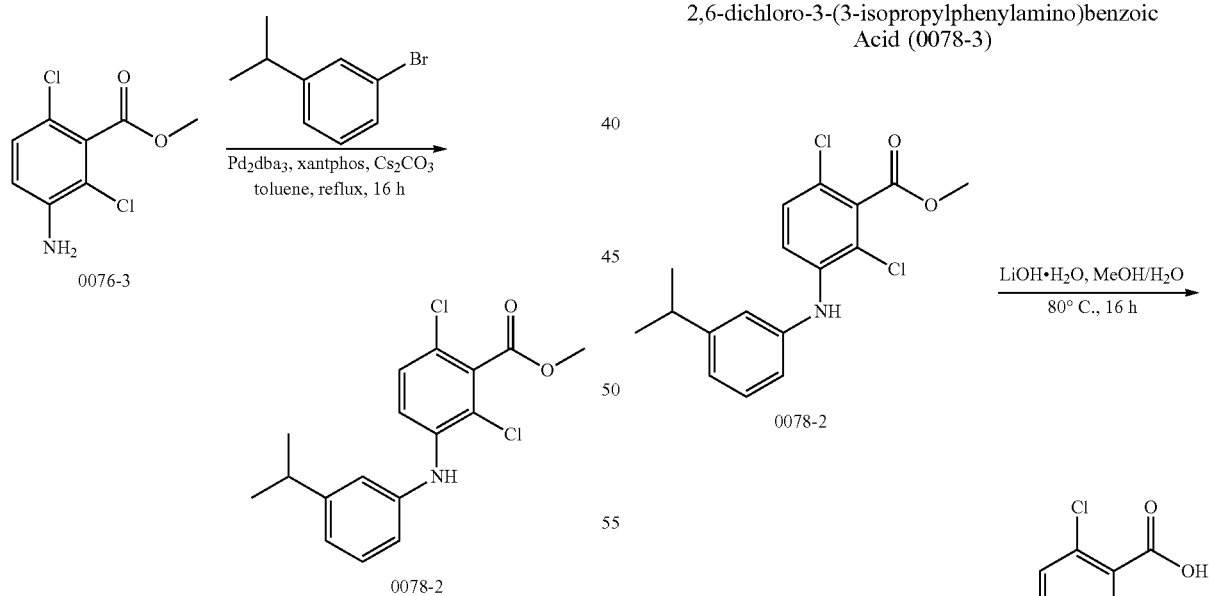

0078-2

To a stirred solution of Pd$_2$(dba)$_3$ (236 mg, 0.41 mmol), Xantphos (475 mg, 0.82 mmol) in toluene (20 mL) was added compound 0076-3 (900 mg, 4.1 mmol), 1-bromo-3-isopropylbenzene (974 mg, 4.92 mmol) and Cs$_2$CO$_3$ (4 g, 12.3 mmol). The mixture was reflux for 16 h. After the consumption of starting material (by LCMS), the reaction solution was added water and extracted with ethyl acetate, the combined organic phases were dried over anhydrous sodium sulfate, filtered, concentrated in vacuo, purified by column to give the product 0078-2 (1 g, 72% yield) as a yellow oil.

The Synthesis of 2,6-dichloro-3-(3-isopropylphenylamino)benzoic Acid (0078-3)

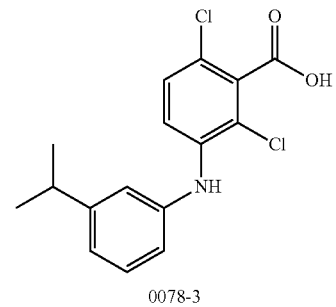

0078-3

The mixture of 0078-3 (500 mg, 1.48 mmol) and LiOH.H₂O (622 mg, 14.8 mmol) in MeOH/H₂O (4/1, 15 mL) was stirred at 80° C. for 16 h. Then the reaction mixture was neutralized with 1 M HCl until pH reached 6. The resulting mixture was concentrated in vacuo, purified by prep-HPLC to give the product 0078-3 (350 mg, 73% yield) as a yellow solid.

The Synthesis of(S)-2-(2,6-dichloro-3-(3-isopropylphenylamino)benzamido)-3-(3-((R)-2,3-dihydro-1H-inden-1-yl)ureido)propanoic Acid (0078-4)

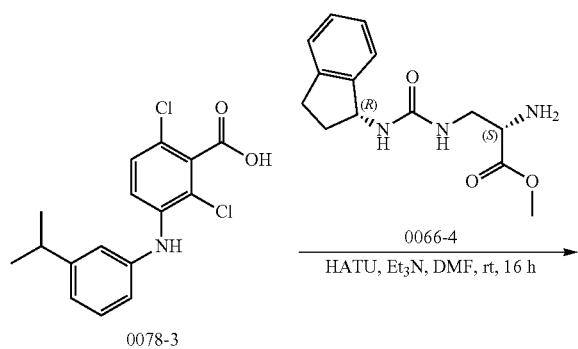

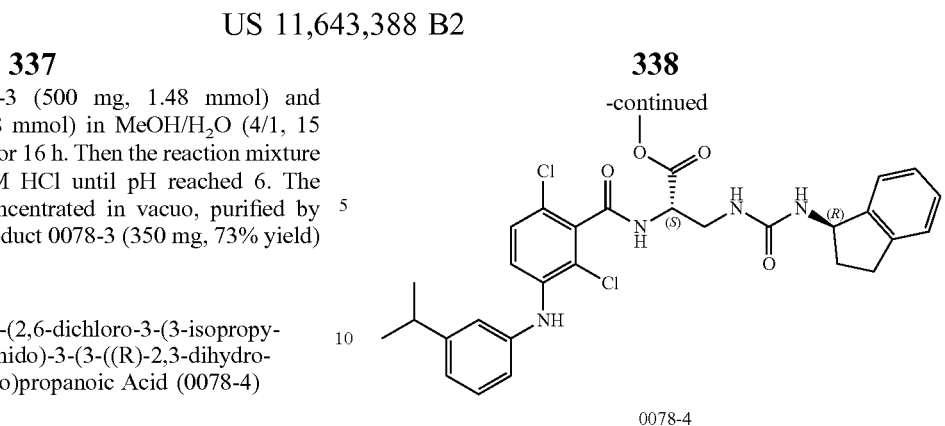

To a stirred solution of compound 0078-3 (350 mg, 1.08 mmol), 0066-4 (300 mg, 1.08 mmol) and HATU (480 mg, 1.26 mmol) in DMF (10 ml) was added TEA (418 mg, 3.24 mmol). The mixture was stirred at room temperature for 16 h. After the consumption of starting material (by LCMS), the reaction solution was added water and extracted with DCM, the combined organic phases were dried over anhydrous sodium sulfate, filtered, concentrated in vacuo, purified by column (DCM:EA=3:1) to give the desired product 0078-4 (250 mg, 39.8% yield) as a white solid.

The Synthesis of (S)-2-(2,6-dichloro-3-(3-isopropylphenylamino)benzamido)-3-(3-((R)-2,3-dihydro-1H-inden-1-yl)ureido)propanoic Acid (SU15210-0078-01)

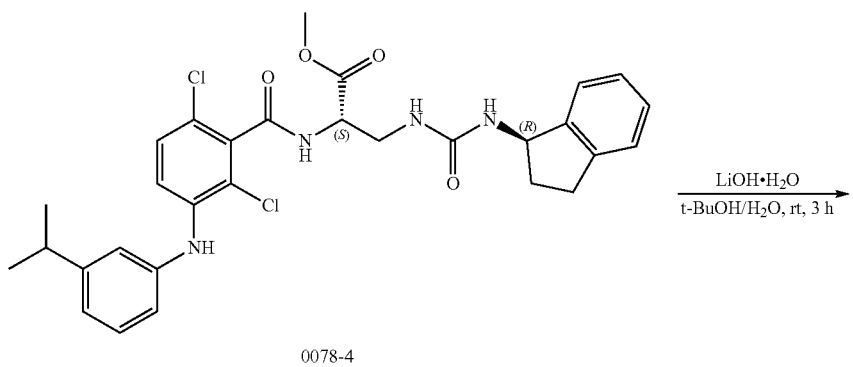

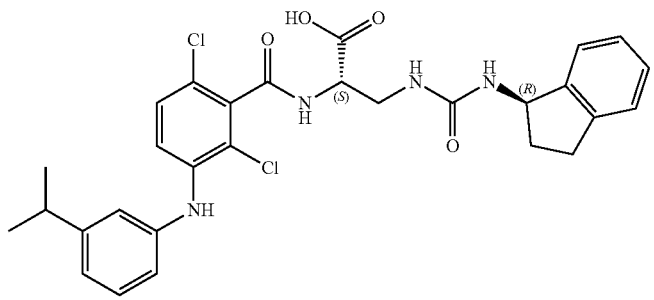

The mixture of 0078-4 (200 mg, 0.35 mmol) and LiOH.H₂O (147 mg, 3.5 mmol) in t-BuOH/H₂O (2/1, 10 mL) was stirred at room temperature for 3 h. Then the reaction mixture was neutralized with 1 M HCl until pH reached 6. The resulting mixture was concentrated in vacuo, purified by prep-HPLC to give the product SU15210-0078-01 (32 mg, 19% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 100%, Rt=1.912 min; MS Calcd.: 569.48; MS Found: 569.3 [M+H]⁺.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 100%, Rt=8.805 min.

¹H NMR (400 MHz, DMSO-d₆) δ 8.45 (bs, 1H), 7.74 (s, 1H), 7.25 (d, J=8.8 Hz, 1H), 7.12-7.19 (m, 6H), 6.99 (s, 1H), 6.88-6.91 (m, 1H), 6.83 (d, J=7.6 Hz, 1H), 6.64 (d, J=8.0 Hz, 1H), 5.92 (s, 1H), 5.06 (q, J=8.0 Hz, 1H), 4.27 (s, 1H), 3.43 (s, 2H), 2.69-2.87 (m, 3H), 2.30-2.37 (m, 1H), 1.60-1.70 (m, 1H), 1.17 (d, J=7.2 Hz, 6H).

SU15210-0080-01

Route for SU15210-0080-01:

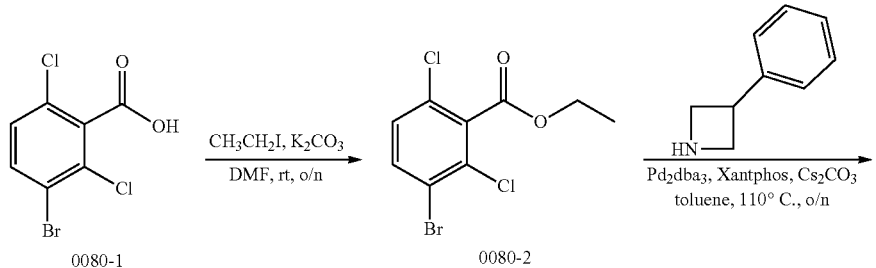

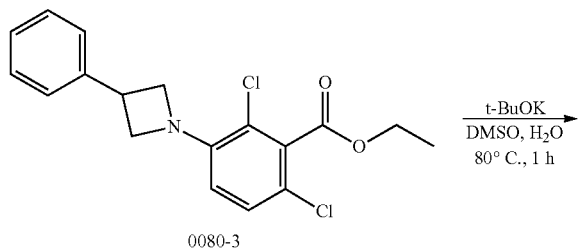

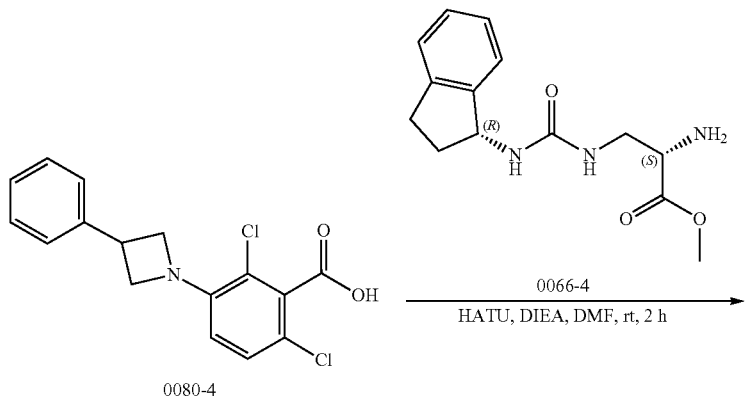

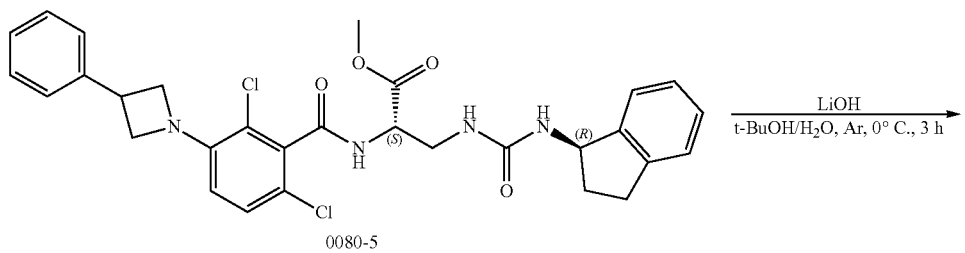

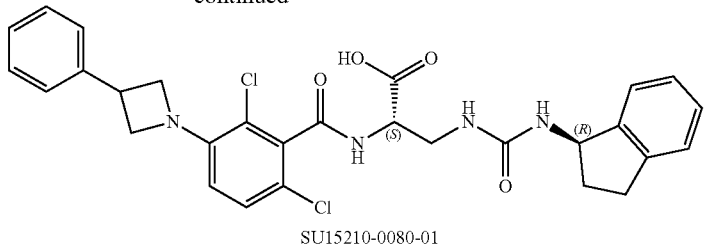

SU15210-0080-01

The Synthesis of Ethyl 3-bromo-2,6-dichlorobenzoate (0080-2)

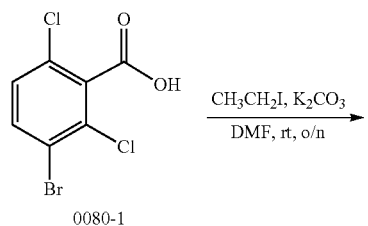

To a solution of 0080-1 (200 mg, 0.74 mmol) in DMF (10 mL) was added $K_2CO_3$ (204 mg, 1.48 mmol) and $CH_3CH_2I$ (127 mg, 0.81 mmol). The mixture was stirred at room temperature for overnight. Filtrated to remove the inorganic salt, the filtrate was concentrated then purified by C.C. (5% to 10% ethyl acetate in petroleum ether) to give 0080-2 (200 mg, 91.5% yield) as colorless oil.

The Synthesis of Tert-Butyl 2-(methylthio)-5,6-dihydropyrimidine-1 (4H)-carboxylate (0080-3)

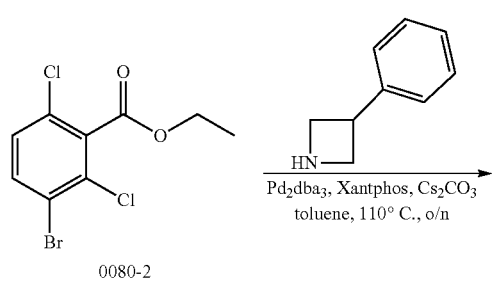

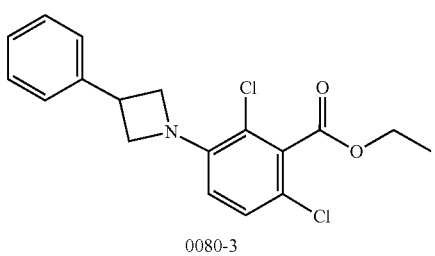

To a solution of 0080-2 (200 mg, 0.67 mmol) in toluene (10 mL) was added 3-phenylazetidine (114 mg, 0.67 mmol), $Cs_2CO_3$ (436 mg, 1.34 mmol), $Pd_2(dba)_3$ (61 mg, 0.067 mmol) and Xantphos (39 mg, 0.067 mmol). The mixture was stirred under Argon at 110° C. for overnight. Filtrated and the filtrate was concentrated then purified by C.C. to give 0080-3 (150 mg, 63.8% yield) as colorless oil.

The Synthesis of 2,6-dichloro-3-(3-phenylazetidin-1-yl)benzoic Acid (0080-4)

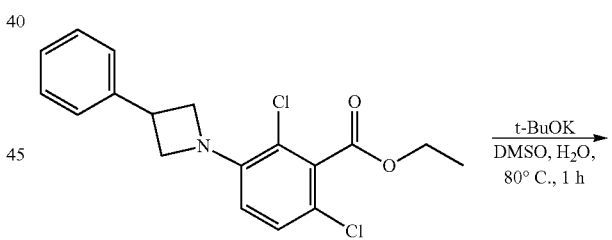

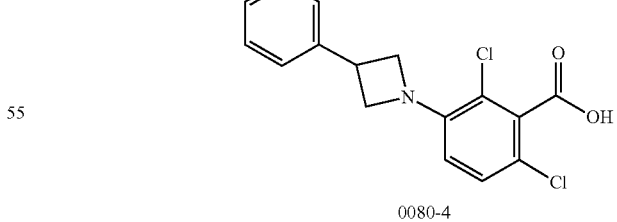

To a solution of 0080-3 (150 mg, 0.43 mmol) in DMSO (5 mL) was added potassium tert-butoxide (72 mg, 0.65 mmol) and water (0.5 mL), the solution was stirred at 80° C. for 1 h. Neutralized with HCl (aq. 2N) to pH~1, then purified by prep-HPLC to get 0080-4 (80 mg, 58% yield) as a light brown solid.

The Synthesis of (S)-methyl 2-(2,6-dichloro-3-(3-phenylazetidin-1-yl)benzamido)-3-(3-((R)-2,3-dihydro-1H-inden-1-yl)ureido)propanoate (0080-5)

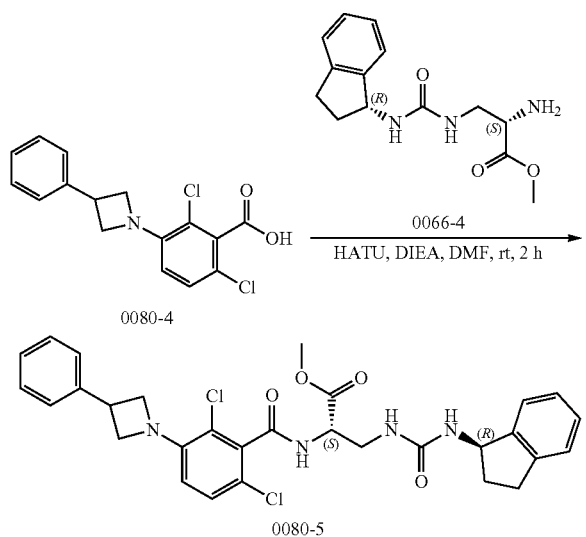

To a solution of 0080-4 (80 mg, 0.25 mmol) in DMF (5.0 mL) was added HATU (95 mg, 0.25 mmol), DIEA (65 mg, 0.50 mmol) and 0066-4 (69 mg, 0.25 mmol). The solution was stirred at room temperature for 2 h. The solution was poured into water (50 mL) and the precipitate was collected by filtration, dried in vacuum to get 0080-5 (90 mg, 62% yield) as a white solid.

The Synthesis of (S)-2-(2,6-dichloro-3-(3-phenylazetidin-1-yl)benzamido)-3-(3-((R)-2,3-dihydro-1H-inden-1-yl)ureido)propanoic Acid (SU15210-0080)

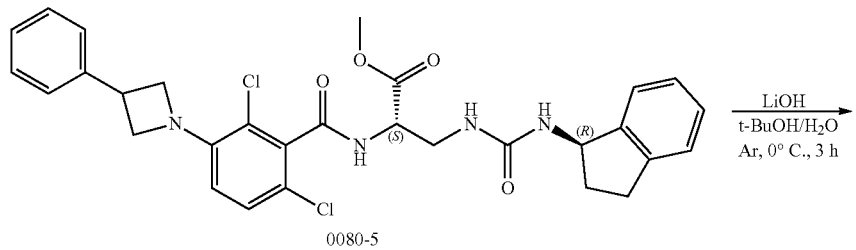

A solution of 0080-5 (90 mg, 0.15 mmol) in t-BuOH (3 mL) and H₂O (1 mL) was added LiOH (7.2 mg, 0.30 mmol) at 0° C. and stirred for 3 h keeping this temperature. The reaction mixture was acidified by HCl (aq, 1N) to pH~2, concentrated and purified by prep-HPLC to give SU15210-0080-01 (35 mg, 40% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 95.6%. Rt=1.249 min; MS Calcd.: 566.1; MS Found: 567.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 95.6%. Rt=3.363 min.

¹HNMR (400 MHz, DMSO-d₆) δ 8.23 (s, 1H), 7.64 (s, 1H), 7.02-7.38 (m, 9H), 6.63 (d, J=8.0 Hz, 2H), 5.91 (s, 1H), 5.01 (q, J=8.4 Hz, 1H), 4.38 (q, J=5.6 Hz, 2H), 3.68-3.92 (m, 4H), 2.82-2.97 (m, 2H), 2.61-2.74 (m, 2H), 2.21-2.33 (m, 2H), 1.57-1.62 (m, 1H).

SU15210-0084-01
Route for SU15210-0084-01:

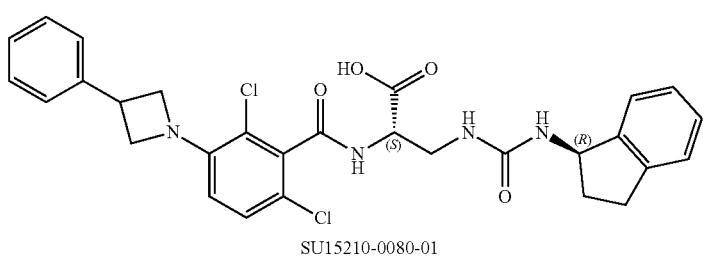

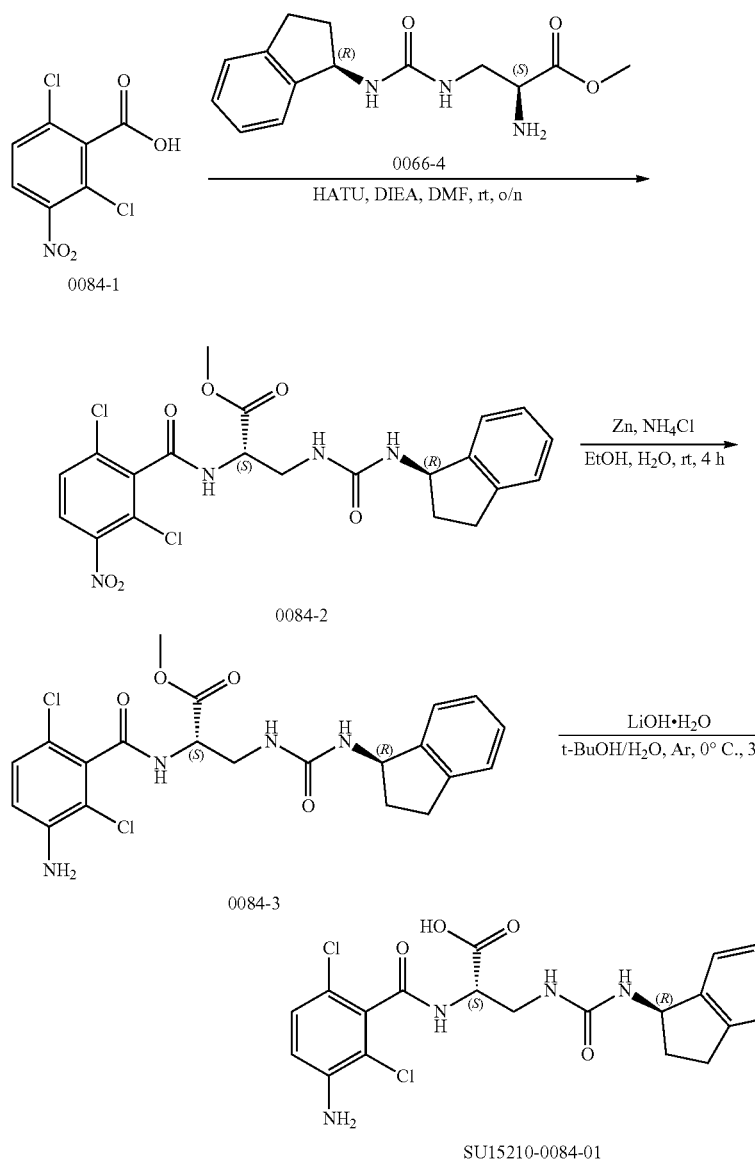
The Synthesis of (S)-methyl 2-(2,6-dichloro-3-nitrobenzamido)-3-(3-((R)-2,3-dihydro-1H-inden-1-yl)ureido)propanoate (0084-2)
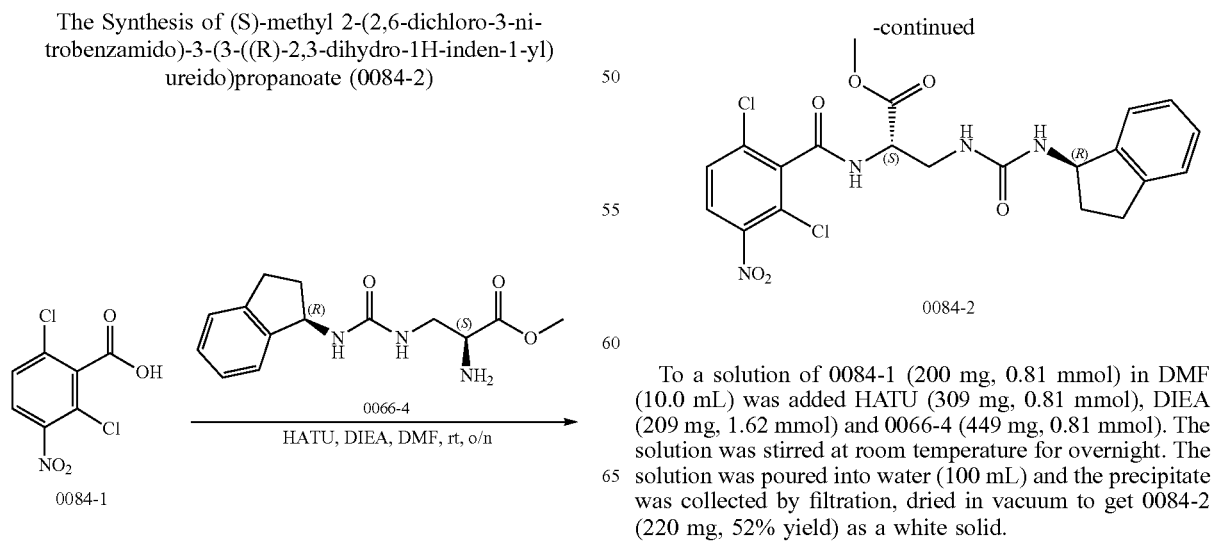
To a solution of 0084-1 (200 mg, 0.81 mmol) in DMF (10.0 mL) was added HATU (309 mg, 0.81 mmol), DIEA (209 mg, 1.62 mmol) and 0066-4 (449 mg, 0.81 mmol). The solution was stirred at room temperature for overnight. The solution was poured into water (100 mL) and the precipitate was collected by filtration, dried in vacuum to get 0084-2 (220 mg, 52% yield) as a white solid.

The Synthesis of (S)-methyl 2-(3-amino-2,6-dichlorobenzamido)-3-(3-((R)-2,3-dihydro-1H-inden-1-yl)ureido)propanoate (0084-3)

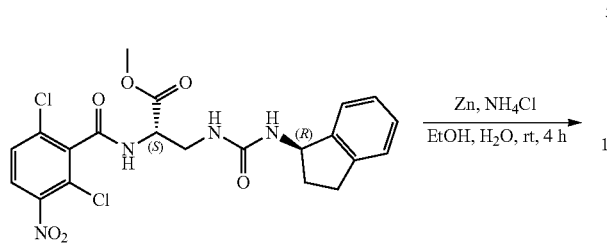

0084-2

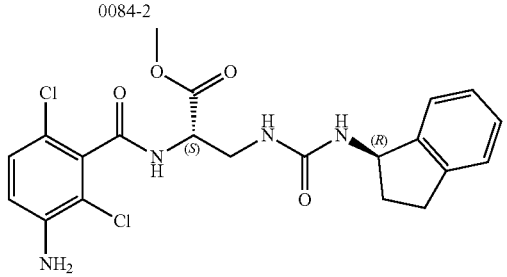

0084-3

To a solution of 0084-2 (220 mg, 0.44 mmol) in EtOH (20 mL) was added sat. NH₄Cl aq. (10 mL) and zinc powder (144 mg, 2.22 mmol), the mixture was stirred at room temperature for 4 h. Filtrated and the filtrate was concentrated to remove the solvent. EA (20 mL) and water (20 mL) was added, then Na₂CO₃ aq. was added to adjust pH to 9. Filtrated to remove the precipitate, the filtrate was extracted with EA (10 mL*2), the organic phase was separated and dried over Na₂SO₄, concentrated then purified by CC (10% to 30% ethyl acetate in petroleum ether) to give 0084-3 (150 mg, 72% yield) as a white solid.

The Synthesis of (S)-2-(3-amino-2,6-dichlorobenzamido)-3-(3-((R)-2,3-dihydro-1H-inden-1-yl)ureido)propanoic Acid (SU15210-0084-01)

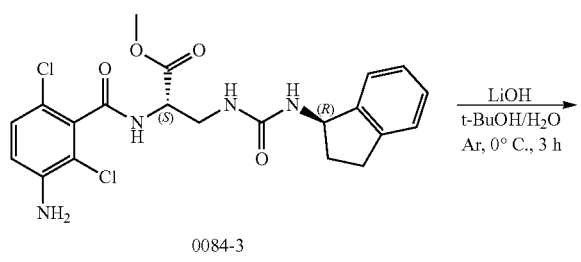

0084-3

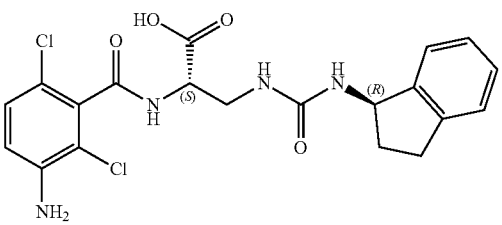

SU15210-0084-01

A solution of 0084-3 (50 mg, 0.11 mmol) in t-BuOH (3 mL) and H₂O (1 mL) was added LiOH (5.3 mg, 0.22 mmol) at 0° C. and stirred for 3 h. Acidified by 1N HCl aq. to pH~2, concentrated and purified by prep-HPLC to give SU15210-0084-01 (20 mg, 41% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 100%. Rt=0.876 min; MS Calcd.: 451.1; MS Found: 452.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=1.749 min.

¹HNMR (400 MHz, DMSO-d₆) δ 8.71 (d, J=6.8 Hz, 1H), 7.16-7.23 (m, 4H), 7.11 (d, J=8.4 Hz, 1H), 6.80 (d, J=8.8 Hz, 1H), 6.57 (d, J=8.4 Hz, 1H), 5.89 (t, J=5.2 Hz, 1H), 5.61 (s, 2H), 5.08 (q, J=8.0 Hz, 1H), 4.41 (q, J=6 Hz, 1H), 3.47-3.52 (m, 2H), 2.84-2.87 (m, 1H), 2.73-2.79 (m, 1H), 2.35-2.50 (m, 1H), 1.65-1.70 (m, 1H).

SU15210-0095-01

Route for SU15210-0095-01:

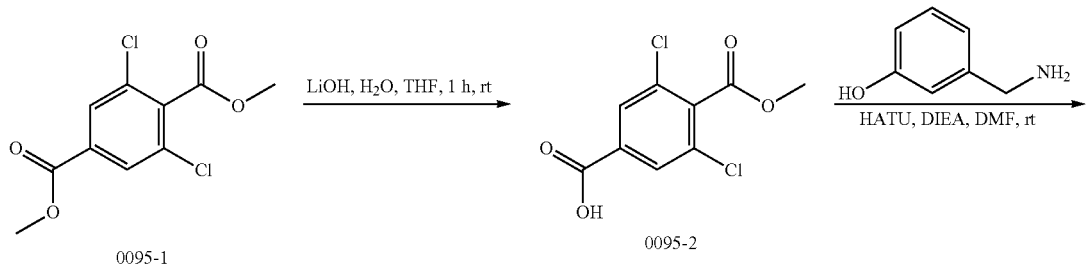

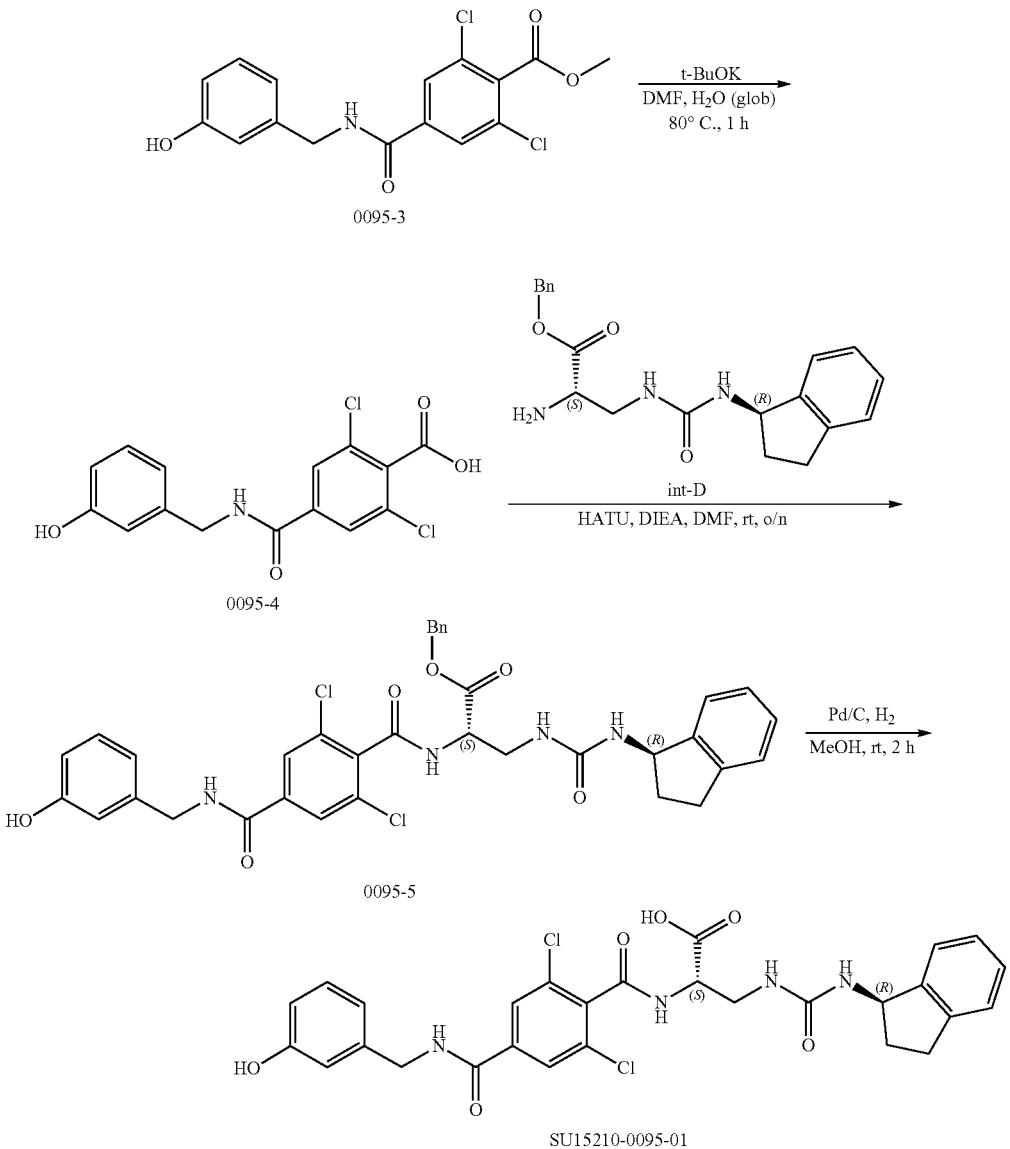
The Synthesis of 3,5-dichloro-4-(methoxycarbonyl)benzoic Acid (0095-2)
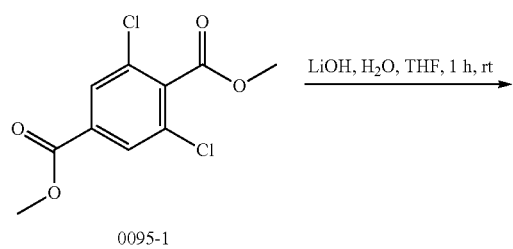
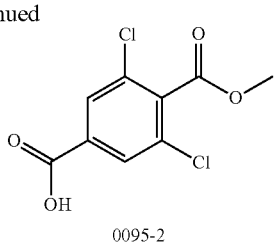
To a solution of 0095-1 (2.0 g, 7.63 mmol) in THF (20 mL) and H₂O (5 mL) was added LiOH (366 mg, 14.3 mmol). The solution was stirred at room temperature for 1 h. Concentrated to remove the solvent, H₂O (20 mL) was added, adjust pH to 1.0 by 1N HCl aq., then collect the precipitate by filtration, dried in vacuum to get 0095-2 (1.6 g, 79% yield) as a white solid.

The Synthesis of Methyl 2,6-dichloro-4-(3-hydroxybenzylcarbamoyl)benzoate (0095-3)

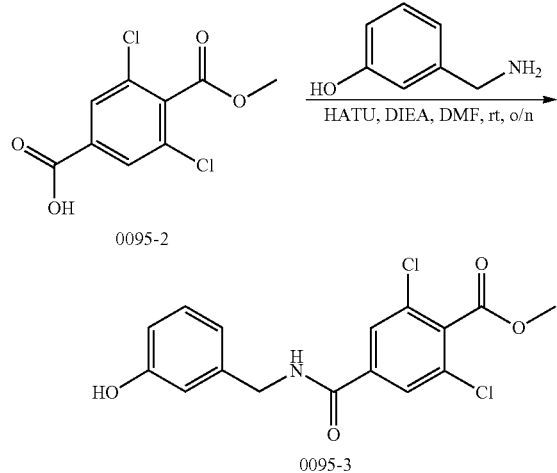

The Synthesis of 2,6-dichloro-4-(3-hydroxybenzylcarbamoyl)benzoic Acid (0095-4)

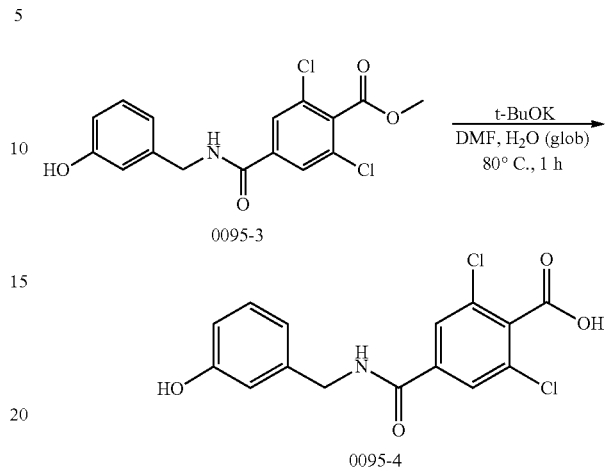

To a solution of 0095-2 (200 mg, 0.80 mmol) in DMF (10.0 mL) was added HATU (305 mg, 0.80 mmol), DIEA (206 mg, 1.60 mmol) and 3-(aminomethyl)phenol (98 mg, 0.80 mmol). The solution was stirred at room temperature for overnight. The solution was poured into water (100 mL) and the precipitate was collected by filtration, then purified by CC (10% to 40% ethyl acetate in petroleum ether) to get 0095-3 (210 mg, 73% yield) as a white solid.

To a solution of 0095-3 (150 mg, 0.43 mmol) in DMSO (5 mL) was added potassium tert-butoxide (96 mg, 0.86 mmol) and water (0.05 mL), the solution was stirred at 80° C. for 1 h. Acidified with 2N HCl aq. to pH~1, then purified by prep-HPLC to get 0095-4 (90 mg, 62% yield) as a white solid.

The Synthesis of (S)-benzyl 2-(2,6-dichloro-4-(3-hydroxybenzylcarbamoyl)benzamido)-3-(3-((R)-2,3-dihydro-1H-inden-1-yl)ureido)propanoate (0095-5)

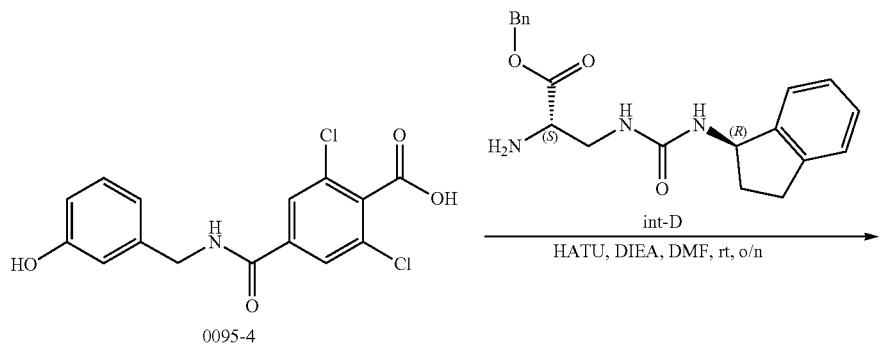

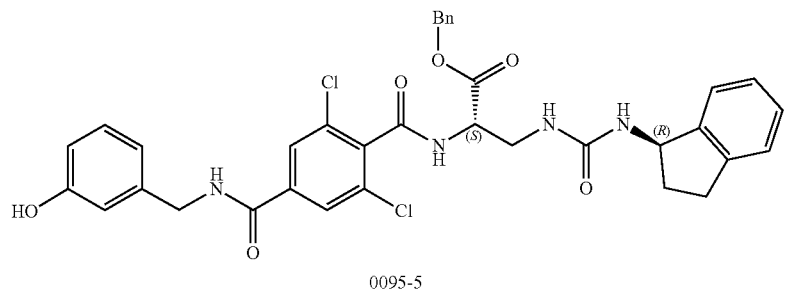

To a solution of 0095-4 (90 mg, 0.26 mmol) in DMF (5.0 mL) was added HATU (100 mg, 0.26 mmol), DIEA (67 mg, 0.52 mmol) and int-D (92 mg, 0.26 mmol). The solution was stirred at room temperature for overnight. The solution was poured into water (50 mL) and the precipitate was collected by filtration, dried in vacuum to get 0095-5 (90 mg, 62% yield) as a white solid.

The Synthesis of (S)-2-(2,6-dichloro-4-(3-hydroxy-benzylcarbamoyl)benzamido)-3-(3-((R)-2,3-dihydro-1H-inden-1-yl)ureido)propanoic Acid (SU15210-0095)

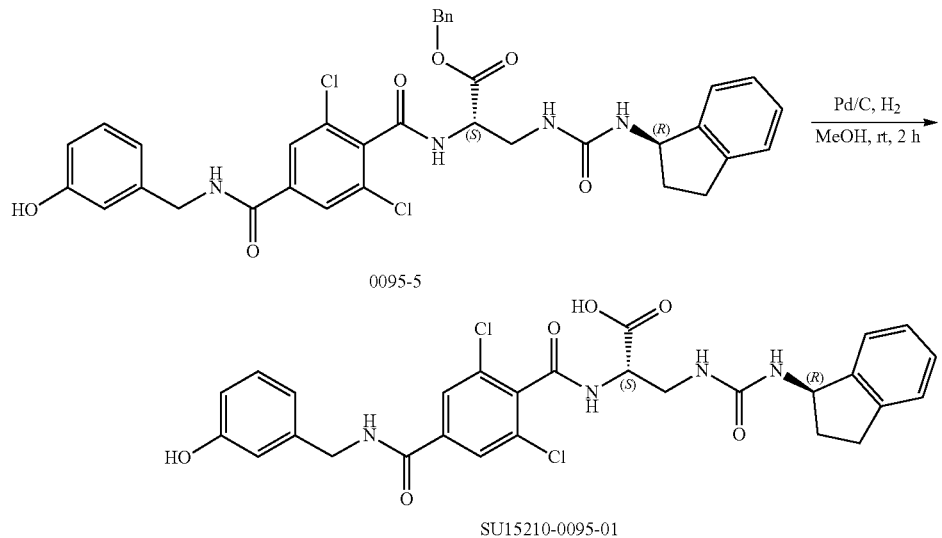

A solution of 0095-5 (90 mg, 0.13 mmol) in MeOH (5 mL) was added Pd/C (10 mg, 10%), the mixture was stirred under $H_2$ at room temperature for 2 h. Filtrated and the filtrate was concentrated and purified by prep-HPLC to get SU15210-0095-01 (40 mg, 51% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [$CH_3CN$] to 0% [water+10 mM TFA] and 100% [$CH_3CN$] in 1.6 min, then under this condition for 1.4 min, finally changed to 95% [water+10 mM TFA] and 5% [$CH_3CN$] in 0.1 min. Purity is 100%. Rt=1.563 min; MS Calcd.: 584.1; MS Found: 585.1 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 100%. Rt=6.819 min.

$^1$HNMR (400 MHz, DMSO-$d_6$) δ 12.79 (br, 1H), 9.33 (s, 1H), 9.26 (t, J=5.6 Hz, 1H), 9.10 (d, J=7.6 Hz, 1H), 7.96 (s, 2H), 7.09-7.22 (m, 5H), 6.71-6.74 (m, 2H), 6.64 (dd, J=8.4, 2.0 Hz, 1H), 6.57 (d, J=8.4 Hz, 1H), 5.87 (t, J=5.6 Hz, 1H), 5.08 (q, J=8.0 Hz, 1H), 4.52 (q, J=8.0 Hz, 1H), 4.40 (d, J=6.0 Hz, 2H), 3.52-3.59 (m, 2H), 2.86-2.90 (m, 1H), 2.73-2.79 (m, 1H), 2.33-2.40 (m, 1H), 1.64-1.70 (m, 1H).

SU15210-0097-01

Route for SU15210-0097-01:

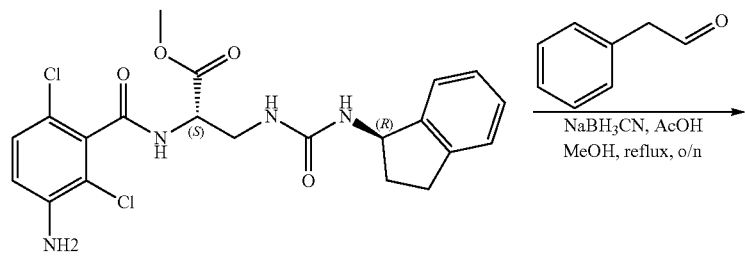

-continued

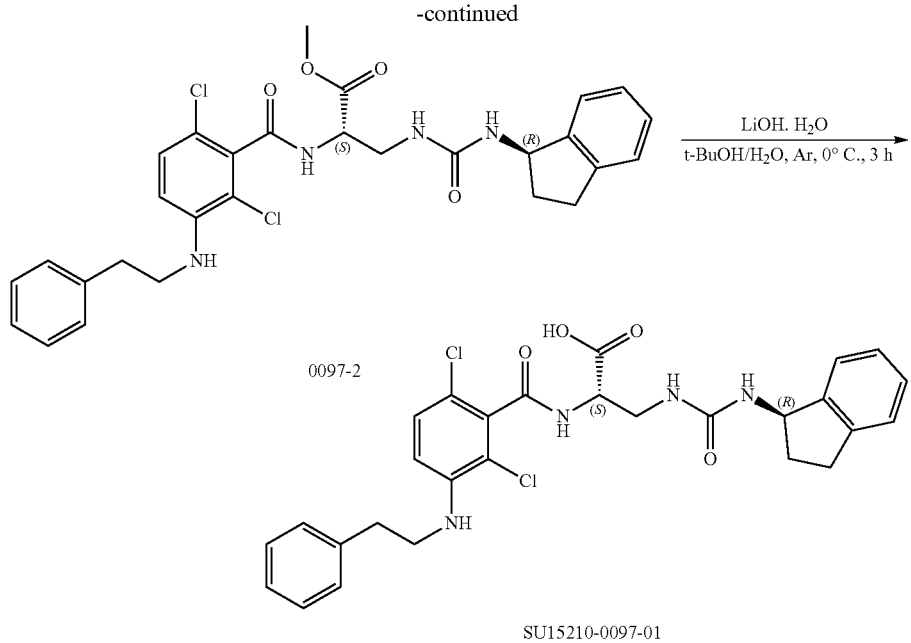

The Synthesis of (S)-methyl 2-(2,6-dichloro-3-(phenethylamino)benzamido)-3-(3-((R)-2,3-dihydro-1H-inden-1-yl)ureido)propanoate (0097-2)

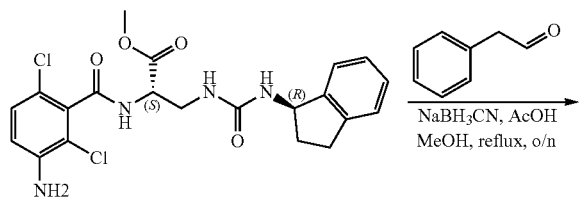

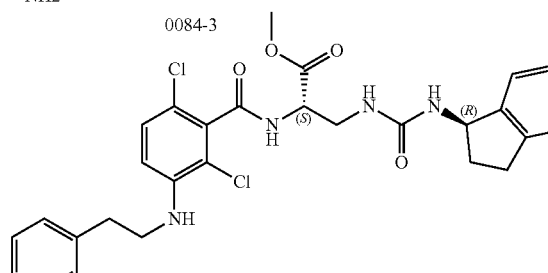

To a solution of 0084-3 (100 mg, 0.18 mmol) in MeOH/AcOH (10:1, 10.0 mL) was added 2-phenylacetaldehyde (25 mg, 0.21 mmol) and NaBH₃CN (15 mg, 0.23 mmol). The solution was stirred at reflux for overnight. Removed the solvent under reduce pressure, the residue was dissolved in DCM (20 mL), then ammonium hydroxide solution was added to adjust pH to 9, the organic layer was separated and washed with water then brine, dried over Na₂SO₄, concentrated and purified by CC (10% MeOH in DCM) to get 0097-2 (70 mg, 57% yield) as a white solid.

The Synthesis of (S)-2-(2,6-dichloro-3-(phenethylamino)benzamido)-3-(3-((R)-2,3-dihydro-1H-inden-1-yl)ureido)propanoic Acid (SU15210-0097-01)

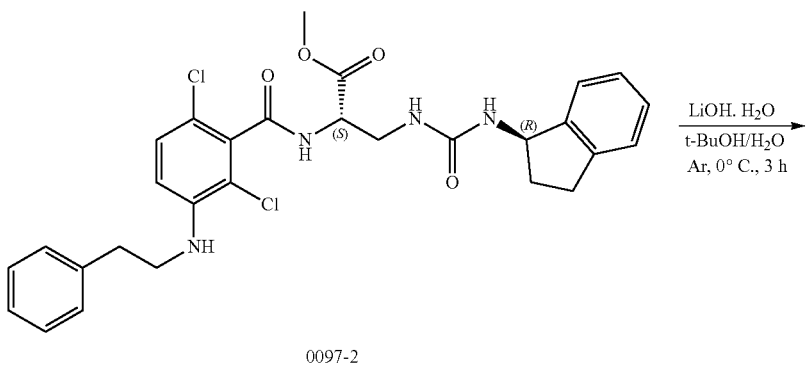

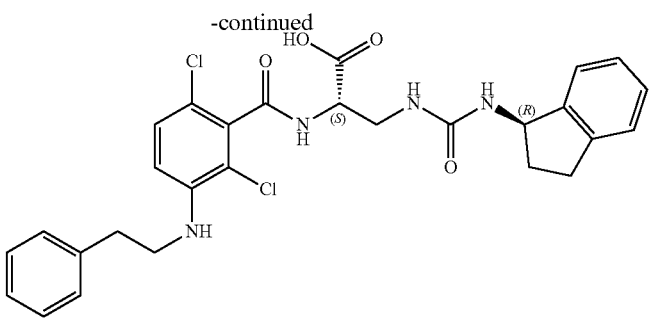

SU15210-0097-01

A solution of 0097-2 (50 mg, 0.09 mmol) in t-BuOH (3 mL) and H₂O (1 mL) was added LiOH (4.3 mg, 0.18 mmol) at 0° C. and stirred for 3 h. Acidified by 1N HCl aq. to pH-2, concentrated and purified by prep-HPLC to get SU15210-0097 (28 mg, 57% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 97.49%. Rt=1.263 min; MS Calcd.: 554.1; MS Found: 555.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=3.326 min.

¹HNMR (400 MHz, DMSO-d₆) δ 12.21 (br, 1H), 8.68 (d, J=7.2 Hz, 1H), 7.08-7.25 (m, 11H), 6.74 (d, J=9.2 Hz, 1H), 6.48 (d, J=8.4 Hz, 1H), 5.81 (t, J=5.2 Hz, 1H), 5.49 (t, J=5.2 Hz, 1H), 5.05 (q, J=8.0 Hz, 1H), 4.35 (q, J=6.0 Hz, 1H), 3.30-3.44 (m, 1H), 3.29-3.42 (m, 3H), 2.76-2.81 (m, 3H), 2.69-2.74 (m, 1H), 2.27-2.30 (m, 1H), 1.58-1.62 (m, 1H).

SU15210-0098-01

Route for SU15210-0098-01:

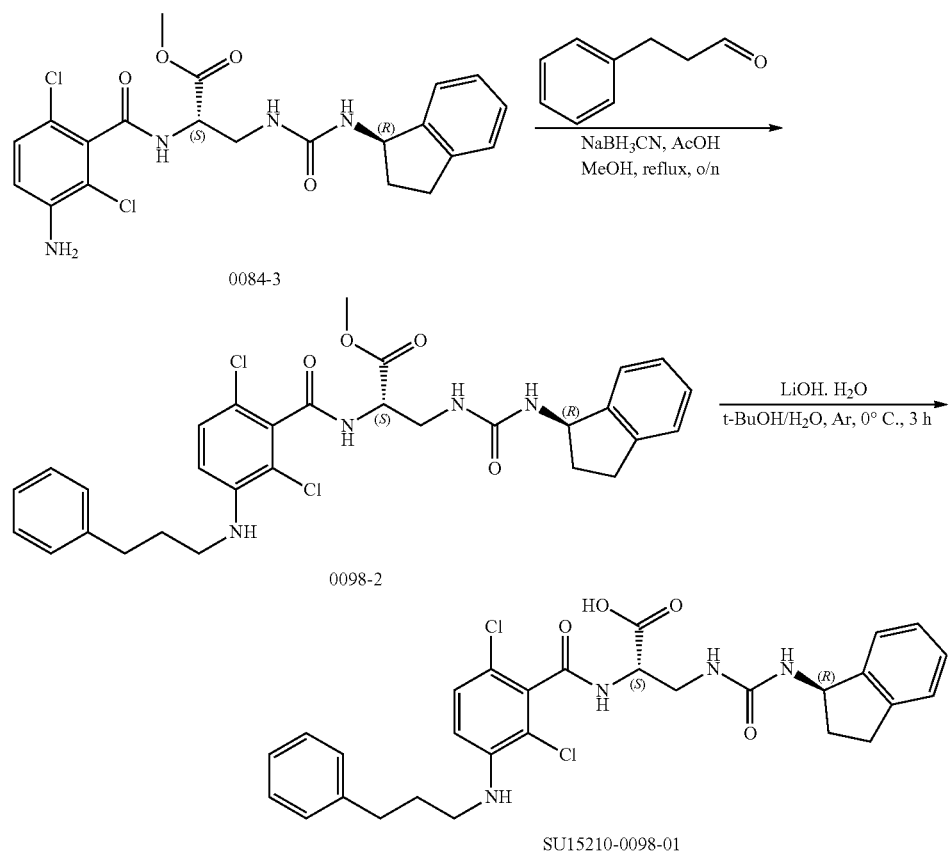

The Synthesis of (S)-methyl 2-(2,6-dichloro-3-(phenethylamino)benzamido)-3-(3-((R)-2,3-dihydro-1H-inden-1-yl)ureido)propanoate (0098-2)

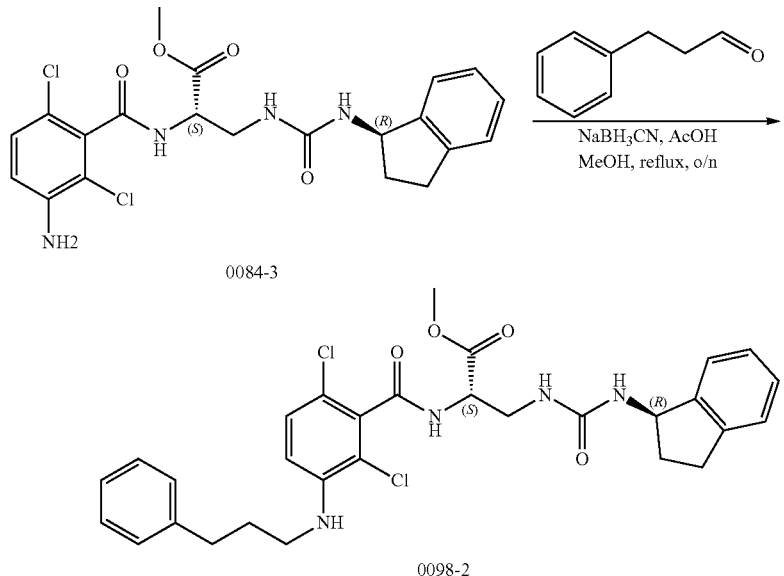

To a solution of 0084-3 (100 mg, 0.18 mmol) in MeOH/AcOH (10:1, 10.0 mL) was added 3-phenylpropanal (28 mg, 0.21 mmol) and NaBH$_3$CN (15 mg, 0.23 mmol). The solution was stirred at reflux for overnight. Remove the solvent under reduce pressure, the residue was dissolved in DCM (20 mL), then ammonium hydroxide solution was added to adjust pH to 9.0, the organic layer was separated and washed with water then brine, dried over Na$_2$SO$_4$, concentrated and purified by CC (10% MeOH in DCM) to get 0098-2 (75 mg, 60% yield) as a white solid.

The Synthesis of (S)-2-(2,6-dichloro-3-(3-phenyl-propylamino)benzamido)-3-(3-((R)-2,3-dihydro-1H-inden-1-yl)ureido)propanoic Acid (SU15210-0098-01)

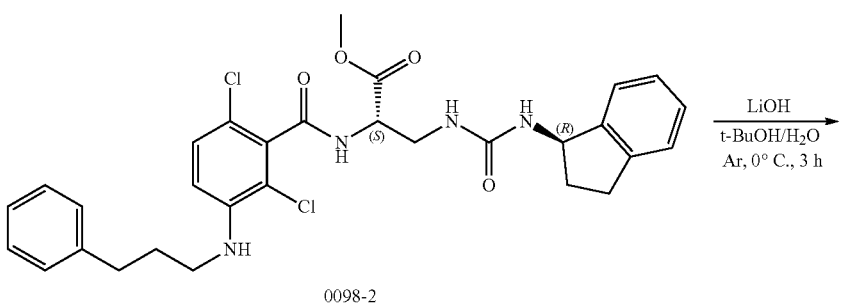

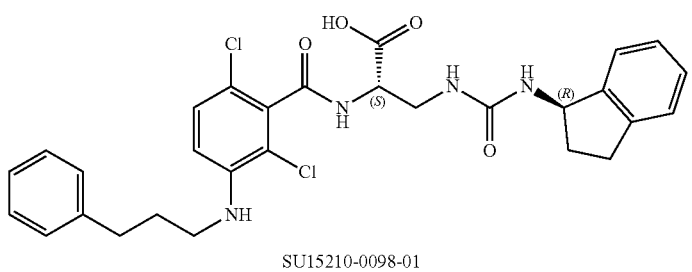

A solution of 0098-2 (50 mg, 0.09 mmol) in t-BuOH (3 mL) and H$_2$O (1 mL) was added LiOH (4.3 mg, 0.18 mmol) at 0° C. and stirred for 3 h. Acidified by 1N HCl aq. to pH-2, concentrated and purified by prep-HPLC to get SU15210-0098 (26 mg, 53% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 98.01%. Rt=1.327 min; MS Calcd.: 568.1; MS Found: 569.1 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=3.583 min.

$^1$H NMR (400 MHz, DMSO-d$_6$) δ 12.23 (br, 1H), 8.76 (d, J=6.8 Hz, 1H), 7.17-7.31 (m, 10H), 6.67 (d, J=8.8 Hz, 1H), 6.55 (d, J=2.4 Hz, 1H), 5.89 (t, J=6.0 Hz, 1H), 5.62 (t, J=6.0 Hz, 1H), 5.10 (q, J=7.6 Hz, 1H), 4.44 (q, J=6.0 Hz, 1H), 3.48-3.51 (m, 1H), 3.30-3.36 (m, 1H), 3.15-3.19 (m, 2H), 2.87-2.89 (m, 1H), 2.73-2.80 (m, 1H), 2.55-2.65 (m, 2H), 2.31-2.40 (m, 1H), 1.79-1.71 (m, 2H), 1.60-1.69 (m, 1H).

SU15210-0099-01

Route for SU15210-0099-01:

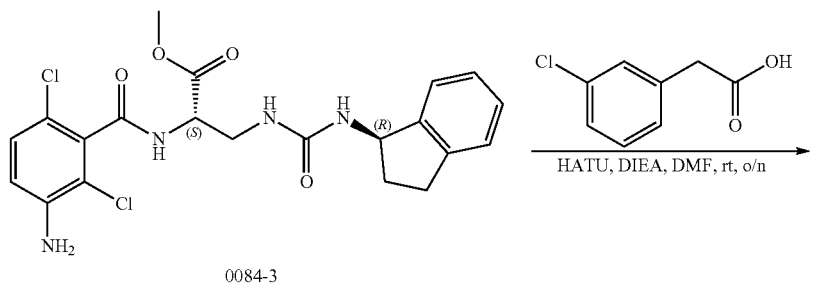

0084-3

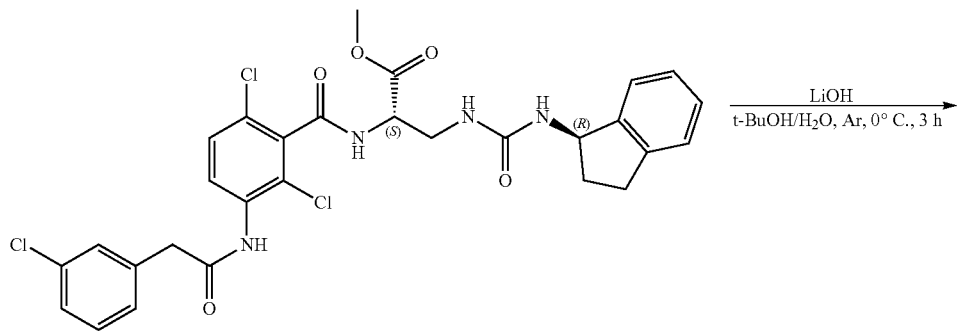

0099-2

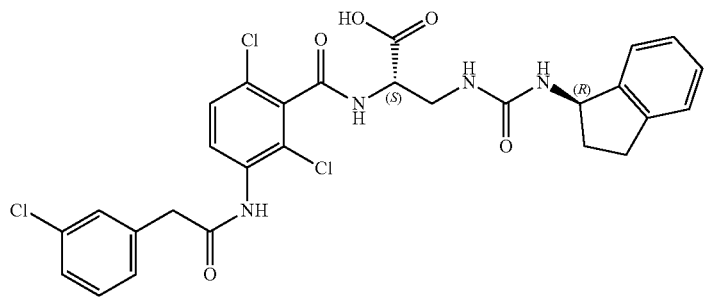

SU15210-0099-01

The Synthesis of (S)-methyl 2-(2,6-dichloro-3-(2-(3-chlorophenyl)acetamido)benzamido)-3-(3-((R)-2,3-dihydro-1H-inden-1-yl)ureido)propanoate (0099-2)

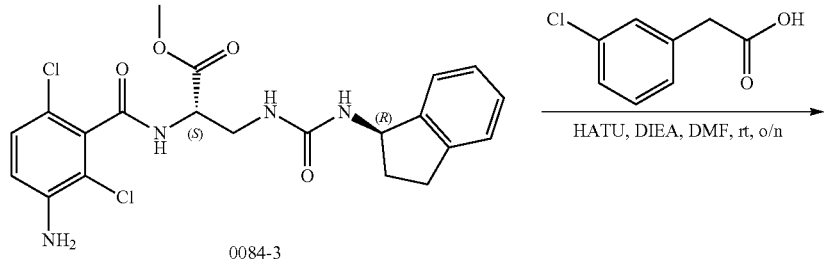

0084-3

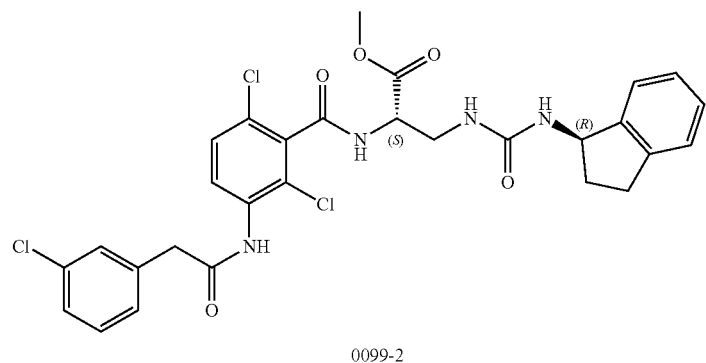

0099-2

To a solution of 2-(3-chlorophenyl)acetic acid (31 mg, 0.18 mmol) in DMF (5.0 mL) was added 0084-3 (100 mg, 0.18 mmol) HATU (68 mg, 0.18 mmol) and DIEA (46 mg, 0.36 mmol). The solution was stirred at room temperature for overnight. Poured the solution into water (50 mL), collect the precipitate by filtration to get the crude product, which was further purified by CC (10% MeOH in DCM) to get 0099-2 (80 mg, 60% yield) as a white solid.

The Synthesis of (S)-2-(2,6-dichloro-3-(2-(3-chlorophenyl)acetamido)benzamido)-3-(3-((R)-2,3-dihydro-1H-inden-1-yl)ureido)propanoic Acid (SU15210-0099-01)

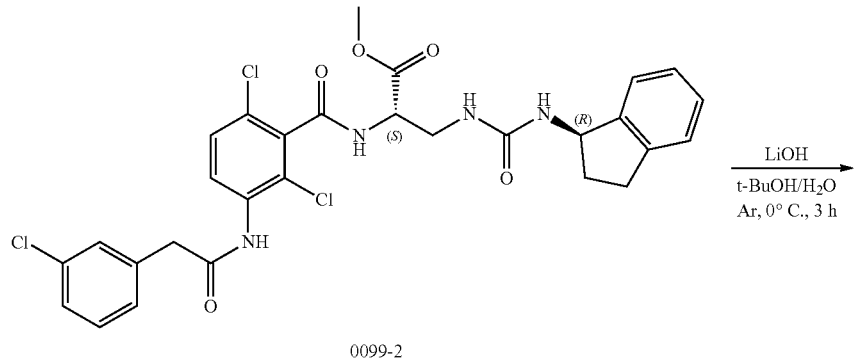

0099-2

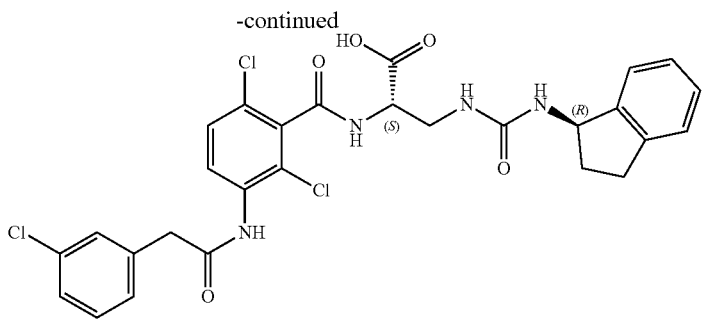

SU15210-0099-01

A solution of 0099-2 (50 mg, 0.09 mmol) in t-BuOH (3 mL) and H₂O (1 mL) was added LiOH (4.3 mg, 0.18 mmol) at 0° C. and stirred for 3 h. Acidified by 1N HCl aq. to pH-2, concentrated and purified by prep-HPLC to get SU15210-0099 (25 mg, 51% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 100%. Rt=1.770 min; MS Calcd.: 602.2; MS Found: 603.2 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=8.560 min.

¹H NMR (400 MHz, DMSO-d₆) δ 12.75 (br, 1H), 9.86 (s, 1H), 8.86 (br, 1H), 7.70 (d, J=8.8 Hz, 1H), 7.41-7.45 (m, 2H), 7.28-7.36 (m, 3H), 7.11-7.20 (m, 4H), 6.56 (d, J=8.4 Hz, 1H), 5.87 (t, J=5.6 Hz, 1H), 5.05 (q, J=8.0 Hz, 1H), 4.39 (q, J=8.0 Hz, 1H), 3.76 (s, 2H), 3.45-3.49 (m, 1H), 3.30-3.37 (m, 1H), 2.81-2.87 (m, 1H), 2.71-2.76 (m, 1H), 2.31-2.37 (m, 1H), 1.62-1.67 (m, 1H).

SU15210-0124-01

Route for SU15210-0124-01:

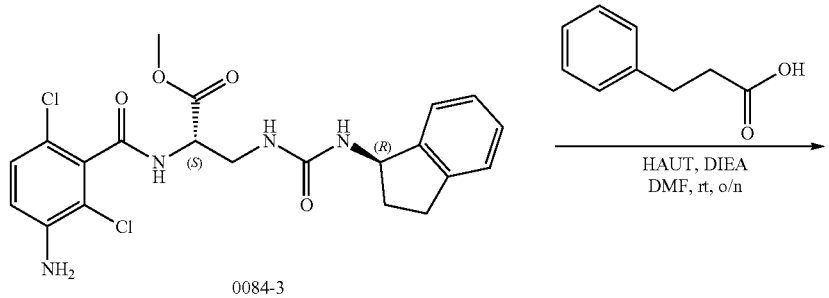

0084-3

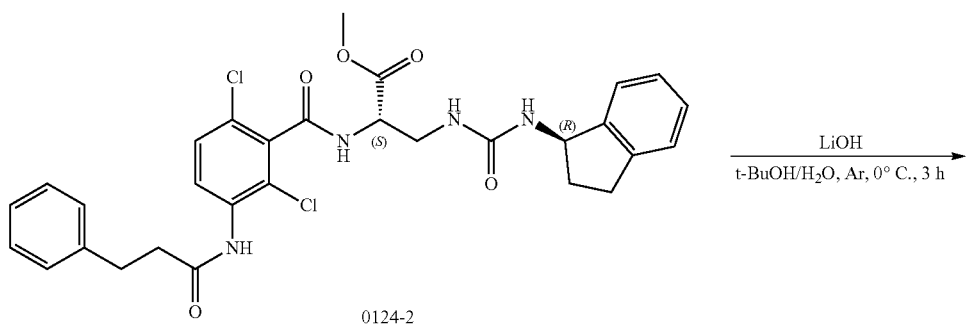

0124-2

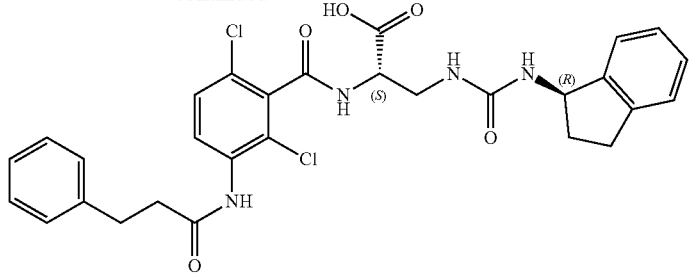

SU15210-0124-01

The Synthesis of (S)-methyl 2-(2,6-dichloro-3-(3-phenylpropanamido)benzamido)-3-(3-((R)-2,3-dihydro-1H-inden-1-yl)ureido)propanoate (0124-2)

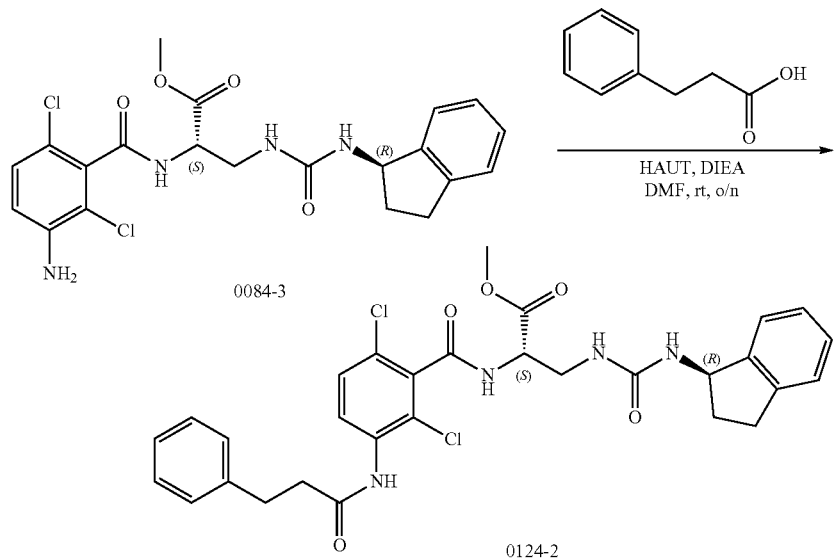

To a solution of 3-phenylpropanoic Acid (27 mg, 0.18 mmol) in DMF (5.0 mL) was added 0084-3 (100 mg, 0.18 mmol) HATU (68 mg, 0.18 mmol) and DIEA (46 mg, 0.36 mmol). The solution was stirred at room temperature for overnight. Poured the solution into water (50 mL), collected the precipitate by filtration to get the crude product, which was further purified by CC (0% to 10% MeOH in DCM) to get 0124-2 (90 mg, 60% yield) as a white solid.

The Synthesis of (S)-2-(2,6-dichloro-3-(3-phenyl-propanamido)benzamido)-3-(3-((R)-2,3-dihydro-1H-inden-1-yl)ureido)propanoic Acid (SU15210-0124-01)

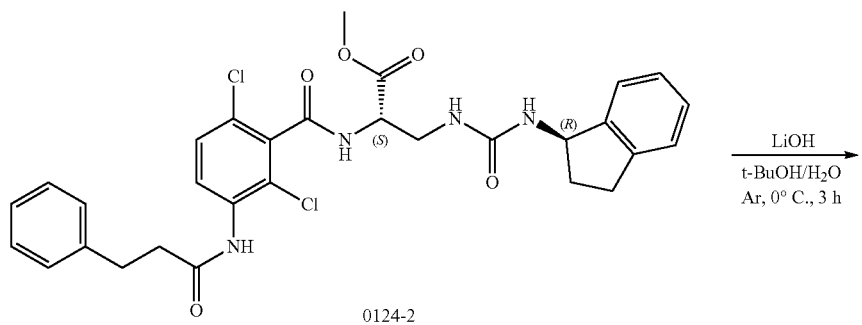

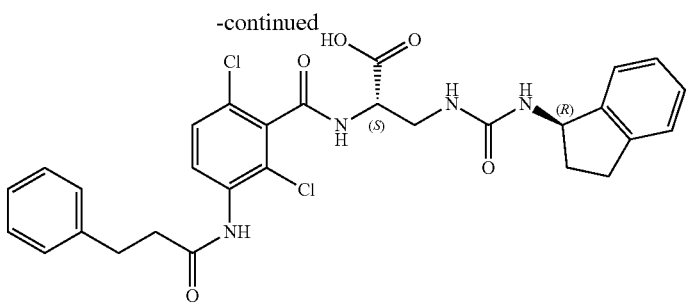

SU15210-0124-01

A solution of 0124-2 (50 mg, 0.08 mmol) in t-BuOH (3 mL) and H₂O (1 mL) was added LiOH (3.8 mg, 0.16 mmol) at 0° C. and stirred for 3 h. Acidified by 1N HCl aq. to pH-2, concentrated and purified by prep-HPLC to get SU15210-0124 (26 mg, 53% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 100%. Rt=1.748 min; MS Calcd.: 582.1; MS Found: 583.1 [M+H]⁺.

Agilent HPLC 1200; Column: Waters X-Bridge C18 (150 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=7.869 min.

$^1$H NMR (400 MHz, DMSO-d₆) δ 9.60 (s, 1H), 8.60 (br, 1H), 7.68 (d, J=8.8 Hz, 1H), 7.42 (d, J=8.8 Hz, 1H), 7.23-7.29 (m, 4H), 7.10-7.19 (m, 5H), 6.61 (d, J=8.0 Hz, 1H), 5.90 (br, 1H), 5.05 (q, J=8.0 Hz, 1H), 4.28 (q, J=6.8 Hz, 1H), 3.39 (br, 2H), 2.81-2.91 (m, 3H), 2.68-2.76 (m, 3H), 2.30-2.37 (m, 1H), 1.62-1.67 (m, 1H).

SU15210-0125-01

Route for SU15210-0125-01:

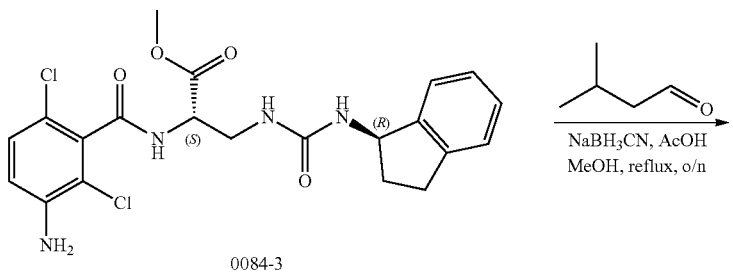

0084-3

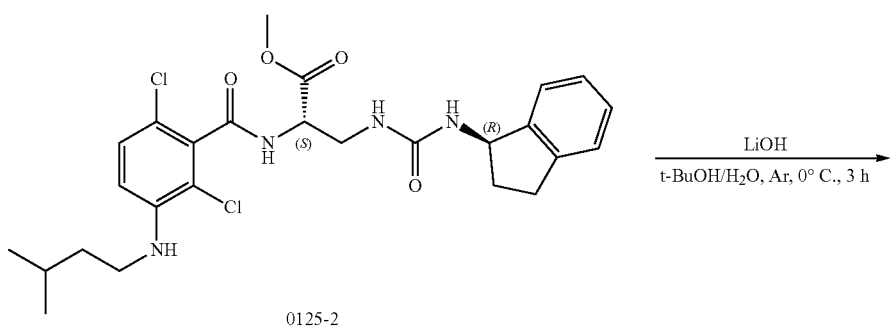

0125-2

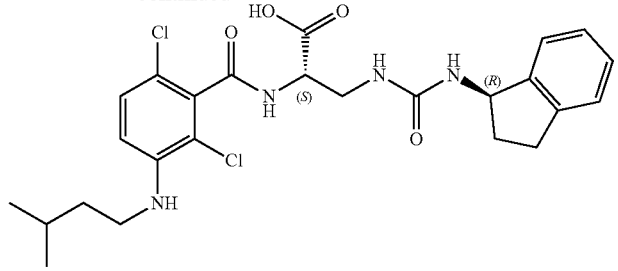

SU15210-0125-01

The Synthesis of (S)-methyl 2-(2,6-dichloro-3-(isopentylamino)benzamido)-3-(3-((R)-2,3-dihydro-1H-inden-1-yl)ureido)propanoate (0125-2)

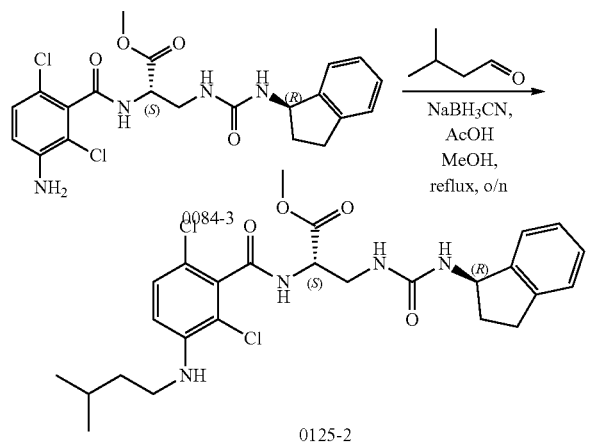

To a solution of 0084-3 (50 mg, 0.11 mmol) in MeOH/AcOH (10:1, 5.0 mL) was added 3-methylbutanal (11 mg, 0.13 mmol) and NaBH₃CN (14 mg, 0.22 mmol). The solution was stirred at reflux for overnight. Remove the solvent under reduce pressure, the residue was dissolved in DCM (20 mL), then ammonium hydroxide solution was added to pH 9, the organic layer was separated and washed with water then brine, dried over Na₂SO₄, concentrated and purified by CC (0% to 10% DCM in MeOH) to get 0125-2 (60 mg, 45% yield) as a white solid.

The Synthesis of (S)-2-(2,6-dichloro-3-(isopentylamino)benzamido)-3-(3-((R)-2,3-dihydro-1H-inden-1-yl)ureido)propanoic Acid (SU15210-0125-01)

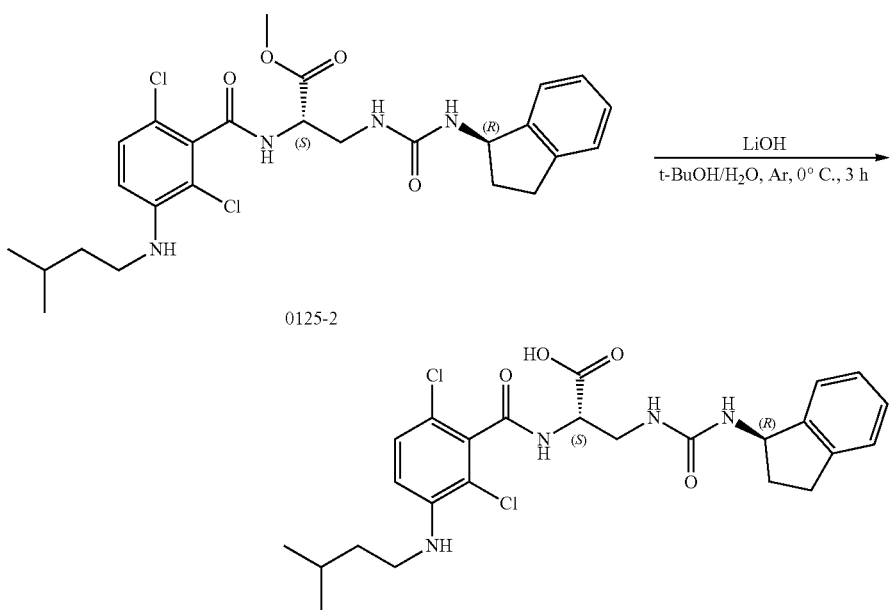

A solution of 0125-2 (26 mg, 0.05 mmol) in t-BuOH (3 mL) and H₂O (1 mL) was added LiOH (2.4 mg, 0.10 mmol) at 0° C. and stirred for 3 h. Acidified by 1N HCl aq. to pH-2, concentrated and purified by prep-HPLC to get SU15210-0125 (15 mg, 59% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 99.23%. Rt=1.479 min; MS Calcd.: 520.1; MS Found: 521.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=3.446 min.

$^1$HNMR (400 MHz, DMSO-d₆) δ 12.59 (br, 1H), 8.66 (s, 1H), 7.08-7.16 (m, 5H), 6.63 (d, J=8.8 Hz, 1H), 6.48 (d, J=8.4 Hz, 1H), 5.82 (t, J=4.0 Hz, 1H), 5.41 (t, J=5.6 Hz, 1H), 5.00 (q, J=8.0 Hz, 1H), 4.35 (q, J=6.8 Hz, 1H), 3.35-3.41 (m, 1H), 3.26-3.30 (m, 1H), 3.08 (t, J=8.0 Hz, 2H), 2.76-2.80 (m, 1H), 2.67-2.70 (m, 1H), 2.28-2.30 (m, 1H), 1.55-1.63 (m, 2H), 1.18-1.30 (m, 2H), 0.79 (d, J=8.0 Hz, 6H).

SU15210-0126-01

Route for SU15210-0126-01:

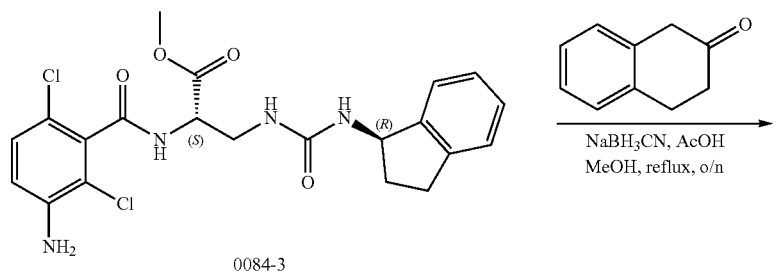

0084-3

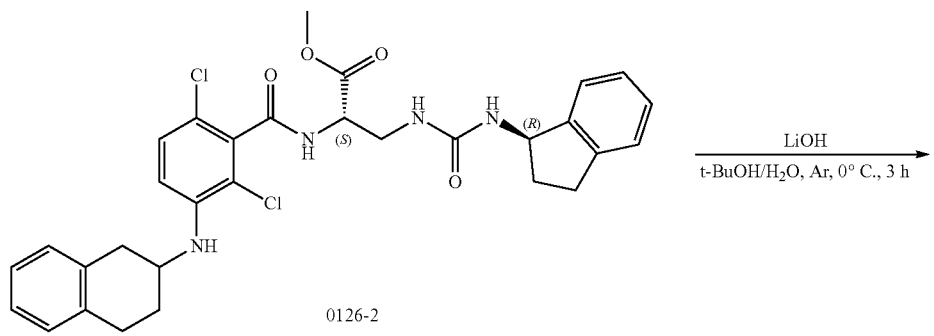

0126-2

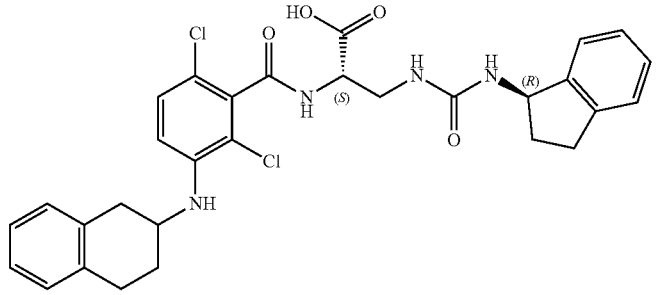

SU15210-0126-01

The Synthesis of (2S)-methyl 2-(2,6-dichloro-3-(1,2,3,4-tetrahydronaphthalen-2-ylamino)benzamido)-3-(3-((R)-2,3-dihydro-1H-inden-1-yl)ureido)propanoate (0126-2)

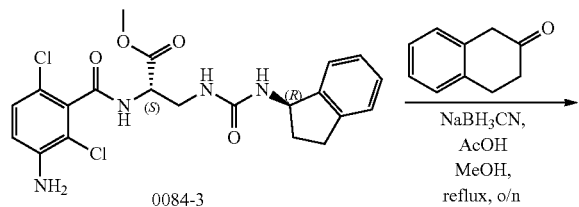

The Synthesis of (2S)-2-(2,6-dichloro-3-(1,2,3,4-tetrahydronaphthalen-2-ylamino)benzamido)-3-(3-((R)-2,3-dihydro-1H-inden-1-yl)ureido)propanoic Acid (SU15210-0126-01)

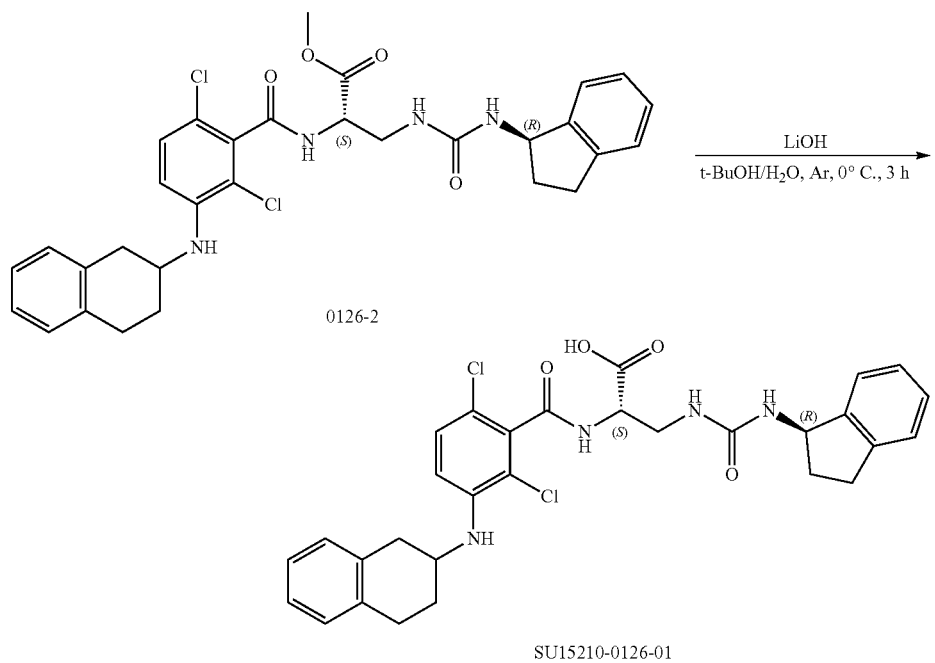

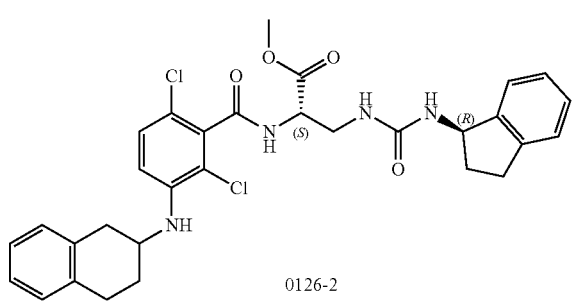

To a solution of 0084-3 (100 mg, 0.18 mmol) in MeOH/AcOH (10:1, 10.0 mL) was added 2-phenylacetaldehyde (25 mg, 0.21 mmol) and NaBH$_3$CN (15 mg, 0.23 mmol). The solution was stirred at reflux for overnight. Removed the solvent under reduce pressure, the residue was dissolved in DCM (20 mL), then ammonium hydroxide solution was added to pH 9, the organic layer was separated and washed with water then brine, dried over Na$_2$SO$_4$, concentrated and purified by CC (10% MeOH in DCM) to get 0126-2 (30 mg, 23% yield) as a white solid.

A solution of 0097-2 (30 mg, 0.05 mmol) in t-BuOH (3 mL) and H$_2$O (1 mL) was added LiOH (2.4 mg, 0.10 mmol) at 0° C. and stirred for 3 h. Acidified by 1N HCl aq. to pH-2, concentrated and purified by prep-HPLC to get SU15210-0126 (12 mg, 41% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 96.63%. Rt=1.336 min; MS Calcd.: 580.2; MS Found: 581.2 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=3.618 min.

¹H NMR (400 MHz, DMSO-d₆) δ 12.59 (br, 1H), 8.70 (d, J=4.8 Hz, 1H), 7.08-7.25 (m, 10H), 6.74 (d, J=9.2 Hz, 1H), 6.48 (d, J=8.4 Hz, 1H), 5.81 (t, J=5.2 Hz, 1H), 5.49 (t, J=5.2 Hz, 1H), 5.05 (q, J=8.0 Hz, 1H), 4.35 (q, J=6.0 Hz, 1H), 3.69-3.78 (m, 1H), 3.42-3.44 (m, 1H), 3.28-3.30 (m, 1H), 2.97-3.01 (m, 1H), 2.65-2.85 (m, 6H), 2.27-2.30 (m, 1H), 1.98-2.02 (m, 1H), 1.58-1.71 (m, 2H).
SU15210-0127-01
Route for SU15210-0127-01:
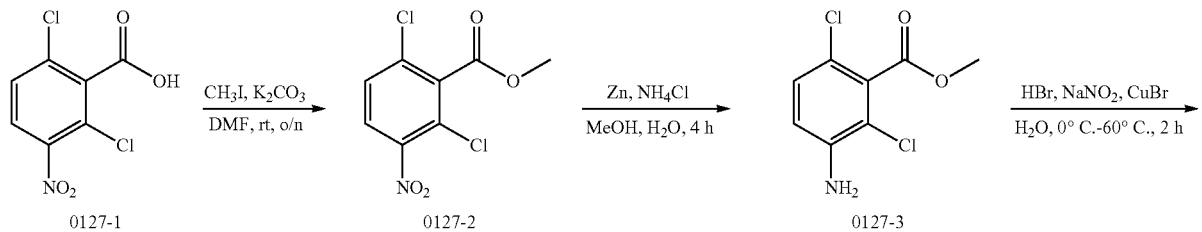
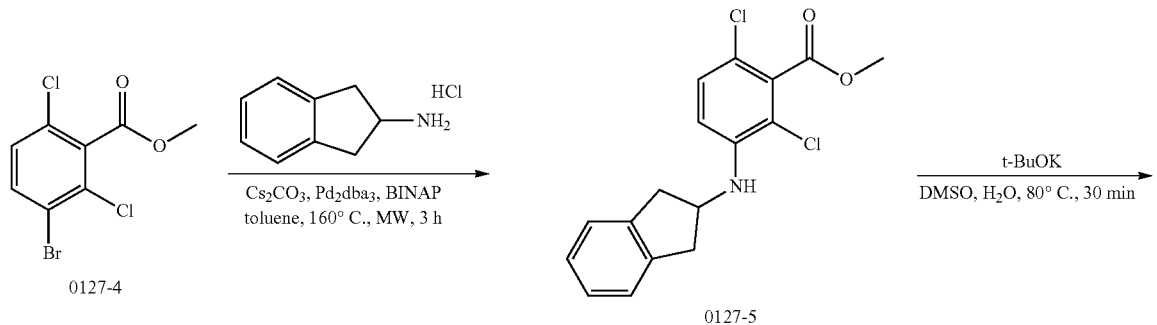
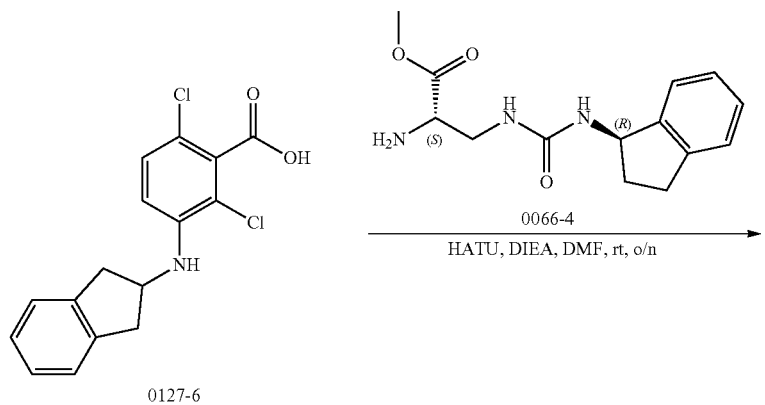
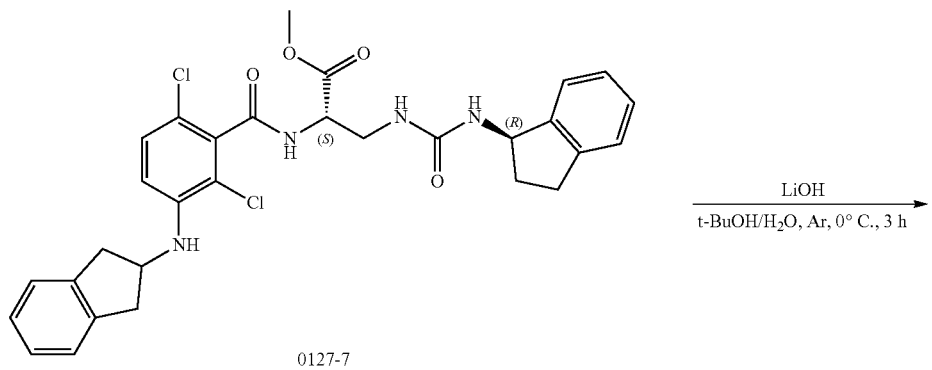

-continued

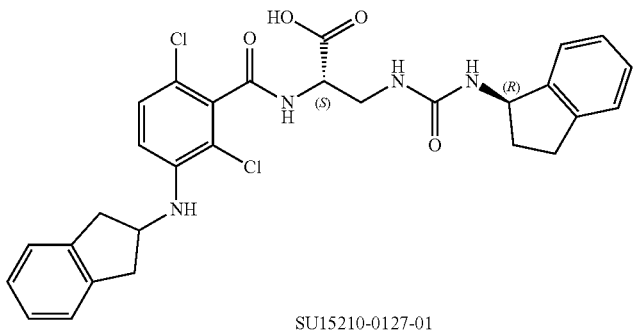

SU15210-0127-01

The Synthesis of Methyl 2,6-dichloro-3-nitrobenzoate (0127-2)

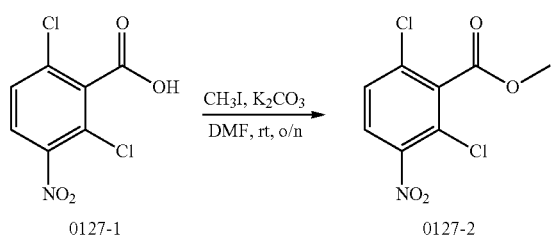

To a solution of 0127-1 (5.0 g, 21.18 mmol) in DMF (40 mL) was K₂CO₃ (5.8 g, 42.36 mmol) and CH₃I (3.2 g, 22.24 mmol). The mixture was stirred at room temperature for overnight. Remove the solid by filtration, the filtrate was concentrated and purified by CC (5% to 10% ethyl acetate in petroleum ether) to get 0127-2 (4.8 g, 90% yield) as a light yellow solid.

The Synthesis of methyl 3-amino-2,6-dichlorobenzoate (0127-3)

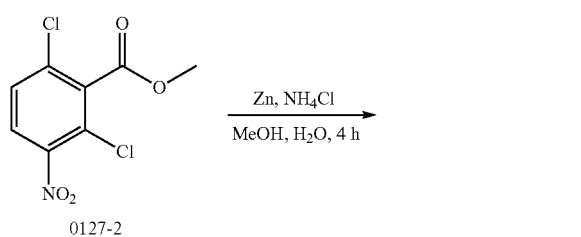

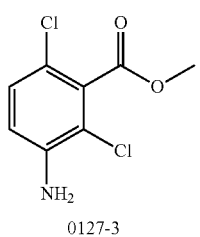

To a solution of 0127-2 (4.8 g, 19.20 mmol) in MeOH/H₂O (2:1, 50 mL) was added NH₄Cl (5.1 g, 96.00 mmol), then zinc powder (6.2 g, 96.00 mmol) was added portion to the solution over 10 min. The mixture was stirred at room temperature for 4 h. Filtrated to remove the extra zinc powder, washed the solid with MeOH (50 mL). The filtrate was concentrated to remove the solvent, the residual was dissolved in EA (50 mL) and water (50 mL), Na₂CO₃ aq. was added to adjust pH to 10, separated the organic phase and washed with water then brine, dried over Na₂SO₄, concentrated to get 0127-3 (3.5 g, 83% yield) as a white solid.

The Synthesis of Methyl 3-bromo-2,6-dichlorobenzoate (0127-4)

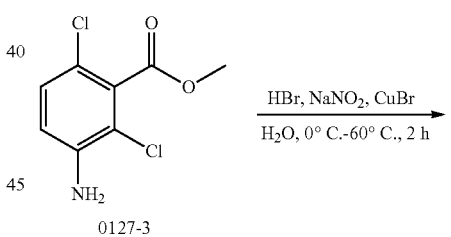

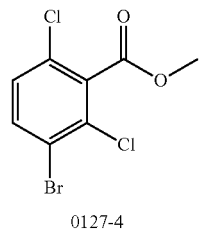

To a solution of 0127-3 (2.0 g, 9.09 mmol) in HBr (33% in acetic acid, 10 mL) and H₂O (10 mL) was added NaNO₂ (63.9 mg, 9.09 mmol) at 0° C., the solution was stirred at 0° C. for 30 min, then CuBr (6.5 g, 45.45 mmol) was added, the solution heated to 60° C. and stirred for 2 h. Cooled to room temperature and filtrated, the filtrate was extracted with DCM (20 mL*2), combined the organic phase and washed with water then brine, dried over Na₂SO₄, concentrated and purified by CC (5% to 10% ethyl acetate in petroleum ether) to get 0127-4 (1.6 g, 62% yield) as a light yellow solid.

The Synthesis of methyl 2,6-dichloro-3-(2,3-dihydro-1H-inden-2-ylamino)benzoate (0127-5)

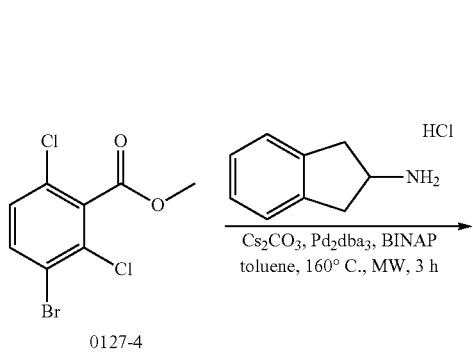

0127-4

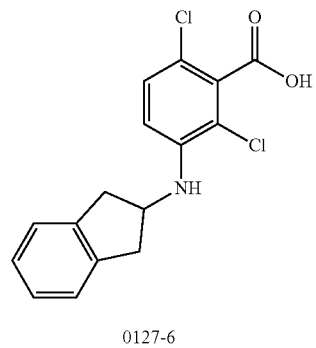

0127-6

To a solution of 0127-5 (210 mg, 0.63 mmol) in DMSO (5 mL) was added t-BuOK (141 mg, 1.26 mmol) and H₂O (0.05 mL), the solution was heated to 80° C. and stirred for 30 min. 1N HCl aq. was added to adjust pH to 1.0, then purified by prep-HPLC to get 0127-6 (110 mg, 55% yield) as a light yellow solid.

The Synthesis of (S)-methyl 2-(2,6-dichloro-3-(2,3-dihydro-1H-inden-2-ylamino)benzamido)-3-(3-((R)-2,3-dihydro-1H-inden-1-yl)ureido)propanoate (0127-7)

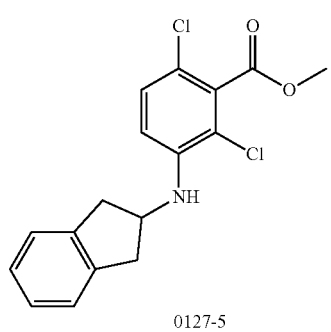

0127-5

To a solution of 0127-4 (500 mg, 1.76 mmol) in toluene (5 mL) was added 2,3-dihydro-1H-inden-2-amine hydrochloride (299 mg, 1.76 mmol), Cs₂CO₃ (1.15 g, 3.52 mmol), Pd₂dba₃ (161 mg, 0.17 mmol) and BINAP (109 mg, 0.17 mmol), the mixture was stirred at 160° C. under microwave for 3 h. Filtrated and concentrated in vacuo, the crude product was purified by CC (5% to 10% ethyl acetate in petroleum ether) to get 0127-5 (210 mg, 35% yield) as a white solid.

The Synthesis of 2,6-dichloro-3-(2,3-dihydro-1H-inden-2-ylamino)benzoic Acid (0127-6)

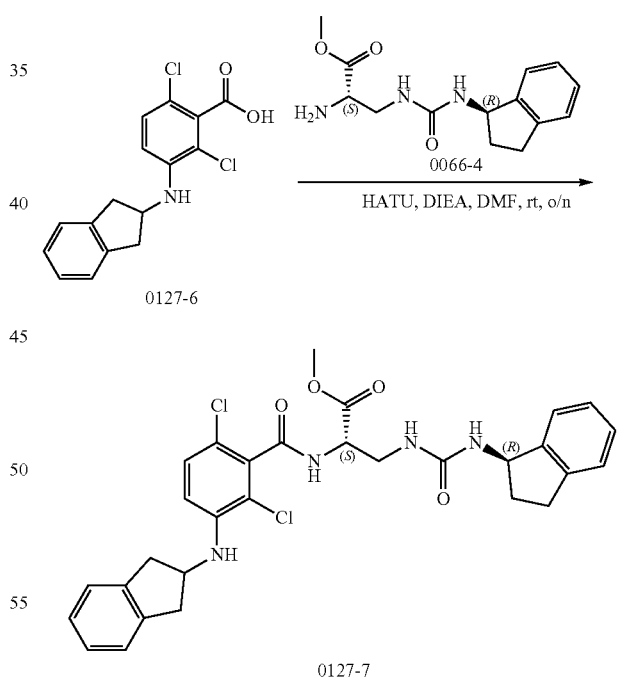

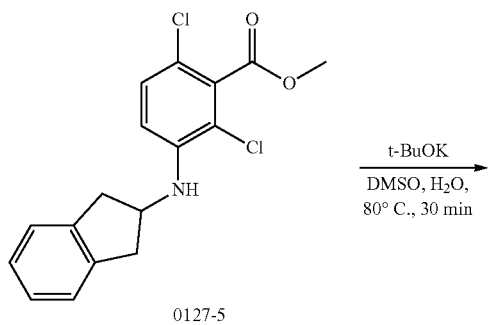

0127-5

To a solution of 0127-6 (100 mg, 0.31 mmol) in DMF (5.0 mL) was added 0066-4 (86 mg, 0.31 mmol) HATU (118 mg, 0.31 mmol) and DIEA (80 mg, 0.62 mmol). The solution was stirred at room temperature for overnight. Poured the solution into water (50 mL), collected the precipitate by filtration to get the crude product, which was further purified by CC (0% to 10% MeOH in DCM) to get 0127-7 (110 mg, 61% yield) as a white solid.

The Synthesis of (S)-2-(2,6-dichloro-3-(2,3-di-hydro-1H-inden-2-ylamino)benzamido)-3-(3-((R)-2,3-dihydro-1H-inden-1-yl)ureido)propanoic Acid (SU15210-0127-01)

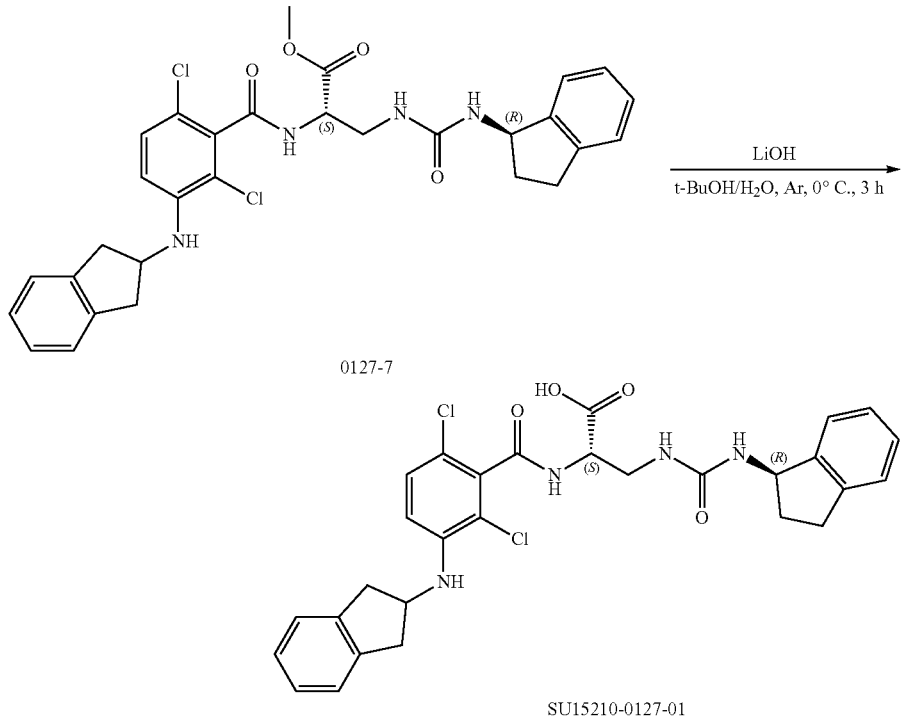

A solution of 0127-7 (50 mg, 0.09 mmol) in t-BuOH (3 mL) and H₂O (1 mL) was added LiOH (4.3 mg, 0.18 mmol) at 0° C. and stirred for 3 h. Acidified by 1N HCl aq. to pH-2, concentrated and purified by prep-HPLC to get SU15210-0127 (22 mg, 45% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 98.06%. Rt=1.905 min; MS Calcd.: 566.2; MS Found: 567.2 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 95.12%. Rt=8.543 min.

¹H NMR (400 MHz, DMSO-d₆) δ 8.62 (br, 1H), 7.10-7.25 (m, 9H), 6.89 (d, J=9.2 Hz, 1H), 6.57 (d, J=8.0 Hz, 1H), 5.88 (br, 1H), 5.56 (d, J=8.0 Hz, 1H), 5.04 (q, J=8.0 Hz, 1H), 4.32-4.37 (m, 2H), 3.44-3.48 (m, 1H), 3.28-3.35 (m, 3H), 2.80-2.97 (m, 3H), 2.50-2.73 (m, 1H), 2.30-2.37 (m, 1H), 1.60-1.69 (m, 1H).

SU15210-0140-01

Synthesis of SU15210-0140-01

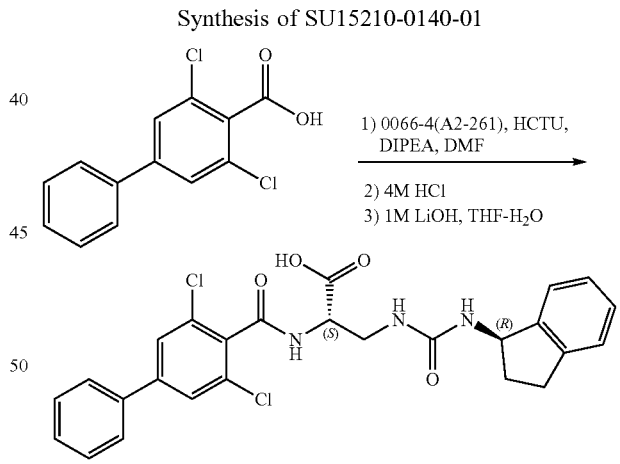

To a stirred solution of Acid (0.5 mmol) and amine (1 eq) in DMF (2 mL) was added DIPEA (2 eq) and HCTU (1 eq). The mixture was stirred for overnight and diluted with ethyl acetate. The organic layer was washed with 1 M HCl, saturated NaHCO₃ and dried over Na₂SO₄. After concentration under reduced pressure, the crude mixture was dissolved in 20% H₂O in THF (3 mL) and 1 M LiOH (1 mL) was added at 0° C. The mixture was stirred for 3 h and neutralized by addition of 1 M HCl. The crude mixture was concentrated and purified by RP-HPLC. ESI-positive; 512.3 (MH+)

SU15210-0145-01

Route for SU15210-0145-01:

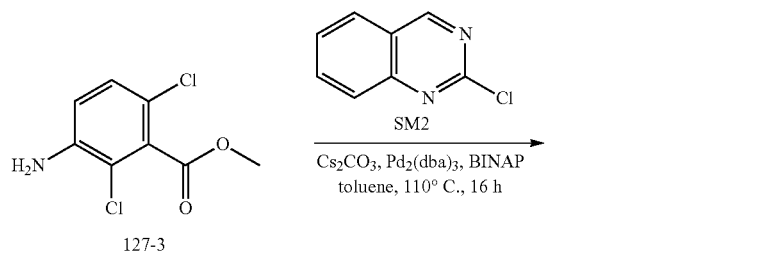
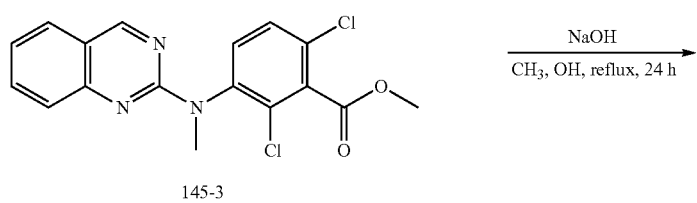
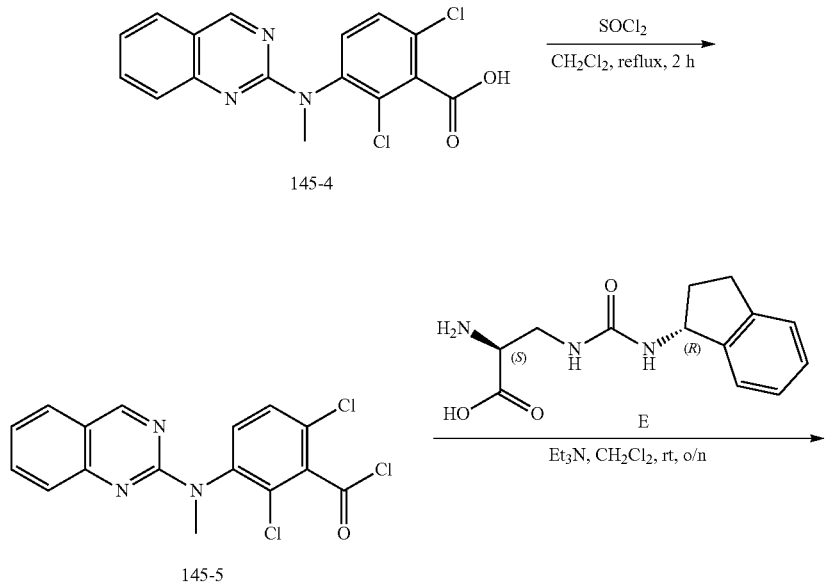
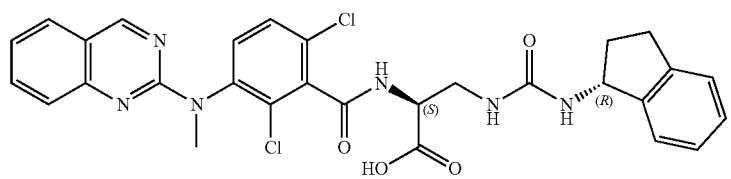
SU15210-0145-01

The Synthesis of Methyl 2,6-dichloro-3-(quinazolin-2-ylamino)benzoate (0145-2)

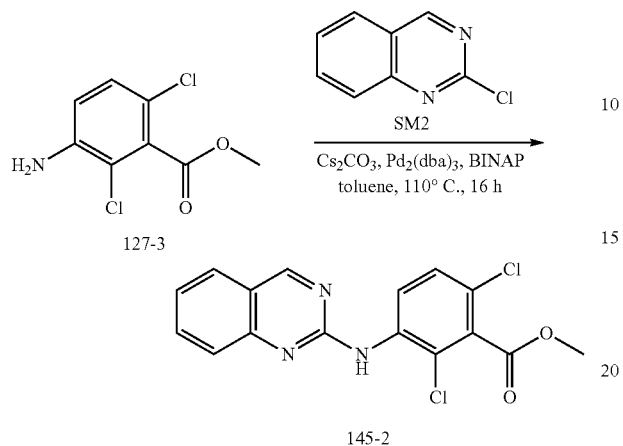

To a solution of 127-3 (440.1 mg, 2.0 mmol) in toluene (20 mL) was added Pd₂(dba)₃ (183.1 mg, 0.2 mmol), BINAP (124.5 mg, 0.2 mmol), Cs₂CO₃ (1.3 g, 4.0 mmol) and SM2 (362.1 mg, 2.2 mmol), the reaction was stirred at 110° C. for 16 h. After the reaction was finished (detected by LCMS), the reaction mixture was concentrated in vacuo, the crude was dissolved in H₂O (30 mL), extracted with EtOAc (30 mL×3), combined the organic layer, dried over anhydrous Na₂SO₄ and filtered, the crude was purified by CC (EtOAc/PE=1:1) to get the product 0145-2 (473.0 mg, 67.9% yield) as a brown solid.

The Synthesis of Methyl 2,6-dichloro-3-(methyl(quinazolin-2-yl)amino)benzoate (0145-3)

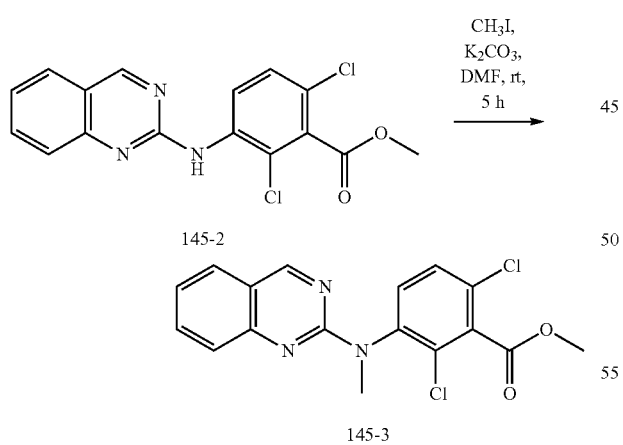

To a solution of methyl 145-2 (473.0 mg, 1.4 mmol) in DMF (10 mL) was added K₂CO₃ (375.5 mg, 2.7 mmol) and CH₃I (289.2 mg, 2.0 mmol), the reaction was stirred at rt for 5 h. After the consumption of starting material (detected by LCMS), the reaction was quenched with H₂O (20 mL), extracted with EtOAc (30 mL×3), combined the organic layer and washed with brine, dried over anhydrous Na₂SO₄, filtered and concentrated, the crude was purified by CC (EtOAc/PE=50%~55%) to give the product 145-3 (490.0 mg, 99.6% yield) as a brown solid.

The Synthesis of 2,6-dichloro-3-(methyl(quinazolin-2-yl)amino)benzoic Acid (0145-4)

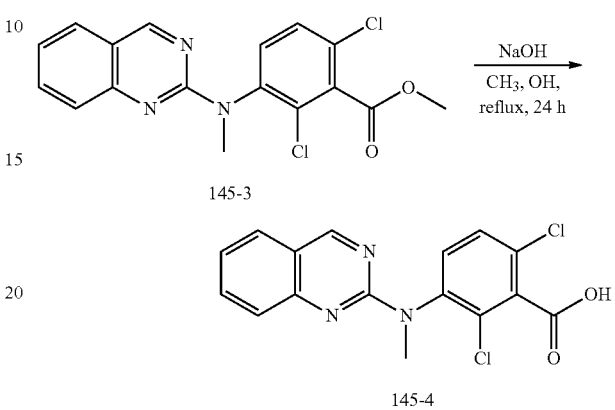

To a solution of methyl 145-3 (463.0 mg, 1.3 mmol) in CH₃OH (10 mL) was added NaOH (255.7 mg, 6.4 mmol), the reaction was stirred at reflux for 24 h. After the reaction was finished (detected by LCMS), the reaction solvent was removed in vacuo, the crude was dissolved with H₂O (20 mL), 1N HCl was added to adjust pH=2~3, extracted with EtOAc (30 mL×3), combined the organic layer, dried over anhydrous Na₂SO₄, filtered and concentrated, the crude 0145-4 (440.0 mg, 98.9% yield) was obtained as white solid and used for next step without further purification.

The Synthesis of 2,6-dichloro-3-(methyl(quinazolin-2-yl)amino)benzoyl chloride (0145-5)

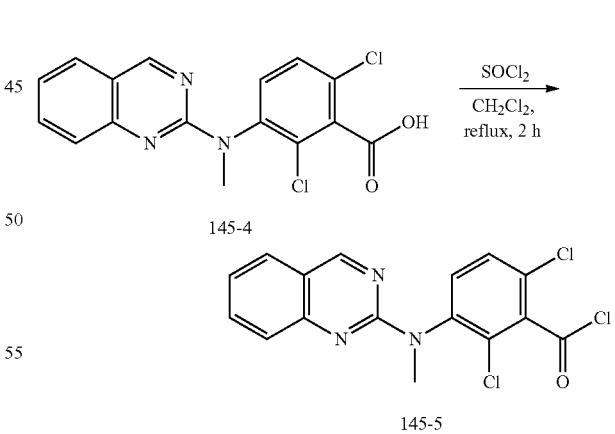

To a solution of 145-4 (174.0 mg, 0.5 mmol) in CH₂Cl₂ (10 mL) was added SOCl₂ (118.9 mg, 1.0 mmol) and DMF (0.05 mL), the reaction was stirred at 45° C. for 2 h. After the consumption of starting material (detected by LCMS), the reaction mixture was concentrated in vacuo, the crude 145-5 (183.0 mg, 99.9% yield) was obtained as a white solid and used for next step without further purification.

The Synthesis of (S)-2-(2,6-dichloro-3-(methyl(quinazolin-2-yl)amino)benzamido)-3-(3-((R)-2,3-dihydro-1H-inden-1-yl)ureido)propanoic Acid (SU15210-0145-01)

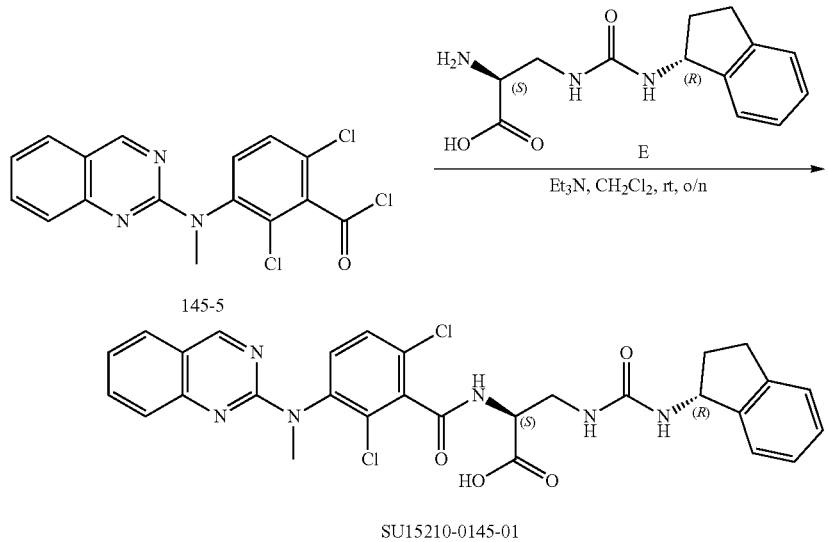

To a solution of E (132.6 mg, 0.5 mmol) in DCM (5 mL) was added Et$_3$N (151.8 mg, 1.5 mmol) and 145-5 (183.3 mg, 0.5 mmol), the reaction was stirred at rt for overnight. After the consumption of starting material (detected by LCMS), the reaction was concentrated in vacuo, the crude was dissolved with H$_2$O (5 mL), 1N HCl was added to adjust pH=2~3, the mixture was purified directly by prep-HPLC to get the product SU15210-0145-01 (120.5 mg, 40.5% yield) as a white solid.

Agilent LCMS 1200-6110, Column: Waters X-Bridge C18 (50 mm *4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity is 100.00%. Rt=1.681 min; MS Calcd.: 592.0; MS Found: 593.2 [M+H]$^+$.

Agilent HPLC 1200; Column: L-column2 ODS (150 mm *4.6 mm*5.0 m); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 100.00%. Rt=7.938 min.

$^1$H NMR (400 MHz, DMSO-d$_6$) δ 12.74 (brs, 1H), 8.96-9.13 (m, 2H), 7.75-7.86 (m, 2H), 7.54-7.64 (m, 3H), 7.33 (t, J=8.0 Hz, 1H), 7.05-7.17 (m, 4H), 6.55 (d, J=8.4 Hz, 1H), 5.83 (s, 1H), 5.04 (q, J=8.0 Hz, 1H), 4.42 (q, J=6.0 Hz, 1H), 3.48-3.54 (m, 1H), 3.44 (s, 3H), 3.31-3.35 (m, 1H), 2.64-2.83 (m, 2H), 2.27-2.31 (m, 1H), 1.57-1.66 (m, 1H).

SU15210-0154-01

Route for SU15210-0154-01:

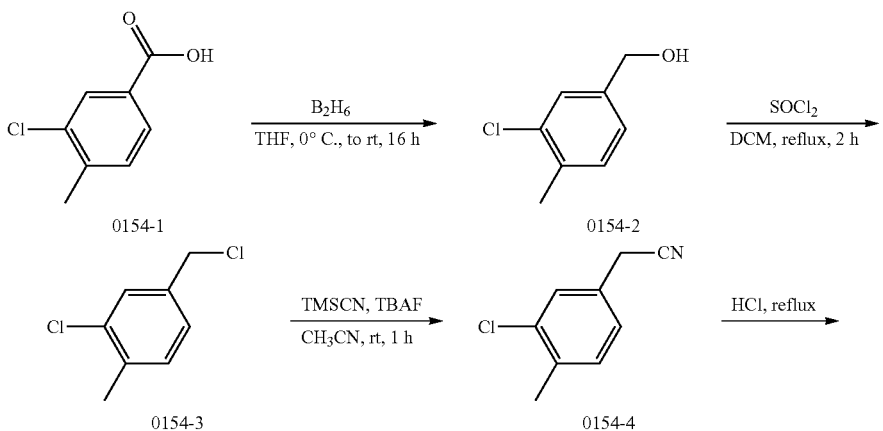

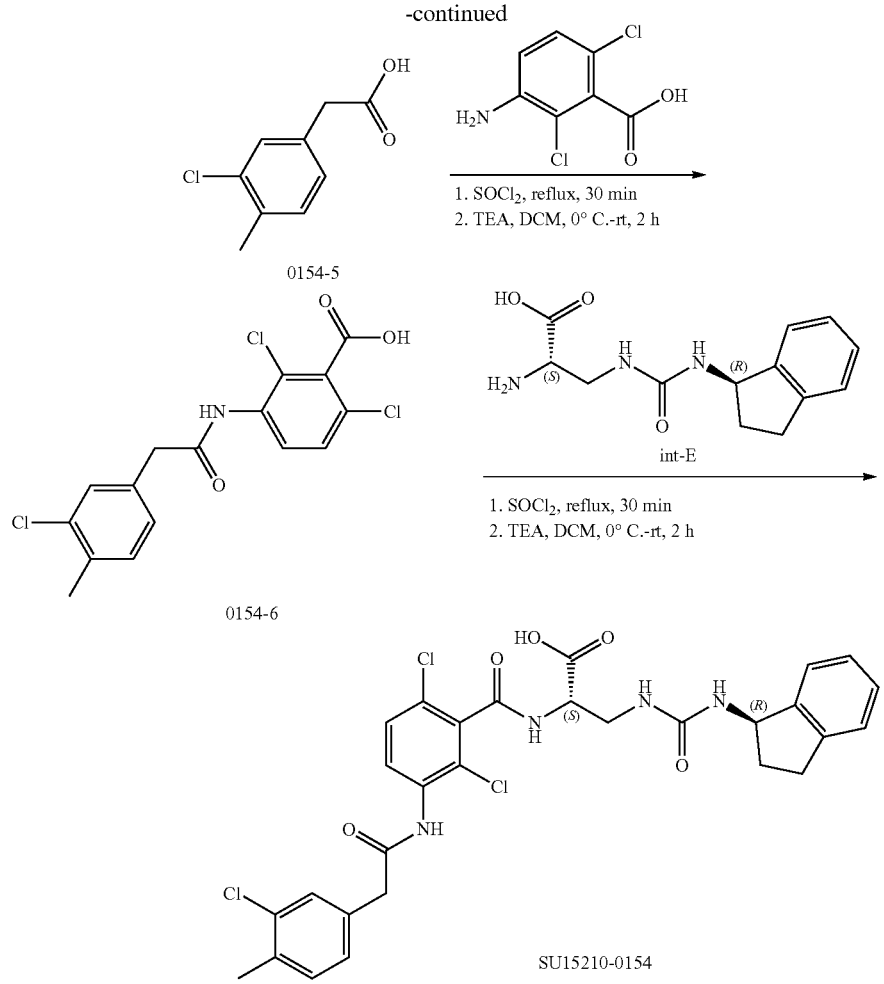

The Synthesis of (3-chloro-4-methylphenyl)methanol (0154-2)

The synthesis of 2-chloro-4-(chloromethyl)-1-methylbenzene (0154-3).

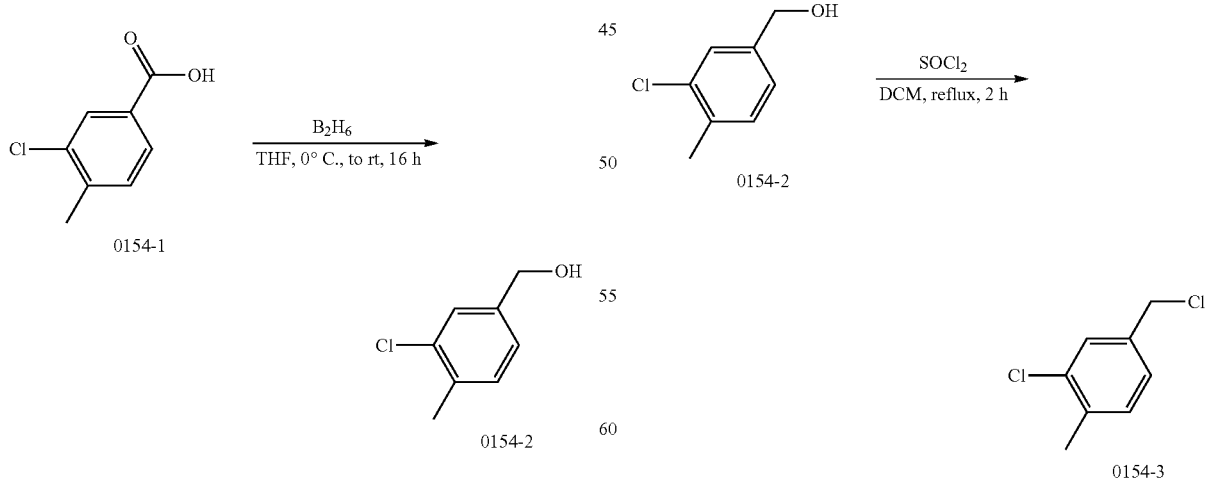

A solution of 0154-1 (5.0 g, 29.31 mmol) in $B_2H_6$ (1 M in THF, 50 mL) was stirred at room temperature for 16 h. Concentrated and purified by CC (10% to 30% ethyl acetate in petroleum ether) to get 0154-2 (3.5 g, 76% yield) as a white solid.

To a solution of 0154-2 (2.0 g, 12.77 mmol) in DCM (20 mL) was added $SOCl_2$ (5 mL), the solution was stirred at reflux for 2 h, concentrated to give 0154-3 (2.3 g, 100% yield) as a white solid.

The Synthesis of 2-(3-chloro-4-methylphenyl)acetonitrile (0154-4)

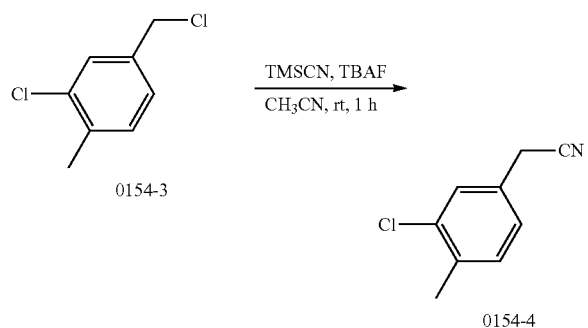

To a solution of 0154-3 (2.3 g, 12.77 mmol) in CH₃CN (30 mL) was added TMSCN (6.4 g, 63.85 mmol) and TBAF (1 M in THF, 13 mL), the solution was stirred at room temperature for 1 h. Water (30 mL) was added, extracted with EA (20 mL*3), combined the organic phase, washed with water then brine, dried over Na₂SO₄, concentrated and purified by CC (10% to 20% ethyl acetate in petroleum ether) to get 0154-4 (1.6 g, 62% yield) as a brown solid.

The Synthesis of 2-(3-chloro-4-methylphenyl)acetic Acid (0154-5)

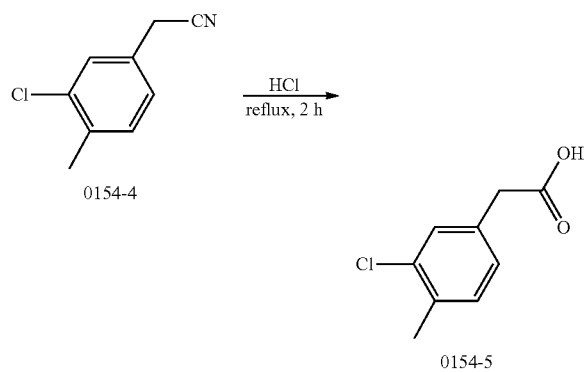

A solution of 0154-4 (1.6 g, 9.66 mmol) in HCl (37%, 10 mL) was stirred at reflux for 2 h, cooled to room temperature and collect the precipitate by filtration, purified by prep-HPLC to give 0154-5 (0.9 g, 50% yield) as a white solid.

The Synthesis of 2,6-dichloro-3-(2,3-dihydro-1H-inden-2-ylamino)benzoic Acid (0154-6)

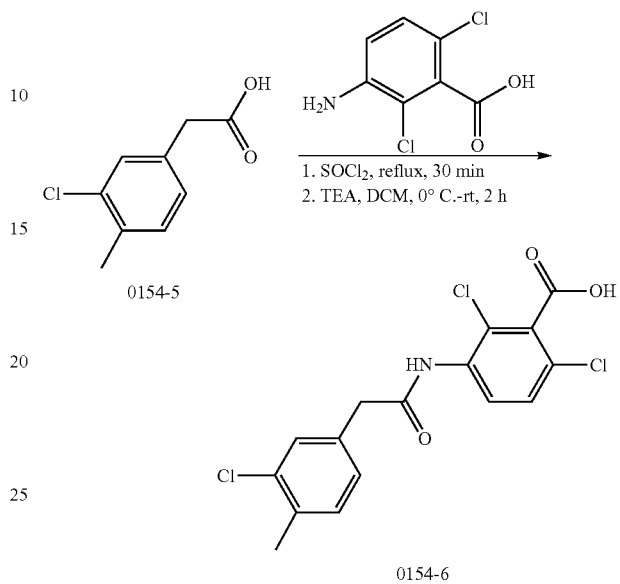

A solution of 0154-5 (200 mg, 1.08 mmol) in SOCl₂ (5 mL) was stirred at reflux for 30 min, concentrated to remove the extra SOCl₂, the residual was then added to a solution of 3-amino-2,6-dichlorobenzoic Acid (223 mg, 1.08 mmol) and TEA (328 mg, 3.24 mmol) in DCM (10 mL) at 0° C., the reaction mixture was then warmed to room temperature and stirred for 2 h. 1N HCl aq. was added to adjust pH to 1.0, separated the organic phase and washed with water then brine, dried over Na₂SO₄, concentrated and purified by prep-HPLC to give 0154-6 (220 mg, 55% yield) as a white solid.

The Synthesis of (S)-2-(2,6-dichloro-3-(2-(3-chloro-4-methylphenyl)acetamido)benzamido)-3-(3-((R)-2,3-dihydro-1H-inden-1-yl)ureido)propanoic Acid (SU15210-0154-01)

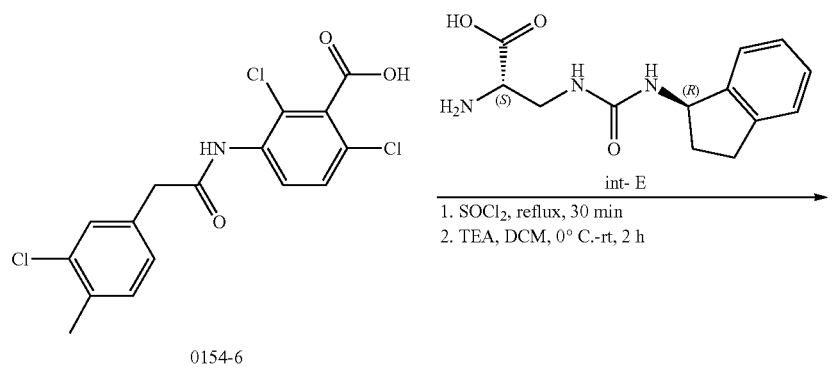

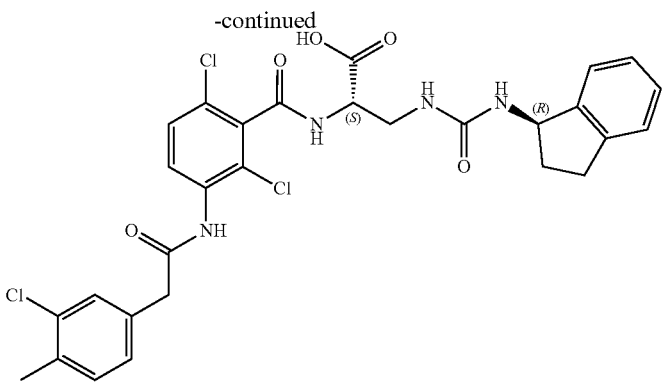

SU15210-0154

A solution of 0154-6 (100 mg, 0.27 mmol) in SOCl$_2$ (5 mL) was stirred at reflux for 30 min, concentrated to remove the extra SOCl$_2$, the residual was then added to a solution of int-E (71 mg, 0.27 mmol) and TEA (82 mg, 0.81 mmol) in DCM (10 mL) at 0° C., the solution was then warmed to room temperature and stirred for 2 h. 1N HCl aq. was added to pH 1, separated the organic phase and washed with water then brine, dried over Na$_2$SO$_4$, concentrated and purified by prep-HPLC to give SU15210-0154-01 (35 mg, 21% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.704 min; MS Calcd.: 616.1; MS Found: 617.1 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 99.77%. Rt=8.089 min.

$^1$H NMR (400 MHz, DMSO-d$_6$) δ 9.83 (s, 1H), 8.86 (br, 1H), 7.69 (d, J=8.8 Hz, 1H), 7.43 (d, J=8.0 Hz, 1H), 7.38 (d, J=1.2 Hz, 1H), 7.27 (d, J=7.6 Hz, 1H), 7.11-7.20 (m, 6H), 6.56 (d, J=8.4 Hz, 1H), 5.85 (t, J=5.2 Hz, 1H), 5.05 (q, J=8.0 Hz, 1H), 4.41 (q, J=6.4 Hz, 1H), 3.45-3.55 (m, 2H), 3.29-3.36 (m, 1H), 2.81-2.87 (m, 1H), 2.70-2.77 (m, 1H), 2.30-2.37 (m, 1H), 2.27 (m, 3H), 1.61-1.67 (m, 1H).

SU15210-0155-01

Route for SU15210-0155-01:

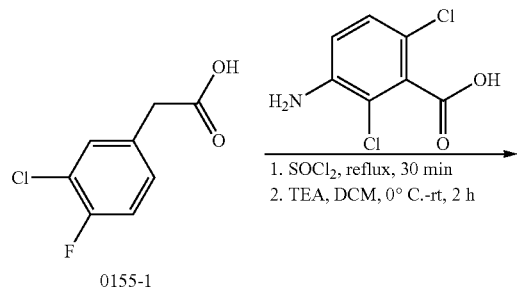

0155-1

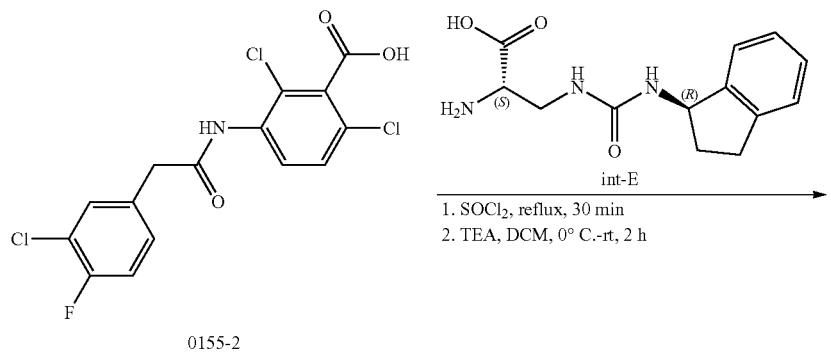

0155-2

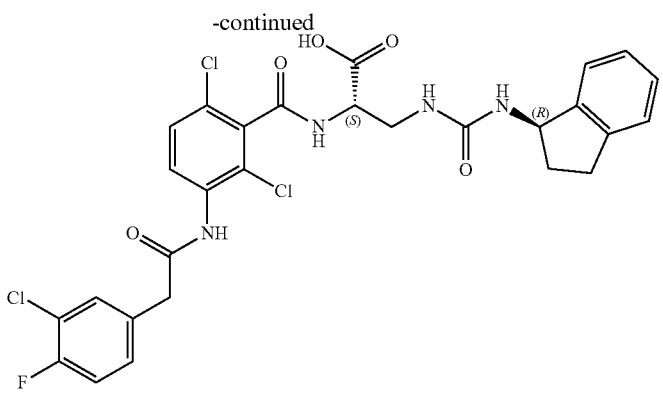

SU15210-0155-01

The Synthesis of 2,6-dichloro-3-(2-(3-chloro-4-fluorophenyl)acetamido)benzoic Acid (0155-2)

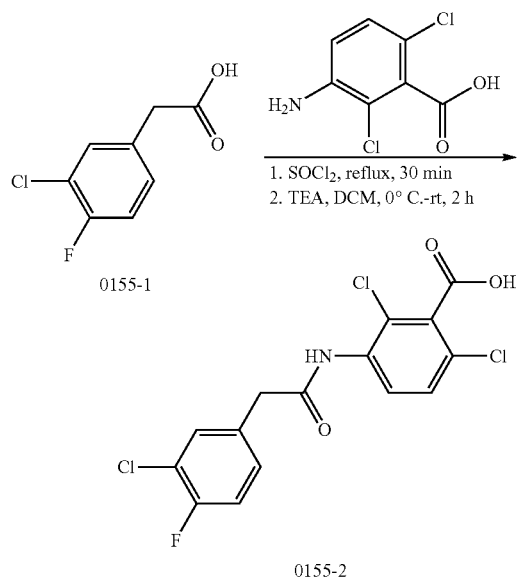

A solution of 0155-1 (500 mg, 2.65 mmol) in SOCl$_2$ (10 mL) was stirred at reflux for 30 min, concentrated to remove the extra SOCl$_2$, the residual was then added to a solution of 3-amino-2,6-dichlorobenzoic Acid (546 mg, 2.65 mmol) and TEA (803 mg, 7.95 mmol) in DCM (10 mL) at 0° C., the solution was then warmed to room temperature and stirred for 2 h. 1N HCl aq. was added to pH 1, separated the organic phase and washed with water then brine, dried over Na$_2$SO$_4$, concentrated and purified by prep-HPLC to give 0155-2 (300 mg, 30% yield) as a white solid.

The Synthesis of (S)-2-(2,6-dichloro-3-(2-(3-chloro-4-fluorophenyl)acetamido)benzamido)-3-(3-((R)-2,3-dihydro-1H-inden-1-yl)ureido)propanoic Acid (SU15210-0155-01)

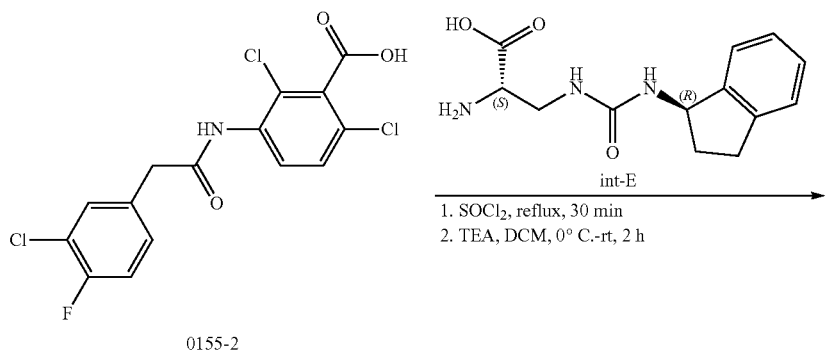

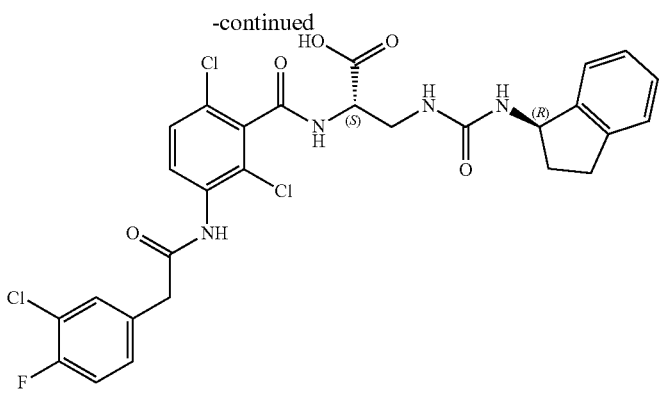

SU15210-0155-01

A solution of 0155-2 (100 mg, 0.27 mmol) in SOCl$_2$ (5 mL) was stirred at reflux for 30 min, concentrated to remove the extra SOCl$_2$, the residual was then added to a solution of int-E (71 mg, 0.27 mmol) and TEA (82 mg, 0.81 mmol) in DCM (10 mL) at 0° C., the solution was then warmed to room temperature and stirred for 2 h. 1N HCl aq. was added to pH 1, separated the organic phase and washed with water then brine, dried over Na$_2$SO$_4$, concentrated and purified by prep-HPLC to give SU15210-0155-01 (21 mg, 13% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.781 min; MS Calcd.: 620.1; MS Found: 621.1 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 99.90%. Rt=8.654 min.

$^1$H NMR (400 MHz, DMSO-d$_6$) δ 12.66 (br, 1H), 9.89 (s, 1H), 9.02 (d, J=7.2 Hz, 1H), 7.72 (d, J=8.8 Hz, 1H), 7.56 (d, J=7.2 Hz, 1H), 7.46 (d, J=8.8 Hz, 1H), 7.32-7.40 (m, 2H), 7.12-7.23 (m, 4H), 6.55 (d, J=8.4 Hz, 1H), 5.86 (t, J=5.6 Hz, 1H), 5.07 (q, J=8.0 Hz, 1H), 4.49 (q, J=7.2 Hz, 1H), 3.77 (s, 2H), 3.50-3.57 (m, 1H), 3.34-3.39 (m, 1H), 2.83-2.90 (m, 1H), 2.70-2.79 (m, 1H), 2.32-2.42 (m, 1H), 1.63-1.71 (m, 1H).

SU15210-0156-01

Route for SU15210-0156-01:

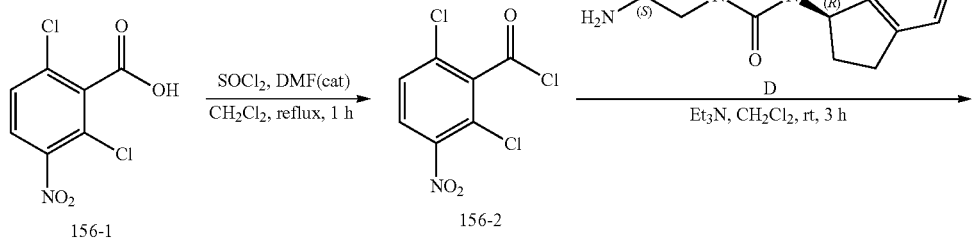

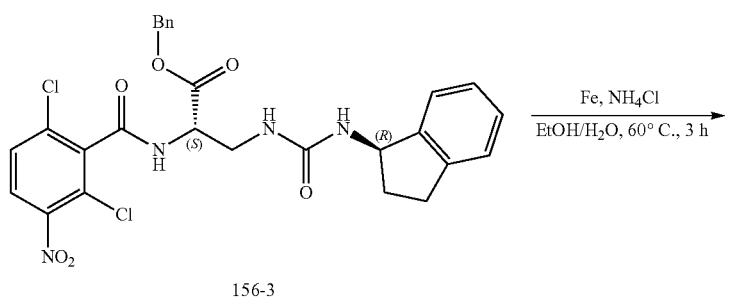

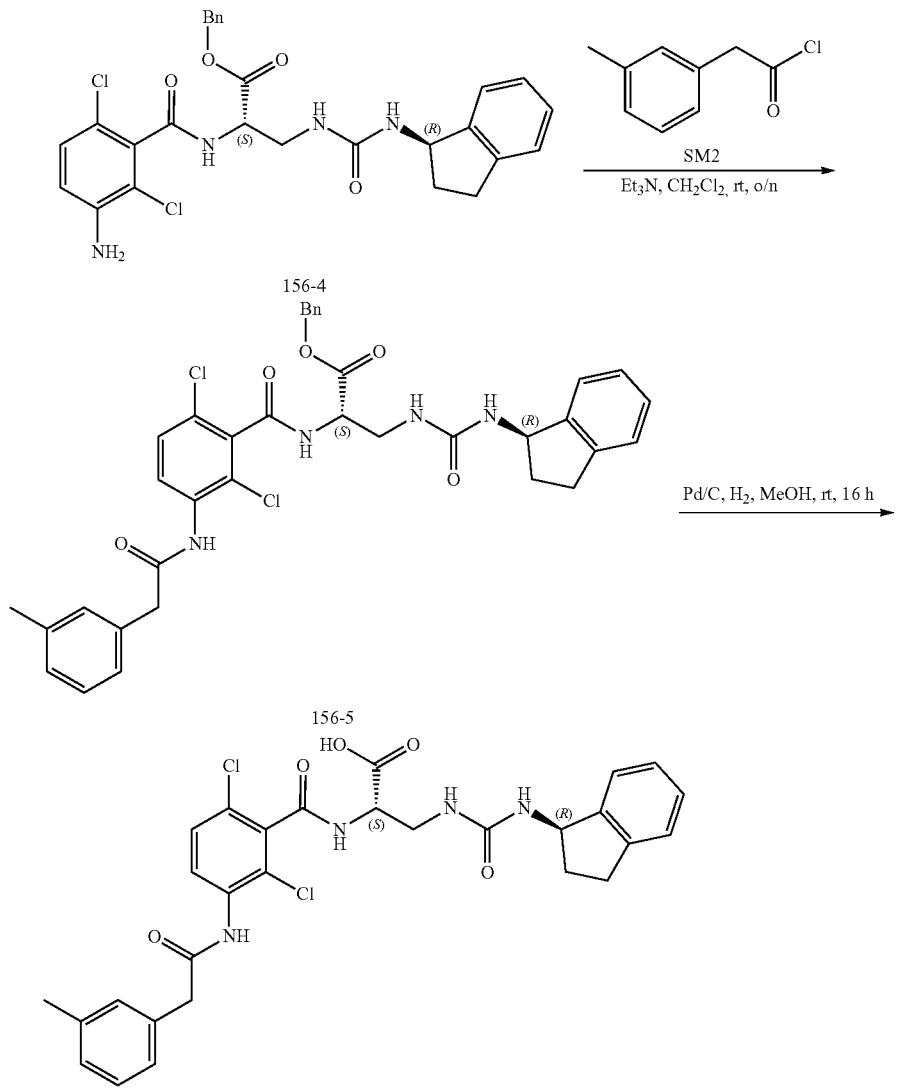

The Synthesis of 2,6-dichloro-3-nitrobenzoyl Chloride (0156-2)

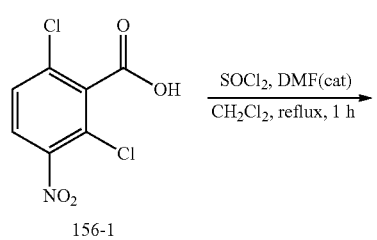

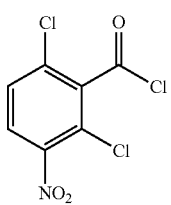

To a solution of 156-1 (236.0 mg, 1.0 mmol) in CH$_2$Cl$_2$ (10 mL) was dropwised SOCl$_2$ (178.5 mg, 1.5 mmol) and DMF (0.05 mL), the reaction was stirred at 45° C. for 1 h. After the consumption of starting material (detected by LCMS), the reaction mixture was concentrated in vacuo, the crude 156-2 (250.0 mg, 99.2% yield) was obtained as a yellow solid and used directly for next step without further purification.

The Synthesis of (S)-benzyl 2-(2,6-dichloro-3-nitrobenzamido)-3-(3-((R)-2,3-dihydro-1H-inden-1-yl)ureido)propanoate (0156-3)

The Synthesis of (S)-benzyl 2-(3-amino-2,6-dichlorobenzamido)-3-(3-((R)-2,3-dihydro-1H-inden-1-yl)ureido)propanoate (0156-4)

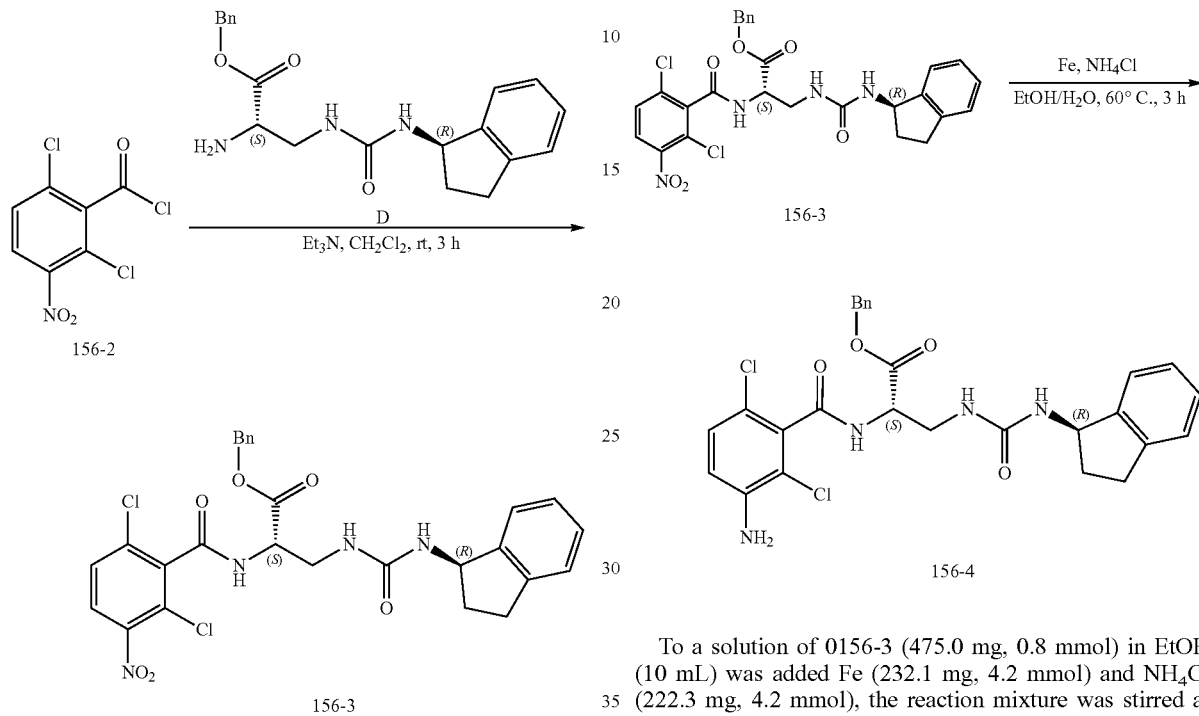

To a solution of D (353.4 mg, 1.0 mmol) in CH$_2$Cl$_2$ (15 mL) was added Et$_3$N (303.6 mg, 3.0 mmol) and 156-2 (254.5 mg, 1.0 mmol), the reaction was stirred at room temperature for 3 h. After the consumption of starting material (detected by LCMS), the reaction was quenched with H$_2$O (20 mL), extracted with CH$_2$Cl$_2$ (20 mL×3), combined the organic layer and washed with brine, dried over anhydrous Na$_2$SO$_4$, filtered and concentrated, the crude was purified by CC (EtOAc/PE=50%~60%) to get the product 156-3 (470.0 mg, 82.3% yield) as a yellow solid.

To a solution of 0156-3 (475.0 mg, 0.8 mmol) in EtOH (10 mL) was added Fe (232.1 mg, 4.2 mmol) and NH$_4$Cl (222.3 mg, 4.2 mmol), the reaction mixture was stirred at 60° C. for 3 h. After the consumption of starting material (detected by LCMS), the reaction mixture was filtered, the filtrate was concentrated in vacuo, the crude was dissolved with H$_2$O (20 mL), extracted with CH$_2$Cl$_2$ (25 mL×3), combine the organic layer and washed with brine, the organic layer was dried over anhydrous Na$_2$SO$_4$, filtered and concentrated to get the product 0156-4 (108.0 mg, 24.0% yield) as a white solid.

The Synthesis of (S)-benzyl 2-(2,6-dichloro-3-(2-(m-tolyl)acetamido)benzamido)-3-(3-((R)-2,3-dihydro-1H-inden-1-yl)ureido)propanoate (0156-5)

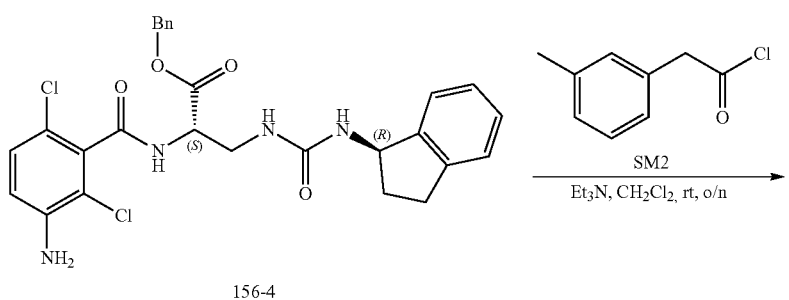

-continued

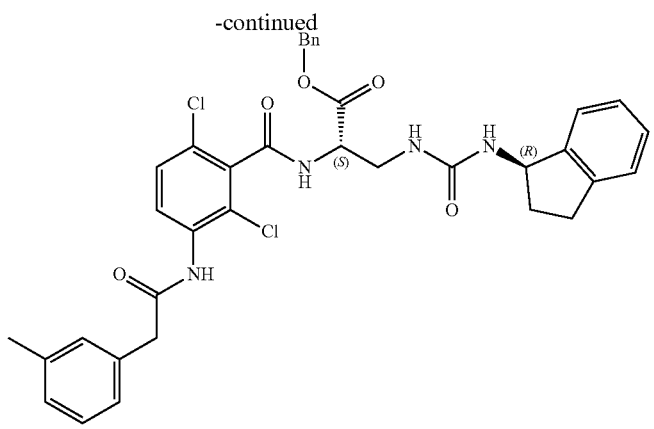

156-5

To a solution of 156-4 (108.0 mg, 0.2 mmol) in CH$_2$Cl$_2$ (5 mL) was added Et$_3$N (60.6 mg, 0.6 mmol) and SM2 (50.5 mg, 0.3 mmol), the reaction mixture was stirred at rt for overnight. After the consumption of starting material (detected by LCMS), the reaction was quenched with H$_2$O (20 mL), extracted with CH$_2$Cl$_2$ (25 mL×3), combined the organic layer, dried over anhydrous Na$_2$SO$_4$, filtered and concentrated, the crude was purified by CC (MeOH/DCM=5%) to get the product 0156-5 (110.0 mg, 81.9% yield) as a white solid.

The Synthesis of (S)-2-(2,6-dichloro-3-(2-m-tolylacetamido)benzamido)-3-(3-((R)-2,3-dihydro-1H-inden-1-yl)ureido)propanoic Acid (SU15210-0156-01)

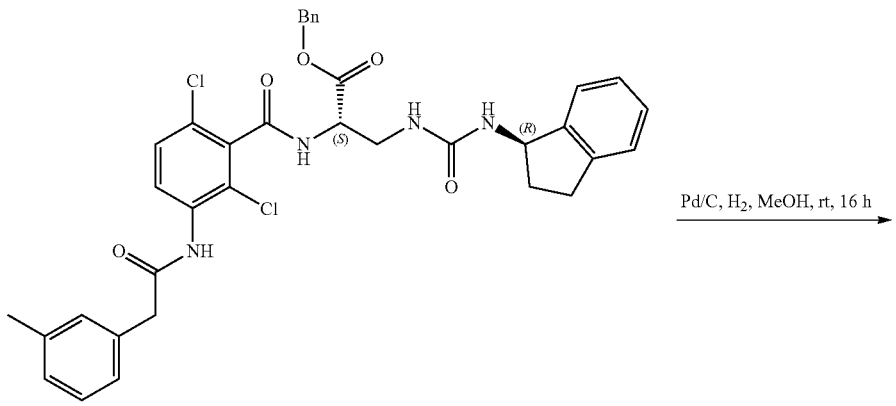

156-5

Pd/C, H$_2$, MeOH, rt, 16 h

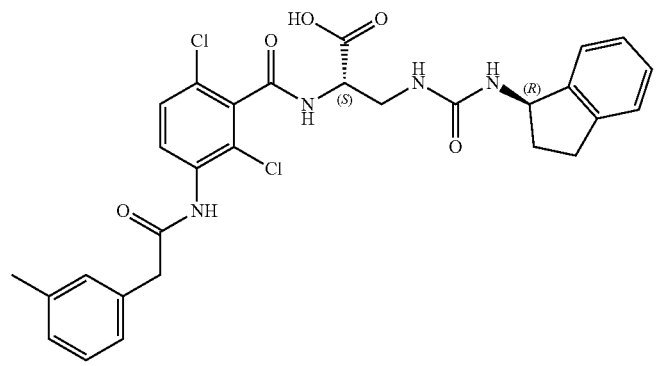

SU15210-0156

To a solution of 156-5 (110.0 mg, 0.2 mmol) in CH$_3$OH (10 mL) was added Pd/C (55.0 mg, 0.5 mmol), the reaction was stirred at rt under H$_2$ atmosphere for 16 h. After the consumption of starting material (detected by LCMS), the reaction mixture was filtered, the filtrate was concentrated in vacuo, the crude was purified by prep-HPLC to give the product SU15210-0156-01 (12.6 mg, 13.2% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 99.04%, Rt=1.638 min; MS Calcd.: 582.0; MS Found: 583.1 [M+H]$^+$.

HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 100.00%, Rt=7.571 min.

$^1$H NMR (400 MHz, DMSO-d$_6$) δ 9.74 (s, 1H), 8.57 (s, 1H), 7.72 (d, J=8.8 Hz, 1H), 7.42 (d, J=8.4 Hz, 1H), 7.11-7.20 (m, 7H), 7.01 (d, J=7.6 Hz, 1H), 6.62 (d, J=8.4 Hz, 1H), 5.90 (s, 1H), 5.05 (q, J=7.6 Hz, 1H), 4.26 (s, 1H), 3.69 (s, 2H), 3.37-3.40 (m, 2H), 2.64-2.88 (m, 2H), 2.29-2.40 (m, 1H), 2.26 (s, 3H), 1.60-1.70 (m, 1H).

SU15210-0158-01

Route for SU15210-0158-01:

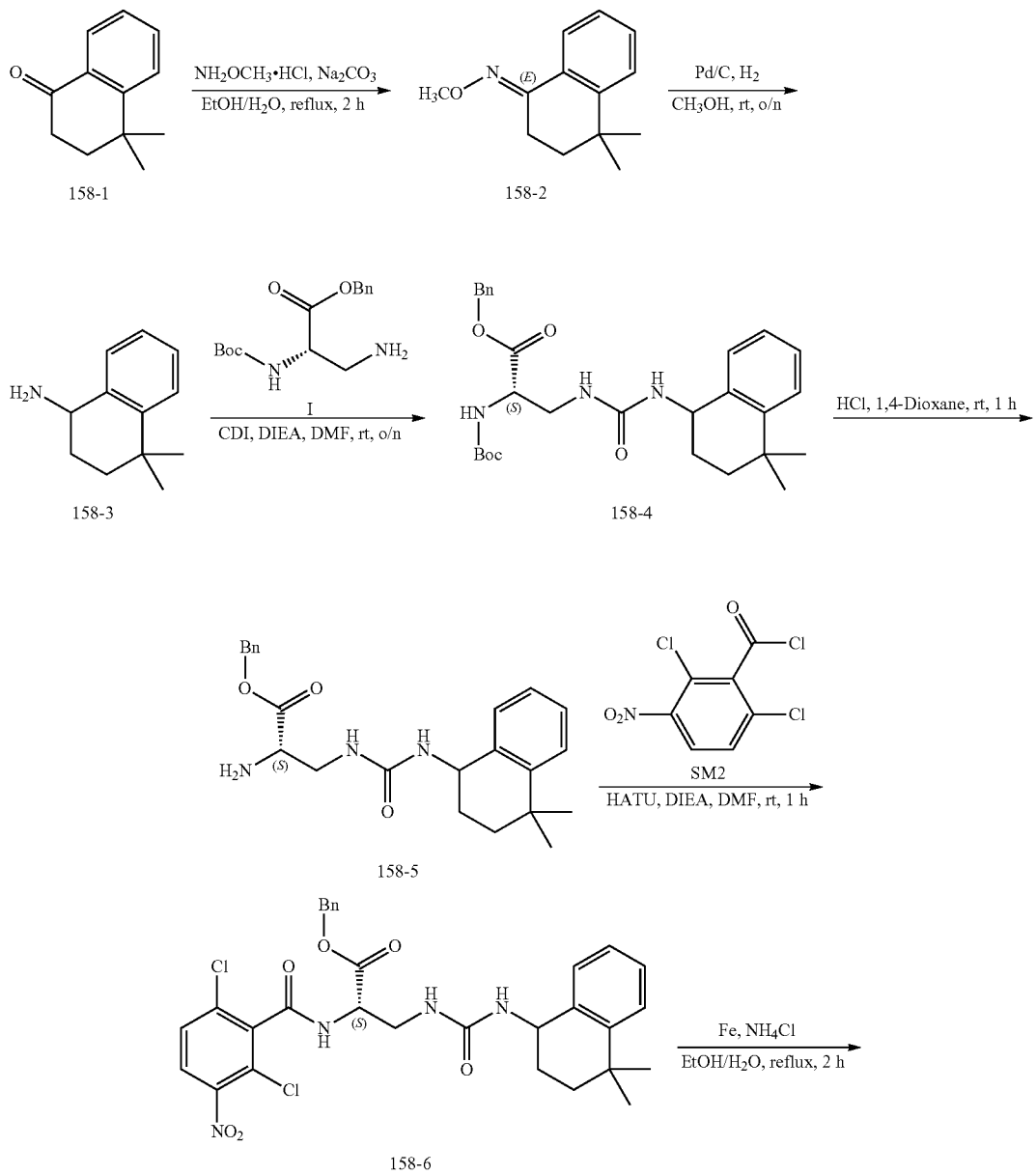

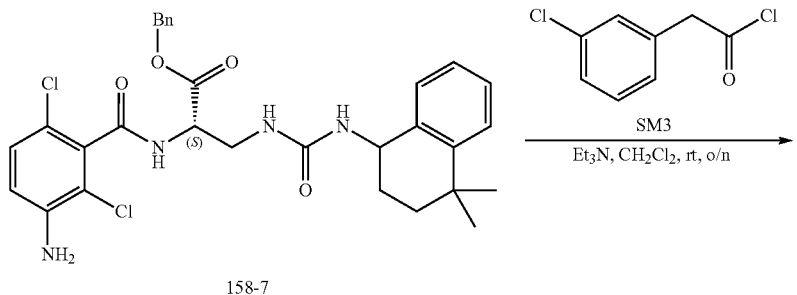
158-7
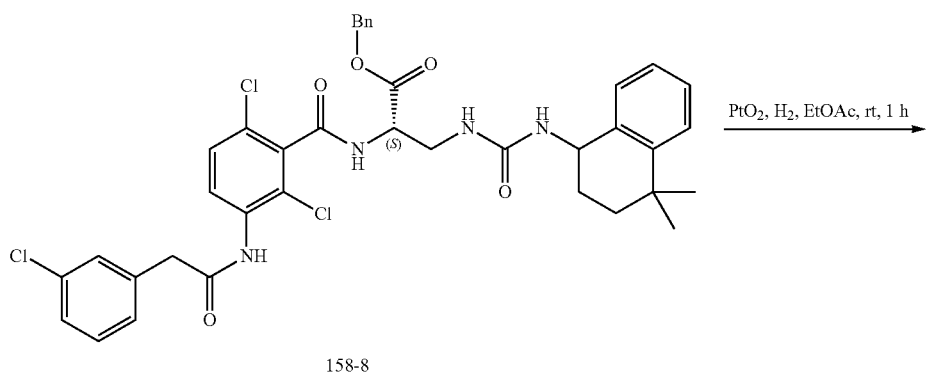
158-8
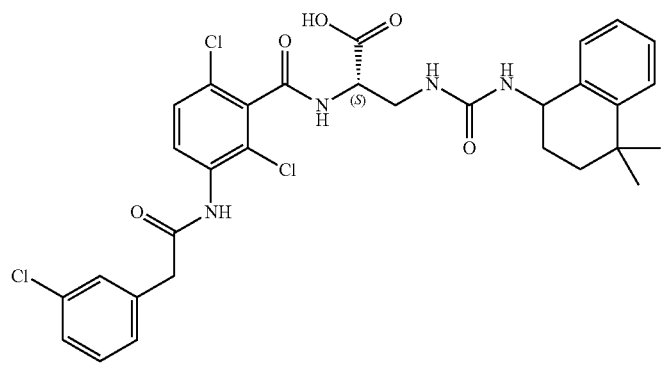
SU15210-0158
The Synthesis of (E)-4,4-dimethyl-3,4-dihydronaphthalen-1(2H)-one O-methyl oxime (0158-2)
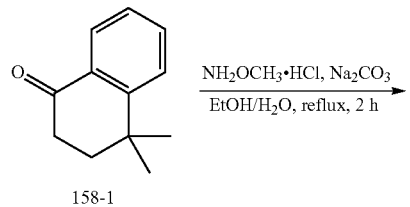
-continued
158-2
To a solution of 158-1 (522.7 mg, 3.0 mmol) in EtOH (10 mL) and H$_2$O (2 mL) was added O-methylhydroxylamine (501.1 mg, 6.0 mmol) and Na$_2$CO$_3$ (318.0 mg, 3.0 mmol), the reaction was stirred at reflux for 2 h. After the consumption of starting material (detected by LCMS), the reaction was concentrated in vacuo, the crude was dissolved with H₂O (20 mL), extracted with EtOAc (25 mL×3), combined the organic layer, dried over anhydrous Na₂SO₄, filtered and concentrated, the crude was purified by CC (EtOAc/PE=15%) to get the product 158-2 (609.0 mg, 99.8% yield) as a white solid.

The Synthesis of 4,4-dimethyl-1,2,3,4-tetrahydronaphthalen-1-amine (158-3)

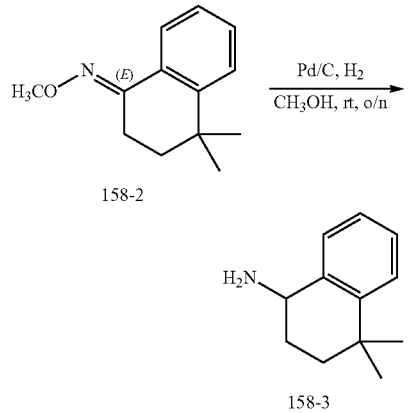

To a solution of 158-2 (609.0 mg, 3.0 mmol) in CH₃OH (20 mL) was added Pd/C (36.4 mg, 0.3 mmol), the reaction was stirred under H₂ atmosphere and at rt for 16 h. After the consumption of starting material (detected by LCMS), the reaction was filtered, the filtrate was concentrated to get the product 158-3 (520.0 mg, 99.0% yield) as brown oil.

The Synthesis of (2S)-benzyl 2-(tert-butoxycarbonylamino)-3-(3-(4,4-dimethyl-1,2,3,4-tetrahydronaphthalen-1-yl)ureido)propanoate (0158-4)

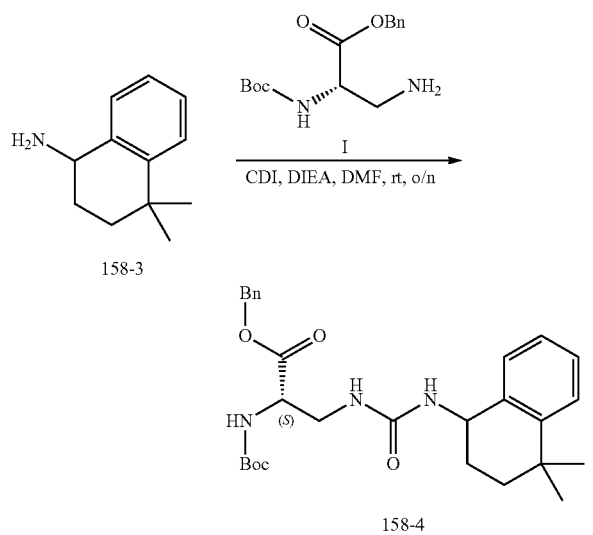

To a solution of 158-3 (262.9 mg, 1.5 mmol) in DMF (5 mL) was added DIPEA (387.7 mg, 3.0 mmol) and CDI (267.6 mg, 1.7 mmol), the mixture was stirred at rt for 1 h. After the reaction was finished (detected by LCMS), I (441.5 mg, 1.5 mmol) was added into the mixture, the reaction was stirred at rt for 16 h. After the reaction was finished (detected by LCMS), the mixture was purified directly by prep-HPLC to get the product 158-4 (390.0 mg, 52.5% yield) as brown oil.

The Synthesis of (2S)-benzyl 2-amino-3-(3-(4,4-dimethyl-1,2,3,4-tetrahydronaphthalen-1-yl)ureido)propanoate (0158-5)

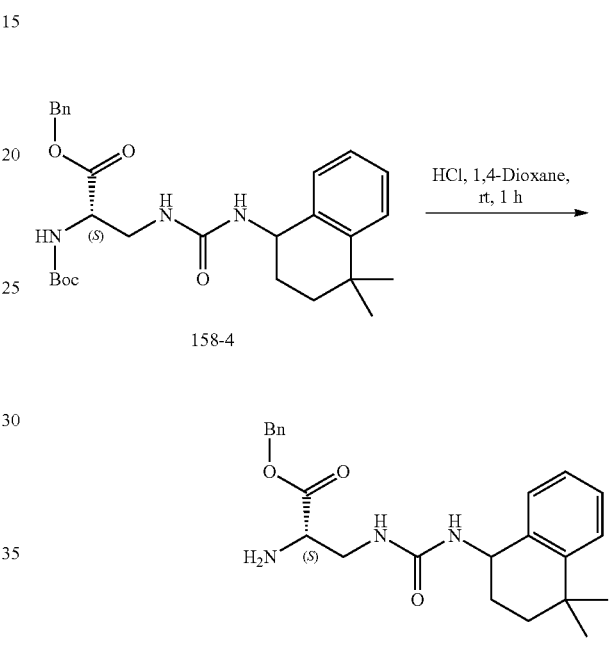

To a solution of 158-4 (390.0 mg, 0.8 mmol) in 1,4-Dioxane (5 mL) was dropwised HCl (4 M in 1,4-Dioxane), the reaction was stirred at rt for 1 h. After the consumption of starting material (detected by LCMS), the reaction mixture was concentrated to get the product 158-5 (310.0 mg, 99.61% yield) as a white solid.

The Synthesis of (2S)-benzyl 2-(2,6-dichloro-3-nitrobenzamido)-3-(3-(4,4-dimethyl-1,2,3,4-tetrahydronaphthalen-1-yl)ureido)propanoate (0158-6)

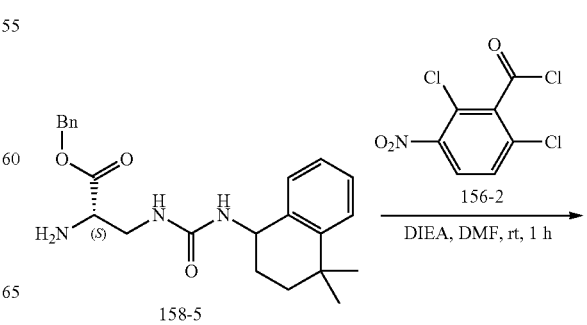

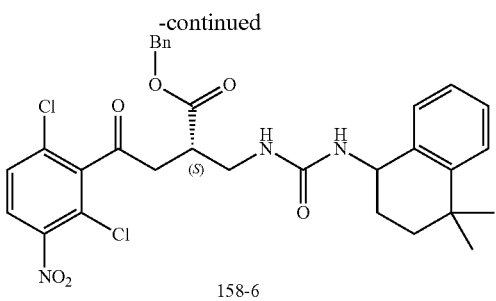

158-6

To a solution of 158-5 (310.0 mg, 0.8 mmol) in DMF (10 mL) was added DIEA (238.0 mg, 2.4 mmol) and 156-2 (299.2 mg, 1.2 mmol), the reaction was stirred at rt for 1 h. After the consumption of starting material (detected by LCMS), the reaction mixture was quenched with $H_2O$ (25 mL), extracted with $CH_2Cl_2$ (25 mL×3), combined the organic layer, dried over anhydrous $Na_2SO_4$, filtered and concentrated, the crude was purified by CC (MeOH/$CH_2Cl_2$=5%) to give the product 158-6 (470.0 mg, 97.7% yield) as yellow solid.

The Synthesis of (2S)-benzyl 2-(3-amino-2,6-dichlorobenzamido)-3-(3-(4,4-dimethyl-1,2,3,4-tetrahydronaphthalen-1-yl)ureido)propanoate (0158-7)

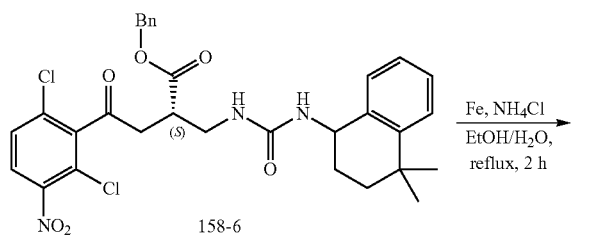

158-6 → Fe, NH4Cl, EtOH/H2O, reflux, 2 h

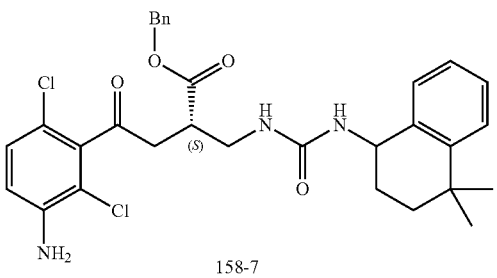

158-7

To a solution of 158-6 (510.0 mg, 0.8 mmol) in EtOH (10 mL) and $H_2O$ (2 mL) was added Fe (232.0 mg, 4.2 mmol) and $NH_4Cl$ (222.0 mg, 4.2 mmol), the reaction mixture was stirred at reflux for 2 h. After the consumption of starting material (detected by LCMS), the reaction mixture was filtered, the filtrate was concentrated in vacuo, the crude was dissolved with $H_2O$ (20 mL), extracted with $CH_2Cl_2$ (30 mL×3), combined the organic layer, dried over anhydrous $Na_2SO_4$, filtered and concentrated to get the product 158-7 (480.0 mg, 98.9% yield) as a white solid.

The Synthesis of (2S)-benzyl 2-(2,6-dichloro-3-(2-(3-chlorophenyl)acetamido)benzamido)-3-(3-(4,4-dimethyl-1,2,3,4-tetrahydronaphthalen-1-yl)ureido)propanoate (0158-8)

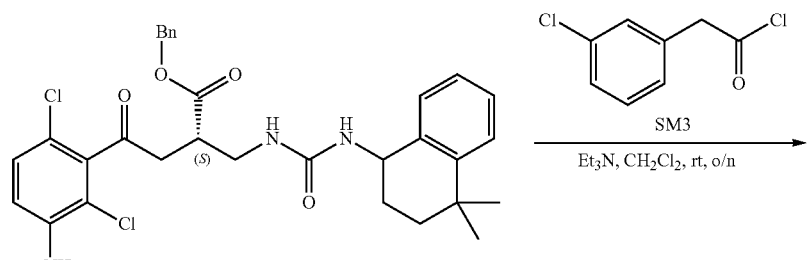

158-7 → SM3, Et3N, CH2Cl2, rt, o/n

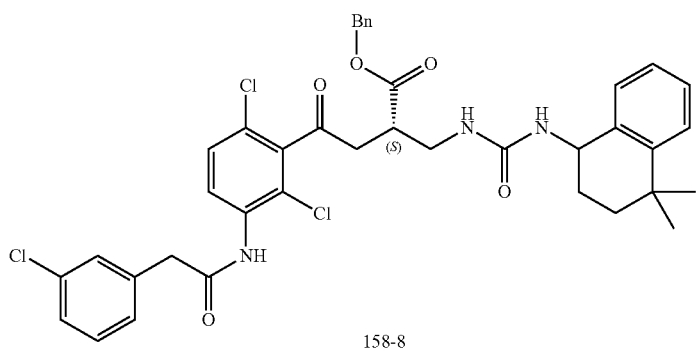

158-8

To a solution of 158-7 (380.0 mg, 0.7 mmol) in CH$_2$Cl$_2$ (10 mL) was added Et$_3$N (197.7 mg, 2.0 mmol) and SM3 (184.7 mg, 1.0 mmol), the reaction mixture was stirred at rt for overnight. After the consumption of starting material (detected by LCMS), the reaction was concentrated in vacuo, the crude was purified by prep-HPLC to get the product 158-8 (360.0 mg, 75.1% yield) as a white solid.

The Synthesis of (2S)-2-(2,6-dichloro-3-(2-(3-chlorophenyl)acetamido)benzamido)-3-(3-(4,4-dimethyl-1,2,3,4-tetrahydronaphthalen-1-yl)ureido)propanoic Acid (SU15210-0158-01)

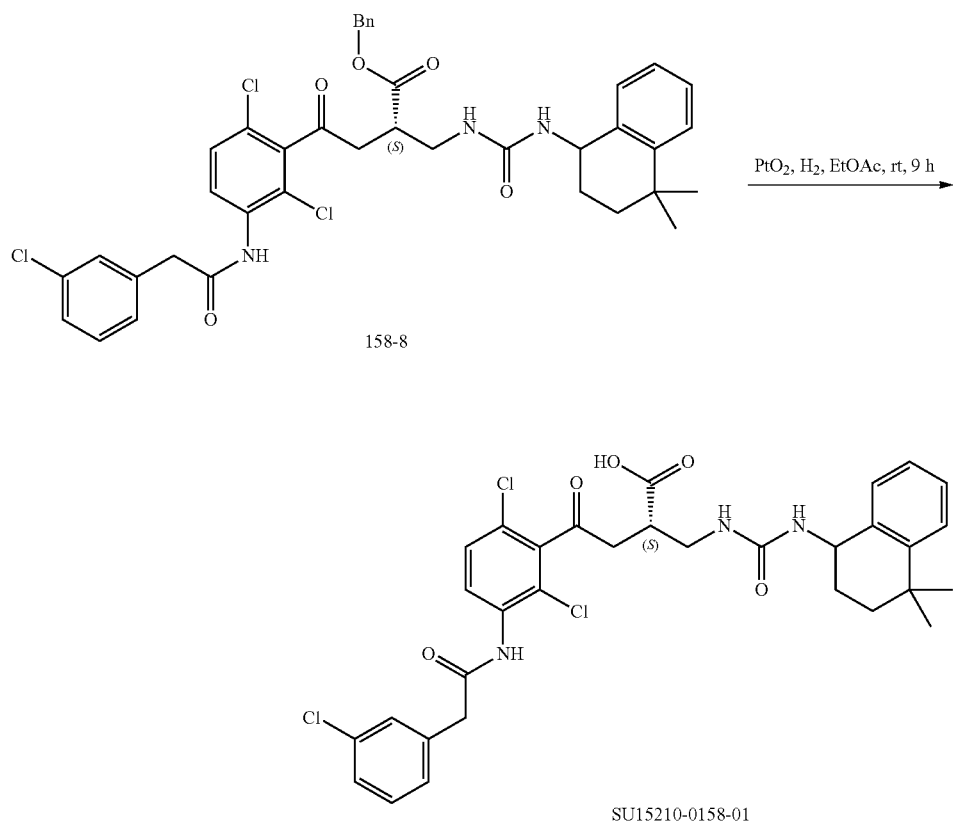

To a solution of 158-8 (50.0 mg, 68.0 umol) in EtOAc (5 mL) was added PtO$_2$ (6.2 mg, 28.0 umol), the reaction was stirred at rt under H$_2$ atmosphere for 9 h. After the consumption of starting material (detected by LCMS), the mixture was filtered and the filtrate was concentrated in vacuo, the crude was purified by prep-HPLC to give the product SU15210-0158-01 (17.0 mg, 38.7% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 100.00%, Rt=1.764 min; MS Calcd.: 644.0; MS Found: 645.1 [M+H]$^+$.

Agilent HPLC 1200; Column: L-column2 ODS (150 mm *4.6 mm*5.0 m); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 98.92%. Rt=9.349 min.

$^1$H NMR (400 MHz, DMSO-d$_6$) δ 12.67 (brs, 1H), 9.89 (s, 1H), 8.92 (s, 1H), 7.72 (d, J=8.8 Hz, 1H), 7.07-7.47 (m, 9H), 6.58-6.62 (m, 1H), 5.81 (d, J=5.6 Hz, 1H), 4.71 (s, 1H), 4.43 (s, 1H), 3.78 (s, 2H), 3.33-3.52 (m, 2H), 1.55-1.87 (m, 4H), 1.26 (s, 3H), 1.22 (s, 3H).

SU15210-0159-01 and SU15210-0197-01
Route for SU15210-0159-01 and SU15210-0197-01:
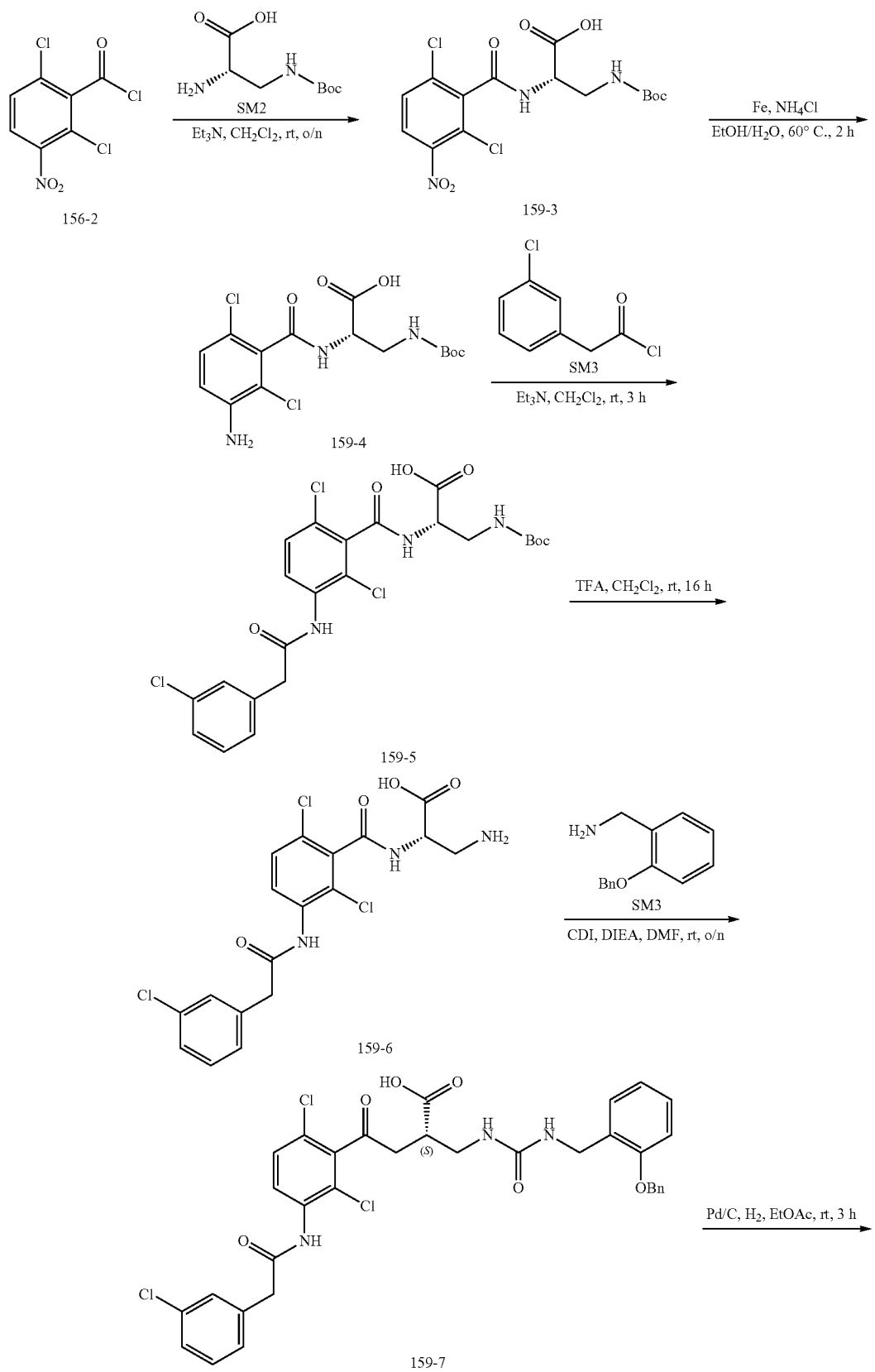

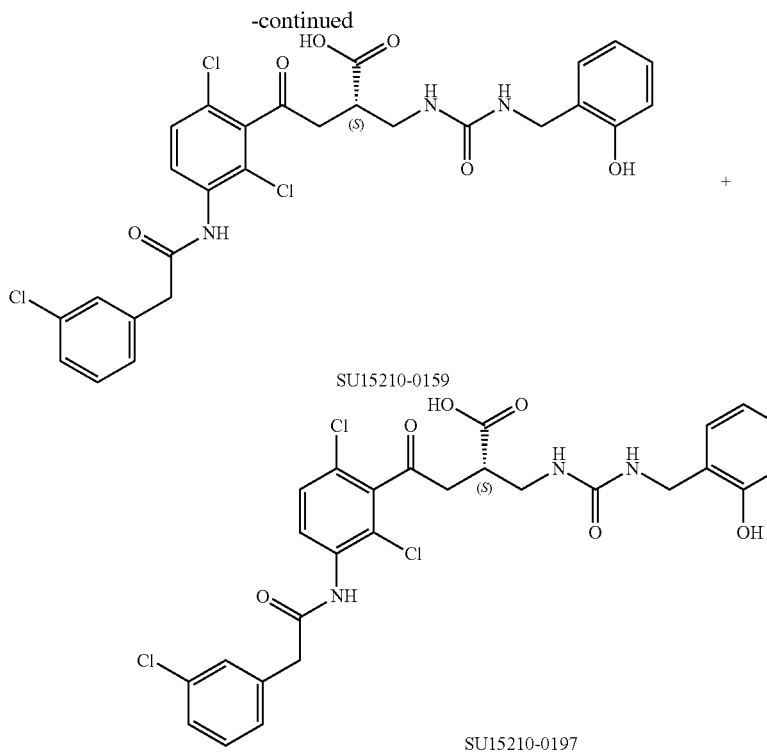

SU15210-0197

The Synthesis of (S)-3-(tert-butoxycarbonylamino)-2-(2,6-dichloro-3-nitrobenzamido)propanoic Acid (159-3)

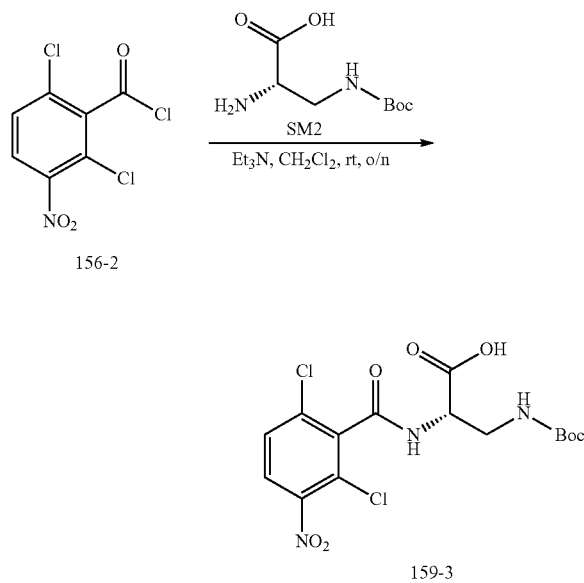

To a solution of SM2 (1.9 g, 9.4 mmol) in CH$_2$Cl$_2$ (50 mL) was added TEA (2.9 g, 28.3 mmol) and 156-2 (2.4 g, 9.4 mmol), the reaction was stirred at rt for overnight. After the reaction was finished (detected by LCMS), the reaction was quenched with H$_2$O (50 mL), 1N HCl was added to adjust pH to 2-3, the mixture was extracted with CH$_2$Cl$_2$ (50 mL×3), combined the organic layer and dried over Na$_2$SO$_4$, filtered and concentrated, the crude was purified by CC (EtOAc/PE=55%) to give the product 159-3 (3.9 g, 97.9% yield) as a white solid.

The Synthesis of (S)-2-(3-amino-2,6-dichlorobenzamido)-3-(tert-butoxycarbonylamino)propanoic Acid (0159-4)

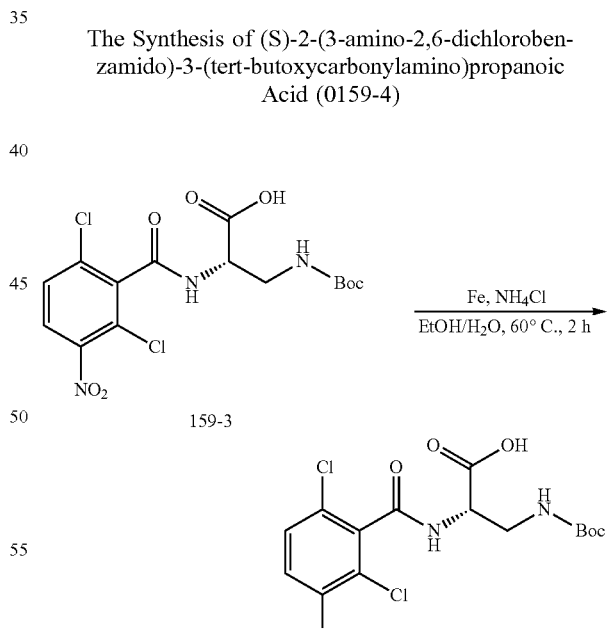

To a solution of 159-3 (754.0 mg, 1.8 mmol) in the mixture solvent of EtOH (10 mL) and H$_2$O (5 mL), was added Fe (498.7 mg, 8.97 mmol7) and NH$_4$Cl (477.6 mg, 8.9 mmol), the reaction was stirred at 60° C. for 2 h. After the consumption of starting material, the reaction was filtered, the filtrate was concentrated in vacuo, the crude dissolved in H$_2$O (5 mL), 1N HCl was dropwised to adjust pH=3~4, the mixture was purified directly by prep-HPLC to get the product 159-4 (445.0 mg, 63.5% yield) as a white solid.

The Synthesis of (S)-3-(tert-butoxycarbonylamino)-2-(2,6-dichloro-3-(2-(3-chlorophenyl)acetamido)benzamido)propanoic Acid (159-5)

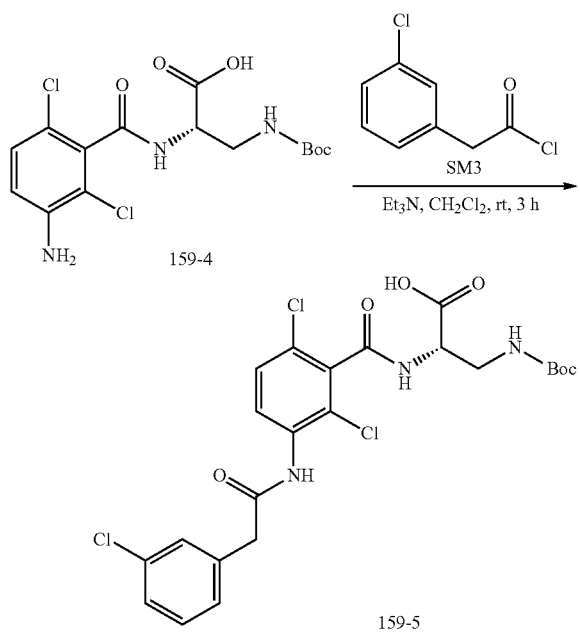

To a solution of 159-4 (431.5 mg, 1.1 mmol) in CH$_2$Cl$_2$ (10 mL) was added Et$_3$N (333.9 mg, 3.3 mmol) and SM3 (321.4 mg, 1.7 mmol), the reaction was stirred at rt for 3 h. After the reaction was finished (detected by LCMS), the reaction solvent was removed in vacuo, the crude was dissolved with H$_2$O (20 mL), 1N HCl was added to pH=2~3, extracted with EtOAc (25 mL×3), combined the organic layer and dried over anhydrous Na$_2$SO$_4$, filtered and concentrated in vacuo, the crude was purified by prep-HPLC to get the product 159-5 (370.0 mg, 61.7% yield) as a white solid.

The Synthesis of (S)-3-amino-2-(2,6-dichloro-3-(2-(3-chlorophenyl)acetamido)benzamido)propanoic Acid (159-6)

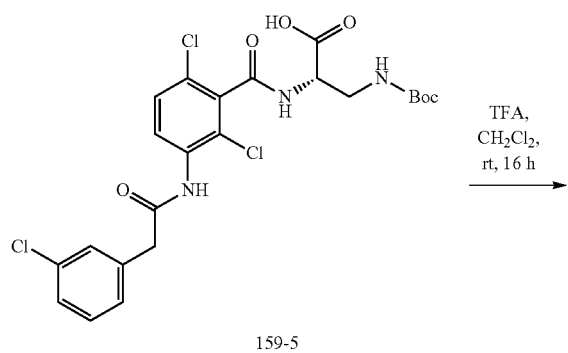

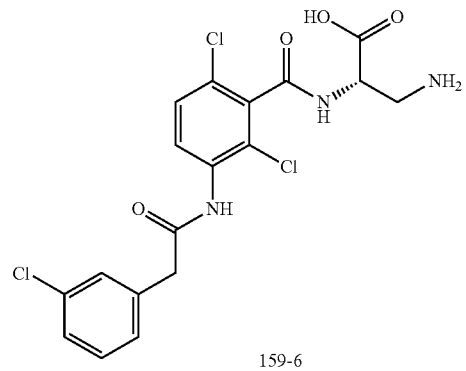

To a solution of 159-5 (420.0 mg, 0.8 mmol) in CH$_2$Cl$_2$ (10 mL) was added TFA (3.0 g, 26.0 mmol), the reaction was stirred at rt for 16 h. After the consumption of starting material (detected by LCMS), the reaction was concentrated in vacuo to the product 159-6 (340.0 mg, 99.2% yield) and used directly for next step without further purification.

The Synthesis of (S)-3-(3-(2-(benzyloxy)benzyl)ureido)-2-(2,6-dichloro-3-(2-(3-chlorophenyl)acetamido)benzamido)propanoic Acid (0159-7)

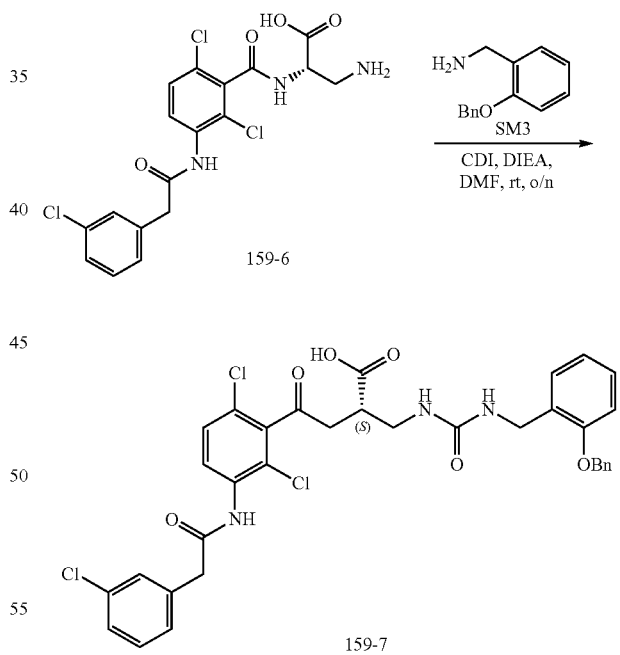

To a solution of SM3 (230.0 mg, 0.7 mmol) in DMF (10 mL) was added DIPEA (277.2 mg, 2.2 mmol) and CDI (127.6 mg, 0.8 mmol), the mixture was stirred at rt for 1 h. After the consumption of starting material (detected by LCMS), 159-6 (318.0 mg, 0.7 mmol) was added to mixture and stirred at rt for overnight. After the reaction was finished (detected by LCMS), the reaction mixture was purified directly by prep-HPLC to get the product 159-7 (375.0 mg, 76.7% yield) as a white solid.

The Synthesis of (S)-2-(2,6-dichloro-3-(2-(3-chlorophenyl)acetamido)benzamido)-3-(3-(2-hydroxybenzyl)ureido)propanoic Acid (SU15210-0159-01) and (S)-2-(2,6-dichloro-3-(2-phenylacetamido)benzamido)-3-(3-(2-hydroxybenzyl)ureido)propanoic Acid (SU15210-0197-01)

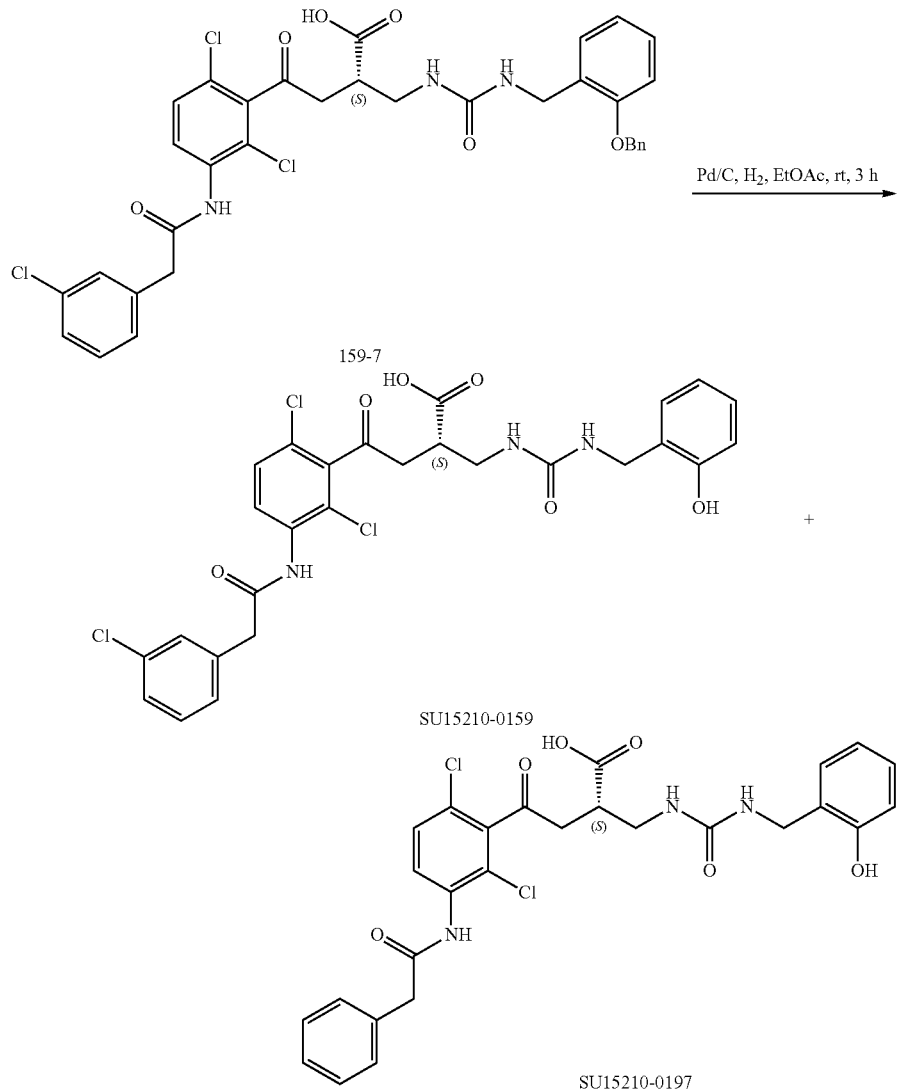

To a solution of 159-7 (136.8 mg, 0.2 mmol) in EtOAc (10 mL) was added Pd/C (137.0 mg, 1.3 mmol), the reaction was stirred at rt under H$_2$ atmosphere for 3 h. After the consumption of starting material (detected by LCMS), the reaction was filtered, the filtrated was concentrated in vacuo, the crude was purified directly by prep-HPLC to get the product SU15210-0159-01 (20.0 mg, 16.8% yield) and SU15210-0197-01 (10.0 mg, 8.9% yield) as a white solid.

SU15210-0159-01

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 97.41%, Rt=1.591 min; MS Calcd.: 592.0; MS Found: 593.0 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 100.00%, Rt=7.270 min.

$^1$H NMR (400 MHz, DMSO-d$_6$) δ 12.67 (brs, 1H), 9.98 (s, 1H), 9.71 (s, 1H), 8.94 (d, J=7.2 Hz, 1H), 7.72 (d, J=8.8 Hz, 1H), 7.44-7.46 (m, 2H), 7.30-7.39 (m, 3H), 7.03-7.10 (m, 2H), 6.71-6.77 (m, 2H), 6.65 (t, J=5.6 Hz, 1H), 6.11 (t, J=5.6 Hz, 1H), 4.41 (q, J=7.2 Hz, 1H), 4.11 (d, J=5.6 Hz, 2H), 3.78 (s, 2H), 3.37-3.47 (m, 2H).

SU15210-0197-01

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 1.6 min, then under this condition for 1.4 min, finally changed to 95% [water+0.05% $NH_4HCO_3$] and 5% [$CH_3CN$+0.05% $NH_4HCO_3$] in 0.05 min and under this condition for 0.7 min), Purity: 98.77%, Rt=1.445 min; MS Calcd.: 558.0; MS Found: 558.7 $[M+H]^+$.

HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 5.0 min, then under this condition for 1.0 min, finally changed to 95% [water+0.05% $NH_4HCO_3$] and 5% [$CH_3CN$+0.05% $NH_4HCO_3$] in 0.1 min and under this condition for 5 min), Purity: 100.00%, Rt=6.668 min.

$^1$H NMR (400 MHz, DMSO-$d_6$) δ 12.76 (brs, 1H), 9.73-9.77 (m, 2H), 8.78 (s, 1H), 7.72 (d, J=8.8 Hz, 1H), 7.42 (d, J=8.8 Hz, 1H), 7.29-7.37 (m, 4H), 7.21-7.25 (m, 1H), 7.01-7.08 (m, 2H), 6.68-6.75 (m, 3H), 6.11 (t, J=5.6 Hz, 1H), 4.34 (q, J=6.8 Hz, 1H), 4.09 (d, J=6.0 Hz, 2H), 3.73 (s, 2H), 3.35-3.43 (m, 2H).

SU15210-0160-01
Route for SU15210-0160-01:

The Synthesis of 2,6-dichloro-3-(3-(2-chlorophenyl)propanamido)benzoic Acid (0160-2)

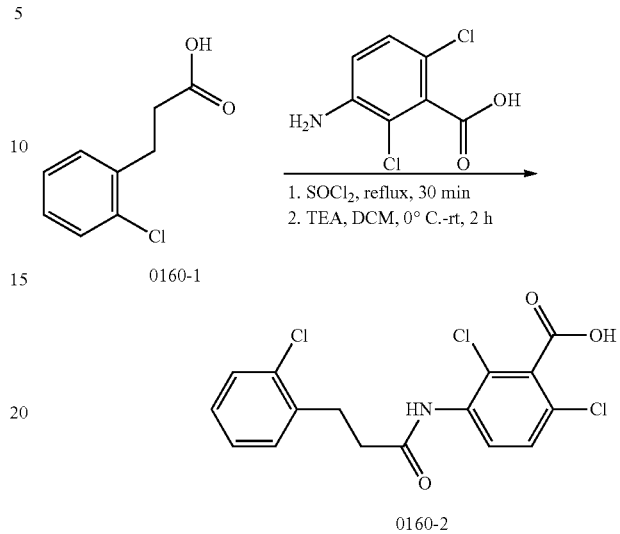

A solution of 0160-1 (300 mg, 1.76 mmol) in $SOCl_2$ (5 mL) was stirred at reflux for 30 min, concentrated to remove the extra $SOCl_2$, the residual was then added to a solution of 3-amino-2,6-dichlorobenzoic Acid (363 mg, 1.76 mmol) and TEA (533 mg, 5.28 mmol) in DCM (10 mL) at 0° C., the solution was then warmed to room temperature and stirred

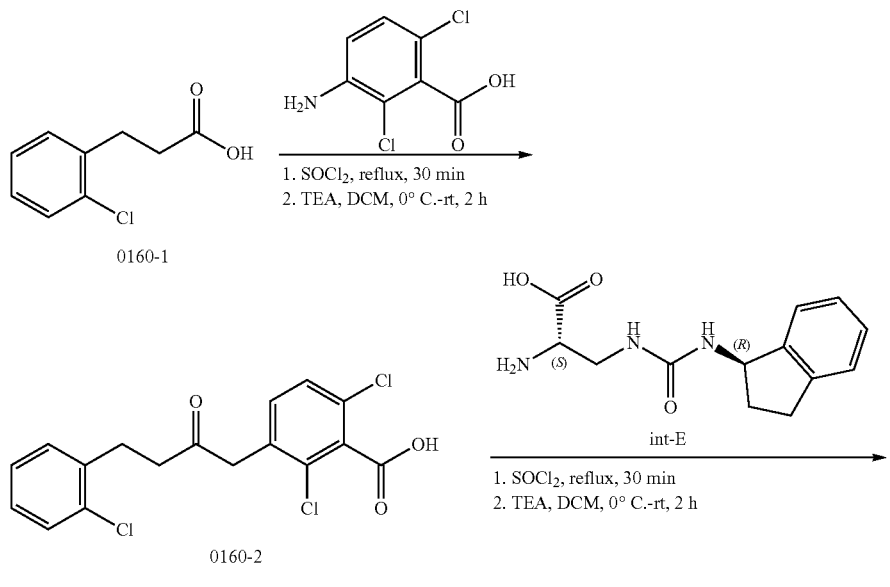

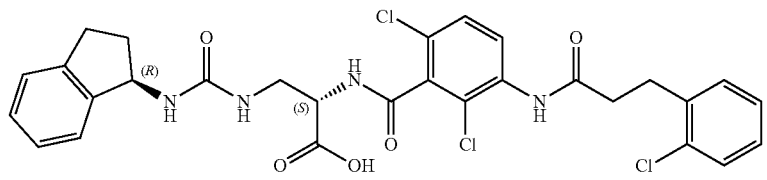

for 2 h. 1N HCl aq. was added to pH 1, separated the organic phase and washed with water then brine, dried over $Na_2SO_4$, concentrated and purified by prep-HPLC to give 0160-2 (400 mg, 63% yield) as a white solid.

The Synthesis of (S)-2-(2,6-dichloro-3-(3-(2-chlorophenyl)propanamido)benzamido)-3-(3-((R)-2,3-dihydro-1H-inden-1-yl)ureido)propanoic Acid (SU15210-0160-01)

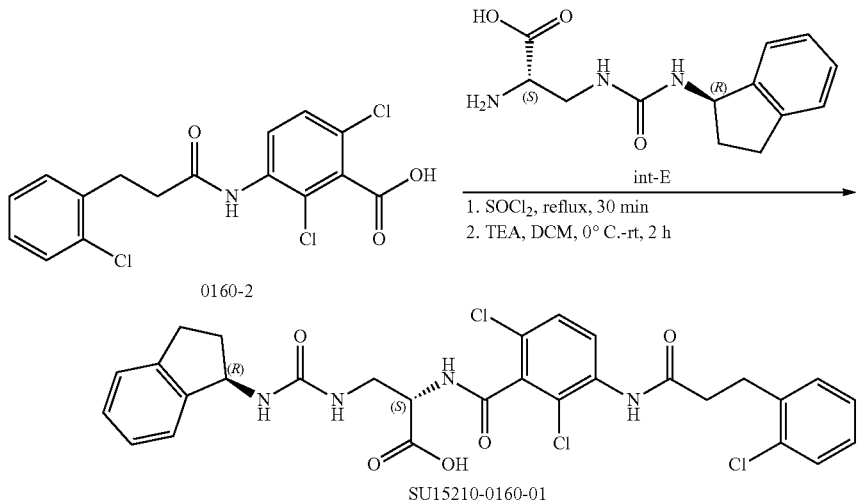

A solution of 0160-2 (100 mg, 0.27 mmol) in $SOCl_2$ (5 mL) was stirred at reflux for 30 min, concentrated to remove the extra $SOCl_2$, the residual was then added to a solution of int-E (71 mg, 0.27 mmol) and TEA (82 mg, 0.81 mmol) in DCM (10 mL) at 0° C., the solution was then warmed to room temperature and stirred for 2 h. 1N HCl aq. was added to pH 1, separated the organic phase and washed with water then brine, dried over $Na_2SO_4$, concentrated and purified by prep-HPLC to give SU15210-0160-01 (21 mg, 13% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [$CH_3CN$] to 0% [water+10 mM TFA] and 100% [$CH_3CN$] in 1.6 min, then under this condition for 1.4 min, finally changed to 95% [water+10 mM TFA] and 5% [$CH_3CN$] in 0.1 min. Purity is 97.11%. Rt=1.701 min; MS Calcd.: 616.1; MS Found: 617.1 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 97.44%. Rt=8.785 min.

$^1$H NMR (400 MHz, DMSO-$d_6$) δ 9.65 (s, 1H), 8.28 (s, 1H), 7.69 (d, J=8.8 Hz, 1H), 7.35-7.44 (m, 3H), 7.20-7.29 (m, 2H), 7.12-7.19 (m, 4H), 6.66 (d, J=8.4 Hz, 1H), 5.94 (br, 1H), 5.05 (q, J=8.0 Hz, 1H), 4.10 (br, 1H), 3.42-3.46 (m, 2H), 3.02 (t, J=7.6 Hz, 2H), 2.80-2.88 (m, 1H), 2.67-2.76 (m, 2H), 2.29-2.37 (m, 1H), 1.62-1.68 (m, 1H).

SU15210-0163-01
Route for SU15210-0163-01:

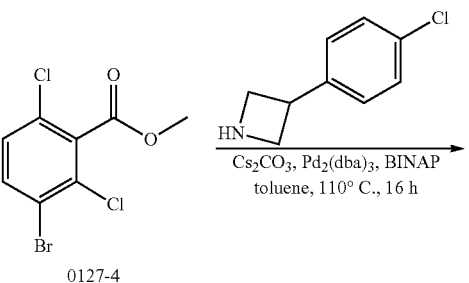

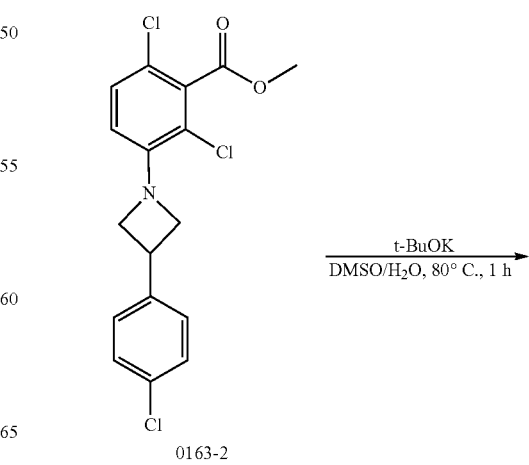

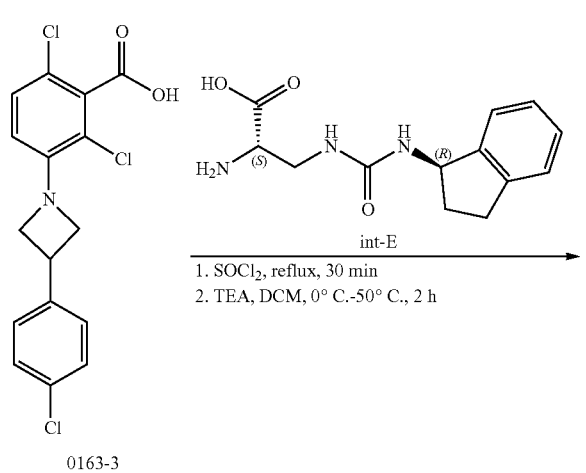

0163-3

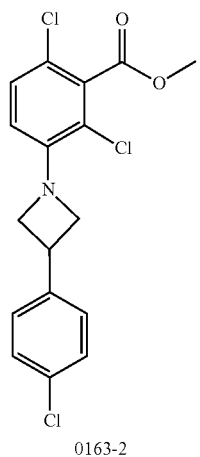

0163-2

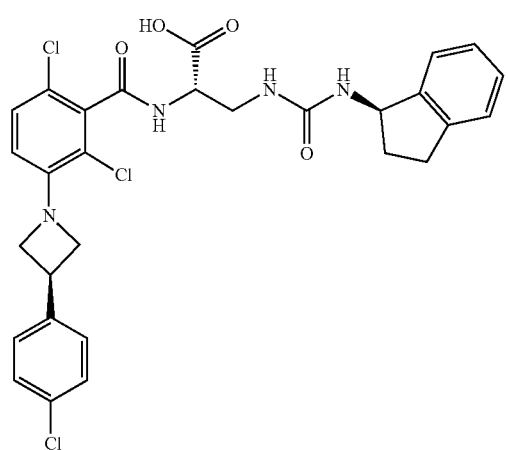

SU15210-0163-01

The Synthesis of Methyl 2,6-dichloro-3-(3-(4-chlorophenyl)azetidin-1-yl)benzoate (0163-2)

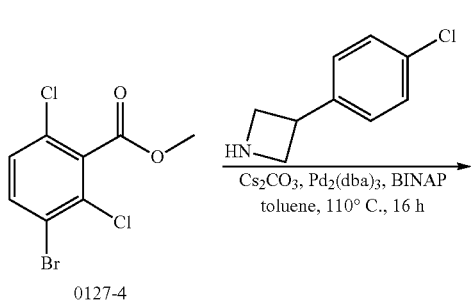

0127-4

To a solution of 0127-4 (200 mg, 0.70 mmol) in toluene (5 mL) was added 3-(4-chlorophenyl)azetidine (118 mg, 0.70 mmol), Cs₂CO₃ (456 mg, 1.40 mmol), Pd₂(dba)₃ (66 mg, 0.07 mmol) and BINAP (45 mg, 0.07 mmol), the mixture was stirred at 110° C. for 16 h. Filtrated and concentrated then purified by CC (5% to 10% ethyl acetate in petroleum ether) to get 0163-2 (210 mg, 80% yield) as a white solid.

The Synthesis of 2,6-dichloro-3-(3-(4-chlorophenyl)azetidin-1-yl)benzoic Acid (0163-3)

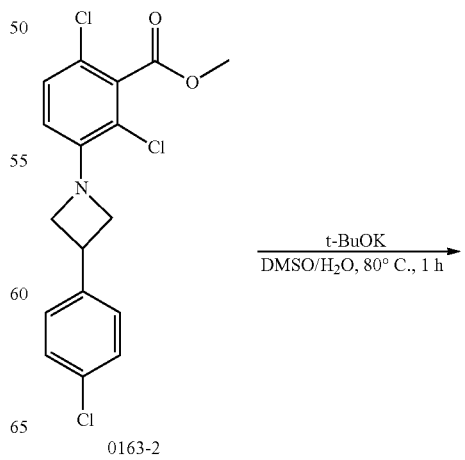

0163-2

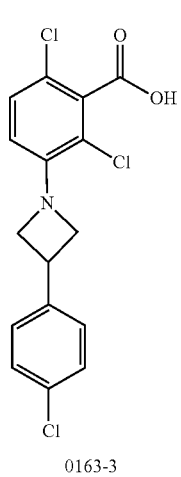

0163-3

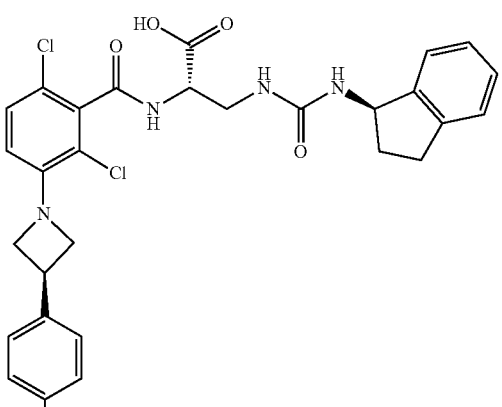

SU15210-0163-01

To a solution of 0163-2 (210 mg, 0.56 mmol) in DMSO (5 mL) was added t-BuOK (127 mg, 1.12 mmol) and H₂O (0.05 mL), the solution was heated to 80° C. and stirred for 1 h. Cooled to room temperature and 1N HCl aq. was added to pH 1, then purified by prep-HPLC to get 0163-3 (110 mg, 69% yield) as a white solid.

The Synthesis of (S)-2-(2,6-dichloro-3-(3-(4-chlorophenyl)azetidin-1-yl)benzamido)-3-(3-((R)-2,3-dihydro-1H-inden-1-yl)ureido)propanoic Acid (SU15210-0163-01)

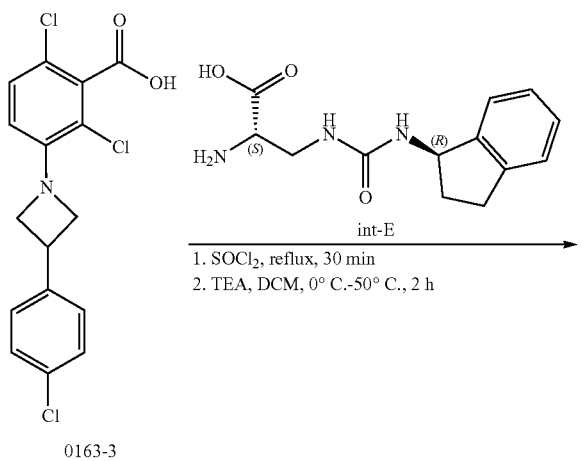

0163-3

1. SOCl₂, reflux, 30 min
2. TEA, DCM, 0° C.-50° C., 2 h int-E

A solution of 0163-3 (110 mg, 0.31 mmol) in SOCl₂ (5 mL) was stirred at reflux for 30 min, concentrated to remove the extra SOCl₂, the residual was then added to a solution of int-E (81 mg, 0.31 mmol) and TEA (94 mg, 0.93 mmol) in DCM (10 mL) at 0° C., the solution was then heated to 50° C. and stirred for 2 h. Cooled to room temperature and 1N HCl aq. was added to pH 1, separated the organic phase and washed with water then brine, dried over Na₂SO₄, concentrated and purified by prep-HPLC to give SU15210-0163-01 (30 mg, 16% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 99.65%. Rt=1.959 min; MS Calcd.: 600.1; MS Found: 601.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 99.63%. Rt=9.766 min.

¹H NMR (400 MHz, DMSO-d₆) δ 8.28 (br, 1H), 7.37-7.44 (m, 4H), 7.28 (d, J=8.8 Hz, 1H), 7.07-7.19 (m, 4H), 6.68 (d, J=8.8 Hz, 1H), 6.63 (d, J=8.0 Hz, 1H), 5.90 (t, J=4.0 Hz, 1H), 5.04 (q, J=8.0 Hz, 1H), 4.39-4.44 (m, 2H), 4.17 (br, 1H), 3.85-3.95 (m, 3H), 3.20-3.40 (m, 2H), 2.50-2.73 (m, 1H), 2.80-2.85 (m, 1H), 2.64-2.75 (m, 1H), 2.28-2.36 (m, 2H), 1.62-1.68 (m, 1H).

SU15210-0165-01
Route for SU15210-0165-01:
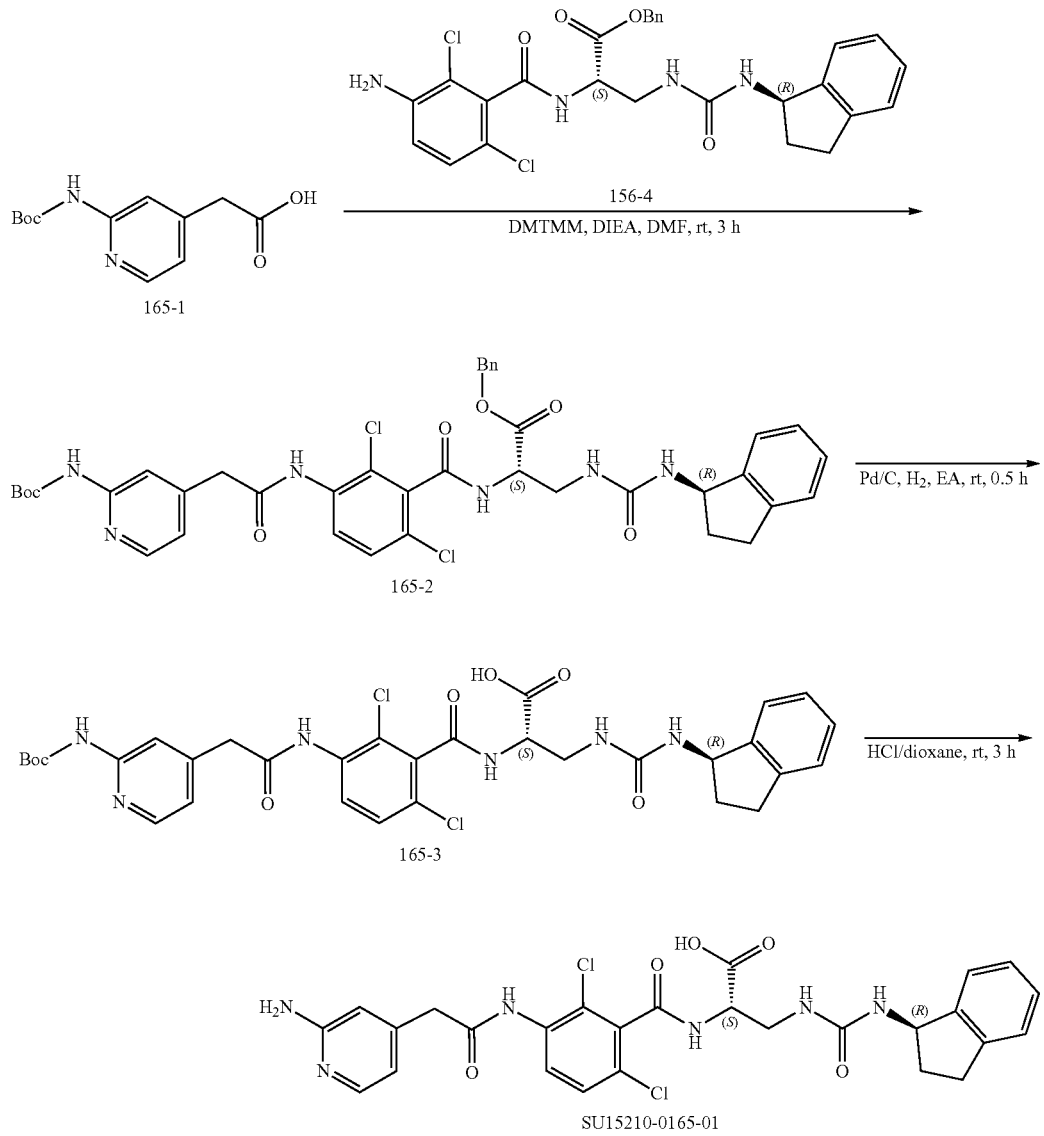
The Synthesis of (S)-benzyl 2-(3-(2-(2-(tert-butoxy-carbonylamino)pyridin-4-yl)acetamido)-2,6-dichlorobenzamido)-3-(3-((R)-2,3-dihydro-1H-inden-1-yl)ureido)propanoate (0165-2)
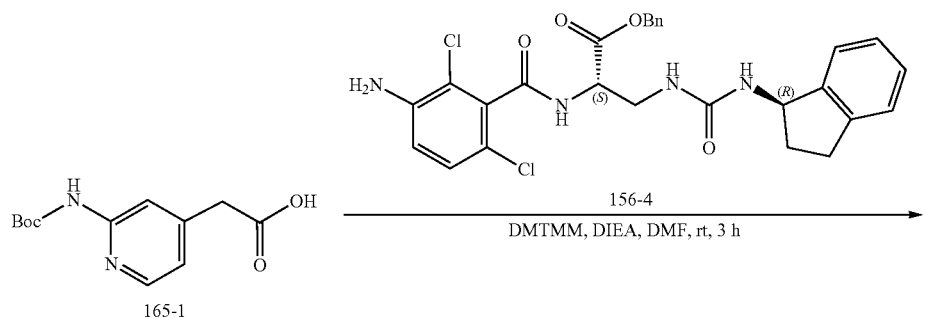

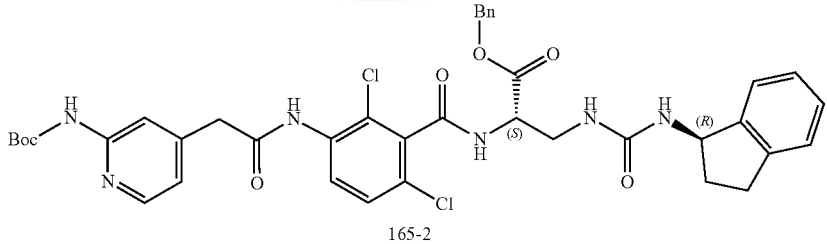

165-2

To a solution of 165-1 (40 mg, 262.90 umol) and 156-4 (142.34 mg, 262.90 umol) in DMF (5 mL) was added DIEA (101.93 mg, 788.70 umol and DMTMM (218.25 mg, 788.70 umol), the solution was stirred at rt for 3 h. After the consumption of starting material (by LCMS), water (10 mL) was added, extracted with ethyl acetate (20 mL×3), washed with water (20 mL×3), dried and concentrated. The crude was purified by pre-HPLC to get 0165-2 (150 mg, 84.46% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 100%. Rt=0.695 min; MS Calcd.: 774.7; MS Found: 775.0 [M+H]$^+$.

The Synthesis of (S)-2-(3-(2-(2-(tert-butoxycarbonylamino)pyridin-4-yl)acetamido)-2,6-dichlorobenzamido)-3-(3-((R)-2,3-dihydro-1H-inden-1-yl)ureido)propanoic Acid (0165-3)

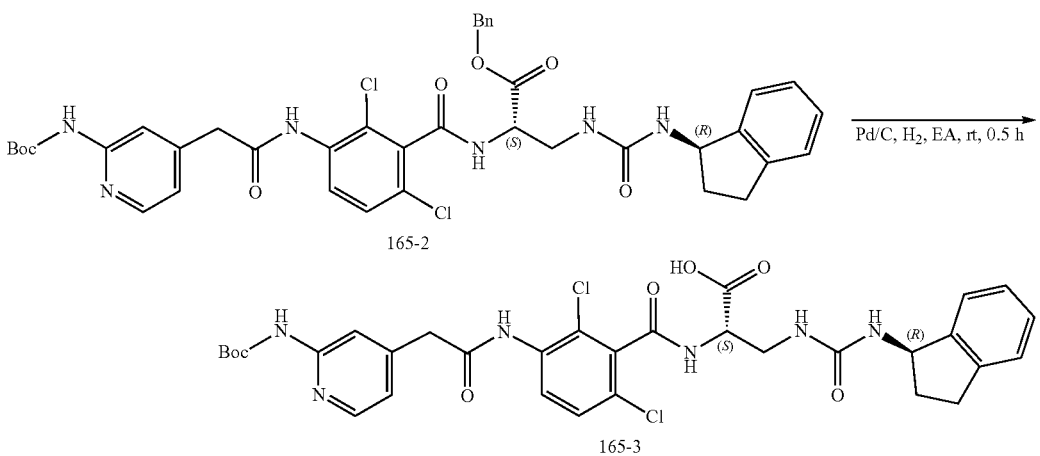

A solution of 0165-2 (99.74 mg, 128.59 umol) in EA (5 mL) was wadded Pd/C (10 mg) and stirred at room temperature for 0.5 h under H$_2$ atmosphere (1.0 atm). After the reaction was complete (by LCMS), the mixture was filtrated, the filtrate was concentrated and purified by pre-HPLC to get 0165-3 (80 mg, 90.75% yield) as a white solid.

The Synthesis of (S)-2-(3-(2-(2-aminopyridin-4-yl)acetamido)-2,6-dichlorobenzamido)-3-(3-((R)-2,3-dihydro-1H-inden-1-yl)ureido)propanoic Acid (SU15210-0165-01)

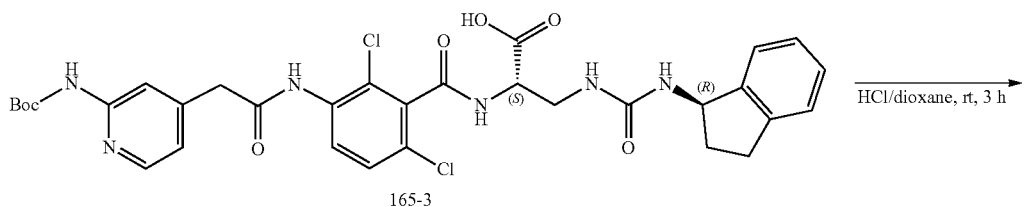

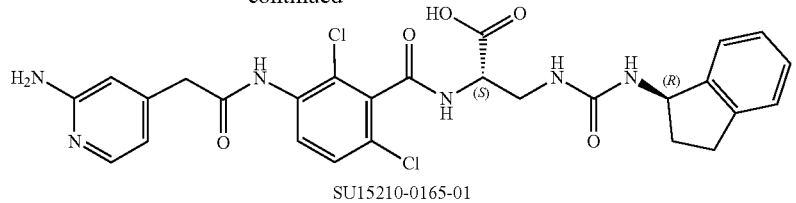

SU15210-0165-01

A solution of 0165-3 (80 mg, 116.69 umol) in HCl/dioxane (20.0 ml), the mixture was stirred at room temperature overnight. After the reaction was completed, the solvent was removed in vacuo, thus was further purified by prep-HPLC to give SU15210-0165-01 (40 mg, 58.55% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.319 min; MS Calcd.: 584.0; MS Found: 587.0 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=5.832 min.

$^1$H NMR (400 MHz, DMSO-d$_6$): δ9.85 (s, 1H), 9.01 (d, J=8.0 Hz, 1H), 7.72-7.81 (m, 2H), 7.47 (d, J=8.0 Hz, 1H), 7.13-7.22 (m, 4H), 6.57 (d, J=8.0 Hz, 1H), 6.40-6.47 (m, 2H), 5.86-5.90 (m, 3H), 5.04-5.11 (m, 1H), 4.46-4.51 (m, 1H), 3.46-3.63 (m, 3H), 2.86-2.89 (m, 2H), 2.30-2.42 (m, 2H), 1.63-1.71 (m, 1H).

SU15210-0167-01

Synthesis of SU15210-0167-01

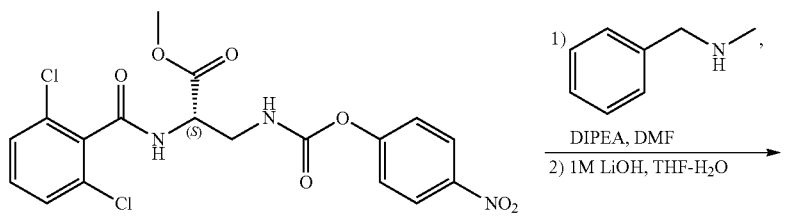

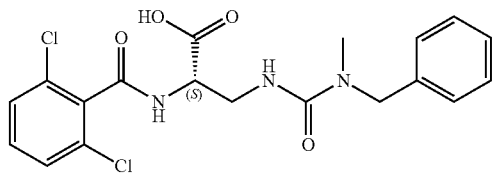

To a stirred solution of O-nitrophenylcarbamate (0.1 mmol) in DMF (1 mL) was added DIPEA (17 uL) and methylbenzylamine (14 uL) and stirred overnight. The mixture was diluted with ethyl acetate. The organic layer was washed with 1 M HCl, saturated NaHCO$_3$ and dried over Na$_2$SO$_4$. After concentration under reduced pressure, the crude product was dissolved in 20% H$_2$O in THF (2.5 mL) and 1 M LiOH (150 uL) was added at 0° C. The mixture was stirred for 3 h and neutralized by addition of 1 M HCl. The crude mixture was concentrated and purified by RP-HPLC. ESI-positive; 424.4 (MH+)

SU15210-0171-01

Synthesis of SU15210-0171-01

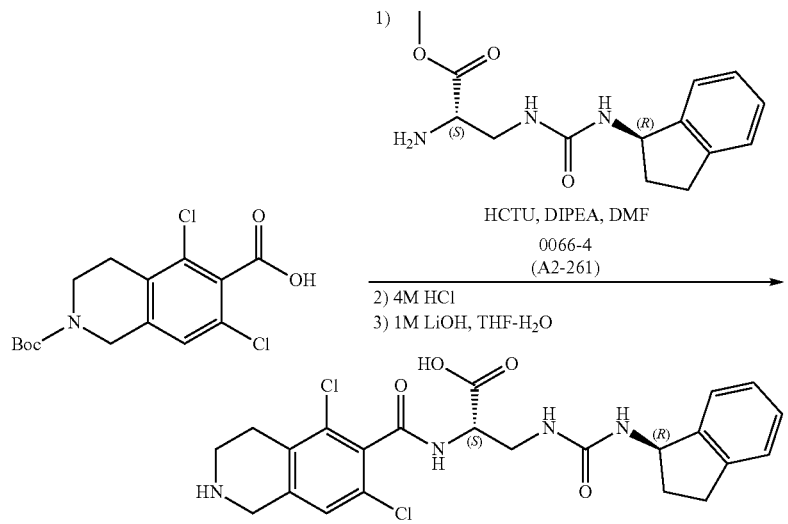

To a stirred solution of amine (1.44 mmol) and Acid (1 eq) in DMF (5 mL) was added DIPEA (3 mmol) and HCTU (1.39 mmol). The mixture was stirred for overnight and diluted with ethyl acetate. The organic layer was washed with 1 M HCl, saturated NaHCO$_3$ and dried over Na$_2$SO$_4$. After concentration under reduced pressure, the crude mixture was treated with 4 M HCl in dioxane (3 mL) and stirred for 3 h. After removal of volatiles under reduced pressure, a portion of the crude HCl salt (76 mg) was dissolved in 20% H$_2$O in THF (5 mL) and 1 M LiOH (250 uL) was added at 0° C. The mixture was stirred for 3 h and neutralized by addition of 1 M HCl. The crude mixture was concentrated and purified by RP-HPLC. ESI-positive; 491.5 (MH+).

SU15210-0172-01

Synthesis of SU15210-0172-01

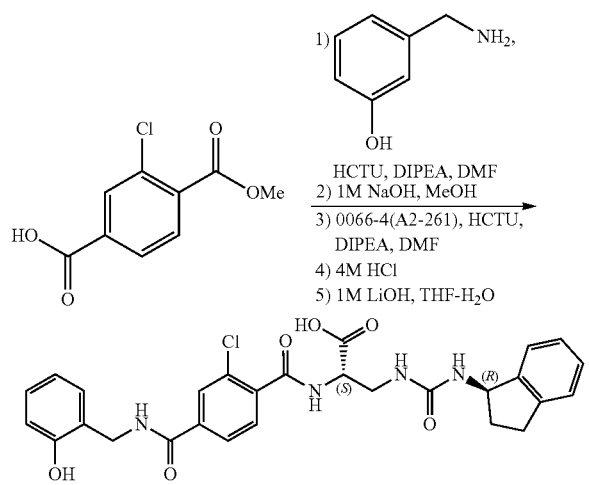

To a stirred solution of amine (1.15 mmol) and Acid (1 eq) in DMF (3 mL) was added DIPEA (2.67 mmol) and HCTU (1.13 mmol). The mixture was stirred for overnight and diluted with ethyl acetate. The organic layer was washed with 1 M HCl, saturated NaHCO$_3$ and dried over Na$_2$SO$_4$. After concentration under reduced pressure, the crude mixture was dissolved in MeOH (5 mL) and treated with 1 M NaOH (1.5 mL). The mixture was neutralized by addition of 1 M HCl and lyophilized. To the acid in DMF (4 mL) was added A2-261 (100 mg, 0.36 mmol), DIPEA (370 uL, 2.12 mmol), and HCTU (0.5 mmol). The mixture was stirred for 4 h and diluted with ethyl acetate. The organic layer was washed with 1 M HCl, saturated NaHCO$_3$ and dried over Na$_2$SO$_4$. After concentration under reduced pressure, the crude mixture was dissolved in 20% H$_2$O in THF (4 mL) and 1 M LiOH (200 uL) was added at 0° C. The mixture was stirred for 3 h and neutralized by addition of 1 M HCl. The crude mixture was concentrated and purified by RP-HPLC. ESI-positive; 551.7 (MH+).

SU15210-0173-01

Synthesis of SU15210-0173-01

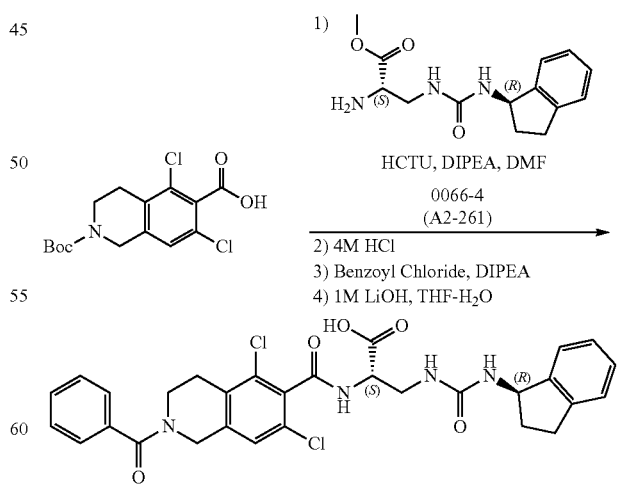

To a stirred solution of amine (1.44 mmol) and acid (1 eq) in DMF (5 mL) was added DIPEA (3 mmol) and HCTU (1.39 mmol). The mixture was stirred for overnight and diluted with ethyl acetate. The organic layer was washed with 1 M HCl, saturated NaHCO₃ and dried over Na₂SO₄. After concentration under reduced pressure, the crude mixture was treated with 4 M HCl in dioxane (3 mL) and stirred for 3 h. After removal of volatiles under reduced pressure, a portion of the crude HCl salt (85 mg) was dissolved in DMF (1 mL) and DIPEA (87 uL) followed by acetyl chloride (28 uL) at rt. The reaction mixture was stirred for 2 h and diluted with ethyl acetate. The organic layer was washed with 1 M HCl, saturated NaHCO₃ and dried over Na₂SO₄. The crude mixture was dissolved in 20% H₂O in THF (5 mL) and 1 M LiOH (200 uL) was added at 0° C. The mixture was stirred for 3 h and neutralized by addition of 1 M HCl. The crude mixture was concentrated and purified by RP-HPLC. ESI-positive; 595.5 (MH+).

SU15210-0174-01

Synthesis of SU15210-0174-01

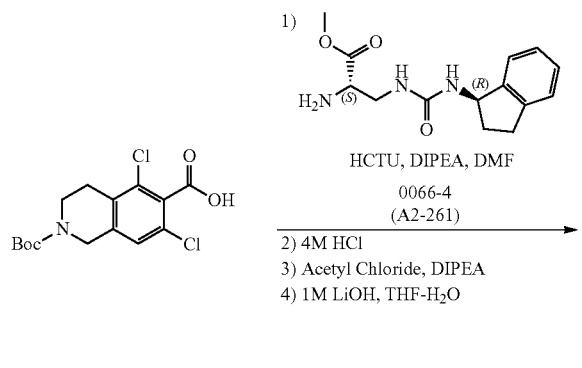

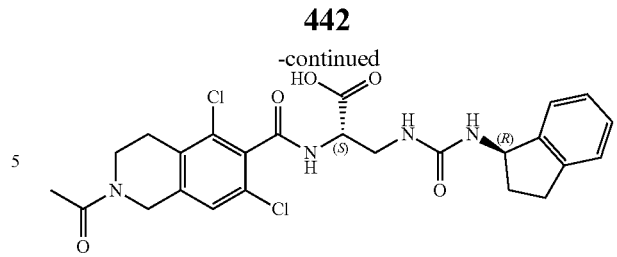

To a stirred solution of amine (1.44 mmol) and Acid (1 eq) in DMF (5 mL) was added DIPEA (3 mmol) and HCTU (1.39 mmol). The mixture was stirred for overnight and diluted with ethyl acetate. The organic layer was washed with 1 M HCl, saturated NaHCO₃ and dried over Na₂SO₄. After concentration under reduced pressure, the crude mixture was treated with 4 M HCl in dioxane (3 mL) and stirred for 3 h. After removal of volatiles under reduced pressure, a portion of the crude HCl salt (82 mg, 0.151 mmol) was dissolved in DMF (1 mL) and DIPEA (87 uL) followed by acetyl chloride (14 uL) at rt. The reaction mixture was stirred for 2 h and diluted with ethyl acetate. The organic layer was washed with 1 M HCl, saturated NaHCO₃ and dried over Na₂SO₄. The crude mixture was dissolved in 20% H₂O in THF (5 mL) and 1 M LiOH (250 uL) was added at 0° C. The mixture was stirred for 3 h and neutralized by addition of 1 M HCl. The crude mixture was concentrated and purified by RP-HPLC. ESI-positive; 533.4 (MH+).

SU15210-0185-01

Route for SU15210-0185-01

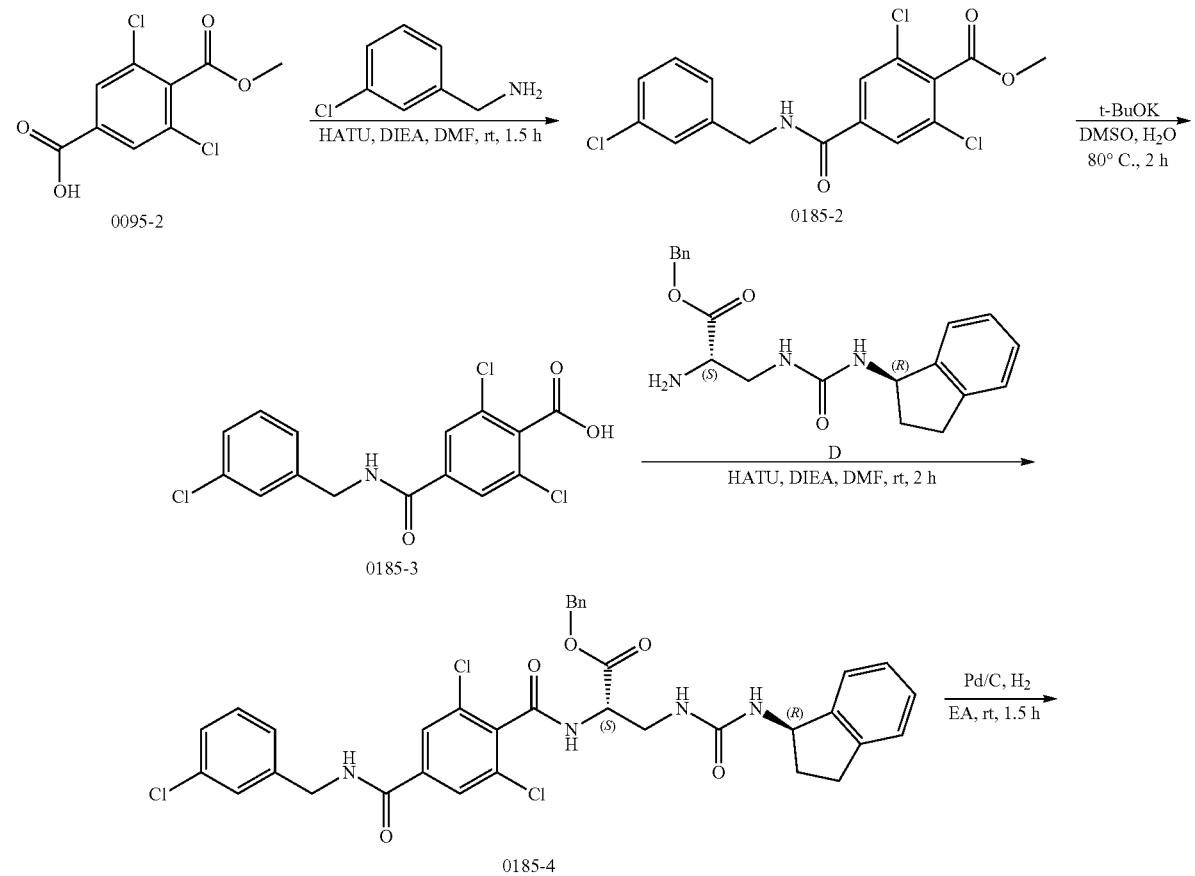

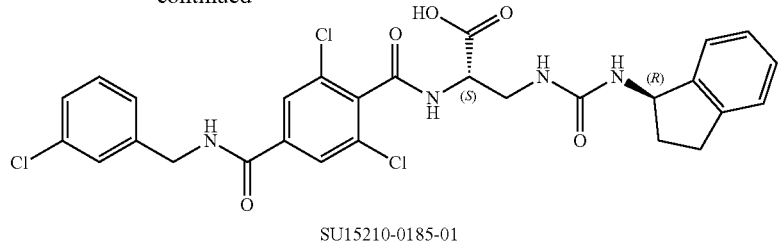

SU15210-0185-01

The Synthesis of Methyl 2,6-dichloro-4-(3-chlorobenzylcarbamoyl)benzoate (0185-2)

The Synthesis of 2,6-dichloro-4-(3-chlorobenzylcarbamoyl)benzoic Acid (0185-3)

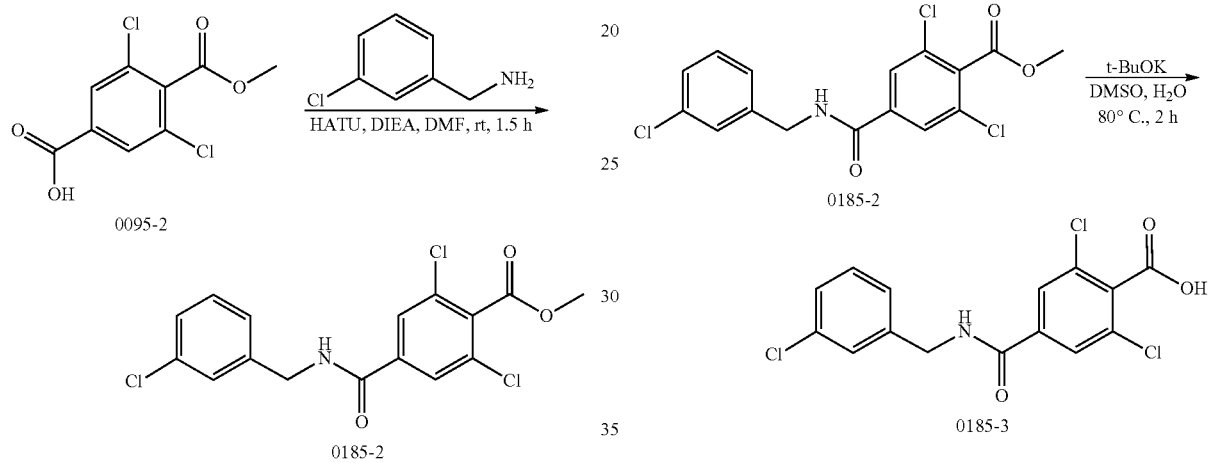

To a solution of compound 0095-2 (200 mg, 803 umol) and (3-chlorophenyl)methanamine (114 mg, 803 umol) in DMF (5 mL) was added DIEA (243 mg, 2.4 mmol) and HATU (613 mg, 1.6 mmol) and the mixture was stirred at room temperature for 1.5 h. After the consumption of starting material (by LCMS), the mixture was quenched with water (20 mL), extracted with EtOAc (20 mL×3), washed the organic layers with water (20 mL), dried over anhydrous sodium sulfate and concentrated on a rotary evaporator. The crude was purified by C.C. (20-40% EtOAc in hexane) to give 0185-2 (248 mg, yield: 82.88%) as a yellow solid.

To a solution of compound 0185-2 (78 mg, 698 umol) in DMSO (4 mL) was added potassium tert-butoxide (78 mg, 698 umol) and the mixture was warmed up to 80° C. for 2 h. After the consumption of starting material (by LCMS), the mixture was quenched with water (10 mL), extracted with EtOAc (20 mL×3), and washed the combined organic layers with water (20 mL×3). The residues was dried over anhydrous sodium sulfate and concentrated in vacuo. The crude product 0185-3 (160 mg, yield: 63.95%) was used for next step without further purification.

The Synthesis of (S)-benzyl 2-(2,6-dichloro-4-(3-chlorobenzylcarbamoyl)benzamido)-3-(3-((R)-2,3-dihydro-1H-inden-1-yl)ureido)propanoate (0185-4)

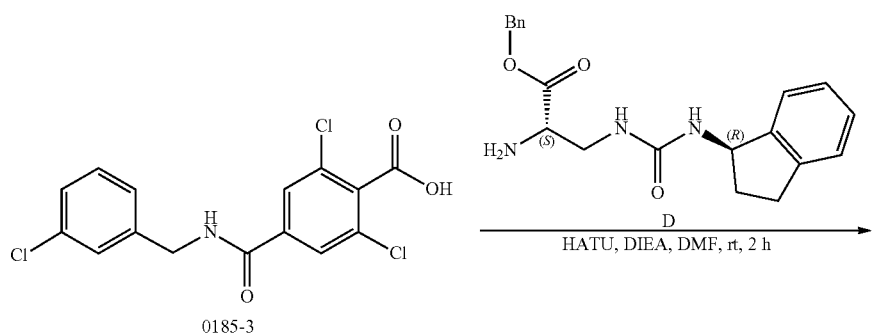

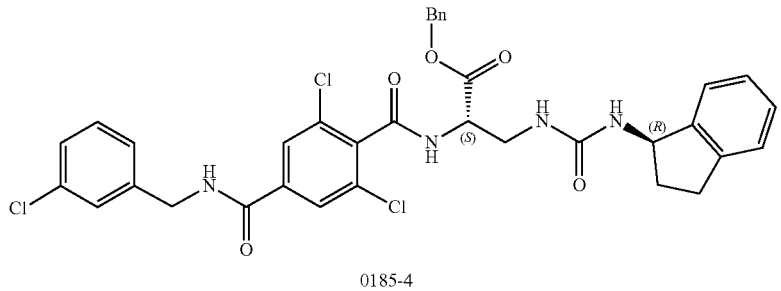

0185-4

To a solution of compound 0185-3 (200 mg, 558 umol) and intermediate D (197 mg, 558 ummol) in DMF (5 mL) was added DIEA (216 mg, 1.67 mmol) and HATU (426 mg, 1.16 mmol) and the mixture was stirred at room temperature for 2 h. After the consumption of starting material (by LCMS), the mixture was quenched with water (10 mL), extracted with EtOAc (20 mL×3), washed the organic layers with water (20 mL×3). The residues was dried over anhydrous sodium sulfate and concentrated on a rotary evaporator. The crude was purified by pre-HPLC to get 0185-4 (175 mg, yield: 45.21%) as a white solid.

The Synthesis of (S)-2-(2,6-dichloro-4-(3-chlorobenzylcarbamoyl)benzamido)-3-(3-((R)-2,3-dihydro-1H-inden-1-yl)ureido)propanoic Acid (SU15210-0185-01)

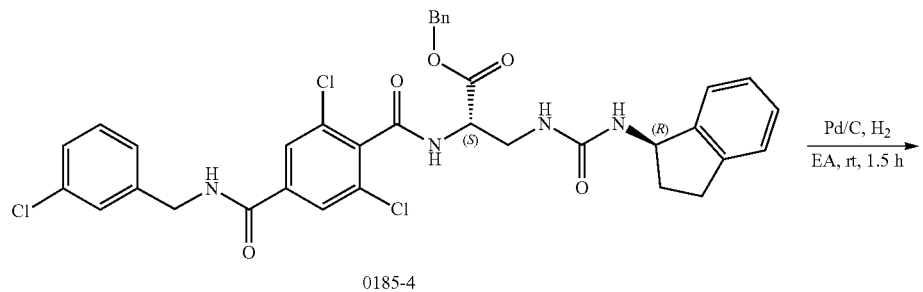

0185-4

Pd/C, H$_2$
EA, rt, 1.5 h

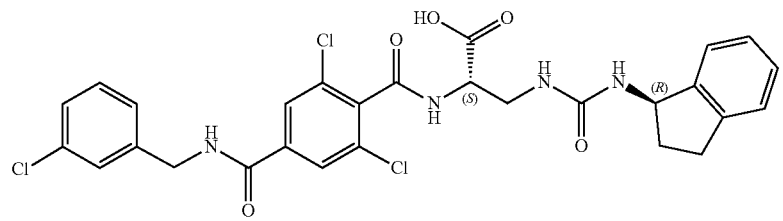

SU15210-0185-01

To a solution of compound 0185-4 (170 mg, 244.96 umol) in EtOAc (4 mL) was added 10% palladium on activated carbon (40 mg, 25 umol) and replaced with hydrogen. The mixture was allowed to stir at rt for 1.5 h. After the consumption of starting material (by LCMS), the mixture was filtered and concentrated in vacuo, the crude was purified by pre-HPLC to give product SU521-0185 (50 mg, yield: 32.3.0%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.659 min; MS Found: 603.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 99.04%, Rt=7.934 min; MS Found: 603.7 [M+H]$^+$.

$^1$H NMR (400 MHz, DMSO-d$_6$) δ 9.31 (t, J=6.0 Hz, 1H), 8.71 (br, 1H), 7.94 (s, 2H), 7.26-7.37 (m, 4H), 7.11 (m, 4H), 6.62 (d, J=8.0 Hz, 1H), 5.90 (s, 1H), 5.03-5.09 (q, 1H), 4.46 (d, J=6.0 Hz, 2H), 4.28 (s, 1H), 3.40 (s, 3H), 2.81-2.87 (m, 1H), 2.68-2.76 (m, 1H), 2.30-2.37 (m, 1H), 1.60-1.70 (m, 1H).

SU15210-0186-01

Route for SU15210-0186-01:

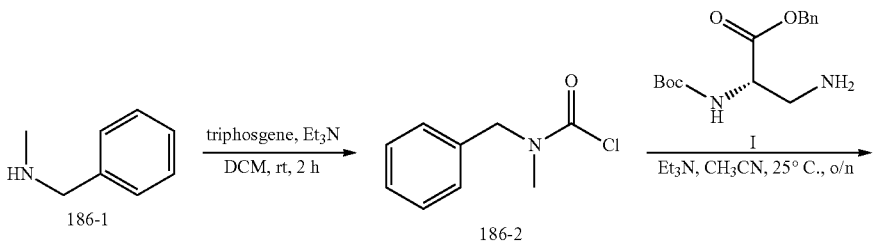

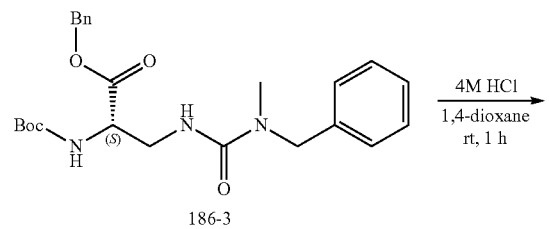

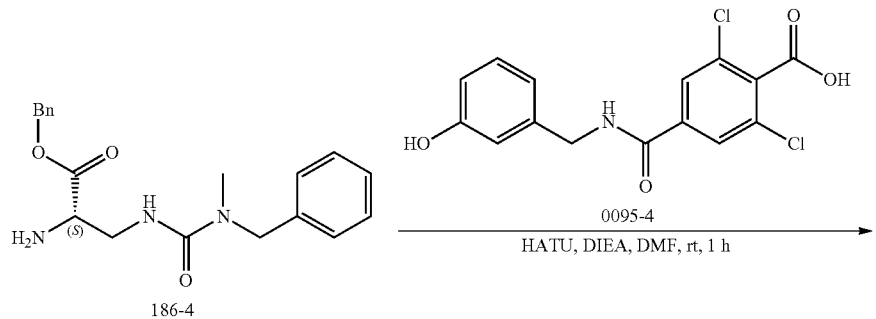

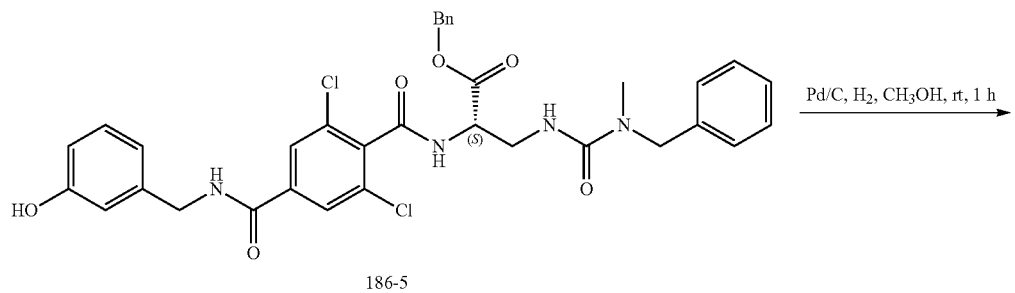

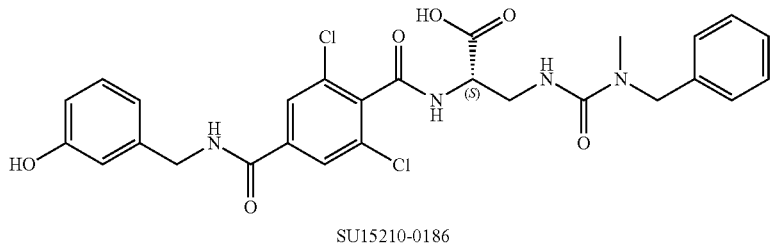

SU15210-0186

The Synthesis of benzyl(methyl)carbamic Chloride (186-2)

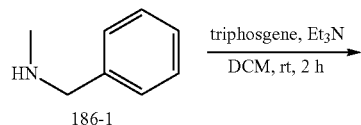

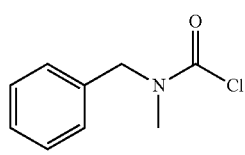

To a solution of 186-1 (424.1 mg, 3.5 mmol) in CH$_2$Cl$_2$ (30 mL) was added TEA (1.1 g, 10.5 mmol), triphosgene (1.04 g, 3.5 mmol) was added in 0° C., the reaction was stirred at rt for 2 h. After the reaction was finished (detected by LCMS), the reaction was quenched with H$_2$O (20 mL), extracted with CH$_2$Cl$_2$ (25 mL×3), combined the organic layer and dried over Na$_2$SO$_4$, filtered and concentrated in vacuo, the crude 186-2 (640.0 mg, 99.6% yield) was obtained as brown oil and used directly for next step without further purification.

The Synthesis of (S)-benzyl 3-(3-benzyl-3-methylureido)-2-(tert-butoxycarbonylamino)propanoate (186-3)

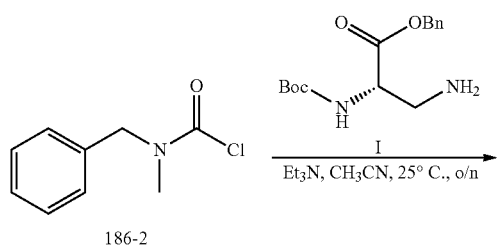

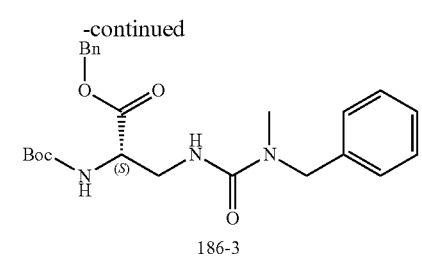

To a solution of I (500.0 mg, 1.7 mmol) in CH$_3$CN (30 mL) was added TEA (343.8 mg, 3.4 mmol) and 186-2 (467.9 mg, 2.6 mmol), the reaction was stirred at 25° C. for 16 h. After the reaction was finished (detected by LCMS), the reaction was concentrated in vacuo, the crude was purified directly by prep-HPLC to get the product 186-3 (140.0 mg, 18.7% yield) as a white solid.

The Synthesis of (S)-benzyl 2-amino-3-(3-benzyl-3-methylureido)propanoate (0186-4)


To a solution of 186-3 (140.0 mg, 0.3 mmol) in 1,4-Dioxane (5 mL) was added HCl (4 M in 1,4-Dioxane), the reaction was stirred at rt for 1 h. After the reaction was finished (detected by LCMS), the reaction was concentrated in vacuo, the crude 186-4 (108.0 mg, 99.8% yield) was obtained as a white solid used directly for next step without further purification.

The Synthesis of (S)-3-(3-benzyl-3-methylureido)-2-(2,6-dichloro-4-(3-hydroxybenzylcarbamoyl)benzamido)propanoate (186-5)

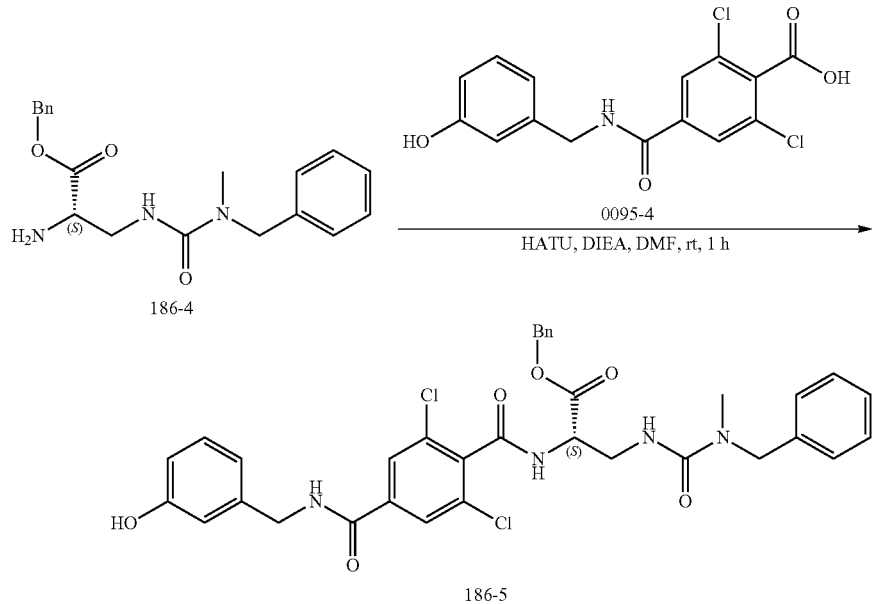

To a solution of 0095-4 (109.6 mg, 0.3 mmol) in DMF (5 mL) was added HATU (167.1 mg, 0.4 mmol), DIPEA (75.7 mg, 0.6 mmol) and 186-4 (100.0 mg, 0.3 mmol), the reaction was stirred at rt for 1 h. After the reaction was finished (detected by LCMS), the reaction was quenched with $H_2O$ (50 mL), extracted with EtOAc (20 mL×3), combined the organic layer and dried over $Na_2SO_4$, filtered and concentrated in vacuo, the crude was purified by prep-HPLC to give the product 186-5 (110.0 mg, 56.6% yield) as a white solid.

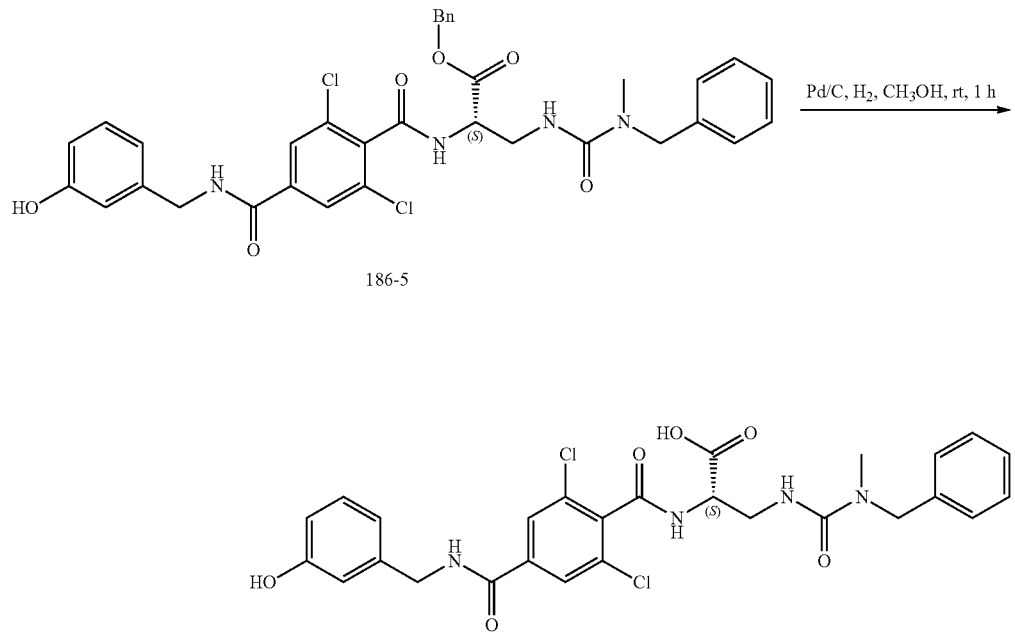

To a solution of 186-5 (100.0 mg, 0.15 mmol) in CH$_3$OH (10 mL) was added Pd/C (100.0 mg, 0.80 mmol), the reaction was stirred at rt under H$_2$ atmosphere for 1 h. After the consumption of starting material (detected by LCMS), the reaction was filtered, the filtrated was concentrated in vacuo, the crude was purified by prep-HPLC to get the product SU15210-0186-01 (35.0 mg, 40.5% yield) as a white solid.

$^1$H NMR (400 MHz, DMSO-d$_6$) δ 12.71 (brs, 1H), 9.36 (s, 1H), 9.27 (t, J=5.6 Hz, 1H), 8.96 (d, J=6.0 Hz, 1H), 7.96 (s, 2H), 7.30-7.34 (m, 2H), 7.19-7.26 (m, 3H), 7.12 (t, J=7.6 Hz, 1H), 6.72-6.74 (m, 2H), 6.62-6.65 (m, 1H), 6.53 (m, 1H), 4.52-4.55 (m, 1H), 4.35-4.50 (m, 4H), 3.38-3.53 (m, 2H), 2.72 (s, 3H).

SU15210-0187-01

Route for SU15210-0187-01:

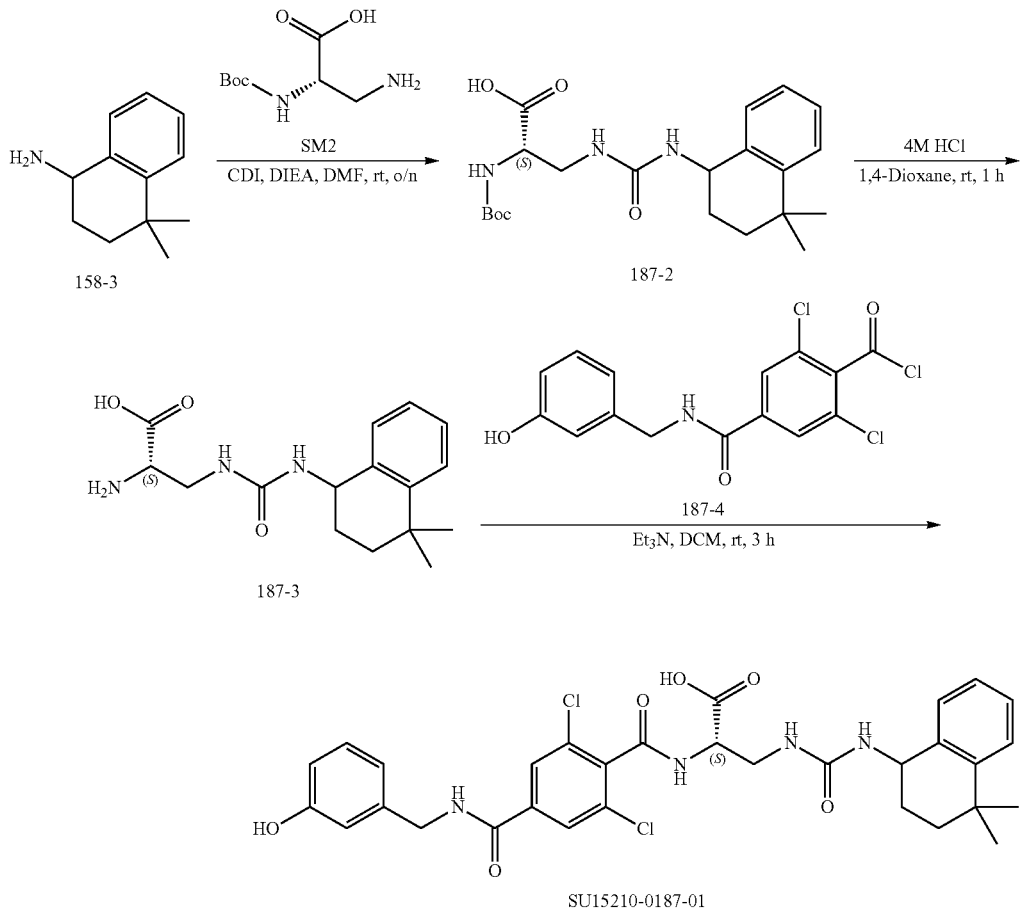

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 99.35%, Rt=1.464 min; MS Calcd.: 572.0; MS Found: 573.2 [M+H]$^+$.

HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 100.00%, Rt=6.462 min.

The Synthesis of (2S)-2-(tert-butoxycarbonylamino)-3-(3-(4,4-dimethyl-1,2,3,4-tetrahydronaphthalen-1-yl)ureido)propanoic Acid (187-2)

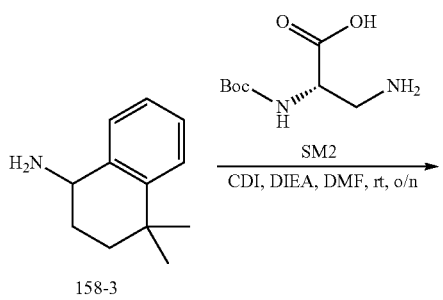

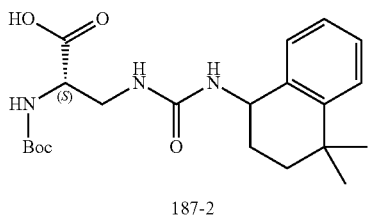

187-2

To a solution of 158-3 (192.8 mg, 1.1 mmol) in DMF (10 mL) was added DIPEA (142.2 mg, 1.1 mmol), CDI (158.4 mg, 1.0 mmol) and SM2 (224.7 mg, 1.1 mmol), the reaction was stirred at rt for overnight. After the reaction was finished (detected by LCMS), the reaction mixture was purified directly by prep-HPLC to get the product 187-2 (245.0 mg, 54.9% yield) as a white solid.

The Synthesis of (2S)-2-amino-3-(3-(4,4-dimethyl-1,2,3,4-tetrahydronaphthalen-1-yl)ureido)propanoic Acid (187-3)

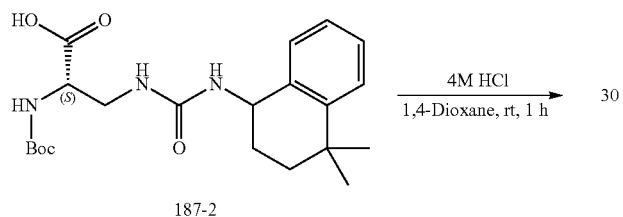

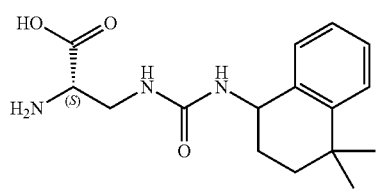

187-3

To a solution of 187-2 (120.0 mg, 0.3 mmol) in HCl (3 mL, 2 M in 1,4-Dioxane), the reaction was stirred at rt for 1 h. After the reaction was finished (detected by LCMS), the reaction was concentrated in vacuo, the crude 187-3 (90.0 mg, 99.6% yield) was get as white solid and used directly for next step without further purification.

The Synthesis of 2,6-dichloro-4-(3-hydroxybenzylcarbamoyl)benzoyl chloride (187-4)

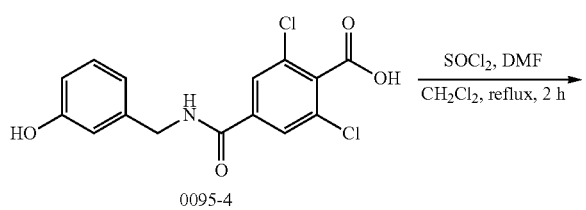

0095-4

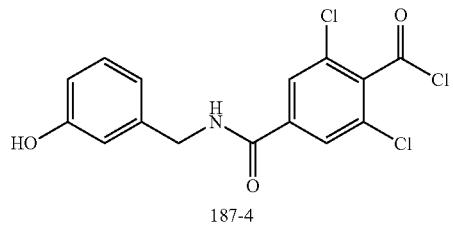

187-4

To a solution of 0095-4 (102.1 mg, 0.3 mmol) in CH$_2$Cl$_2$ (5 mL) was dropwised thionyl chloride (43.0 mg, 0.4 mmol) and a tip of DMF, the reaction was stirred at reflux for 2 h. After the reaction was finished (detected by LCMS), the reaction was concentrated in vacuo, the crude 187-4 (107.0 mg, 99.5% yield) was obtained as brown oil and used directly for next step without further purification.

The Synthesis of (2S)-2-(2,6-dichloro-4-(3-hydroxybenzylcarbamoyl)benzamido)-3-(3-(4,4-dimethyl-1,2,3,4-tetrahydronaphthalen-1-yl)ureido)propanoic Acid (SU15210-0187-01)

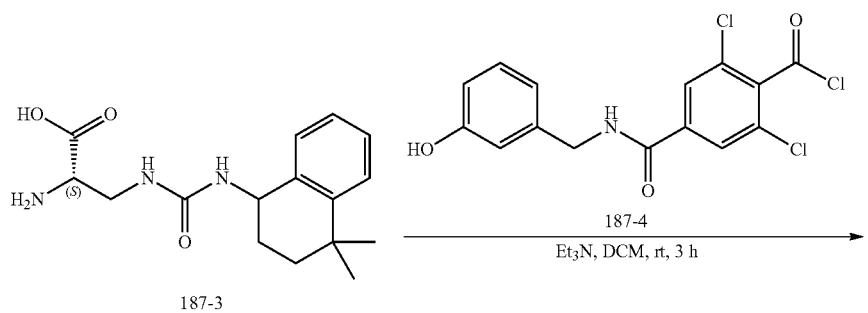

-continued

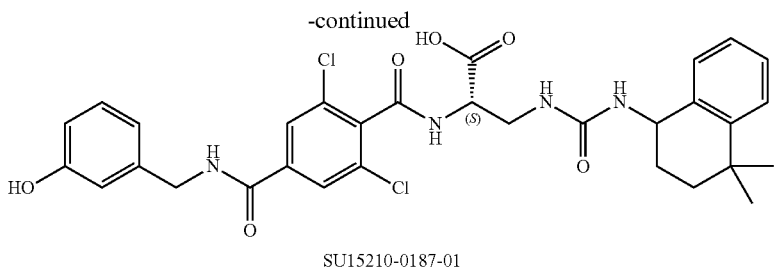

SU15210-0187-01

To a solution of 187-3 (92.0 mg, 0.3 mmol) in $CH_2Cl_2$ (5 mL) was added TEA (90.0 mg, 0.9 mmol) and 187-4 (108.0 mg, 0.3 mmol), the reaction was stirred at rt for 3 h. After the reaction was finished (detected by LCMS), the reaction solvent was removed in vacuo, the crude was purified directly by prep-HPLC to get the product SU15210-0187-01 (29.0 mg, 15.4% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 1.6 min, then under this condition for 1.4 min, finally changed to 95% [water+0.05% $NH_4HCO_3$] and 5% [$CH_3CN$+0.05% $NH_4HCO_3$] in 0.05 min and under this condition for 0.7 min), Purity: 100.00%, Rt=1.589 min; MS Calcd.: 626.0; MS Found: 626.8 $[M+H]^+$.

HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 5.0 min, then under this condition for 1.0 min, finally changed to 95% [water+0.05% $NH_4HCO_3$] and 5% [$CH_3CN$+0.05% $NH_4HCO_3$] in 0.1 min and under this condition for 5 min), Purity: 100.00%, Rt=7.474 min.

$^1$H NMR (400 MHz, DMSO-$d_6$) δ 9.36 (s, 1H), 9.23 (t, J=5.6 Hz, 1H), 8.53 (s, 1H), 7.93 (s, 2H), 7.30 (d, J=8.0 Hz, 1H), 7.04-7.18 (m, 4H), 6.60-6.72 (m, 4H), 5.85 (s, 1H), 4.68-4.72 (m, 1H), 4.38 (d, J=5.6 Hz, 2H), 4.21 (d, J=6.0 Hz, 1H), 3.31-3.44 (m, 2H), 1.53-1.83 (m, 4H), 1.23 (s, 3H), 1.20 (s, 3H).

SU15210-0188-01
Route for SU15210-0188-01:

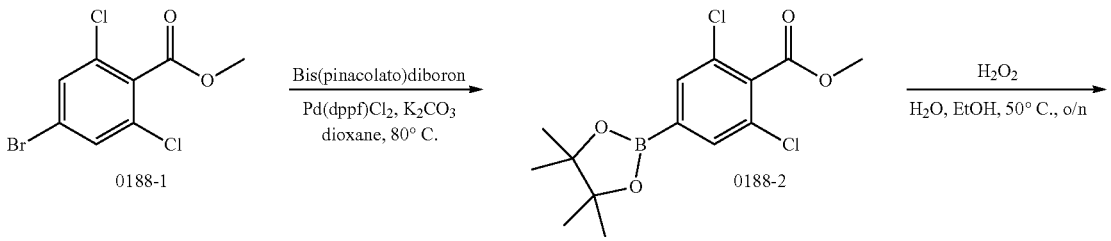

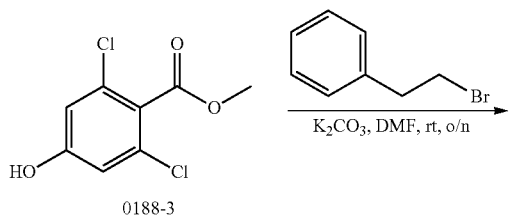

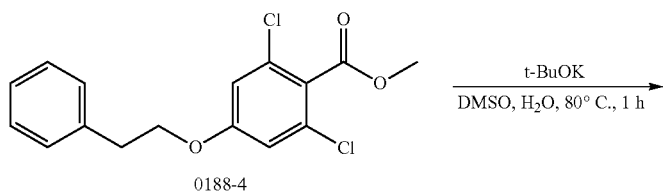

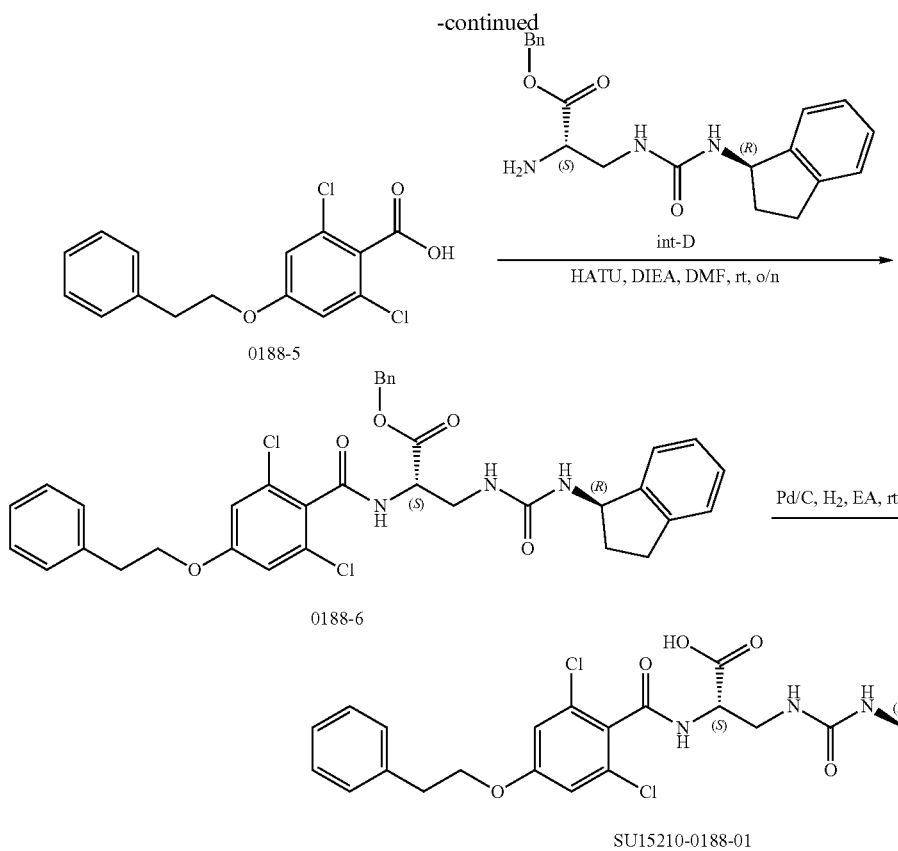

The Synthesis of Methyl 2,6-dichloro-4-(4,4,5,5-tetramethyl-1,3,2-dioxaborolan-2-yl)benzoate (0188-2)

The Synthesis of Methyl 2,6-dichloro-4-hydroxybenzoate (0188-3)

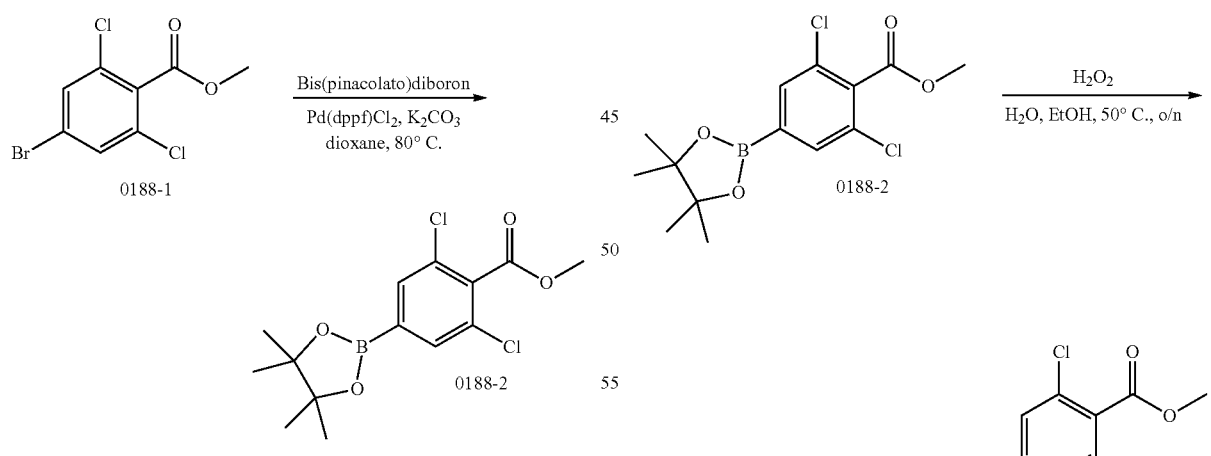

To a solution of 0188-1 (500 mg, 1.76 mmol) in dioxane (10 mL) was added bis(pinacolato)diboron (894 mg, 3.52 mmol), K₂CO₃ (486 mg, 3.52 mmol) and Pd(dppf)Cl₂ (132 mg, 0.18 mmol). The mixture was stirred at 80° C. for overnight. Remove the solid by filtration, the filtrate was concentrated and purified by CC (5% to 10% ethyl acetate in petroleum ether) to get 0188-2 (330 mg, 57% yield) as a white solid.

To a solution of 0188-2 (380 mg, 1.15 mmol) in EtOH/H₂O (2:1, 10 mL) was added H₂O₂ (30% w/w, 5 mL). The solution was stirred at 50° C. for overnight. Concentrated and purified by reverse-flash to get 0188-3 (120 mg, 55% yield) as a white solid.

461
The Synthesis of Methyl 2,6-dichloro-4-phenethoxybenzoate (0188-4)

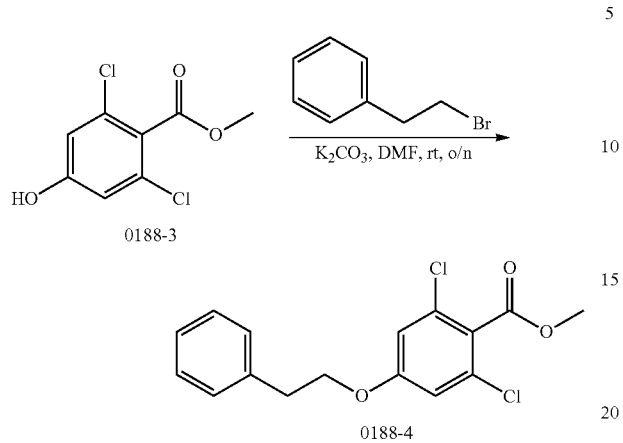

To a solution of 0188-3 (120 mg, 0.55 mmol) in DMF (10 mL) was added K₂CO₃ (150 mg, 1.10 mmol) and (2-bromoethyl)benzene (153 mg, 0.83 mmol), the solution was stirred at room temperature for overnight. Filtrated to remove the solid, the filtrate was concentrated and purified by CC (10% to 20% ethyl acetate in petroleum ether) to get 0188-4 (120 mg, 68% yield) as colorless oil.

462
The Synthesis of 2,6-dichloro-4-phenethoxybenzoic Acid (0188-5)

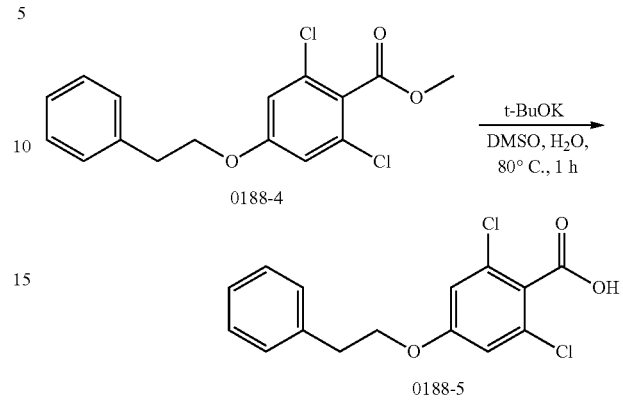

To a solution of 0188-4 (120 mg, 0.37 mmol) in DMSO (5 mL) was added t-BuOK (83 mg, 0.74 mmol) and H₂O (0.05 mL), the solution was heated to 80° C. and stirred for 1 h. 1N HCl aq. was added to pH 1, then purified by prep-HPLC to get 0188-5 (40 mg, 35% yield) as a light brown solid.

The Synthesis of (S)-benzyl 2-(2,6-dichloro-4-phenethoxybenzamido)-3-(3-((R)-2,3-dihydro-1H-inden-1-yl)ureido)propanoate (0188-6)

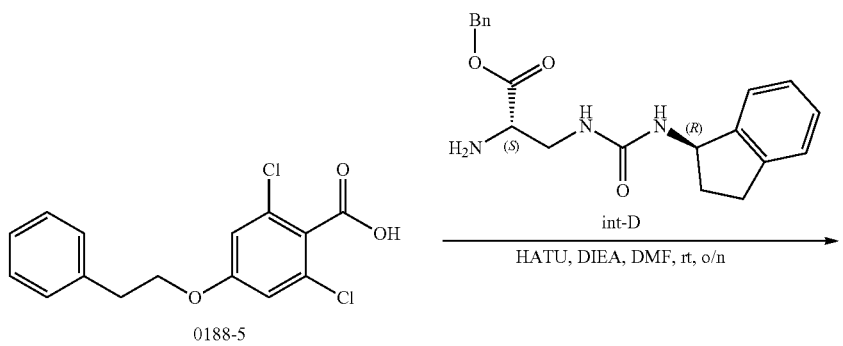

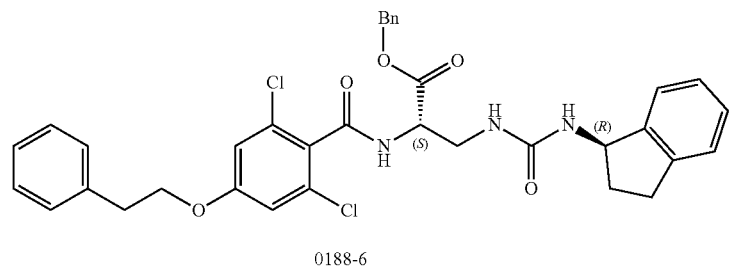

To a solution of 0188-5 (40 mg, 0.13 mmol) in DMF (5.0 mL) was added int-D (46 mg, 0.13 mmol), HATU (50 mg, 0.13 mmol) and DIEA (34 mg, 0.26 mmol). The solution was stirred at room temperature for overnight. Poured the solution into water (50 mL), collect the precipitate by filtration to get the crude product then further purified by CC (0% to 10% MeOH in DCM) to get 0188-6 (30 mg, 36% yield) as a white solid.

The Synthesis of (S)-2-(2,6-dichloro-4-phenethoxy-benzamido)-3-(3-((R)-2,3-dihydro-1H-inden-1-yl)ureido)propanoic Acid (SU15210-0188-01)

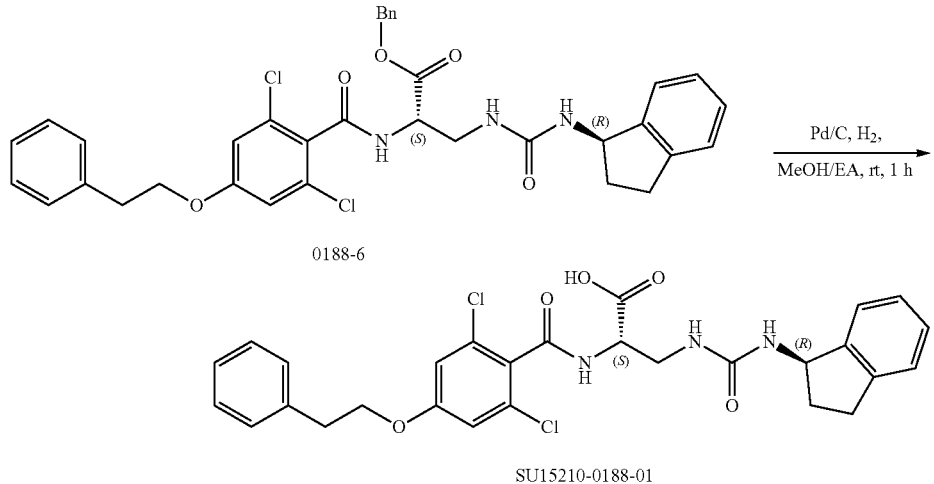

To a solution of 0188-6 (30 mg, 0.05 mmol) in MeOH/EA (1:1, 5.0 mL) was added Pd/C (5 mg). The mixture was stirred at room temperature for 1 h. Filtrated and the filtrate was concentrated and purified by prep-HPLC to get SU15210-0188-01 (6 mg, 23% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.904 min; MS Calcd.: 555.2; MS Found: 556.2 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 99.81%. Rt=9.367 min.

$^1$H NMR (400 MHz, DMSO-d$_6$) δ 12.67 (br, 1H), 8.87 (d, J=7.6 Hz, 1H), 7.30-7.33 (m, 4H), 7.14-7.25 (m, 5H), 7.11 (s, 2H), 6.57 (d, J=8.4 Hz, 1H), 5.88 (t, J=5.6 Hz, 1H), 5.07 (q, J=8.0 Hz, 1H), 4.45 (q, J=5.6 Hz, 1H), 4.28 (t, J=6.8 Hz, 2H), 3.48-3.56 (m, 2H), 3.03 (t, J=5.6 Hz, 2H), 2.80-2.90 (m, 1H), 2.72-2.79 (m, 1H), 2.32-2.38 (m, 1H), 1.63-1.69 (m, 1H).

SU15210-0189-01
Route for SU15210-0189-01

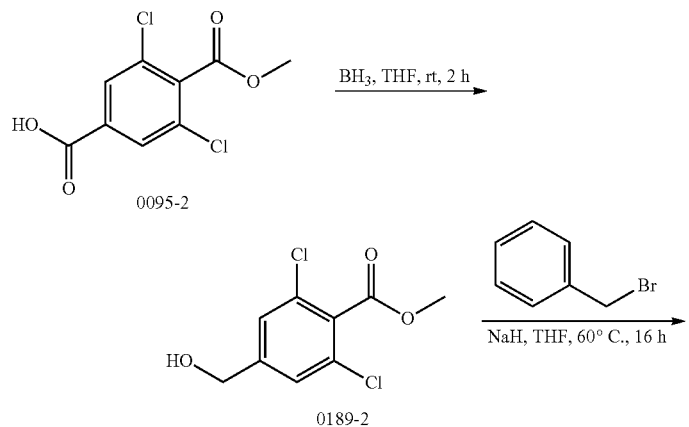

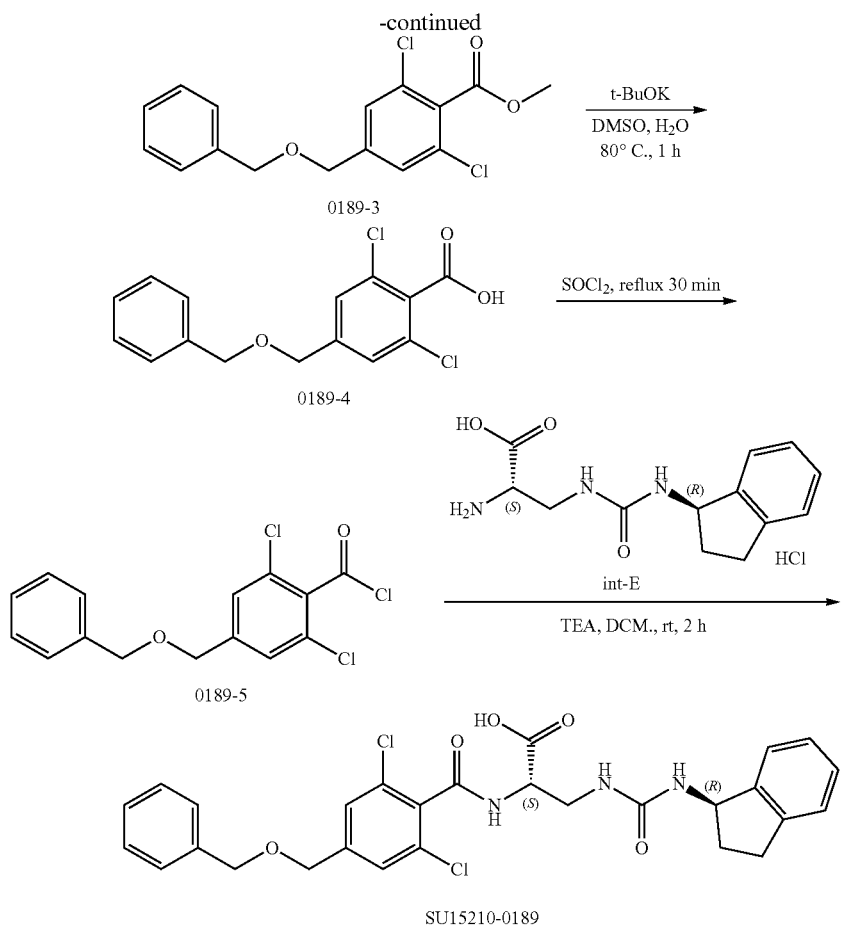

The Synthesis of Methyl 2,6-dichloro-4-(hydroxymethyl)benzoate (0189-2)

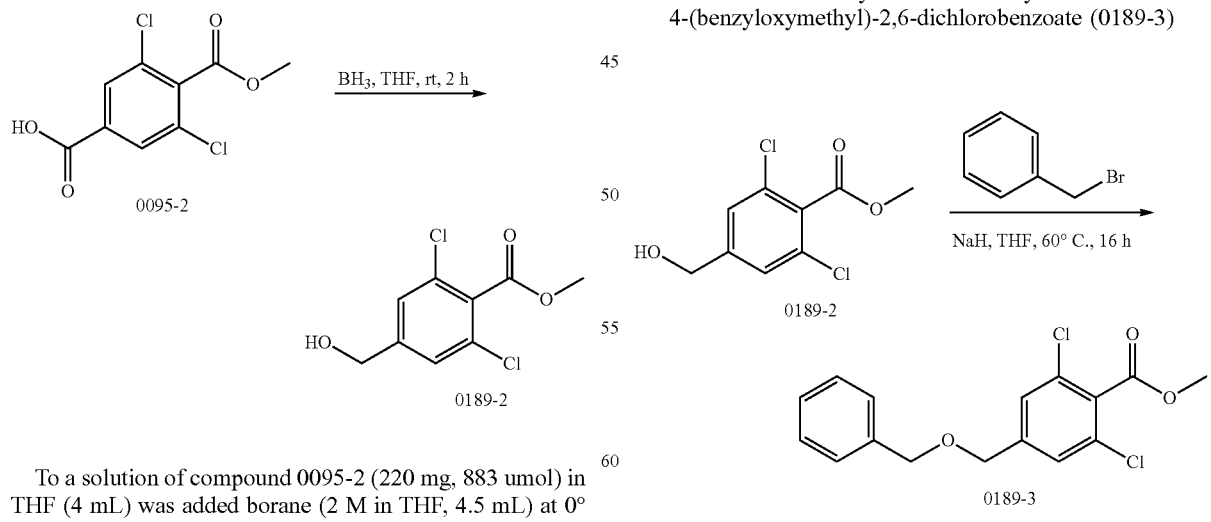

To a solution of compound 0095-2 (220 mg, 883 umol) in THF (4 mL) was added borane (2 M in THF, 4.5 mL) at 0° C., then allowed to warm up to room temperature and to stir for 2 h. After the consumption of starting material (by LCMS), the mixture was quenched with 20 mL HCl (1N). The solution was extracted with EA (20 mL×3) and dried over anhydrous sodium sulfate and concentrated on a rotary evaporator to give 0189-2 (205 mg, yield: 98.73%) as a white solid. The crude product was used for next step without purification.

The Synthesis of Methyl 4-(benzyloxymethyl)-2,6-dichlorobenzoate (0189-3)

To a solution of 0189-2 (205 mg, 872 umol) in THF (10 mL) was cooled in a ice bath and sodium hydride (20 mg, 2.62 mmol) was added, the mixture was stirred for 15 min and warmed to room temperature. Then (bromomethyl)

benzene (298 mg, 1.74 mmol) was added and the mixture was heat to 60° C. for overnight. After the consumption of the starting material, the mixture was quenched with water (20 mL), extracted with EtOAc (20 mL×3), dried over anhydrous sodium sulfate and filtered. The residue was concentrated and purified by pre-HPLC to get 0189-3 (260 mg, yield: 91.68%) as a white solid.

The Synthesis of 4-(benzyloxymethyl)-2,6-dichlorobenzoic Acid (0189-4)

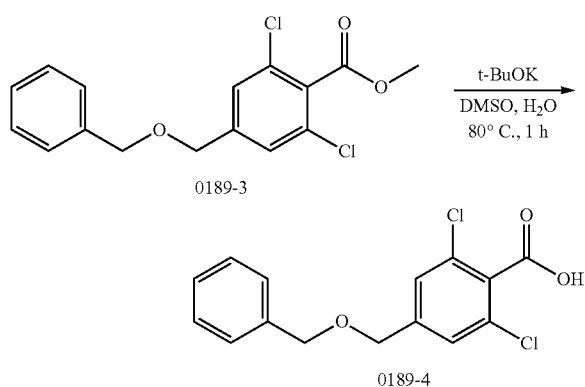

To a solution of compound 0189-3 (260 mg, 800 umol) in DMSO (4 mL) was added potassium tert-butoxide (89.72 mg, 800 umol) and the mixture was heat to 80° C. for 1 h. After the consumption of the starting material (by LCMS), the mixture was purified by pre-HPLC to give 0189-4 (175 mg, yield: 70.34%) as a white solid.

The Synthesis of 4-(benzyloxymethyl)-2,6-dichlorobenzoyl Chloride (0189-5)

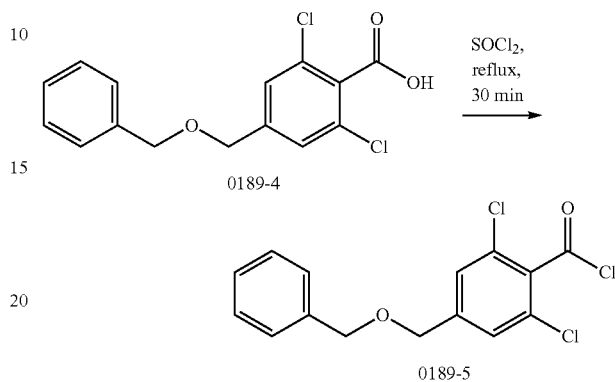

To a solution of 0189-4 (175 mg, 562 umol) in thionyl chloride (3 mL) was heated to reflux for 30 min. After the consumption of starting material (by LCMS), the mixture was concentrated under reduced pressure to give 0189-5 (185 mg, yield: 100%). The crude product was used for next step immediately.

The Synthesis of(S)-2-(4-(benzyloxymethyl)-2,6-dichlorobenzamido)-3-(3-((R)-2,3-dihydro-1H-inden-1-yl)ureido)propanoic Acid (SU15210-0189)

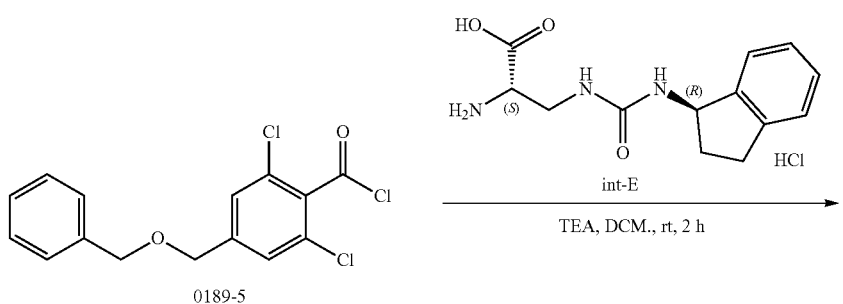

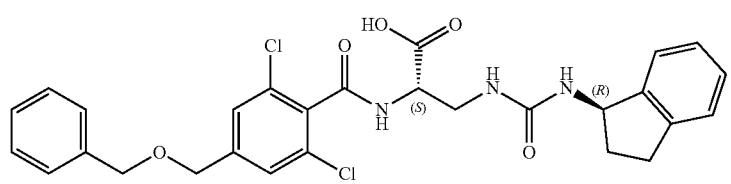

SU15210-0189-01

To a solution of compound int-E (148 mg, 562 umol) in DCM (5 mL) was added DIEA (285 mg, 2.81 mmol) at 0° C., then 189-5 (185 mg, 562 umol) was added into the mixture. This mixture was allowed to stir at room temperature for 2 hours. After the consumption of the starting material, the mixture was concentrated in vacuo and purified by pre-HPLC to get SU15210-0189 (77 mg, yield: 24.60%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH$_3$CN] to 0% water [0.05% TFA] and 100% [CH$_3$CN] in 1.6 min, then under this condition for 1.4 min, finally changed to 95% water [0.05% TFA] and 5% [CH$_3$CN] in 0.1 min and under this condition for 0.7 min), Purity: 100%, Rt=1.865 min; MS Found: 556.2 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH$_3$CN] to 0% water [0.05% TFA] and 100% [CH$_3$CN] in 10 min, then under this condition for 5 min, finally changed to 95% water [0.05% TFA] and 5% [CH$_3$CN] in 0.1 min and under this condition for 0.7 min), Purity: 100%, Rt=9.109 min; MS Found: 556.2 [M+H]$^+$.

$^1$H NMR (400 MHz, DMSO-d$_6$) δ 12.67 (br, 1H), 8.96 (d, J=7.2 Hz, 1H), 7.45 (s, 2H), 7.23-7.38 (m, 5H), 7.11-7.20 (m, 4H), 6.54 (d, J=8.4 Hz, 1H), 5.85 (t, J=6.0 Hz, 1H), 5.06 (q, J=8.0 Hz, 1H), 4.53-4.54 (m, 4H), 4.44-4.49 (m, 1H), 3.49-3.55 (m, 1H), 2.81-2.88 (m, 1H), 2.69-2.77 (m, 1H), 2.27-2.38 (m, 2H), 1.60-1.67 (m, 1H).

SU15210-0190-01

Route for SU15210-0190-01:

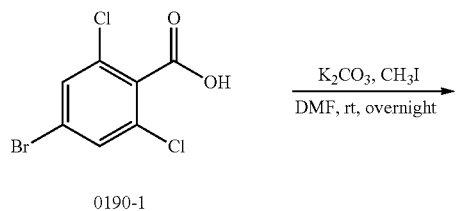

0190-1

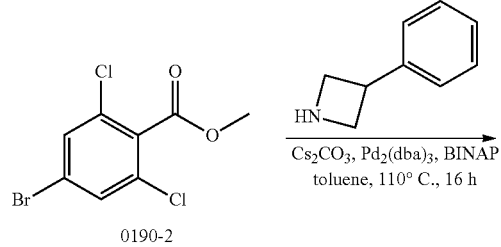

0190-2

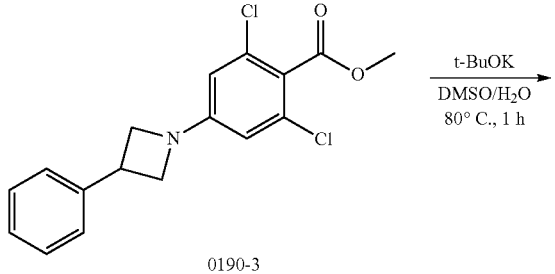

0190-3

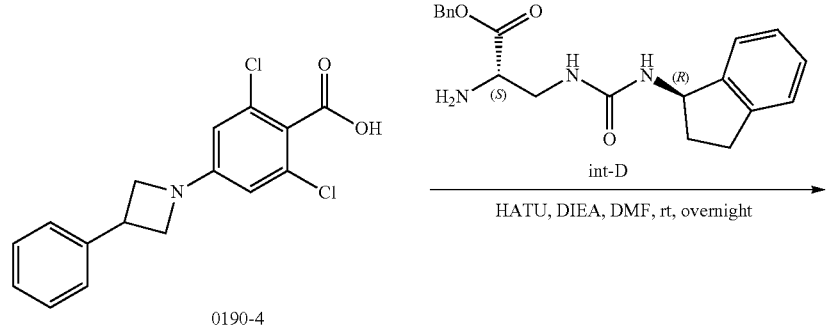

0190-4

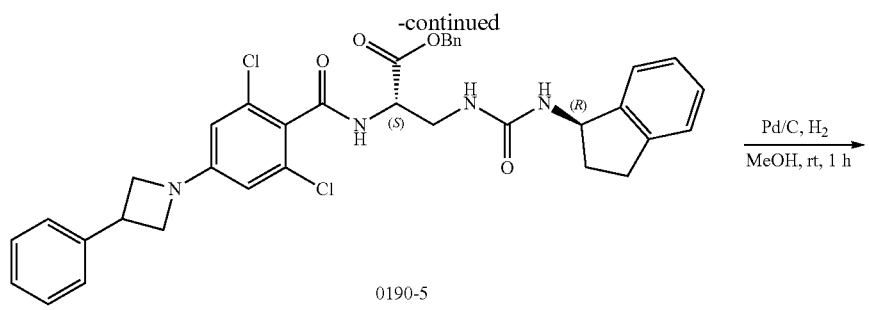

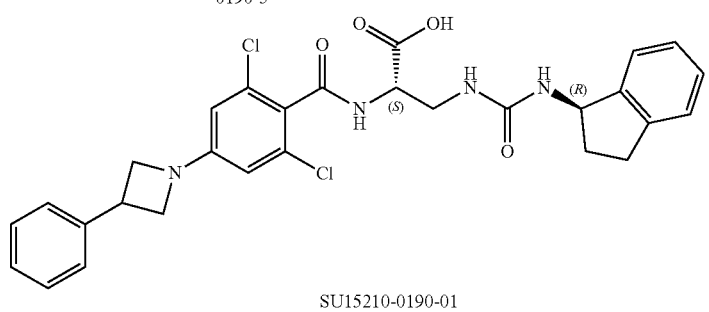

The Synthesis of Methyl 4-bromo-2,6-dichloro-benzoate (0190-2)

The Synthesis of Methyl 2,6-dichloro-4-(3-phenylazetidin-1-yl)benzoate (0190-3)

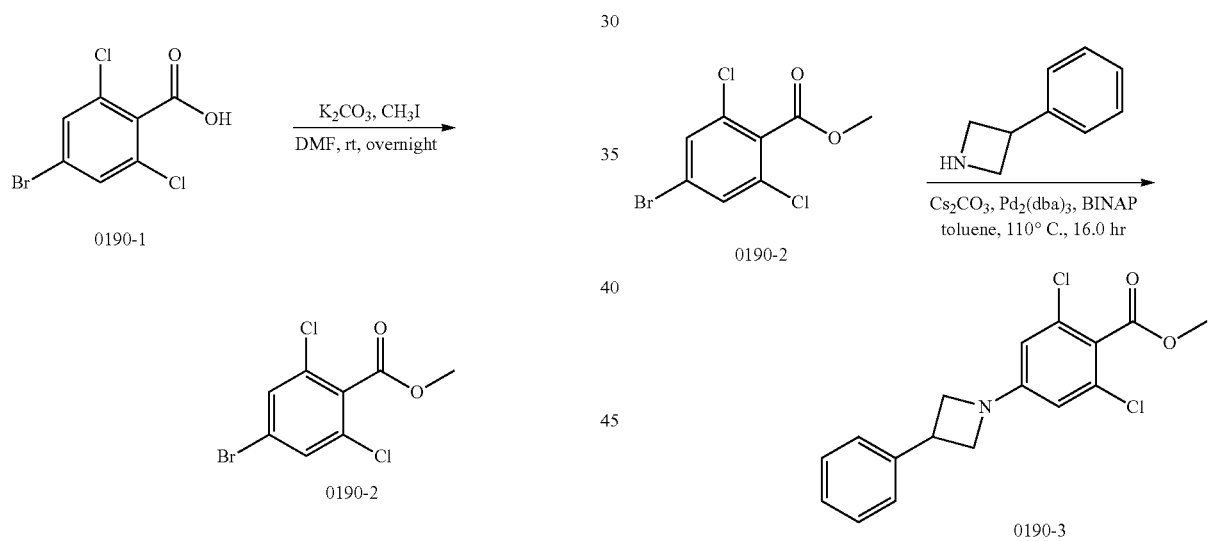

To a solution of 0190-1 (2.00 g, 7.41 mmol) and CH₃I (1.05 g, 7.41 mmol) in DMF (5 mL), was added K₂CO₃ (1.54 g, 11.11 mmol) and the mixture was stirred at room temperature for overnight. After the reaction was finished, water was added and the mixture was filtered and the liquid layer was extracted with EA (20 mL×3), the organic phase was combined and washed with water then brine, dried over Na₂SO₄, concentrated and purified by prep-HPLC to get 0190-2 (2.0 g, 95.06% yield) as a white solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 93.35%. Rt=0.853 min; MS Calcd.: 282.7; MS Found: 283.7 [M+H]⁺.

To a solution of 0190-2 (260 mg, 915.71 umol) and 3-phenylazetidine (121.96 mg, 915.71 umol) in toluene (5 mL) was added Cs₂CO₃ (895.07 mg, 2.75 mmol), Pd₂(dba)₃ (83.85 mg, 91.57 umol) and BINAP (57.02 mg, 91.57 umol), the solution was stirred at 110° C. for 16.0 hours under nitrogen atmosphere. After the reaction was finished, the mixture was filtered and the filtrate was concentrated to get the crude product 0190-3 (300 mg, 97.44% yield) as a yellow solid.

Agilent LCMS 1200-6120, Column: Halo C18 (30 mm*4.6 mm*2.7 μm); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5%

[CH₃CN] in 0.01 min. Purity is 67.59%. Rt=0.921 min; MS Calcd.: 335.7; MS Found: 336.7 [M+H]⁺.

The Synthesis of 2,6-dichloro-4-(3-phenylazetidin-1-yl)benzoic Acid (0190-4)

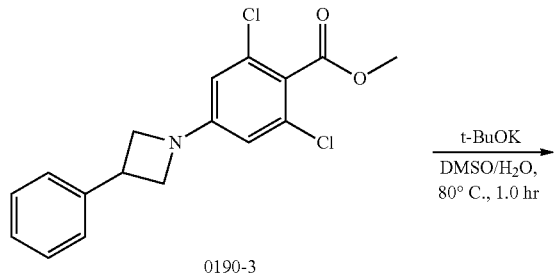

To a solution of 0190-3 (350 mg, 1.04 mmol) in DMSO (5 mL) and one drop of water, t-BuOK (175.22 mg, 1.56 mmol) was added and the solution was stirred at room temperature for 80° C. for 1 hour. After the reaction was finished, diluted hydrochloric acid was added in to adjust the pH to 3-4, then the solution was purified by prep-HPLC directly to get 0190-4 (130 mg, 38.76% yield) as a yellow solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 94.04%. Rt=0.780 min; MS Calcd.: 321.7; MS Found: 322.7 [M+H]⁺.

The Synthesis of Benzyl (2R)-3-(2,3,3a,7a-tetrahydro-1H-inden-2-ylcarbamoylamino)-2-[[2,6-dichloro-4-(3-phenylazetidin-1-yl)benzoyl]amino]propanoate (0190-5)

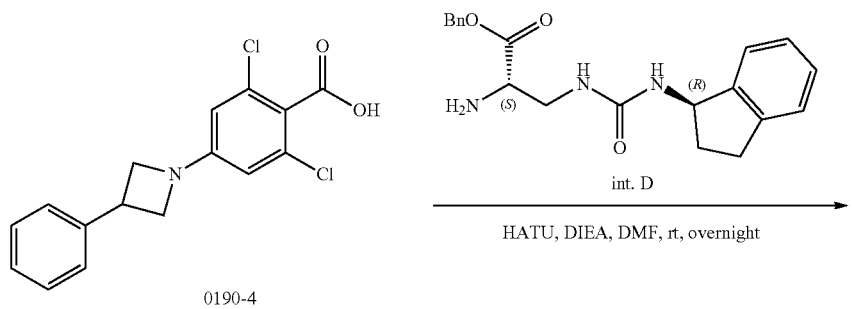

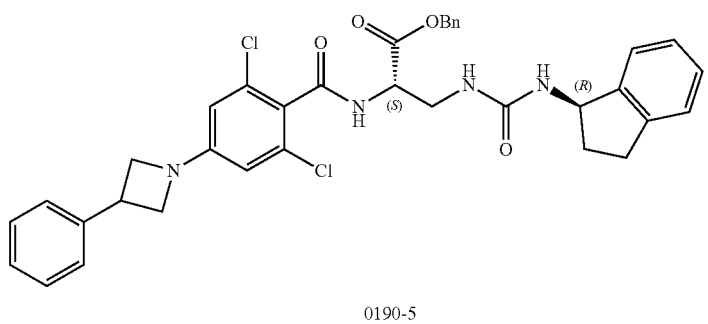

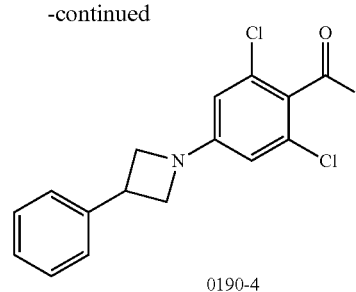

To a solution of 0190-4 (50 mg, 155.19 umol) and int.D (55.16 mg, 155.19 umol) in DMF (2 mL) was added HATU (88.51 mg, 232.79 umol) and DIEA (40.11 mg, 310.38 umol), the solution was stirred at room temperature for overnight. Purified by prep-HPLC directly to get 0190-5 (40 mg, 39.08% yield) as a white solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 64.82%. Rt=0.929 min; MS Calcd.: 656.7; MS Found: 657.7 [M+H]⁺.

The Synthesis of (2S)-3-(2,3,3a,7a-tetrahydro-1H-inden-2-ylcarbamoylamino)-2-[[2,6-dichloro-4-(3-phenylazetidin-1-yl)benzoyl]amino]propanoic acid (SU15210-0190-01)

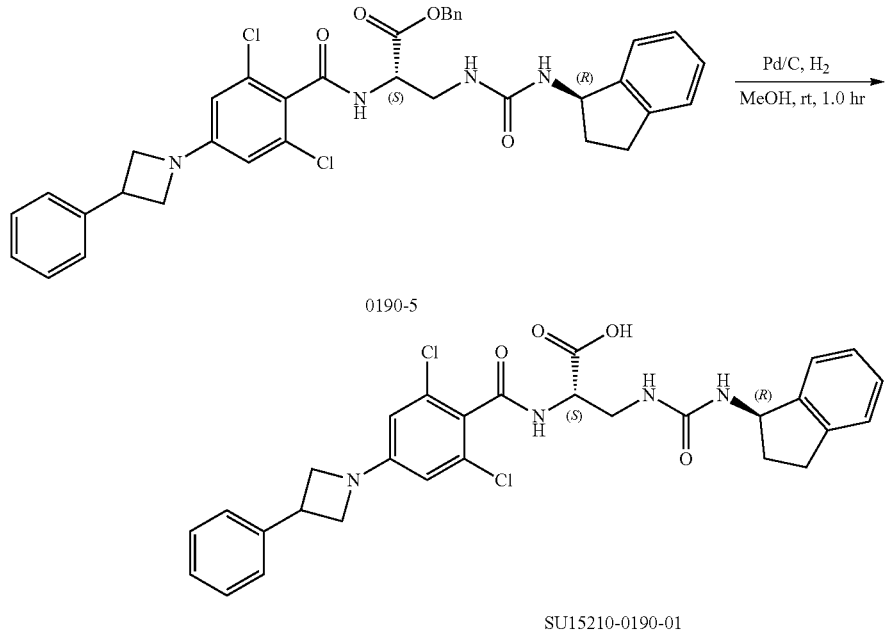

A solution of 0190-5 (40 mg, 60.64 umol) in MeOH (5 mL) was added Pd/C (20 mg, 142.21 umol), the solution was stirred at room temperature for 1.0 hour under hydrogen atmosphere (1.0 atm). After the reaction was finished, the mixture was filtered and washed by MeOH for three times, then the solution was concentrated and purified by prep-HPLC to get the product SU15210-0190-01 (3 mg, 8.69% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 96.6%. Rt=1.913 min; MS Calcd.: 566.7; MS Found: 567.7 [M+H]$^+$.

Agilent HPLC 1200; Column: Waters X-Bridge C18 (150 mm*4.6 mm*3.5 μm); Column Temperature: 40° C.; Flow Rate: 1.0 mL/min; Mobile Phase: from 95% [water+0.1% TFA] and 5% [CH$_3$CN] to 0% [water+0.1% TFA] and 100% [CH$_3$CN] in 10 min, then under this condition for 5 min, finally changed to 95% [water+0.1% TFA] and 5% [CH$_3$CN] in 0.1 min and under this condition for 5 min. Purity is 93.29%. Rt=9.457 min.

$^1$H NMR (400 MHz, DMSO-d$_6$) δ 8.76 (d, J=7.6 Hz, 1H), 7.15-7.38 (m, 10H), 6.59 (d, J=8.4 Hz, 1H), 6.54 (s, 2H), 5.89 (t, J=6.4 Hz, 1H), 5.07 (q, J=8.4 Hz, 1H), 4.41-4.43 (m, 1H), 4.31 (t, J=8.0 Hz, 2H), 3.94-4.01 (m, 1H), 3.86 (t, J=6.4 Hz, 2H), 3.49-3.56 (m, 1H), 2.67-2.90 (m, 2H), 2.33-2.40 (m, 1H), 1.62-1.71 (m, 1H).

SU15210-0191-01
Route for SU15210-0191-01:

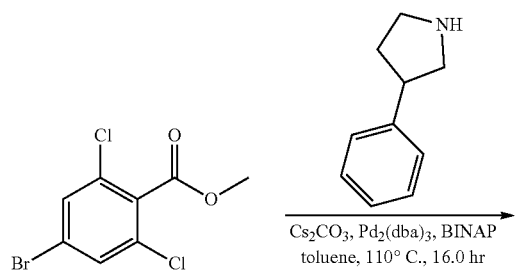

-continued
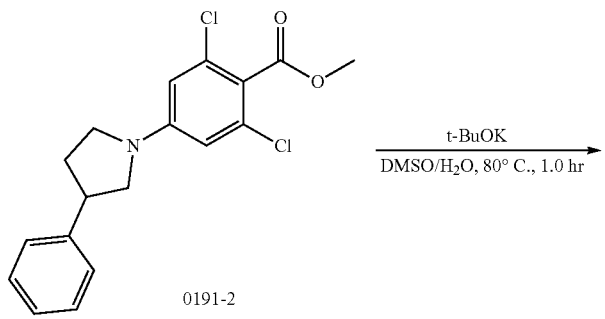
0191-2
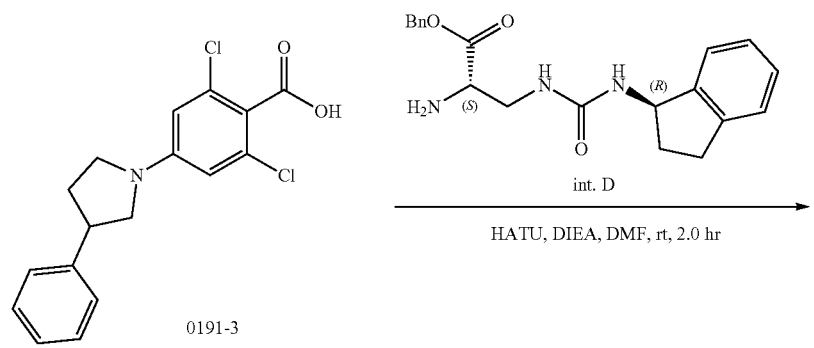
0191-3
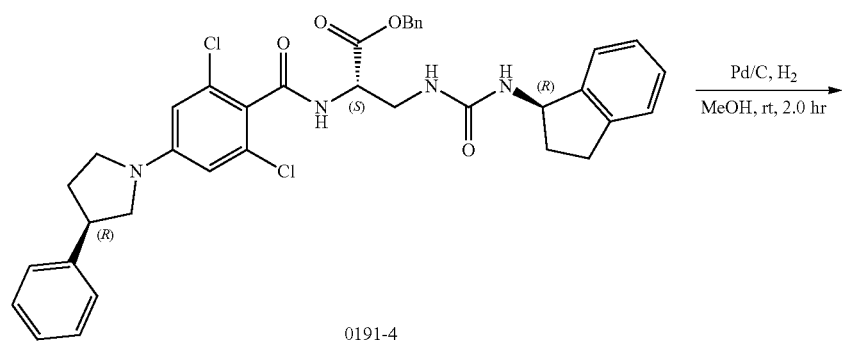
0191-4
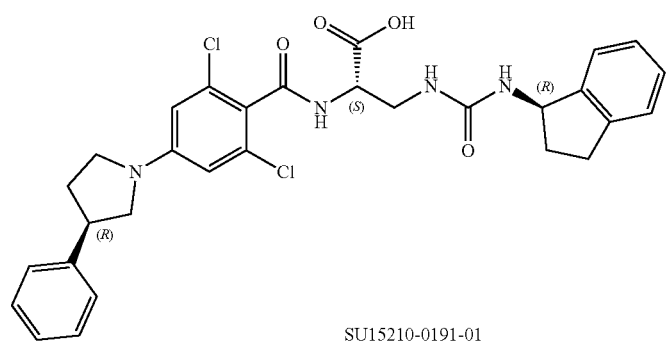
SU15210-0191-01

The Synthesis of Methyl 2,6-dichloro-4-(3-phenylpyrrolidin-1-yl)benzoate (0191-2)

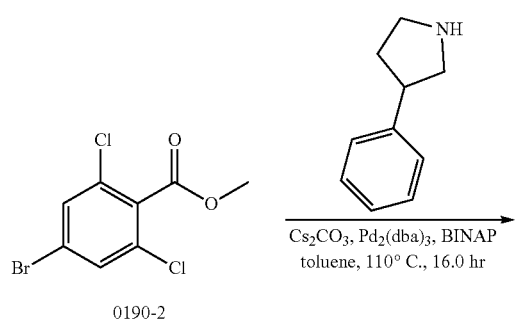

The Synthesis of 2,6-dichloro-4-(3-phenylpyrrolidin-1-yl)benzoic Acid (0191-3)

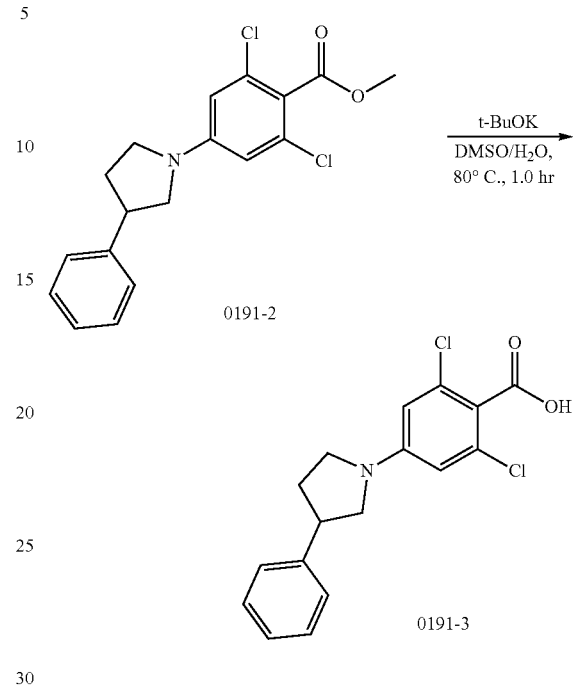

To a solution of 0190-2 (1.0 g, 6.52 mmol) and 3-phenylpyrrolidine (518.20 mg, 3.52 mmol) in toluene (5 mL) was added Cs₂CO₃ (3.44 g, 10.57 mmol), Pd₂(dba)₃ (322.51 mg, 352.19 umol) and BINAP (219.30 mg, 352.19 umol) at room temperature. The reaction mixture was then heated to 110° C. and stirred for 16.0 hours. After the reaction was finished, the mixture was filtered, then the solution was removed in vacuum and concentrated to get 0191-2 (0.58 g, 47.02% yield) as brown oil.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 77.52%. Rt=0.940 min; MS Calcd.: 349.7; MS Found: 350.7 [M+H]⁺.

To a solution of 0191-2 (0.58 g, 1.66 mmol) in the mixture of DMSO (5 mL) and two drops of water was added t-BuOK (278.73 mg, 2.48 mmol), the solution was stirred at 80° C. for 1.0 hour. After the reaction was finished, diluted hydrochloric acid was added in to adjust the pH to 3-4, then the solution was purified by pre-HPLC to get 0191-3 (200 mg, 35.92% yield) as a yellow solid.

Agilent LCMS 1200-6120, Column: Halo C18 (30 mm*4.6 mm*2.7 μm); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 100%. Rt=0.806 min; MS Calcd.: 335.7; MS Found: 336.7 [M+H]⁺.

The Synthesis of Benzyl (2R)-3-(2,3,3a,7a-tetrahydro-1H-inden-2-ylcarbamoylamino)-2-[[2,6-dichloro-4-(3-phenylpyrrolidin-1-yl)benzoyl]amino]propanoate (0191-4)

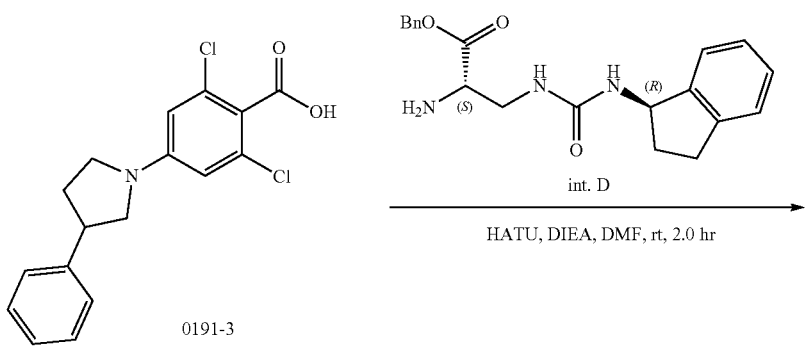

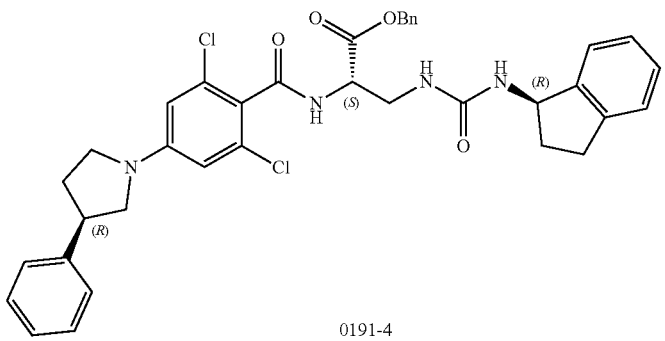

0191-4

To a solution of 0191-3 (100 mg, 297.43 μmol) and int.D (105 mg, 297.43 μmol) in DMF (5 mL) was added HATU (169.64 mg, 446.15 μmol) and DIEA (38.44 mg, 297.43 μmol), the mixture was stirred at room temperature for 2.0 hours. After the reaction was finished, the solution was concentrated in vacuo and purified by pre-HPLC to get 0191-4 (50 mg, 24.96% yield) as a white solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 78.05%. Rt=0.945 min; MS Calcd.: 670.7; MS Found: 671.7 [M+H]$^+$.

The Synthesis of (2R)-3-(2,3,3a,7a-tetrahydro-1H-inden-2-ylcarbamoylamino)-2-[[2,6-dichloro-4-(3-phenylpyrrolidin-1-yl)benzoyl]amino]propanoic acid (SU15210-0191-01)

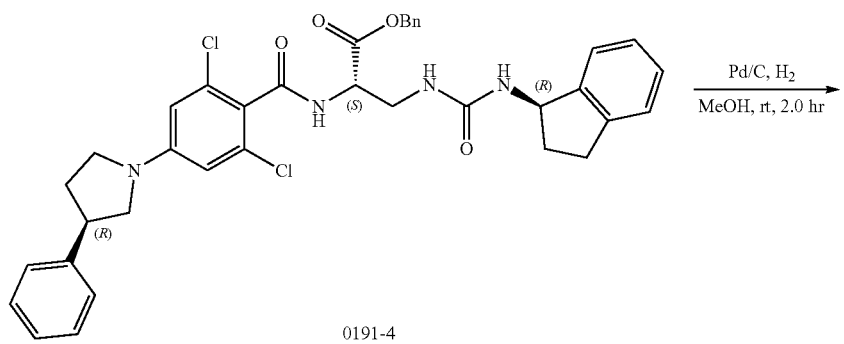

0191-4

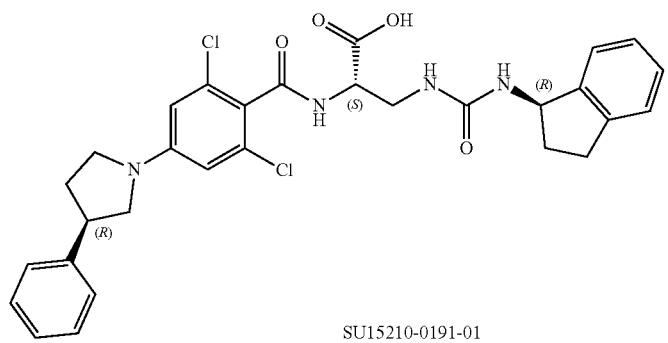

SU15210-0191-01

To a solution of 0191-4 (50 mg, 74.23 mol) in MeOH (5 mL) was added Pd/C (20.85 mg, 148.45 μmol) and the mixture was stirred at temperature for 2.0 hours under hydrogen atmosphere (1.0 atm). After the reaction was finished, the mixture was filtered and the solution was concentrated and purified by pre-HPLC to get SU15210-0191-01 (8.0 mg, 18.47% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [$CH_3CN$] to 0% [water+10 mM TFA] and 100% [$CH_3CN$] in 1.6 min, then under this condition for 1.4 min, finally changed to 95% [water+10 mM TFA] and 5% [$CH_3CN$] in 0.1 min. Purity is 98.40%. Rt=1.941 min; MS Calcd.: 580.7; MS Found: 581.7 $[M+H]^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% TFA] and 5% [$CH_3CN$] to 0% [water+0.1% TFA] and 100% [$CH_3CN$] in 10 min, then under this condition for 5 min, finally changed to 95% [water+0.1% TFA] and 5% [$CH_3CN$] in 0.1 min and under this condition for 5 min. Purity is 98.66%. Rt=9.693 min.

$^1$H NMR (400 MHz, DMSO-$d_6$) δ 8.70 (d, J=6.8 Hz, 1H), 7.33 (d, J=4.8 Hz, 5H), 7.14-7.26 (m, 6H), 6.58-6.59 (m, 4H), 5.90 (t, J=5.4 Hz, 1H), 5.08 (t, J=8.4 Hz, 1H), 4.41 (t, J=7.6 Hz, 1H), 3.75 (t, J=8.6 Hz, 1H), 2.67-2.90 (m, 3H), 2.33-2.40 (m, 4H), 2.01-2.11 (m, 1H), 1.62-1.70 (m, 1H), 1.15-1.24 (m, 1H).

SU15210-0192-01

Route for SU15210-0192-01

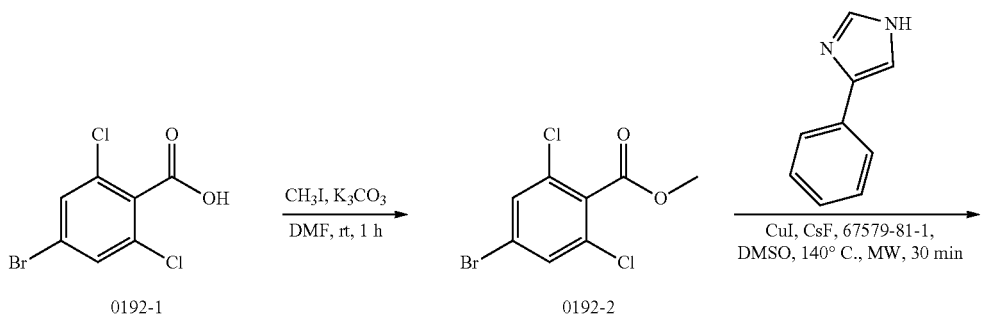

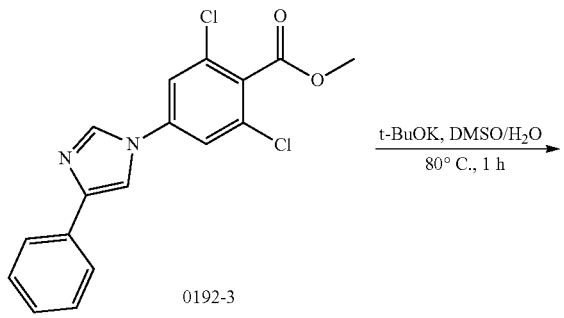

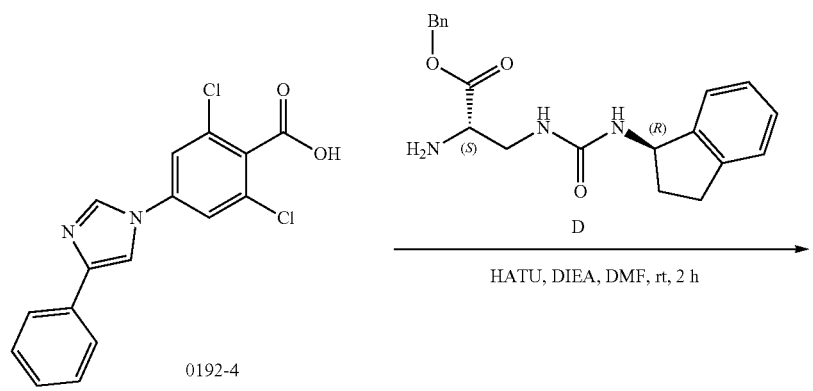

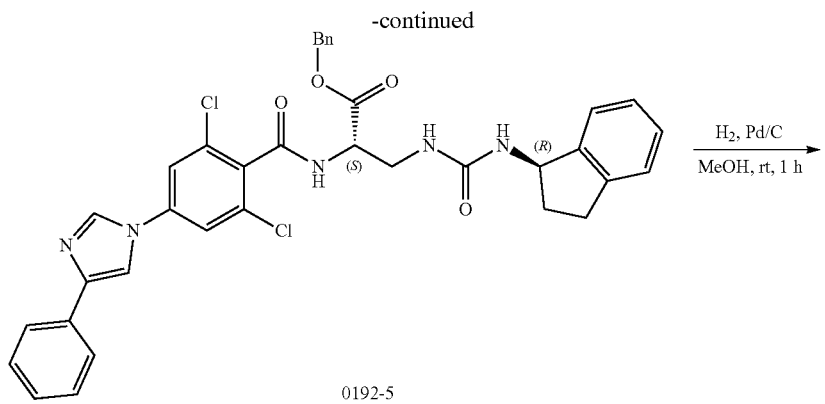

0192-5

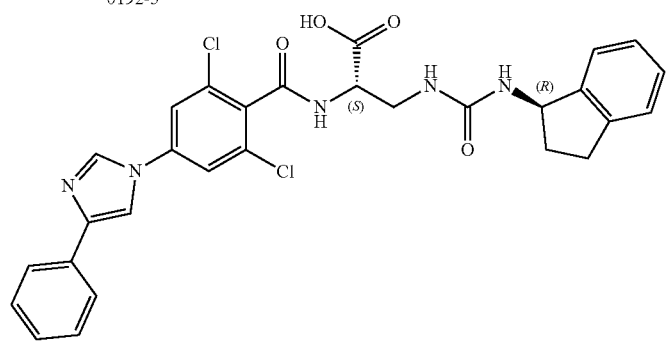

SU15210-0192-01

The Synthesis of Methyl 4-bromo-2,6-dichlorobenzoate (0192-2)

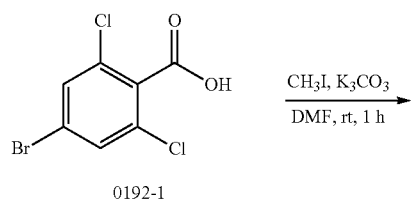

0192-1

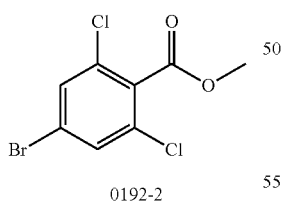

0192-2

To a solution of compound 0192-1 (1.0 g, 3.70 mmol) in DMF (10 mL) was added iodomethane (789 mg, 5.56 mmol) and potassium carbonate (1.02 g, 7.41 mmol). This mixture was allowed to stir at room temperature for 1 h. After the consumption of starting material (by LCMS), water (20 mL) was added, extracted with EtOAc (20 mL×3). The combined organic layers was washed with water (20 mL×3), dried over anhydrous sodium sulfate, filtered and concentrated to get 0192-2 (1.0 g, yield: 95.06%) as a light yellow solid.

The Synthesis of Methyl 2,6-dichloro-4-(4-phenyl-1H-imidazol-1-yl)benzoate (0192-3)

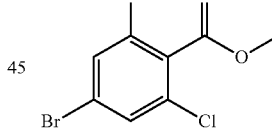

0192-2

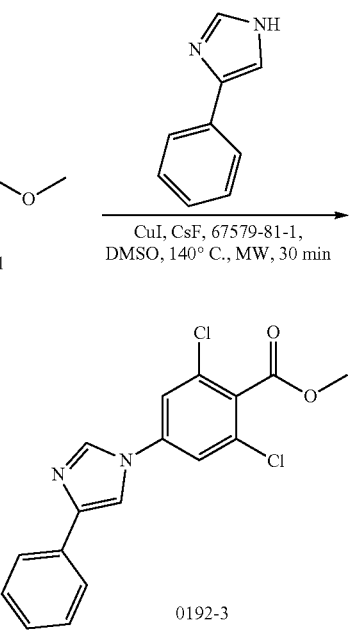

0192-3

To a solution of compound 0192-2 (600 mg, 2.11 mmol) in DMSO (10 mL) was added 4-phenyl-1H-imidazole (274 mg, 1.90 mmol), copper (I) iodode (40 mg, 0.211 mmol), cesium fluoride (641 mg, 4.22 mmol) and (1S, 2S)—N1, N2-dimethylcyclohexane (150.07 mg, 1.06 mmol) in vacuum tube filled with Ar through microwave at 140° C. for 0.5 h. After the radiation, the mixture was quenched with water (20 mL), extracted with EtOAc (20 mL×3). The residue was dried over anhydrous sodium sulfate, filtered and concentrated. This crude was purified by C.C. (20-25% EtOAc in hexane) to give 0192-3 (200 mg, yield: 27.3%) as a white solid.

The Synthesis of 2,6-dichloro-4-(4-phenyl-1H-imidazol-1-yl)benzoic Acid (0192-4)

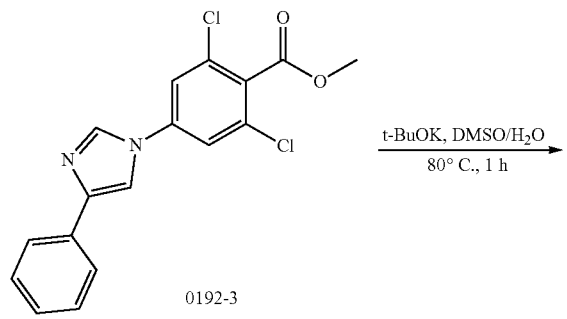

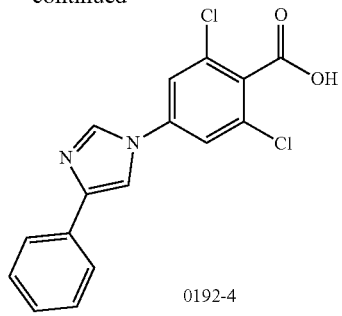

To a solution of compound 0192-3 (190 mg, 547 umol) in DMSO (4 mL) was added a solution of potassium tert-butoxide (123 mg, 1.09 mmol) in water (0.25 mL). The reaction mixture was heated to 80° C. for 1 h. After the consumption of the starting material, this mixture was purified by pre-HPLC to give 0192-4 (140 mg, yield: 76.8%) as a white solid.

The Synthesis of (S)-benzyl 2-(2,6-dichloro-4-(4-phenyl-1H-imidazol-1-yl)benzamido)-3-(3-((R)-2,3-dihydro-1H-inden-1-yl)ureido)propanoate (0192-5)

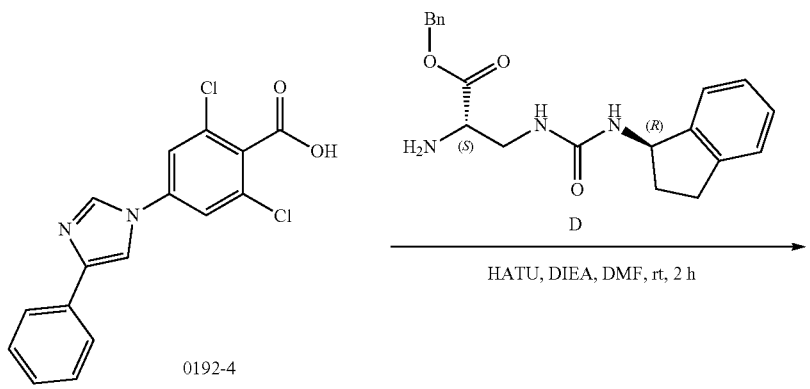

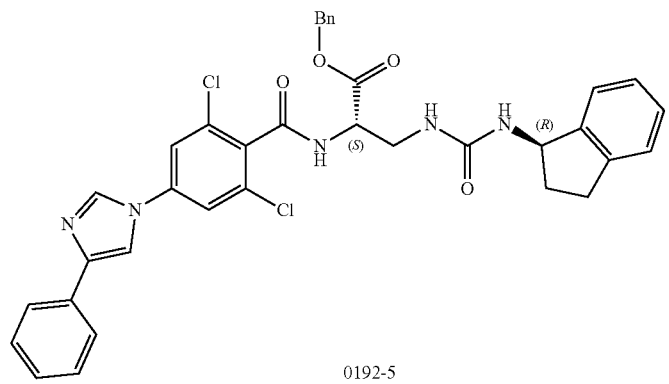

To a solution of compound 0192-4 (190 mg, 570.28 umol) in DMF (10 mL) was added HATU (436 mg, 1.14 mmol), DIEA (221 mg, 1.71 mmol) and the mixture was stirred for 15 min and then intermediate D (302 mg, 855.42 umol) was added and the reaction was stirred at rt for 2 h. After the consumption of starting material, the reaction was quenched with water (20 mL) and extracted with EtOAc (30 mL×3). The combined organic layers was washed with water and concentrated. The crude was purified by HPLC to get 0192-5 (200 mg, yield: 52.4%) as a white solid.

The Synthesis of (S)-2-(2,6-dichloro-4-(4-phenyl-1H-imidazol-1-yl)benzamido)-3-(3-((R)-2,3-dihydro-1H-inden-1-yl)ureido)propanoic Acid (SU15210-0192-01)

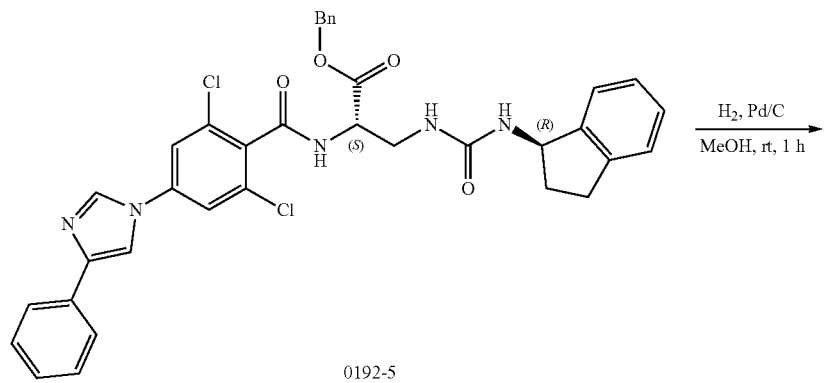

0192-5

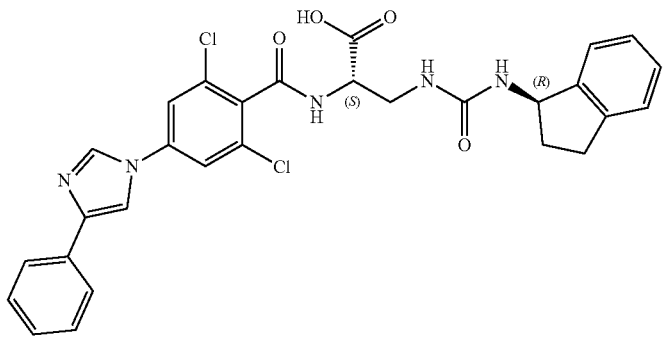

SU15210-0192-01

To a solution of compound 0192-5 (190 mg, 284 umol) in MeOH (5 mL) was added 10% palladium on activated carbon (43 mg, 28 umol) and replaced with hydrogen. The mixture was allowed to stir at room temperature for 1 h. After the consumption of starting material (by LCMS), the mixture was filtered and concentrated in vacuo, the crude was purified by pre-HPLC to give product SU15210-0192-01 (55 mg, yield: 33.5%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH$_3$CN] to 0% water [0.05% TFA] and 100% [CH$_3$CN] in 1.6 min, then under this condition for 1.4 min, finally changed to 95% water [0.05% TFA] and 5% [CH$_3$CN] in 0.1 min and under this condition for 0.7 min), Purity: 99.54%, Rt=1.622 min; MS Found: 578.2 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH$_3$CN] to 0% water [0.05% TFA] and 100% [CH$_3$CN] in 10 min, then under this condition for 5 min, finally changed to 95% water [0.05% TFA] and 5% [CH$_3$CN] in 0.1 min and under this condition for 0.7 min), Purity: 97.94%, Rt=7.371 min; MS Found: 578.2 [M+H]$^+$.

$^1$H NMR (400 MHz, DMSO-d$_6$) δ 12.78 (br, 1H), 9.06 (d, J=7.6 Hz, 1H), 8.56 (s, 1H), 8.51 (s, 1H), 8.05 (s, 2H), 7.85 (d, J=7.2 Hz, 2H), 7.42 (t, J=7.6 Hz, 2H), 7.15-7.29 (m, 5H), 6.61 (d, J=8.4 Hz, 1H), 5.90 (s, 1H), 5.07-5.13 (q, 1H), 4.48-4.53 (q, 1H), 3.52-3.60 (m, 1H), 2.84-2.91 (m, 1H), 2.72-2.80 (m, 1H), 2.30-2.44 (m, 1H), 1.63-1.75 (m, 1H).

491
Route for SU15210-0208-01
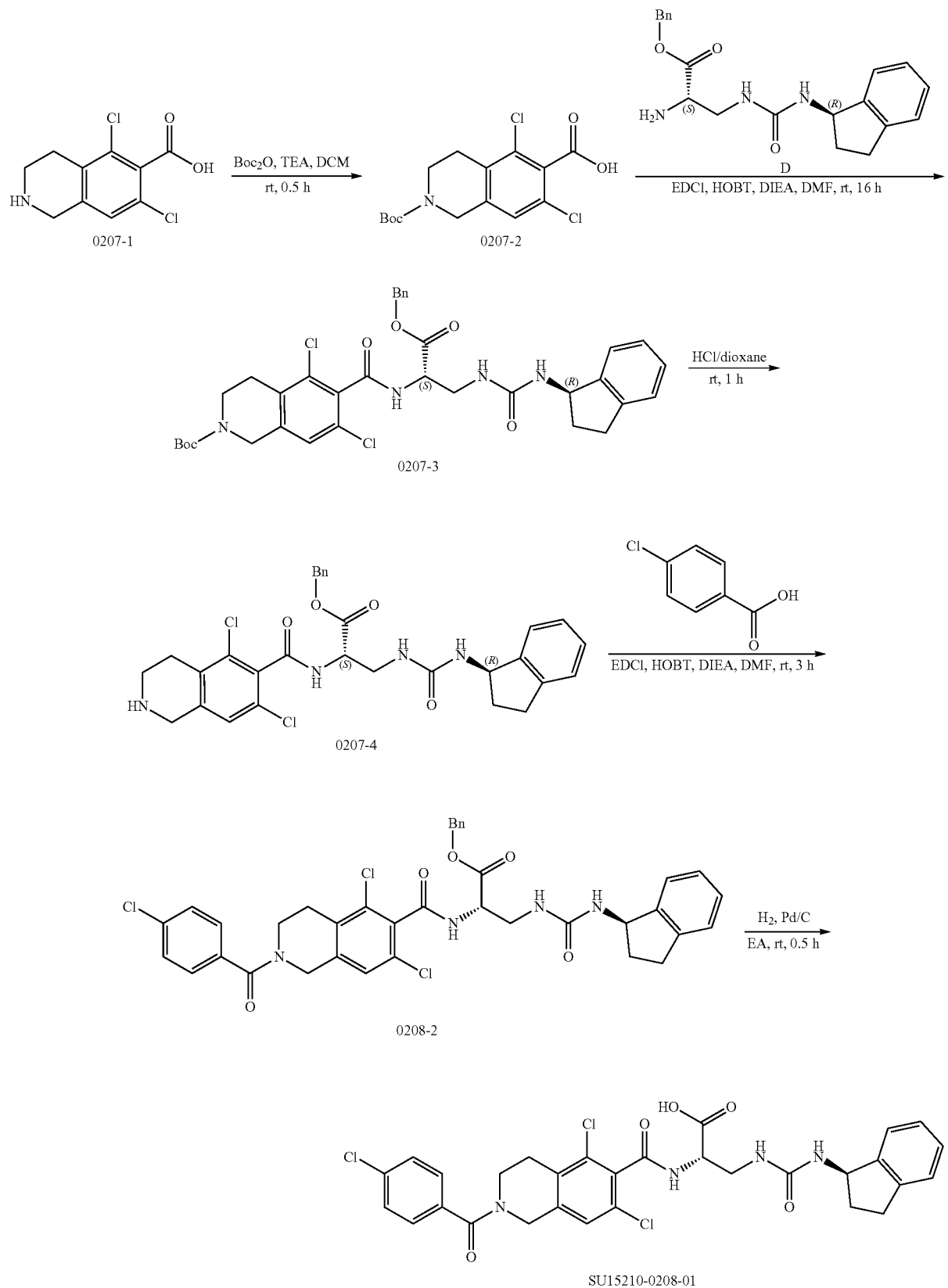

The Synthesis of 2-(tert-butoxycarbonyl)-5,7-dichloro-1,2,3,4-tetrahydroisoquinoline-6-carboxylic Acid (0207-2)

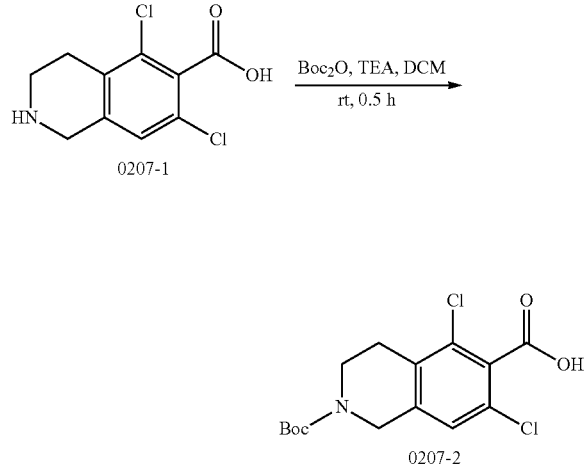

To a solution of compound 0207-1 (2.5 g, 10 mmol) in DCM (30 mL) was added TEA (2.06 g, 20 mmol) and Di-tert-butyl dicarbonate (2.44 g, 11 mmol), and the mixture was stirred room temperature for 0.5 h. After the consumption of starting material (by LCMS), the mixture was quenched by water (30 mL), extracted with DCM (30 mL×3), dried over anhydrous sodium sulfate, filtered and concentrated under reduced pressure to get 0207-2 (3.0 g, yield: 85.30%) as a yellow oil.

The Synthesis of Tert-Butyl 6-((S)-1-(benzyloxy)-3-(3-((R)-2,3-dihydro-1H-inden-1-yl)ureido)-1-oxopropan-2-ylcarbamoyl)-5,7-dichloro-3,4-dihydroisoquinoline-2 (1H)-carboxylate (0207-3)

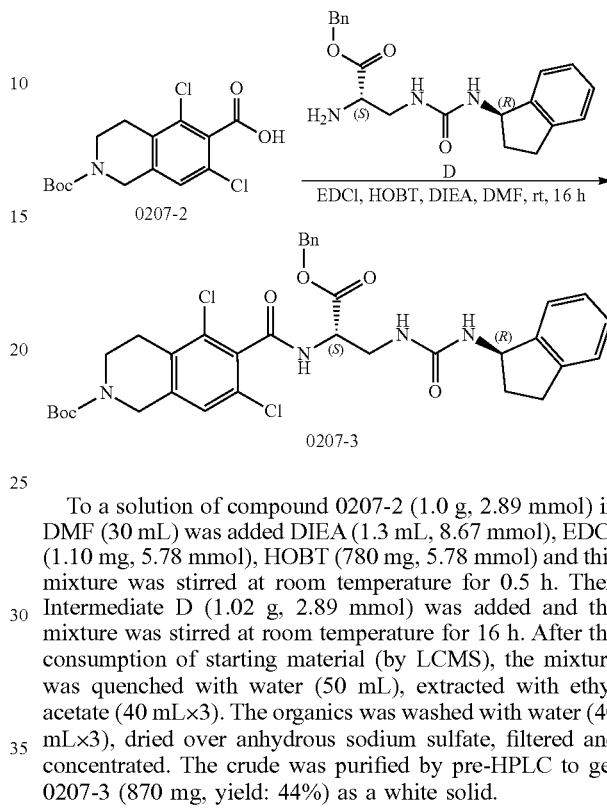

To a solution of compound 0207-2 (1.0 g, 2.89 mmol) in DMF (30 mL) was added DIEA (1.3 mL, 8.67 mmol), EDCI (1.10 mg, 5.78 mmol), HOBT (780 mg, 5.78 mmol) and this mixture was stirred at room temperature for 0.5 h. Then Intermediate D (1.02 g, 2.89 mmol) was added and the mixture was stirred at room temperature for 16 h. After the consumption of starting material (by LCMS), the mixture was quenched with water (50 mL), extracted with ethyl acetate (40 mL×3). The organics was washed with water (40 mL×3), dried over anhydrous sodium sulfate, filtered and concentrated. The crude was purified by pre-HPLC to get 0207-3 (870 mg, yield: 44%) as a white solid.

The Synthesis of (S)-benzyl 2-(5,7-dichloro-1,2,3,4-tetrahydroisoquinoline-6-carboxamido)-3-(3-((R)-2,3-dihydro-1H-inden-1-yl)ureido)propanoate (0207-4)

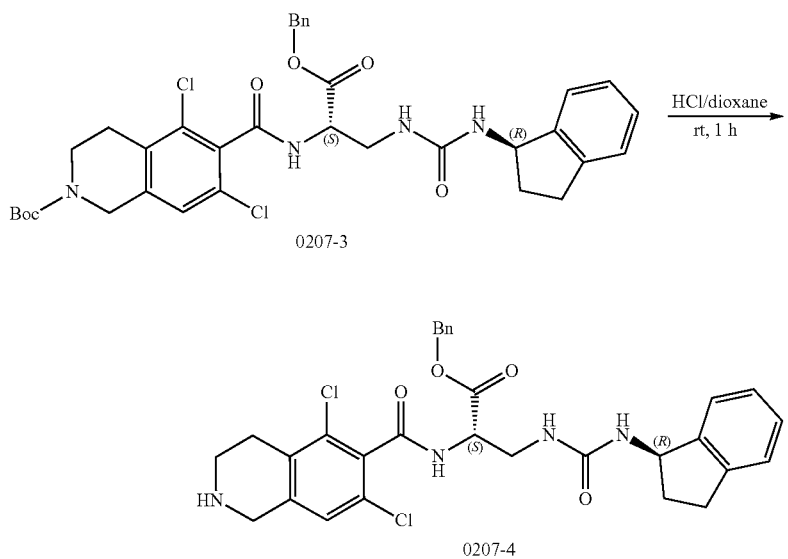

To the solution of compound 0207-3 (870 mg, 1.28 mmol) in 1,4-dioxane (10 mL) was added HCl (5 mL, 2.0N in dioxane) and this mixture was stirred at room temperature for 1 h. After the consumption of starting material (by LCMS), the solution was concentrated to give 0207-4 (740 mg, yield: 99.70%) as a white solid without purification.

The Synthesis of (S)-benzyl 2-(5,7-dichloro-2-(4-chlorobenzoyl)-1,2,3,4-tetrahydroisoquinoline-6-carboxamido)-3-(3-((R)-2,3-dihydro-1H-inden-1-yl)ureido)propanoate (0208-2)

To a solution of compound 4-chlorobenzoic Acid (33 mg, 208 umol) in DMF (10 mL) was added DIEA (73 mg, 568 umol), EDCI (73 mg, 378 umol) and HOBT (73 mg, 378 umol). The mixture was stirred at room temperature for 15 min, 0207-4 (110 mg, 189 umol) was added into this mixture and the mixture was stirred at room temperature for overnight. After the consumption of starting material (by LCMS), this mixture was quenched with water (20 mL), extracted with ethyl acetate (20 mL×3). The organics was washed with water (20 mL×3), dried over anhydrous sodium sulfate, filtered and concentrated. The crude was purified by pre-HPLC to get 0208-2 (80 mg, yield: 59%) as a white solid.

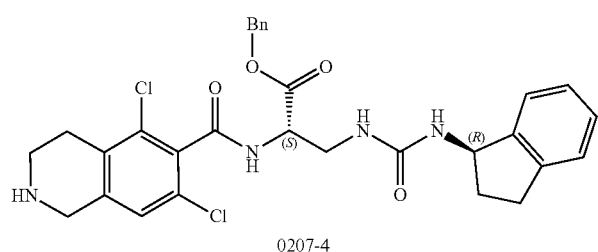

0207-4

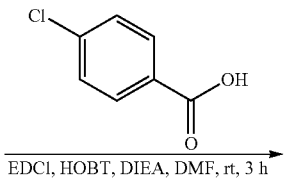

EDCl, HOBT, DIEA, DMF, rt, 3 h

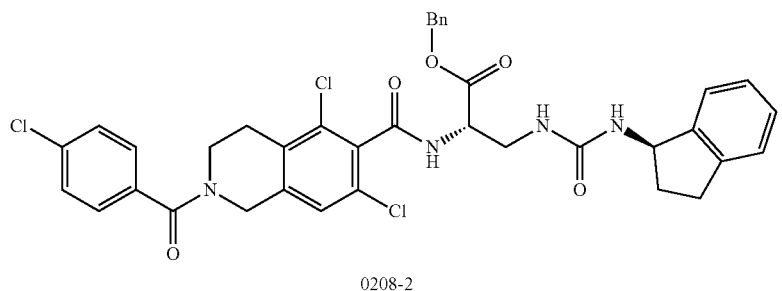

0208-2

The Synthesis of (S)-2-(5,7-dichloro-2-(4-chlorobenzoyl)-1,2,3,4-tetrahydroisoquinoline-6-carboxamido)-3-(3-((R)-2,3-dihydro-1H-inden-1-yl)ureido) propanoic Acid (SU15210-0208-01)

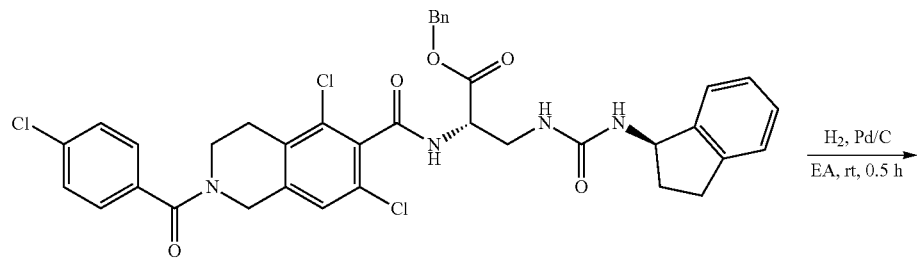

0208-2

H$_2$, Pd/C
EA, rt, 0.5 h

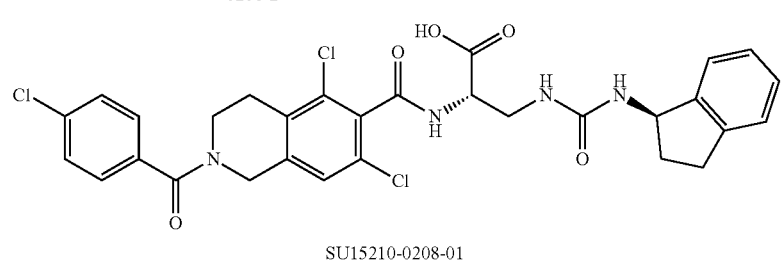

SU15210-0208-01

To a solution of compound 0208-2 (70 mg, 97 umol) in ethyl acetate (5 mL) was added 5% Pd on activated C (20 mg) and replaced with H$_2$ for 0.5 h. After the consumption of starting material (by LCMS), this mixture was filtered, concentrated under reduced pressure. The crude product was purified by pre-HPLC to get SU15210-0208-01 (11 mg, yield: 18%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH$_3$CN] to 0% water [0.05% TFA] and 100% [CH$_3$CN] in 1.6 min, then under this condition for 1.4 min, finally changed to 95% water [0.05% TFA] and 5% [CH$_3$CN] in 0.1 min and under this condition for 0.7 min), Purity: 100%, Rt=1.788 min; MS Found: 629.0 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH$_3$CN] to 0% water [0.05% TFA] and 100% [CH$_3$CN] in 10 min, then under this condition for 5 min, finally changed to 95% water [0.05% TFA] and 5% [CH$_3$CN] in 0.1 min and under this condition for 0.7 min), Purity: 99.88%, Rt=8.766 min; MS Found: 629.0 [M+H]$^+$.

$^1$H NMR (400 MHz, DMSO-d$_6$) δ 12.66 (br, 1H), 8.86 (s, 1H), 7.54-7.61 (m, 5H), 7.13-7.38 (m, 4H), 6.59 (d, J=4.4 Hz, 1H), 5.90 (s, 1H), 5.07 (q, J=8.0 Hz, 1H), 4.80 (s, 1H), 4.61 (s, 1H), 4.42-4.47 (m, 1H), 3.89 (s, 1H), 3.60 (s, 1H), 3.49-3.55 (m, 1H), 2.71-2.90 (m, 4H), 2.32-2.39 (m, 1H), 1.62-1.72 (m, 1H).

Route for SU15210-0209-01

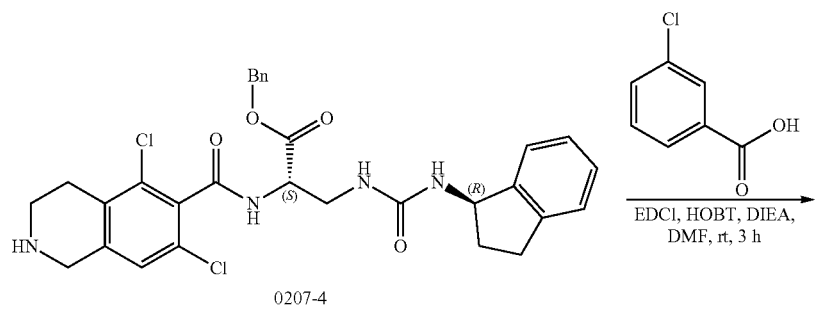

0207-4

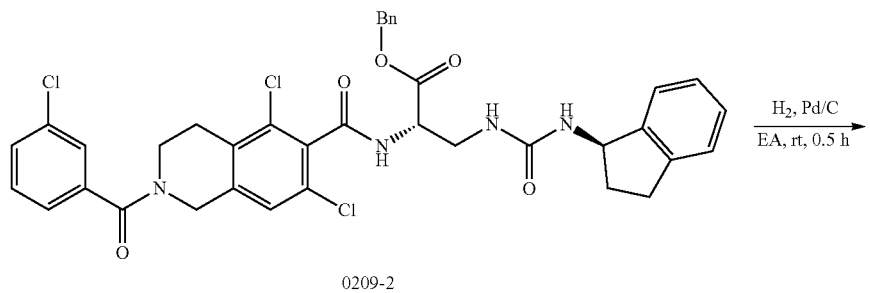

0209-2

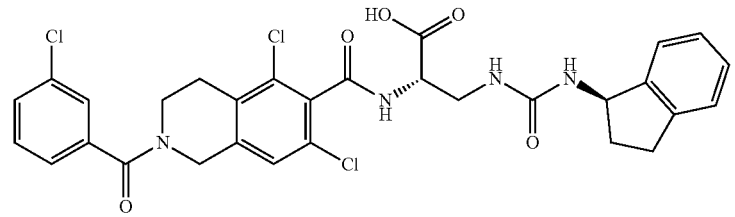

SU15210-0209-01

DMSO—d$_6$ as solvent

The Synthesis of (S)-benzyl 2-(5,7-dichloro-2-(3-chlorobenzoyl)-1,2,3,4-tetrahydroisoquinoline-6-carboxamido)-3-(3-((R)-2,3-dihydro-1H-inden-1-yl)ureido)propanoate (0209-2)

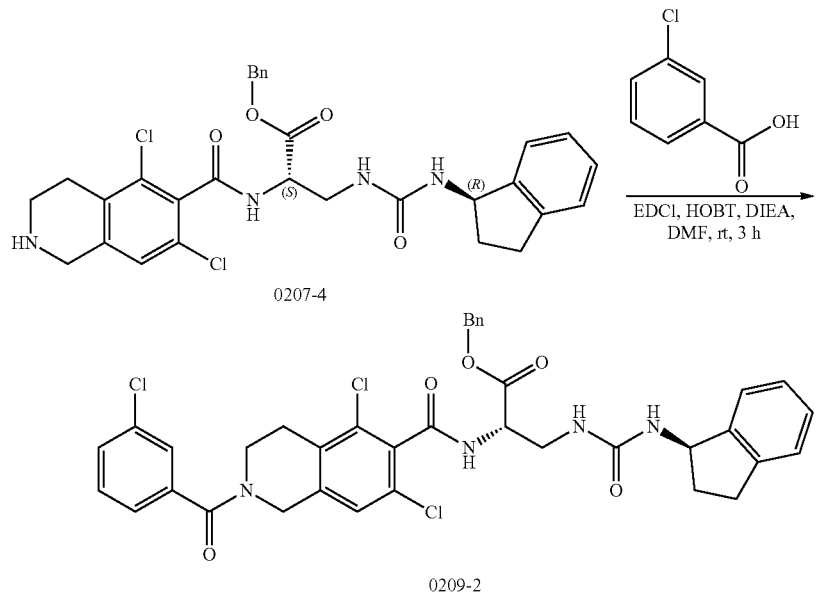

To a solution of 3-chlorobenzoic Acid (30 mg, 189 umol) in DMF (5 mL) was added DIEA (74 mg, 567 umol), EDCI (73 mg, 378 umol) and HOBT (73 mg, 378 umol). The reaction was stirred at room temperature for 15 min, 0207-4 (110 mg, 189 umol) was added into this mixture and the mixture was stirred at room temperature for overnight. After the consumption of starting material (by LCMS), water (100 mL) was added, extracted with ethyl acetate (20 mL×3), washed with water (20 mL×3), dried and concentrated. The crude was purified by pre-HPLC to get 0209-2 (70 mg, yield: 51.39%) as a white solid.

The Synthesis of (S)-2-(5,7-dichloro-2-(3-chlorobenzoyl)-1,2,3,4-tetrahydroisoquinoline-6-carboxamido)-3-(3-((R)-2,3-dihydro-1H-inden-1-yl)ureido) propanoic Acid (SU15210-0209-01)

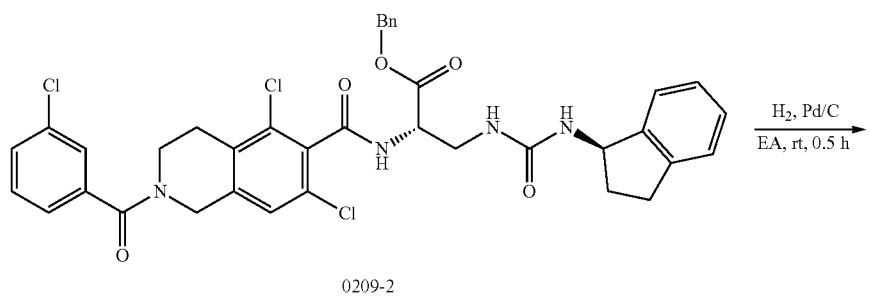

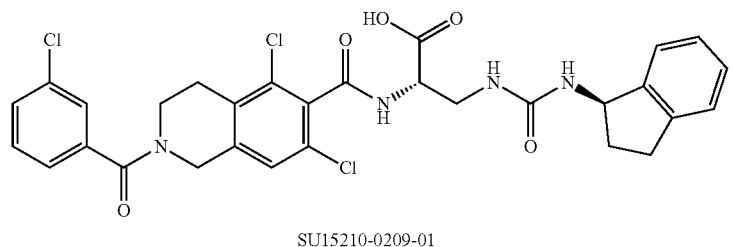

To a solution of compound 0209-2 (60 mg, 83 umol) in ethyl acetate (5 mL) was added 5% Pd on activated C (18 mg) and replaced with $H_2$. The mixture was stirred at room temperature for 0.5 h. After the consumption of starting material, this mixture was filtered, concentrated. The crude product was purified by pre-HPLC to get SU15210-0209-01 (11 mg, yield: 20.96%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [$CH_3CN$] to 0% water [0.05% TFA] and 100% [$CH_3CN$] in 1.6 min, then under this condition for 1.4 min, finally changed to 95% water [0.05% TFA] and 5% [$CH_3CN$] in 0.1 min and under this condition for 0.7 min), Purity: 100%, Rt=1.792 min; MS Found: 629.2 $[M+H]^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [$CH_3CN$] to 0% water [0.05% TFA] and 100% [$CH_3CN$] in 10 min, then under this condition for 5 min, finally changed to 95% water [0.05% TFA] and 5% [$CH_3CN$] in 0.1 min and under this condition for 0.7 min), Purity: 100%, Rt=8.720 min; MS Found: 629.2 $[M+H]^+$.

$^1$H NMR (400 MHz, DMSO-$d_6$) δ 12.64 (br, 1H), 8.86 (s, 1H), 7.49-7.58 (m, 5H), 7.13-7.23 (m, 4H), 6.59 (d, J=4.4 Hz, 1H), 5.90 (s, 1H), 5.07 (q, J=8.0 Hz, 1H), 4.81 (s, 1H), 4.60 (s, 1H), 4.41-4.46 (m, 1H), 3.89 (s, 1H), 3.48-3.58 (m, 2H), 2.67-2.90 (m, 4H), 2.32-2.41 (m, 1H), 1.62-1.75 (m, 1H).

SU15210-0210-01
Route for SU15210-0210-01

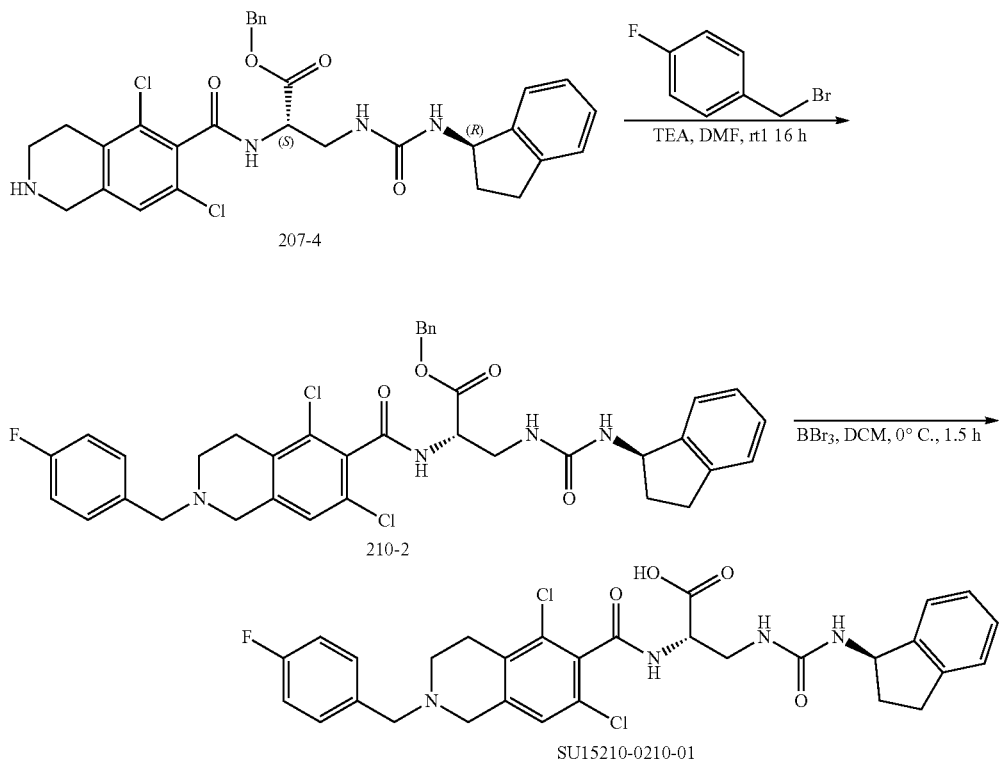

The Synthesis of (S)-benzyl 2-(5,7-dichloro-2-(4-fluorobenzyl)-1,2,3,4-tetrahydroisoquinoline-6-carboxamido)-3-(3-((R)-2,3-dihydro-1H-inden-1-yl)ureido)propanoate (0210-2)

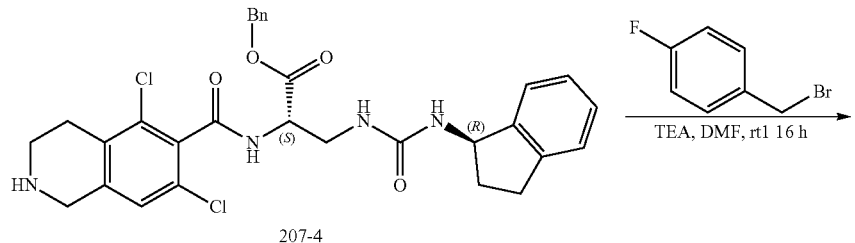

-continued

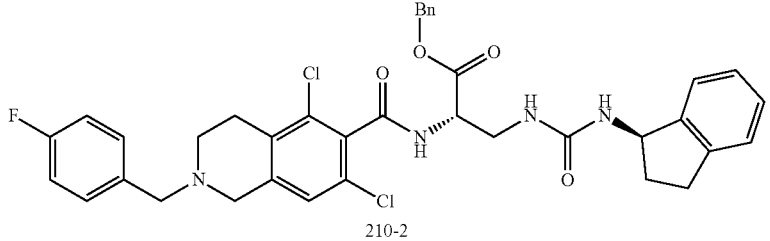

210-2

To a solution of 0207-4 (110 mg, 189 umol) in DMF (2 mL) was added 1-(bromomethyl)-4-fluoro-benzene (54 mg, 284 umol) and TEA (38 mg, 378 umol), the reaction mixture was allowed to stir at room temperature for overnight. After the consumption of starting material (by LCMS), the mixture was concentrated under reduced pressure and purified by pre-HPLC to give 0210-2 (80 mg, yield: 61%) as a white solid.

The Synthesis of (S)-2-(5,7-dichloro-2-(4-fluorobenzyl)-1,2,3,4-tetrahydroisoquinoline-6-carboxamido)-3-(3-((R)-2,3-dihydro-1H-inden-1-yl)ureido) propanoic Acid (SU15210-0210-01)

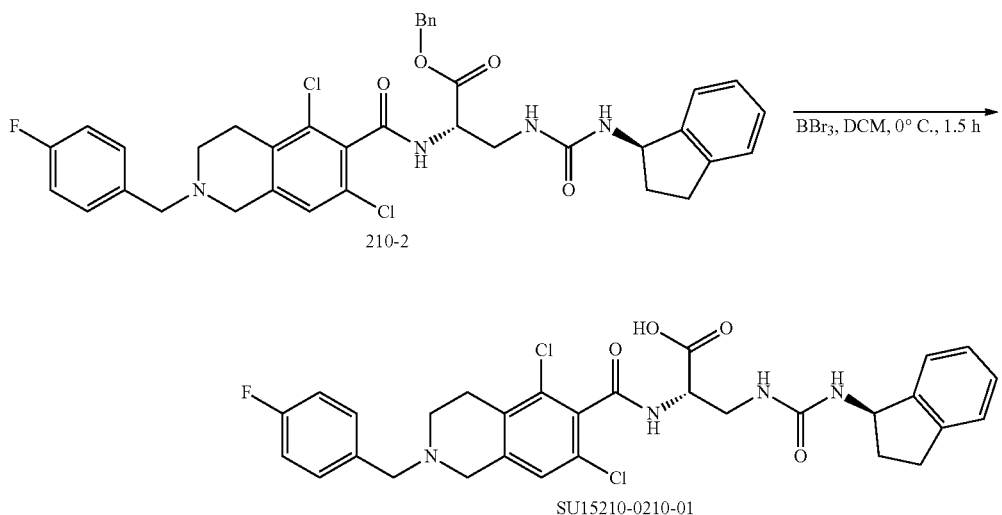 [SMILES: O=C(NC[C@H](NC(=O)c1c(Cl)cc2c(c1Cl)CCN(Cc1ccc(F)cc1)C2)C(=O)OCc1ccccc1)N[C@@H]1CCc2ccccc21 ; O=C(NC[C@H](NC(=O)c1c(Cl)cc2c(c1Cl)CCN(Cc1ccc(F)cc1)C2)C(=O)O)N[C@@H]1CCc2ccccc21]

To a solution of compound 0210-2 (60 mg, 87 umol) in DCM (5 mL) was added a solution of boron tribromide in DCM (1 M, 0.9 mL) at an ice bath and the mixture was stirred at this temperature for 1.5 h. After the consumption of starting material (by LCMS), the mixture was concentrated under reduced pressure and purified by pre-HPLC to give SU15210-0210-01 (15 mg, yield: 28.8%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.734 min; MS Found: 599.2 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 100%, Rt=8.287 min; MS Found: 599.2 [M+H]$^+$.

$^1$H NMR (400 MHz, DMSO-d$_6$) δ 8.49 (s, 1H), 7.37-7.40 (m, 2H), 7.14-7.25 (m, 7H), 6.66 (d, J=8.0 Hz, 1H), 5.92 (s, 1H), 5.07 (q, J=8.0 Hz, 1H), 4.28-4.33 (m, 1H), 3.51-3.65 (m, 5H), 2.84-2.90 (m, 1H), 2.67-2.78 (m, 5H), 2.31-2.39 (m, 1H), 1.64-1.69 (m, 1H).

$^1$H NMR (400 MHz, DMSO-d$_6$+D$_2$O) δ 7.38-7.42 (m, 2H), 7.15-7.25 (m, 7H), 5.07 (t, J=7.6 Hz, 1H), 4.40 (t, J=6.0 Hz, 1H), 3.65 (s, 2H), 3.50-3.57 (m, 3H), 3.34-3.39 (m, 1H), 2.84-2.90 (m, 1H), 2.70-2.79 (m, 5H), 2.34-2.40 (m, 1H), 1.65-1.70 (m, 1H).

SU15210-0211-01
Route for SU15210-0211-01:
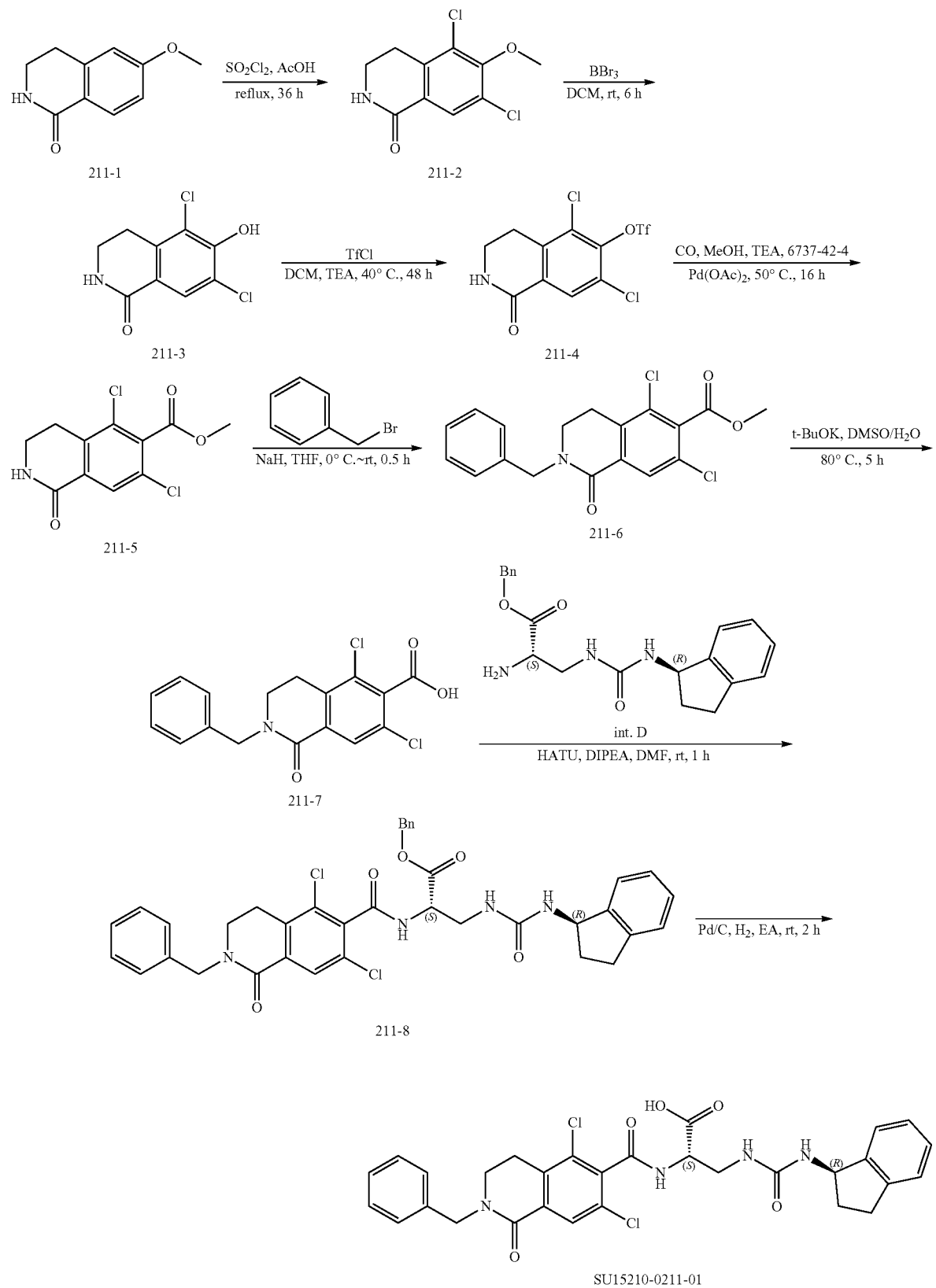
SU15210-0211-01

The Synthesis of 5,7-dichloro-6-methoxy-3,4-dihydroisoquinolin-1 (2H)-one (211-2)

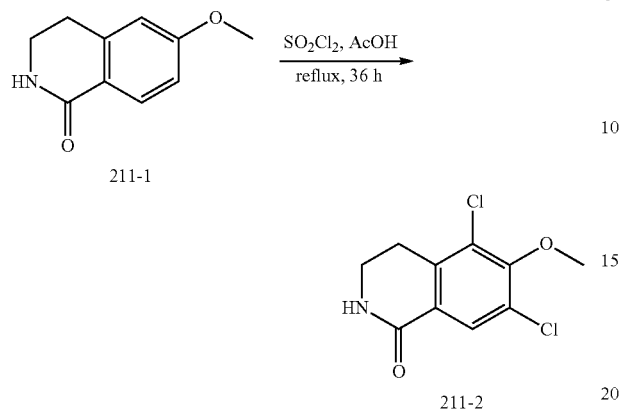

To a solution of 211-1 (5 g, 28.24 mmol) in AcOH (20 mL) was added SO$_2$Cl$_2$ (15.12 g, 112.96 mmol) at room temperature. The reaction mixture was then heated to reflux and stirred for 36 h. After the reaction was finished, the mixture was slowly poured into the ice-water, the product was precipitated to give 211-2 (4 g, 58% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 76.04%. Rt=0.618 min; MS Calcd.: 246.1; MS Found: 246.2 [M+H]$^+$.

The Synthesis of 5,7-dichloro-6-hydroxy-3,4-dihydroisoquinolin-1 (2H)-one (211-3)

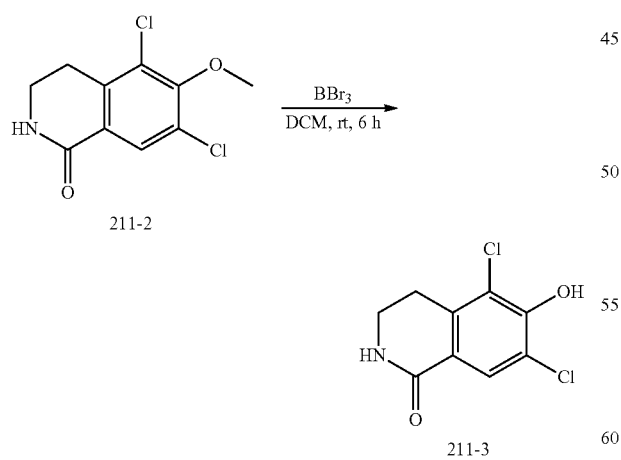

To a stirred solution of 211-2 (4 g, 16.33 mmol) in DCM (20 mL) was added BBr$_3$ (8.09 g, 32.66 mmol), and the reaction mixture was stirred at room temperature for 6 hours until the reaction was complete. The reaction was then cooled to 0° C., and quenched by the slow addition of methanol. The solvents were removed under reduced pressure to give 211-3 (3.5 g, yield: 93%) as a dark light yellow solid, which was used without further purification.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 96.22%. Rt=0.471 min; MS Calcd.: 232.1; MS Found: 232.2 [M+H]$^+$.

The Synthesis of 5,7-dichloro-1-oxo-1,2,3,4-tetrahydroisoquinolin-6-yl trifluoromethanesulfonate (211-4)

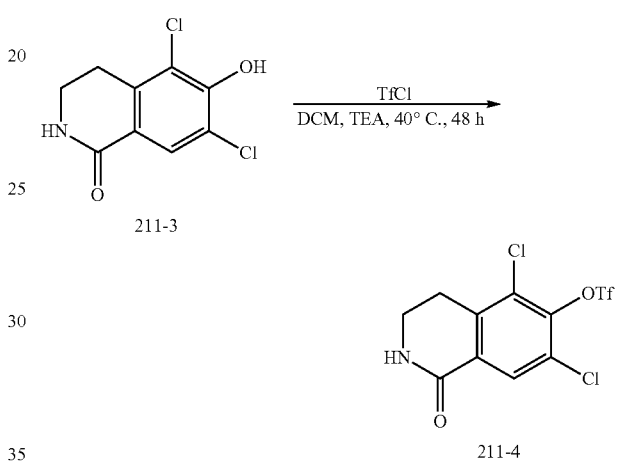

A solution of 211-3 (3.5 g, 15.15 mmol), TfCl (12.72 g, 75.75 mmol) and Et$_3$N (45.45 mmol) in CH$_2$Cl$_2$ (20 mL) was stirred at 40° C. for 2 d until the reaction was complete. The solvent was removed in vacuum and the crude product was purified by flash column chromatography (silica gel, PE/EA=2:1) to give 211-4 (1000 mg, yield: 18%) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 100%. Rt=1.870 min; MS Calcd.: 379.2; MS Found: 380.3 [M+H]$^+$.

The Synthesis of Methyl 5,7-dichloro-1-oxo-1,2,3,4-tetrahydroisoquinoline-6-carboxylate (211-5)

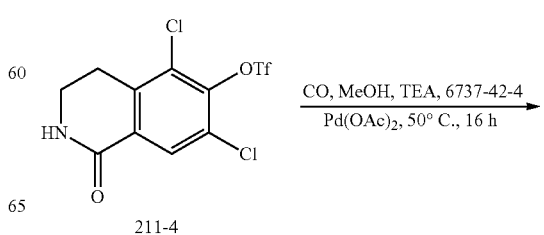

-continued

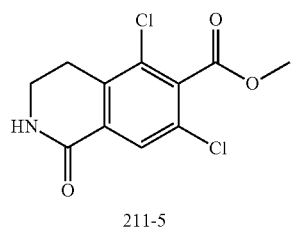

211-5

A solution of 211-4 ((1 g, 2.75 mmol), Pd(OAc)$_2$ (31 mg, 0.14 mmol), 6737-42-4 (1.13 g, 2.75 mmol), TEA (5.5 mmol) in MeOH/DMF (1/1 v/v, 20 mL) was stirred at 50° C. for 16 h under CO atmosphere (3 Mpa). After the consumption of starting material (by LCMS), the solution was concentrated in vacuo, purified by column (PE:EA=15: 1) to give the product 211-5 (200 mg, 27% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 95.11%. Rt=1.430 min; MS Calcd.: 274.1; MS Found: 274.1 [M+H]$^+$.

The Synthesis of Methyl 2-benzyl-5,7-dichloro-1-oxo-1,2,3,4-tetrahydroisoquinoline-6-carboxylate (211-6)

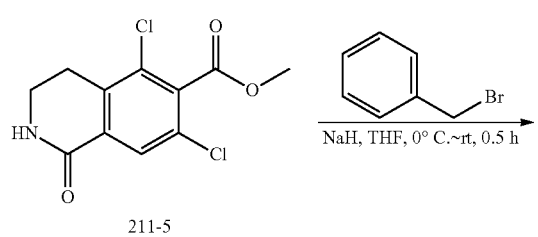

211-5

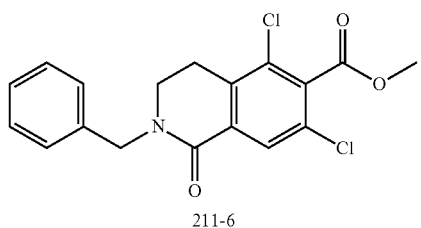

211-6

To a solution of 211-5 (200 mg, 0.73 mmol) in DMF (3 mL) was added NaH (60%, 59 mg, 1.46 mmol) and BnBr (136 mg, 0.8 mmol), the mixture was stirred at rt for 0.5 h. After the reaction was finished (detected by LCMS), 10 mL H$_2$O was added to quench the reaction, extracted with EtOAc (40 mL×3), combined the organic layer, dried over anhydrous Na$_2$SO$_4$, filtered and concentrated, the crude was purified by CC to get the product 211-6 (150 mg, 57% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 40.0%. Rt=0.810 min; MS Calcd.: 364.2; MS Found: 364.2 [M+H]$^+$.

The Synthesis of 2-benzyl-5,7-dichloro-1-oxo-1,2,3,4-tetrahydroisoquinoline-6-carboxylic Acid (211-7)

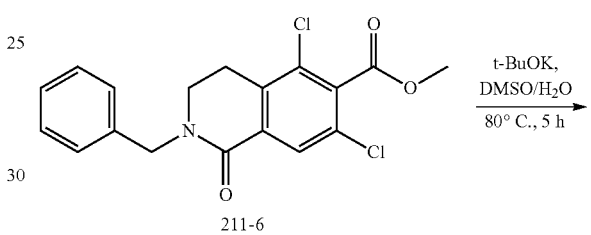

211-6

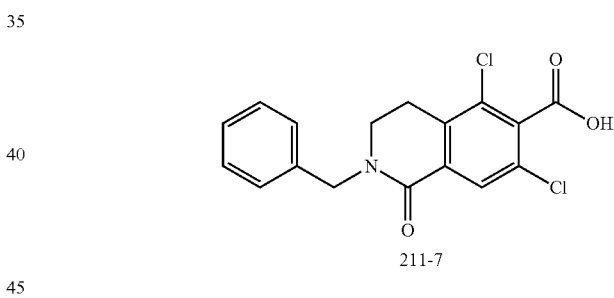

211-7

To a solution of 211-6 (150 mg, 0.41 mmol) in H$_2$O (1 mL) and DMSO (3 mL) was added t-BuOK (138 mg, 1.23 mmol). The mixture was stirred at 80° C. for 5 h. After the reaction was finished, the solvent was removed in vacuum, the residual was dissolved in water (5 mL) and EA (5 mL), acidified by 1N HCl aq. to pH-2, the organic layer was then separated and the water phase was extracted with EA (5 mL×3), the organic phase was combined and washed with water then brine, dried over Na$_2$SO$_4$, concentrated and purified by pre-HPLC to get 211-7 (120 mg, 84% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 62.60%. Rt=0.659 min; MS Calcd.: 350.2; MS Found: 350.2 [M+H]$^+$.

The Synthesis of (S)-benzyl 2-(2-benzyl-5,7-dichloro-1-oxo-1,2,3,4-tetrahydroisoquinoline-6-carboxamido)-3-(3-((R)-2,3-dihydro-1H-inden-1-yl)ureido)propanoate (211-8)

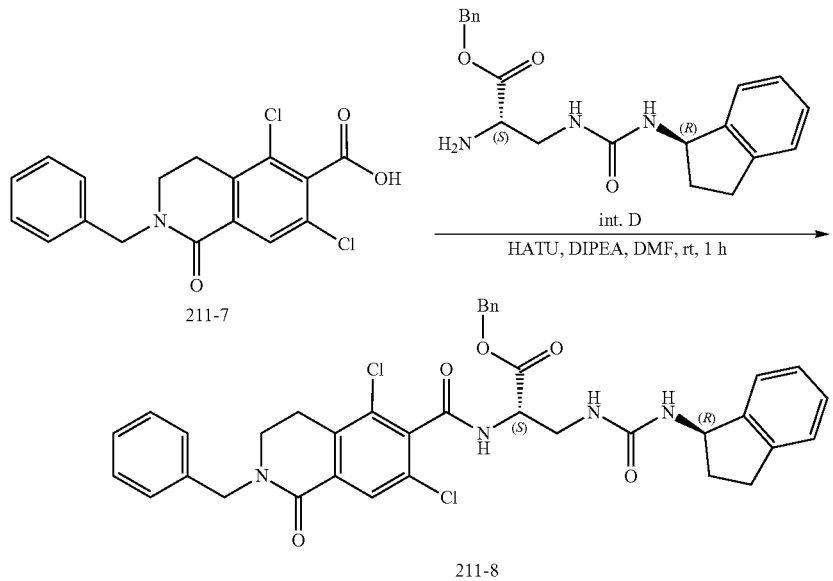

To a solution of 211-7 (120 mg, 0.34 mmol) in DMF (3 mL) was added DIEA (132 mg, 1.02 mmol), HATU (131 mg, 0.34 mmol). The reaction was stirred at room temperature for 15 min, int.D (120 mg, 0.34 mmol) was added into this mixture and the mixture was stirred at room temperature for overnight. After the consumption of starting material (by LCMS), water (10 mL) was added, extracted with ethyl acetate (10 mL×3), washed with water (10 mL×3), dried and concentrated. The crude was purified by pre-HPLC to get 211-8 (26 mg, 11% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 44.64%. Rt=1.888 min; MS Calcd.: 685.6; MS Found: 685.2 [M+H]$^+$.

The Synthesis of (S)-2-(2-benzyl-5,7-dichloro-1-oxo-1,2,3,4-tetrahydroisoquinoline-6-carboxamido)-3-(3-((R)-2,3-dihydro-1H-inden-1-yl)ureido)propanoic Acid (SU15210-0211-01)

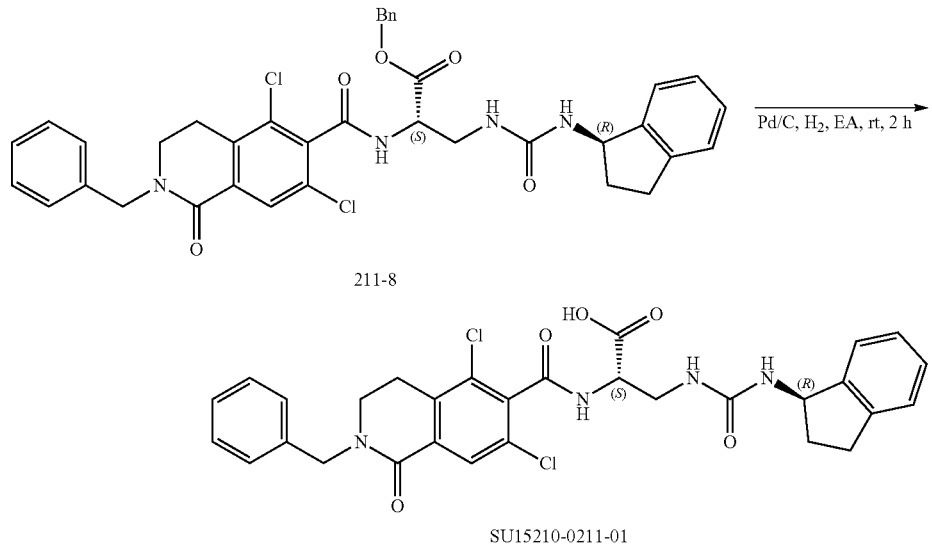

To a solution of compound 211-8 (26 mg, 0.04 mmol) in ethyl acetate (3 mL) was added 5% Pd on activated carbon (3 mg) and replaced with $H_2$. The mixture was stirred at room temperature for 2 h. After the consumption of starting material, this mixture was filtered, concentrated. The crude product was purified by pre-HPLC to get SU15210-0211-01 (10 mg, 41% yield) as yellow oil.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [$CH_3CN$] to 0% [water+10 mM TFA] and 100% [$CH_3CN$] in 0.8 min, then under this condition for 0.4 min, finally changed to 95% [water+10 mM TFA] and 5% [$CH_3CN$] in 0.01 min. Purity is 98.03%. Rt=1.687 min; MS Calcd.: 595.5; MS Found: 597.2 $[M+H]^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min.

$^1$H NMR (400 MHz, DMSO-$d_6$) δ 8.92 (s, 1H), 7.98 (s, 1H), 7.33-7.44 (m, 5H), 7.27-7.19 (m, 4H), 6.71 (d, J=8.0 Hz, 1H), 5.97 (s, 1H), 5.14 (q, J=8.0 Hz, 1H), 4.79 (s, 2H), 4.49 (m, 1H), 3.62-3.55 (m, 5H), 3.12-3.07 (m, 2H), 2.97-2.89 (m, 1H), 2.85-2.76 (m, 1H), 2.45-2.38 (m, 1H), 1.76-1.70 (m, 1H).

SU15210-0214-01

Route for SU15210-0214-01

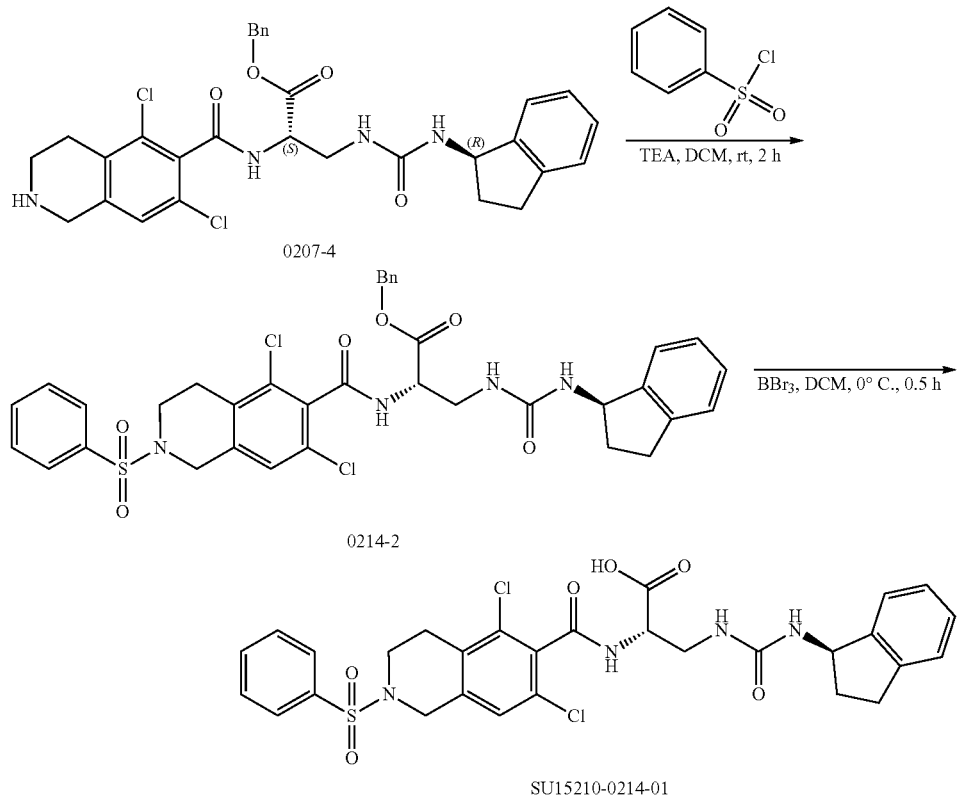

The Synthesis of (S)-benzyl 2-(5,7-dichloro-2-(phenylsulfonyl)-1,2,3,4-tetrahydroisoquinoline-6-carboxamido)-3-(3-((R)-2,3-dihydro-1H-inden-1-yl)ureido)propanoate (0214-2)

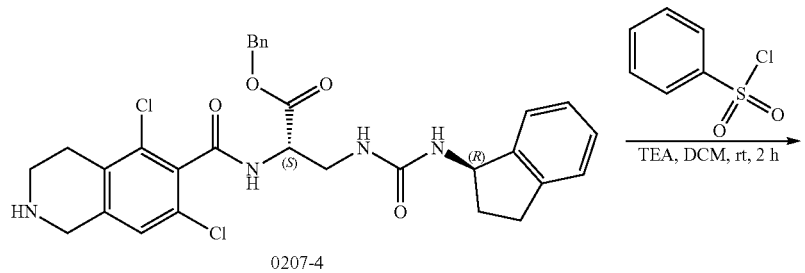

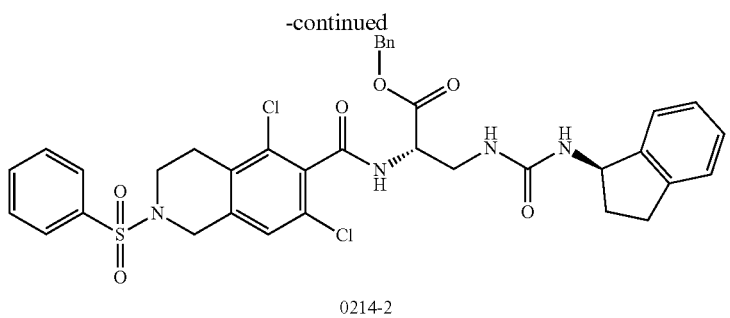

0214-2

To a solution of compound 0207-4 (50 mg, 86 umol) in DCM (2 mL) was added TEA (26 mg, 256 umol) and benzenesulfonyl chloride (152 mg, 860 umol), and this mixture was stirred at room temperature for 2 h. After the consumption of starting material (by LCMS), the mixture was concentrated and the crude was purified by pre-HPLC to get 0214-2 (45 mg, yield: 72.5%) as a white solid.

The Synthesis of (S)-2-(5,7-dichloro-2-(phenylsulfonyl)-1,2,3,4-tetrahydroisoquinoline-6-carboxamido)-3-(3-((R)-2,3-dihydro-1H-inden-1-yl)ureido)propanoic Acid (SU15210-0214-01)

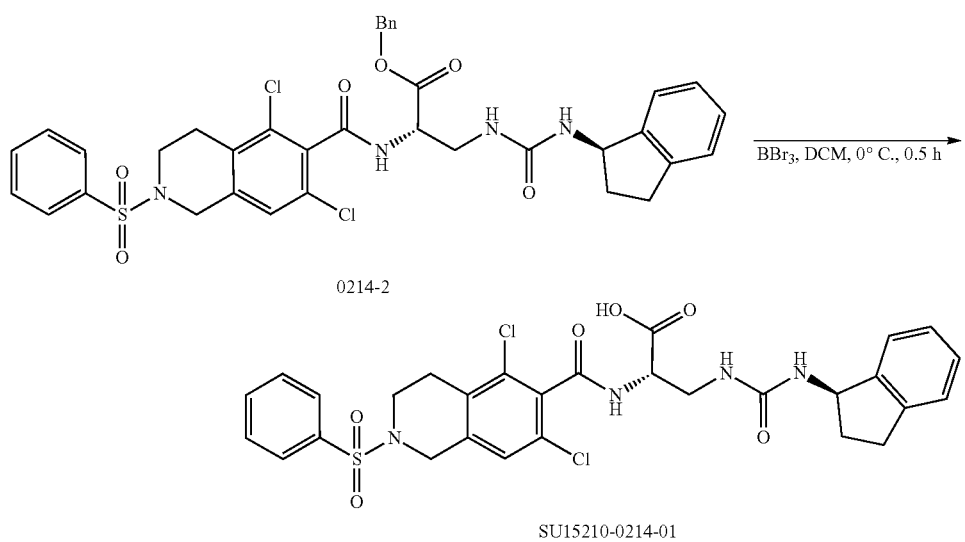

To a solution of compound 0214-2 (30 mg, 42 umol) in DCM (2 mL) was added a solution of boron tribromide in DCM (1 M, 0.5 mL) at an ice bath and the mixture was stirred at this temperature for 0.5 h. After the consumption of starting material (by LCMS), the mixture was concentrated under reduced pressure and purified by pre-HPLC to give SU15210-0214-01 (6 mg, yield: 22.9%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH$_3$CN] to 0% water [0.05% TFA] and 100% [CH$_3$CN] in 1.6 min, then under this condition for 1.4 min, finally changed to 95% water [0.05% TFA] and 5% [CH$_3$CN] in 0.1 min and under this condition for 0.7 min), Purity: 100%, Rt=1.759 min; MS Found: 631.1 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH$_3$CN] to 0% water [0.05% TFA] and 100% [CH$_3$CN] in 10 min, then under this condition for 5 min, finally changed to 95% water [0.05% TFA] and 5% [CH$_3$CN] in 0.1 min and under this condition for 0.7 min), Purity: 100%, Rt=8.485 min; MS Found: 631.1 [M+H]$^+$.

$^1$H NMR (400 MHz, DMSO-d$_6$) δ 8.92 (d, J=7.2 Hz, 1H), 7.81-7.83 (m, 2H), 7.71-7.75 (m, 1H), 7.64-7.67 (m, 2H), 7.43 (s, 1H), 7.13-7.23 (m, 4H), 6.55-6.58 (m, 1H), 5.87 (t, J=5.6 Hz, 1H), 5.06 (q, J=8.0 Hz, 1H), 4.46 (m, 1H), 4.26 (s, 2H), 3.49-3.55 (m, 1H), 3.37-3.38 (m, 2H), 3.31 (s, 2H), 2.83-2.90 (m, 1H), 2.67-2.79 (m, 3H), 2.31-2.37 (m, 1H), 1.61-1.71 (m, 1H).

SU15210-0217-01
Route for SU15210-0217-01:
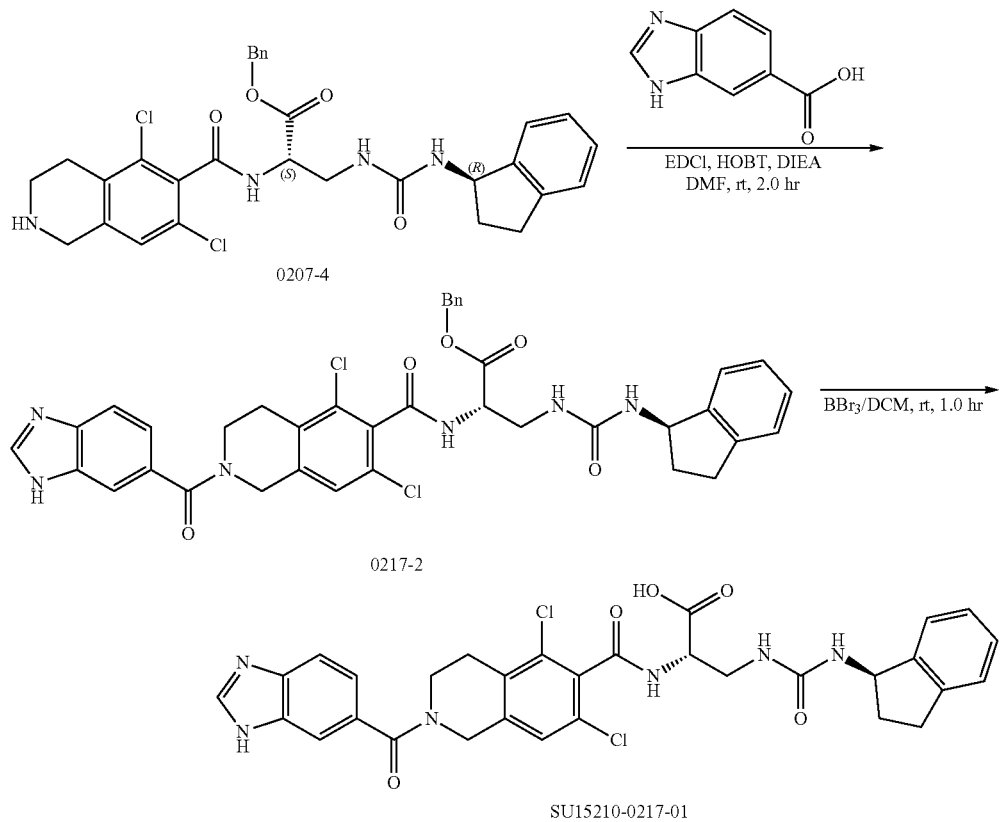
The Synthesis of Benzyl (2S)-2-[[2-(3H-benzimidazole-5-carbonyl)-5,7-dichloro-3,4-dihydro-1H-isoquinoline-6-carbonyl]amino]-3-[[(1R)-indan-1-ycarbamoylamino]propanoate (0217-2)
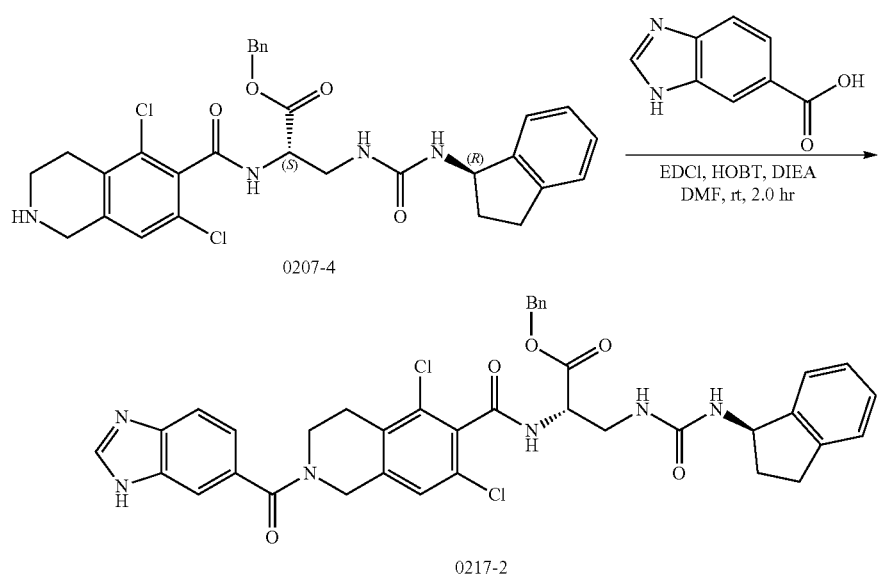

To a solution of 0207-4 (40.0 mg, 68.79 μmol) and 3H-benzimidazole-5-carboxylic acid (11.15 mg, 68.79 μmol) in DMF (5 mL) was added EDCI (15.82 mg, 82.55 μmol), HOBT (11.15 mg, 82.55 μmol) and DIPEA (13.34 mg, 103.18 μmol) at room temperature. The reaction mixture was stirred at rt for 2.0 h. After the reaction was finished, the solvent was concentrated and purified by prep-HPLC to get 0217-2 (20.0 mg, 40.07% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+0.2% NH$_3$ 7 M in MeOH] and 5% [CH$_3$CN] to 0% [water+0.2% NH$_3$ 7 M in MeOH] and 100% [CH$_3$CN] in 1.6 min, then under this condition for 1.4 min, finally changed to 95% [water+0.2% NH$_3$ 7 M in MeOH] and 5% [CH$_3$CN] in 0.1 min and under this condition for 0.7 min. Purity is 97.57%. Rt=1.989 min; MS Calcd.: 724.3; MS Found: 725.3 [M+H]$^+$.

The Synthesis of (2S)-2-[[2-(3H-benzimidazole-5-carbonyl)-5,7-dichloro-3,4-dihydro-1H-isoquinoline-6-carbonyl]amino]-3-[[(1R)-indan-1-yl]carbamoylamino]propanoic Acid (SU15210-0217-01)

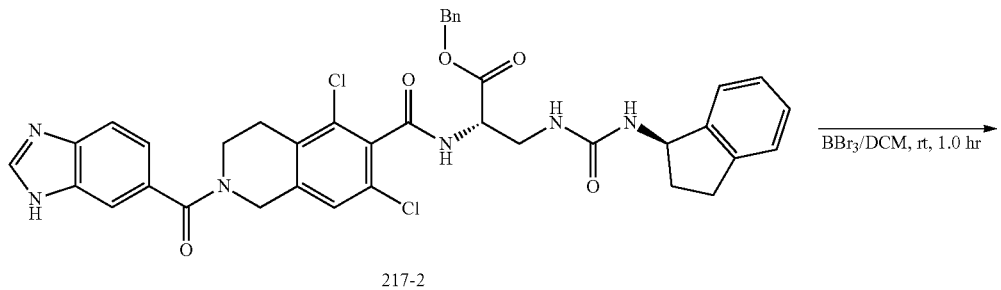

217-2

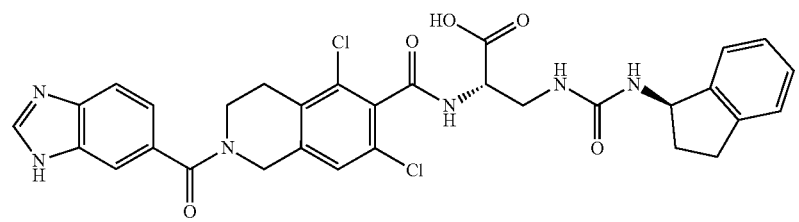

SU15210-0217-01

To a solution of 0217-2 (20.0 mg, 27.56 μmol) was dissolved in BBr$_3$/DCM (1.0N, 5 ml) and the solution was stirred at room temperature for 1.0 hour, after the reaction was finished, the solution was concentrated and purified by prep-HPLC to get SU15210-0217-01 (5.0 mg, 28.55% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+0.2% NH$_3$ 7 M in MeOH] and 5% [CH$_3$CN] to 0% [water+0.2% NH$_3$ 7 M in MeOH] and 100% [CH$_3$CN] in 1.6 min, then under this condition for 1.4 min, finally changed to 95% [water+0.2% NH$_3$ 7 M in MeOH] and 5% [CH$_3$CN] in 0.1 min and under this condition for 0.7 min. Purity is 98.38%. Rt=1.398 min; MS Calcd.: 635.7; MS Found: 637.2 [M+H]$^+$.

Agilent HPLC 1200; Column: Waters X-Bridge C18 (50 mm*4.6 mm*3.5 μm); Column Temperature: 40° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 97.90%. Rt=6.245 min.

$^1$H NMR (400 MHz, DMSO-d$_6$) δ 12.68 (s, 1H), 8.33 (s, 1H), 7.61-7.74 (m, 2H), 7.32-7.45 (m, 2H), 7.11-7.26 (m, 4H), 6.67 (s, 1H), 5.93 (s, 1H), 5.08 (q, J=7.6 Hz, 1H), 4.77 (s, 2H), 4.26 (s, 1H), 3.76 (s, 2H), 3.42 (s, 2H), 2.67-2.90 (m, 5H), 2.33-2.39 (m, 1H), 1.62-1.72 (m, 1H), 1.23 (s, 1H).

SU15210-0219
Route for SU15210-0219
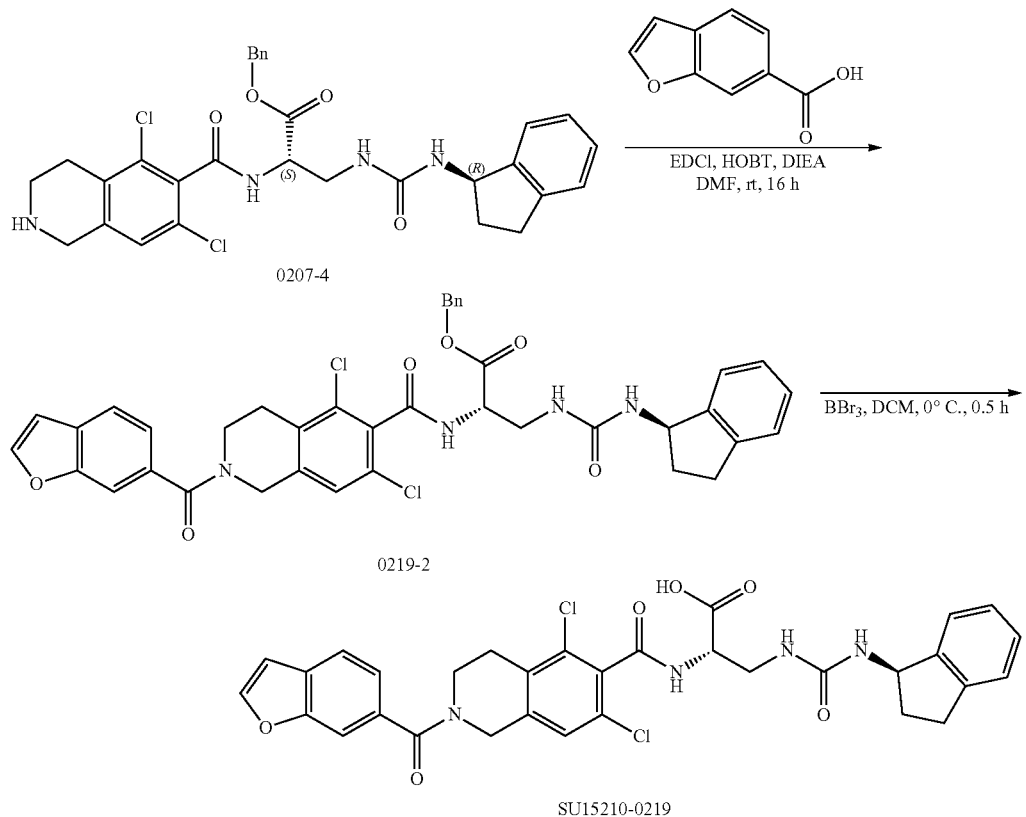
SU15210-0219
The Synthesis of (S)-benzyl 2-(5,7-dichloro-2-(3-chlorobenzoyl)-1,2,3,4-tetrahydroisoquinoline-6-carboxamido)-3-(3-((R)-2,3-dihydro-1H-inden-1-yl)ureido)propanoate (0219-2)
To a solution of benzofuran-6-carboxylic Acid (28 mg, 172 umol) in DMF (2 mL) was added DIEA (67 mg, 344 umol), EDCI (66 mg, 344 umol) and HOBT (46 mg, 344 umol). The reaction mixture was stirred at room temperature for 15 min, 0207-4 (100 mg, 172 umol) was added into this
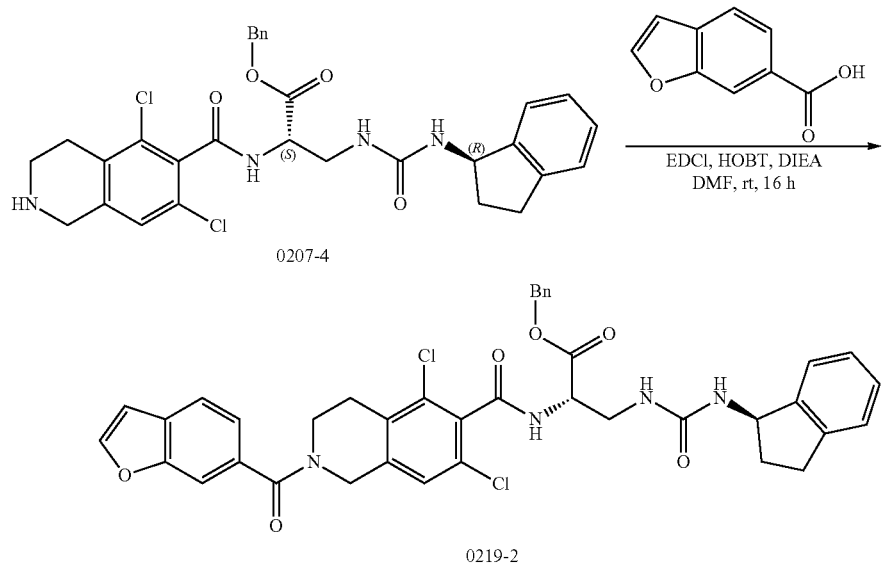

mixture and the mixture was stirred at room temperature for overnight. After the consumption of starting material (by LCMS), water (10 mL) was added, extracted with ethyl acetate (20 mL×3), washed with water (20 mL×3), dried and concentrated. The crude was purified by pre-HPLC to get 0219-2 (55 mg, yield: 44.9%) as a white solid.

The Synthesis of (S)-2-(5,7-dichloro-2-(3-chlorobenzoyl)-1,2,3,4-tetrahydroisoquinoline-6-carboxamido)-3-(3-((R)-2,3-dihydro-1H-inden-1-yl)ureido) propanoic Acid (SU15210-0219)

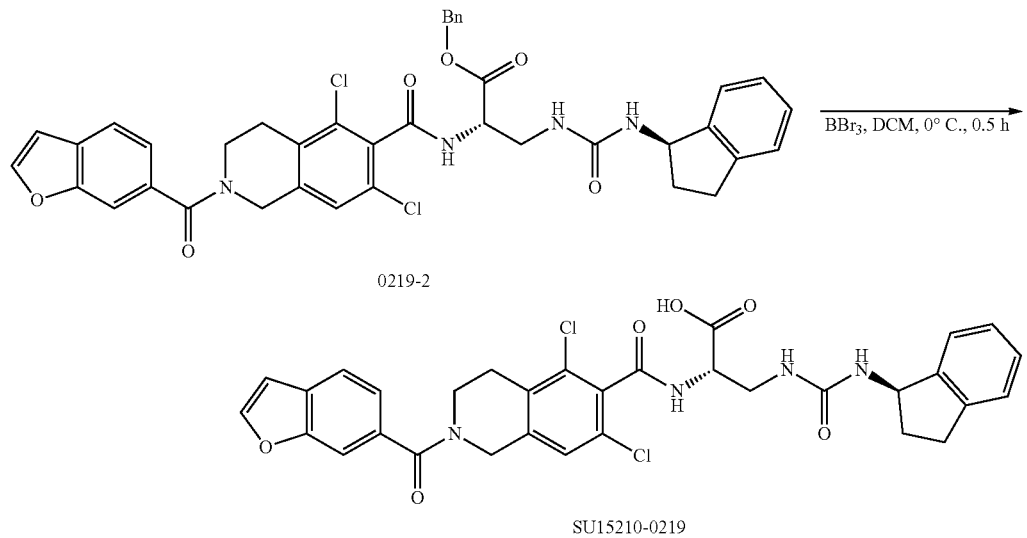

To a solution of compound 0219-2 (35 mg, 49 umol) in DCM (2 mL) was added a solution of boron tribromide in DCM (1 M, 0.5 mL) at an ice bath and the mixture was still stirred at this temperature for 0.5 h. After the consumption of starting material (by LCMS), the mixture was concentrated under reduced pressure and purified by pre-HPLC to give SU15210-0219 (10 mg, yield: 32.7%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.549 min; MS Found: 365.2 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 99.27%, Rt=7.441 min; MS Found: 635.2 [M+H]$^+$.

$^1$H NMR (400 MHz, DMSO-d$_6$) δ 8.25 (br, 1H), 8.12 (d, J=2.0 Hz, 1H), 7.70-7.77 (m, 2H), 7.50 (br, 1H), 7.35 (d, J=6.8 Hz, 1H), 7.13-7.25 (m, 5H), 7.05-7.06 (m, 1H), 6.67 (d, J=8.0 Hz, 1H), 5.91 (s, 1H), 5.07 (q, J=8.0 Hz, 1H), 4.78 (s, 2H), 4.19 (m, 1H), 2.68-2.90 (m, 6H), 2.32-2.38 (m, 1H), 1.66-1.70 (m, 1H).

SU15210-0221
Route for SU15210-0221

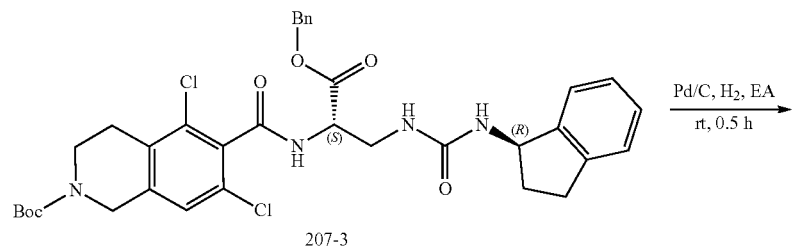

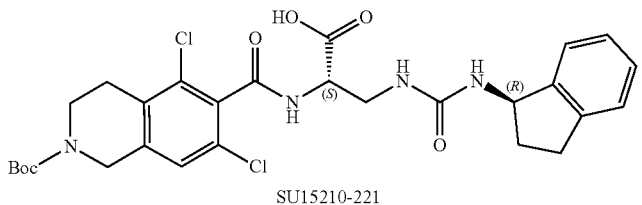

SU15210-221

The Synthesis of (S)-2-(2-(tert-butoxycarbonyl)-5,7-dichloro-1,2,3,4-tetrahydroisoquinoline-6-carboxamido)-3-(3-((R)-2,3-dihydro-1H-inden-1-yl)ureido)propanoic Acid (SU15210-0221)

To a solution of compound 0207-3 (45 mg, 66 umol) in ethyl acetate (3 mL) was added 10% Pd on activated C (10 mg) and replaced with H₂ (1.0 atm). The mixture was stirred at room temperature for 0.5 h. After the consumption of starting material (by LCMS), this mixture was filtered, concentrated. The crude was purified by pre-HPLC to get SU15210-0221 (16 mg, yield: 30.7%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH₃CN] to 0% water [0.05% TFA] and 100% [CH₃CN] in 1.6 min, then under this condition for 1.4 min, finally changed to 95% water [0.05% TFA] and 5% [CH₃CN] in 0.1 min and under this condition for 0.7 min), Purity: 100%, Rt=1.837 min; MS Found: 591.1 [M+H]⁺.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH₃CN] to 0% water [0.05% TFA] and 100% [CH₃CN] in 10 min, then under this condition for 5 min, finally changed to 95% water [0.05% TFA] and 5% [CH₃CN] in 0.1 min and under this condition for 0.7 min), Purity: 100%, Rt=8.926 min; MS Found: 591.1 [M+H]⁺.

¹H NMR (400 MHz, DMSO-d₆) δ 8.87 (d, J=6.4 Hz, 1H), 7.43 (s, 1H), 7.13-7.23 (m, 4H), 6.58 (d, J=8.4 Hz, 1H), 5.88 (t, J=5.6 Hz, 1H), 5.07 (q, J=8.0 Hz, 1H), 4.53 (s, 2H), 4.42-4.48 (m, 1H), 3.60 (t, J=5.6 Hz, 2H), 3.49-3.55 (m, 1H), 3.31 (s, 1H), 2.83-2.90 (m, 1H), 2.67-2.79 (m, 3H), 2.32-2.39 (m, 1H), 1.62-1.72 (m, 1H), 1.42 (s, 9H).

SU15210-0222
Route for SU15210-0222

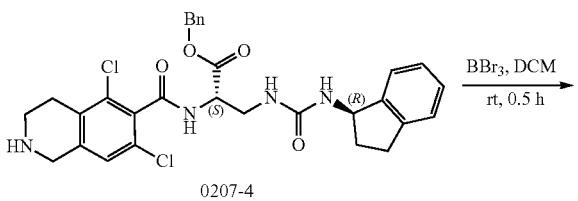

0207-4

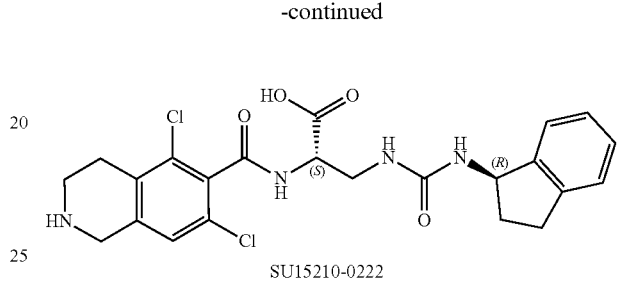

SU15210-0222

The Synthesis of(S)-2-(5,7-dichloro-1,2,3,4-tetrahydroisoquinoline-6-carboxamido)-3-(3-((R)-2,3-dihydro-1H-inden-1-yl)ureido)propanoic Acid (SU15210-0222)

To a solution of compound 0207-4 (50 mg, 86 umol) in DCM (2 mL) was added a solution of boron tribromide in DCM (1 M, 0.5 mL) at an ice bath and the mixture was still stirred at this temperature for 0.5 h. After the consumption of starting material (by LCMS), the mixture was concentrated under reduced pressure and purified by pre-HPLC to give SU15210-0222 (3 mg, yield: 7.1%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% water [0.05% TFA] and 5% [CH₃CN] to 0% water [0.05% TFA] and 100% [CH₃CN] in 1.6 min, then under this condition for 1.4 min, finally changed to 95% water [0.05% TFA] and 5% [CH₃CN] in 0.1 min and under this condition for 0.7 min), Purity: 99.02%, Rt=1.340 min; MS Found: 491.0 [M+H]⁺.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% water [0.05% TFA] and 5% [CH₃CN] to 0% water [0.05% TFA] and 100% [CH₃CN] in 10 min, then under this condition for 5 min, finally changed to 95% water [0.05% TFA] and 5% [CH₃CN] in 0.1 min and under this condition for 0.7 min), Purity: 93.90%, Rt=5.704 min; MS Found: 491.0 [M+H]⁺.

¹H NMR (400 MHz, DMSO-d₆) δ 9.00 (d, J=6.4 Hz, 1H), 7.45 (s, 1H), 7.14-7.23 (m, 4H), 6.55-6.60 (m, 1H), 5.92-5.95 (m, 1H), 5.07 (q, J=8.0 Hz, 1H), 4.44-4.49 (m, 1H), 4.26 (s, 2H), 3.48-3.56 (m, 1H), 3.37-3.40 (m, 1H), 2.85-2.90 (m, 3H), 2.67-2.79 (m, 1H), 2.27-2.33 (m, 1H), 1.63-1.70 (m, 1H).

SU15210-0223-01
Route for SU15210-0223-01:
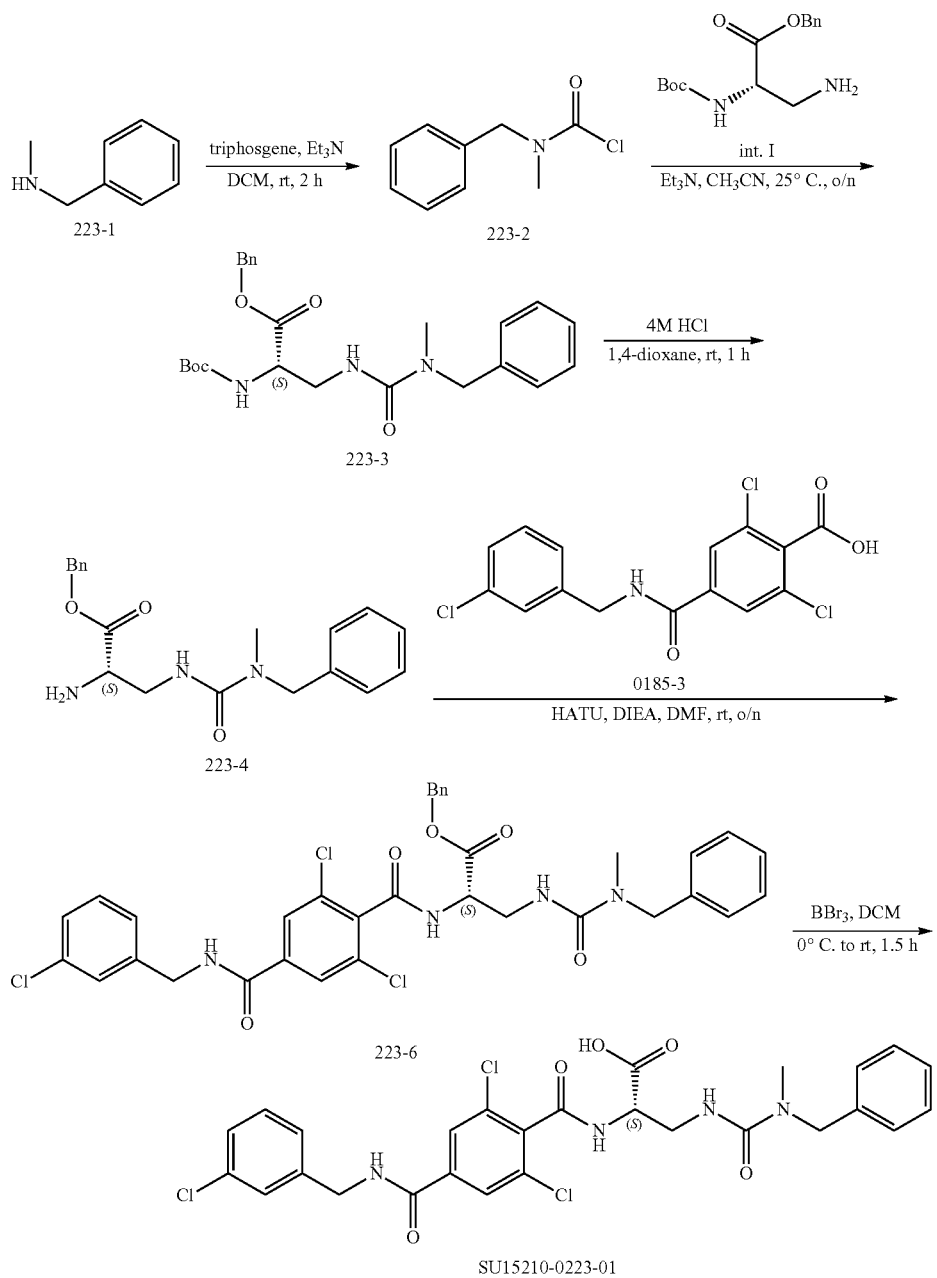
The Synthesis of benzyl(methyl)carbamic Chloride (223-2)
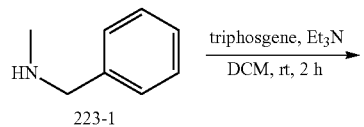
-continued
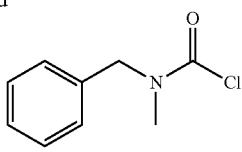
To a mixture of 223-1 (121 mg, 998.51 umol) and TEA (202 mg, 2.00 mmol) in dichloromethane (5 mL) was added triphosgene (148 mg, 498.74 umol) and stirred at room temperature for 2 h. After the reaction was finished (detected by TLC (ethyl acetate), the mixture was just concentrated in vacuo and used next step directly without further purification.

The Synthesis of (S)-benzyl 3-(3-benzyl-3-methylureido)-2-(tert-butoxycarbonylamino)propanoate (223-3)

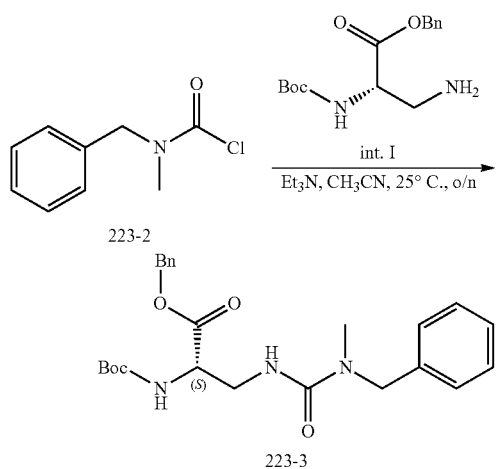

To a mixture of 223-2 (183 mg, 996.54 umol) in acetonitrile (10 mL) was added int. I (245 mg, 832.36 umol) and TEA (168.07 mg, 1.66 mmol) then the reaction mixture was stirred at room temperature for 16 h. After the reaction was finished, the mixture was concentrated then purified by Prep-HPLC to give benzyl 223-3 (100 mg, 27.27% yield) as light-yellow oil.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity is 89.19%. Rt=2.212 min; MS Calcd.: 441.2; MS Found: 442.1 [M+H]$^+$.

The Synthesis of (S)-benzyl 2-amino-3-(3-benzyl-3-methylureido)propanoate (223-4)

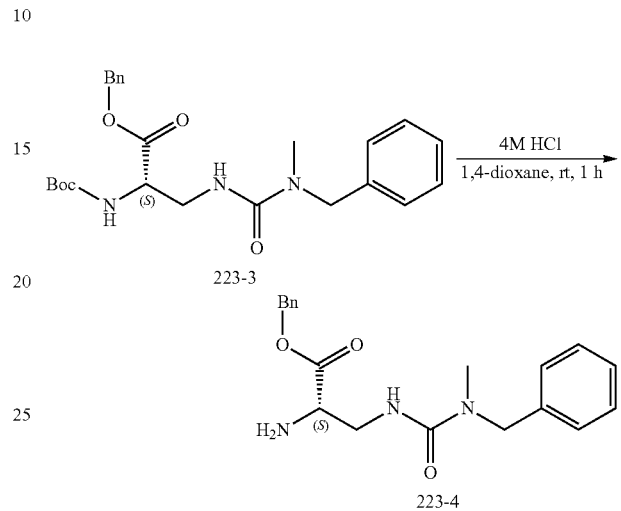

To a solution of 223-3 (100 mg, 226.49 umol) in 1,4-Dioxane (1 mL) was added 4 M HCl in 1,4-dioxane (226.49 umol, 1 mL) and then stirred at room temperature for 1 h. After the reaction was finished, then concentrated in vacuo and used to next step directly without further purification.

The Synthesis of (S)-benzyl 3-(3-benzyl-3-methylureido)-2-(2,6-dichloro-4-(3-chlorobenzylcarbamoyl)benzamido)propanoate (223-6)

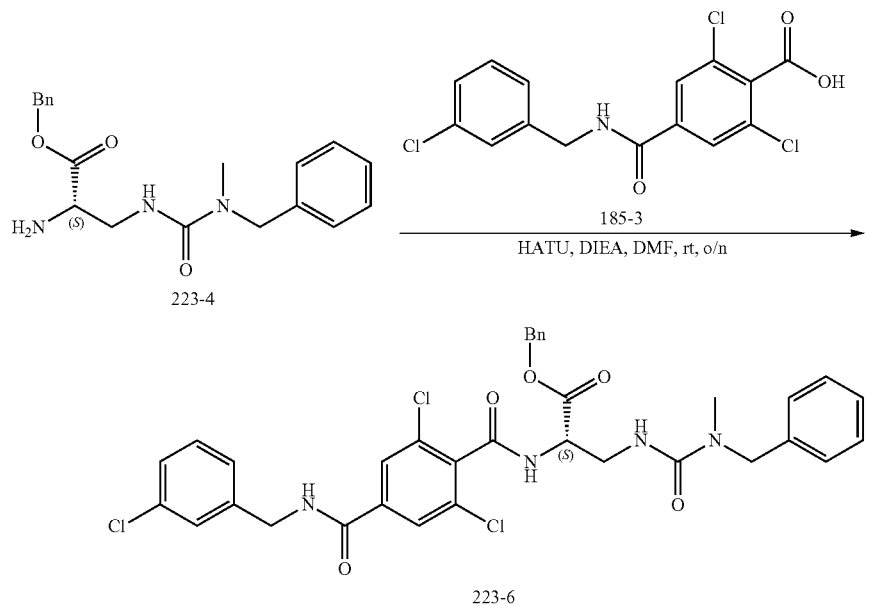

To a mixture of 223-4 (77 mg, 225.54 umol), 185-3 (81 mg, 225.88 umol) and HATU (129 mg, 337.48 umol) in DMF (5 mL) was added DIPEA (117 mg, 905.29 umol) and stirred at room temperature for 16 h. Then the mixture was diluted with water and extracted by ethyl acetate (20 mL×2). The combined organic layers was washed with brine (10 mL×2), dried over sodium sulfate, and concentrated. The residue was purified by Prep-TLC (petroleum ether/ethyl acetate=1/1) twice to give 223-6 (73 mg, 47.46% yield) as light-yellow oil.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity is 100%. Rt=2.286 min; MS Calcd.: 680.1; MS Found: 681.0 [M+H]$^+$.

The Synthesis of (S)-3-(3-benzyl-3-methylureido)-2-(2,6-dichloro-4-(3-chlorobenzylcarbamoyl)benzamido)propanoic Acid (SU15210-0223-01)

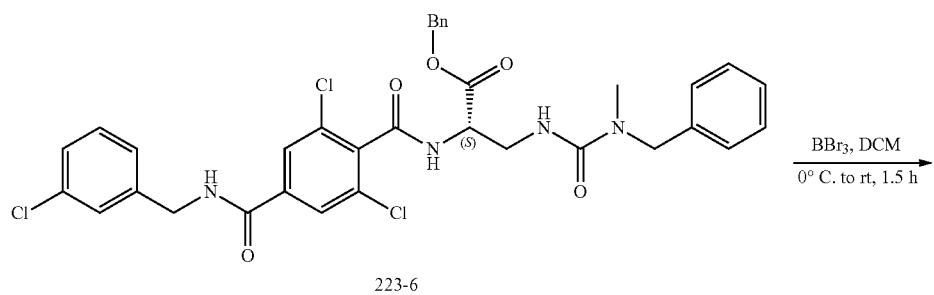

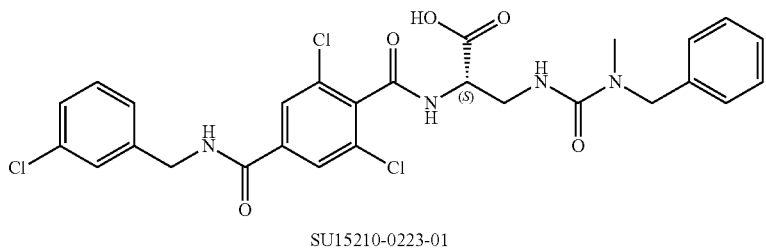

To a solution of 223-6 (73 mg, 107.04 umol) in CH$_2$Cl$_2$ (5 mL) was added BBr$_3$ (80.45 mg, 321.12 umol) at 0° C. and stirred at room temperature for 1.5 h. Then the mixture was diluted with water and extracted by CH$_2$Cl$_2$ (10 mL×2). The combined organic layers were washed with brine (10 mL×2), dried over sodium sulfate, and concentrated. The residue was purified by Prep-HPLC to give the target compound SU15210-0223-01 (20 mg, 31.57% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity is 100%. Rt=1.674 min; MS Calcd.: 590.1; MS Found: 590.6 [M]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=7.255 min.

$^1$H NMR (400 MHz, DMSO-d$_6$) δ 9.33 (t, J=6.0 Hz, 1H), 8.64-8.70 (br, 1H), 7.96 (s, 2H), 7.28-7.40 (m, 6H), 7.20-7.26 (m, 4H), 6.67-6.75 (m, 1H), 4.48-4.49 (m, 2H), 4.36-4.42 (m, 2H), 3.45-3.48 (m, 1H), 3.31 (s, 2H), 2.73 (s, 3H).

SU15210-0224-01

Route for SU15210-0224-01:

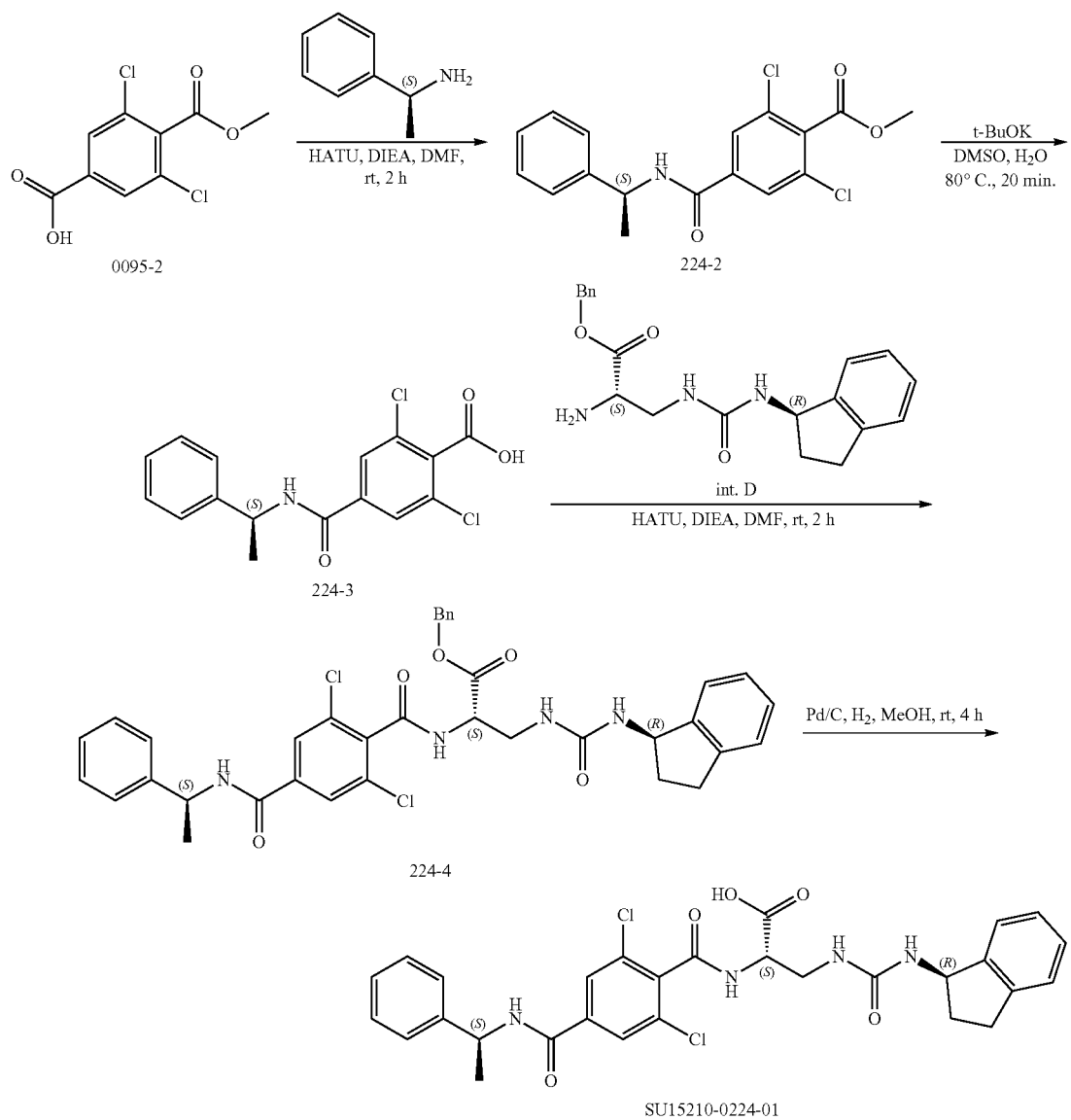

The Synthesis of (S)-methyl 2,6-dichloro-4-(1-phenylethylcarbamoyl)benzoate (224-2)

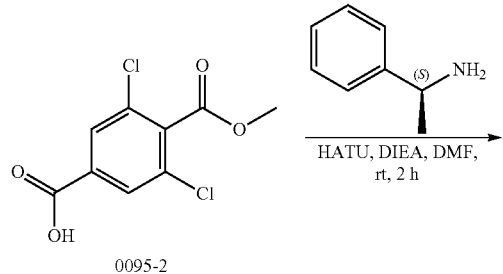

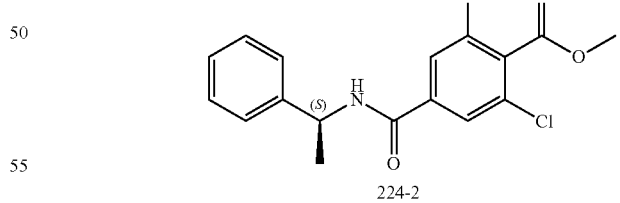

A solution of 0095-2 (400 mg, 1.60 mmol) in DMF (20 mL) was added HATU (610 mg, 1.60 mmol) and DIEA (621 mg, 4.81 mmol). After the reaction mixture was stirred for 15 min at room temperature, (S)-1-phenylethanamine (194 mg, 1.60 mmol) in DMF (5 mL) was added slowly. Then the solution was stirred at room temperature for 2 h. Concentrated and purified by pre-HPLC directly to give 224-2 (520 mg, 91.9% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+ 10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Rt=2.223 min; MS Calcd.: 351.1; MS Found: 351.9 [M+H]⁺.

The Synthesis of (S)-2,6-dichloro-4-(1-phenylethyl-carbamoyl)benzoic Acid (224-3)

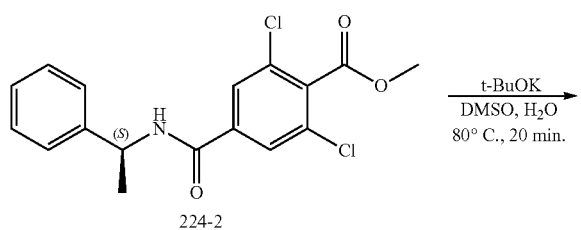

To a solution of 224-2 (500 mg, 1.42 mmol) in DMSO (10 mL) and H₂O (100 μL) was added tert-butyl potassium (318 mg, 2.84 mmol), the solution was heated to 80° C. and stirred for 20 min. After the consumption of starting material (by LCMS), the mixture was quenched with water (10 mL), extracted with EtOAc (20 mL×3), and washed the combined organic layers with water (20 mL×3). The residues was dried over anhydrous sodium sulfate and concentrated in vacuo. The crude product was purified by pre-HPLC to give 224-3 (410 mg, 30% yield) as colorless oil.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+ 10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Rt=1.325 min; MS Calcd.: 337.0; MS Found: 338.0 [M+H]⁺.

The Synthesis of (S)-benzyl 2-(2,6-dichloro-4-((S)-1-phenylethylcarbamoyl)benzamido)-3-(3-((R)-2,3-dihydro-1H-inden-1-yl)ureido)propanoate (224-4)

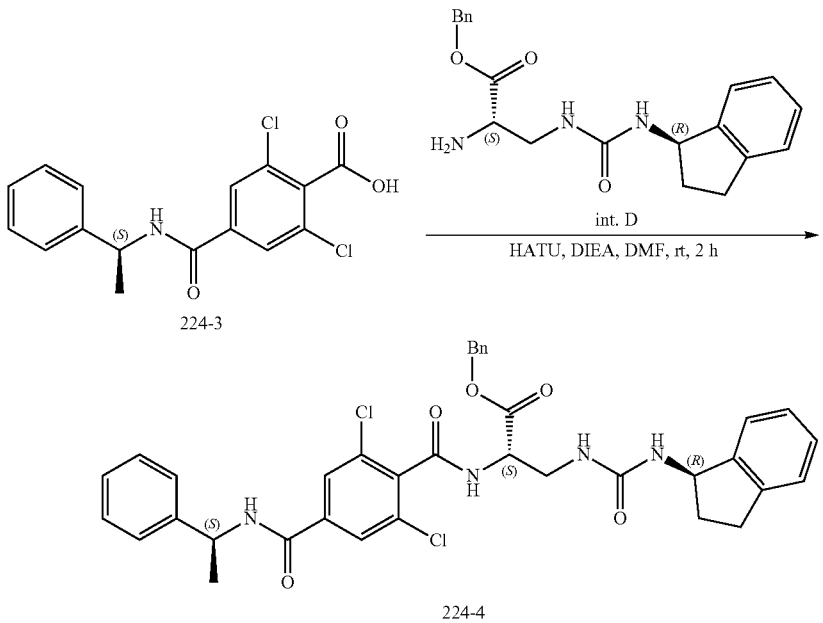

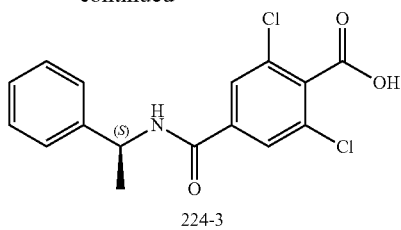

A solution of 224-3 (50.0 mg, 0.148 mmol) in DMF (10 mL) was added HATU (56.2 mg, 0.148 mmol) and DIEA (57.2 mg, 0.443 mmol). After the reaction mixture was stirred at room temperature for 15 min, int.D (52.3 mg, 0.148 mmol) in DMF (2 mL) was added slowly. Then the solution was stirred at room temperature for 2 h. Concentrated and purified by pre-HPLC directly to give 224-4 (49.1 mg, 49.3% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+ 10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Rt=2.249 min; MS Calcd.: 672.2; MS Found: 673.2 [M+H]⁺.

The Synthesis of (S)-2-(2,6-dichloro-4-((S)-1-phenylethylcarbamoyl)benzamido)-3-(3-((R)-2,3-dihydro-1H-inden-1-yl)ureido)propanoic Acid (SU15210-0224-01)

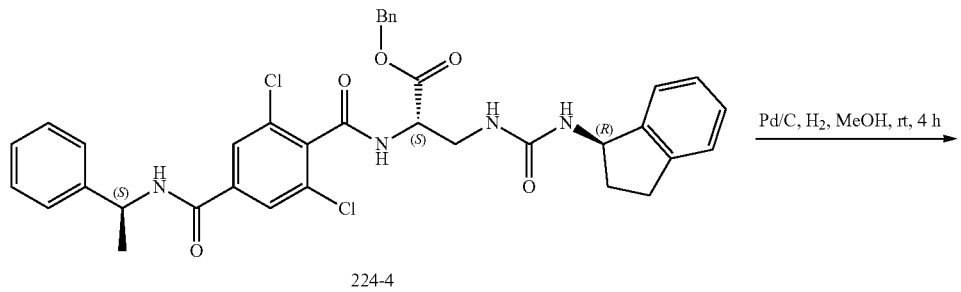

224-4

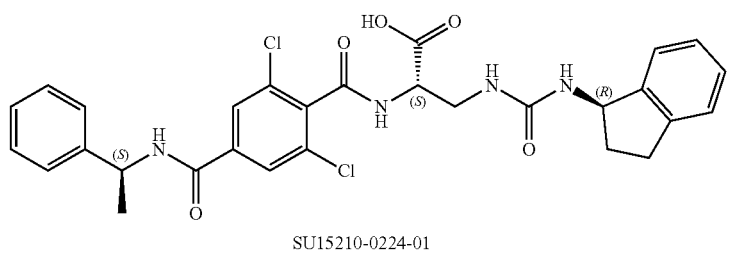

SU15210-0224-01

A solution of 224-4 (49.1 mg, 0.073 mmol) in CH₃OH (5 mL) was added Pd/C (5.00 mg) and stirred at room temperature for 4 h under H₂ atmosphere (1.0 atm). After the reaction was complete (by LCMS), the mixture was filtrated, the filtrate was concentrated and purified by prep-HPLC to get SU15210-0224-01 (25.0 mg, 58.9% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity is 100%. Rt=1.620 min; MS Calcd.: 582.1; MS Found: 583.1 [M+H]⁺.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity is 100%. Rt=7.685 min.

¹H NMR (400 MHz, DMSO-d₆) δ 9.08 (d, J=8 Hz, 1H), 8.91 (s, 1H), 7.97 (s, 2H), 7.15-7.39 (m, 10H), 6.62 (s, 1H), 5.90 (s, 1H), 5.07-5.16 (m, 2H), 4.41 (br, 1H), 3.48 (s, 1H), 2.75-2.86 (m, 2H), 2.32-2.37 (m, 1H), 1.64-1.69 (m, 1H), 1.48 (d, J=7.2 Hz, 3H).

SU15210-0225-01

Route for SU15210-0225-01

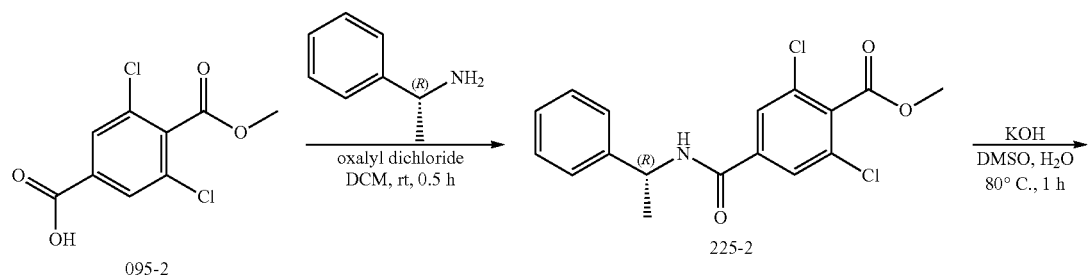

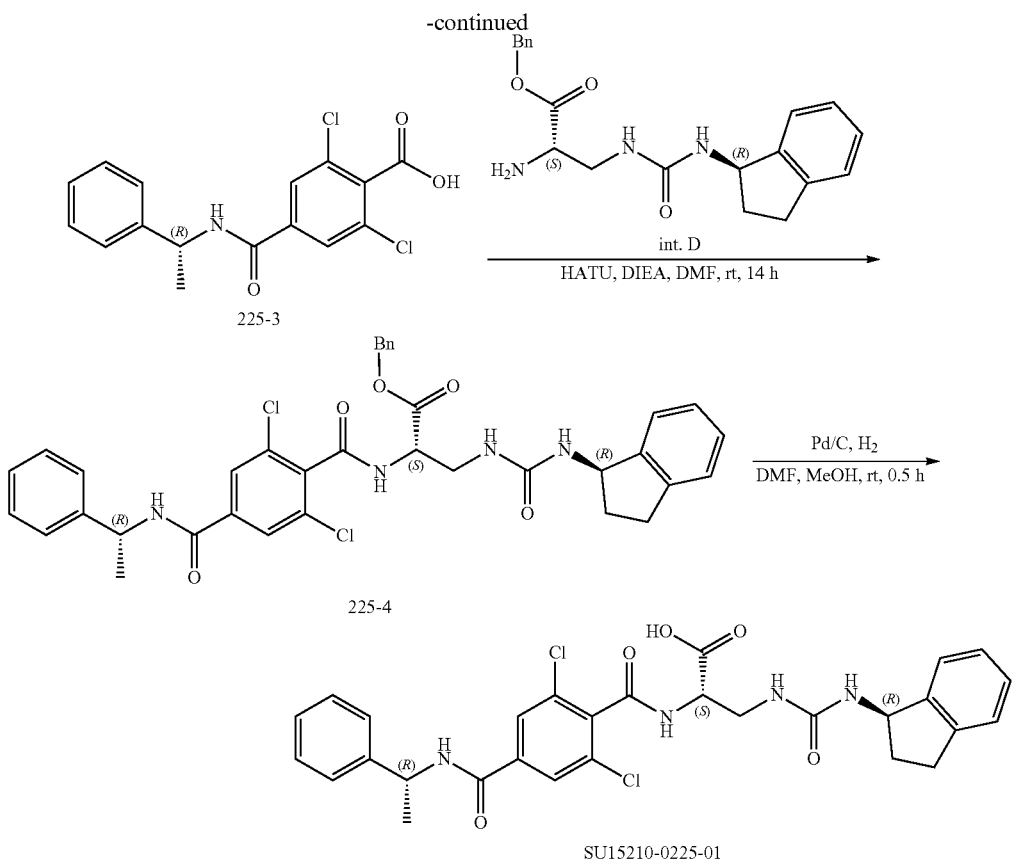

The Synthesis of (R)-methyl 2,6-dichloro-4-(1-phenylethylcarbamoyl)benzoate (225-2)

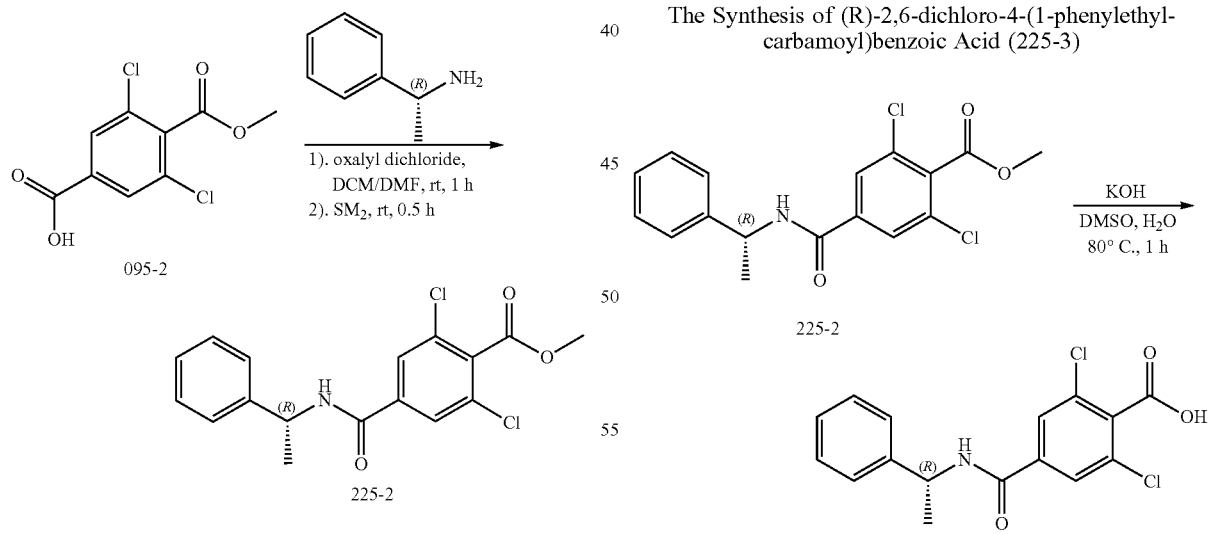

To a mixture of 095-2 (0.25 g, 1.00 mmol) and oxalyl dichloride (255 mg, 2.01 mmol) in DCM (5 mL) was added DMF (1 drop). After stirring at room temperature for 1 h, the reaction mixture was concentrated and dissolved in DCM (10 mL). (1R)-1-phenylethanamine (122 mg, 1.01 mmol) and DIEA (390 mg, 3.02 mmol) was added and stirred for 0.5 h, then added water, the aqueous phase was extracted with dichloromethane, the combined organic phases were dried over anhydrous sodium sulfate, filtered, concentrated in vacuo and purified with pre-TLC to give 225-2 (277 mg, yield: 78.6%) as brown oil.

The Synthesis of (R)-2,6-dichloro-4-(1-phenylethylcarbamoyl)benzoic Acid (225-3)

To a stirred solution of 225-2 (277 mg, 786.46 umol) in DMSO (3 mL) and $H_2O$ (1.5 mL) was added KOH (46.33 mg, 825.78 umol), the mixture was stirred at 80° C. for 1 h, purified with pre-HPLC to give 225-3 (183 mg, 68.81% yield) as a white solid.

The Synthesis of (S)-benzyl 2-(2,6-dichloro-4-((R)-1-phenylethylcarbamoyl)benzamido)-3-(3-((R)-2,3-dihydro-1H-inden-1-yl)ureido)propanoate (225-4)

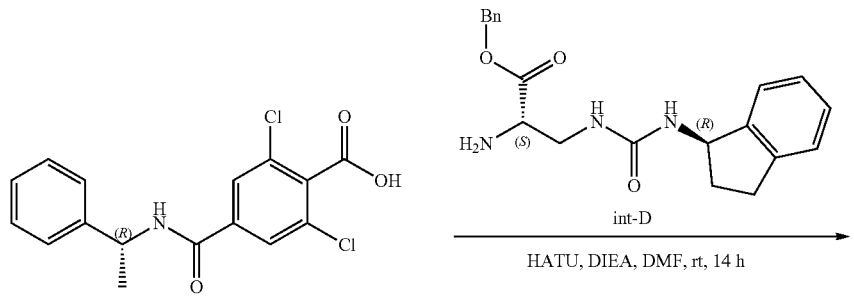

To a stirred solution of int. D (188.11 mg, 532.25 umol) in DMF (4 mL) was added 225-3 (150 mg, 443.54 umol), DIPEA (171.97 mg, 1.33 mmol) and HATU (252.97 mg) the mixture was stirred at rt for 14 h, purified by pre-HPLC to give 225-4 (96 mg, 32.13% yield) as a white solid.

The Synthesis of (S)-2-(2,6-dichloro-4-((R)-1-phenylethylcarbamoyl)benzamido)-3-(3-((R)-2,3-dihydro-1H-inden-1-yl)ureido)propanoic Acid (SU15210-0225-01)

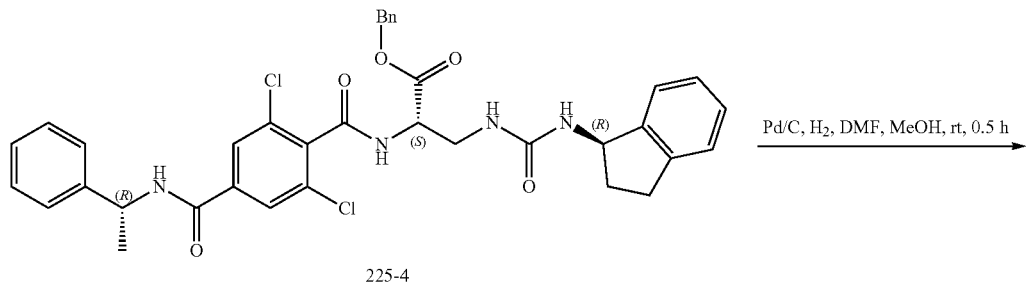

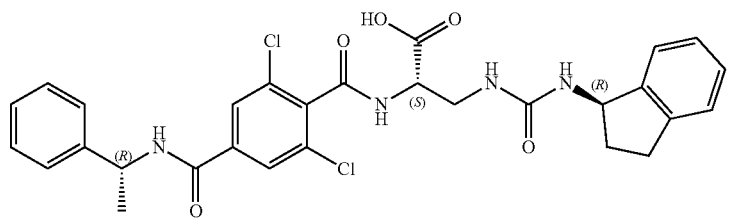

To a solution of 225-4 (110.00 mg, 163.31 umol) in DMF (8 mL) and MeOH (32 mL) was added Pd/C (10 mg), the mixture was stirred under hydrogen atmosphere (1 atm) at room temperature for 0.5 h, filtrated, concentrated and purified by pre-HPLC to give SU15210-0225-01 (49 mg, 51.43% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: A: Water (0.05% TFA) B: ACN (0.05% TFA); Gradient: B from 5% to 100% for 1.6 min and hold 100% for 1.4 min. Purity: 99.04%, Rt=1.756 min; MS Calcd.: 582.14; MS Found: 583.2 [M+H]$^+$.

HPLC (Agilent HPLC 1200, Column: WATERS XBridge (150 mm*4.6 mm*3.5 um); Column Temperature: 40° C.; Flow Rate: 1.0 mL/min; Mobile Phase: A: Water (0.05% TFA) B: ACN (0.05% TFA); Gradient: Pump1:B from 5% to 100% for 10 min and hold 100% for 5.0 min. Purity: 100%, Rt=8.461 min.

$^1$H NMR (400 MHz, DMSO-d$_6$) δ 12.61 (br, 1H), 9.08-9.12 (m, 2H), 7.98 (s, 2H), 9.31-7.39 (m, 4H), 7.16-7.25 (m, 5H), 6.58 (d, J=8.4 Hz, 1H), 5.88 (t, J=5.6 Hz, 1H), 5.06-5.18 (m, 2H), 4.51 (q, J=7.6 Hz, 1H), 3.53-3.59 (m, 1H), 3.32-3.39 (m, 1H), 2.71-2.91 (m, 2H), 2.33-2.41 (m, 1H), 1.62-1.72 (m, 1H), 1.48 (d, J=7.2 Hz, 3H).

SU15210-0226-01

Route for SU15210-0226-01

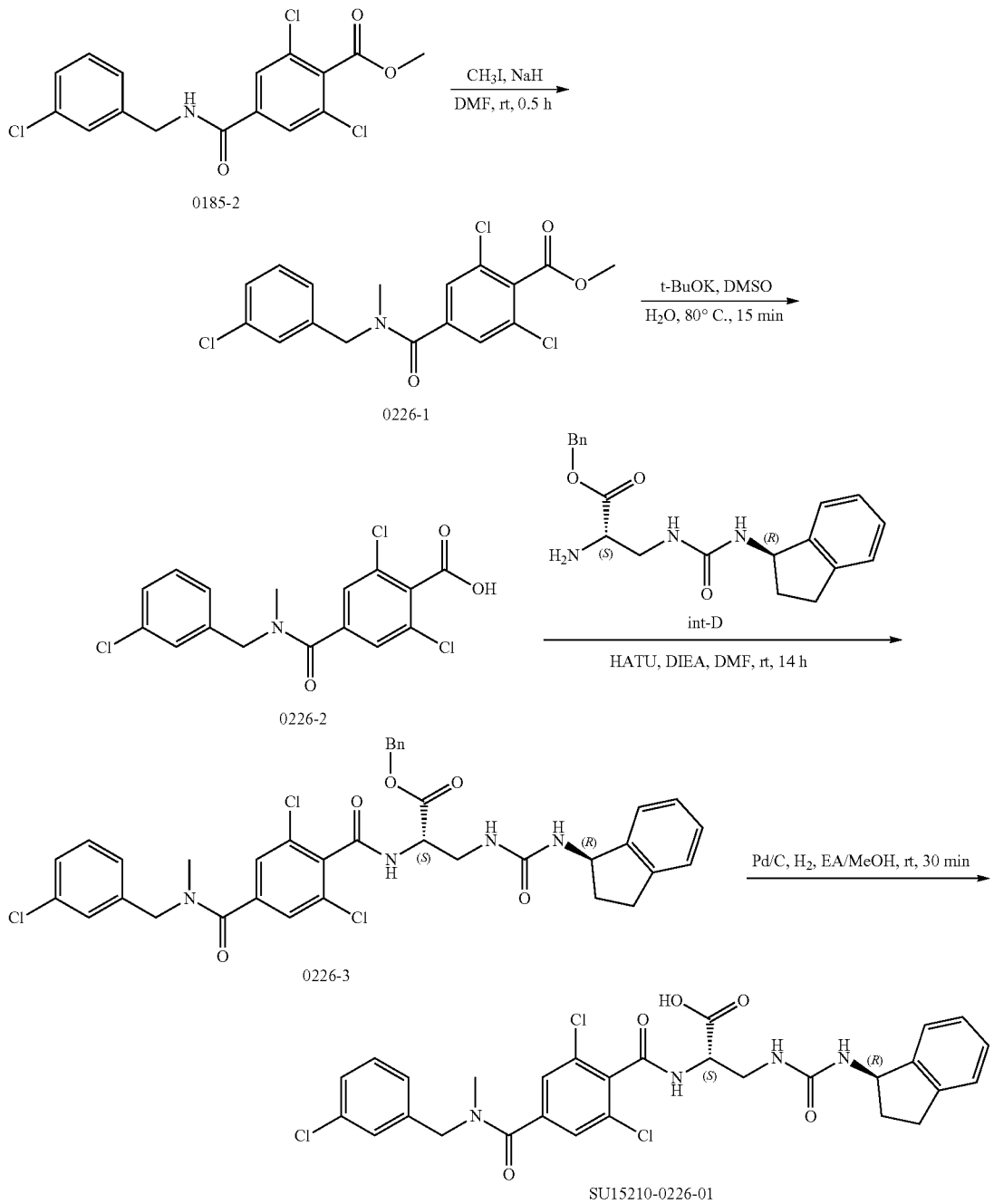

The Synthesis of methyl 2,6-dichloro-4-((3-chlorobenzyl)(methyl)carbamoyl)benzoate (0226-1)

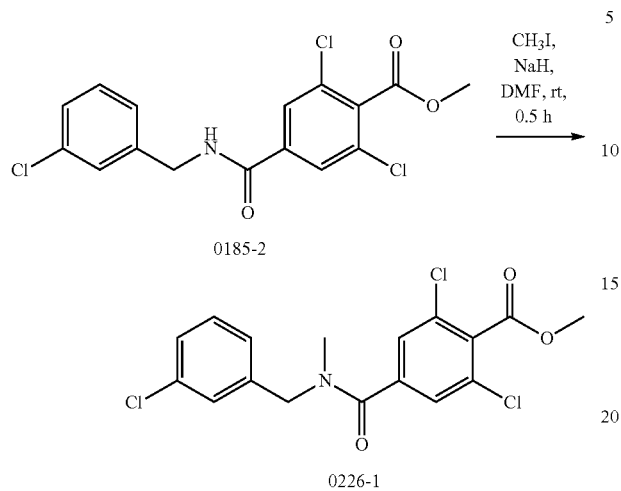

Sodium hydride (70 mg, 1.83 mmol, 60% dispersion in mineral oil) was added to a stirred solution of 0185-2 (450 mg, 1.21 mmol) in DMF (5 mL) at rt. After stirring for 15 min, iodomethane (343 mg, 2.42 mmol) was added and the reaction mixture was stirred for another 0.5 h at room temperature. The reaction mixture was diluted with water (20 ml), extracted ethyl acetate (20 mL×2). The combined organic layers were washed with brine (10 mL×2), dried over sodium sulfate, and concentrated to give 0226-1 (450 mg, 96.37% yield) as an off-white solid.

The Synthesis of 2,6-dichloro-4-((3-chlorobenzyl)(methyl)carbamoyl)benzoic Acid (0226-2)

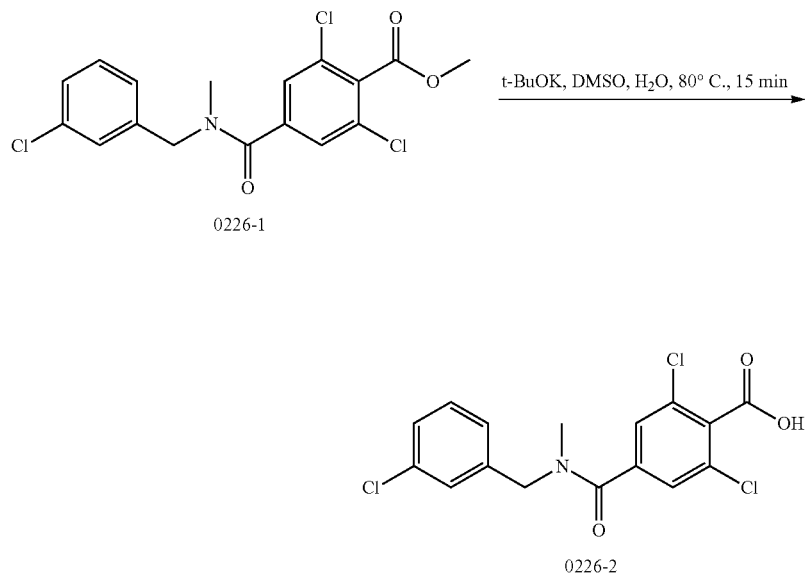

The mixture of 0226-1 (410 mg, 1.06 mmol), potassium 2-methylpropan-2-olate (119 mg, 1.06 mmol) and water (1 drop) in DMSO (4 mL) was stirred at 80° C. for 15 min. The reaction mixture was diluted with water (20 ml), extracted ethyl acetate (30 mL×2). The combined organic layers were washed with brine (10 mL×2), dried over sodium sulfate, and concentrated. The residue was purified by reverse flash column to give 0226-2 (249 mg, 63.02% yield) as colorless oil.

The Synthesis of (S)-benzyl 2-(2,6-dichloro-4-((3-chlorobenzyl)(methyl)carbamoyl)benzamido)-3-(3-((R)-2,3-dihydro-1H-inden-1-yl)ureido)propanoate (0226-3)

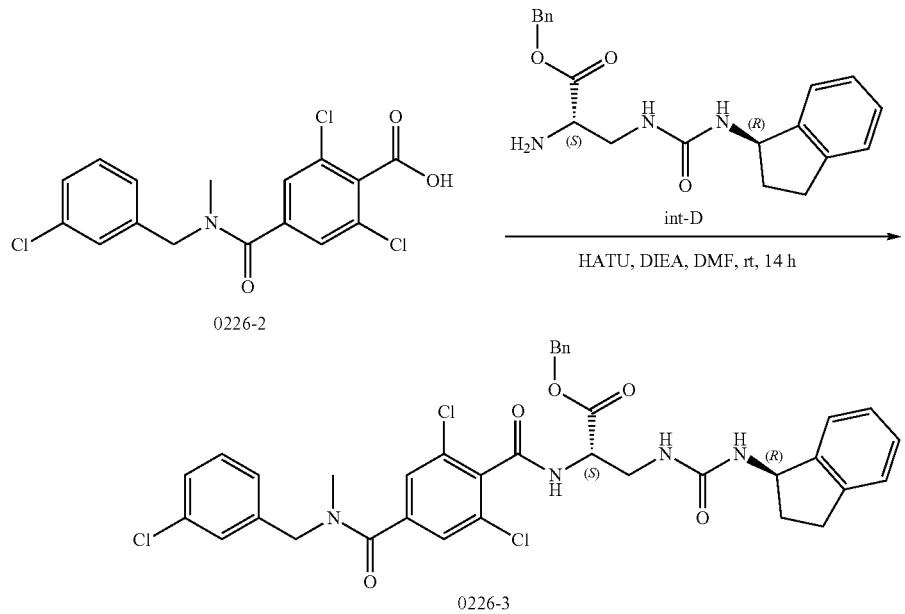

To a stirred solution of 0226-2 (188 mg, 504.52 umol) in DMF (3 mL) was added int.D (178.31 mg, 504.52 umol), DIPEA (195.61 mg, 1.51 mmol) and HATU (287.75 mg, 756.78 umol) the mixture was stirred at rt for 14 h, purified with pre-HPLC to give 0226-3 (121 mg, 33.87% yield) as a white solid.

The Synthesis of (S)-2-(2,6-dichloro-4-((3-chlorobenzyl)(methyl)carbamoyl)benzamido)-3-(3-((R)-2,3-dihydro-1H-inden-1-yl)ureido)propanoic Acid (SU15210-0226-01)

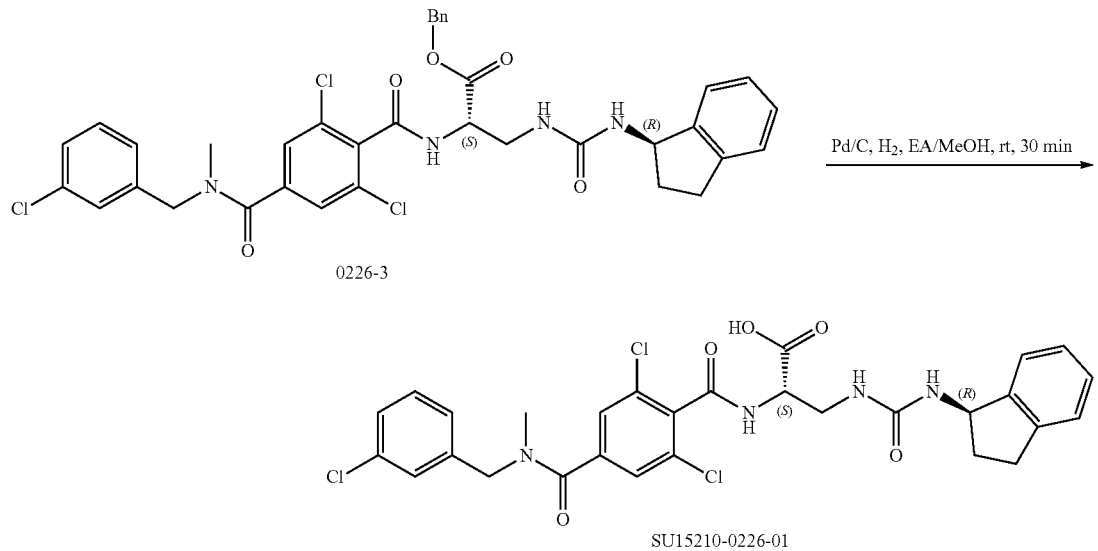

To a solution of 0226-3 (110 mg, 155.36 umol) in MeOH (12 mL) and Ethyl acetate (24 mL) was added Pd/C (20 mg), the mixture was stirred under hydrogen atmosphere (1 atm) at room temperature for 0.5 h, filtrated, concentrated and purified by pre-HPLC to give SU15210-0226-01 (67 mg, 69.79% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: A: Water (0.05% TFA) B: ACN (0.05% TFA); Gradient: B from 5% to 100% for 1.6 min and hold 100% for 1.4 min; Purity: 99.82%, Rt=1.794 min; MS Calcd.: 616.10; MS Found: 617.2 [M+H]$^+$.

HPLC (Agilent HPLC 1200, Column: WATERS XBridge (150 mm*4.6 mm*3.5 um); Column Temperature: 40° C.; Flow Rate: 1.0 mL/min; Mobile Phase: A: Water (0.05% TFA) B: ACN (0.05% TFA); Gradient: Pump1:B from 5% to 100% for 10 min and hold 100% for 5.0 min. Purity: 100%, Rt=8.719 min.

$^1$H NMR (400 MHz, DMSO-d$_6$) δ 9.00-9.08 (m, 1H), 7.59-7.66 (m, 2H), 7.31-7.45 (m, 4H), 7.17-7.23 (m, 4H), 6.53-6.59 (m, 1H), 5.85-5.87 (m, 1H), 5.8-5.11 (m, 1H), 4.66 (s, 1H), 4.45-4.53 (m, 2H), 3.54-3.57 (m, 1H), 3.32-3.36 (m, 1H), 2.85-2.89 (m, 4H), 2.68-2.79 (m, 1H), 2.35-2.39 (m, 1H), 1.62-1.72 (m, 1H).

SU15210-0227-01

Route for SU15210-0227-01:

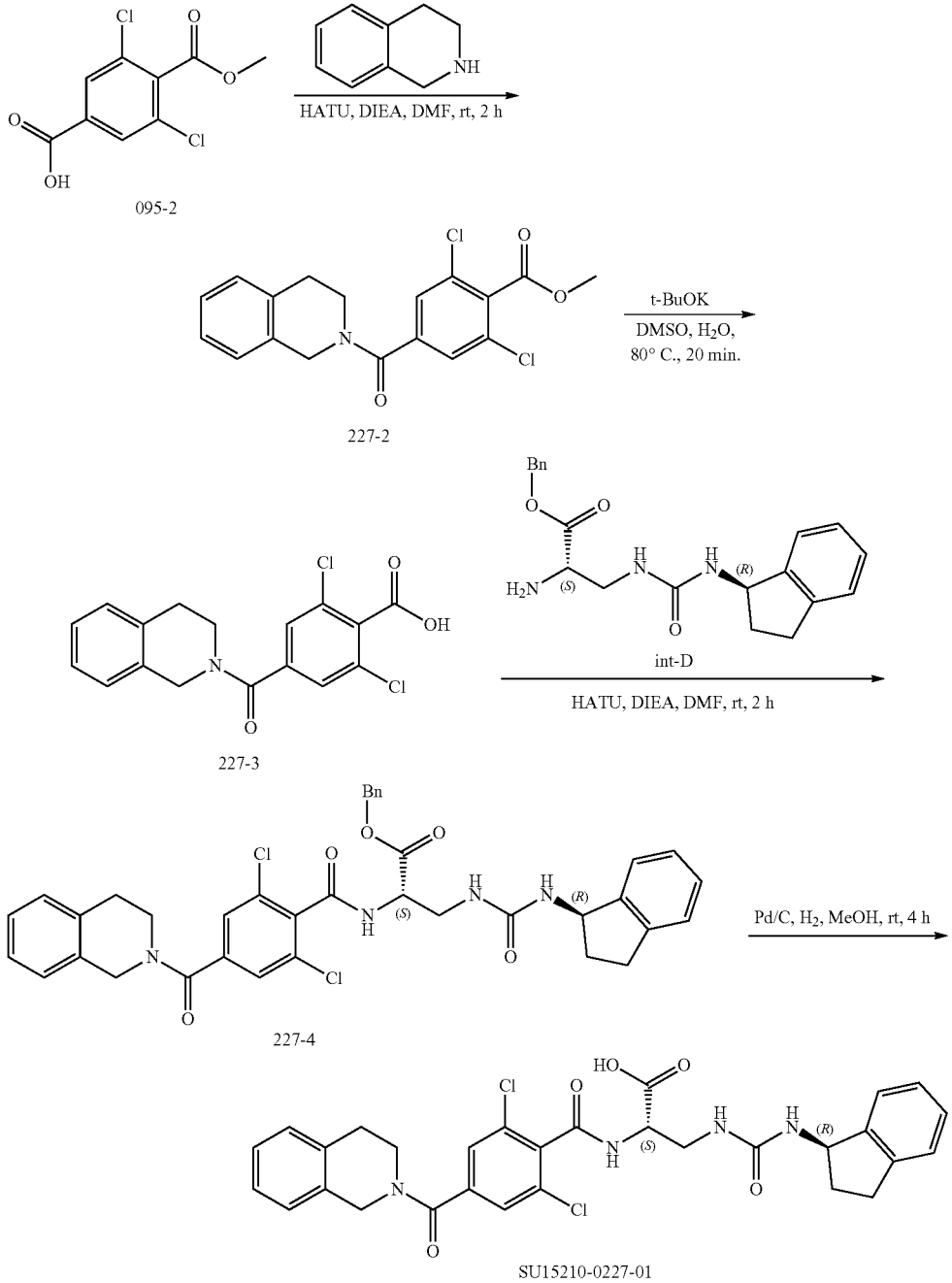

551
The Synthesis of methyl 2,6-dichloro-4-(1,2,3,4-tetrahydroisoquinoline-2-carbonyl)benzoate (227-2)

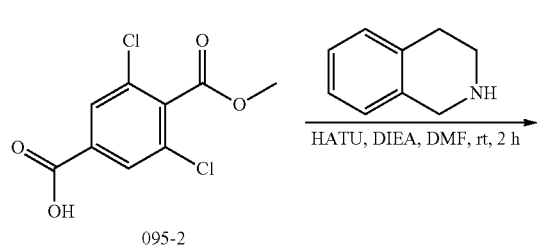

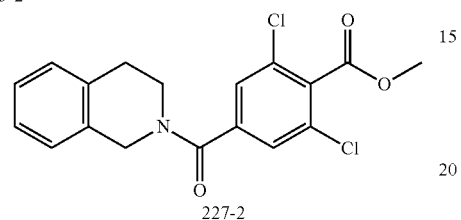

A solution of 095-2 (400 mg, 1.60 mmol) in DMF (20 mL) were added HATU (610 mg, 1.60 mmol) and DIEA (621 mg, 4.81 mmol). After the reaction mixture was stirred for 15 min at room temperature, 1,2,3,4-tetrahydroisoquinoline (194 mg, 1.60 mmol) in DMF (5 mL) was added slowly. Then the solution was stirred at room temperature for 2 h. Concentrated and purified by pre-HPLC directly to get methyl 227-2 (350 mg, 60.2% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Rt=2.205 min; MS Calcd.: 363.0; MS Found: 364.0 [M+H]$^+$.

552
The Synthesis of 2,6-dichloro-4-(1,2,3,4-tetrahydroisoquinoline-2-carbonyl)benzoic Acid (227-3)

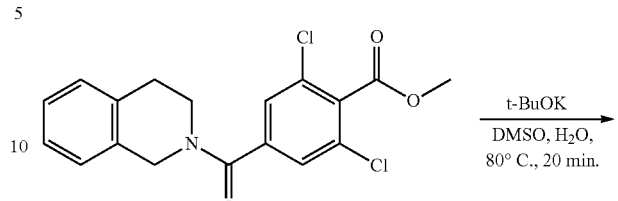

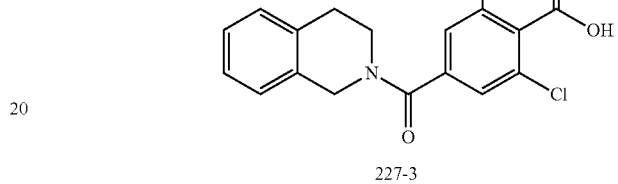

To a solution of 227-2 (350 mg, 0.965 mmol) in DMSO (10 mL) and H$_2$O (100 μL) was added tert-butyl potassium (216 mg, 1.93 mmol), the solution was heated to 80° C. and stirred for 20 min. After the consumption of starting material (by LCMS), the mixture was quenched with water (10 mL), extracted with EtOAc (20 mL×3), and washed the combined organic layers with water (20 mL×3). The residues was dried over anhydrous sodium sulfate and concentrated in vacuo. The crude product was purified by pre-HPLC to give 227-3 (110 mg, 32.6% yield) as colorless oil.

The Synthesis of (S)-benzyl 2-(2,6-dichloro-4-(1,2,3,4-tetrahydroisoquinoline-2-carbonyl)benzamido)-3-(3-((R)-2,3-dihydro-1H-inden-1-yl)ureido)propanoate (227-4)

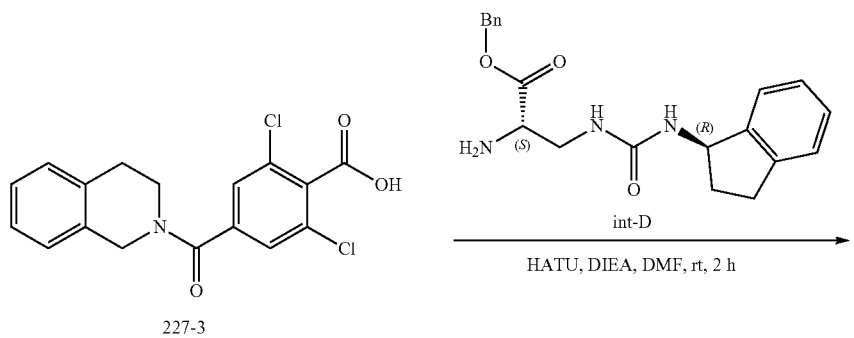

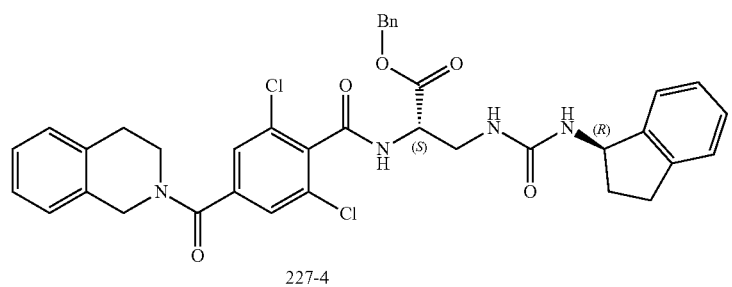

A solution of 227-3 (110 mg, 0.315 mmol) in DMF (20 mL) was added HATU (120 mg, 0.315 mmol) and DIEA (112 mg, 0.945 mmol). After the reaction mixture was stirred for 15 min at room temperature, int.D (111 mg, 0.315 mmol) in DMF (2 mL) was added slowly. Then the solution was stirred at room temperature for 2 h. Concentrated and purified by prep-HPLC directly to get 227-4 (120 mg, 55.6% yield) as a white solid.

The Synthesis of(S)-2-(2,6-dichloro-4-(1,2,3,4-tetra-hydroisoquinoline-2-carbonyl)benzamido)-3-(3-((R)-2,3-dihydro-1H-inden-1-yl)ureido)propanoic Acid (SU15210-0227-01)

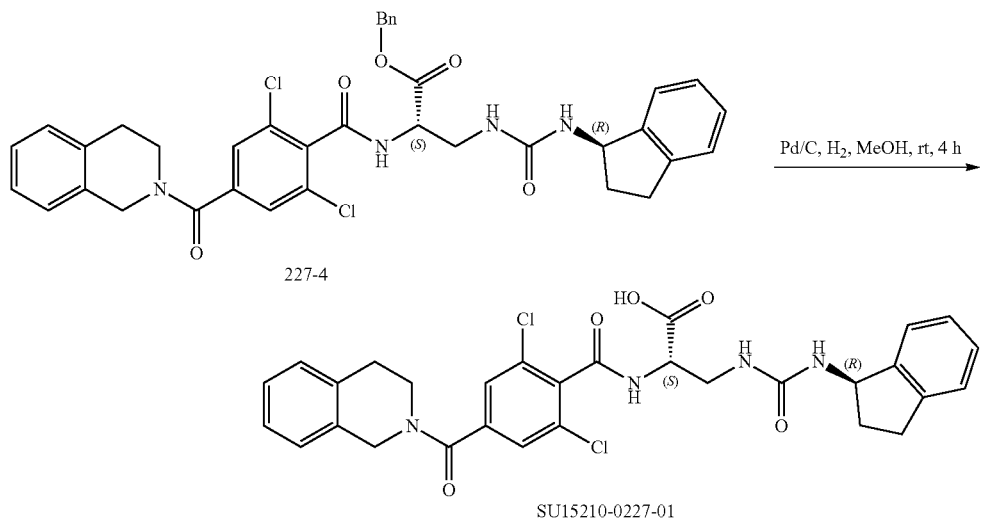

A solution of 227-4 (120 mg, 0.175 mmol) in CH$_3$OH (10 mL) was added Pd/C (10 mg) and stirred at room temperature for 4 h under H$_2$ atmosphere (1.0 atm). After the reaction was complete (by LCMS), the mixture was filtrated, the filtrate was concentrated and purified by prep-HPLC to give SU15210-0227-01 (43.1 mg, 41.4% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity is 100%. Rt=1.587 min; MS Calcd.: 594.1; MS Found: 595.1 [M+H]$^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity is 100%. Rt=7.619 min.

$^1$H NMR (400 MHz, DMSO-d$_6$) δ 8.61 (s, 1H), 7.60 (s, 1H), 7.57 (s, 1H), 7.13-7.27 (m, 10H), 6.65 (s, 1H), 5.92 (s, 1H), 5.05-5.11 (m, 1H), 4.76 (s, 1H), 4.54 (s, 1H), 4.30 (s, 1H), 3.82 (s, 1H), 3.54 (s, 2H), 2.74-2.90 (m, 5H), 2.33-2.38 (m, 1H), 1.65-1.70 (m, 1H).

SU15210-0228-01

Route for SU15210-0228-01:

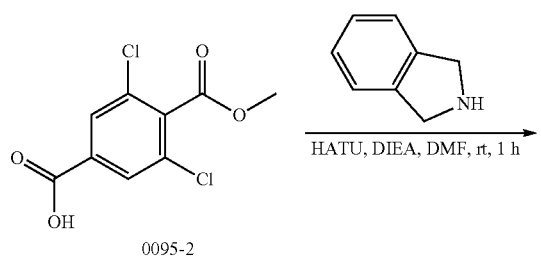

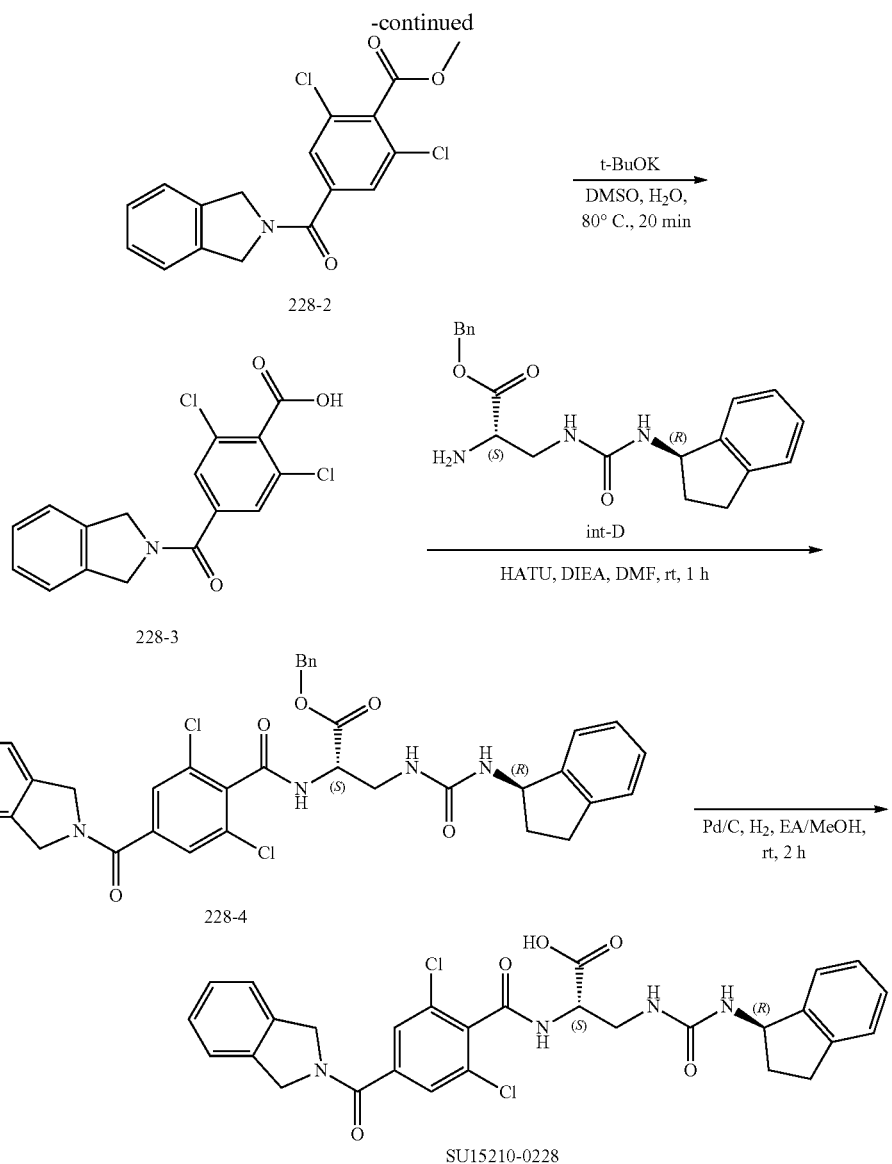

The Synthesis of Methyl 2,6-dichloro-4-(isoindoline-2-carbonyl)benzoate (0228-2)

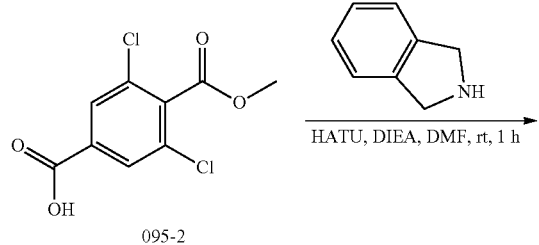

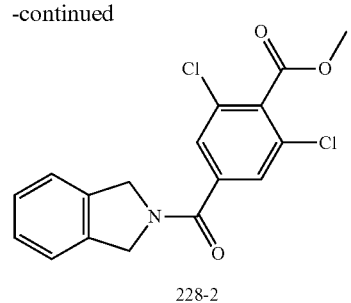

To a solution of 095-2 (250 mg, 1.00 mmol) in DMF (5 mL) was added isoindoline (119.62 mg, 1.00 mmol), HATU (138.14 mg, 361.38 umol) and DIEA (46.71 mg, 361.38 umol) at room temperature. The reaction mixture was stirred at rt for 1 hr. After the reaction was finished, the solvent was dissolved in water (20 mL) and EA (20 mL), the organic layer was then separated and the water phase was extracted with EA (20 mL×3), the organic phase was combined and washed with water then brine, dried over Na₂SO₄, concentrated and purified by pre-HPLC to get 0228-2 (300 mg, 85.34% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 92.12%. Rt=0.755 min; MS Calcd.: 349.03; MS Found: 350.2 [M+H]⁺.

The Synthesis of
2,6-dichloro-4-(isoindoline-2-carbonyl)benzoic Acid
(0228-3)

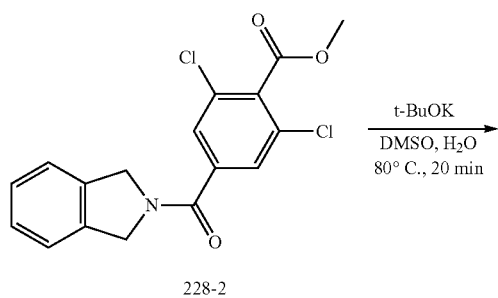

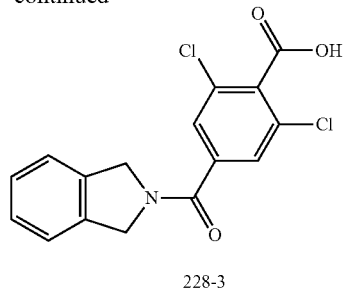

To a solution of 0228-2 (300 mg, 856.66 umol) in H₂O (0.3 mL) and DMSO (3 mL) was added t-BuOK (96.13 mg, 856.66 umol), the solution was stirred at 80° C. for 20 min, After the reaction was finished, the solvent was removed in vacuum, the residual was dissolved in water (20 mL) and EA (20 mL), acidified by 1N HCl aq. to pH-2, the organic layer was then separated and the water phase was extracted with EA (20 mL×3), the organic phase was combined and washed with water then brine, dried over Na₂SO₄, concentrated and purified by pre-HPLC to get 0228-3 (250 mg, 86.81% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 92.12%. Rt=0.616 min; MS Calcd.: 335.0; MS Found: 336.0 [M+H]⁺.

The Synthesis of (S)-benzyl 2-(2,6-dichloro-4-(isoindoline-2-carbonyl)benzamido)-3-(3-((R)-2,3-dihydro-1H-inden-1-yl)ureido)propanoate (0228-4)

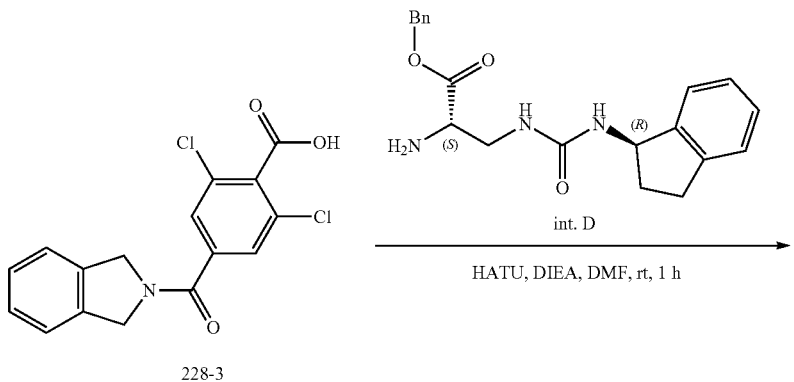

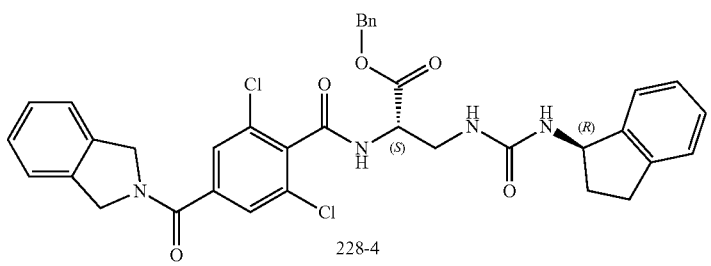

To a solution of 228-3 (250 mg, 743.67 umol) in DMF (5 mL) was added int.D (262.82 mg, 743.67 umol), HATU (284.27 mg, 743.67 umol) and DIEA (144.17 mg, 1.12 mmol), the mixture was stirred at room temperature for 1 h. After the consumption of starting material (by LCMS), water (10 mL) was added, extracted with ethyl acetate (20 mL×3), washed with water (20 mL×3), dried and concentrated. The crude was purified by pre-HPLC to get 228-4 (300 mg, 60.07% yield) as a white solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [$CH_3CN$] to 0% [water+10 mM TFA] and 100% [$CH_3CN$] in 0.8 min, then under this condition for 0.4 min, finally changed to 95% [water+10 mM TFA] and 5% [$CH_3CN$] in 0.01 min. Purity is 100%. Rt=0.785 min; MS Calcd.: 670.1; MS Found: 671.1[M+H]$^+$.

The Synthesis of (S)-2-(2,6-dichloro-4-(isoindoline-2-carbonyl)benzamido)-3-(3-((R)-2,3-dihydro-1H-inden-1-yl)ureido)propanoic Acid (SU15210-0228)

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [$CH_3CN$] to 0% [water+10 mM TFA] and 100% [$CH_3CN$] in 1.6 min, then under this condition for 1.4 min, finally changed to 95% [water+10 mM TFA] and 5% [$CH_3CN$] in 0.1 min. Purity is 100%. Rt=1.670 min; MS Calcd.: 580.13; MS Found: 581.3 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 100%. Rt=7.550 min.

$^1$H NMR (400 MHz, DMSO-$d_6$): δ7.72 (s, 2H), 7.29-7.41 (m, 5H), 7.15-7.22 (m, 5H), 6.71 (d, J=8.0 Hz, 1H), 5.96 (d,

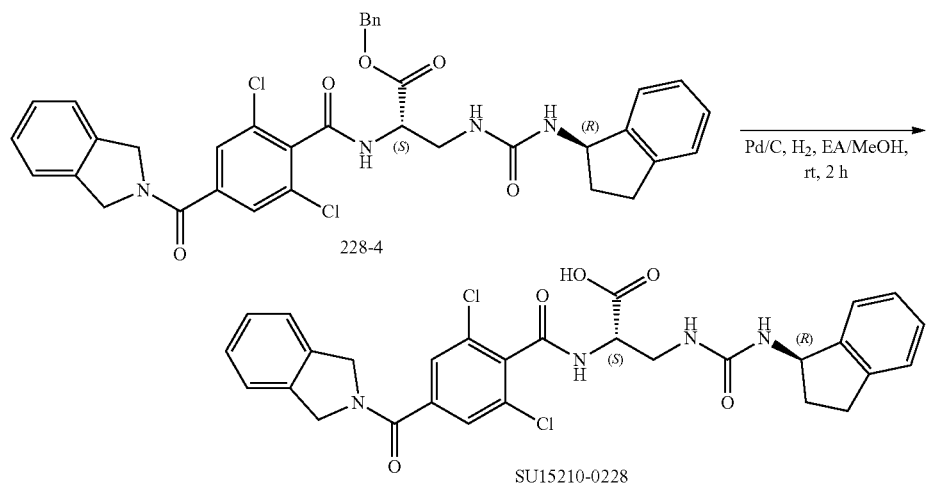

A solution of 228-4 (100 mg, 148.91 umol) in EA (2 mL) and MeOH (1 mL) was added Pd/C (10 mg) and stirred at room temperature for 2 h under $H_2$ atmosphere (1.0 atm). After the reaction was complete (by LCMS), the mixture was filtrated, the filtrate was concentrated and purified by pre-HPLC to get SU15210-0228 (50 mg, 57.75% yield) as a white solid.

J=8.0 Hz, 1H), 5.05-5.11 (m, 1H), 4.84 (s, 2H), 4.78 (s, 2H), 4.15 (br, 1H), 3.48-3.51 (m, 1H), 2.84-2.89 (m, 1H), 2.66-2.78 (m, 1H), 2.33-2.39 (m, 2H), 1.65-1.7 (m, 1H).

SU15210-0234-01

Route for SU15210-0234-01:

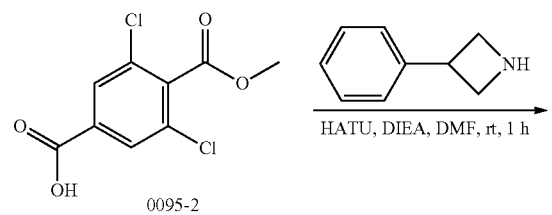

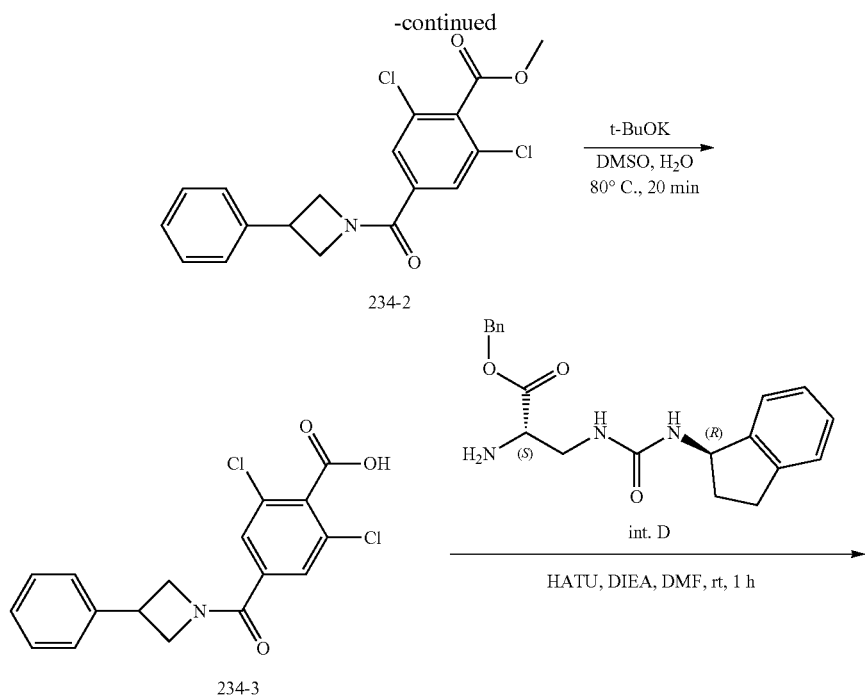
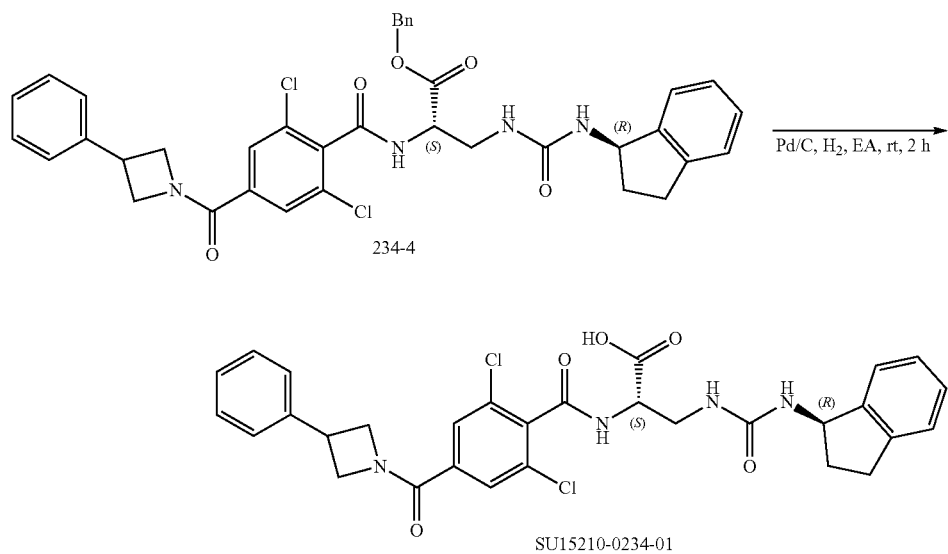
The Synthesis of Methyl 2,6-dichloro-4-(3-phenylazetidine-1-carbonyl)benzoate (0234-2)
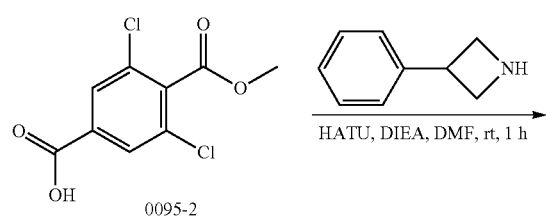
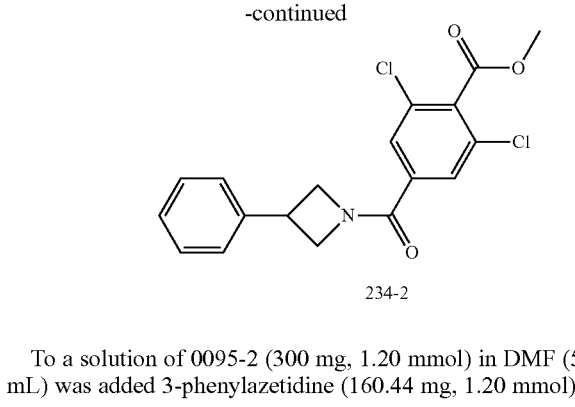
To a solution of 0095-2 (300 mg, 1.20 mmol) in DMF (5 mL) was added 3-phenylazetidine (160.44 mg, 1.20 mmol), HATU (460.45 mg, 1.20 mmol) and DIEA (155.68 mg, 1.20 mmol). The reaction mixture was stirred at rt for 1 hr. After the reaction was finished, the solvent was removed in vacuum, the organic layer was then separated and the water phase was extracted with EA (20 mL×3), the organic phase was combined and washed with water then brine, dried over Na$_2$SO$_4$, concentrated and purified by pre-HPLC to get 234-2 (400 mg, 91.17% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 92.12%. Rt=0.777 min; MS Calcd.: 363.0; MS Found: 364.2 [M+H]$^+$.

The Synthesis of 2,6-dichloro-4-(3-phenylazetidine-1-carbonyl)benzoic Acid (0234-3)

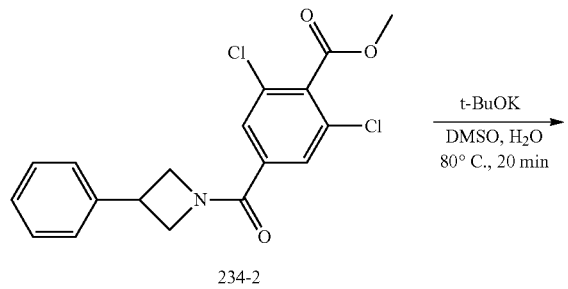

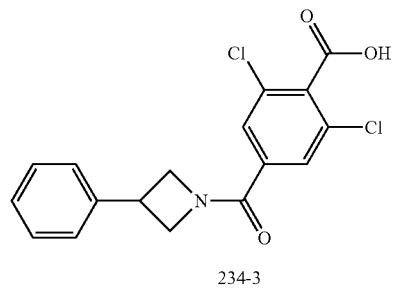

To a solution of 0234-2 (200 mg, 551 umol) in H$_2$O (0.4 mL) and DMSO (4 mL) was added t-BuOK (67.78 mg, 604.03 umol). The mixture was stirred at 80° C. for 20 min. After the reaction was finished, the solvent was removed in vacuum, the residual was dissolved in water (20 mL) and EA (20 mL), Acidified by 1N HCl aq. to pH-2, the organic layer was then separated and the water phase was extracted with EA (20 mL×3), the organic phase was combined and washed with water then brine, dried over Na$_2$SO$_4$, concentrated and purified by pre-HPLC to get 234-3 (150 mg, 78.00% yield) as yellow oil.

The Synthesis of Benzyl (2S)-2-[[2,6-dichloro-4-(3-phenylazetidine-1-carbonyl)benzoyl]amino]-3-[[[(1S)-indan-1-yl]carbamoylamino]propanoate (0234-4)

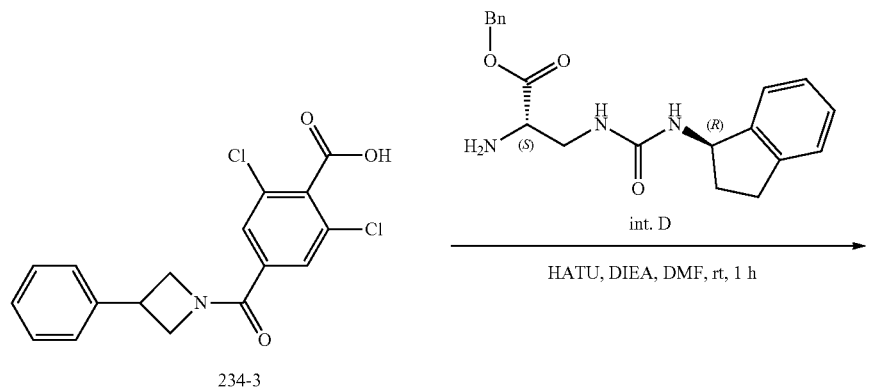

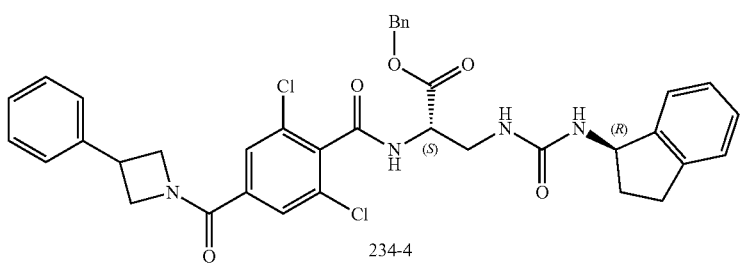

To a solution of 0234-3 (80 mg, 1.52 mmol) in DMF (5 mL) was added int.D (80.74 mg, 228.44 umol), HATU (87.32 mg, 228.44 umol) and DIEA (59.05 mg, 456.89 umol), the mixture was stirred at room temperature for 1 h. After the consumption of starting material (by LCMS), water (10 mL) was added, extracted with ethyl acetate (20 mL×3), washed with water (20 mL×3), dried and concentrated. The crude was purified by pre-HPLC to get 0234-4 (80 mg, 51.08% yield) as yellow oil.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 100%. Rt=0.797 min; MS Calcd.: 684.1; MS Found: 686.1 [M+H]$^+$.

The Synthesis of (2S)-2-(2,6-dichlorobenzamido)-3-(2-(6-guanidinochroman-4-ylamino)acetamido)propanoic Acid (SU15210-0234-01)

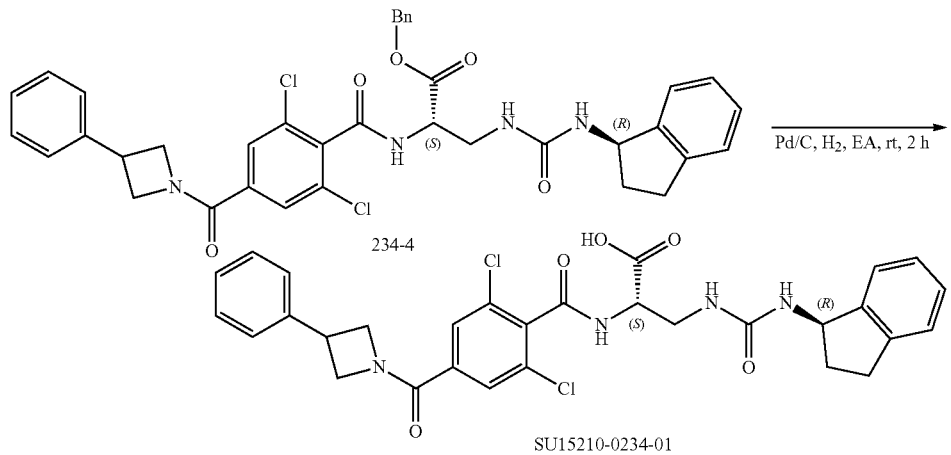

A solution of 234-4 (80 mg, 116.69 umol) in EA (2 mL) and MeOH (1 mL) was added Pd/C (10 mg) and stirred at room temperature for 2 h under H$_2$ atmosphere (1.0 atm). After the reaction was complete (by LCMS), the mixture was filtrated, the filtrate was concentrated and purified by pre-HPLC to get SU15210-0234 (50 mg, 71.96% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.717 min; MS Calcd.: 594.1; MS Found: 597.2 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=7.678 min.

$^1$H NMR (400 MHz, DMSO-d$_6$): δ 7.73 (s, 2H), 7.35-7.44 (m, 5H), 7.15-7.29 (m, 5H), 6.64 (d, J=8.0 Hz, 1H), 5.91 (t, J=4 Hz, 1H), 5.04-5.10 (m, 1H), 4.65-4.69 (m, 1H), 4.41-4.51 (m, 2H), 3.91-4.04 (m, 2H), 3.42 (s, 2H), 2.83-2.89 (m, 1H), 2.67-2.78 (m, 1H), 2.32-2.42 (m, 2H), 1.62-1.71 (m, 1H).

SU15210-0235-01
Route for SU15210-0235-01:

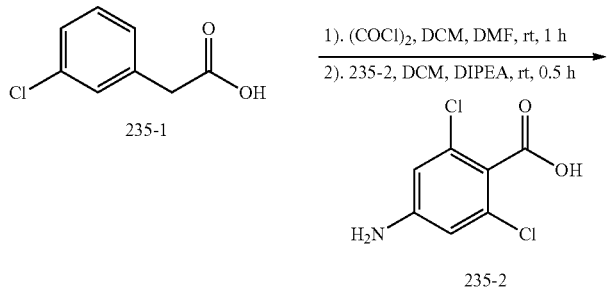

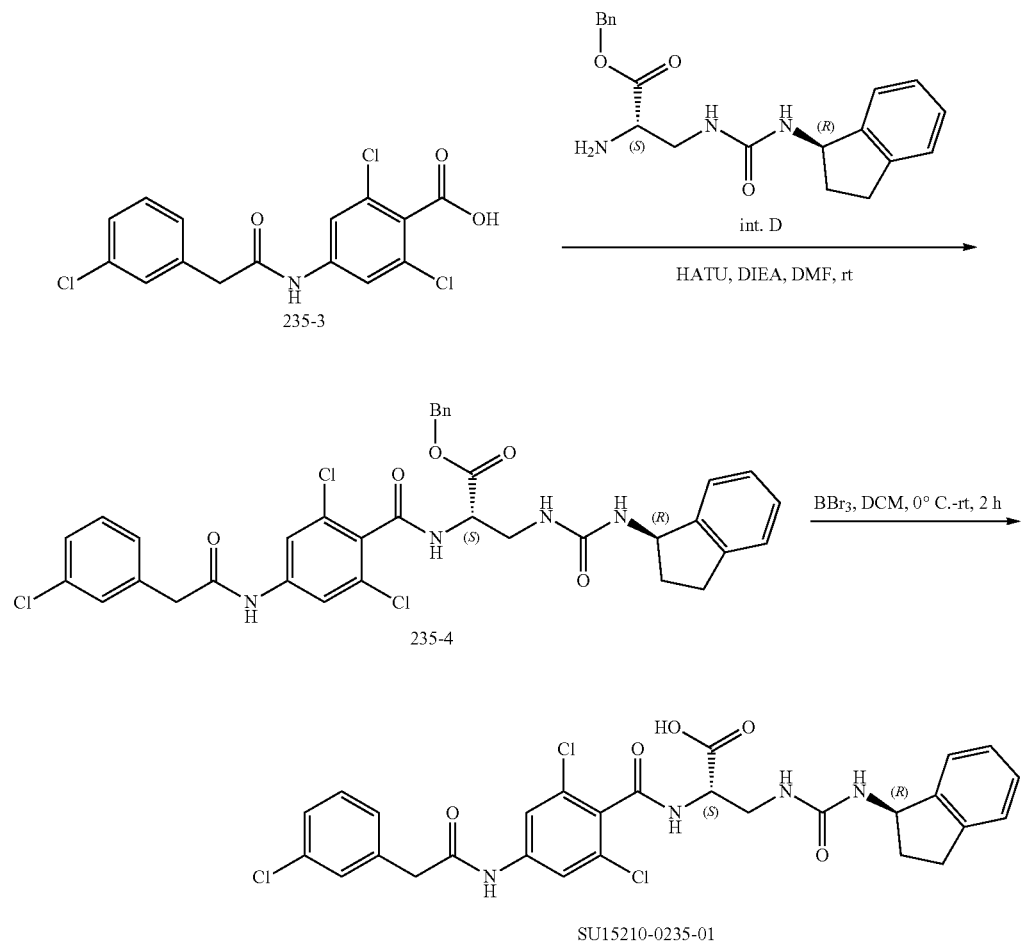

The Synthesis of 2,6-dichloro-4-(2-(3-chlorophenyl)acetamido)benzoic Acid (235-3)

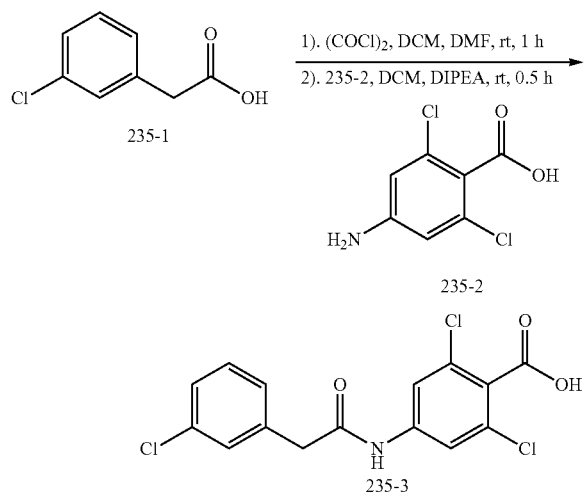

To a mixture of 235-1 (307 mg, 1.80 mmol) and oxalyl dichloride (457 mg, 3.60 mmol) in $CH_2Cl_2$ (20 mL) was added DMF (1 drop). After stirring at room temperature for 1 h, the reaction mixture was concentrated and dissolved in $CH_2Cl_2$ (10 mL). 235-2 (372 mg, 1.81 mmol) and DIPEA (698 mg, 5.40 mmol) was added to the solution and stirred at room temperature for 0.5 h. The reaction mixture was concentrated and the residue was purified by Prep-HPLC to give compound 235-3 (354 mg, 54.85% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity is 100%. Rt=1.396 min; MS Calcd.: 357.0; MS Found: 358.0 $[M+H]^+$.

The Synthesis of (S)-benzyl 2-(2,6-dichloro-4-(2-(3-chlorophenyl)acetamido)benzamido)-3-(3-((R)-2,3-dihydro-1H-inden-1-yl)ureido)propanoate (235-4)

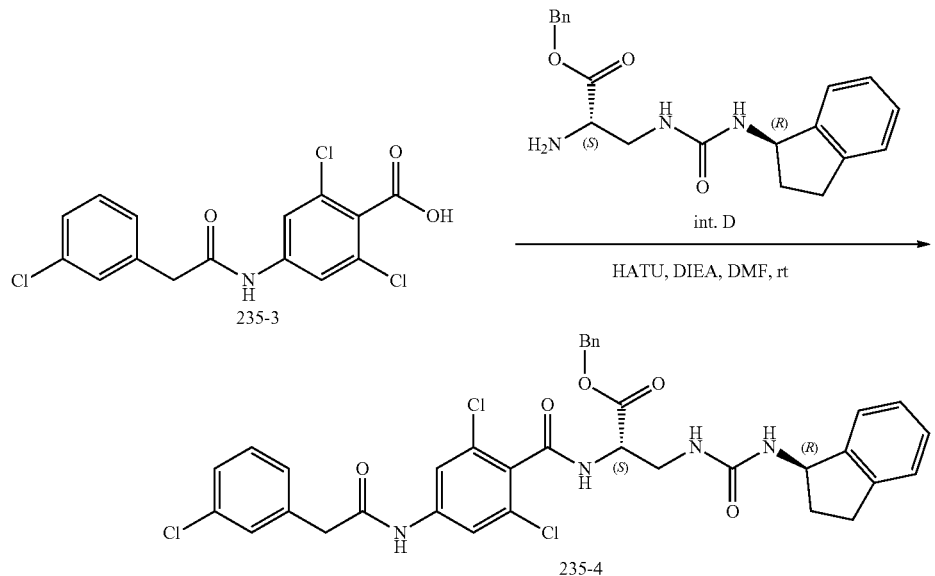

To a mixture of 235-3 (142 mg, 395.98 umol), int.D (140.00 mg, 396.14 umol) and HATU (226.00 mg, 591.24 umol) in DMF (10 mL) was added DIPEA (152.00 mg, 1.18 mmol) and stirred at room temperature for 16 h. Then the mixture was diluted with water and extracted by ethyl acetate (20 mL×2). The combined organic layers were washed with brine (10 mL×2), dried over sodium sulfate, and concentrated. The residue was purified by Prep-TLC (petroleum ether/ethyl acetate=2/3) twice then Prep-HPLC to give the target compound 235-4 (47 mg, 67.72 umol, 17.10% yield) as a white solid.

Agilent LCMS 1200-6120, Column: Phenomenex Kinetex EVO C18 (50 mm*4.6 mm*2.6 m); Column Temperature: 40° C.; Flow Rate: 2.3 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.75 min, then under this condition for 0.8 min, finally changed to 95% [water+10 mM $NH_4HCO_3$] and 5% [$CH_3CN$] in 0.1 min and under this condition for 0.1 min. Purity is 99.02%. Rt=1.885 min; MS Calcd.: 692.1; MS Found: 693.2 $[M+H]^+$.

The synthesis of (S)-2-(2,6-dichloro-4-(2-(3-chlorophenyl)acetamido)benzamido)-3-(3-((R)-2,3-dihydro-1H-inden-1-yl)ureido)propanoic Acid (SU15210-0235-01)

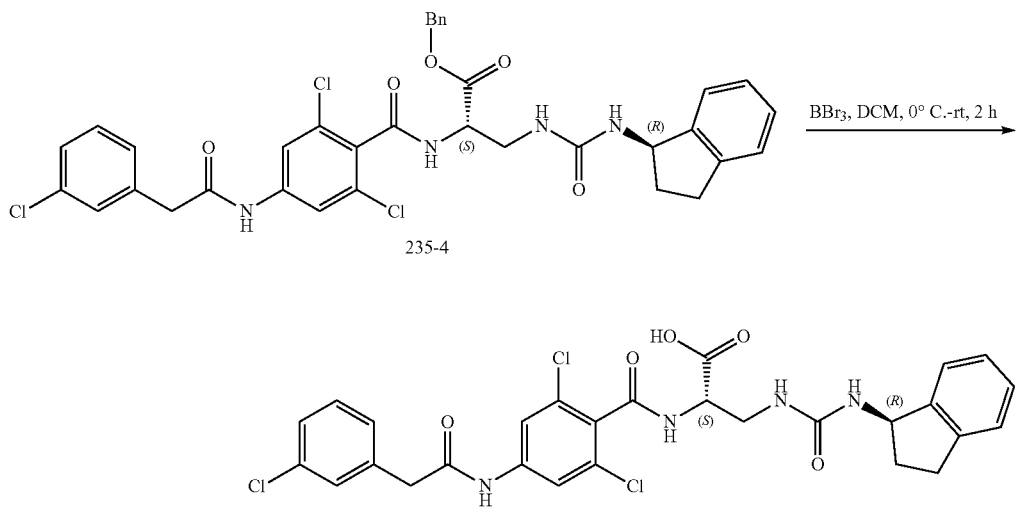

To a solution of 235-4 (47 mg, 67.72 umol) in CH₂Cl₂ (10 mL) was added BBr₃ (52 mg, 207.57 umol) at 0° C., then stirred at room temperature for 2 h. The reaction was finished which was detected by LCMS and concentrated. Then the residue was purified by Prep-HPLC to give the target compound SU15210-0235-01 (25 mg, 61.13% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity is 98.69%. Rt=1.750 min; MS Calcd.: 602.1; MS Found: 603.2 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=7.375 min.

¹HNMR (400 MHz, DMSO-d₆) δ 10.58 (s, 1H), 7.69 (s, 2H), 7.32-7.40 (m, 3H), 7.17-7.19 (m, 1H), 7.15-7.22 (m, 4H), 6.56-6.69 (br, 1H), 5.87-5.95 (br, 1H), 5.04-5.08 (m, 1H), 4.26-4.28 (br, 1H), 3.72 (s, 2H), 3.37-3.41 (m, 2H), 3.27-3.31 (m, 2H), 2.83-2.89 (m, 1H), 2.67-2.78 (m, 1H), 2.32-2.38 (m, 1H), 1.64-1.69 (m, 1H).

SU15210-0066-4
Route for SU15210-0066-4

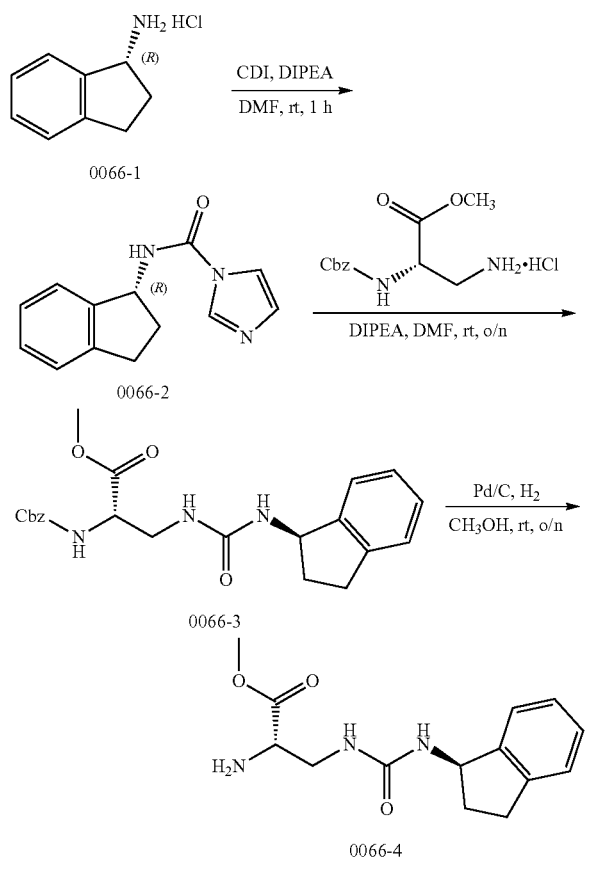

The Synthesis of (S)-methyl 2-(((benzyloxy)carbonyl)amino)-3-(3-((R)-2,3-dihydro-1H-inden-1-yl)ureido)propanoate (0066-3)

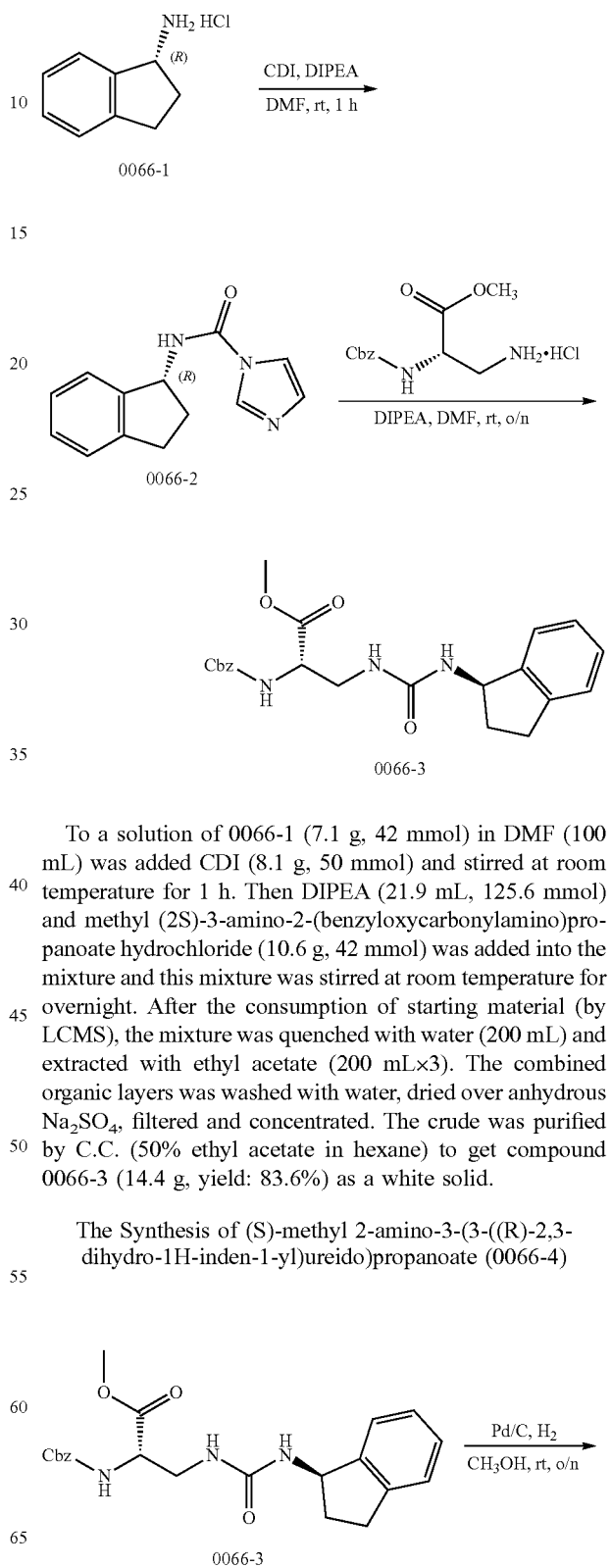

To a solution of 0066-1 (7.1 g, 42 mmol) in DMF (100 mL) was added CDI (8.1 g, 50 mmol) and stirred at room temperature for 1 h. Then DIPEA (21.9 mL, 125.6 mmol) and methyl (2S)-3-amino-2-(benzyloxycarbonylamino)propanoate hydrochloride (10.6 g, 42 mmol) was added into the mixture and this mixture was stirred at room temperature for overnight. After the consumption of starting material (by LCMS), the mixture was quenched with water (200 mL) and extracted with ethyl acetate (200 mL×3). The combined organic layers was washed with water, dried over anhydrous Na₂SO₄, filtered and concentrated. The crude was purified by C.C. (50% ethyl acetate in hexane) to get compound 0066-3 (14.4 g, yield: 83.6%) as a white solid.

The Synthesis of (S)-methyl 2-amino-3-(3-((R)-2,3-dihydro-1H-inden-1-yl)ureido)propanoate (0066-4)

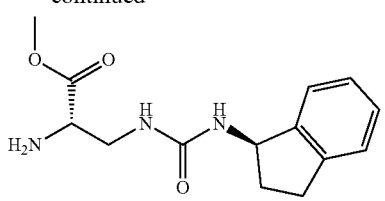

0066-4

To a solution of compound 0066-3 (16.4 g, 40 mmol) in methanol (150 mL) was added 10% Pd on activated Carbon (1.6 g) and replaced with H₂ (1.0 atm). This mixture was stirred at room temperature for overnight. After the consumption of starting material (by LCMS), the mixture was filtered and the filtrate was concentrated in a vacuo to get 0066-4 (10.1 g, yield: 91.4%) as a white solid.

SU15210-0002-06-Bn (int.A):

Route for SU15210-0002-06-Bn (int.A):

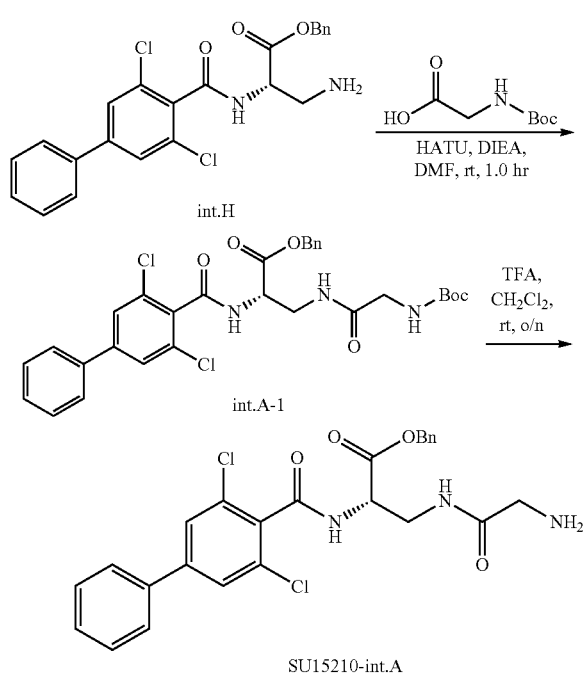

SU15210-int.A

The Synthesis of Benzyl (2S)-3-[[2-(tert-butoxycarbonylamino)acetyl]amino]-2-[(2,6-dichloro-4-phenyl-benzoyl)amino]propanoate (int.A-1)

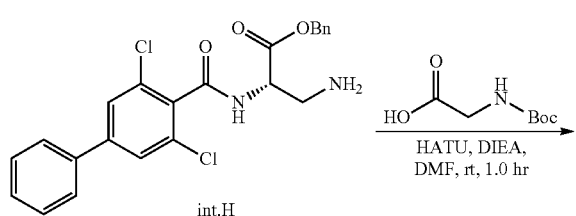

int.H

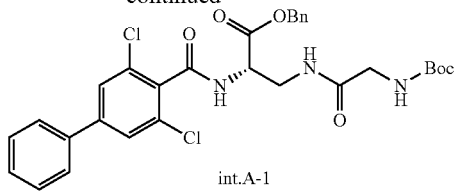

int.A-1

To a solution of int.H (620.00 mg, 1.40 mmol) and BOC-Glycine (245.00 mg, 1.40 mmol) in DMF (5 mL) was added HATU (797.64 mg, 2.10 mmol) and DIEA (361.49 mg, 2.80 mmol) at room temperature. The reaction mixture was stirred at room temperature for 1.0 hour. After the reaction was finished, the solvent was poured into water (50 mL), the precipitate was filtrated then dried and purified by CC (10% to 30% ethyl acetate in petroleum ether) to get int.A-1 (600.00 mg, 71.45% yield) as a white solid.

Agilent LCMS 1200-6120, Column: Halo C18 (50 mm*4.6 mm*2.6 m); Column Temperature: 45° C.; Flow Rate: 2.3 mL/min; Mobile Phase: from 95% [water+10 mM NH₄HCO₃] and 5% [CH₃CN] to 0% [water+10 mM NH₄HCO₃] and 100% [CH₃CN] in 1.75 min, then under this condition for 0.80 min, finally changed to 95% [water+10 mM NH₄HCO₃] and 5% [CH₃CN] in 0.20 min. Purity is 99.31%. Rt=1.864 min; MS Calcd.: 599.7; MS Found: 600.7 [M+H]⁺.

The Synthesis of Benzyl (2S)-3-[(2-aminoacetyl)amino]-2-[(2,6-dichloro-4-phenyl-benzoyl)amino]propanoate (SU15210-int.A)

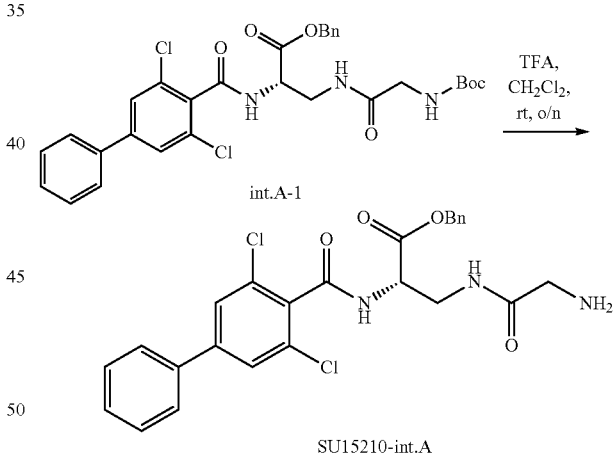

SU15210-int.A

To a solution of int.A-1 in DCM (5 mL) was added TFA (170.89 mg, 1.50 mmol), the solution was stirred at room temperature for overnight. After the reaction was finished, the solution was concentrated and the crude product was dissolved in water. The solution was basified with Na₂CO₃ to pH 10, then the solution was washed by EA for three times, the EA layer was concentrated and purified by prep-HPLC to get SU15210-int.A (450 mg, 90.01% yield) as a white solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity is 96.04%. Rt=0.626 min; MS Calcd.: 499.7; MS Found: 500.7 [M+H]⁺.

SU15210-int-B

Route for SU15210-int-B:

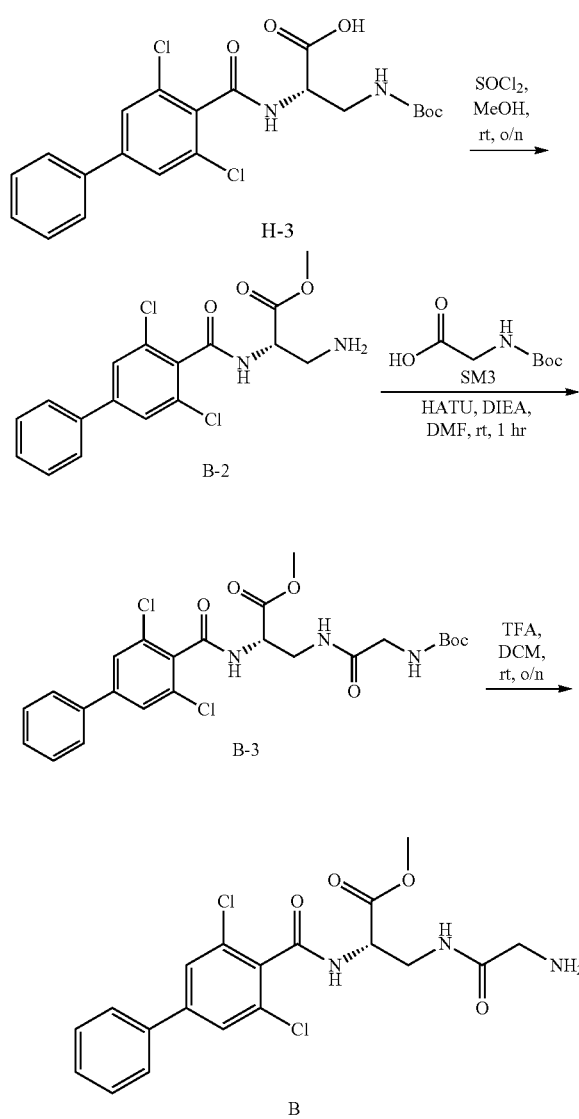

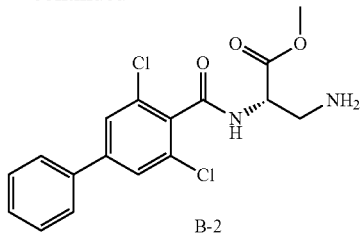

To a solution of int.H-3 (2.0 g, 4.42 mmol) in MeOH (20 mL) was added SOCl₂ (5 mL), the solution was stirred at room temperature for overnight. After the reaction was finished, concentrated to give int.B-2 (1.8 g, 100% yield) as a white solid and used directly for the next step.

The Synthesis of (S)-methyl 3-(2-(tert-butoxycarbonylamino)acetamido)-2-(3,5-dichlorobiphenyl-4-ylcarboxamido)propanoate (int.B-3)

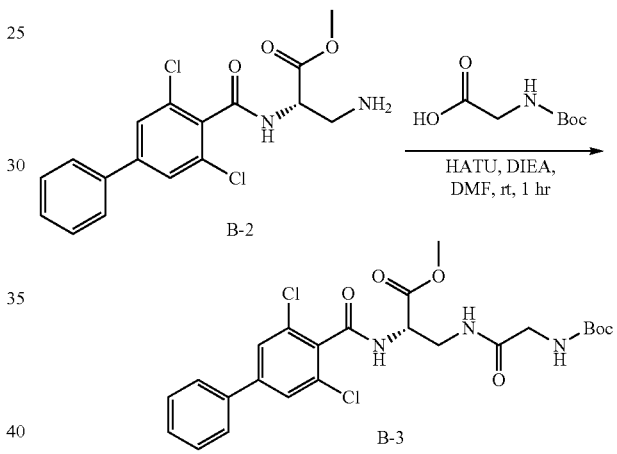

To a solution of int.B-2 (1.8 g, 4.42 mmol) and BOC-Glycine (0.8 g, 4.42 mmol) in DMF (10 mL) was added HATU (1.7 g, 4.42 mmol) and DIEA (1.7 g, 13.26 mmol) at room temperature. The reaction mixture was stirred at room temperature for 1.0 hour. After the reaction was finished, the solvent was poured into water (100 mL) and the precipitate was collected by filtration. The solid was then dried and purified by CC (10% to 30% ethyl acetate in petroleum ether) to get int.B-3 (1.9 g, 82% yield) as a white solid.

The Synthesis of (S)-methyl 3-(2-(tert-butoxycarbonylamino)acetamido)-2-(3,5-dichlorobiphenyl-4-ylcarboxamido)propanoate (SU15210-int.B)

The Synthesis of (S)-methyl 3-amino-2-(3,5-dichlorobiphenyl-4-ylcarboxamido)propanoate (int.B-2)

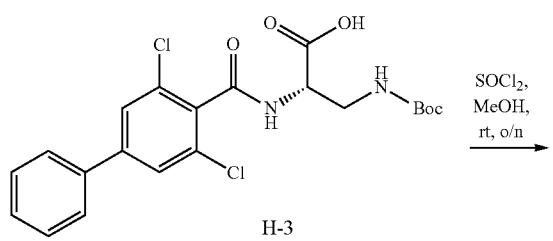

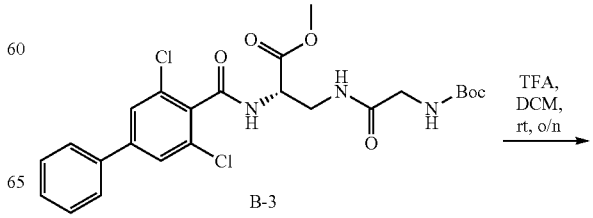

-continued

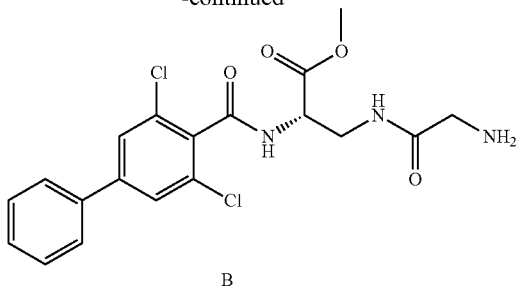

B

To a solution of int.B-3 (1.9 g, 3.63 mmol) in DCM (10 mL) was added TFA (2 mL), the solution was stirred at room temperature for overnight. After the reaction was finished, the solution was concentrated and the crude product was dissolved in water. The solution was basified with $Na_2CO_3$ to pH 10, then the solution was washed by EA for three times, the EA layer was separated and washed with water then brine, dried over $Na_2SO_4$, concentrated and purified by prep-HPLC to get SU15210-int.B (1.4 g, 91% yield) as a white solid.

Agilent LCMS 1200-6120, Column: Halo C18 (30 mm*4.6 mm*2.7 m); Column Temperature: 40° C.; Flow Rate: 3.0 mL/min; Mobile Phase: from 95% [water+10 mM TFA] and 5% [$CH_3CN$] to 0% [water+10 mM TFA] and 100% [$CH_3CN$] in 0.8 min, then under this condition for 0.4 min, finally changed to 95% [water+10 mM TFA] and 5% [$CH_3CN$] in 0.01 min. Purity is 98.81%. Rt=0.561 min; MS Calcd.: 423.1; MS Found: 424.1 $[M+H]^+$.

Intermediate D

Route for the intermediate D:

The Synthesis of (S)-benzyl 2-(tert-butoxycarbonylamino)-3-(3-((R)-2,3-dihydro-1H-inden-1-yl)ureido)propanoate (D-2)

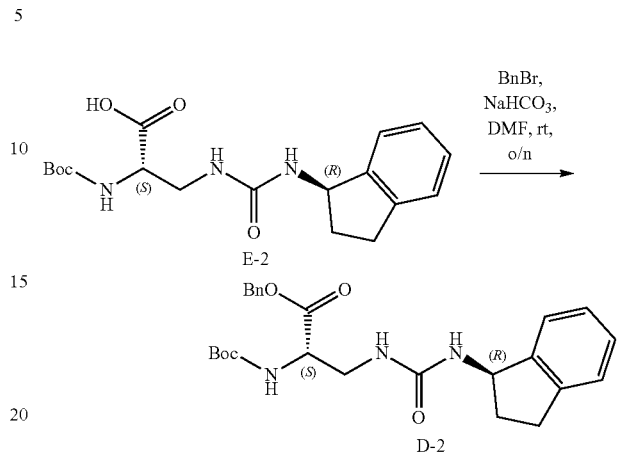

To a solution of E-2 (2.6 g, 7.2 mmol) in DMF (30 mL) was added $NaHCO_3$ (1.2 g, 14.4 mmol) and BnBr (1.8 g, 10.8 mmol), the mixture was stirred at rt for overnight. After the reaction was finished (detected by LCMS), 250 mL $H_2O$ was added to quench the reaction, extracted with EtOAc (40 mL×3), combined the organic layer, dried over anhydrous $Na_2SO_4$, filtered and concentrated, the crude was purified by CC to get the product D-2 (3.1 g, 95.6% yield) as white solid.

The Synthesis of (S)-benzyl 2-amino-3-(3-((R)-2,3-dihydro-1H-inden-1-yl)ureido)propanoate (D)

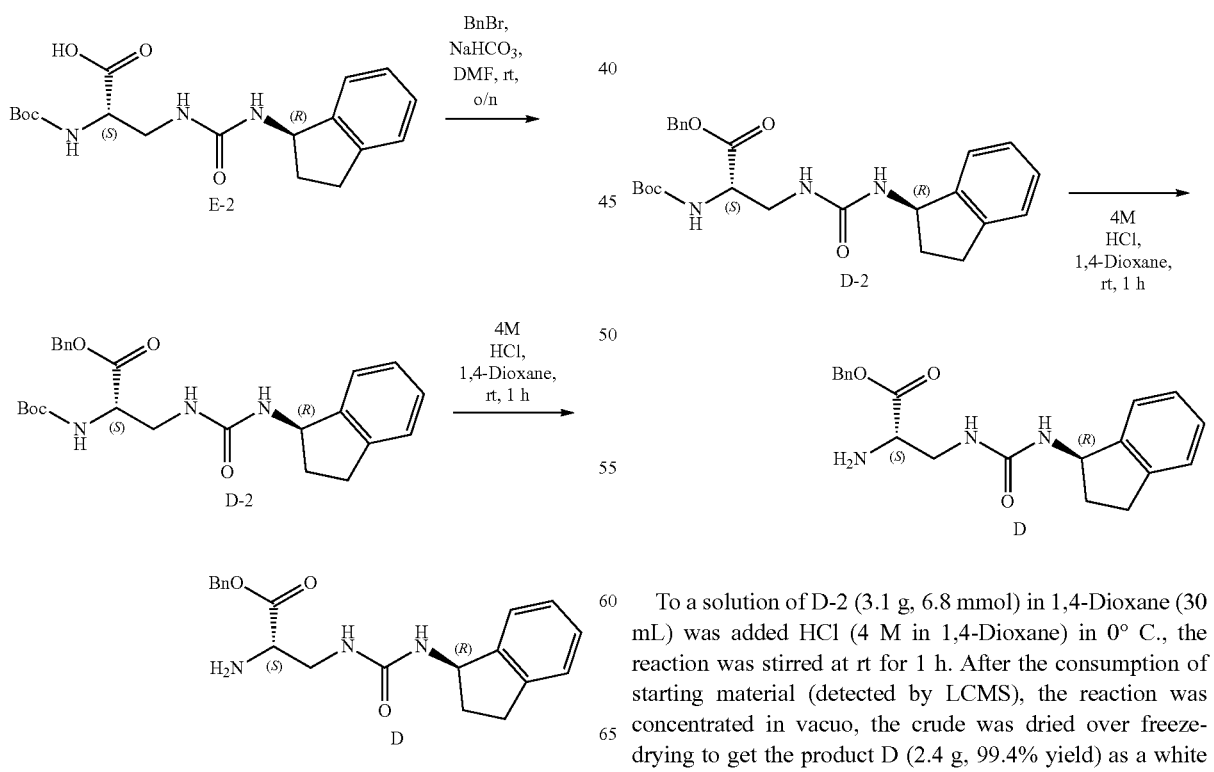

To a solution of D-2 (3.1 g, 6.8 mmol) in 1,4-Dioxane (30 mL) was added HCl (4 M in 1,4-Dioxane) in 0° C., the reaction was stirred at rt for 1 h. After the consumption of starting material (detected by LCMS), the reaction was concentrated in vacuo, the crude was dried over freeze-drying to get the product D (2.4 g, 99.4% yield) as a white solid.

Intermediate E

Route for the intermediate E:

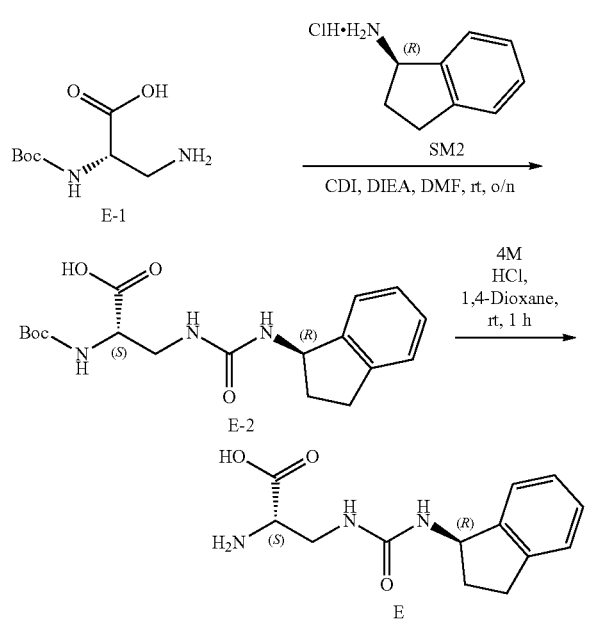

The Synthesis of (S)-2-(tert-butoxycarbonylamino)-3-(3-((R)-2,3-dihydro-1H-inden-1-yl)ureido)propanoic Acid (E-1)

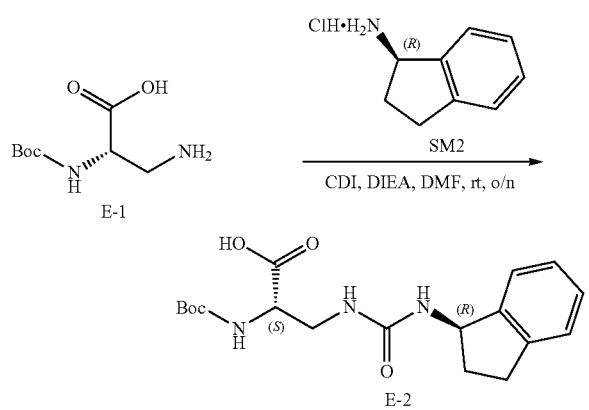

To a solution of SM2 (3.4 g, 20.0 mmol) in DMF (50 mL) was added DIEA (7.7 g, 60.0 mmol) and CDI (3.6 g, 22.0 mmol), the mixture was stirred at rt for 1 h. After the reaction was finished (detected by LCMS), E-1 (4.1 g, 20.0 mmol) was added into the reaction mixture, the reaction was stirred at rt for overnight. After the reaction was finished (detected by LCMS), 250 mL H$_2$O was added to quench the reaction, 1N HCl was added to pH=2~3, extracted with EtOAc (50 mL×3), combined the organic layer, dried over anhydrous Na$_2$SO$_4$, filtered and concentrated, the crude was purified by prep-HPLC to get the product E-2 (5.2 g, 71.6% yield) as a white solid.

The Synthesis of (S)-2-amino-3-(3-((R)-2,3-dihydro-1H-inden-1-yl)ureido)propanoic Acid (E)

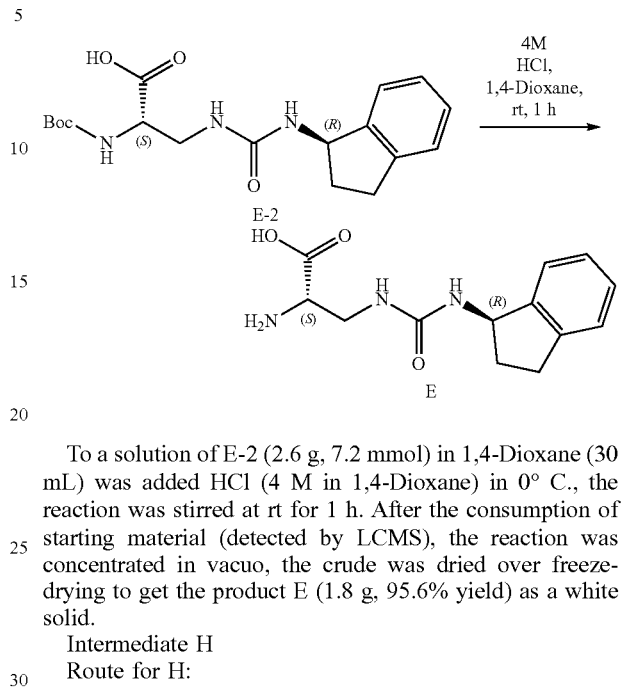

To a solution of E-2 (2.6 g, 7.2 mmol) in 1,4-Dioxane (30 mL) was added HCl (4 M in 1,4-Dioxane) in 0° C., the reaction was stirred at rt for 1 h. After the consumption of starting material (detected by LCMS), the reaction was concentrated in vacuo, the crude was dried over freeze-drying to get the product E (1.8 g, 95.6% yield) as a white solid.

Intermediate H

Route for H:

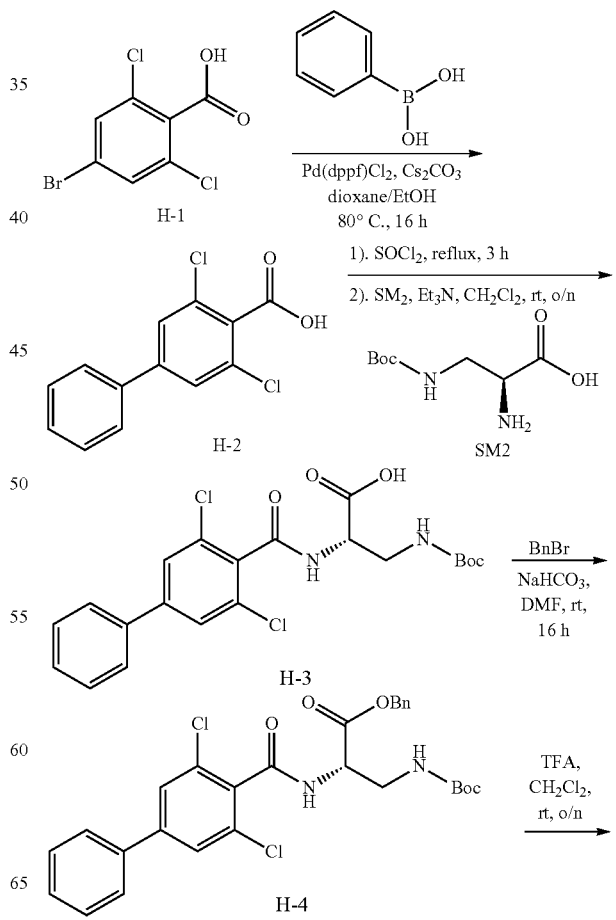

-continued

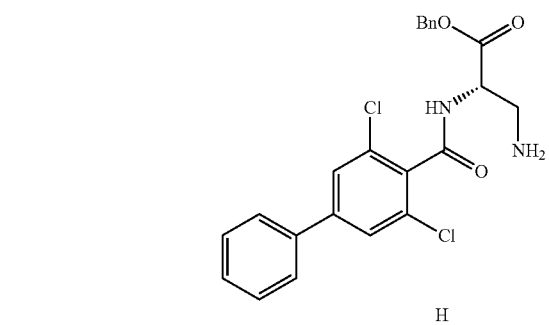

H

The Synthesis of 3,5-dichlorobiphenyl-4-carboxylic Acid (H-2)

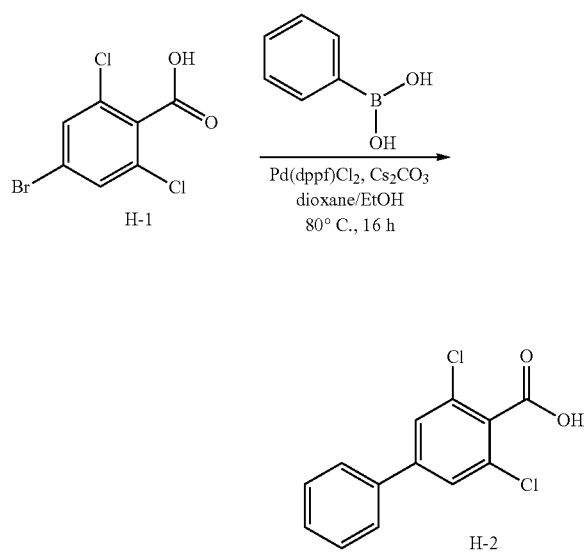

To a mixture of H-1 (5.36 g, 19.86 mmol), phenylboronic Acid (2.42 g, 19.86 mmol) and Pd(dppf)Cl$_2$ (14.53 g, 19.86 mmol) in dioxane/EtOH (10/1) (55 mL) was added Cs$_2$CO$_3$ (6.47 g, 19.86 mmol) and stirred at 80° C. for 16 h. After the reaction was finished (detected by LCMS), then the mixture was concentrated in vacuo and used next step directly without further purification.

Agilent LCMS 1200-6120, Column: Phenomenex Kinetex EVO C18 (50 mm*4.6 mm*2.6 m); Column Temperature: 40° C.; Flow Rate: 2.3 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.75 min, then under this condition for 0.8 min, finally changed to 95% [water+10 mM NH$_4$HCO$_3$] and 5% [CH$_3$CN] in 0.1 min and under this condition for 0.1 min. Rt=1.170 min; MS Calcd.: 266.0; MS Found: 284.1 [M+NH$_4$]$^+$.

The Synthesis of (S)-3-(tert-butoxycarbonylamino)-2-(3,5-dichlorobiphenyl-4-ylcarboxamido)propanoic Acid (H-3)

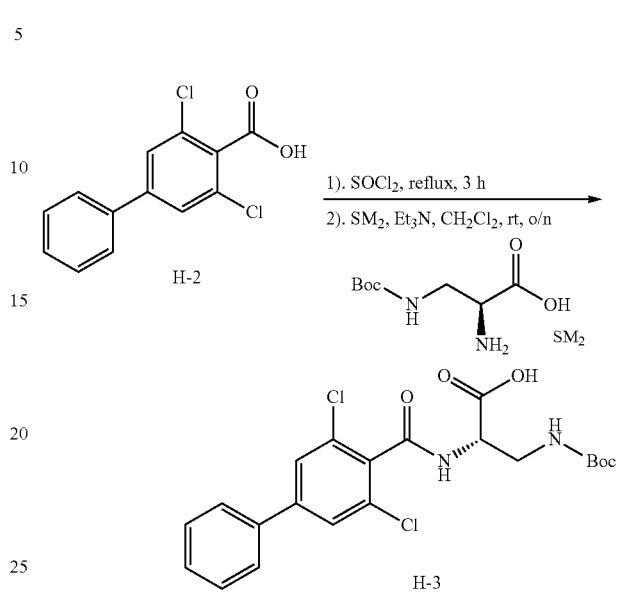

A solution of H-2 (5.32 g, 19.92 mmol) in SOCl$_2$ (15 mL) was reflux for 3 h, and then the mixture was concentrated to dryness and dissolved in dichloromethane (25 mL), TEA (8.06 g, 79.67 mmol) and SM$_2$ (4.07 g, 19.92 mmol) was added to above. The mixture was stirred at room temperature for 16 h and then diluted with water and extracted by CH$_2$Cl$_2$ (80 mL×2). The combined organic layers were washed with brine (30 mL×2), dried over sodium sulfate, and concentrated. The residue was purified by column chromatography (MeOH/CH$_2$Cl$_2$=1/10) to give the target compound H-3 (6 g, 13.24 mmol, 66.45% yield) as a black solid.

Agilent LCMS 1200-6120, Column: Phenomenex Kinetex EVO C18 (50 mm*4.6 mm*2.6 m); Column Temperature: 40° C.; Flow Rate: 2.3 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.75 min, then under this condition for 0.8 min, finally changed to 95% [water+10 mM NH$_4$HCO$_3$] and 5% [CH$_3$CN] in 0.1 min and under this condition for 0.1 min. Purity is 87.88%. Rt=1.355 min; MS Calcd.: 452.1; MS Found: 353.2 [M−100+H]$^+$.

The Synthesis of (S)-benzyl 3-(tert-butoxycarbonylamino)-2-(3,5-dichlorobiphenyl-4-ylcarboxamido)propanoate (H-4)

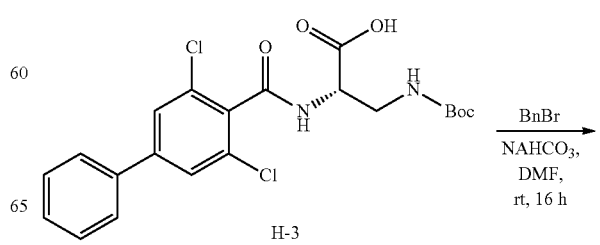

The Synthesis of (S)-benzyl 3-amino-2-(3,5-dichlorobiphenyl-4-ylcarboxamido)propanoate (H)

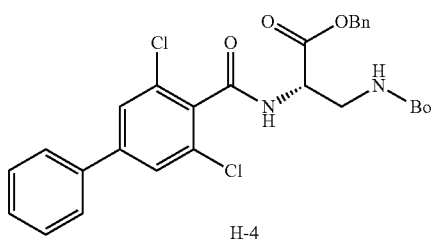

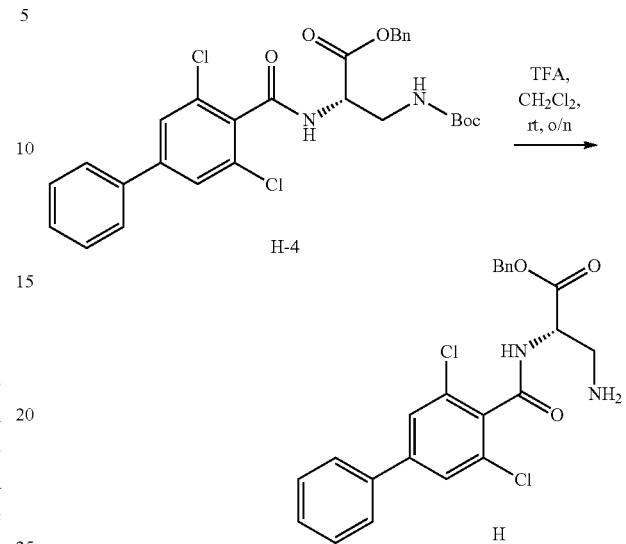

To a mixture of H-3 (6 g, 13.24 mmol) and bromoethylbenzene (2.26 g, 13.24 mmol) in DMF (30 mL) was added $NaHCO_3$ (1.67 g, 19.85 mmol) and stirred at room temperature for 16 h. Then the mixture was diluted with water and extracted by ethyl acetate (50 mL×2). The combined organic layers were washed with brine (30 mL×2), dried over sodium sulfate, and concentrated. The residue was purified by column chromatography (petroleum ether/ethyl acetate=1/3) to give the target compound H-4 (3.6 g, 6.83 mmol, 51.57% yield) as a yellow solid.

Agilent LCMS 1200-6120, Column: Phenomenex Kinetex EVO C18 (50 mm*4.6 mm*2.6 m); Column Temperature: 40° C.; Flow Rate: 2.3 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.75 min, then under this condition for 0.8 min, finally changed to 95% [water+10 mM $NH_4HCO_3$] and 5% [$CH_3CN$] in 0.1 min and under this condition for 0.1 min. Purity is 96.94%. Rt=1.984 min; MS Calcd.: 542.1; MS Found: 443.2 [M−100+H]$^+$.

To a mixture of H-4 (3.6 g, 6.83 mmol) in $CH_2Cl_2$ (15 mL) was added TFA (4.44 g, 38.94 mmol) and stirred at room temperature for 16 h. After the reaction was finished and then concentrated to give H (2.8 g, 96.00% yield) as yellow oil.

Agilent LCMS 1200-6120, Column: Phenomenex Kinetex EVO C18 (50 mm*4.6 mm*2.6 m); Column Temperature: 40° C.; Flow Rate: 2.3 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.75 min, then under this condition for 0.8 min, finally changed to 95% [water+10 mM $NH_4HCO_3$] and 5% [$CH_3CN$] in 0.1 min and under this condition for 0.1 min. Purity is 96.94%. Rt=1.749 min; MS Calcd.: 442.1; MS Found: 443.2 [M+H]$^+$.

Example 3: Biological Data

TABLE 1

Biological data. α2β1 Cell Adhesion IC$_{50}$: A: <0.5 μM, B: 0.5-1 μM, C: 1-5 μM, D: >5 μM. d.r.: diastereomeric ratio.

| Compound | α2β1 Cell Adhesion IC$_{50}$ | α4β1 Cell Adhesion IC$_{50}$ (nM) | Plasma Stab(h) % rem/ 60 min | Met Stab(h) % rem/ 45 min | Caco-2 Permeability A-B/B-A/ efflux | Kinetic Solubility (Aq, μM) | d.r. |
|---|---|---|---|---|---|---|---|
| SU15210-0186-01 | A | | | | 2.2/1.5/0.67 | | |
| SU15210-0095-01 | A | 21090 | 99.4 | 99.6 | 3.2/1.6/0.49 | | |
| SU15210-0185-01 | A | | | | 2.2/5.53/2.6 | | |
| SU15210-0099-01 | A | | 85.84 | 72.3 | 2.7/20.1/7.4 | 66.9 | 99:5 |
| SU15210-0187-01 | A | | | | | | |
| SU15210-0124-01 | A | 21000 | | | | | 98:2 |
| SU15210-0098-01 | A | 32340 | | | | | |
| SU15210-0173-01 | A | | 108 | 65 | 0.8/6.8/7.6 | | |
| SU15210-0076-01 | A | 2897 | 55.6 | 96.3 | 0.2/24.2/97 | | 78:22 |

TABLE 1-continued

Biological data. α2β1 Cell Adhesion IC$_{50}$: A: <0.5 μM, B: 0.5-1 μM, C: 1-5 μM, D: >5 μM. d.r.: diastereomeric ratio.

| Compound | α2β1 Cell Adhesion IC$_{50}$ | α4β1 Cell Adhesion IC$_{50}$ (nM) | Plasma Stab(h) % rem/ 60 min | Met Stab(h) % rem/ 45 min | Caco-2 Permeability A-B/B-A/ efflux | Kinetic Solubility (Aq, μM) | d.r. |
|---|---|---|---|---|---|---|---|
| SU15210-0080-01 | A | 37040 | | | | | |
| SU15210-0172-01 | A | | | | | | |
| SU15210-0159-01 | A | | | | | | |
| SU15210-0167-01 | A | 83910 | | | | | |
| SU15210-0155-01 | B | | | | | | |
| SU15210-0084-01 | B | | | | | | |
| SU15210-0189-01 | B | | | | | | |
| SU15210-0156-01 | B | | | | | | |
| SU15210-0078-01 | B | | | | | | 79:4:4:3:1 |
| SU15210-0192-01 | C | | | | | | |
| SU15210-0188-01 | C | | | | | | |
| SU15210-0163-01 | C | | | | | | |
| SU15210-0126-01 | C | | | | | | |
| SU15210-0154-01 | C | | | | | | |
| SU15210-0174-01 | C | | | | | | |
| SU15210-0097-01 | C | | | | | | |
| SU15210-0125-01 | C | | | | | | |
| SU15210-0140-01 | D | | | | | | |
| SU15210-0171-01 | D | | | | | | |
| SU15210-0190-01 | D | | | | | | |
| SU15210-0191-01 | D | | | | | | |
| SU15210-0208-01 | A | | | | | | |
| SU15210-0209-01 | A | | | | | | |
| SU15210-0210-01 | C | | | | | | |
| SU15210-0211-01 | A | | | | | | |
| SU15210-0214-01 | C | | | | | | |
| SU15210-0223-01 | A | | | | | | |
| SU15210-0224-01 | C | | | | | | |
| SU15210-0225-01 | A | | | | | | |
| SU15210-0226-01 | B | | | | | | |
| SU15210-0227-01 | B | | | | | | |
| SU15210-0228-01 | C | | | | | | |
| SU15210-0234-01 | A | | | | | | |
| SU15210-0235-01 | A | | | | | | |

Example 4: Additional Compounds and Characterization Data

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

SU15210-0242-01

Route for SU15210-0242-01

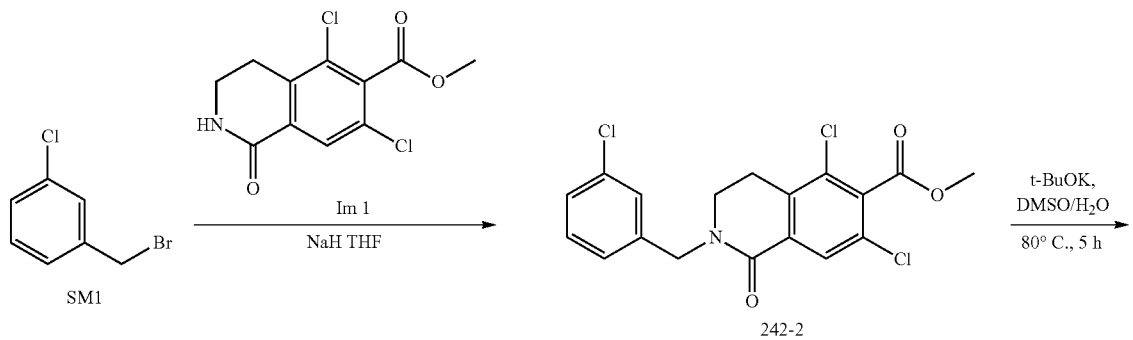

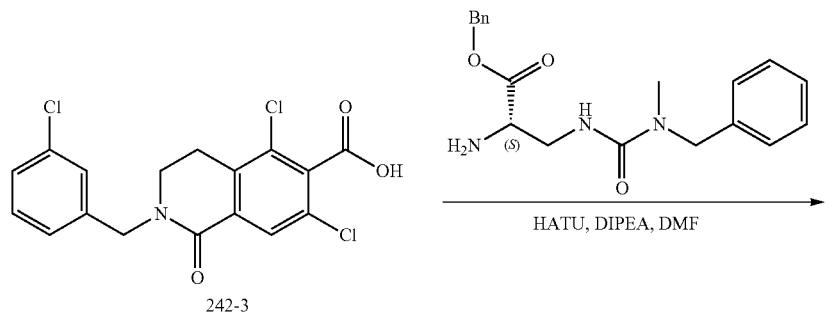

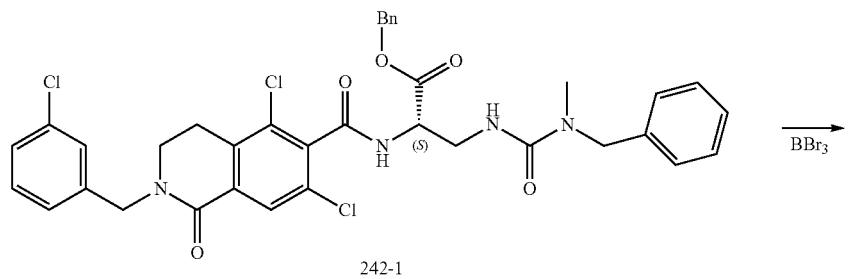

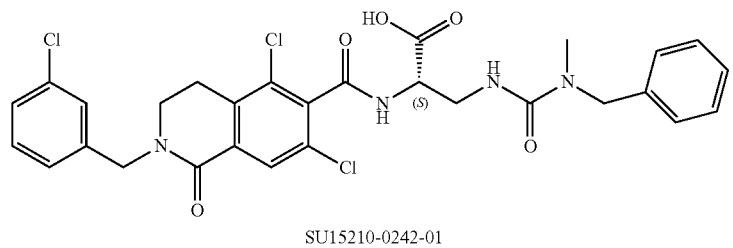

SU15210-0242-01

589

Methyl 5,7-dichloro-2-(3-chlorobenzyl)-1-oxo-1,2,3,4-tetrahydroisoquinoline-6-carboxylate (242-2)

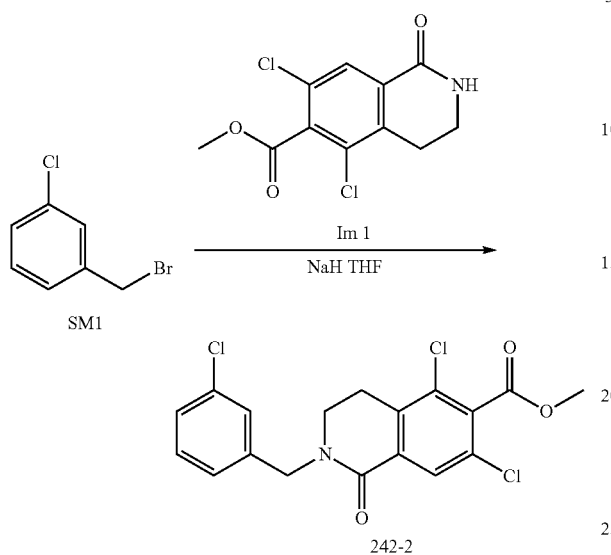

To a 50 mL 3-neck round flask, IM1 (160 mg, 579.47 umol) and tetrahydrofuran (20 mL) was added, it was cooled to 0° C. and then NaH (100 mg, 2.61 mmol, 60% purity) was added, it was replaced with N₂, the reaction mixture was stirred at RT for 45 min, then SM1 (119.07 mg, 579.47 umol) was added, it was stirred at RT overnight, then it was diluted with water, extracted with EA, dried with Na₂SO₄, concentrated to get crude oil, and it was purified by silica gel column (PE:EA=10:1) to afford 242-2 (230 mg, 574.02 umol, 99.06% yield). $^1$H NMR (400 MHz, CDCl₃) δ 8.15 (s, 1H), 7.32-7.27 (m, 3H), 7.23-7.14 (m, 1H), 4.75 (s, 2H), 4.00 (s, 3H), 3.51 (t, J=6.7 Hz, 2H), 3.04 (t, J=6.7 Hz, 2H).

590

5,7-dichloro-2-(3-chlorobenzyl)-1-oxo-1,2,3,4-tetrahydroisoquinoline-6-carboxylic Acid (242-3)

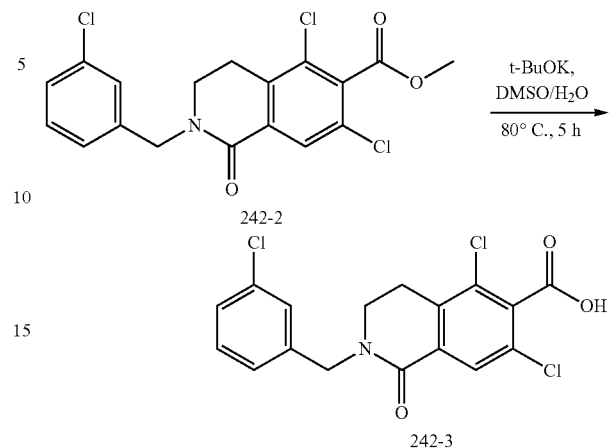

Potassium 2-methylpropan-2-olate (177.32 mg, 1.58 mmol) was added to the mixture of 242-2 (210 mg, 526.76 umol) in DMSO (4 mL) and water (1 mL), it was stirred at 80° C. for 4 h until the reaction was completed, then it was diluted with water, adjusted the pH=2 with HCl (2 M), extracted with EA, dried with Na₂SO₄ to get crude oil, it was purified by prep-HPLC to afford 242-3 (130 mg, 337.98 umol).

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10 mM NH₄HCO₃] and 5% [CH3CN] to 5% [water+10 mM NH₄HCO₃] and 95% [CH₃CN] in 2 min, then under this condition for 2 min. Purity is 98.78%. Rt=1.78 min; MS Calcd.: 383.9; MS Found: 383.7 [M+H]⁺.

(S)-benzyl-3-(3-benzyl-3-methylureido)-2-(5,7-dichloro-2-(3-chlorobenzyl)-1-oxo-1,2,3,4-tetrahydroisoquinoline-6-carboxamido)propanoate (242-1)

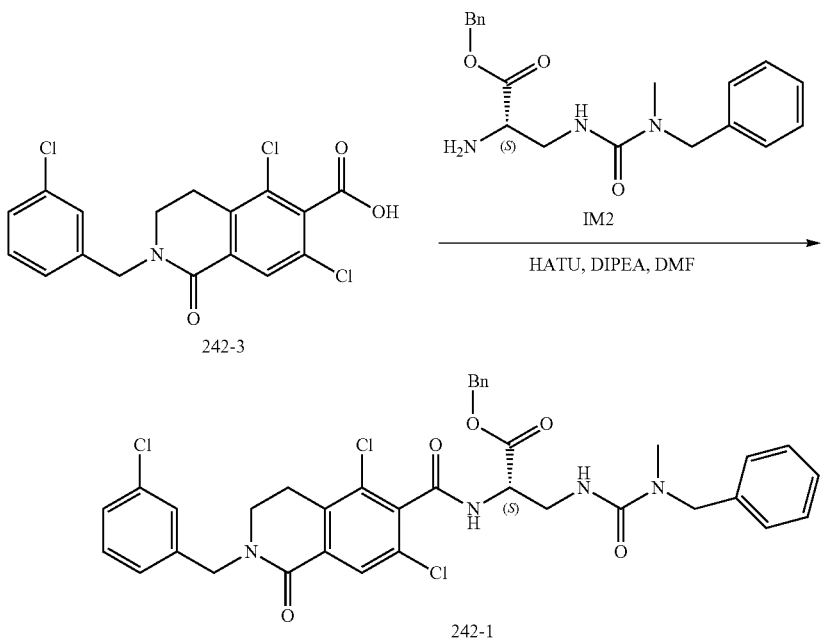

A mixture of 242-3 (110 mg, 285.98 umol), IM2 (98 mg, 285.98 umol), HATU (163.97 mg, 428.97 umol), DIPEA (110.88 mg, 857.94 umol, 149.43 uL) in DMF was stirred at RT for 4 h until the reaction was completed, then it was diluted with water, extracted with EA, dried with $Na_2SO_4$, purified by silica gel column (PE:EA=2:1) to afford 242-1 (70 mg, 98.87 umol, 34.57% yield).

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10 mM $NH_4HCO_3$] and 5% [$CH_3CN$] to 5% [water+10 mM $NH_4HCO_3$] and 95% [$CH_3CN$] in 2 min, then under this condition for 2 min. Purity is 97.17%. Rt=2.72 min; MS Calcd.: 707.1; MS Found: 706.6 $[M+H]^+$.

(S)-3-(3-benzyl-3-methylureido)-2-(5,7-dichloro-2-(3-chlorobenzyl)-1-oxo-1,2,3,4-tetrahydroisoquinoline-6-carboxamido)propanoic Acid (SU15210-0242-01)

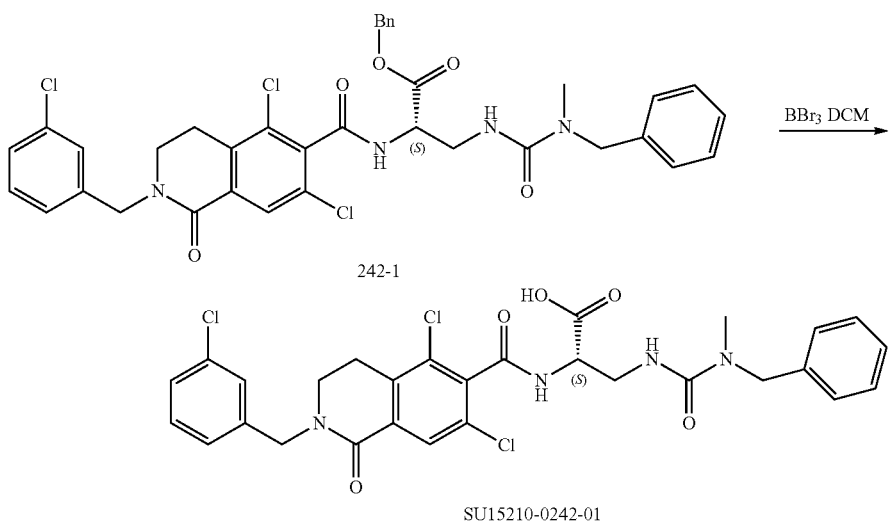

Tribromoborane (84.92 mg, 338.97 umol) was added to the solution of 242-1 (60 mg, 84.74 umol) in dichloromethane (3 mL), and it was stirred at RT for 1.5 h until it was completed by TLC, then it was quenched with water, extracted with EA, dried with $Na_2SO_4$, concentrated to get crude oil, and then it was purified by prep-HPLC to afford SU15210-0242-01 (25 mg, 40.46 umol, 47.74% yield).

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10 mM $NH_4HCO_3$] and 5% [$CH_3CN$] to 5% [water+10 mM $NH_4HCO_3$] and 95% [$CH_3CN$] in 2 min, then under this condition for 2 min. Purity is 95.11%. Rt=2.175 min; MS Calcd.: 616.1; MS Found: 616.7 $[M+H]^+$.

$^1$H NMR (400 MHz, DMSO) δ 8.43 (s, 1H), 7.91 (s, 1H), 7.31 (dd, J=37.5, 30.0 Hz, 9H), 6.73 (s, 1H), 4.72 (s, 2H), 4.41 (q, J=15.6 Hz, 2H), 4.25 (d, J=6.6 Hz, 1H), 3.57 (s, 5H), 3.03 (t, J=6.7 Hz, 2H), 2.74 (s, 3H).

SU15210-0243-01

Route for SU15210-0243-4:

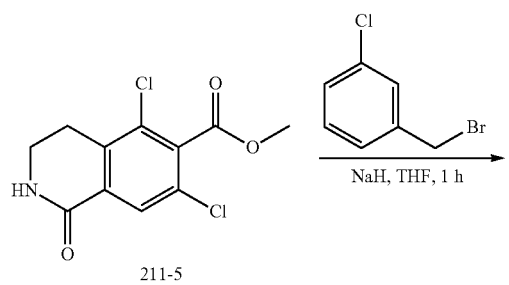

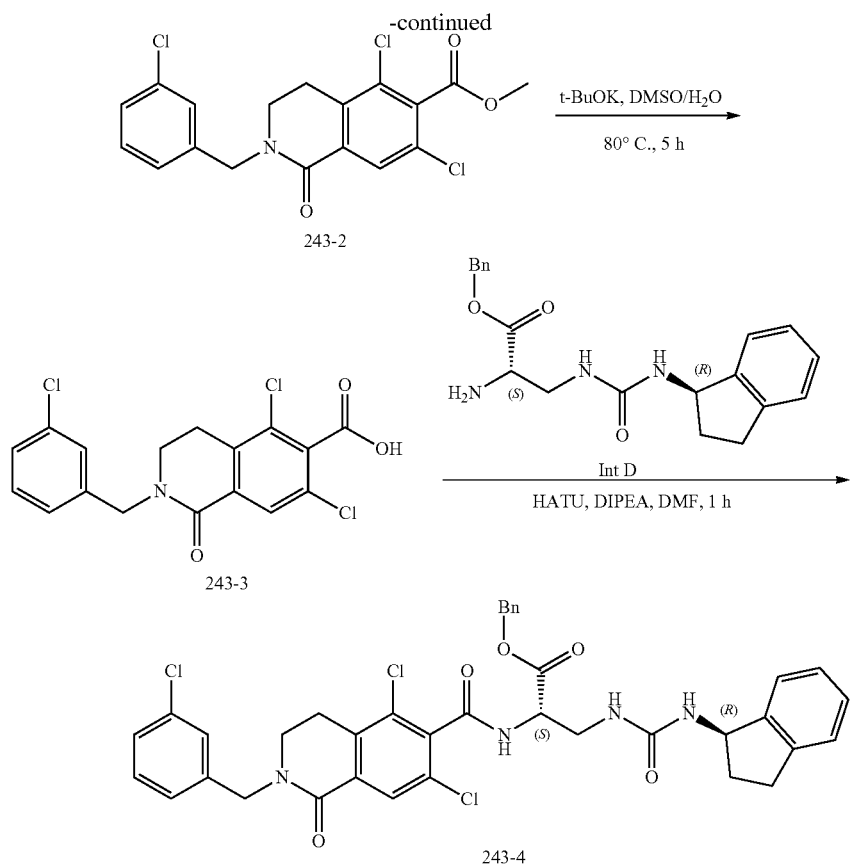

1. The Synthesis of methyl 5,7-dichloro-2-(3-chlorobenzyl)-1-oxo-1,2,3,4-tetrahydroisoquinoline-6-carboxylate (0243-2)

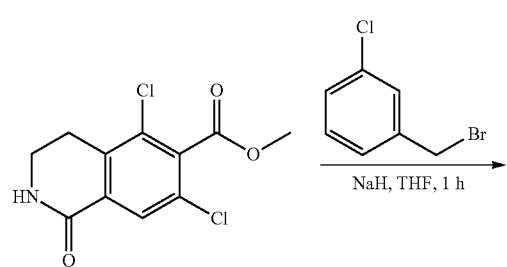

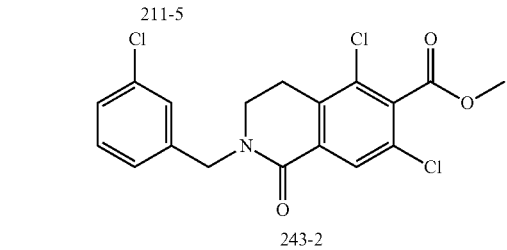

A solution of 211-5 (150 mg, 547.25 umol) and NaH (26.27 mg, 1.09 mmol, 60% in mineral oil) in anhydrous THF (4 mL) was stirred for 10 min at 0° C. 1-(Bromomethyl)-3-chlorobenzene (112.45 mg, 547.25 umol) in solution in anhydrous THF (2 mL) was added at 0° C. The reaction mixture was stirred for 1 h. And then water (100 mL) was added. The mixture was extracted with EA (2×100 mL). The combined organic layers were washed with brine (2×50 mL), dried over Na$_2$SO$_4$, filtered, and concentrated to give 243-2 (200 mg, 91.67% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 92.12%. Rt=0.850 min; MS Calcd.: 397.0; MS Found: 398.2 [M+H]$^+$.

2. The Synthesis of 5,7-dichloro-2-(3-chlorobenzyl)-1-oxo-1,2,3,4-tetrahydroisoquinoline-6-carboxylic Acid (0243-3)

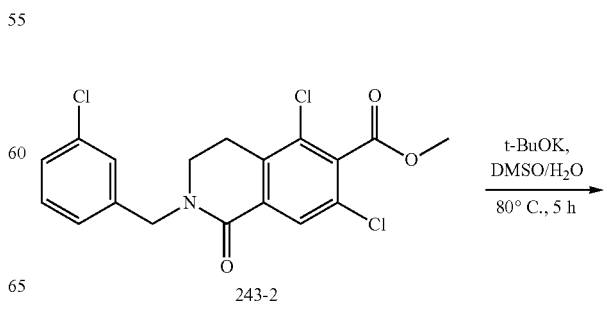

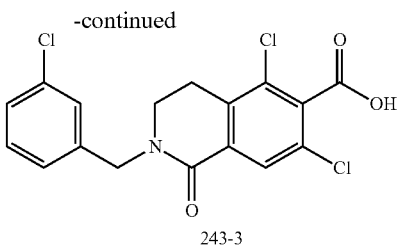

To a solution of 0243-2 (200 mg, 501.67 umol) in DMSO (5 mL) and one drop of water, t-BuOK (112.59 mg, 1.00 mmol) was added and the solution was stirred at room temperature for 80° C. for 5 h. After the reaction was finished, diluted hydrochloric acid was added in to adjust the pH to 3-4, then the solution was purified by prep-HPLC directly to get 0243-3 (150 mg, 77.73% yield) as a yellow solid.

Agilent LCMS 1200-6120, Column: Halo C18 (50 mm*4.6 mm*2.7 m); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 92.12%. Rt=0.710 min; MS Calcd.: 382.9; MS Found: 384.2 [M+H]$^+$.

3. The Synthesis of (S)-benzyl 2-(5,7-dichloro-2-(3-chlorobenzyl)-1-oxo-1,2,3,4-tetrahydroisoquinoline-6-carboxamido)-3-(3-((R)-2,3-dihydro-1H-inden-1-yl)ureido)propanoate (0243-4)

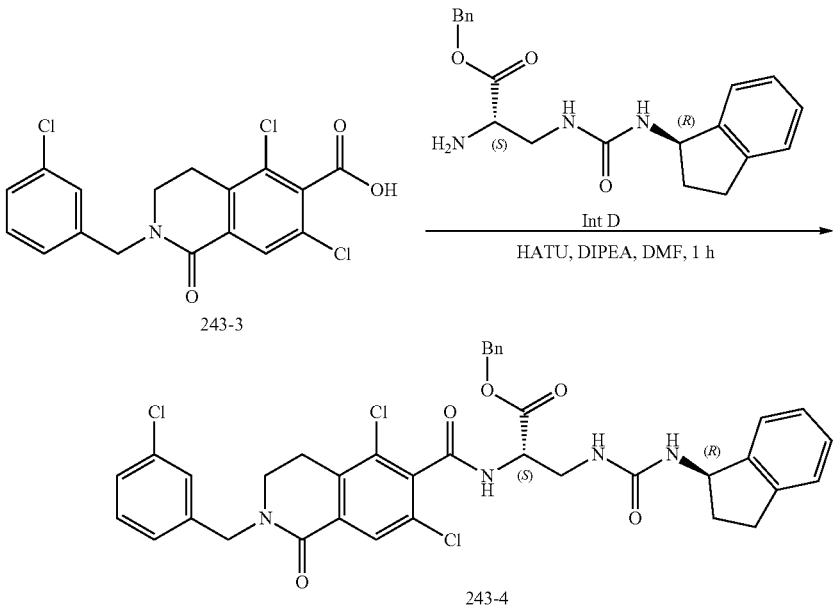

To a solution of 0243-3 (150 mg, 389.97 umol) and int.D (137.82 mg, 389.97 umol) in DMF (5 mL) was added HATU (149.07 mg, 389.97 umol) and DIEA (100.80 mg, 779.95 umol), the solution was stirred at room temperature for overnight. Purified by prep-HPLC directly to get 0243-4 (250 mg, 87.10% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=2.349 min; MS Calcd.: 718.1; MS Found: 721.2 [M+H]$^+$.

$^1$H NMR (400 MHz, d$_6$-DMSO): δ 8.95 (t, J=8 Hz, 1H), 7.91 (s, 1H), 7.32-7.46 (m, 8H), 7.27-7.29 (m, 1H), 7.12-7.23 (m, 4H), 6.68 (d, J=8 Hz, 1H), 6.23 (d, J=8 Hz, 1H), 5.05-5.20 (m, 3H), 4.72 (s, 2H), 4.53-4.58 (m, 1H), 3.65 (s, J=4 Hz, 2H), 3.54-3.58 (m, 2H), 3.01-3.09 (m, 2H), 2.83-2.90 (m, 1H), 2.71-2.79 (m, 1H), 2.32-2.39 (m, 1H), 1.62-1.72 (m, 1H).

4. The Synthesis of (2S)-2-[[5,7-dichloro-2-[(3-chlorophenyl)methyl]-1-oxo-3,4-dihydroisoquinoline-6-carbonyl]amino]-3-[[(1R)-indan-1-yl]carbamoylamino]propanoic Acid (SU15210-0243-01)

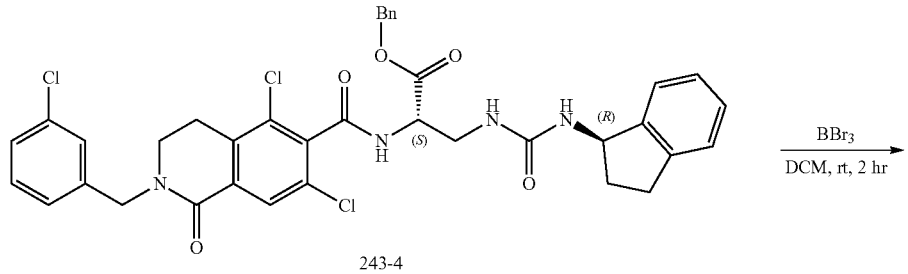

243-4

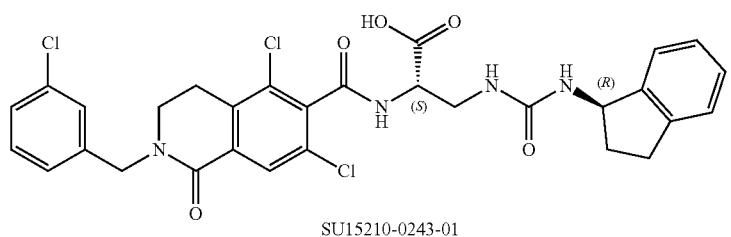

SU15210-0243-01

A mixture of benzyl (2S)-2-[[5,7-dichloro-2-[(3-chlorophenyl)methyl]-1-oxo-3,4-dihydroisoquinoline-6-carbonyl]amino]-3-[[(1R)-indan-1-yl]carbamoylamino]propanoate (20 mg, 27.78 umol), and tribromoborane (20.88 mg, 83.33 umol) in dichloromethane (2 mL) was stirred at rt, 2 hr. After the consumption of starting material (by LCMS), water (10 mL) was added, extracted with dichloromethane (10 mL×3), washed with water (10 mL×3), dried and concentrated. The crude material was purified by prep-HPLC to provide SU15210-0243-01 (5.01 mg, 7.95 umol) as a white solid. $^1$H NMR (400 MHz, DMSO) δ 8.92 (s, 1H), 7.98 (s, 1H), 7.33 (dddd, J=14.2, 9.1, 6.8, 4.1 Hz, 8H), 6.93 (d, J=8.0 Hz, 1H), 6.25 (d, J=5.8 Hz, 1H), 5.10 (dd, J=15.8, 7.7 Hz, 1H), 4.78 (s, 2H), 4.08 (s, 2H), 3.63 (dd, J=20.9, 14.2 Hz, 2H), 3.11 (t, J=6.7 Hz, 2H), 3.00-2.87 (m, 1H), 2.81 (dd, J=16.2, 7.9 Hz, 1H), 2.47-2.35 (m, 1H), 1.78-1.65 (m, 1H), 1.30 (s, 1H).

SU15210-0244-01

Route for SU15210-0244-01

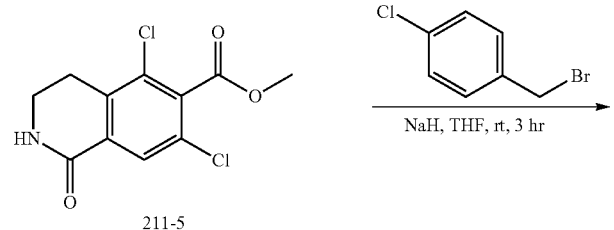

211-5

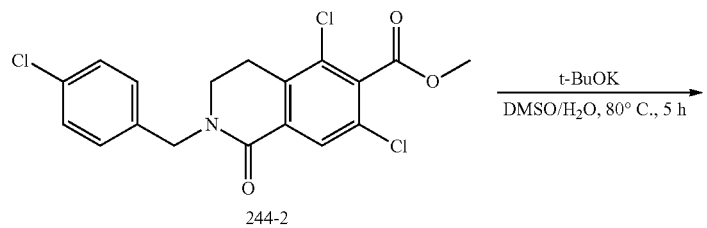

244-2

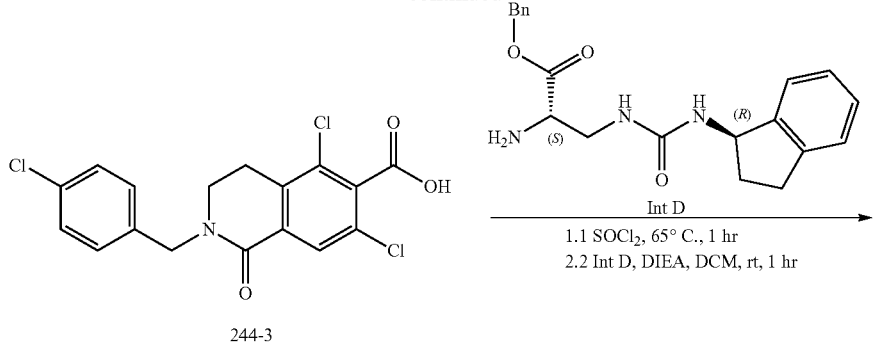

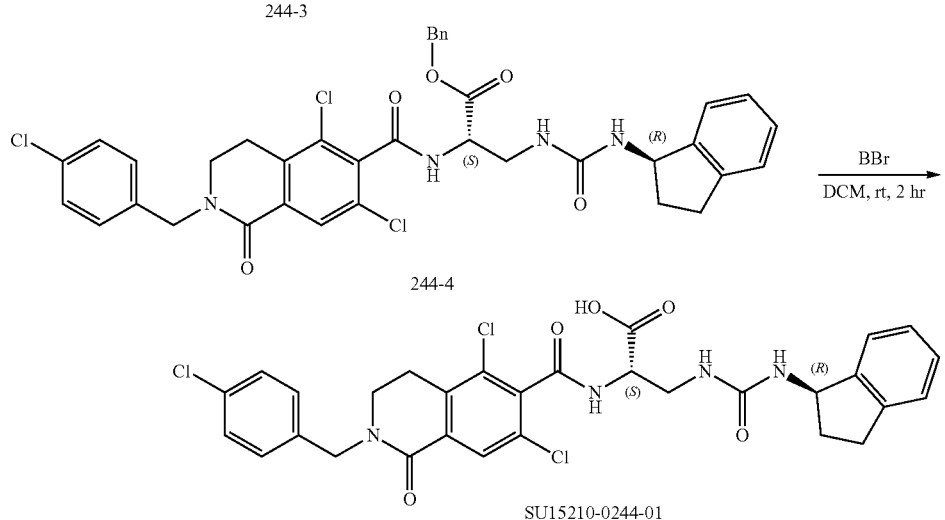

The Synthesis of methyl 5,7-dichloro-2-[(4-chlorophenyl)methyl]-1-oxo-3,4-dihydroisoquinoline-6-carboxylate (244-2)

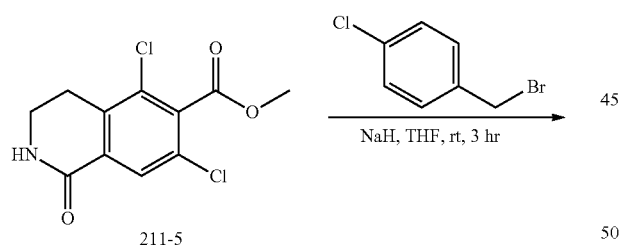

A mixture of methyl 5,7-dichloro-1-oxo-3,4-dihydro-2H-isoquinoline-6-carboxylate (500 mg, 1.82 mmol) and sodium hydride (291.86 mg, 7.30 mmol, 60% purity) in THF (5 mL) was stirred at rt, 1 hr. After 1-(bromomethyl)-4-chloro-benzene (374.83 mg, 1.82 mmol) was added to the reaction, than the mixture was allowed to warm to rt for 2 hr. The reaction mixture was partitioned between ethyl acetate (30 mL) and water (30 mL), and the organic layer was washed with water (30 mL, twice) and brine, dried over anhydrous magnesium sulfate and filtered. The residue after concentration of the filtrate was purified by silica gel column to give 244-2 (500 mg, 68.76% yield) as a while solid.

The Synthesis of 5,7-dichloro-2-[(4-chlorophenyl)methyl]-1-oxo-3,4-dihydroisoquinoline-6-carboxylic Acid (244-3)

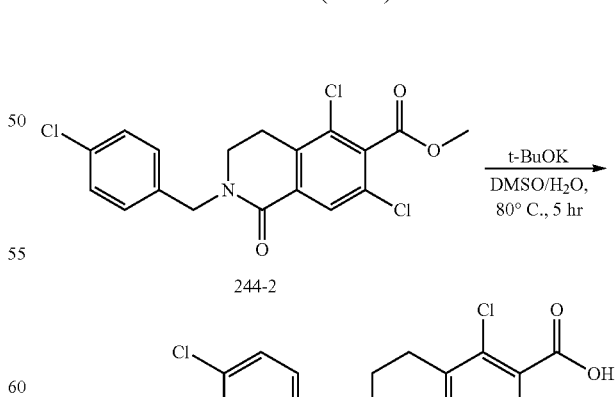

A mixture of methyl 5,7-dichloro-2-[(4-chlorophenyl)methyl]-1-oxo-3,4-dihydroisoquinoline-6-carboxylate (250 mg, 627.09 umol) and potassium 2-methylpropan-2-olate (211.10 mg, 1.88 mmol) in Dimethyl Sulfoxide (10 mL) and water (2 mL) was stirred at 80° C., 5 hr. After the reaction was finished, the solvent was removed under vacuum, the residual was dissolved in water (5 mL) and EA (5 mL), acidified by 1N HCl aq. to pH-2, the organic layer was then separated and the water phase was extracted with EA (5 mL×3), the organic phase was combined and washed with water then brine, dried over Na₂SO₄, concentrated the organic phase to obtain the crude light yellow 244-3 (347 mg, 93.51% yield).

The Synthesis of benzyl (2S)-2-[[5,7-dichloro-2-[(4-chlorophenyl)methyl]-1-oxo-3,4-dihydroisoquinoline-6-carbonyl]amino]-3-[[(1R)-indan-1-yl]carbamoylamino]propanoate (244-3)

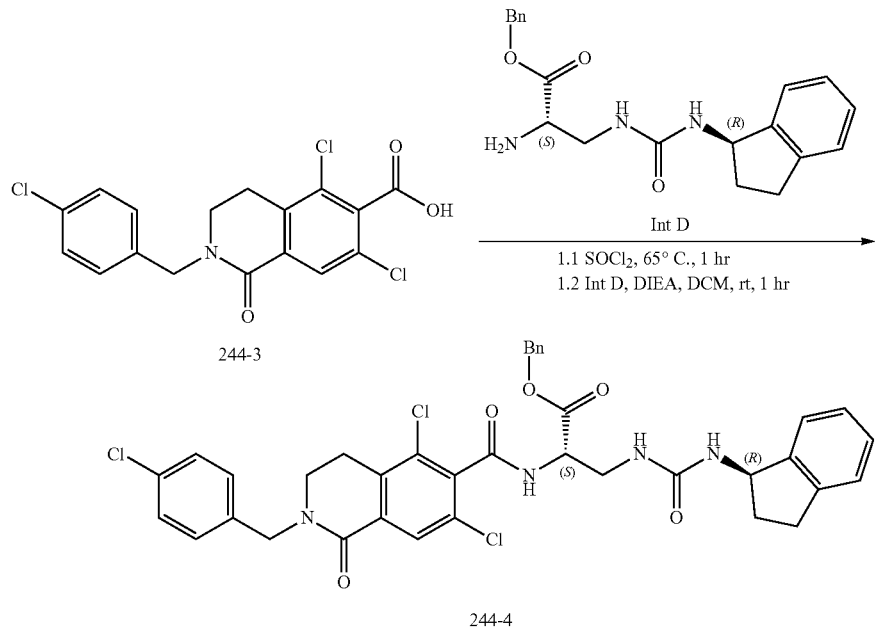

3-1. A mixture of 5,7-dichloro-2-[(4-chlorophenyl)methyl]-1-oxo-3,4-dihydroisoquinoline-6-carboxylic Acid (170 mg, 441.97 umol) in thionyl chloride (10 mL) was stirred at 65° C., 1 hr. This reaction mixture was concentrated under vacuum and used without further purification.

3-2. A mixture of benzyl (2S)-2-amino-3-[[(1R)-indan-1-yl]carbamoylamino]propanoate (156.20 mg, 441.97 umol) and N-ethyl-N-isopropyl-propan-2-amine (171.36 mg, 1.33 mmol, 230.95 uL) in dichloromethane (10 mL) was added to the crude product from 1.1, the reaction was then stirred at rt 1 hr, concentrated and purified by pre-HPLC to provide 244-4 (23 mg, 7.23% yield) as a white solid.

The Synthesis of benzyl (2S)-2-[[5,7-dichloro-2-[(4-chlorophenyl)methyl]-1-oxo-3,4-dihydroisoquinoline-6-carbonyl]amino]-3-[[(1R)-indan-1-yl]carbamoylamino]propanoic Acid (SU15210-0244-01)

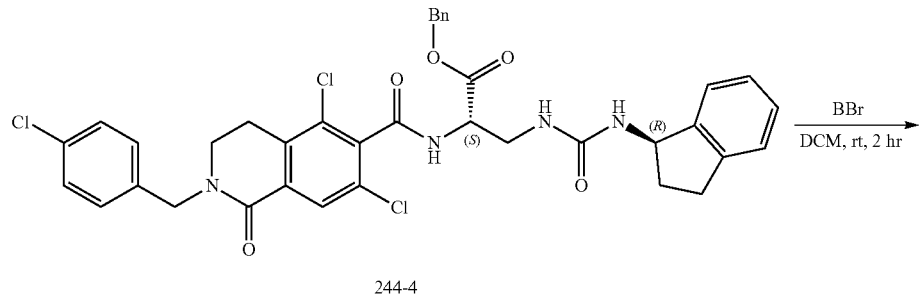

-continued

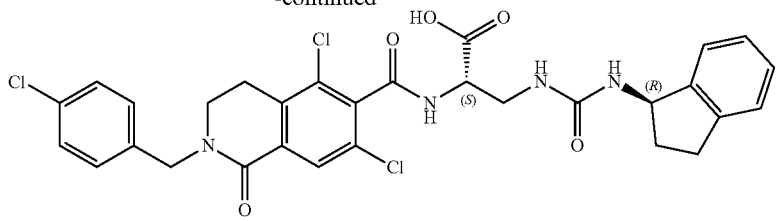

SU15210-0244-01

A mixture of benzyl (2S)-2-[[5,7-dichloro-2-[(4-chlorophenyl)methyl]-1-oxo-3,4-dihydroisoquinoline-6-carbonyl]amino]-3-[[(1R)-indan-1-yl]carbamoylamino]propanoate (23 mg, 31.94 umol) (23 mg, 27.78 umol), and tribromoborane (20.88 mg, 83.33 umol) in dichloromethane (2 mL) was stirred at rt, 2 hr. After the consumption of starting material (by LCMS), water (10 mL) was added, extracted with dichloromethane (10 mL×3), washed with water (10 mL×3), dried and concentrated. The crude was purified by pre-HPLC to provide SU15210-0244-01 (3.20 mg, 24.85% yield) as a white solid.

SU15210-0245-01

Route for SU15210-0245-01:

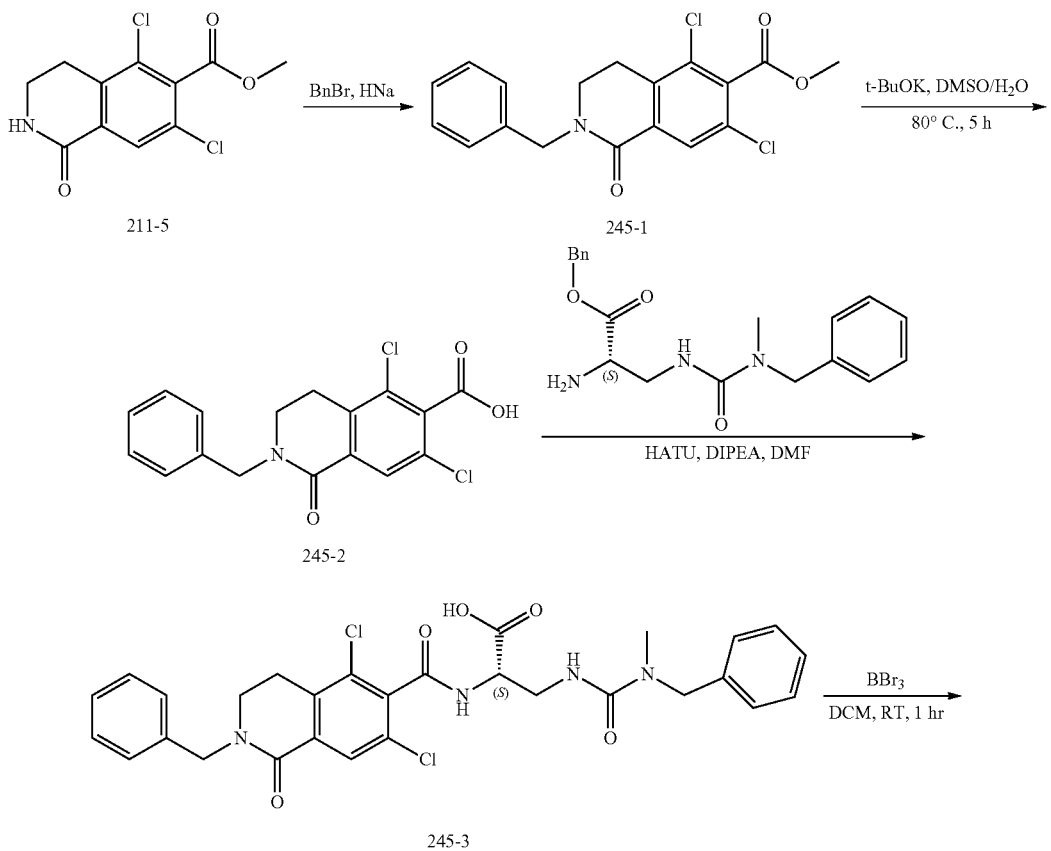

1. Synthesis of 245-1

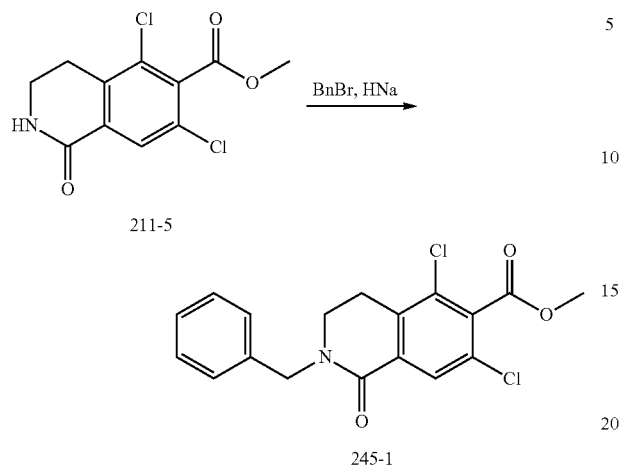

To a solution of 211-5 (200 mg, 729.66 umol) in THF (5 mL), then sodium hydride (70.04 mg, 2.92 mmol) was added at 0° C. The reaction was stirred for 15 min, after bromomethylbenzene (124.80 mg, 729.66 umol, 86.66 uL) was added. Then the reaction was stirred at rt for 2 hr. LCMS showed the reaction was completed. The solvent was concentrated. Extracted with EA (20 ml*2), dired over $Na_2SO_4$, filtered and concentrated to give crude product, the crude product was purified by CC (PE:EA=5:1) to give 245-1 (230 mg, 631.48 umol, 86.54% yield).

2. Synthesis of 245-2

To a solution of methyl 245-1 (230 mg, 631.48 umol) and potassium 2-methylpropan-2-olate (212.58 mg, 1.89 mmol) in DMSO (5 mL) and $H_2O$ (1 mL). The reaction was stirred at 80° C. for 5 hr. LCMS showed the raw materials was disappeared. The solvent was concentrated. Extracted with EA (20 ml*2), dried over $Na_2SO_4$, filtered, concentrated to give 245-2 (250 mg, 499.72 umol, 70% purity) as a yellow oil.

3. Synthesis of 245-3

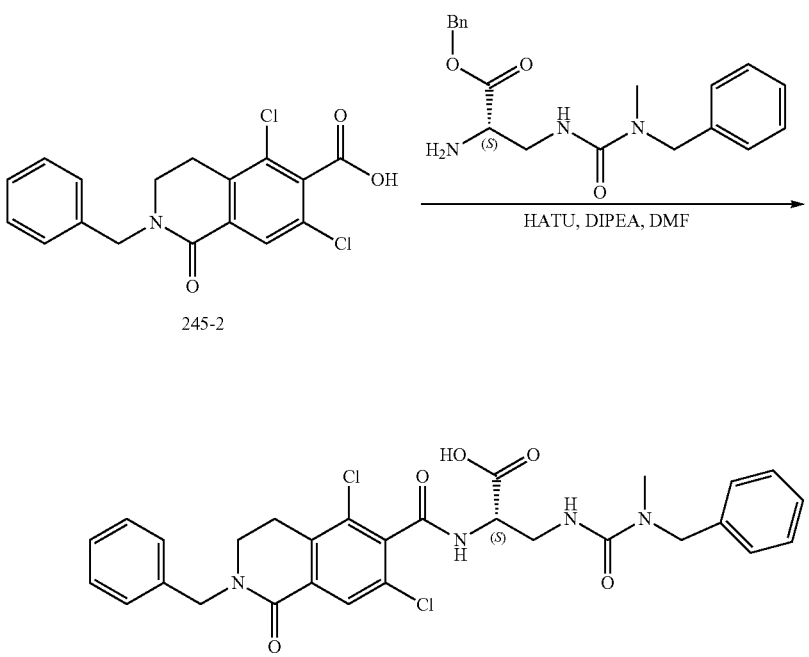

To a solution of 2-benzyl-5,7-dichloro-1-oxo-3,4-dihydroisoquinoline-6-carboxylic acid (139.02 mg, 396.97 umol), N-ethyl-N-isopropyl-propan-2-amine (136.81 mg, 1.06 mmol, 184.39 uL) and [dimethylamino(triazolo[4,5-b]pyridin-3-yloxy)methylene]-dimethyl-ammonium hexafluorophosphate (150.94 mg, 396.97 umol) in DMF (5 mL), then 245-2 (100 mg, 264.65 umol, HCl) was added. The reaction was stirred at rt for 1 hr. LCMS showed the raw material was disappeared. The solvent was purified prep-hplc to give 245-3 (30 mg, 44.54 umol, 16.83% yield).

4. Synthesis of SU15210-0245-01

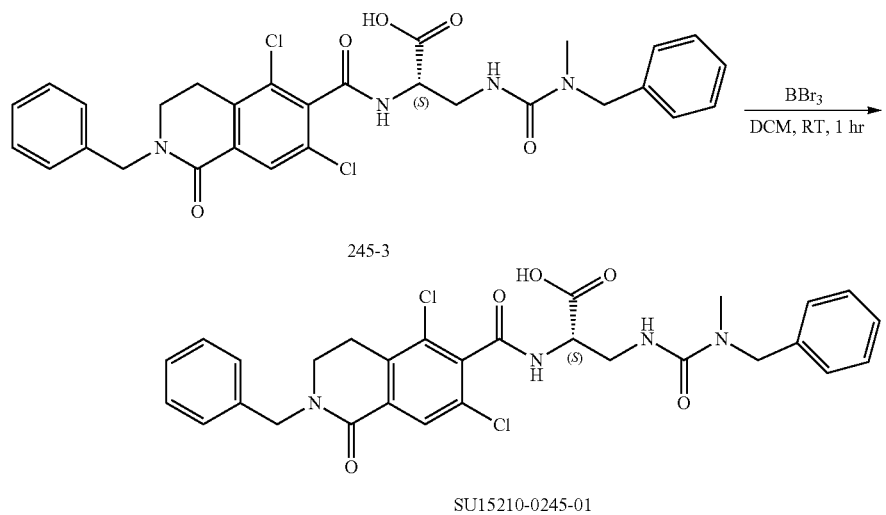

To a solution of 245-3 (30 mg, 44.54 umol) in DCM (5 mL), then tribromoborane (16.74 mg, 66.81 umol) was added slowly. The reaction was stirred at rt for 1 hr. LCMS show the raw material was disappeared. The solvent was concentrated. The residue was purified by prep-HPLC to give (2S)-2-[(2-benzyl-5,7-dichloro-1-oxo-3,4-dihydroisoquinoline-6-carbonyl)amino]-3-[[benzyl(methyl)carbamoyl]amino]propanoic Acid (8.49 mg, 14.55 umol, 32.67% yield). $^1$H NMR (400 MHz, DMSO) δ 8.58 (s, 1H), 7.91 (s, 1H), 7.38-7.28 (m, 7H), 7.27-7.19 (m, 3H), 6.69 (s, 1H), 4.72 (s, 2H), 4.39 (dt, J=26.2, 13.1 Hz, 4H), 3.58-3.45 (m, 5H), 3.02 (t, J=6.7 Hz, 2H), 2.73 (s, 3H), 2.00 (dd, J=14.9, 7.2 Hz, 1H).

SU15210-0251
Route for SU15210-0251

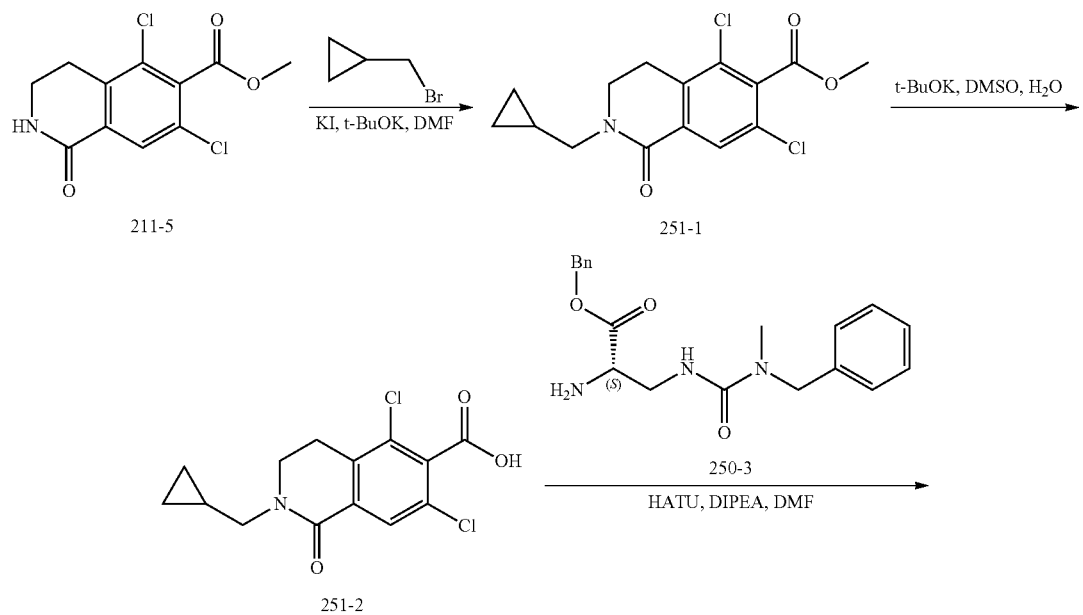

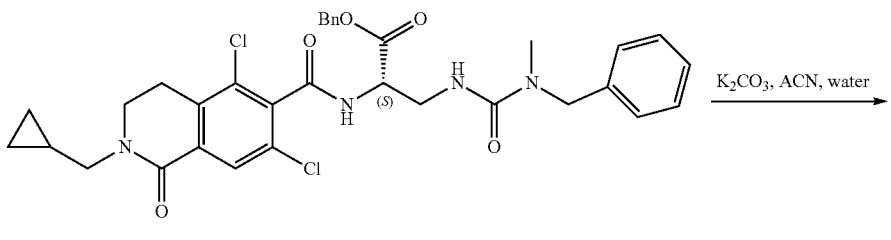

251-3

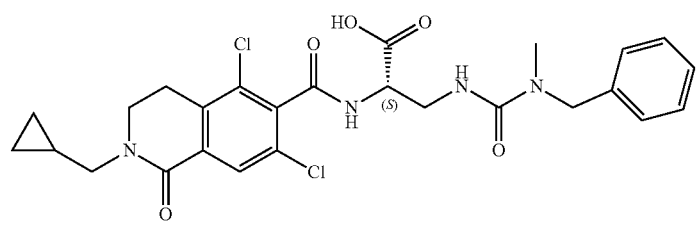

SU15210-0251

The Synthesis of methyl 5,7-dichloro-2-(cyclopropylmethyl)-1-oxo-3,4-dihydroisoquinoline-6-carboxylate (251-1)

The Synthesis of 5,7-dichloro-2-(cyclopropylmethyl)-1-oxo-3,4-dihydroisoquinoline-6-carboxylic Acid (251-2)

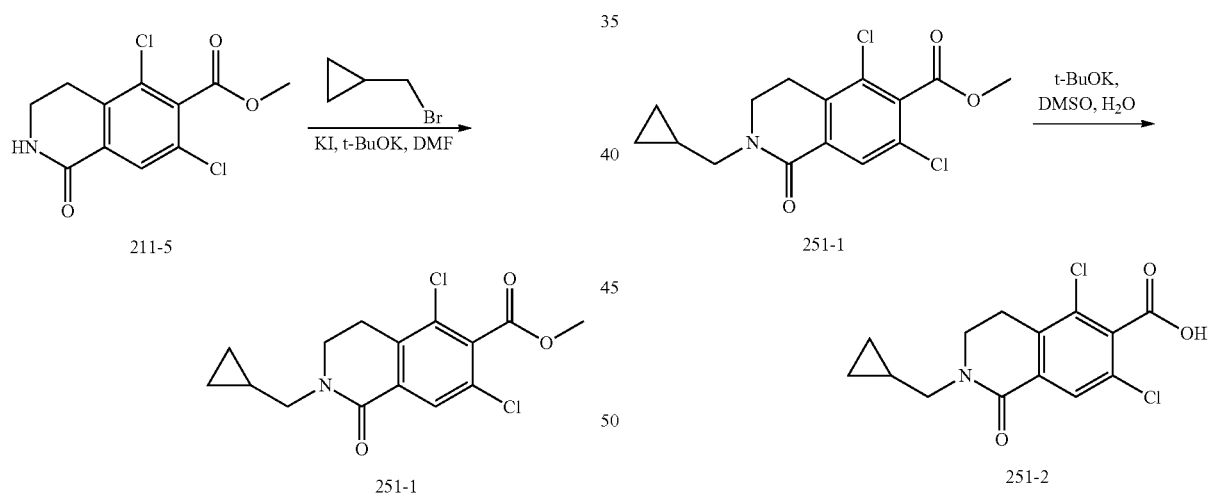

A mixture of methyl 5,7-dichloro-1-oxo-3,4-dihydro-2H-isoquinoline-6-carboxylate (300 mg, 1.09 mmol), bromomethylcyclopropane (177.31 mg, 1.31 mmol), potassium iodide (218.03 mg, 1.31 mmol, 69.88 uL) and Potassium tert-butoxide (245.63 mg, 2.19 mmol) in N,N-dimethylformamide (3 mL) was stirred at 80° C. for 5 hr. The reaction mixture was partitioned between ethyl acetate (30 mL) and water (30 mL), and the organic layer was washed with water (30 mL, twice) and brine, dried over anhydrous magnesium sulfate and filtered. The residue after concentration of the filtrate was purified by silica gel column to give 251-1 (242 mg, 737.38 umol, 67.37% yield) as a while solid.

A mixture of methyl 5,7-dichloro-2-(cyclopropylmethyl)-1-oxo-3,4-dihydroisoquinoline-6-carboxylate (242 mg, 737.38 umol) and Potassium tert-butoxide (289.60 mg, 2.58 mmol) in water (2 mL) and Dimethyl sulfoxide (20 mL) was stirred at 80° C. for overnight. After the reaction was finished, the solvent was removed under vacuum, the residual was dissolved in water (5 mL) and EA (5 mL), acidified by 1N HCl aq. to pH 2, the organic layer was then separated and the water phase was extracted with EA (5 mL×3), the organic phase was combined and washed with water then brine, dried over $Na_2SO_4$, concentrated the organic phase to obtain the white solid 251-2 (211 mg, 671.63 umol, 91.08% yield).

The Synthesis of benzyl (2S)-3-[[benzyl(methyl)carbamoyl]amino]-2-[[5,7-dichloro-2-(cyclopropylmethyl)-1-oxo-3,4-dihydroisoquinoline-6-carbonyl]amino]propanoate (251-3)

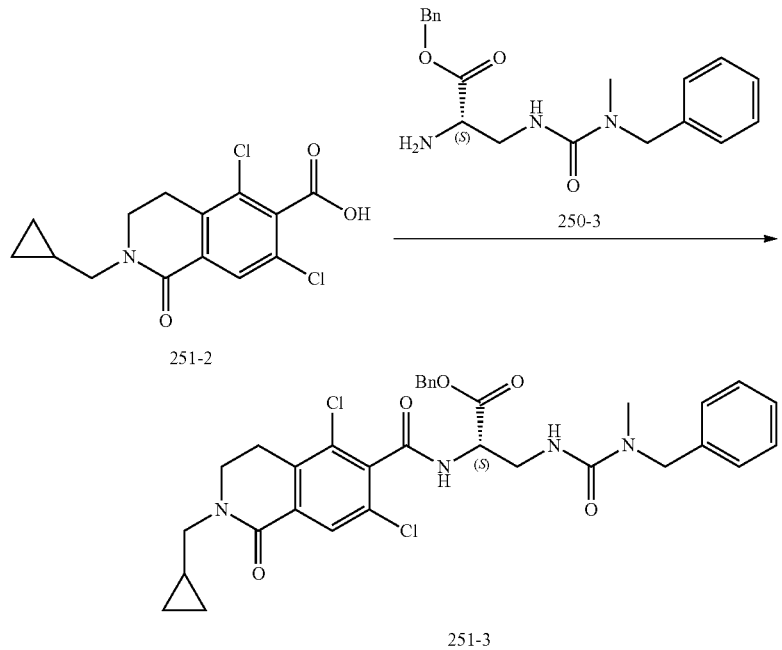

3-1. A mixture of 5,7-dichloro-2-(cyclopropylmethyl)-1-oxo-3,4-dihydroisoquinoline-6-carboxylic Acid (47.85 mg, 152.31 umol) in thionyl chloride (5 mL) was stirred at 80° C. for 1 hr. Then the reaction solution was evaporated under reduced pressure.

3-2. A mixture of benzyl (2S)-2-amino-3-[[benzyl(methyl)carbamoyl]amino]propanoate (40 mg, 117.16 umol) and N,N-diethylethanamine (35.57 mg, 351.49 umol) in dichloromethane (10 mL) was stirred at 0° C. for 3 min. After 1.1 was added and the reaction was stirred at rt for 1 hr. After the reaction was quenched with $H_2O$ (20 mL), extracted with $CH_2Cl_2$ (30 mL*3), combined the organic layer and dried over $Na_2SO_4$, filtered and concentrated in vacuo, the crude 251-3 (54 mg, 84.70 umol, 72.29% yield) was obtained as brown and used directly for next step without further purification.

The Synthesis of (2S)-3-[[benzyl(methyl)carbamoyl]amino]-2-[[5,7-dichloro-2-(cyclopropylmethyl)-1-oxo-3,4-dihydroisoquinoline-6-carbonyl]amino]propanoic Acid (SU15210-0251)

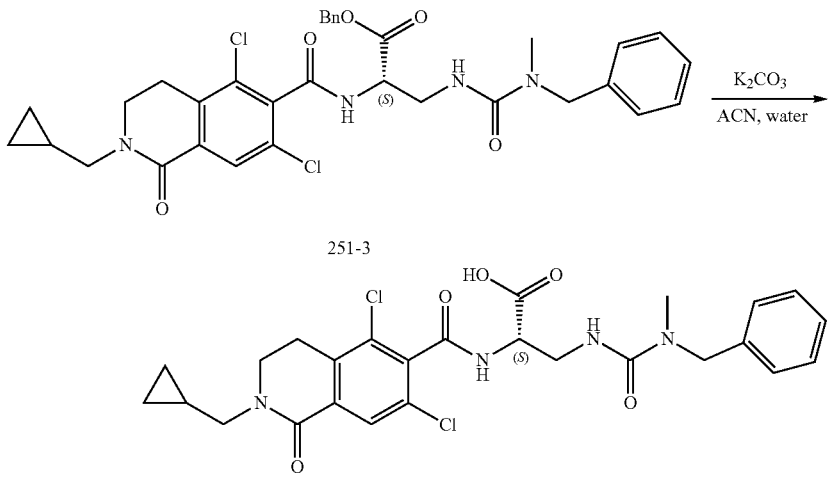

A mixture of benzyl (2S)-3-[[benzyl(methyl)carbamoyl]amino]-2-[[5,7-dichloro-2-(cyclopropylmethyl)-1-oxo-3,4-dihydroisoquinoline-6-carbonyl]amino]propanoate (34 mg, 53.33 umol) and Potassium carbonate (22.11 mg, 159.99 umol, 9.66 uL) was dissolved in acetonitrile (10 mL) and water (1 mL) and the resulting reaction mixture was stirred at rt 4 h. Then, the reaction solution was dried, dissolved in methanol and prepared by liquid phase to provide SU15210-0251 (1.7 mg, 3.11 umol, 5.82% yield) as white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.606 min; MS Found: 546.8 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 92.70%, Rt=8.034 min.

$^1$H NMR (400 MHz, MeOD) δ 7.96 (s, 1H), 7.35-7.20 (m, 6H), 4.65-4.42 (m, 4H), 3.78-3.65 (m, 4H), 3.47 (t, J=5.2 Hz, 2H), 3.11 (t, J=6.8 Hz, 2H), 2.84 (s, 3H), 1.12 (tt, J=12.1, 6.9 Hz, 1H), 0.59-0.51 (m, 2H), 0.33 (q, J=4.8 Hz, 2H).

SU15210-0257

Route for SU15210-0257

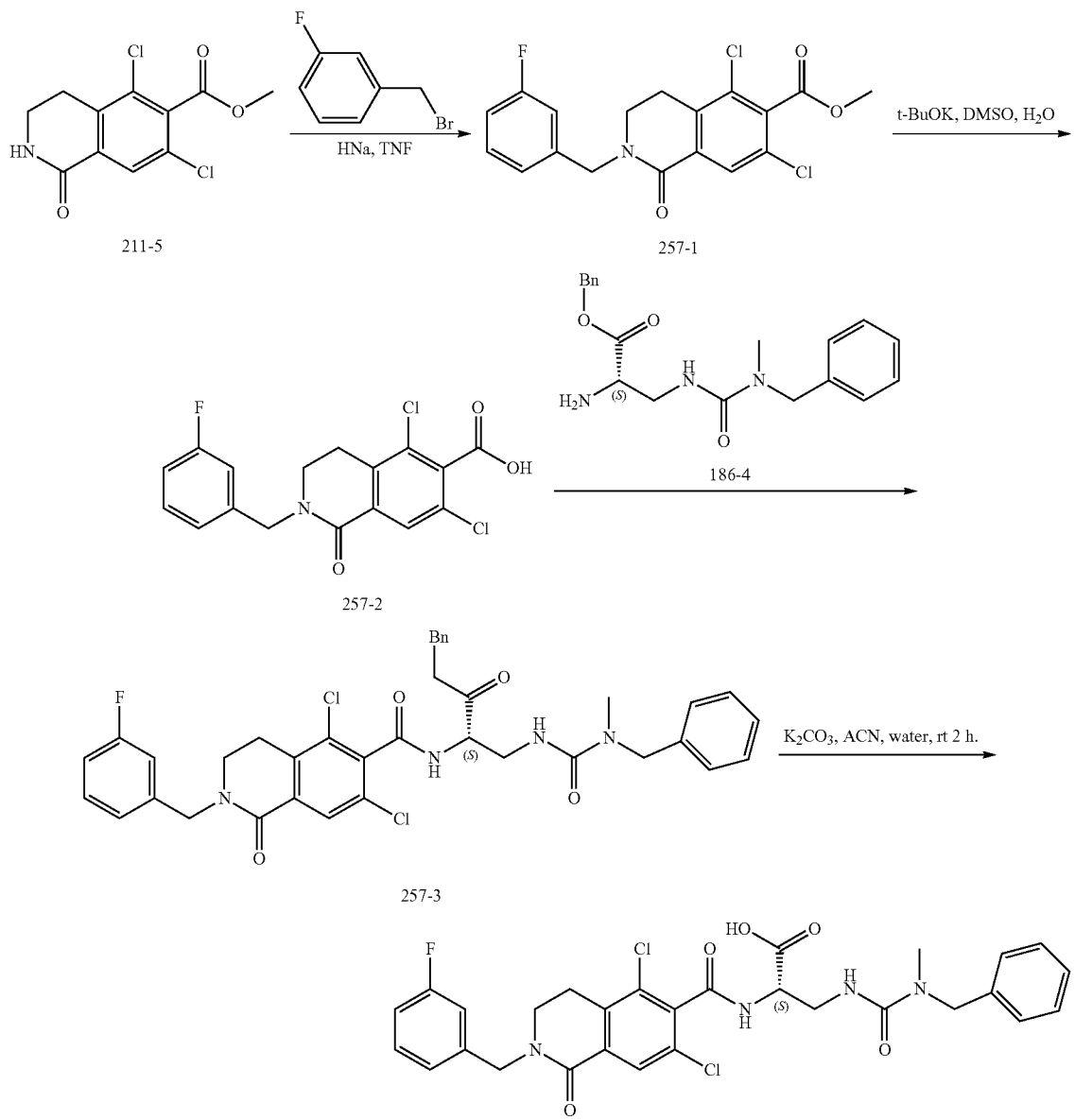

1. The Synthesis of methyl 5,7-dichloro-2-[(3-fluorophenyl)methyl]-1-oxo-3,4-dihydroisoquinoline-6-carboxylate (257-1)

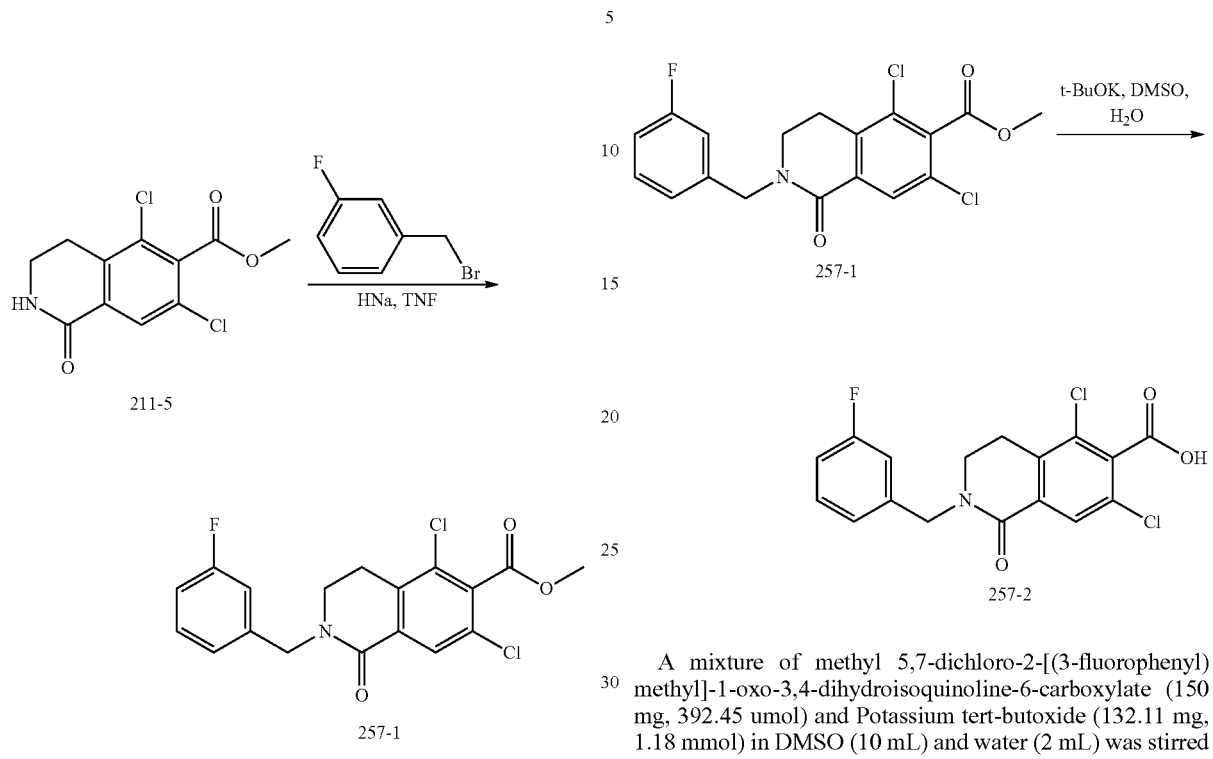

A mixture of methyl 5,7-dichloro-1-oxo-3,4-dihydro-2H-isoquinoline-6-carboxylate (150 mg, 0.55 mmol) in tetrahydrofuran (20 mL) was stirred at 0° C. for 3 min. Afterwards, sodium hydride (65.66 mg, 1.64 mmol, 60% purity) was added, and the reaction stirred at rt for 2 hrs. The reaction mixture was partitioned between ethyl acetate (30 mL) and water (30 mL), and the organic layer was washed with water (30 mL, twice) and brine, dried over anhydrous magnesium sulfate and filtered. The residue after concentration of the filtrate was purified by silica gel column to give 257-1 (150 mg, 0.39 mmol, 71.77% yield) as a while solid.

2. The Synthesis of 5,7-dichloro-2-[(3-fluorophenyl)methyl]-1-oxo-3,4-dihydroisoquinoline-6-carboxylic Acid (275-2)

A mixture of methyl 5,7-dichloro-2-[(3-fluorophenyl)methyl]-1-oxo-3,4-dihydroisoquinoline-6-carboxylate (150 mg, 392.45 umol) and Potassium tert-butoxide (132.11 mg, 1.18 mmol) in DMSO (10 mL) and water (2 mL) was stirred at 80° C. for 5 hr. After the reaction was finished, the solvent was removed under vacuum, the residual was dissolved in water (5 mL) and EA (5 mL), acidified by 1N HCl aq. to pH-2, the organic layer was then separated and the water phase was extracted with EA (5 mL×3), the organic phase was combined and washed with water then brine, dried over Na$_2$SO$_4$. The organic phase was then concentrated to obtain the crude light yellow oil 275-2 (119 mg, 323.21 umol, 82.36% yield).

3. The Synthesis of benzyl (2S)-3-[[benzyl(methyl)carbamoyl]amino]-2-[[5,7-dichloro-2-[(3-fluorophenyl)methyl]-1-oxo-3,4-dihydroisoquinoline-6-carbonyl]amino]propanoate (257-3)

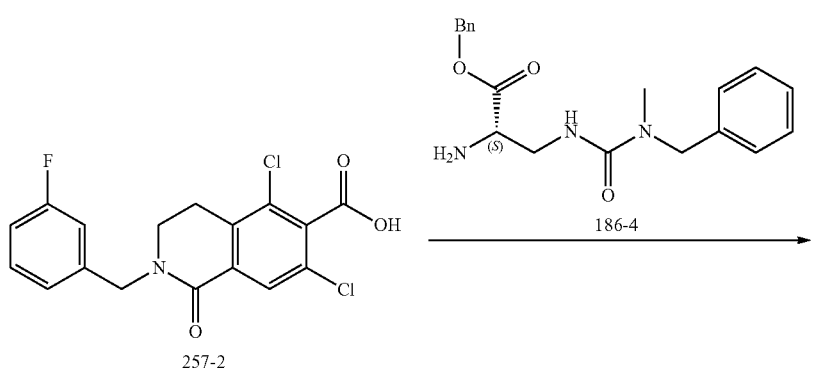

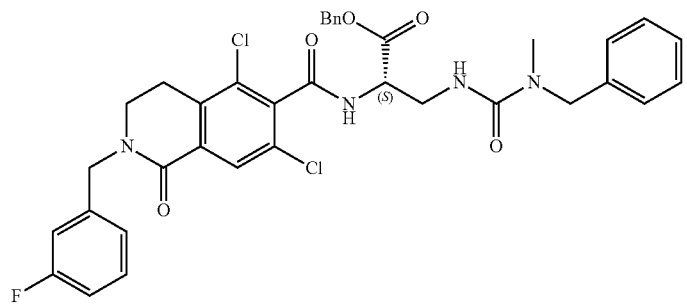

257-3

3.1 A mixture of 5,7-dichloro-2-[(3-fluorophenyl)methyl]-1-oxo-3,4-dihydroisoquinoline-6-carboxylic Acid (86.28 mg, 234.33 umol) was dissolved in thionyl chloride (5 mL) and then stirred at 80° C. for 1 h. The resulting reaction mixture was then concentrated under reduced pressure.

3.2 A mixture of benzyl (2S)-2-amino-3-[[benzyl(methyl)carbamoyl]amino]propanoate (40 mg, 117.16 umol) and N,N-diethylethanamine (35.57 mg, 351.49 umol) in dichloromethane (10 mL) was stirred at 0° C. for 3 min. Afterwards, 1.1 was added and the reaction was stirred at rt for 1 hr. After the reaction was completed (detected by LCMS), the reaction was quenched with $H_2O$ (50 mL), extracted with EtOAc (20 mL×3), combined the organic layer and dried over $Na_2SO_4$, filtered and concentrated in vacuo. The crude was purified by prep TLC to give the product 257-3 (47 mg, 67.96 umol, 58.00% yield) as a light yellow oil.

4. The Synthesis of (2S)-3-[[benzyl(methyl)carbamoyl]amino]-2-[[5,7-dichloro-2-[(3-fluorophenyl)methyl]-1-oxo-3,4-dihydroisoquinoline-6-carbonyl]amino]propanoic Acid (SU15210-0257)

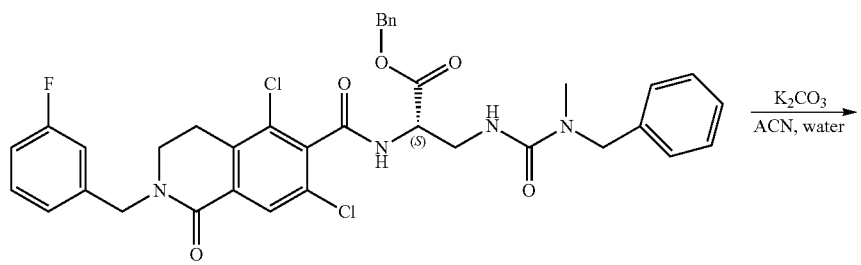

257-3

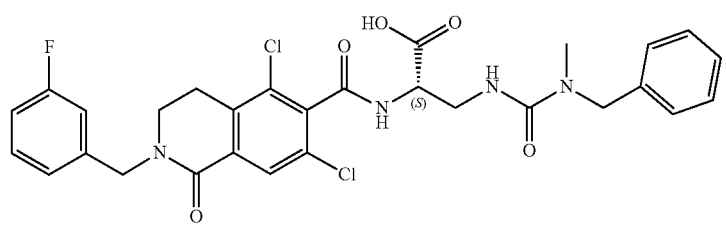

SU15210-0257

A mixture of benzyl (2S)-3-[[benzyl(methyl)carbamoyl]amino]-2-[[5,7-dichloro-2-[(3-fluorophenyl)methyl]-1-oxo-3,4-dihydroisoquinoline-6-carbonyl]amino]propanoate (42 mg, 60.73 umol) and dipotassium carbonate (25.18 mg, 182.19 umol, 11.00 uL) was dissolved in acetonitrile (10 mL) and water (1 mL) and then stirred at rt 2 h. The resulting reaction solution was dried, dissolved in methanol and prepared by liquid phase to provide SU15210-0257 (5.91 mg, 9.83 umol, 16.18% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=2.070 min; MS Found: 600.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 96.75%, Rt=7.693 min.

$^1$H NMR (400 MHz, MeOD) δ 8.00 (s, 1H), 7.43-6.96 (m, 10H), 4.77 (s, 2H), 4.59 (d, J=15.2 Hz, 1H), 4.41 (d, J=15.4 Hz, 2H), 3.84 (s, 2H), 3.58 (t, J=6.7 Hz, 2H), 3.05 (t, J=6.5 Hz, 2H), 2.87 (s, 3H).

SU15210-0265

Route for SU15210-0265

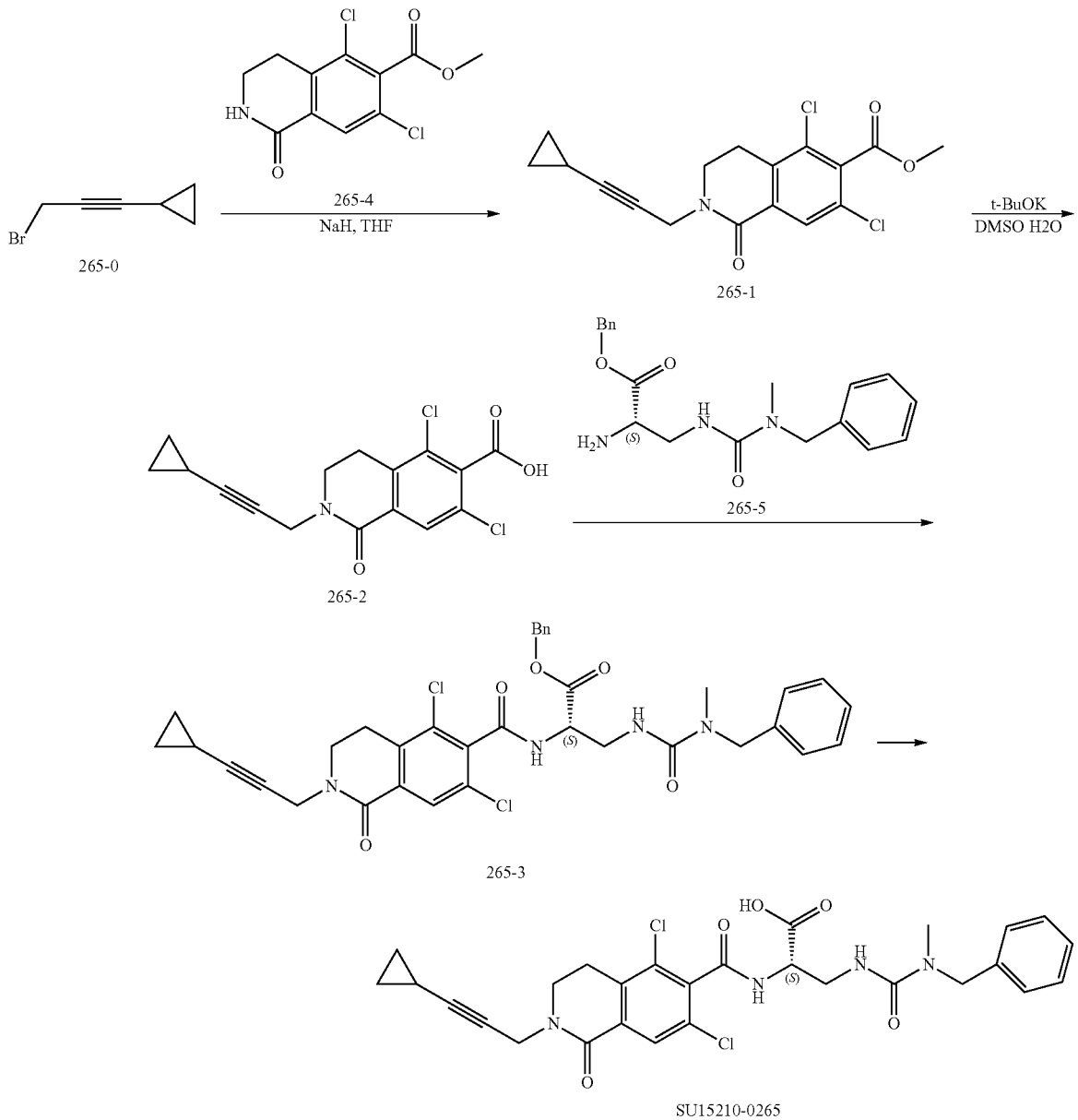

SU15210-0265

1. Methyl 5,7-dichloro-2-(3-cyclopropylprop-2-ynyl)-1-oxo-1,2,3,4-tetrahydroisoquinoline-6-carboxylate

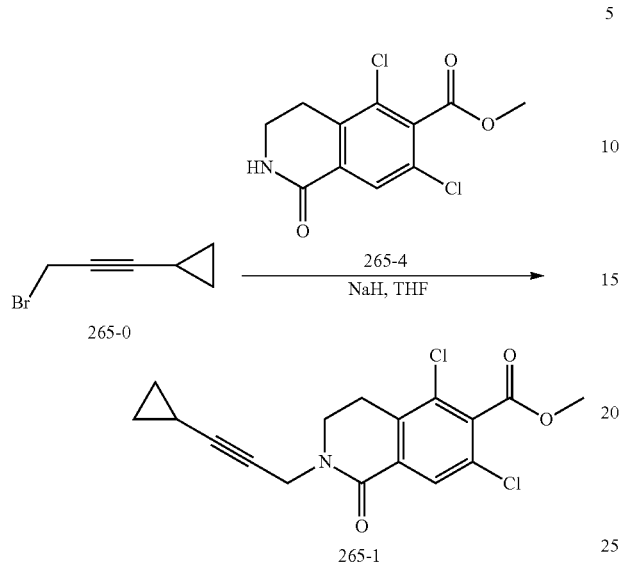

To a 25 mL round bottomed flask, 265-4 (140 mg, 510.76 umol) was added to THE (5 mL), and then was cooled down to 0° C. Then, NaH (36.77 mg, 1.53 mmol) was added, and the resulting reaction mixture was stirred at rt for 1 h, followed by the addition of 265-0 (97.47 mg, 612.92 umol) and the resulting reaction mixture was stirred at rt for 3 h. When all the start material was consumed, the reaction was quenched with water, extracted with EA, dried with $Na_2SO_4$, concentrated to provide a crude oil which was purified by silica gel column to afford 265-1 (110 mg, 312.31 umol, 61.15% yield) as white powder.

2. 5,7-dichloro-2-(3-cyclopropylprop-2-ynyl)-1-oxo-1,2,3,4-tetrahydroisoquinoline-6-carboxylic Acid

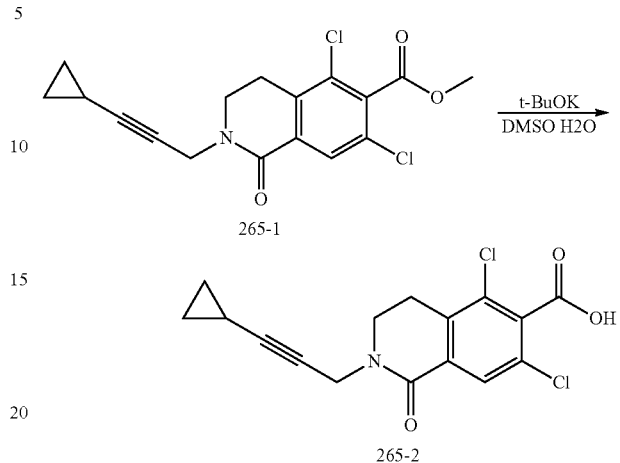

To a mixture of 265-1 (90 mg, 255.53 umol) and potassium; 2-methylpropan-2-olate (86.02 mg, 766.59 umol) was dissolved in DMSO (4 mL) and $H_2O$ (1 mL), and the resulting reaction mixture was stirred at 80° C. overnight. Analytical TLC showed the start material was consumed and the reaction was quenched with water, adjusted to pH 1 with HCl, extracted with EA, dried with $Na_2SO_4$, concentrated to provide a crude oil which was purified by prep-HPLC to afford 265-2 (20 mg, 59.14 umol, 23.14% yield) as white solid.

3. (S)-benzyl 3-(3-benzyl-3-methylureido)-2-(5,7-dichloro-2-(3-cyclopropylprop-2-ynyl)-1-oxo-1,2,3,4-tetrahydroisoquinoline-6-carboxamido)propanoate

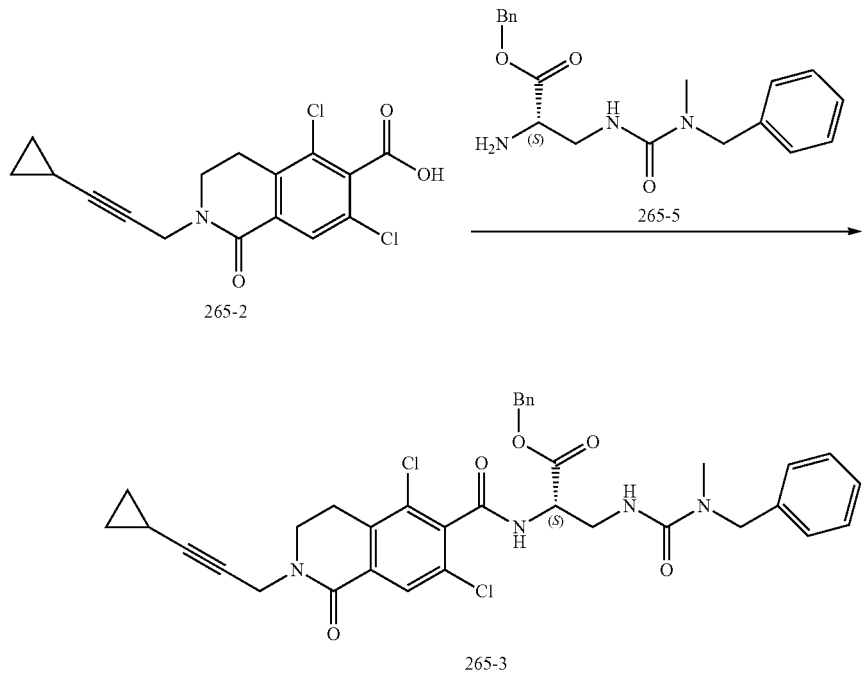

A mixture of 265-2 (16 mg, 47.31 umol), DIPEA (12.23 mg, 94.62 umol, 16.48 uL), and HATU (27.13 mg, 70.97 umol) were dissolved in DMF (10 mL) and was subsequently stirred at rt for 15 min, before 265-5 (16.15 mg, 47.31 umol) was added. The resulting reaction mixture was stirred at rt overnight, LCMS detected the target mass, and the reaction was quenched with water, extracted with EA, dried with Na$_2$SO$_4$, concentrated to provide the crude oil 265-3 (25 mg, 37.79 umol, 79.87% yield) which was used to next step without further purification.

4. (S)-3-(3-benzyl-3-methylureido)-2-(5,7-dichloro-2-(3-cyclopropylprop-2-ynyl)-1-oxo-1,2,3,4-tetrahydroisoquinoline-6-carboxamido)propanoic Acid prep-HPLC to afford SU15210-0265 (2.15 mg, 3.76 umol) as white solid.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 90.7%, Rt=8.173 min; MS Found: 570.7 [M+H]$^+$.

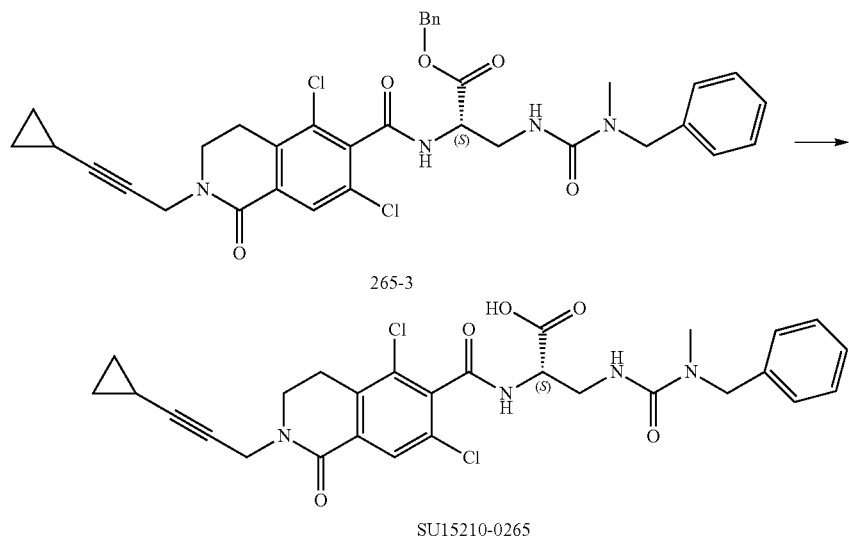

A mixture of 265-3 (25 mg, 37.79 umol) and dipotassium carbonate (52.23 mg, 377.89 umol, 22.81 uL) were dissolved in ACN (50 mL) and water (10 mL) and then stirred at rt overnight. LCMS showed target mass, and the resulting reaction mixture was diluted with water, extracted with EA, concentrated to provide a crude oil, which was purified by $^1$H NMR (400 MHz, MeOD) δ 8.03 (s, 1H), 7.49-7.13 (m, 9H), 4.76 (s, 1H), 4.61-4.40 (m, 3H), 4.22 (dd, J=7.1, 0.8 Hz, 2H), 3.79-3.56 (m, 4H), 3.08 (t, J=6.7 Hz, 2H), 2.82 (s, 3H), 1.29 (t, J=7.1 Hz, 3H).

SU15210-0270-01
Route for SU15210-0270-01

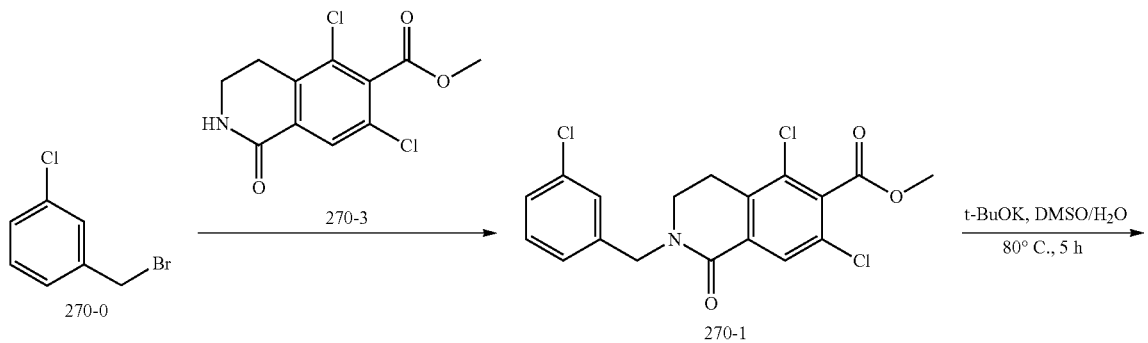

-continued

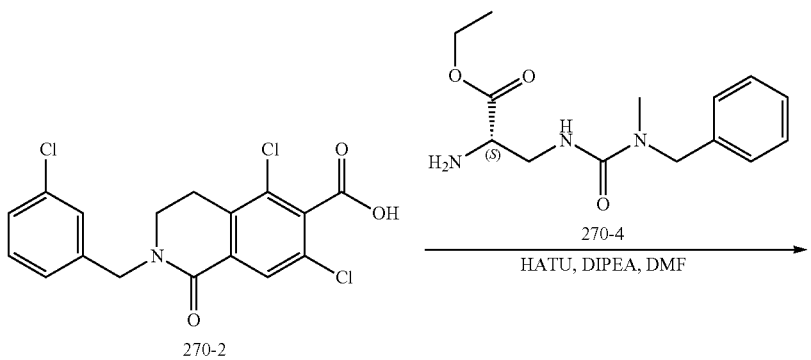

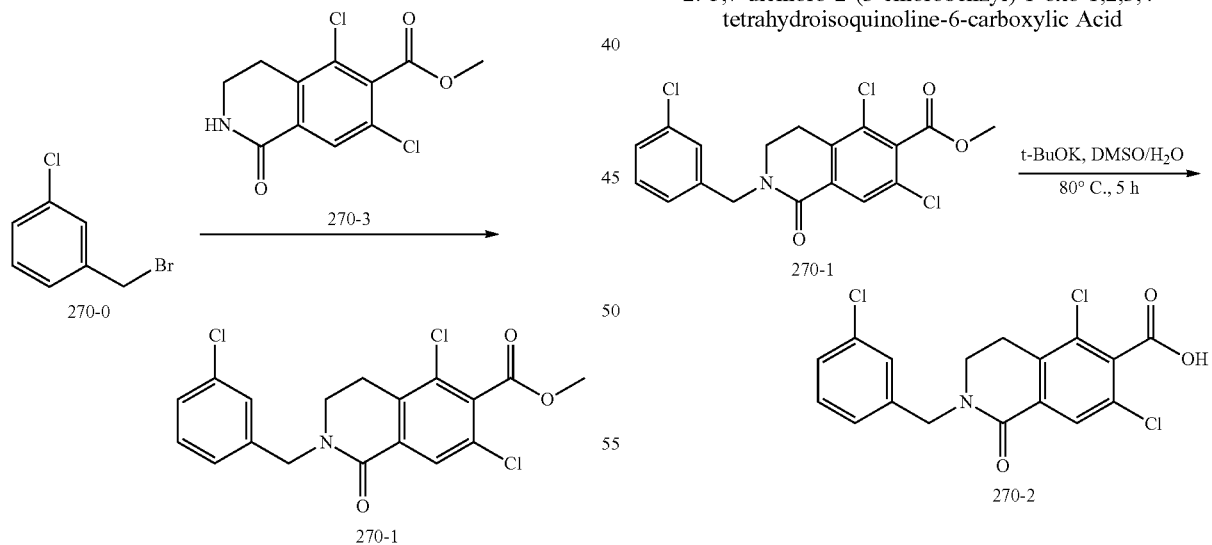

SU15210-0270-01

1. Methyl 5,7-dichloro-2-(3-chlorobenzyl)-1-oxo-1,2,3,4-tetrahydroisoquinoline-6-carboxylate To a 50 mL 3-neck round bottomed flask, 270-3 (170 mg, 615.68 umol) and tetrahydrofuran (50 mL) were added, the reaction was then cooled to 0° C., and NaH (106.26 mg, 2.66 mmol, 60% purity) was added under $N_2$ atmosphere, and the reaction mixture was stirred at RT for 45 min. Then 270-0 (139.16 mg, 677.25 umol, 88.64 uL) was added, and the resulting reaction mixture was stirred at RT overnight before dilution with water, extraction with EA and concentration of the crude material under reduced pressure. This crude material was purified by silica gel column to afford 270-1 (206 mg, 514.12 umol, 83.50% yield) as yellow oil.

2. 5,7-dichloro-2-(3-chlorobenzyl)-1-oxo-1,2,3,4-tetrahydroisoquinoline-6-carboxylic Acid Potassium-2-methylpropan-2-olate (157.06 mg, 1.40 mmol) was added to 270-1 (186 mg, 466.55 umol) dissolved in methylsulfinylmethane (20 mL) and water (5 mL), the resulting reaction mixture was stirred at 80° C. or 4 h, then was diluted with water, acidified to pH=2, extracted with EA, dried with $Na_2SO_4$ to provide the crude oil following concentration under reduced pressure. This crude material was purified by prep-HPLC to afford 270-2 (170 mg, 441.97 umol, 94.73% yield) as a yellow oil.

3. (S)-ethyl 3-(3-benzyl-3-methylureido)-2-(5,7-dichloro-2-(3-chlorobenzyl)-1-oxo-1,2,3,4-tetrahydroisoquinoline-6-carboxamido)propanoate

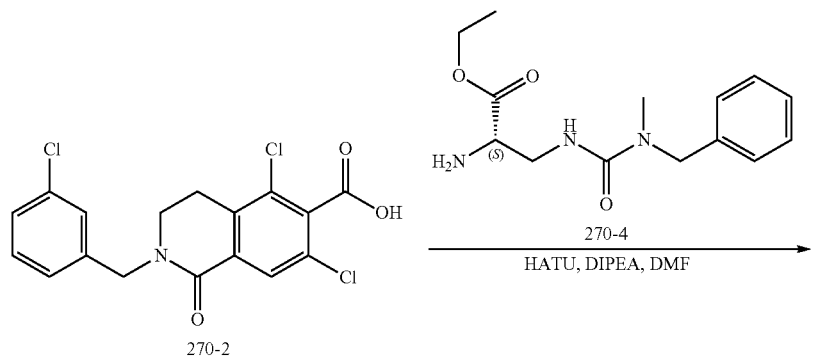

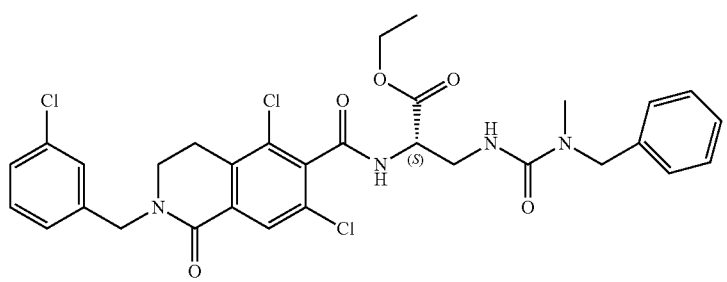

A mixture of 270-2 (250 mg, 646.57 umol) HATU (370.72 mg, 969.85 umol) and DIPEA (167.13 mg, 1.29 mmol, 225.24 uL) in DMF (50 mL) was stirred at rt for 15 min, then 270-4 (180.61 mg, 646.57 umol) was added. The resulting reaction mixture was stirred at rt overnight, then quenched with water, extracted with EA, dried with $Na_2SO_4$, concentrated to provide crude oil. This crude material was purified by prep-HPLC to afford SU15210-0270-01 (45 mg, 69.45 umol, 10.74% yield) as yellow solid.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 98.1%, Rt=10.37 min; MS Found: 644.7 [M+H]+.

1H NMR (400 MHz, MeOD) δ 8.03 (s, 1H), 7.49-7.13 (m, 9H), 4.76 (s, 1H), 4.61-4.40 (m, 3H), 4.22 (dd, J=7.1, 0.8 Hz, 2H), 3.79-3.56 (m, 4H), 3.08 (t, J=6.7 Hz, 2H), 2.82 (s, 3H), 1.29 (t, J=7.1 Hz, 3H).

SU15210-0279-01
Route for SU15210-0279-01

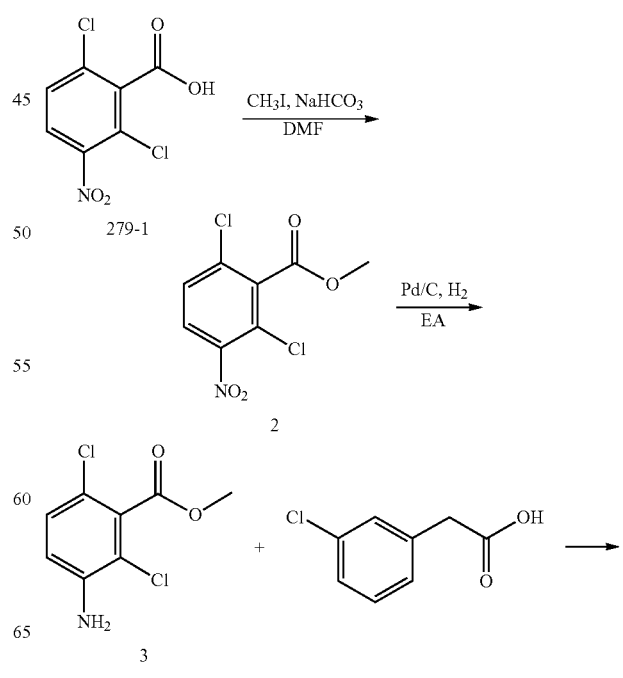

-continued

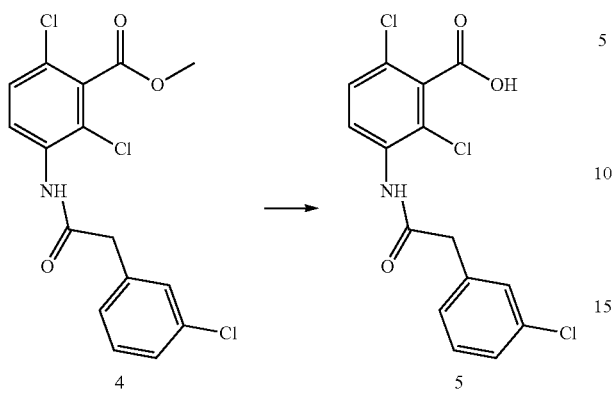

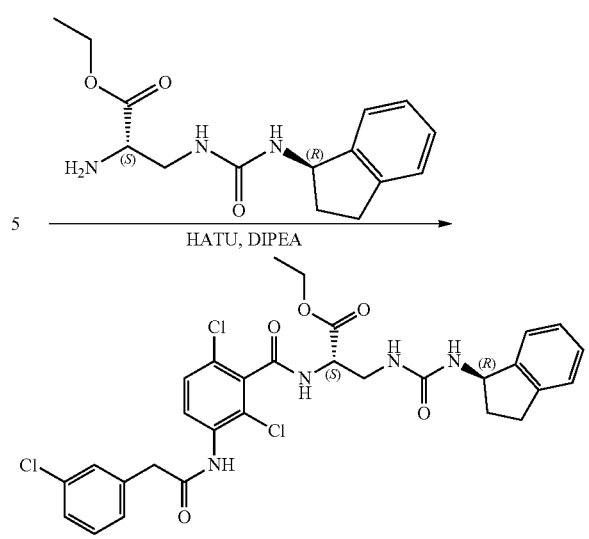

The Synthesis of methyl
2,6-dichloro-3-nitro-benzoate (2)

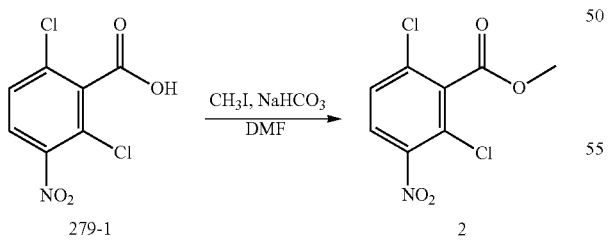

To a mixture of 2,6-dichloro-3-nitro-benzoic Acid (400 mg, 1.69 mmol) and CH$_3$I (240.67 mg, 1.69 mmol) in DMF (10 mL) was added NaHCO$_3$ (427.10 mg, 5.08 mmol). After the reaction mixture stirred at rt for 3 h, it was then diluted with 100 mL water and 100 mL DCM. The organic phase was concentrated under reduced pressure to afford 2 (420 mg, 99% yield) as an clear oil.

The Synthesis of methyl
3-amino-2,6-dichloro-benzoate (3)

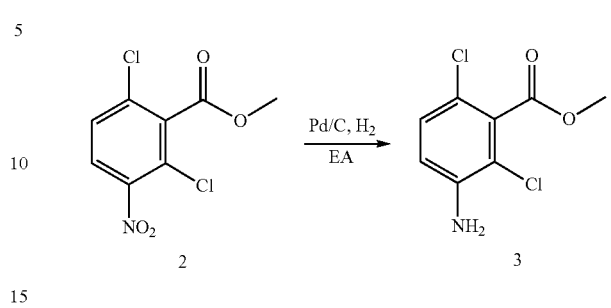

To a solution of methyl 2,6-dichloro-3-nitro-benzoate (420 mg, 1.68 mmol) in EA (20 mL) was added Pd/C (100 mg, 823.38 umol). After stirring at rt under H$_2$ for 36 hr, the reaction mixture was filtered and concentrated to afford 3 (370 mg, 63.8% yield) as a white solid.

The Synthesis of methyl 2,6-dichloro-3-[[2-(3-chlorophenyl)acetyl]amino]benzoate (4)

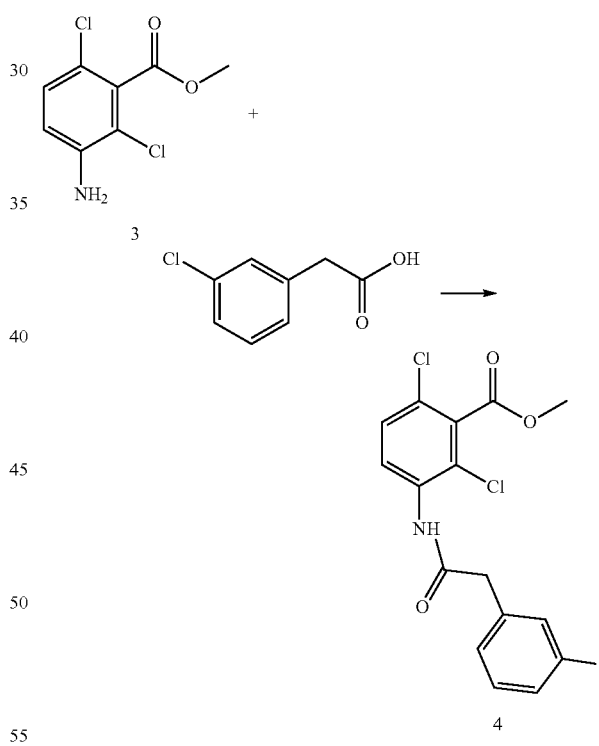

A solution of 2-(3-chlorophenyl) acetic Acid (542.67 mg, 3.18 mmol) in SOCl$_2$ (604.77 mg, 10 mL) was refluxed under N$_2$ for 2 h and then evaporated to remove SOCl$_2$. Then the residue was added to a mixture of methyl 3-amino-2,6-dichloro-benzoate (350 mg, 1.59 mmol) and K$_2$CO$_3$ (482.84 mg, 3.50 mmol, 665.07 uL) in THF (20 mL). After stirring at rt for 2 h, the reaction mixture was diluted with 100 mL water and 100 mL DCM. The organic phase was concentrated under reduced pressure to afford 4 (540 mg, 91.2% yield) as a crude white solid.

The Synthesis of 2,6-dichloro-3-[[2-(3-chlorophenyl)acetyl]amino]benzoic Acid (5)

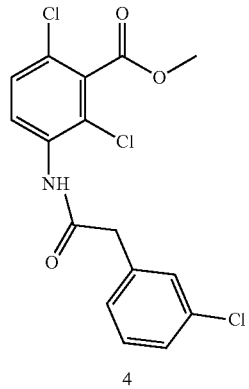

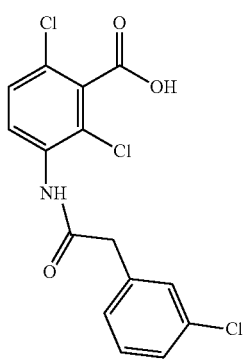

A mixture of methyl 2,6-dichloro-3-[[2-(3-chlorophenyl)acetyl]amino]benzoate (540 mg, 1.45 mmol) and LiI (969.81 mg, 7.25 mmol, 13.74 uL) suspended in pyridine (20 mL) and then stirred at 115° C. for 17 hr. The reaction mixture subsequently was concentrated and purified by prep-HPLC to afford 5 (190 mg, 36.5% yield) as a white solid.

The Synthesis of ethyl rac-(2S)-2-[[2,6-dichloro-3-[[2-(3-chlorophenyl)acetyl]amino]benzoyl]amino]-3-[[rac-(1R)-indan-1-yl]carbamoylamino]propanoate (SU15210-0279-01)

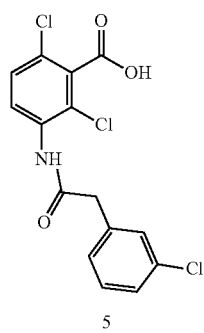
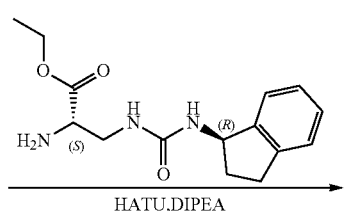

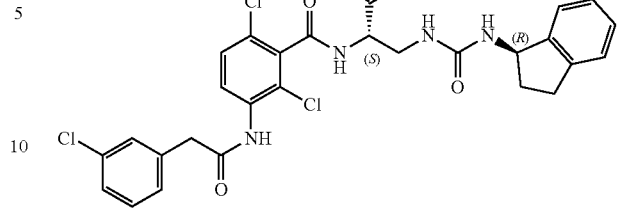

SU15210-0279-01

To a solution of 2,6-dichloro-3-[[2-(3-chlorophenyl)acetyl]amino]benzoic Acid (180 mg, 501.95 μmol), HATU (190.86 mg, 501.95 μmol) and DIPEA (194.61 mg, 1.51 mmol, 262.28 μL) in DMF (5 mL) was added ethyl rac-(2S)-2-amino-3-[[rac-(1R)-indan-1-yl]carbamoylamino]propanoate (146.24 mg, 501.95 μmol). After stirred at rt for 1 h, the reaction solution was purified by prep-HPLC to afford SU15210-0279-01 (95 mg, 27.85% yield) as a white solid.

$^1$H NMR (400 MHz, DMSO) δ 9.91 (s, 1H), 9.12 (d, J=7.3 Hz, 1H), 7.73 (d, J=8.8 Hz, 1H), 7.50-7.41 (m, 2H), 7.33 (tt, J=7.2, 6.5 Hz, 3H), 7.25-7.10 (m, 6H), 6.57 (d, J=8.3 Hz, 1H), 5.91 (t, J=6.0 Hz, 1H), 5.07 (dd, J=16.0, 8.1 Hz, 1H), 4.53 (dd, J=13.4, 7.4 Hz, 1H), 4.21-4.05 (m, 2H), 3.78 (s, 2H), 3.60-3.47 (m, 1H), 2.87 (ddd, J=15.6, 8.5, 2.9 Hz, 1H), 2.72 (ddd, J=17.2, 10.2, 5.2 Hz, 1H), 2.42-2.29 (m, 1H), 1.67 (ddd, J=17.2, 12.5, 8.8 Hz, 1H), 1.23 (t, J=7.1 Hz, 3H).

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 93.68%, Rt=3.091 min; MS Found: 632.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 92.96%, Rt=9.860 min.

SU15210-0280

Route for SU15210-0280

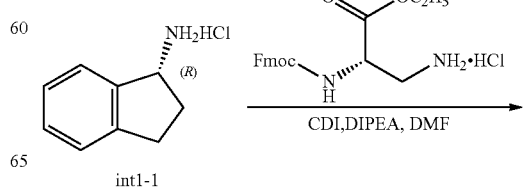

int1-1

633
-continued
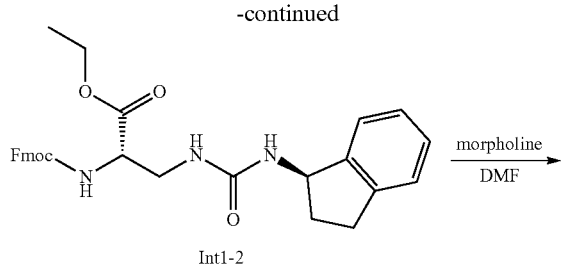
Int1-2
634
-continued
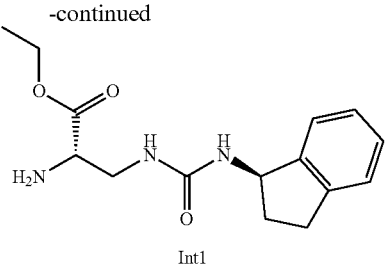
Int1
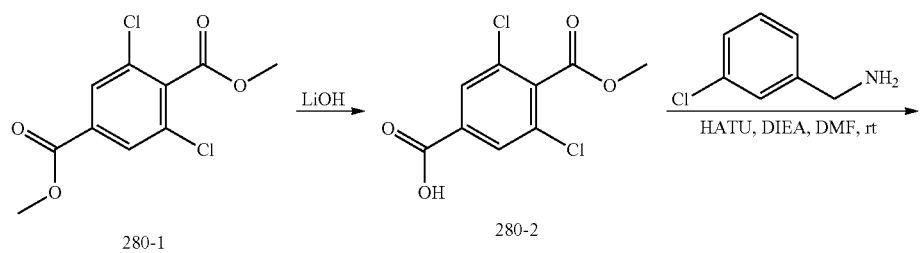
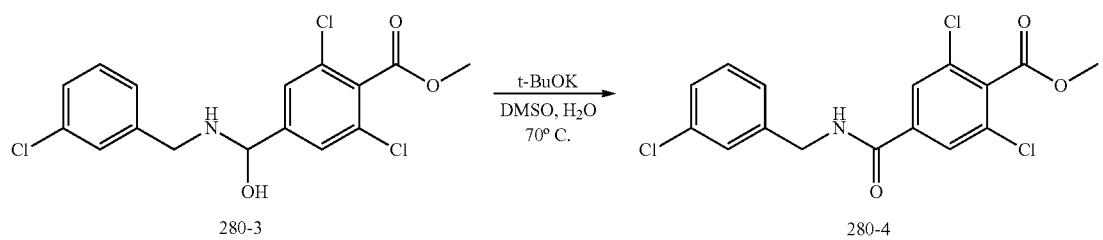
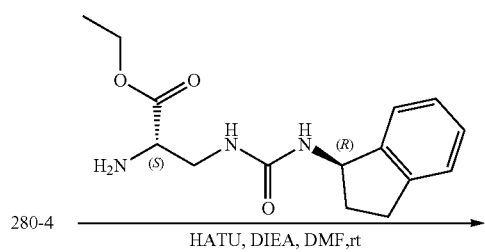
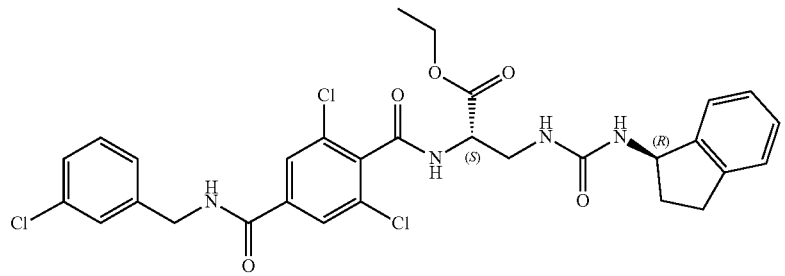
SU15210-0280

1. The Synthesis of (S)-ethyl 2-(((9H-fluoren-9-yl)methoxy)carbonylamino)-3-(3-((R)-2,3-dihydro-1H-inden-1-yl)ureido)propanoate (int1-2)

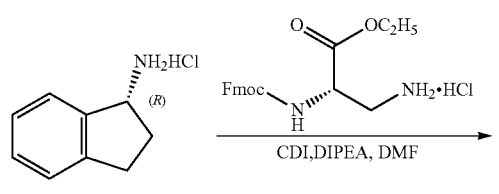

To a solution of (1R)-indan-1-amine; hydrochloride (500 mg, 2.95 mmol) in DMF (20 mL) was added CDI (509.10 mg, 3.54 mmol). The reaction mixture was stirred at rt for 1 hr, then DIPEA (1.14 g, 8.84 mmol, 1.54 mL) and ethyl (2S)-3-amino-2-(9H-fluoren-9-ylmethoxycarbonylamino) propanoate hydrochloride (1.15 g, 2.95 mmol) were added. After stirring at rt for 16 hr, the mixture was quenched with $H_2O$ (100 mL) and extracted with EA (100 mL), the organic layer was concentrated under reduced pressure and purified by silica gel column (PE:EA=1:1) to obtain (S)-ethyl 2-(((9H-fluoren-9-yl)methoxy) carbonylamino)-3-(3—((R)-2,3-dihydro-1H-inden-1-yl) ureido) propanoate (1.0 g, 1.95 mmol, 66.07% yield) as a white solid.

2. The Synthesis of (S)-ethyl 2-amino-3-(3-((R)-2,3-dihydro-1H-inden-1-yl) ureido)propanoate (int-1)

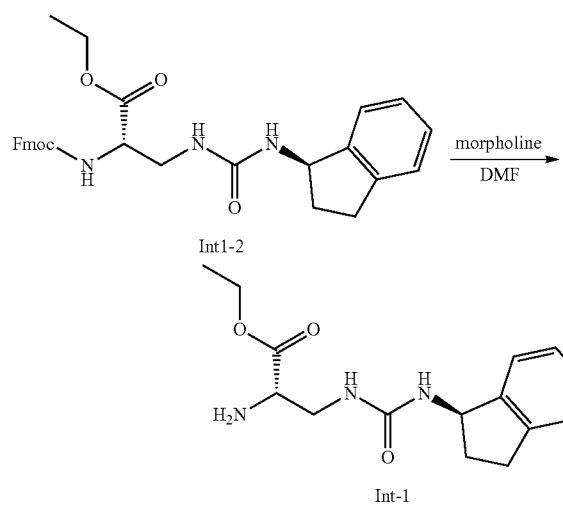

To a solution of obtained (S)-ethyl 2-(((9H-fluoren-9-yl)methoxy)carbonylamino)-3-(3-((R)-2,3-dihydro-1H-inden-1-yl) ureido)propanoate (1.0 g, 1.95 mmol) in DMF (5 mL) was added morpholine (1 mL) and the reaction was stirred at rt for 1 hr. Following concentration under reduced pressure, the crude material was purified by silica gel column (PE:EA=1:1) to obtain (S)-ethyl 2-amino-3-(3-((R)-2,3-dihydro-1H-inden-1-yl) ureido)propanoate (300 mg, 1.03 mmol, 52.88% yield).

3. The Synthesis of 3,5-dichloro-4-methoxycarbonyl-benzoic Acid (280-2)

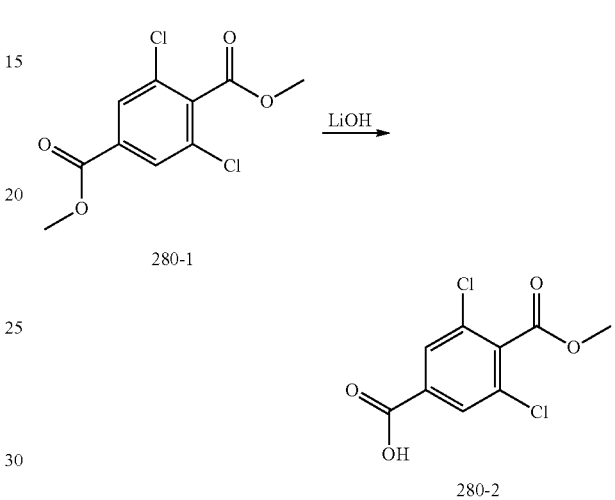

To a mixture of dimethyl 2,6-dichlorobenzene-1,4-dicarboxylate (650 mg, 2.47 mmol) in THF (10 mL) and $H_2O$ (4 mL) was added LiOH (118.35 mg, 4.94 mmol). Then this mixture was stirred at rt for 1 hr before the pH was Adjusted to ~4 with 1N HCl solution and EA was added. The organic layer was concentrated to obtain 3,5-dichloro-4-methoxycarbonyl-benzoic acid (550 mg, 2.21 mmol, 89.38% yield) as a white solid.

4. The Synthesis of methyl 2,6-dichloro-4-(3-chlorobenzylcarbamoyl)benzoate (280-3)

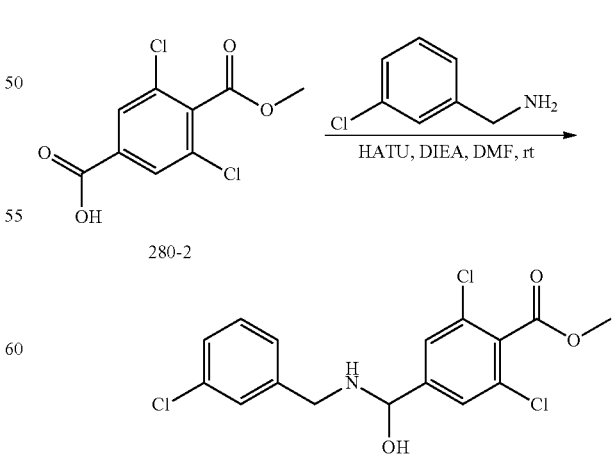

To a solution of compound 280-2 (550 mg, 2.21 mmol) and (3-chlorophenyl) methanamine (314 mg, 2.21 mmol) in DMF (10 mL) was added DIEA (855 mg, 6.63 mmol) and HATU (1.68 g, 4.42 mmol) and the mixture was stirred at rt for 1.5 h. This mixture was quenched with water (50 mL), extracted with EtOAc (50 mL×3), dried over anhydrous sodium sulfate and concentrated under reduced pressure. The crude was purified by silica gel column (PE:EA=4:1) to obtain to give 280-3 (220 mg, 0.59 mmol, yield: 26.69%) as a yellow solid.

The Synthesis of 2,6-dichloro-4-(3-chlorobenzylcarbamoyl)benzoic Acid (280-4)

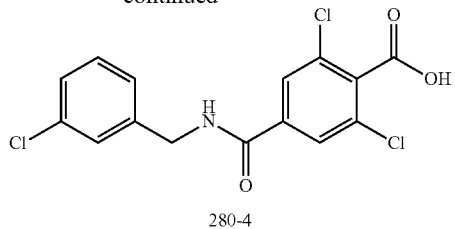

280-4

To a solution of compound 280-3 (220 mg, 0.59 mmol) in DMSO (8 mL) and H₂O (0.5 mL) was added potassium tert-butoxide (132.5 mg, 1.18 mmol) and the mixture was stirred at 70° C. for 2 h. Then this mixture was quenched with water (50 mL), extracted with EtOAc (20 mL×3), and washed the combined organic layers with water (50 mL×3). The residues was dried over anhydrous sodium sulfate and concentrated in vacuo. The crude product 280-4 (130 mg, 362.52 umol, 61.40% yield) was used for next step without further purification.

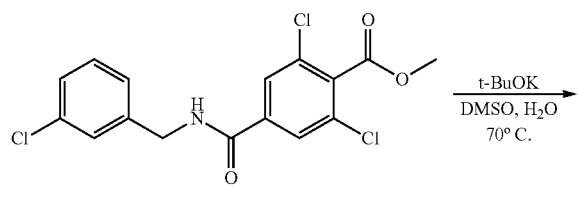

The Synthesis of (S)-ethyl 2-(2,6-dichloro-4-(3-chlorobenzylcarbamoyl)benzamido)-3-(3-((R)-2,3-dihydro-1H-inden-1-yl)ureido)propanoate (SU15210-0280)

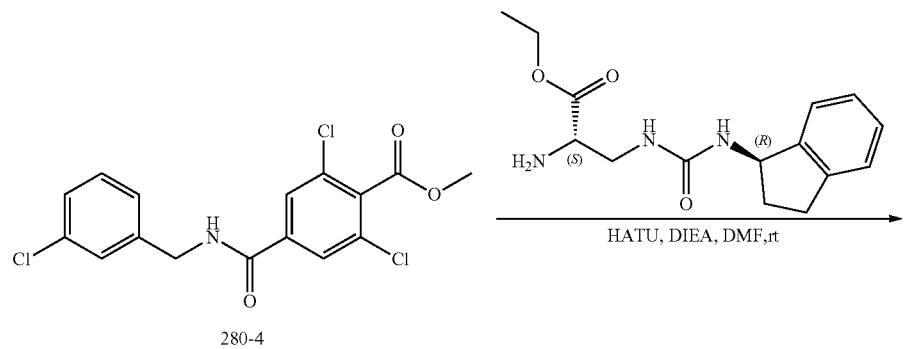

280-4

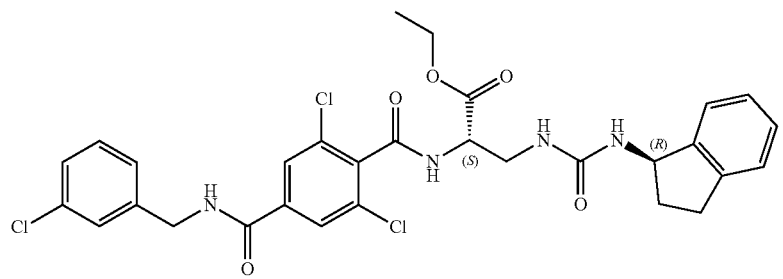

SU15210-0280

To a solution of compound 280-4 (130 mg, 362.52 umol) and Int1 (105.62 mg, 362.5 umol) in DMF (10 mL) was added DIEA (140 mg, 1.1 mmol) and HATU (207 mg, 543.8 umol) and the mixture was stirred at room temperature for 16 h. The mixture was quenched with water (50 mL), extracted with EA (50 mL×3), washed the organic layers with water (50 mL×3). The residues was dried over anhydrous sodium sulfate and concentrated. The crude was purified by pre-HPLC to provide SU15210-0280 (94.9 mg, 150.17 umol, 41.43% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=2.333 min; MS Found: 630.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 97.12%, Rt=9.990 min.

$^1$H NMR (400 MHz, DMSO) δ 9.32 (t, J=5.9 Hz, 1H), 9.20 (d, J=7.4 Hz, 1H), 7.97 (s, 2H), 7.47-7.27 (m, 4H), 7.27-7.09 (m, 4H), 6.57 (d, J=8.4 Hz, 1H), 5.90 (s, 1H), 5.08 (q, J=7.9 Hz, 1H), 4.56 (dd, J=13.4, 7.4 Hz, 1H), 4.48 (d, J=5.8 Hz, 2H), 4.19-4.09 (m, 2H), 3.55 (dt, J=18.5, 6.2 Hz, 1H), 2.87 (ddd, J=15.9, 8.8, 3.2 Hz, 1H), 2.82-2.70 (m, 1H), 2.41-2.28 (m, 1H), 2.00 (dd, J=14.8, 7.1 Hz, 1H), 1.68 (dq, J=12.4, 8.7 Hz, 1H), 1.24 (d, J=5.0 Hz, 3H).

SU15210-0289
Route for SU15210-0289

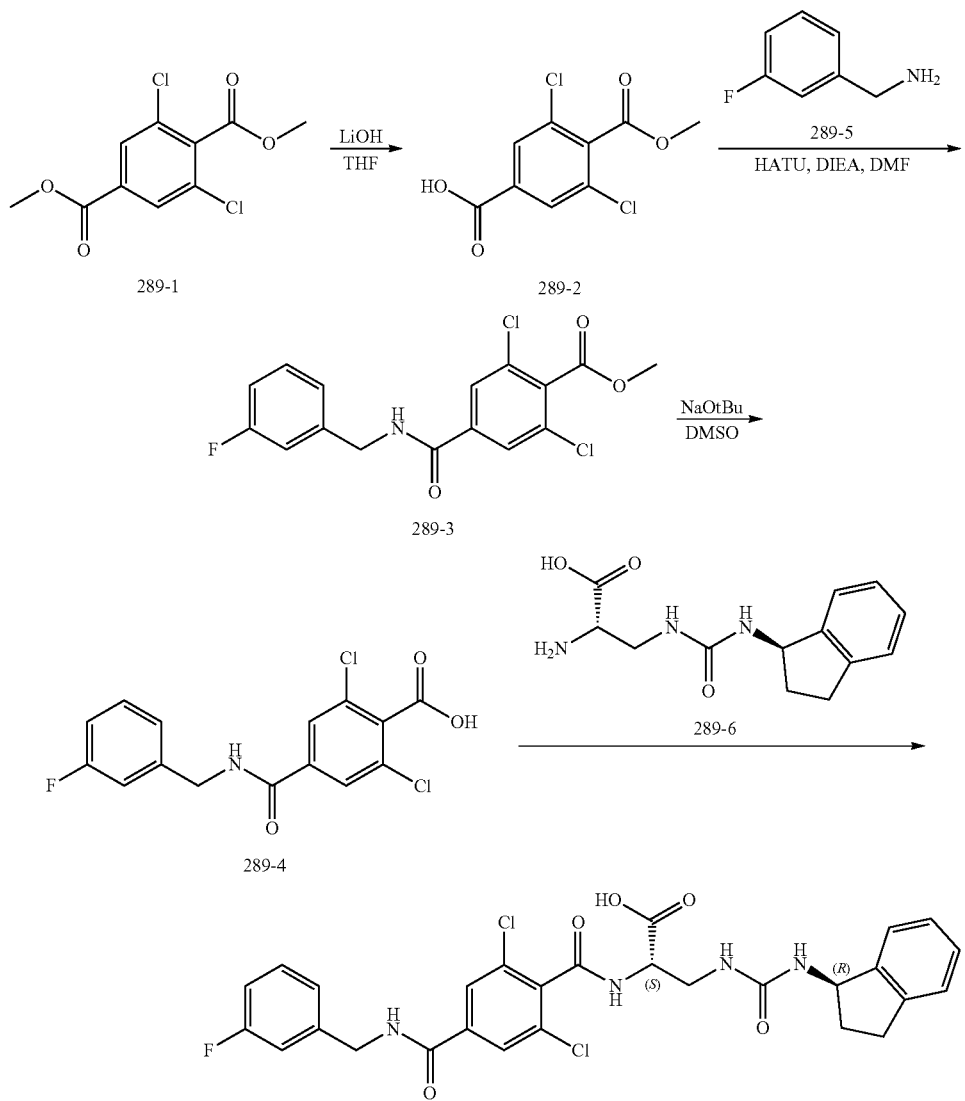

SU15210-0289

1. 3,5-dichloro-4-(methoxycarbonyl)benzoic Acid

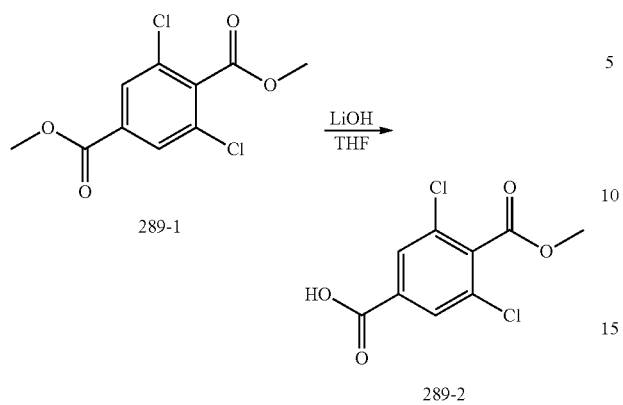

To a solution of 290-1 (90.36 mg, 343.49 μmol) in THF (5 mL) and water (2 mL), LiOH (41.13 mg, 1.72 mmol) was added and the resulting reaction mixture was stirred at rt for 1 h. Analytical TLC showed the start material was consumed, and the reaction was quenched with water, extracted with EA, concentrated to obtain product 290-2 (102 mg, 409.56 μmol, 119.23% yield) as white solid, it was used to next step without further purification.

2. methyl 2,6-dichloro-4-(3-fluorobenzylcarbamoyl)benzoate

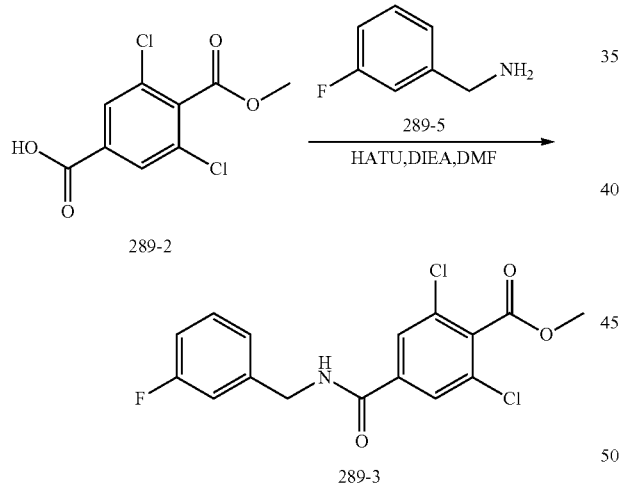

To a solution of 289-2 (100 mg, 401.53 μmol) and 289-5 (51.25 mg, 409.56 μmol, 46.72 μL) in DMF (6.69 mL), HATU (460.45 mg, 1.20 mmol) and DIPEA (259.47 mg, 2.01 mmol, 349.70 μL) were added, and the resulting reaction mixture was stirred at rt for 3 h. At which point LCMS showed target MW present, and the reaction mixture was diluted with water, extracted with EA, concentrated to provide crude product 289-3 (160 mg, 449.22 μmol, 111.88% yield) as yellow oil, this material was used to next step without further purification.

3. 2,6-dichloro-4-(3-fluorobenzylcarbamoyl)benzoic Acid

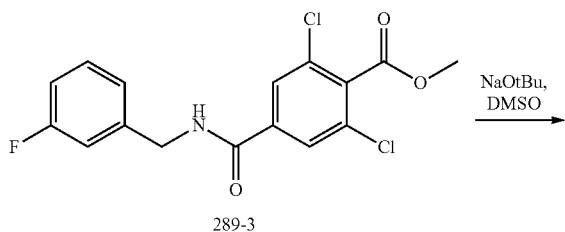

To a solution of 289-3 (160 mg, 449.22 μmol) in DMSO (7 mL) and water (2 mL), t-BuOK (504.08 mg, 4.49 mmol) was added, and the reaction mixture was stirred at 70° C. for 3 h, then it was diluted with water, the pH was adjusted to ~1, extracted with EA, dried with Na$_2$SO$_4$, concentrated under reduced pressure to afford 289-4 (105 mg, 306.88 μmol, 68.32% yield) as light yellow solid, it was used to next step without further purification.

4. (S)-2-(2,6-dichloro-4-(3-fluorobenzylcarbamoyl) benzamido)-3-(3-((R)-2,3-dihydro-1H-inden-1-yl) ureido)propanoic Acid

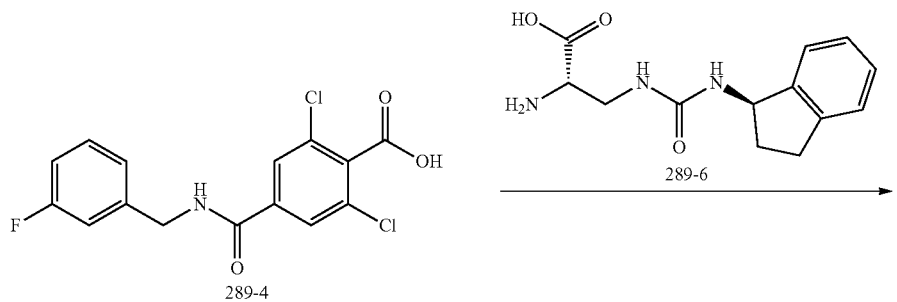

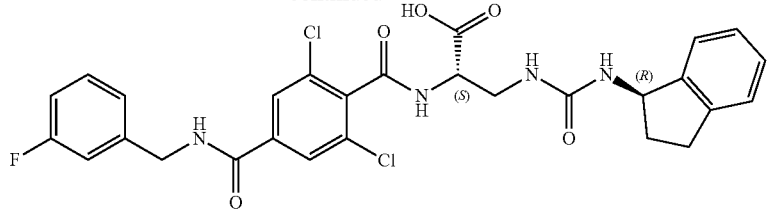

SU15210-0289

To a solution of 289-4 (20 mg, 58.45 μmol) in DMF (40.51 mL), HATU (22.34 mg, 58.45 μmol) and DIPEA (22.66 mg, 175.36 μmol, 30.54 μL) were added, and this reaction mixture was stirred at rt for 1.5 h. Then 289-6 (20 mg, 58.45 μmol) was added, and the reaction mixture was stirred at rt for 48 h. LCMS detected the target MW present, then the reaction was filtered, and the filtrate was purified by prep-HPLC to afford SU15210-0289 (3 mg, 5.11 μmol, 8.74% yield) as white powder.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 97.7%, Rt=7.931 min; MS Found: 584.7 [M−H]$^+$.

$^1$H NMR (400 MHz, DMSO) δ 9.31 (t, J=5.9 Hz, 1H), 8.70 (s, 1H), 7.96 (s, 2H), 7.48-7.31 (m, 1H), 7.31-6.98 (m, 4H), 6.63 (d, J=8.3 Hz, 1H), 5.92 (s, 1H), 5.08 (d, J=8.2 Hz, 1H), 4.43 (t, J=37.9 Hz, 3H), 3.43 (s, 2H), 2.85 (dd, J=8.6, 3.2 Hz, 1H), 2.81-2.69 (m, 1H), 2.40-2.26 (m, 1H), 1.68 (dd, J=12.5, 8.5 Hz, 1H).

SU15210-0290-01
Route for SU15210-0290-01

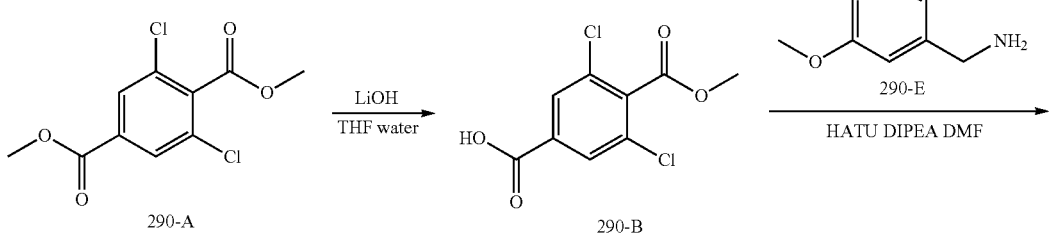

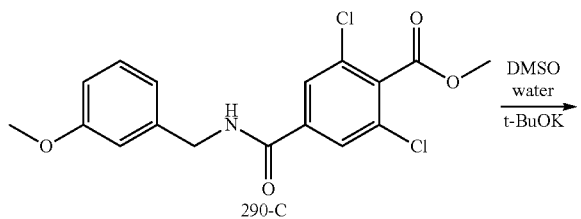

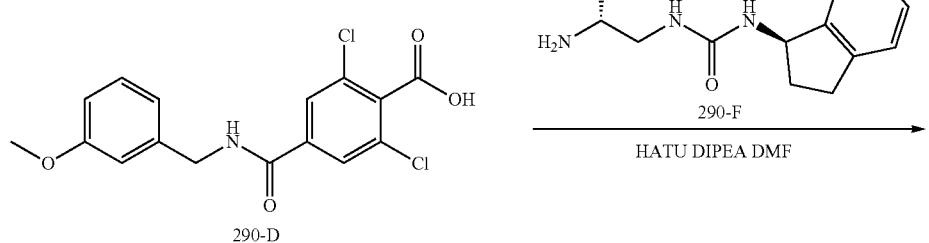

-continued

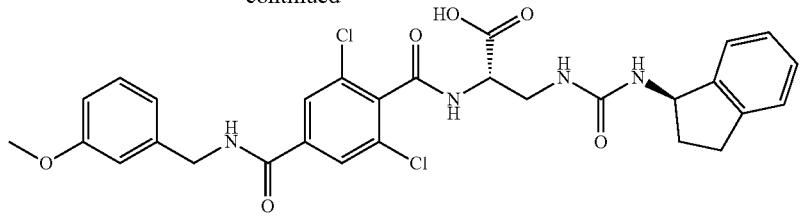

SU15210-0290-01

1. 3,5-dichloro-4-(methoxycarbonyl)benzoic Acid

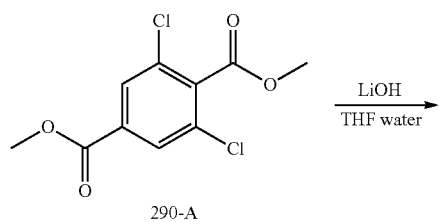

To a solution of 290-A (90.36 mg, 343.49 μmol) in THF (5 mL) and water (2 mL), LiOH (41.13 mg, 1.72 mmol) was added and the resulting reaction mixture was stirred at rt for 1 h. TLC then showed the start material was consumed, and the reaction was quenched with water, extracted with EA, concentrated to provide product 290-B (102 mg, 409.56 μmol, 119.23% yield) as white solid which was used to next step without further purification.

2. Methyl 2,6-dichloro-4-(3-methoxybenzylcarbamoyl)benzoate

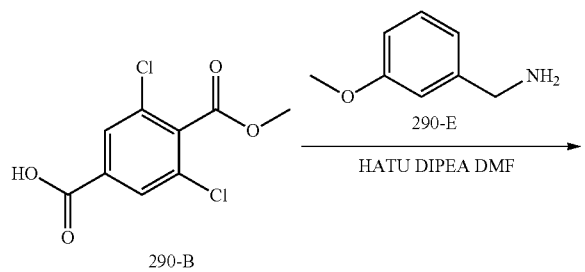

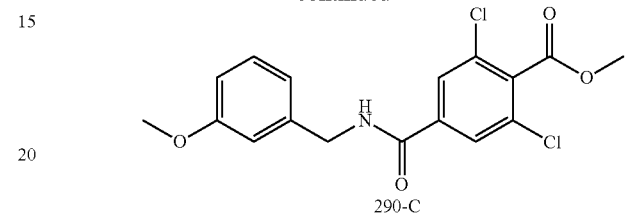

To a solution of 290-E (28.68 mg, 209.07 μmol, 26.75 μL), 290-B (50 mg, 190.06 mol) in DMF (10 mL), HATU (217.95 mg, 570.18 μmol) and DIPEA (122.82 mg, 950.30 μmol, 165.53 μL) were added, and the resulting reaction mixture was stirred at rt for 14 hr, then was quenched with water, extracted with EA, dried with $Na_2SO_4$, concentrated to provide a crude oil, which was purified by silica gel column (PE:EA=10:1) to afford 290-C (64 mg, 167.44 μmol, 88.10% yield) as white solid.

3. 2,6-dichloro-4-(3-methoxybenzylcarbamoyl)benzoic Acid

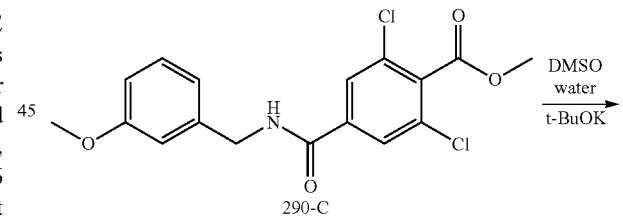

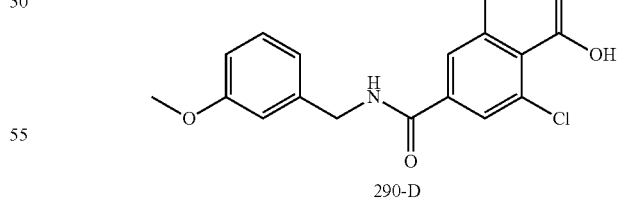

To a solution of 290-C (70 mg, 183.13 μmol) in DMSO (5 mL) and Water (1 mL), t-BuOK (61.65 mg, 549.40 μmol) was added, and the resulting reaction mixture was stirred at 70° C. for 3 hr, then pH was adjusted to ~1 with aq. HCl, extracted with EA, dried with $Na_2SO_4$, concentrated to provide product 290-D (60 mg, 169.40 μmol, 92.50% yield) as yellow solid. This material was used to next step without further purification.

4. (S)-2-(2,6-dichloro-4-(3-methoxybenzylcarbamoyl)benzamido)-3-(3-((R)-2,3-dihydro-1H-inden-1-yl)ureido)propanoic Acid

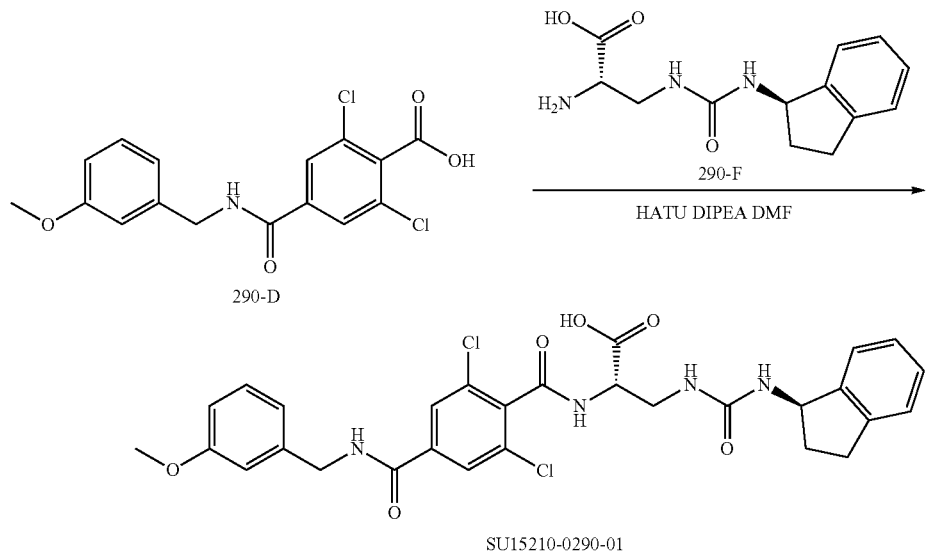

290-D

SU15210-0290-01

To a solution of 290-D (25 mg, 70.58 μmol) in DMF (4.99 mL), HATU (26.98 mg, 70.58 μmol) and DIPEA (9.12 mg, 70.58 μmol, 12.29 μL) were added, and the resulting reaction mixture was stirred at rt for 1.5 h. Then 290-F (22.47 mg) was added, and the reaction was stirred at rt overnight. LCMS detected the target Mass, then the reaction mixture was filtered and the filtrate was then collected. This material was purified by prep-HPLC to afford SU15210-0290-01 (6 mg, 9.98 μmol, 14.13% yield) as white solid.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 99.8%, Rt=7.903 min; MS Found: 598.7 $[M+H]^+$.

$^1$H NMR (400 MHz, DMSO) δ 9.26 (t, J=5.9 Hz, 1H), 8.60 (s, 1H), 7.95 (s, 2H), 7.20 (dddd, J=14.0, 11.3, 8.3, 4.6 Hz, 5H), 6.96-6.75 (m, 3H), 6.65 (d, J=8.3 Hz, 1H), 5.93 (s, 1H), 5.08 (q, J=8.0 Hz, 1H), 4.45 (d, J=5.8 Hz, 2H), 4.28 (d, J=6.4 Hz, 1H), 3.74 (s, 3H), 3.43 (s, 2H), 2.87 (ddd, J=15.6, 8.6, 3.0 Hz, 1H), 2.81-2.65 (m, 1H), 2.36 (dtd, J=10.8, 7.6, 3.3 Hz, 1H), 1.75-1.58 (m, 1H).

SU15210-0291

Route for SU15210-0291

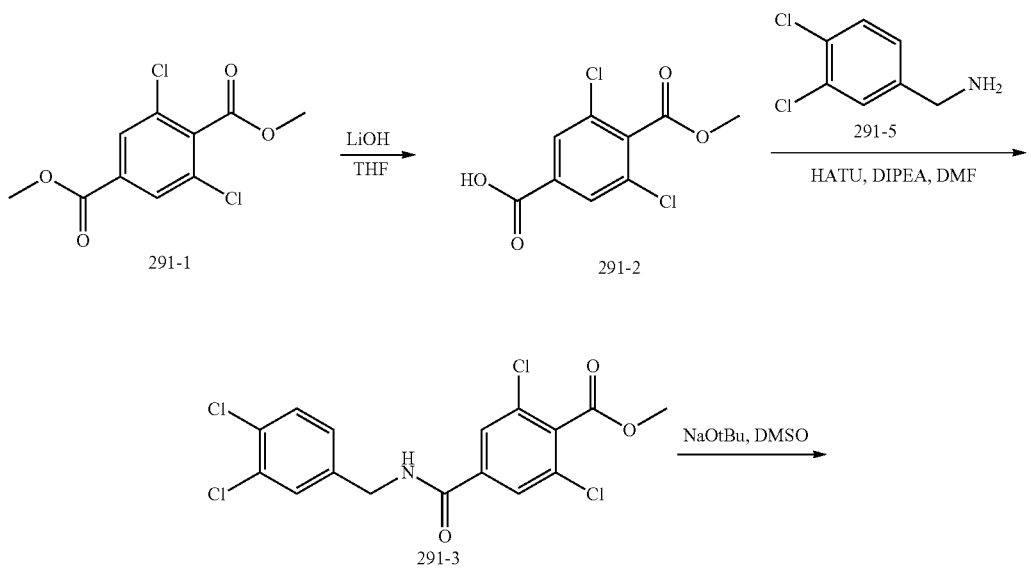

-continued

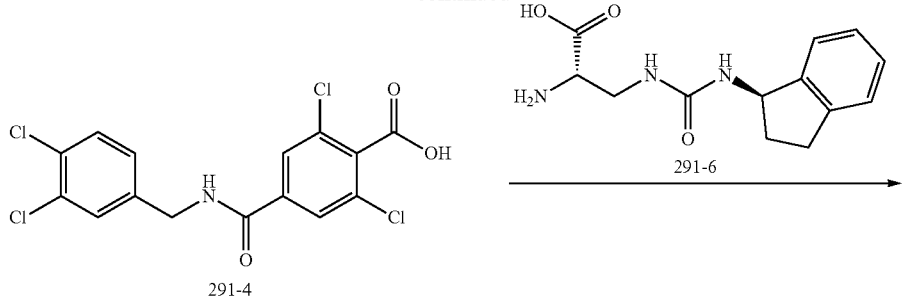

1. 3,5-dichloro-4-(methoxycarbonyl)benzoic Acid

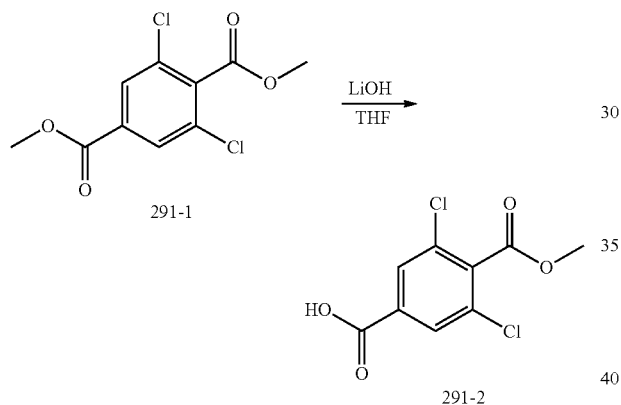

To a solution of 291-1 (80 mg) in THF (5 mL) and Water (2 mL), LiOH (41.13 mg, 1.72 mmol) was added, and the resulting reaction mixture was stirred at rt for 1 h. Analytical TLC showed the start material was consumed, and the reaction was quenched with water, extracted with EA, concentrated to provide product 291-2 (120 mg) as white solid, it was used to next step without further purification.

2. Methyl 2,6-dichloro-4-(3,4-dichlorobenzylcarbamoyl)benzoate

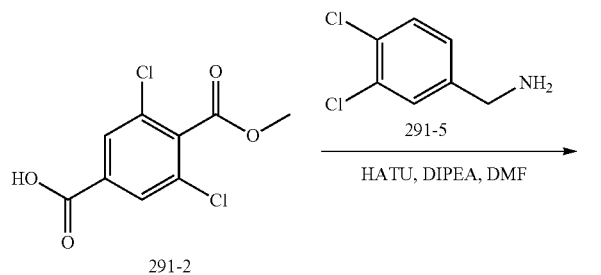

-continued

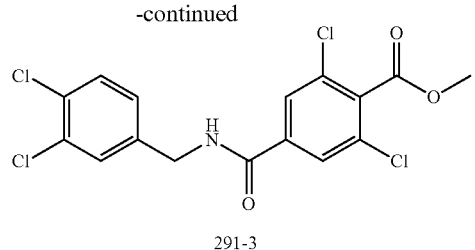

To a solution of 291-2 (80 mg) and 291-5 (101 mg) in DMF (6.69 mL), HATU (460.45 mg, 1.20 mmol) and DIPEA (259.47 mg, 2.01 mmol, 349.70 μL) were added, and the resulting reaction mixture was stirred at rt for 3 h. LCMS showed target Mass present, and the reaction mixture was diluted with water, extracted with EA, concentrated to provide crude product, which was purified by preparatory TLC to afford 291-3 (110 mg) as yellow oil.

3. 2,6-dichloro-4-(3,4-dichlorobenzylcarbamoyl)benzoic Acid

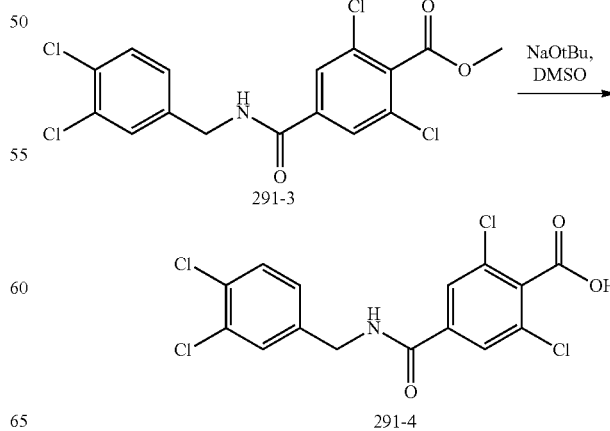

To a solution of 291-3 (100 mg, 449.22 mol) in DMSO (7 mL) and water (2 mL), t-BuOK (504.08 mg, 4.49 mmol) was added, and the resulting reaction mixture was stirred at 70° C. for 3 h, then diluted with water, the pH was adjusted to ~1, extracted with EA, dried with $Na_2SO_4$, concentrated to afford 291-4 (90 mg) as light yellow solid, it was used to next step without further purification.

4. (S)-2-(2,6-dichloro-4-(3,4-dichlorobenzylcarbamoyl)benzamido)-3-(3-((R)-2,3-dihydro-1H-inden-1-yl)ureido)propanoic Acid

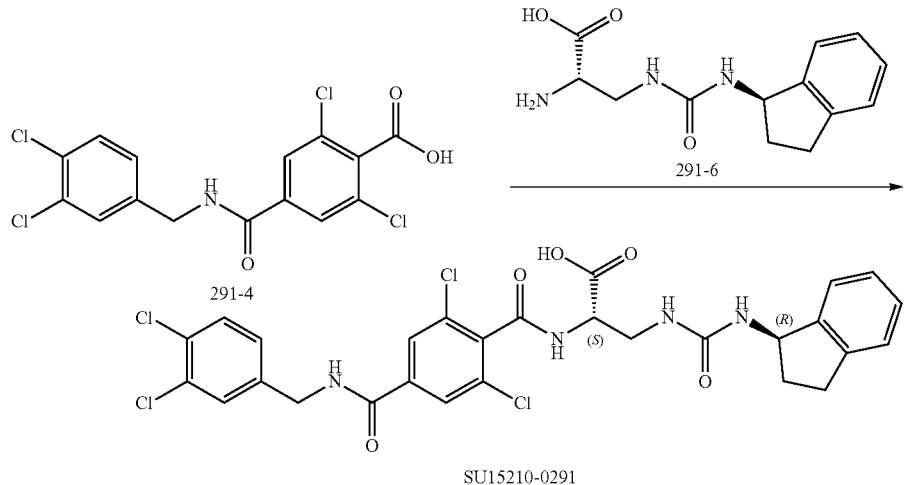

To a solution of 291-4 (25 mg) in DMF (40.51 mL), HATU (22.34 mg, 58.4 μmol) and DIPEA (22.66 mg, 175.36 μmol, 30.54 μL) were added, and the resulting reaction mixture was stirred at rt for 1.5 h. Then 291-6 (20 mg) was added, and the reaction was stirred at rt for 48 h. LCMS detected the target Mass, then the reaction mixture was filtered, and the filtrate was collected and purified by prep-HPLC to afford SU15210-0291 (6 mg) as white solid.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 97.7%, Rt=7.931 min; MS Found: 584.7 [M−H]$^+$.

$^1$H NMR (400 MHz, DMSO) δ 9.39 (t, J=5.8 Hz, 1H), 8.71 (s, 1H), 8.02 (d, J=10.9 Hz, 2H), 7.66 (d, J=8.3 Hz, 2H), 7.51-7.13 (m, 4H), 6.71 (d, J=8.2 Hz, 1H), 5.99 (s, 1H), 5.14 (dd, J=16.1, 8.2 Hz, 1H), 4.54 (d, J=5.7 Hz, 2H), 4.37 (d, J=6.3 Hz, 1H), 3.50 (s, 3H), 2.93 (ddd, J=15.5, 8.6, 3.0 Hz, 1H), 2.79 (dt, J=28.8, 10.7 Hz, 1H), 2.47-2.34 (m, 1H), 1.74 (dq, J=12.4, 8.7 Hz, 1H).

SU15210-0292

Route for SU15210-0292

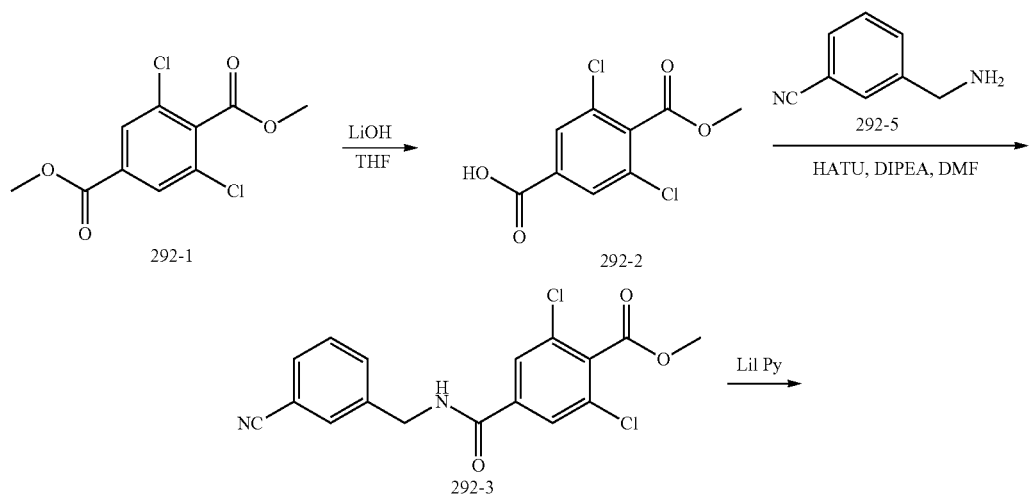

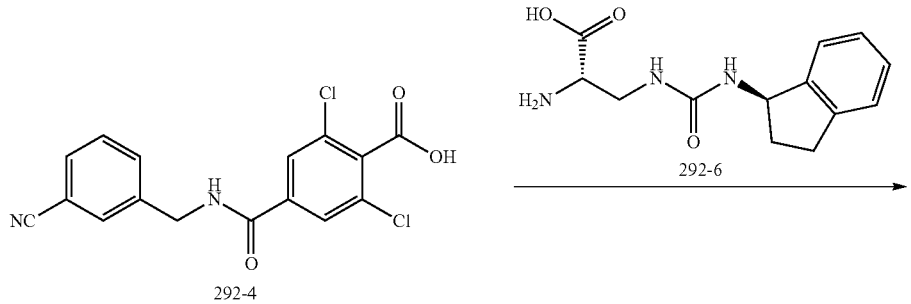

1. 3,5-dichloro-4-(methoxycarbonyl)benzoic Acid

2. Methyl 2,6-dichloro-4-(3-cyanobenzylcarbamoyl)benzoate

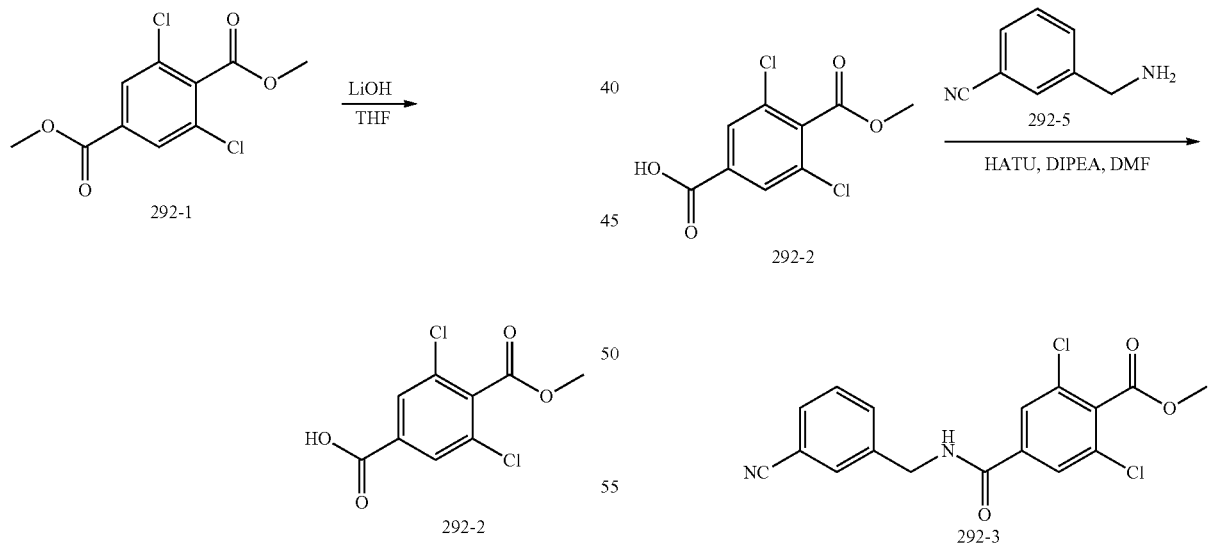

To a solution of 292-1 (80 mg) in THF (5 mL) and Water (2 mL), LiOH (41.13 mg, 1.72 mmol) was added, and the resulting reaction mixture was stirred at rt for 1 h. Analytical TLC showed the start material was consumed, and the reaction was quenched with water, extracted with EA, concentrated to provide product 292-2 (120 mg) as white solid which was used to next step without further purification.

To a solution of 292-2 (100 mg) and 292-5 (101 mg) in DMF (6.69 mL), HATU (460.45 mg, 1.20 mmol) and DIPEA (259.47 mg, 2.01 mmol, 349.70 μL) were added, and the resulting reaction mixture was stirred at rt for 3 h. Analytical LCMS showed target Mass, then the reaction was diluted with water, extracted with EA, concentrated to provide crude product, which was purified by preparatory TLC to afford 293-3 (90 mg) as yellow oil.

3. 2,6-dichloro-4-(3-cyanobenzylcarbamoyl)benzoic Acid

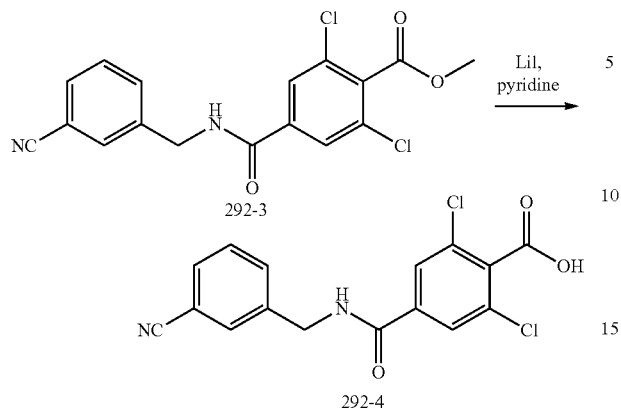

To a solution of 292-3 (90 mg) in pyridine (5 mL), LiI (67 mg) was added, and the resulting reaction mixture was stirred at rt overnight. Then the reaction was diluted with water, the pH was adjusted to ~1, extracted with EA, dried with $Na_2SO_4$, concentrated under reduced pressure to afford 292-4 (76 mg) as light yellow solid which was used to next step without further purification.

4. (S)-2-(2,6-dichloro-4-(3-cyanobenzylcarbamoyl)benzamido)-3-(3-((R)-2,3-dihydro-1H-inden-1-yl)ureido)propanoic Acid

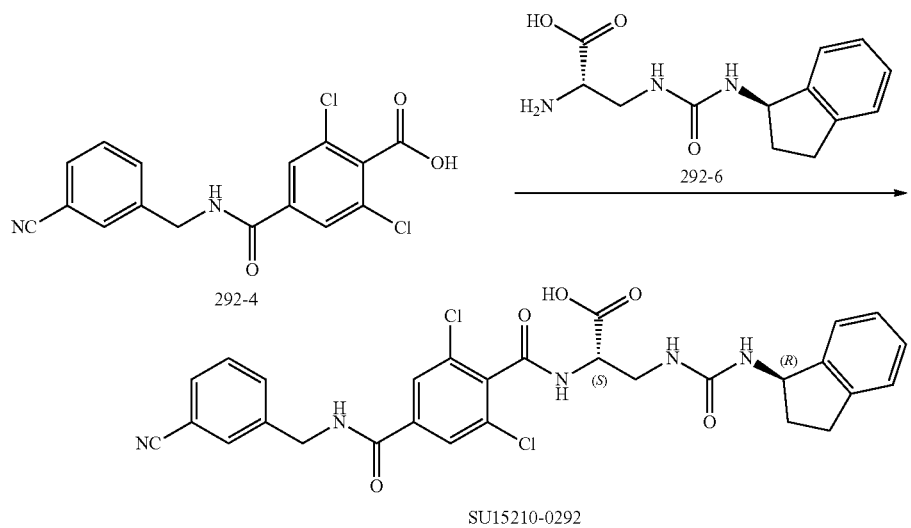

To a solution of 292-4 (25 mg) in DMF (40.51 mL), HATU (22.34 mg, 58.45 µmol) and DIPEA (22.66 mg, 175.36 µmol, 30.54 µL) were added, and the resulting reaction mixture was stirred at rt for 1.5 h. Then 292-6 (20 mg) was added, and the reaction was stirred at rt for 48 h. LCMS detected the target Mass, pH was adjusted to ~2, and the resulting mixture was extracted with EA, dried with $Na_2SO_4$, concentrated to provide the crude oil. This material was purified by prep-HPLC to afford SU15210-0292 (10 mg) as white solid.

HPLC (Agilent LCMS 1200-6120, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 99.0%, Rt=7.818 min; MS Found: 593.7 $[M+H]^+$.

$^1$H NMR (400 MHz, DMSO) δ 9.35 (t, J=5.5 Hz, 1H), 8.56 (s, 1H), 8.16-7.41 (m, 5H), 7.19 (dd, J=17.7, 5.3 Hz, 3H), 6.67 (d, J=7.9 Hz, 1H), 5.94 (s, 1H), 5.08 (d, J=7.8 Hz, 1H), 4.41 (dd, J=103.7, 5.6 Hz, 3H), 3.43 (s, 4H), 2.98-2.65 (m, 2H), 2.42-2.13 (m, 1H), 1.81-1.54 (m, 1H).

SU15210-0293
Route for SU15210-0293

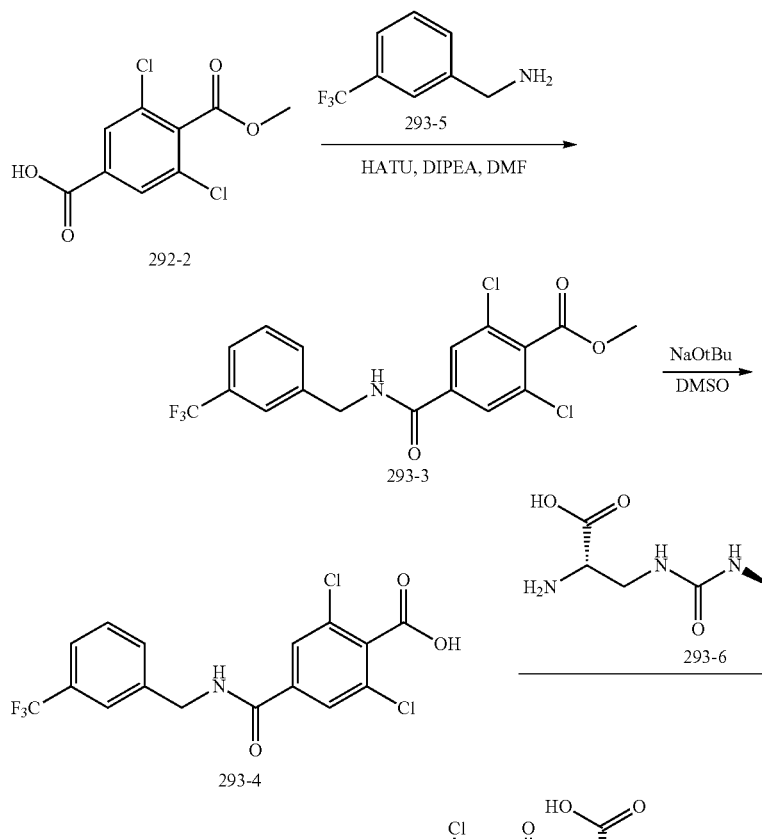

1. Methyl 2,6-dichloro-4-(3-(trifluoromethyl)benzyl-carbamoyl)benzoate

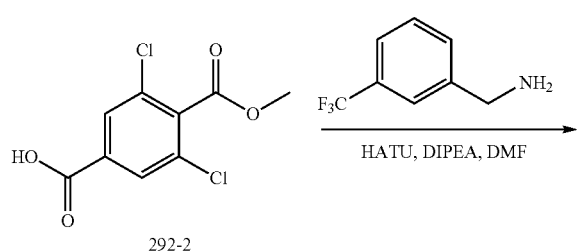

To a solution of 289-2 (80 mg) and 293-5 (101 mg) in DMF (6.69 mL), HATU (460.45 mg, 1.20 mmol) and DIPEA (259.47 mg, 2.01 mmol, 349.70 μL) were added, and the resulting reaction mixture was stirred at rt for 3 h. Then LCMS showed target Mass, and the reaction was diluted with water, extracted with EA, concentrated to provide the crude product which was purified by preparatory TLC to afford 293-3 (120 mg) as yellow oil.

2. 2,6-dichloro-4-(3-(trifluoromethyl)benzylcarbam-oyl)benzoic Acid

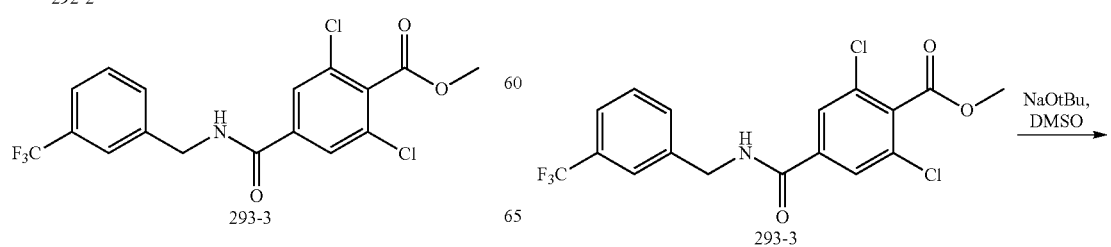

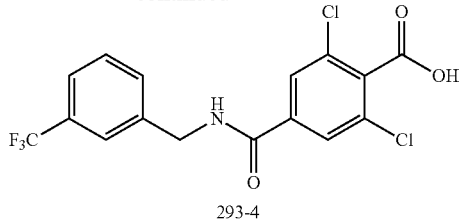

293-4

To a solution of 293-3 (120 mg, 449.22 μmol) in DMSO (7 mL) and water (2 mL), t-BuOK (504.08 mg, 4.49 mmol) was added, and the resulting reaction mixture was stirred at 70° C. for 3 h. Then it was diluted with water, pH was adjusted to ~1, extracted with EA, dried with Na$_2$SO$_4$, concentrated to afford 293-4 (100 mg) as light yellow solid which was used to next step without further purification.

3. (S)-2-(2,6-dichloro-4-(3-(trifluoromethyl)benzyl-carbamoyl)benzamido)-3-(3-((R)-2,3-dihydro-1H-inden-1-yl)ureido)propanoic Acid

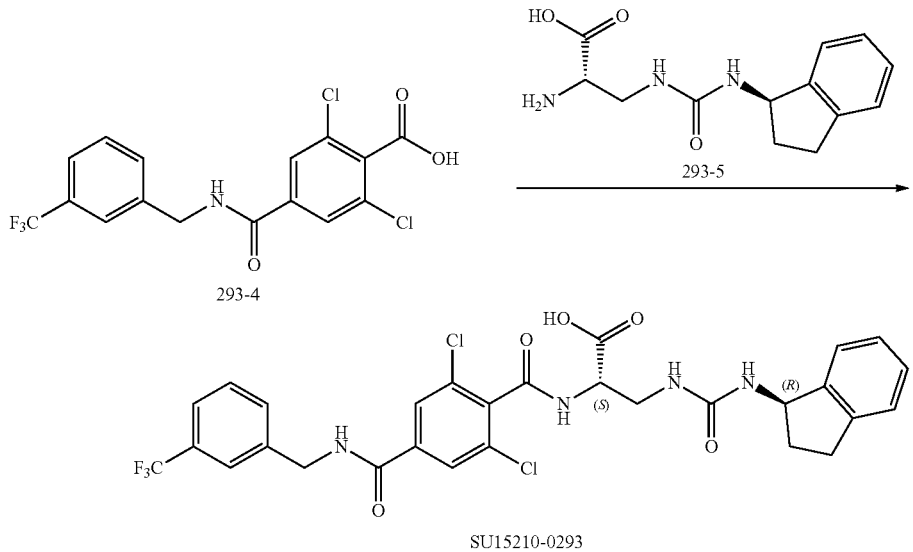

SU15210-0293

To a solution of 293-4 (25 mg) in DMF (40.51 mL), HATU (22.34 mg, 58.45 mol) and DIPEA (22.66 mg, 175.36 μmol, 30.54 μL) were added, and the resulting reaction mixture was stirred at rt for 1.5 h, then 293-6 (20 mg) was added, and the reaction was stirred at rt for 48 h. LCMS detected the target Mass, then it was filtered, and the filtrate was purified by prep-HPLC to afford SU15210-0293 (4 mg) as white solid.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 97.7%, Rt=7.931 min; MS Found: 584.7 [M−H]$^+$.

$^1$H NMR (400 MHz, DMSO) δ 9.31 (t, J=5.9 Hz, 1H), 8.70 (s, 1H), 7.96 (s, 2H), 7.48-7.31 (m, 1H), 7.31-6.98 (m, 4H), 6.63 (d, J=8.3 Hz, 1H), 5.92 (s, 1H), 5.08 (d, J=8.2 Hz, 1H), 4.43 (t, J=37.9 Hz, 3H), 3.43 (s, 2H), 2.85 (dd, J=8.6, 3.2 Hz, 1H), 2.81-2.69 (m, 1H), 2.40-2.26 (m, 1H), 1.68 (dd, J=12.5, 8.5 Hz, 1H).

SU15210-0294

Route for SU15210-0294

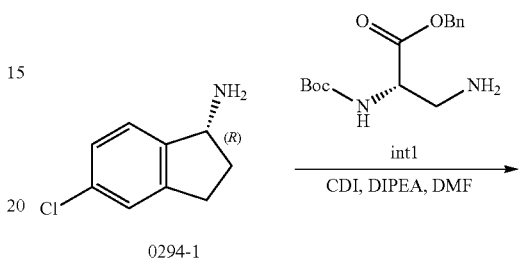

0294-1

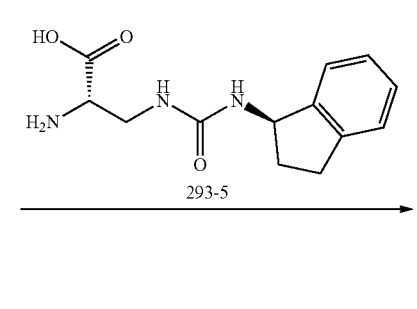

0294-2

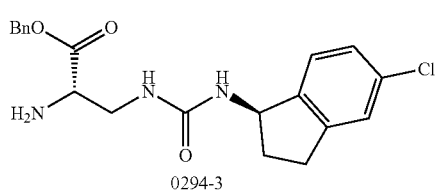

0294-3

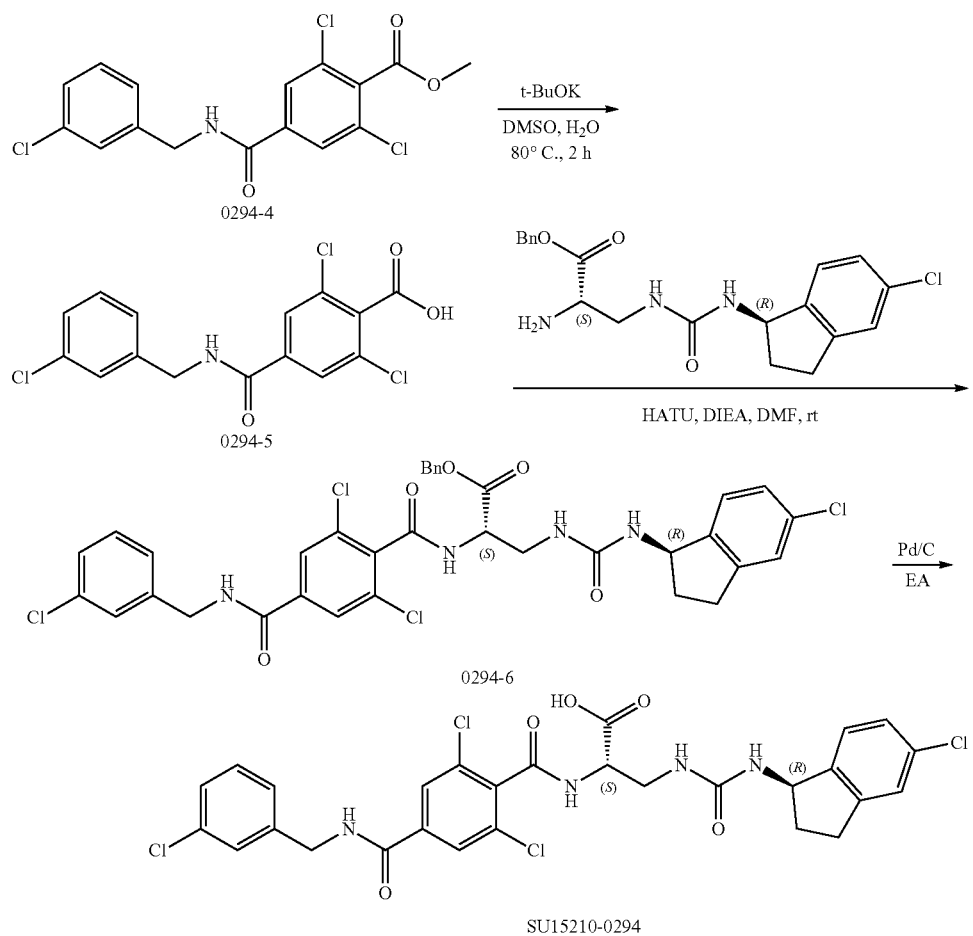

1. Synthesis of(S)-benzyl 2-(tert-butoxycarbonylamino)-3-(3-((R)-5-chloro-2,3-dihydro-1H-inden-1-yl)ureido)propanoate (0294-2)

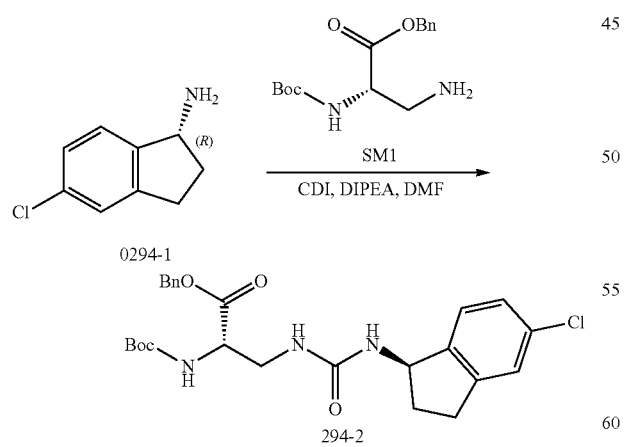

To a solution of (R)-5-chloro-2,3-dihydro-1H-inden-1-amine; hydrochloride (70 mg, 343.0 umol) in DMF (3 mL) was added CDI (66.7 mg, 411.6 umol) and the reaction stirred at rt for 2 hr. Then, DIPEA (133.0 mg, 1.03 mmol) and (S)-benzyl-3-amino-2-(tert-butoxycarbonyl amino)propanoate (101.0 mg, 343.0 umol) were added and the resulting reaction mixture stirred at rt for 16 hr. Then this mixture was quenched with H₂O (100 mL) and extracted with EA (100 mL), the organic layer was washed with brine for 3 times. Following concentration under reduced pressure this material purified by silica gel column (PE:EA=5:1) to obtain 0294-2 (70 mg, 143.5 umol, 41.82% yield) as a light yellow solid.

2. (S)-benzyl 2-amino-3-(3-((R)-5-chloro-2,3-dihydro-1H-inden-1-yl)ureido) propanoate (0294-3)

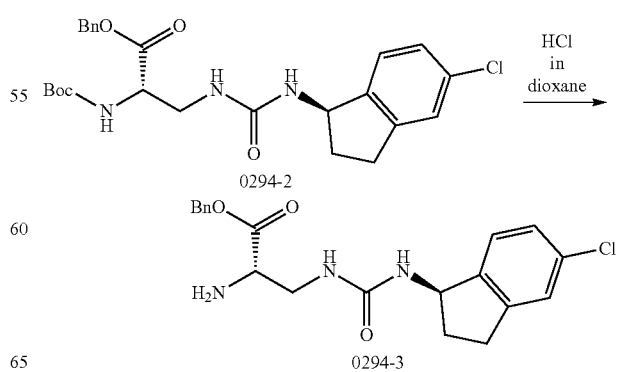

To a solution of obtained 0294-2 (70 mg, 143.45 μmol) in HCl/dioxane (5 mL) was stirred at rt for 2 hr. The reaction mixture was then concentrated under reduced pressure to obtain 0294-3 (55 mg, 141.80 μmol, 98.85% yield) as a light yellow solid.

3. The synthesis of 2,6-dichloro-4-(3-chlorobenzylcarbamoyl)benzoic Acid (0185-3)

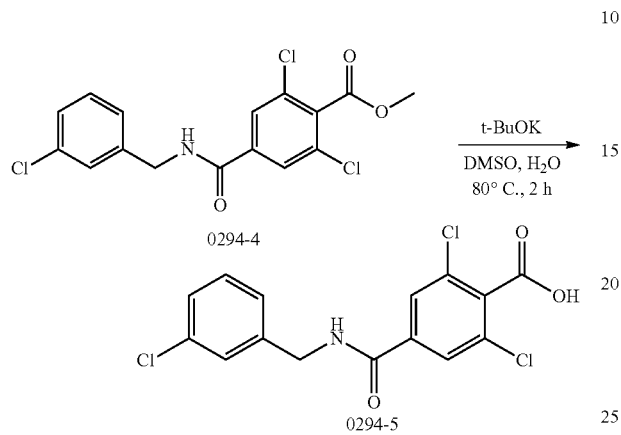

To a solution of compound 0294-4 (300 mg, 805.09 μmol) in DMSO (5 mL) and H₂O (1 mL) was added Potassium t-Butoxide (180.68 mg, 1.61 mmol). Then the mixture was stirred at 80° C. for 2 hr, the pH was adjusted to ~3 with 1N HCl solution and extracted with EA (150 mL) and water (150 mL). Concentration under reduced pressure gave product 0294-5 (270 mg, 752.92 μmol, 93.52% yield) which was used for next step without further purification.

4. The Synthesis of (S)-benzyl 3-(3-((R)-5-chloro-2,3-dihydro-1H-inden-1-yl) ureido)-2-(2,6-dichloro-4-(3-chlorobenzylcarbamoyl)benzamido)propanoate (0294-6)

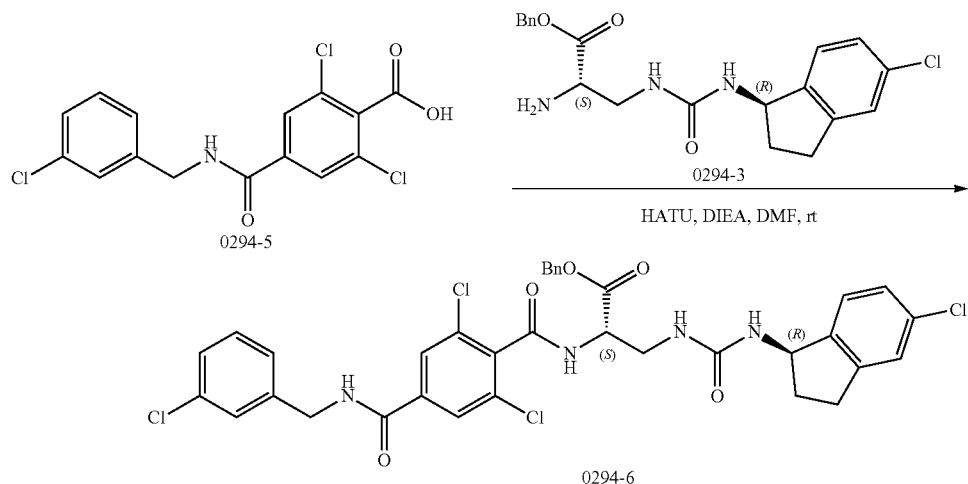

To a solution of compound 0294-5 (51 mg, 142.22 μmol) and 0294-3 (55.16 mg, 142.22 μmol) in DMF (2 mL) was added DIEA (55.14 mg, 426.66 μmol) and HATU (81.11 mg, 213.33 μmol) and the mixture was stirred at room temperature for 16 h. This mixture was then quenched with water (50 mL), extracted with EA (50 mL). The organic layer was washed with brine (50 mL×3), and the residue was dried over anhydrous sodium sulfate and concentrated on a rotary evaporator. The crude was purified by silica gel column (DCM:MeOH=10:1) to obtain 0294-6 (60 mg, 82.37 μmol, 57.92% yield) as a light yellow solid.

5. The Synthesis of (S)-3-(3-((R)-5-chloro-2,3-dihydro-1H-inden-1-yl)ureido)-2-(2,6-dichloro-4-(3-chlorobenzylcarbamoyl)benzamido)propanoic Acid (SU15210-0294)

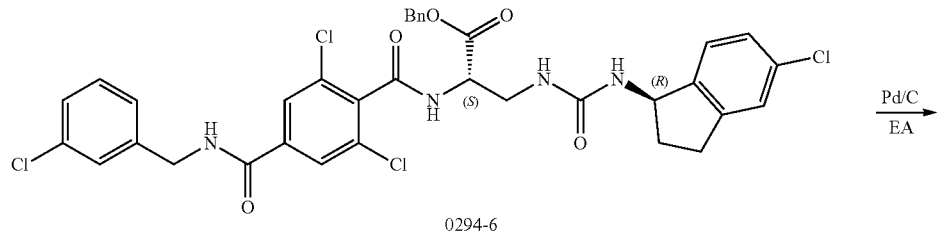

0294-6

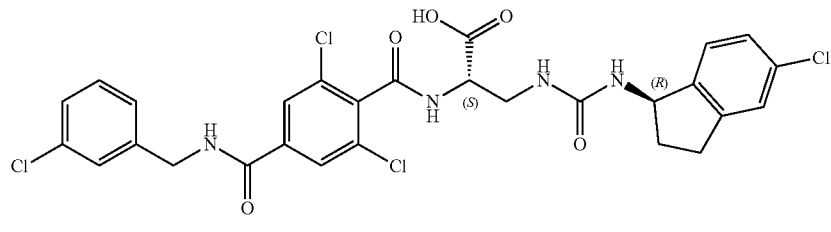

SU15210-0294

To a solution of compound 0294-6 (40 mg, 54.91 μmol) in EA (20 mL) was added 10% palladium on activated carbon (100 mg). The mixture was allowed to stir at rt for 2 h under hydrogen at 1 atmosphere. The mixture was filtered and concentrated under reduced pressure. The crude was purified by pre-HPLC to give product SU15210-0294 (7.03 mg, 11.01 μmol, 20.06% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 95.75%, Rt=2.089 min; MS Found: 638.5 $[M+H]^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 95.02%, Rt=9.946 min.

$^1$H NMR (400 MHz, DMSO) δ 9.31 (t, J=5.9 Hz, 1H), 8.62 (s, 1H), 7.95 (s, 2H), 7.38 (dd, J=9.1, 6.0 Hz, 2H), 7.34-7.26 (m, 3H), 7.23-7.16 (m, 2H), 6.69 (d, J=8.2 Hz, 1H), 5.95 (s, 1H), 5.05 (q, J=8.1 Hz, 1H), 4.48 (d, J=5.8 Hz, 2H), 4.27 (s, 1H), 2.96-2.80 (m, 3H), 2.75 (dt, J=16.7, 8.4 Hz, 1H), 2.37 (ddd, J=12.5, 7.8, 4.7 Hz, 1H), 2.00 (dd, J=14.7, 6.9 Hz, 1H), 1.71 (tt, J=17.5, 8.9 Hz, 1H).

SU15210-0301

Route for SU15210-0301

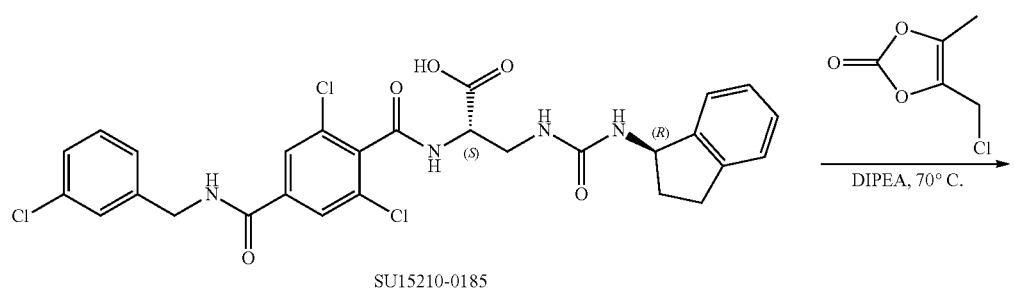

SU15210-0185

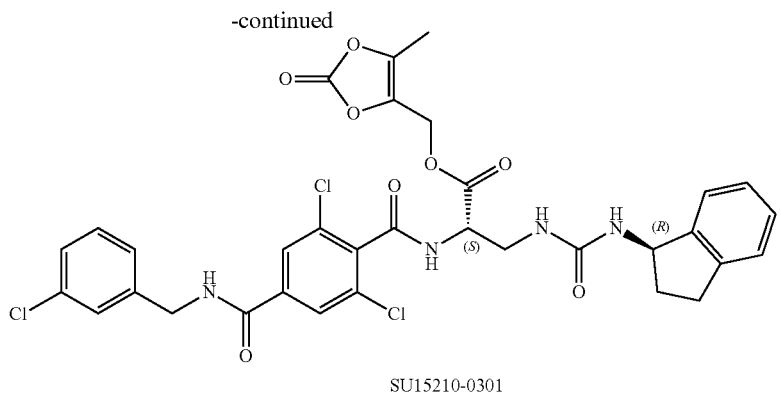

SU15210-0301

1. The Synthesis of (S)-(5-methyl-2-oxo-1,3-dioxol-4-yl)methyl 2-(2,6-dichloro-4-(3-chlorobenzylcarbamoyl)benzamido)-3-(3-((R)-2,3-dihydro-1H-inden-1-yl)ureido)propanoate (SU15210-0301)

To a mixture of SU15210-0185 (25 mg, 41.40 μmol) in DMF (4 mL) was added 4-(chloromethyl)-5-methyl-1,3-dioxol-2-one (30.75 mg, 206.99 μmol) and DIPEA (26.75 mg, 206.99 μmol, 36.05 μL). Then the mixture was stirred at 70° C. for 3 hr before the target Mass was detected by LCMS. The mixture was then concentrated under reduced pressure and purified by Prep-HPLC to give SU15210-0185 (13.18 mg, 18.41 μmol, 44.47% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 92.09%, Rt=2.634 min; MS Found: 716.5 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 92.62%, Rt=9.985 min.

$^1$H NMR (400 MHz, MeOD) δ 7.90 (s, 2H), 7.41-7.07 (m, 8H), 5.16 (t, J=7.5 Hz, 1H), 5.03 (s, 2H), 4.79 (dd, J=7.1, 5.7 Hz, 2H), 4.53 (s, 2H), 3.67 (ddd, J=21.4, 14.1, 6.4 Hz, 2H), 2.93 (ddd, J=15.7, 8.6, 3.3 Hz, 1H), 2.87-2.72 (m, 1H), 2.57-2.39 (m, 1H), 2.18 (s, 3H), 1.75 (dq, J=12.6, 8.6 Hz, 1H).

SU15210-0302
Route for SU15210-0302

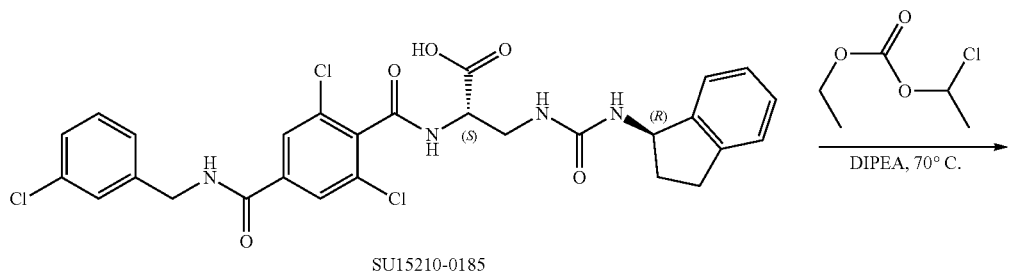

SU15210-0185

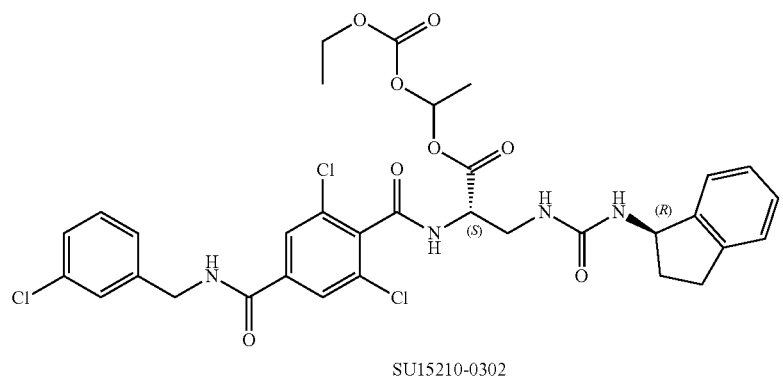

SU15210-0302

1. The Synthesis of (2S)-1-(ethoxycarbonyloxy) ethyl 2-(2,6-dichloro-4-(3-chlorobenzylcarbamoyl) benzamido)-3-(3-((R)-2,3-dihydro-1H-inden-1-yl) ureido)propanoate (SU15210-0302)

To a mixture of SU15210-0185 (25 mg, 41.40 μmol) in DMF (4 mL) was added 1-chloroethyl ethyl carbonate (31.58 mg, 206.99 μmol) and DIPEA (26.75 mg, 206.99 μmol, 36.05 L). Then the mixture was stirred at 70° C. for 3 hr before the desired Mass was detected by LCMS. The mixture was then concentrated under reduced pressure and purified by Prep-HPLC to give SU15210-0185 (11.06 mg, 15.36 μmol, 37.11% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=2.843 min; MS Found: 720.5 $[M+H]^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 97.58%, Rt=10.260 min.

$^1$H NMR (400 MHz, MeOD) δ 7.90 (s, 2H), 7.37-7.14 (m, 8H), 6.86-6.70 (m, 1H), 5.17 (t, J=7.6 Hz, 1H), 4.81-4.77 (m, 1H), 4.54 (s, 2H), 4.25-4.07 (m, 2H), 3.66 (dddd, J=30.8, 22.0, 14.2, 6.5 Hz, 2H), 2.94 (ddd, J=15.7, 8.7, 3.4 Hz, 1H), 2.87-2.72 (m, 1H), 2.57-2.38 (m, 1H), 1.76 (dq, J=12.6, 8.4 Hz, 1H), 1.54 (dd, J=5.4, 0.7 Hz, 3H), 1.27 (td, J=7.1, 4.6 Hz, 3H).

Example 5: Additional Biological Data

TABLE 2

| Biological data. | |
|---|---|
| Compound | α2β1 Cell Adhesion $IC_{50}$ |
| SU15210-0242-01 | A |
| SU15210-0243-01 | D |
| SU15210-0244-01 | D |
| SU15210-0245-01 | D |
| SU15210-0251 | C |
| SU15210-0265 | D |
| SU15210-0270-01 | B |
| SU15210-0280 | C |
| SU15210-0289 | A |
| SU15210-0290-01 | A |
| SU15210-0291 | A |
| SU15210-0292 | A |
| SU15210-0293 | A |
| SU15210-0294 | B |

A: <0.5 μM,
B: 0.5-1 μM,
C: 1-5 μM,
D: >5 μM.

REFERENCES

1. Holgate S T. J Allergy Clin Immunol 2011. 128 (495-505).
2. Brightling C E, Gupta S, Gonem S, Siddiqui S. Clin Exp Allergy 2012. 42 (638-649).
3. Benayoun L, Druilhe A, Dombret M C, Aubier M, Pretolani M. Am J Respir Crit Care Med 2003. 167 (1360-1368).
4. Chiba Y, Nakazawa S, Todoroki M, Shinozaki K, Sakai H, Misawa M. Am J Respir Cell Mol Biol 2009. 40 (159-167).
5. Berger P, Girodet P O, Begueret H, et al. FASEB J 2003. 17 (2139-2141).
6. Kudo M, Melton A, Chen C, Engler M, Huang K, Rin X, Wang Y, Bernstein X, Li J, Atabai K, Huang X, Sheppard D. Nat. Med 2012. 18 (547-554).

What is claimed is:

1. A compound, or a pharmaceutically acceptable salt thereof or a prodrug thereof, having the formula:

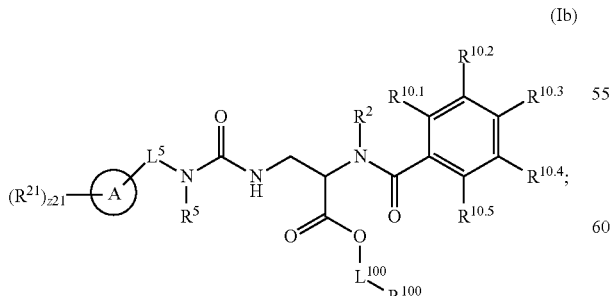

(Ib)

wherein
Ring A is cycloalkyl, heterocycloalkyl, aryl, or heteroaryl;
$R^2$ is hydrogen or substituted or unsubstituted alkyl;
$R^5$ is hydrogen or unsubstituted $C_1$-$C_3$ alkyl;
$L^5$ is a bond or unsubstituted $C_1$-$C_3$ alkylene;
$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $-C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $C(O)R^{10.2C}$, $-C(O)OR^{10.2C}$, $C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, $-L^{10.2}-R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $-C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$, $-L^{10.3}-R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$, $-L^{10.4}-R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $-NR^{10.5A}C(O)OR^{10.5C}$, $-NR^{10.5A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $SR^{21D}$, $-R^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, $-C(S)-$, substituted or unsubstituted alkylene, or substituted or unsubstituted heteroalkylene;

$R^{22}$, $R^{23}$, and $R^{24}$ are independently substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, $-CX^{100}_3$, $-CHX^{100}_2$, $-CH_2X^{100}$, $-OCX^{100}_3$, $-OCH_2X^{100}$, $-OCHX^{100}_2$, $-CN$, $-SO_{n100}R^{100D}$, $-SO_{v100}NR^{100A}R^{100B}$, $-NHC(O)NR^{100A}R^{100B}$, $-N(O)_{m100}$, $-NR^{100A}R^{100B}$, $-C(O)R^{100C}$, $-C(O)OR^{100C}$, $-C(O)NR^{100A}R^{100B}$, $-OR^{100D}$, $-SR^{100D}$, $-NR^{100A}SO_2R^{100D}$, $-NR^{100A}C(O)R^{100C}$, $-NR^{100A}C(O)OR^{100C}$, $-NR^{100A}OR^{100C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.4A}$, $R^{10.4B}$, $R^{10.4C}$, $R^{10.4D}$, $R^{10.5A}$, $R^{10.5B}$, $R^{10.5C}$, $R^{10.5D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl;

$R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, n21, and n100 are independently an integer from 0 to 4;

m10.1, m10.2, m10.3, m10.4, m10.5, m21, m100, v10.1, v10.2, v10.3, v10.4, v10.5, v21, and v100 are independently 1 or 2;

$X^{10.1}$, $X^{10.2}$, $X^{10.3}$, $X^{10.4}$, $X^{10.5}$, $X^{21}$, and $X^{100}$ are independently —F, —Cl, —Br, or —I;

z21 is an integer from 0 to 11;

wherein at least one of $R^{10.1}$ or $R^{10.5}$ is not hydrogen; and wherein at least one of $R^{10.2}$, $R^{10.3}$, or $R^{10.4}$ is -$L^{10.2}$-$R^{22}$, -$L^{10.3}$-$R^{23}$, or -$L^{10.4}$-$R^{24}$ respectively.

2. The compound of claim 1, wherein
$L^{10.3}$ is a bond, —NH—, —O—, —C(O)—, —NHC(O)O—, —NHS(O)$_2$—, or substituted or unsubstituted 2 to 5 membered heteroalkylene;

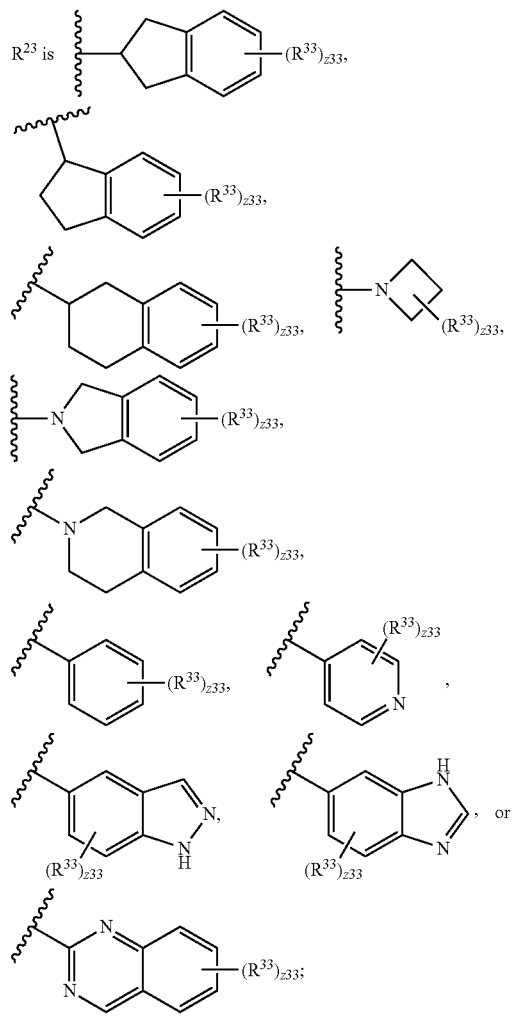

and
z33 is an integer from 0 to 10.

3. A pharmaceutical composition comprising a compound of claim 1, or a pharmaceutically acceptable salt thereof or a prodrug thereof, and a pharmaceutically acceptable excipient.

4. A method of treating asthma, the method comprising administering to a subject in need thereof an effective amount of a compound of claim 1, or a pharmaceutically acceptable salt thereof or a prodrug thereof.

5. A method of treating an inflammatory disease, the method comprising administering to a subject in need thereof an effective amount of a compound of claim 1, or a pharmaceutically acceptable salt thereof or a prodrug thereof.

6. A method of treating an autoimmune disease, the method comprising administering to a subject in need thereof an effective amount of a compound of claim 1, or a pharmaceutically acceptable salt thereof or a prodrug thereof.

7. A compound, or a pharmaceutically acceptable salt thereof or a prodrug thereof, having the formula:

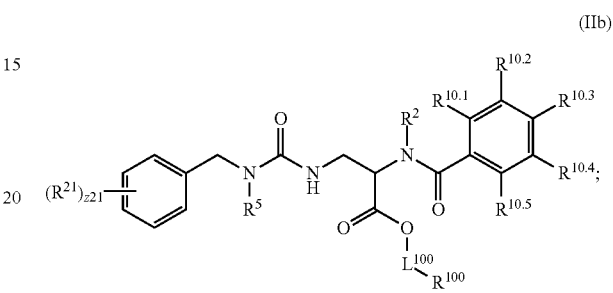

(IIb)

wherein
$R^2$ is hydrogen or substituted or unsubstituted alkyl;
$R^5$ is unsubstituted $C_1$-$C_3$ alkyl;
$R^{10.1}$ is hydrogen, halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10.1}R^{10.1D}$, —$SO_{v10.1}NR^{10.1A}R^{10.1B}$, —$NHC(O)NR^{10.1A}R^{10.1B}$, —$N(O)_{m10.1}$, —$NR^{10.1A}R^{10.1B}$, —$C(O)R^{10.1C}$, —$C(O)OR^{10.1C}$, —$C(O)NR^{10.1A}R^{10.1B}$, —$OR^{10.1D}$, —$SR^{10.1D}$, —$NR^{10.1A}SO_2R^{10.1D}$, —$NR^{10.1A}C(O)R^{10.1C}$, —$NR^{10.1A}C(O)OR^{10.1C}$, —$NR^{10.1A}OR^{10.1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$ is hydrogen, halogen, —$CX^{10.2}_3$, —$CHX^{10.2}_2$, —$CH_2X^{10.2}$, —$OCX^{10.2}_3$, —$OCH_2X^{10.2}$, —$OCHX^{10.2}_2$, —CN, —$SO_{n10.2}R^{10.2D}$, —$SO_{v10.2}NR^{10.2A}R^{10.2B}$, —$NHC(O)NR^{10.2A}R^{10.2B}$, —$N(O)_{m10.2}$, —$NR^{10.2A}R^{10.2B}$, $C(O)R^{10.2C}$, —$C(O)OR^{10.2C}$, —$C(O)NR^{10.2A}R^{10.2B}$, —$OR^{10.2D}$, —$SR^{10.2D}$, —$NR^{10.2A}SO_2R^{10.2D}$, —$R^{10.2A}C(O)R^{10.2C}$, —$NR^{10.2A}C(O)OR^{10.2C}$, —$NR^{10.2A}OR^{10.2C}$, —$N_3$, -$L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, —$CX^{10.3}_3$, —$CHX^{10.3}_2$, —$CH_2X^{10.3}$, —$OCX^{10.3}_3$, —$OCH_2X^{10.3}$, —$OCHX^{10.3}_2$, —CN, —$SO_{n10.3}R^{10.3D}$, —$SO_{v10.3}NR^{10.3A}R^{10.3B}$, —$NHC(O)NR^{10.3A}R^{10.3B}$, —$N(O)_{m10.3}$, —$NR^{10.3A}R^{10.3B}$, —$C(O)R^{10.3C}$, —$C(O)OR^{10.3C}$, —$C(O)NR^{10.3A}R^{10.3B}$, —$OR^{10.3D}$, —$SR^{10.3D}$, —$NR^{10.3A}SO_2R^{10.3D}$, —$NR^{10.3A}C(O)R^{10.3C}$, —$NR^{10.3A}C(O)OR^{10.3C}$, —$NR^{10.3A}OR^{10.3C}$, —$N_3$, -$L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.4}$ is hydrogen, halogen, $-CX^{10.4}_3$, $-CHX^{10.4}_2$, $-CH_2X^{10.4}$, $-OCX^{10.4}_3$, $-OCH_2X^{10.4}$, $-OCHX^{10.4}_2$, $-CN$, $-SO_{n10.4}R^{10.4D}$, $-SO_{v10.4}NR^{10.4A}R^{10.4B}$, $-NHC(O)NR^{10.4A}R^{10.4B}$, $-N(O)_{m10.4}$, $-NR^{10.4A}R^{10.4B}$, $-C(O)R^{10.4C}$, $-C(O)OR^{10.4C}$, $-C(O)NR^{10.4A}R^{10.4B}$, $-OR^{10.4D}$, $-SR^{10.4D}$, $-NR^{10.4A}SO_2R^{10.4D}$, $-NR^{10.4A}C(O)R^{10.4C}$, $-NR^{10.4A}C(O)OR^{10.4C}$, $-NR^{10.4A}OR^{10.4C}$, $-N_3$, $-L^{10.4}-R^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $-SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $-NR^{10.5A}C(O)OR^{10.5C}$, $-NR^{10.5A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $C(O)R^{21C}$, $-C(O)OR^{21C}$, $-C(O)NR^{21A}R^{21B}$, $-OR^{21D}$, $-SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$, $L^{10.3}$, and $L^{10.4}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, substituted or unsubstituted alkylene, or substituted or unsubstituted heteroalkylene;

$R^{22}$, $R^{23}$ and $R^{24}$ are independently substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, $-CX^{100}_3$, $-CHX^{100}_3$, $-CH_2X^{100}$, $-OCX^{100}_3$, $-OCH_2X^{100}$, $-OCHX^{100}_2$, $-CN$, $-SO_{n100}R^{100D}$, $-SO_{v100}NR^{100A}R^{100B}$, $-NHC(O)NR^{100A}R^{100B}$, $-N(O)_{m100}$, $-NR^{100A}R^{100B}$, $-C(O)R^{100C}$, $-C(O)OR^{100C}$, $-C(O)NR^{100A}R^{100B}$, $-OR^{100D}$, $-SR^{100D}$, $-NR^{100A}SO_2R^{100D}$, $-NR^{100A}C(O)R^{100C}$, $-NR^{100A}C(O)OR^{100C}$, $-NR^{100A}OR^{100C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.4A}$, $R^{10.4B}$, $R^{10.4C}$, $R^{10.4D}$, $R^{10.5A}$, $R^{10.5B}$, $R^{10.5C}$, $R^{10.5D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl;

$R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.2, n10.3, n10.4, n10.5, n21, and n100 are independently an integer from 0 to 4;

m10.1, m10.2, m10.3, m10.4, m10.5, m21, m100, v10.1, v10.2, v10.3, v10.4, v10.5, v21, and v100 are independently 1 or 2;

$X^{10.1}$, $X^{10.2}$, $X^{10.3}$, $X^{10.4}$, $X^{10.5}$, $X^{21}$, and $X^{100}$ are independently $-F$, $-Cl$, $-Br$, or $-I$;

z21 is an integer from 0 to 5; and wherein at least one of $R^{10.1}$ or $R^{10.5}$ is not hydrogen.

8. A compound, or a pharmaceutically acceptable salt thereof or a prodrug thereof, having the formula:

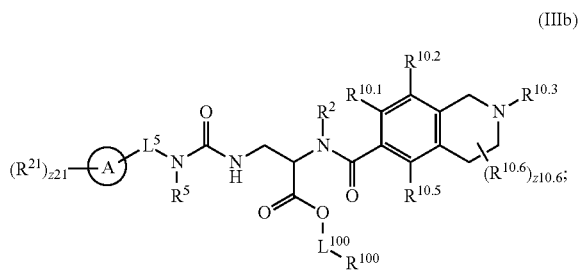
(IIIb)

wherein

Ring A is cycloalkyl, heterocycloalkyl, aryl, or heteroaryl;
$R^2$ is hydrogen or substituted or unsubstituted alkyl;
$R^5$ is hydrogen or unsubstituted $C_1$-$C_3$ alkyl;
$L^5$ is a bond or unsubstituted $C_1$-$C_3$ alkylene;
$R^{10.1}$ is hydrogen, halogen, $-CX^{10.1}_3$, $-CHX^{10.1}_2$, $-CH_2X^{10.1}$, $-OCX^{10.1}_3$, $-OCH_2X^{10.1}$, $-OCHX^{10.1}_2$, $-CN$, $-SO_{n10.1}R^{10.1D}$, $-SO_{v10.1}NR^{10.1A}R^{10.1B}$, $-NHC(O)NR^{10.1A}R^{10.1B}$, $-N(O)_{m10.1}$, $-NR^{10.1A}R^{10.1B}$, $C(O)R^{10.1C}$, $-C(O)OR^{10.1C}$, $-C(O)NR^{10.1A}R^{10.1B}$, $-OR^{10.1D}$, $-SR^{10.1D}$, $-NR^{10.1A}SO_2R^{10.1D}$, $-NR^{10.1A}C(O)R^{10.1C}$, $-NR^{10.1A}C(O)OR^{10.1C}$, $-NR^{10.1A}OR^{10.1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$ is hydrogen, halogen, $-CX^{10.2}_3$, $-CHX^{10.2}_2$, $-CH_2X^{10.2}$, $-OCX^{10.2}_3$, $-OCH_2X^{10.2}$, $-OCHX^{10.2}_2$, $-CN$, $-SO_{n10.2}R^{10.2D}$, $-SO_{v10.2}NR^{10.2A}R^{10.2B}$, $-NHC(O)NR^{10.2A}R^{10.2B}$, $-N(O)_{m10.2}$, $-NR^{10.2A}R^{10.2B}$, $C(O)R^{10.2C}$, $-C(O)OR^{10.2C}$, $C(O)NR^{10.2A}R^{10.2B}$, $-OR^{10.2D}$, $-SR^{10.2D}$, $-NR^{10.2A}SO_2R^{10.2D}$, $-NR^{10.2A}C(O)R^{10.2C}$, $-NR^{10.2A}C(O)OR^{10.2C}$, $-NR^{10.2A}OR^{10.2C}$, $-N_3$, -$L^{10.2}$-$R^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.3}$ is hydrogen, halogen, $-CX^{10.3}_3$, $-CHX^{10.3}_2$, $-CH_2X^{10.3}$, $-OCX^{10.3}_3$, $-OCH_2X^{10.3}$, $-OCHX^{10.3}_2$, $-CN$, $-SO_{n10.3}R^{10.3D}$, $-SO_{v10.3}NR^{10.3A}R^{10.3B}$, $-NHC(O)NR^{10.3A}R^{10.3B}$, $-N(O)_{m10.3}$, $-NR^{10.3A}R^{10.3B}$, $C(O)R^{10.3C}$, $-C(O)OR^{10.3C}$, $-C(O)NR^{10.3A}R^{10.3B}$, $-OR^{10.3D}$, $-SR^{10.3D}$, $-NR^{10.3A}SO_2R^{10.3D}$, $-NR^{10.3A}C(O)R^{10.3C}$, $-NR^{10.3A}C(O)OR^{10.3C}$, $-NR^{10.3A}OR^{10.3C}$, $-N_3$, -$L^{10.3}$-$R^{23}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.5}$ is hydrogen, halogen, $-CX^{10.5}_3$, $-CHX^{10.5}_2$, $-CH_2X^{10.5}$, $-OCX^{10.5}_3$, $-OCH_2X^{10.5}$, $-OCHX^{10.5}_2$, $-CN$, $-SO_{n10.5}R^{10.5D}$, $SO_{v10.5}NR^{10.5A}R^{10.5B}$, $-NHC(O)NR^{10.5A}R^{10.5B}$, $-N(O)_{m10.5}$, $-NR^{10.5A}R^{10.5B}$, $-C(O)R^{10.5C}$, $-C(O)OR^{10.5C}$, $-C(O)NR^{10.5A}R^{10.5B}$, $-OR^{10.5D}$, $-SR^{10.5D}$, $-NR^{10.5A}SO_2R^{10.5D}$, $-NR^{10.5A}C(O)R^{10.5C}$, $-NR^{10.5A}C(O)OR^{10.5C}$, $-NR^{10.5A}OR^{10.5C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.6}$ is independently oxo, halogen, $-CX^{10.6}_3$, $-CHX^{10.6}_2$, $-CH_2X^{10.6}$, $-OCX^{10.6}_3$, $-OCH_2X^{10.6}$, $-OCHX^{10.6}_2$, $-CN$, $-SO_{n10.6}R^{10.6D}$, $-SO_{v10.6}NR^{10.6A}R^{10.6B}$, $-NHC(O)NR^{10.6A}R^{10.6B}$, $-N(O)_{m10.6}$, $-NR^{10.6A}R^{10.6B}$, $-C(O)R^{10.6C}$, $-C(O)OR^{10.6C}$, $-C(O)NR^{10.6A}R^{10.6B}$, $-OR^{10.6D}$, $-SR^{10.6D}$, $-NR^{10.6A}SO_2R^{10.6D}$, $-NR^{10.6A}C(O)R^{10.6C}$, $-NR^{10.6A}C(O)OR^{10.6C}$, $-NR^{10.6A}OR^{10.6C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21D}$, $-SO_{v21}NR^{21A}R^{21B}$, $-NHC(O)NR^{21A}R^{21B}$, $-N(O)_{m21}$, $-NR^{21A}R^{21B}$, $-C(O)R^{21C}$, $-C(O)OR^{21C}$, $-C(O)NR^{21A}R^{21B}$, $-OR^{21D}$, $SR^{21D}$, $-NR^{21A}SO_2R^{21D}$, $-NR^{21A}C(O)R^{21C}$, $-NR^{21A}C(O)OR^{21C}$, $-NR^{21A}OR^{21C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{10.2}$ and $L^{10.3}$ are independently a bond, $-NH-$, $-S-$, $-O-$, $-C(O)-$, $-C(O)O-$, $-OC(O)-$, $-NHC(O)-$, $-C(O)NH-$, $-NHC(O)O-$, $-OC(O)NH-$, $-NHC(O)NH-$, $-NHC(NH)NH-$, $-S(O)_2-$, $-NHS(O)_2-$, $-S(O)_2NH-$, substituted or unsubstituted alkylene, or substituted or unsubstituted heteroalkylene;

$R^{22}$ and $R^{23}$ are independently substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, or unsubstituted heterocycloalkylene, substituted or unsubstituted arylene, or substituted or unsubstituted heteroarylene;

$R^{100}$ is hydrogen, halogen, $-CX^{100}_3$, $-CHX^{100}_2$, $-CH_2X^{100}$, $-OCX^{100}_3$, $-OCH_2X^{100}$, $-OCHX^{100}_2$, $-CN$, $-SO_{n100}R^{100D}$, $-SO_{v100}NR^{100A}R^{100B}$, $-NHC(O)NR^{100A}R^{100B}$, $-N(O)_{m100}$, $-NR^{100A}R^{100B}$, $-C(O)R^{100C}$, $-C(O)OR^{100C}$, $-C(O)NR^{100A}R^{100B}$, $-OR^{100D}$, $-SR^{100D}$, $-NR^{100A}SO_2R^{100D}$, $-NR^{100A}C(O)R^{100C}$, $-NR^{100A}C(O)OR^{100C}$, $-NR^{100A}OR^{100C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.2A}$, $R^{10.2B}$, $R^{10.2C}$, $R^{10.2D}$, $R^{10.3A}$, $R^{10.3B}$, $R^{10.3C}$, $R^{10.3D}$, $R^{10.5A}$, $R^{10.5B}$, $R^{10.5C}$, $R^{10.5D}$, $R^{10.6A}$, $R^{10.6B}$, $R^{10.6C}$, $R^{10.6D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, $-NHC(O)$ H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.2A}$ and $R^{10.2B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{10.6A}$ and $R^{10.6B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.2, n10.3, n10.5, n10.6, n21, and n100 are independently an integer from 0 to 4;

m10.1, m10.2, m10.3, m10.5, m10.6, m21, m100, v10.1, v10.2, v10.3, v10.5, v10.6, v21, and v100 are independently 1 or 2;

$X^{10.1}$, $X^{10.2}$, $X^{10.3}$, $X^{10.5}$, $X^{10.6}$, $X^{21}$, and $X^{100}$ are independently —F, —Cl, —Br, or —I;

z10.6 is an integer from 0 to 6;

z21 is an integer from 0 to 11; and wherein at least one of $R^{10.1}$ or $R^{10.5}$ is not hydrogen.

9. A compound, or a pharmaceutically acceptable salt thereof or a prodrug thereof, having the formula:

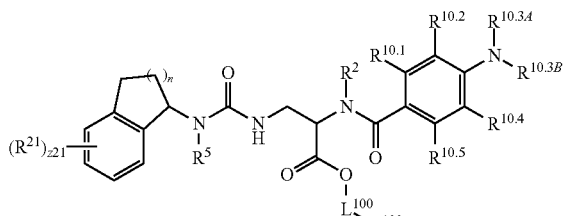

or

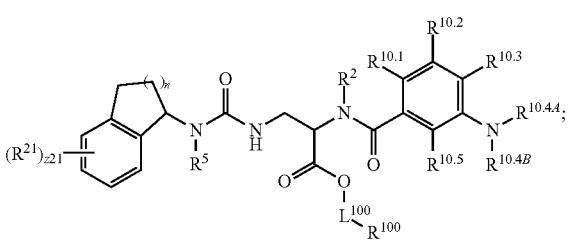

wherein $R^2$ is hydrogen or substituted or unsubstituted alkyl;

$R^5$ is hydrogen or unsubstituted C$_1$-C$_3$ alkyl;

$R^{10.1}$ is hydrogen, halogen, —CX$^{10.1}_3$, —CHX$^{10.1}_2$, —CH$_2$X$^{10.1}$, —OCX$^{10.1}_3$, —OCH$_2$X$^{10.1}$, —OCHX$^{10.1}_2$, —CN, —SO$_{n10.1}$R$^{10.1D}$, —SO$_{v10.1}$NR$^{10.1A}$R$^{10.1B}$, —NHC(O)NR$^{10.1A}$R$^{10.1B}$, —N(O)$_{m10.1}$, —NR$^{10.1A}$R$^{10.1B}$, —C(O)R$^{10.1C}$, —C(O)OR$^{10.1C}$, —C(O)NR$^{10.1A}$R$^{10.1B}$, —OR$^{10.1D}$, —SR$^{10.1D}$, —NR$^{10.1A}$SO$_2$R$^{10.1D}$, —NR$^{10.1A}$C(O)R$^{10.1C}$, —NR$^{10.1A}$C(O)OR$^{10.1C}$, —NR$^{10.1A}$OR$^{10.1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.2}$, $R^{10.3}$, and $R^{10.4}$ are independently hydrogen, halogen, or —CF$_3$;

$R^{10.5}$ is hydrogen, halogen, —CX$^{10.5}_3$, —CHX$^{10.5}_2$, —CH$_2$X$^{10.5}$, —OCX$^{10.5}_3$, —OCH$_2$X$^{10.5}$, —OCHX$^{10.5}_2$, —CN, —SO$_{n10.5}$R$^{10.5D}$, SO$_{v10.5}$NR$^{10.5A}$R$^{10.5B}$, —NHC(O)NR$^{10.5A}$R$^{10.5B}$, —N(O)$_{m10.5}$, —NR$^{10.5A}$R$^{10.5B}$, —C(O)R$^{10.5C}$, —C(O)OR$^{10.5C}$, —C(O)NR$^{10.5A}$R$^{10.5B}$, —OR$^{10.5D}$, —SR$^{10.5D}$, —NR$^{10.5A}$SO$_2$R$^{10.5D}$, —NR$^{10.5A}$C(O)R$^{10.5C}$, —NR$^{10.5A}$C(O)OR$^{10.5C}$, —NR$^{10.1A}$OR$^{10.5C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21}$ is independently oxo, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O)R$^{21C}$, —C(O)OR$^{21C}$, —C(O)NR$^{21A}$R$^{21B}$, —OR$^{21D}$, —SR$^{21D}$, —NR$^{21A}$SO$_2$R$^{21D}$, —NR$^{21A}$C(O)R$^{21C}$, —NR$^{21A}$C(O)OR$^{21C}$, —NR$^{21A}$OR$^{21C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^{100}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is hydrogen, halogen, —CX$^{100}_3$, —CHX$^{100}$, —CH$_2$X$^{100}$, —OCX$^{100}_3$, —OCH$_2$X$^{100}$, —OCHX$^{100}_2$, —CN, —SO$_{n100}$R$^{100D}$, —SO$_{v100}$NR$^{100A}$R$^{100B}$, —NHC(O)NR$^{100A}$R$^{100B}$, —N(O)$_{m100}$, —NR$^{100A}$R$^{100B}$, —C(O)R$^{100C}$, —C(O)OR$^{100C}$, —C(O)NR$^{100A}$R$^{100B}$, —OR$^{100D}$, —SR$^{100D}$, —NR$^{100A}$SO$_2$R$^{100D}$, —NR$^{100A}$C(O)R$^{100C}$, —NR$^{100A}$C(O)OR$^{100C}$, —NR$^{100A}$OR$^{100C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10.1A}$, $R^{10.1B}$, $R^{10.1C}$, $R^{10.1D}$, $R^{10.3A}$, $R^{10.3B}$, $R^{10.4A}$, $R^{10.4B}$, $R^{10.5A}$, $R^{10.5B}$, $R^{10.5C}$, $R^{10.5D}$, $R^{21A}$, $R^{21B}$, $R^{21C}$, $R^{21D}$, $R^{100A}$, $R^{100B}$, $R^{100C}$, and $R^{100D}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10.1A}$ and $R^{10.1B}$ substituents bonded to the same nitrogen atom may be joined to form a substituted or unsubstituted heterocycloalkyl or substituted or unsubstituted heteroaryl; $R^{10.3A}$ and $R^{10.3B}$ substituents bonded to the same nitrogen atom may be joined to form a substituted or unsubstituted heterocycloalkyl or substituted or unsubstituted heteroaryl; $R^{10.4A}$ and $R^{10.4B}$ substituents bonded to the same nitrogen atom may be joined to form a substituted or unsubstituted heterocycloalkyl or substituted or unsubstituted heteroaryl; $R^{10.5A}$ and $R^{10.5B}$ substituents bonded to the same nitrogen atom may be joined to form a substituted or unsubstituted heterocycloalkyl or substituted or unsubstituted heteroaryl; $R^{21A}$ and $R^{21B}$ substituents bonded to the same nitrogen atom may be joined to form a substituted or unsubstituted heterocycloalkyl or substituted or unsubstituted heteroaryl; $R^{100A}$ and $R^{100B}$ substituents bonded to the same nitrogen atom may be joined to form a substituted or unsubstituted heterocycloalkyl or substituted or unsubstituted heteroaryl;

n10.1, n10.5, n21, and n100 are independently an integer from 0 to 4;

m10.1, m10.5, m21, m100, v10.1, v10.5, v21, and v100 are independently 1 or 2;

$X^{10.1}$, $X^{10.5}$, $X^{21}$, and $X^{100}$ are independently —F, —Cl, —Br, or —I;

z21 is an integer from 0 to 9;

n is an integer from 0 to 3; and wherein at least one of $R^{10.1}$ or $R^{10.5}$ is not hydrogen.

10. The compound of claim 1, wherein

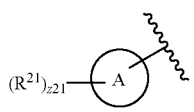

is

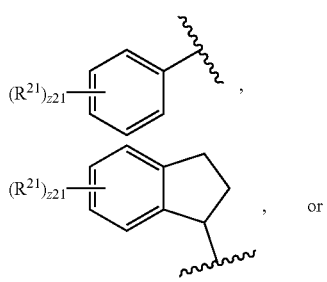, or

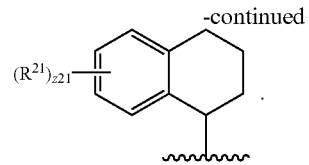

11. The compound of claim 1, wherein $R^2$ is hydrogen or unsubstituted $C_1$-$C_3$ alkyl.

12. The compound of claim 1, wherein $R^{10.1}$ is halogen, substituted or unsubstituted $C_1$-$C_5$ alkyl, or substituted or unsubstituted 2 to 5 membered heteroalkyl.

13. The compound of claim 1, wherein $R^{10.1}$ is —Cl.

14. The compound of claim 1, wherein $L^{10.3}$ is a bond, —NH—, —O—, —C(O)—, —NHC(O)O—, —NHS(O)₂—,

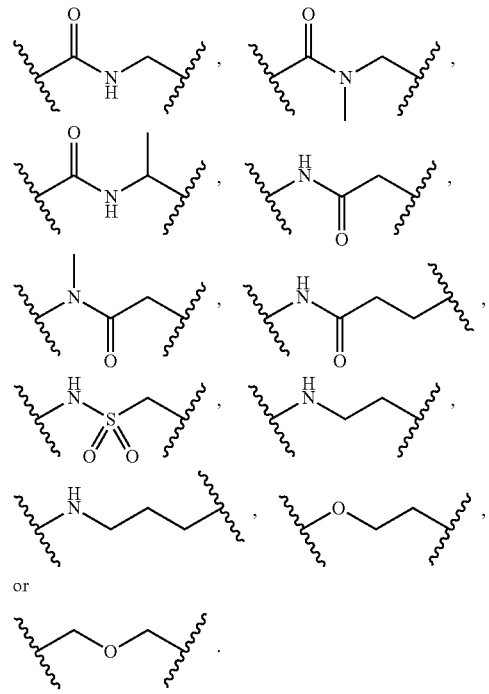

15. The compound of claim 1, wherein
$R^{23}$ is $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; and $R^{33}$ is independently oxo, halogen, —CCl₃, —CBr₃, —CF₃, —CI₃, —CH₂Cl, —CH₂Br, —CH₂F, —CH₂I, —CHCl₂, —CHBr₂, —CHF₂, —CHI₂, —CN, —OH, —NH₂, —COOH, —CONH₂, —NO₂, —SH, —SO₃H, —OSO₃H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCBr₃, —OCF₃, —OCI₃, —OCH₂Cl, —OCH₂Br, —OCH₂F, —OCH₂I, —OCHCl₂, —OCHBr₂, —OCHF₂, —OCHI₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

16. The compound of claim 15, wherein $R^{33}$ is independently halogen, —CF₃, —OH, —NH₂, substituted or unsubstituted $C_1$-$C_4$ alkyl, substituted or unsubstituted 2 to 5 membered heteroalkyl, or substituted or unsubstituted phenyl.

17. The compound of claim 1, wherein $R^{23}$ is

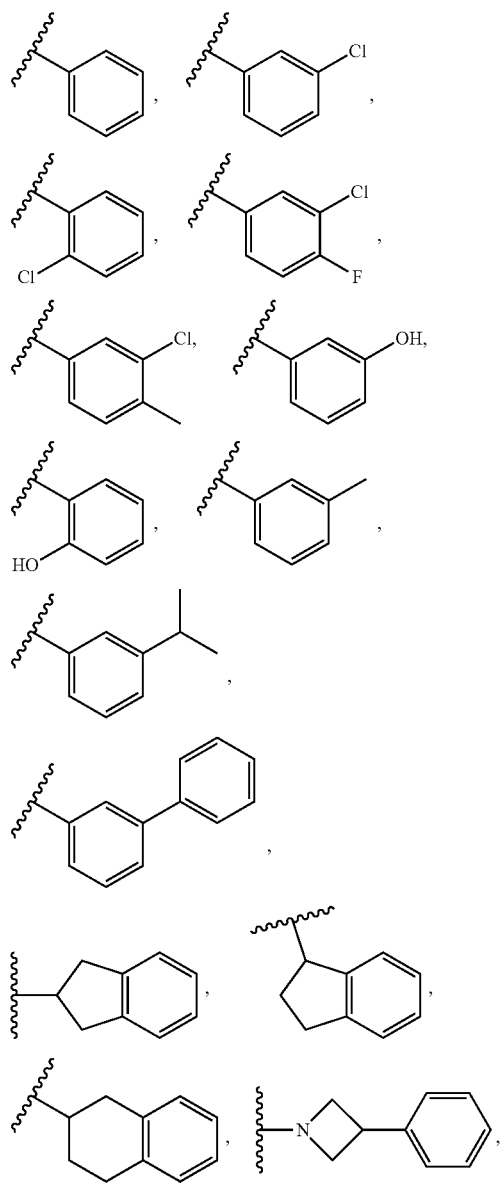
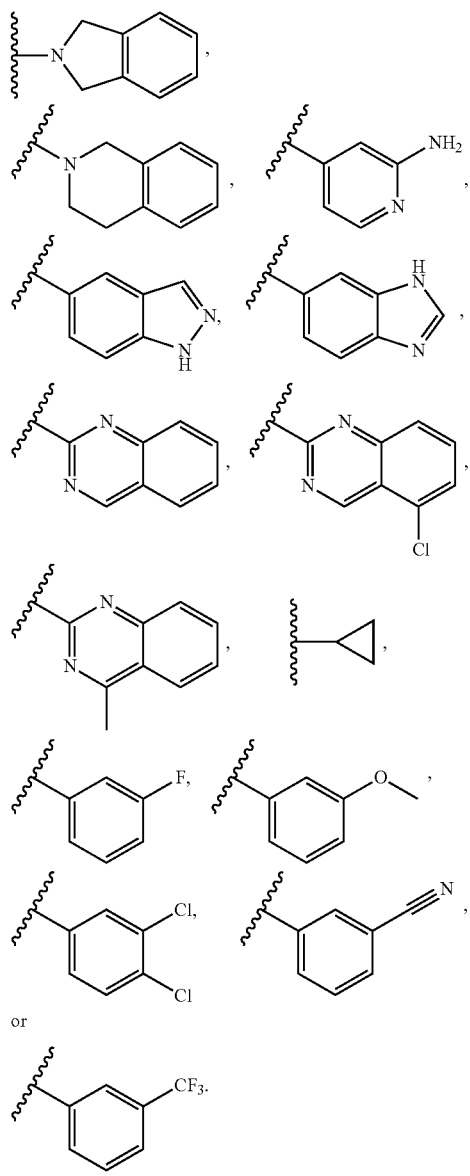

18. The compound of claim 1, wherein $R^{10.5}$ is hydrogen, halogen, substituted or unsubstituted $C_1$-$C_5$ alkyl, or substituted or unsubstituted 2 to 5 membered heteroalkyl.
19. The compound of claim 1, wherein $R^{10.5}$ is —Cl.
20. The compound of claim 1, having the formula

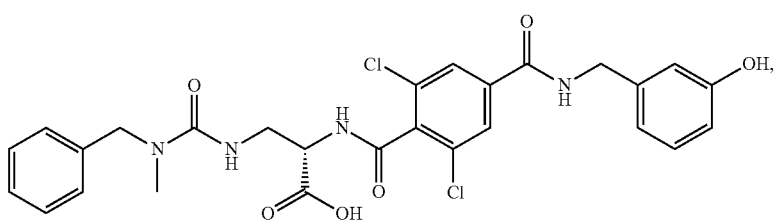

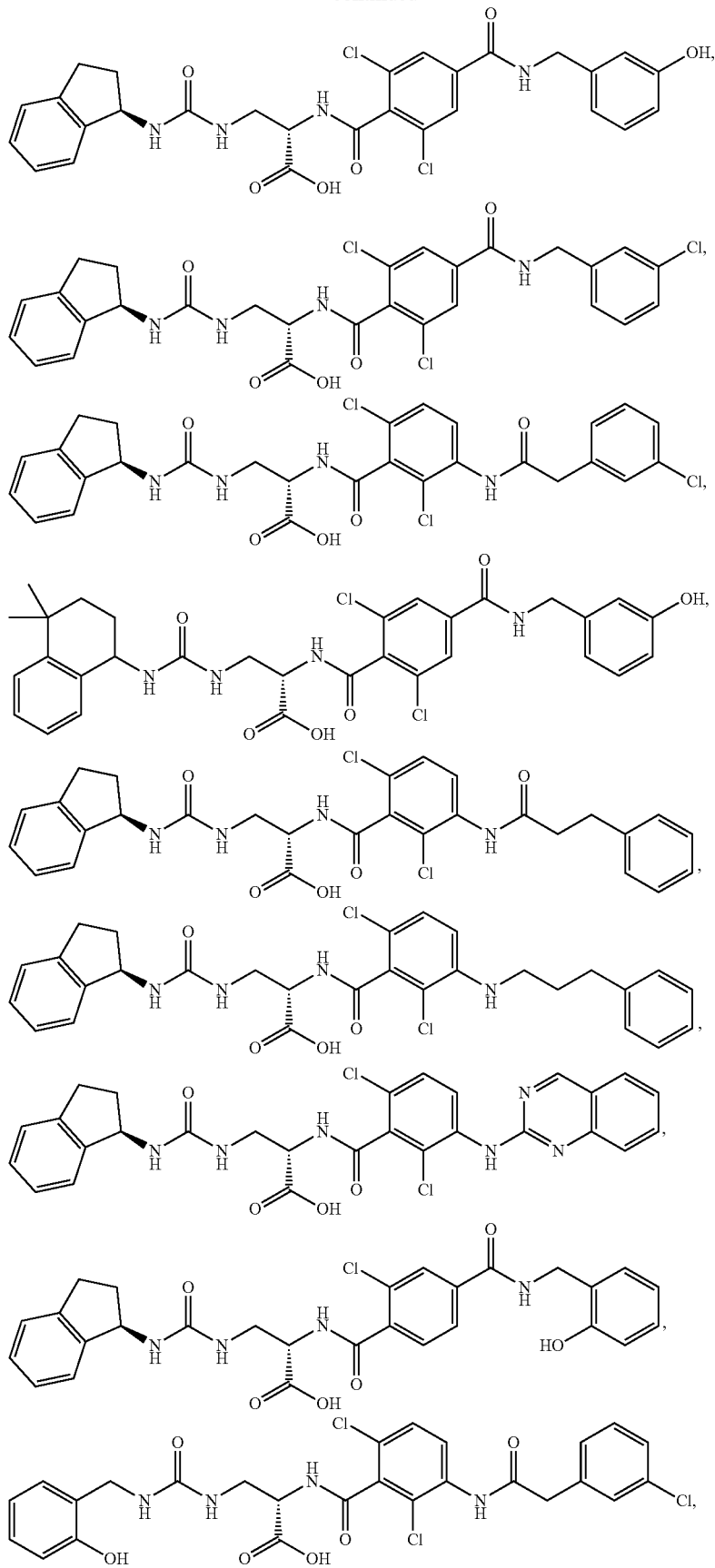

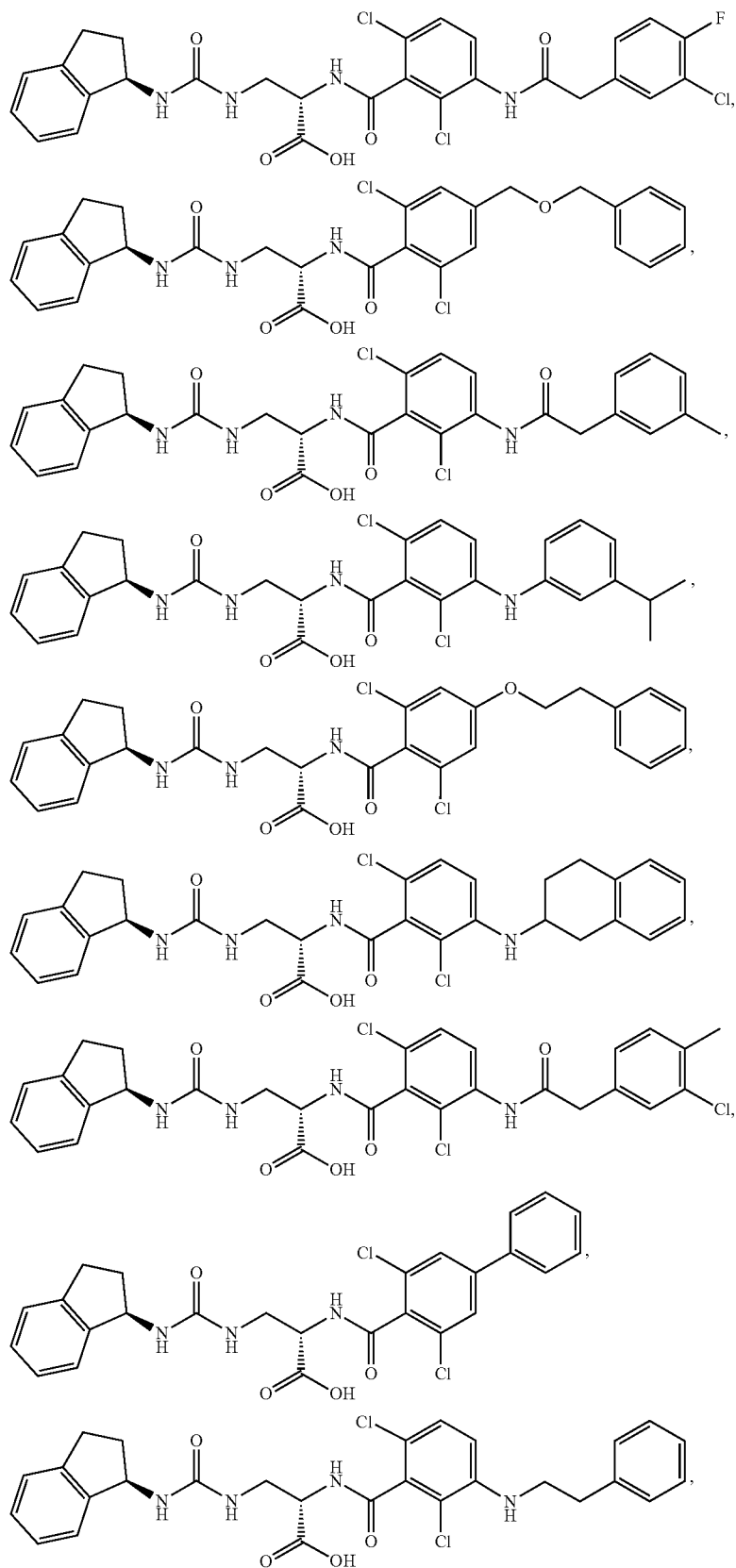

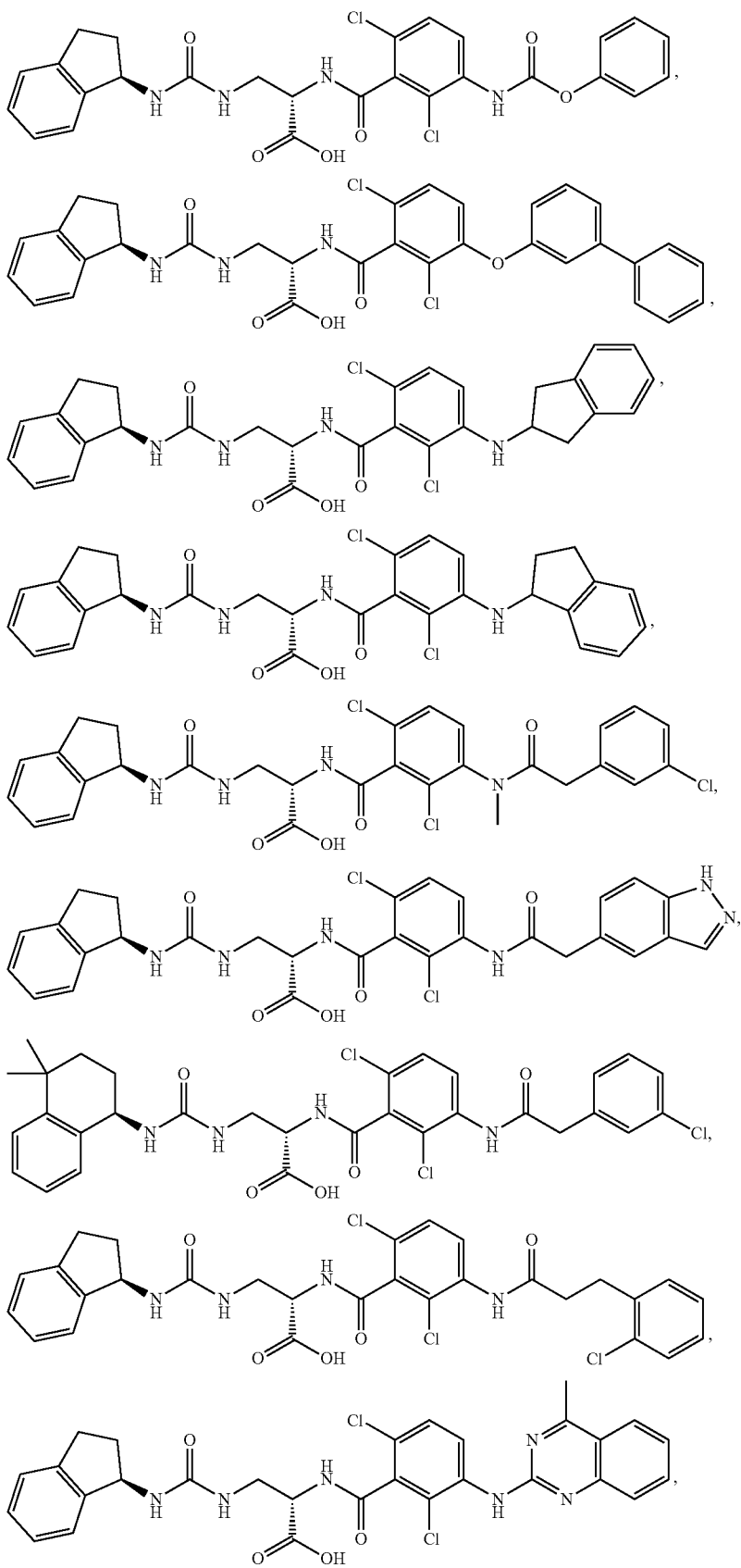

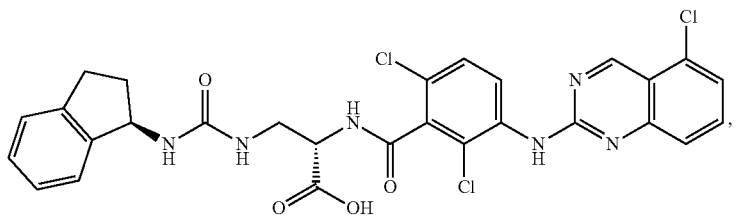
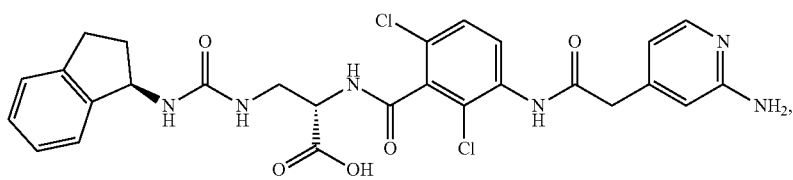
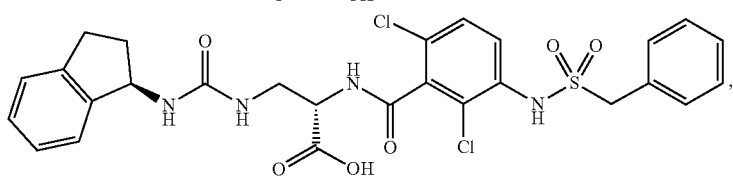
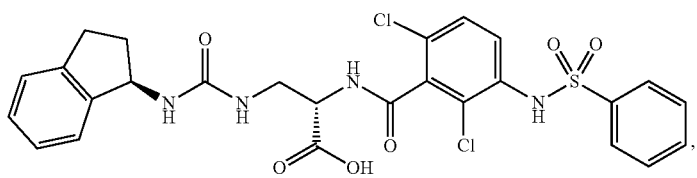
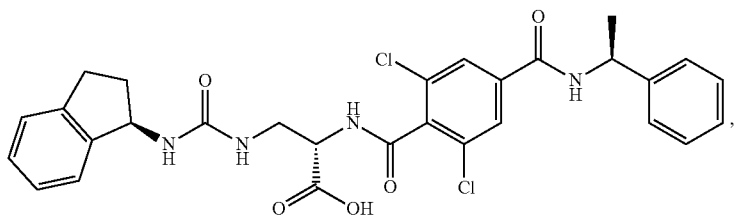
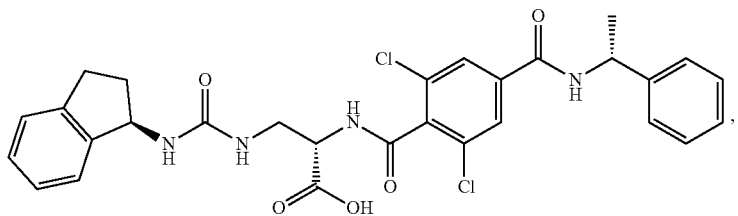
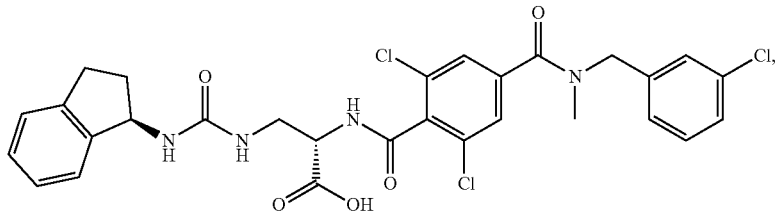
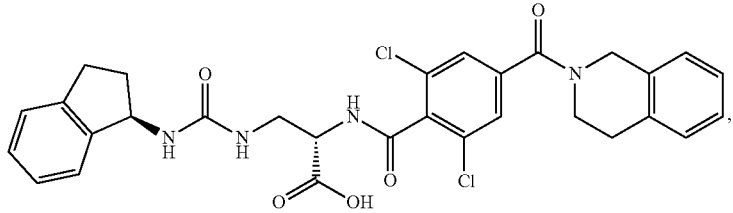

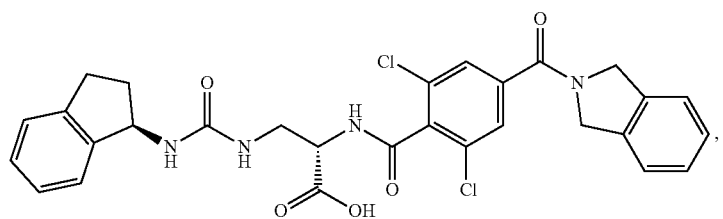
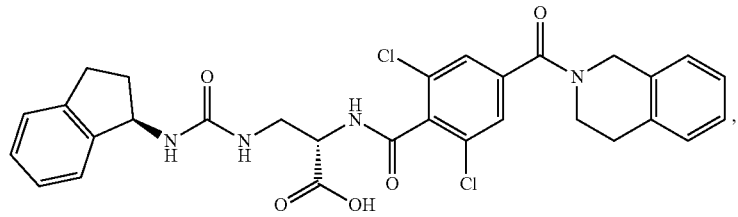
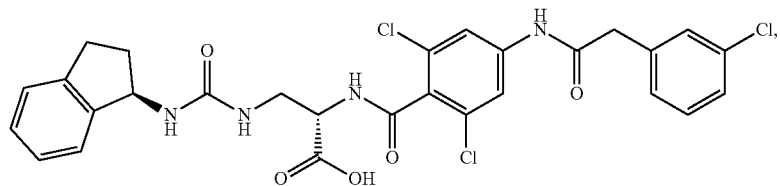
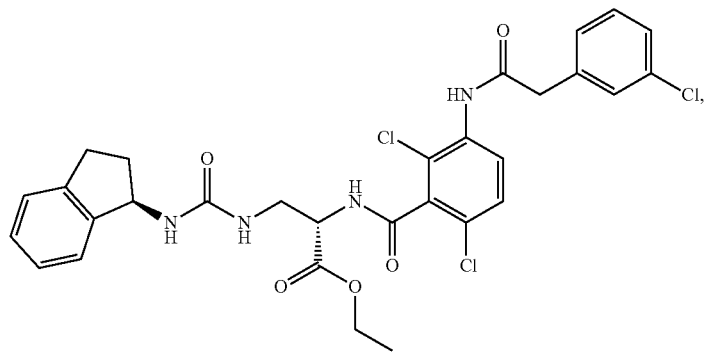
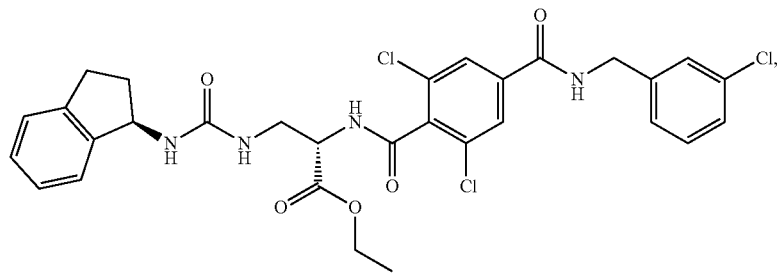
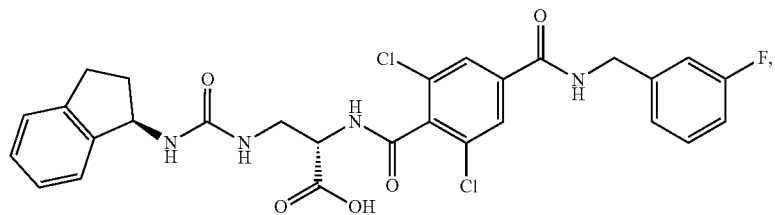
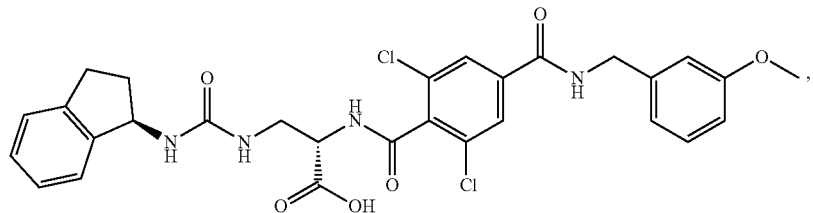

-continued
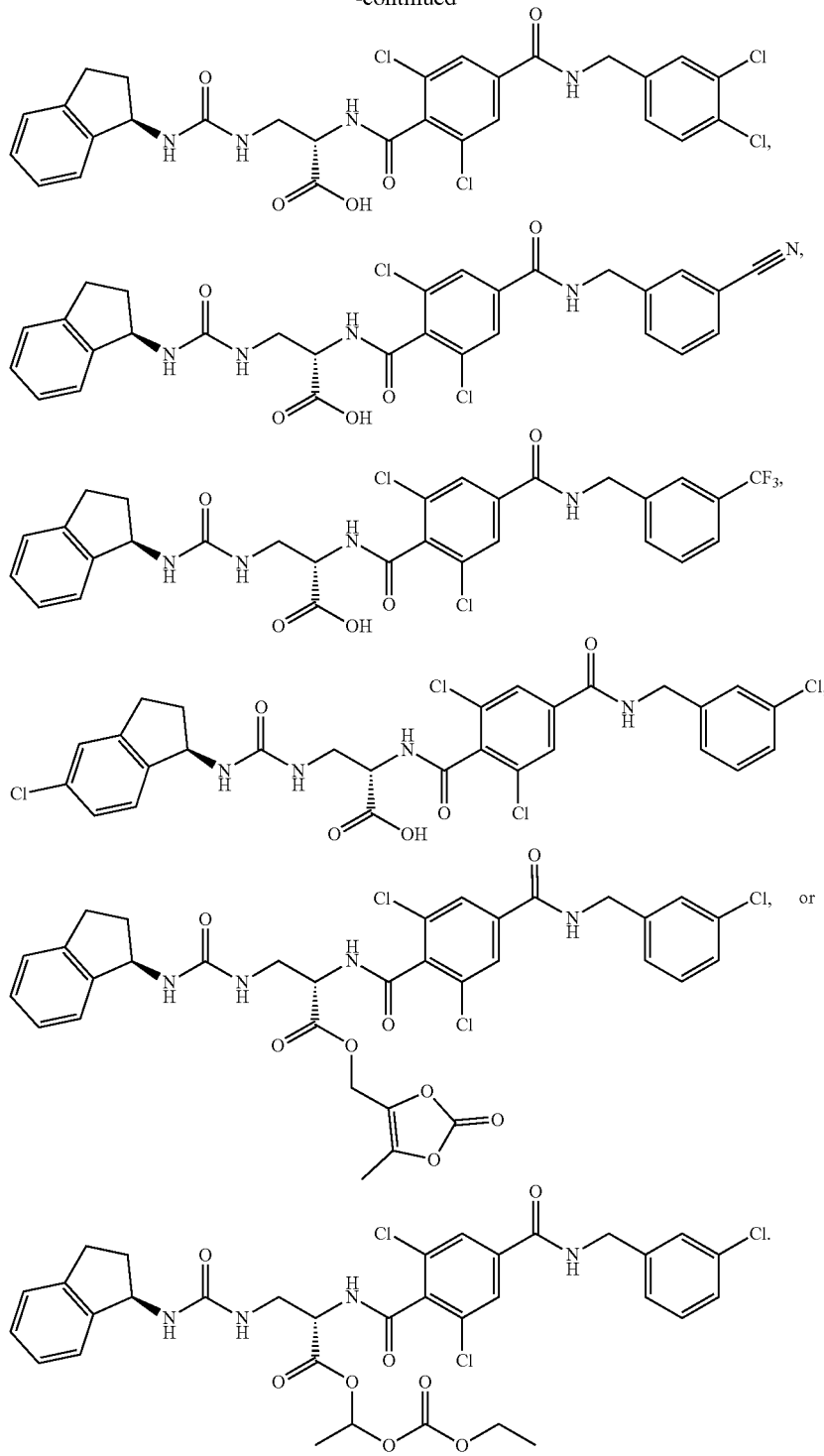
* * * * *

UNITED STATES PATENT AND TRADEMARK OFFICE
CERTIFICATE OF CORRECTION

PATENT NO. : 11,643,388 B2
APPLICATION NO. : 17/246014
DATED : May 9, 2023
INVENTOR(S) : Dean Sheppard et al.

Page 1 of 1

It is certified that error appears in the above-identified patent and that said Letters Patent is hereby corrected as shown below:

In the Specification

In Column 679, Line 44, delete "Ser Ala Val Thr Thr Val Val Asn Pro Lys Tyr Glu Gly Lys Ala" and insert -- Ser Ala Val Thr Thr Val Val Asn Pro Lys Tyr Glu Gly Lys --, therefor.

Signed and Sealed this
Twenty-fourth Day of October, 2023

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 1181
<212> TYPE: PRT
<213> ORGANISM: Artificial Sequence
<220> FEATURE:
<223> OTHER INFORMATION: Synthetic polypeptide

<400> SEQUENCE: 1

Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
                20                  25                  30

Gly Leu Pro Glu Ala Lys Ile Phe Ser Gly Pro Ser Ser Glu Gln Phe
            35                  40                  45

Gly Tyr Ala Val Gln Gln Phe Ile Asn Pro Lys Gly Asn Trp Leu Leu
        50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
```

```
                    85                  90                  95
Leu Gln Thr Ser Thr Ser Ile Pro Asn Val Thr Glu Met Lys Thr Asn
                100                 105                 110
Met Ser Leu Gly Leu Ile Leu Thr Arg Asn Met Gly Thr Gly Gly Phe
                115                 120                 125
Leu Thr Cys Gly Pro Leu Trp Ala Gln Cys Gly Asn Gln Tyr Tyr
130                 135                 140
Thr Thr Gly Val Cys Ser Asp Ile Ser Pro Asp Phe Gln Leu Ser Ala
145                 150                 155                 160
Ser Phe Ser Pro Ala Thr Gln Pro Cys Pro Ser Leu Ile Asp Val Val
                165                 170                 175
Val Val Cys Asp Glu Ser Asn Ser Ile Tyr Pro Trp Asp Ala Val Lys
                180                 185                 190
Asn Phe Leu Glu Lys Phe Val Gln Gly Leu Asp Ile Gly Pro Thr Lys
                195                 200                 205
Thr Gln Val Gly Leu Ile Gln Tyr Ala Asn Asn Pro Arg Val Val Phe
                210                 215                 220
Asn Leu Asn Thr Tyr Lys Thr Lys Glu Glu Met Ile Val Ala Thr Ser
225                 230                 235                 240
Gln Thr Ser Gln Tyr Gly Gly Asp Leu Thr Asn Thr Phe Gly Ala Ile
                245                 250                 255
Gln Tyr Ala Arg Lys Tyr Ala Tyr Ser Ala Ser Gly Gly Arg Arg
                260                 265                 270
Ser Ala Thr Lys Val Met Val Val Thr Asp Gly Glu Ser His Asp
                275                 280                 285
Gly Ser Met Leu Lys Ala Val Ile Asp Gln Cys Asn His Asp Asn Ile
                290                 295                 300
Leu Arg Phe Gly Ile Ala Val Leu Gly Tyr Leu Asn Arg Asn Ala Leu
305                 310                 315                 320
Asp Thr Lys Asn Leu Ile Lys Glu Ile Lys Ala Ile Ala Ser Ile Pro
                325                 330                 335
Thr Glu Arg Tyr Phe Phe Asn Val Ser Asp Glu Ala Ala Leu Leu Glu
                340                 345                 350
Lys Ala Gly Thr Leu Gly Glu Gln Ile Phe Ser Ile Glu Gly Thr Val
                355                 360                 365
Gln Gly Gly Asp Asn Phe Gln Met Glu Met Ser Gln Val Gly Phe Ser
                370                 375                 380
Ala Asp Tyr Ser Ser Gln Asn Asp Ile Leu Met Leu Gly Ala Val Gly
385                 390                 395                 400
Ala Phe Gly Trp Ser Gly Thr Ile Val Gln Lys Thr Ser His Gly His
                405                 410                 415
Leu Ile Phe Pro Lys Gln Ala Phe Asp Gln Ile Leu Gln Asp Arg Asn
                420                 425                 430
His Ser Ser Tyr Leu Gly Tyr Ser Val Ala Ala Ile Ser Thr Gly Glu
                435                 440                 445
Ser Thr His Phe Val Ala Gly Ala Pro Arg Ala Asn Tyr Thr Gly Gln
                450                 455                 460
Ile Val Leu Tyr Ser Val Asn Glu Asn Gly Asn Ile Thr Val Ile Gln
465                 470                 475                 480
Ala His Arg Gly Asp Gln Ile Gly Ser Tyr Phe Gly Ser Val Leu Cys
                485                 490                 495
Ser Val Asp Val Asp Lys Asp Thr Ile Thr Asp Val Leu Leu Val Gly
                500                 505                 510
```

Ala Pro Met Tyr Met Ser Asp Leu Lys Lys Glu Gly Arg Val Tyr
            515                 520                 525

Leu Phe Thr Ile Lys Lys Gly Ile Leu Gly Gln His Gln Phe Leu Glu
        530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
        915                 920                 925

Lys Ile Pro Leu Leu Tyr Asp Ala Glu Ile His Leu Thr Arg Ser Thr
930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
            965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
            995                 1000                1005

Val Gln Thr Asp Lys Ala Gly Asp Ile Ser Cys Asn Ala Asp Ile
    1010                1015                1020

Asn Pro Leu Lys Ile Gly Gln Thr Ser Ser Val Ser Phe Lys
    1025                1030                1035

Ser Glu Asn Phe Arg His Thr Lys Glu Leu Asn Cys Arg Thr Ala
    1040                1045                1050

Ser Cys Ser Asn Val Thr Cys Trp Leu Lys Asp Val His Met Lys
    1055                1060                1065

Gly Glu Tyr Phe Val Asn Val Thr Thr Arg Ile Trp Asn Gly Thr
    1070                1075                1080

Phe Ala Ser Ser Thr Phe Gln Thr Val Gln Leu Thr Ala Ala Ala
    1085                1090                1095

Glu Ile Asn Thr Tyr Asn Pro Glu Ile Tyr Val Ile Glu Asp Asn
    1100                1105                1110

Thr Val Thr Ile Pro Leu Met Ile Met Lys Pro Asp Glu Lys Ala
    1115                1120                1125

Glu Val Pro Thr Gly Val Ile Ile Gly Ser Ile Ala Gly Ile
    1130                1135                1140

Leu Leu Leu Leu Ala Leu Val Ala Ile Leu Trp Lys Leu Gly Phe
    1145                1150                1155

Phe Lys Arg Lys Tyr Glu Lys Met Thr Lys Asn Pro Asp Glu Ile
    1160                1165                1170

Asp Glu Thr Thr Glu Leu Ser Ser
    1175                1180

<210> SEQ ID NO 2
<211> LENGTH: 799
<212> TYPE: PRT
<213> ORGANISM: Artificial Sequence
<220> FEATURE:
<223> OTHER INFORMATION: Synthetic polypeptide

<400> SEQUENCE: 2

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

```
Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
            130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
```

-continued

| | 515 | | | | 520 | | | | 525 | | |
|---|---|---|---|---|---|---|---|---|---|---|---|
| Gly | Glu | Cys | Val | Cys | Gly | Gln | Cys | Val | Cys | Arg | Lys | Arg | Asp | Asn | Thr |
| | 530 | | | | 535 | | | | 540 | | |

Asn Glu Ile Tyr Ser Gly Lys Phe Cys Glu Cys Asp Asn Phe Asn Cys
545                550                555                560

Asp Arg Ser Asn Gly Leu Ile Cys Gly Gly Asn Gly Val Cys Lys Cys
                565                570                575

Arg Val Cys Glu Cys Asn Pro Asn Tyr Thr Gly Ser Ala Cys Asp Cys
            580                585                590

Ser Leu Asp Thr Ser Thr Cys Glu Ala Ser Asn Gly Gln Ile Cys Asn
        595                600                605

Gly Arg Gly Ile Cys Glu Cys Gly Val Cys Lys Cys Thr Asp Pro Lys
    610                615                620

Phe Gln Gly Gln Thr Cys Glu Met Cys Gln Thr Cys Leu Gly Val Cys
625                630                635                640

Ala Glu His Lys Glu Cys Val Gln Cys Arg Ala Phe Asn Lys Gly Glu
            645                650                655

Lys Lys Asp Thr Cys Thr Gln Glu Cys Ser Tyr Phe Asn Ile Thr Lys
        660                665                670

Val Glu Ser Arg Asp Lys Leu Pro Gln Pro Val Gln Pro Asp Pro Val
    675                680                685

Ser His Cys Lys Glu Lys Asp Val Asp Cys Trp Phe Tyr Phe Thr
690                695                700

Tyr Ser Val Asn Gly Asn Asn Glu Val Met Val His Val Val Glu Asn
705                710                715                720

Pro Glu Cys Pro Thr Gly Pro Asp Ile Ile Pro Ile Val Ala Gly Val
            725                730                735

Val Ala Gly Ile Val Leu Ile Gly Leu Ala Leu Leu Leu Ile Trp Lys
        740                745                750

Leu Leu Met Ile Ile His Asp Arg Arg Glu Phe Ala Lys Phe Glu Lys
    755                760                765

Glu Lys Met Asn Ala Lys Trp Asp Thr Gly Glu Asn Pro Ile Tyr Lys
770                775                780

Ser Ala Val Thr Thr Val Val Asn Pro Lys Tyr Glu Gly Lys Ala
785                790                795